(12) United States Patent
Håkansson

(10) Patent No.: US 10,881,709 B2
(45) Date of Patent: *Jan. 5, 2021

(54) IMMUNE SYSTEM MODULATORS AND COMPOSITIONS

(71) Applicant: Canimguide Therapeutics AB, Lund (SE)

(72) Inventor: Leif Håkansson, Höllviken (SE)

(73) Assignee: CANIMGUIDE THERAPEUTICS AB, Lund (SE)

( * ) Notice: Subject to any disclaimer, the term of this patent is extended or adjusted under 35 U.S.C. 154(b) by 0 days.

This patent is subject to a terminal disclaimer.

(21) Appl. No.: 15/555,029

(22) PCT Filed: Mar. 2, 2016

(86) PCT No.: PCT/US2016/020510
§ 371 (c)(1),
(2) Date: Aug. 31, 2017

(87) PCT Pub. No.: WO2016/144650
PCT Pub. Date: Sep. 15, 2016

(65) Prior Publication Data
US 2018/0177842 A1    Jun. 28, 2018

Related U.S. Application Data

(60) Provisional application No. 62/129,669, filed on Mar. 6, 2015.

(51) Int. Cl.
| | | |
|---|---|---|
| *A61K 38/00* | (2006.01) | |
| *A61K 38/10* | (2006.01) | |
| *A61K 38/38* | (2006.01) | |
| *A61K 9/00* | (2006.01) | |
| *A61K 47/02* | (2006.01) | |
| *A61P 37/06* | (2006.01) | |
| *A61P 35/04* | (2006.01) | |
| *A61K 38/08* | (2019.01) | |

(52) U.S. Cl.
CPC ............ *A61K 38/10* (2013.01); *A61K 9/0009* (2013.01); *A61K 9/0019* (2013.01); *A61K 38/08* (2013.01); *A61K 38/385* (2013.01); *A61K 47/02* (2013.01); *A61P 35/04* (2018.01); *A61P 37/06* (2018.01); *A61K 38/00* (2013.01)

(58) Field of Classification Search
CPC ..................................................... A61K 38/00
See application file for complete search history.

(56) References Cited

U.S. PATENT DOCUMENTS

| | | | |
|---|---|---|---|
| 6,703,491 | B1 | 3/2004 | Homburger et al. |
| 7,745,391 | B2 | 6/2010 | Mintz et al. |
| 7,960,126 | B2 | 6/2011 | Håkansson et al. |
| 8,133,688 | B2 | 3/2012 | Håkansson et al. |
| 9,120,874 | B2 | 9/2015 | Håkansson et al. |
| 9,657,059 | B2 | 5/2017 | Håkansson |
| 2004/0031072 | A1 | 2/2004 | La Rosa et al. |
| 2007/0031847 | A1 | 2/2007 | Cargill et al. |
| 2012/0227131 | A1 | 9/2012 | Abad et al. |
| 2012/0309015 | A1 | 12/2012 | Finan et al. |
| 2014/0161812 | A1 | 6/2014 | Håkansson et al. |
| 2016/0046702 | A1 | 2/2016 | Håkansson et al. |
| 2017/0298096 | A1 | 10/2017 | Håkansson |

FOREIGN PATENT DOCUMENTS

| | | |
|---|---|---|
| EP | 1 806 364 A2 | 7/2007 |
| WO | WO 2002/088307 | 11/2002 |
| WO | WO 2003/106621 | 12/2003 |
| WO | WO 2004/022097 | 3/2004 |
| WO | WO 2004/046306 | 6/2004 |
| WO | WO 2006/013472 | 2/2006 |
| WO | WO 2007/133290 | 11/2007 |
| WO | WO 2008/136736 A2 | 11/2008 |
| WO | WO 2009/047360 | 4/2009 |
| WO | WO 2011/119484 | 9/2011 |
| WO | WO 2015/035332 | 3/2015 |
| WO | WO 2016/144650 | 9/2016 |

OTHER PUBLICATIONS

Håkansson (J. Transl. Med. 2019, 17 (Suppl. 1):16; Abstract #01; pp. 1-18).*
EPO Communication dated Dec. 19, 2017 in European Application No. 14771713.6.
International Preliminary Report on Patentability dated Mar. 15, 2016 in Application No. PCT/US2014/054612.
International Preliminary Report on Patentability in International Application No. PCT/US2016/020510 dated Sep. 12, 2017.
International Search Report and Written Opinion dated Dec. 17, 2014 in Application No. PCT/US2014/054612.
International Search Report and Written Opinion dated May 31, 2016 in Application No. PCT/US2016/020510.
Summary of BLAST searches for "FFVKL," "FFVKLS," "TFFVKL," "TFFVKLS," "KKLDTFFVKLSLFTER" and "KKLDTFFVKLSLFTER" for against database entries present in Apr. 2012, in 9 pages.
GenBank: AAD02558.1 "PGPS/NH17, partial [Petunia x hybrids]" Submitted Feb. 23, 1998, in 1 page.
GenBank: AAY03652,1, "Sequence 193 from patent U.S. Pat. No. 6861256" dated Mar. 1, 2005, in 1 page.
GenBank: ABH73247.1. "Sequence 193 from patent U.S. Pat. No. 7041437" dated May 9, 2006, in 1 page.
GenBank: ABT82318.1. Sequence 169788 from patent U.S. Pat. No. 7214786. dated May 8, 2007, in 1 page.

(Continued)

*Primary Examiner* — Stephen L Rawlings
(74) *Attorney, Agent, or Firm* — Knobbe, Martens Olson and Bear, LLP

(57) ABSTRACT

The present invention described herein relates to molecules and compositions that interact with molecules that suppress the immune system. More specifically, embodiments described herein concern the discovery, manufacture, and use of compositions that remove immunosuppression the immune system by binding to immunoregulatory peptides that interact with receptors on immune cells, compositions that can stimulate immune cells, and compositions that are cytotoxic to tumor cells.

10 Claims, 106 Drawing Sheets

Specification includes a Sequence Listing.

(56) References Cited

OTHER PUBLICATIONS

GenBank: ACC54912.1. "Sec61 gamma subunit alpha, partial [Xenopus borealis]" Submitted Feb. 4, 2008, in 1 page.
GenBank: AEE26217.1, "mechanosensitive ion channel family protein [*Francisella cf. tularensis* subsp. *Novicida 3523*]" Submitted Feb. 14, 2011, in 2 pages.
GenBank: AER13808.1, "NAD+-dependent glyceraldehyde-3-phosphate dehydrogenase, partial [Crepidomanes minutum]" Submitted Nov. 20, 2010, in 1 page.
GenBank: AER13809,1, "NAD+-dependent glyceraldehyde-3-phosphate dehydrogenase, partial [Crepidomanes minutum]" Submitted Nov. 20, 2010, in 1 page.
GenBank: AER13806.1, "NAD+-dependent glyceraldehyde-3-phosphate dehydrogenase, partial [Crepidomanes fallax]" Submitted Nov. 20, 2010, in 1 page.
GenBank: AEV00298.1. "Sequence 159416 from patent U.S. Pat. No. 8067671." dated Nov. 29, 2011, in 1 page.
GenBank: AEY43457.1, "Sequence 159416 from patent U.S. Pat. No. 8088976." dated Jan. 3, 2012, in 1 page.
GenBank: CBA05911.1. "hypothetical protein predicted by Glimmer/Critica [Neisseria meningitidis alpha275]" Submitted Sep. 13, 2007, in 1 page.
GenBank: CBA07448,1. "hypothetical protein predicted by Glimmer/Critica [Neisseria meningitidis alpha153]" Submitted Sep. 13, 2007, in 1 page.
GenBank: EDK23255,1. hypothetical protein RUMTOR_02533 [Ruminococcus torques ATCC 27756]. Submitted Feb. 3, 2007, in 2 pages.
GenBank: EDM02489.1. "rCG36896, partial [Rattus norvegicus]" Submitted Jul. 5, 2006, in 1 page.
GenBank: EEH01101.1. "conserved hypothetical protein [Borreliella finlandensis]" Submitted Jan. 30, 2008, in 1 page.
GenBank: EFV64484.1. "putative transposase [Neisseria meningitides H44/76]" Submitted Dec. 29, 2010, in 1 page.
GenBank: EGV62334.1. "hypothetical protein CANTEDRAFT_126106 [Candida tenuis ATCC 10573]" Submitted May 9, 2011, in 2 pages.
GenBank: GAA79446.1. "hypothetical protein P20495_1947 [*Pseudoalteromonas* sp. *BSi20495*]" Submitted Oct. 24, 2011, in 1 page.
NCBI Reference Sequence: YP_169980.1, corresponding to Gene ID: 3190887. FTT_0992 hypothetical protein [*Francisella tularensis* subsp. *Tularensis SCHU S4*] Submitted Aug. 13, 2009, in 2 pages.
NCBI Reference Sequence: ZP_01968952.1. "hypothetical protein RUMTOR_02533 {Ruminococcus torques ATCC 27756]" Submitted Mar. 26, 2007, in 2 pages.
NCBI Reference Sequence: ZP_03772822.1. "conserved hypothetical protein [*Borrelia* sp. *SV1*]" Submitted Nov. 20, 2010, in 1 page.
NCBI Reference Sequence: ZP_09243197.1. "hypothetical protein P20495_1947 [*Pseudoalteromonas* sp. *BSi20495*]" Submitted Dec. 6, 2011, in 1 page.
Genbank: AAU76211.1, "Sequence 57156 from patent U.S. Pat. No. 6703491" Submitted Mar. 9, 2004, in 1 page.
Genbank: AAU60963.1, "Sequence 41908 from patent U.S. Pat. No. 6703491" Submitted Mar. 9, 2004, in 1 page.
Genbank: EGQ19313.1, "hypothetical protein HMPREF9372_3709 [Sporosarcina newyorkensis 2681]" Submitted Apr. 29, 2011, in 2 pages.
Genbank: YP_004444039, "hypothetical protein AGROH133_12330 [*Agrobacterium* sp. *H133*]" Submitted May 9, 2011, in 1 page.
Genbank: ADY66948.1, "hypothetical protein AGROH133_12330 [*Agrobacterium* sp. *H133*]" Submitted Oct. 1, 2010, in 1 page.
NCBI Reference Sequence: ZP_03783719, "hypothetical protein RUMHYD_03198 [Blautia hydrogenotrophica DSM 10507]" Submitted Jan. 14, 2009, in 2 pages.
Genbank: EEG47914.1, "TIGR00268 family protein [Blautia hydrogenotrophica DSM 10507]" Submitted Jan. 14, 2009, in 2 pages.

Genbank: YP_584917, "PepSYassociated TM helix [Cupriavidus metallidurans CH34]" Submitted Apr. 18, 2006, in 2 pages.
Genbank: ABF09648.1, "PepSYassociated TM helix [Cupriavidus metallidurans CH34]" Submitted Feb. 3, 2010, in 2 pages.
Genbank: ADT21006.1, "Sequence 42411 from U.S. Pat. No. 7834146" Submitted Nov. 16, 2010, in 1 page.
Genbank: AFA96582.1, "Sequence 42411 from U.S. Pat. No. 8106174" submitted Jan. 31, 2012, in 1 page.
Genbank: ABT54594.1, "Sequence 142064 from U.S. Pat. No. 7214786" submitted May 8, 2007, in 1 page.
Genbank: AAL69330.1, "inorganic pyrophosphatase, partial [Ochrobactrum anthropi ATCC 49188]" submitted Sep. 7, 2001, 1 page.
NCBI Reference Sequence: XP_009859504.1, corresponding to Genbank: LOC100181353, "Predicted: sodium/calcium exchanger 2-like [Ciona intestinalis]" dated Oct. 24, 2014, and to Applicant's knowledge, the indicated reference sequence was indexed on BLAST at least as of Apr. 2012, in 2 pages.
Genbank: YP_005416505, "pyrophosphateenergized proton pump [Rhodospirillum photometricum DSM 122]" submitted Feb. 2, 2012, in 2 pages.
Genbank: CCG07535.1, "Pyrophosphateenergized proton pump [Pararhodospirillum photornetricum DSM 122]" submitted Feb. 2, 2012, in 2 pages.
NCBI Reference Sequence: ZP_04679926.1, "Vtype H(+)translocating pyrophosphatase [Ochrobactrum intermedium LMG 3301]" submitted Nov. 10, 2010, in 1 page.
Genbank: EEQ95432.1, "Vtype H(+)translocating pyrophosphatase [Ochrobactrum intermedium LMG 3301]" submitted in May 15, 2009, in 2 pages.
NCBI Reference Sequence: XP_003463117.1, corresponding to Gene ID: 100724157, "Predicted: origin recognition complex subunit 1 [Cavia porcellus]", dated Jul. 14, 2015, and to Applicant's knowledge, the indicated reference sequence was indexed on BLAST at least as of Apr. 2012, In 2 pages.
NCBI Reference Sequence: XP_003128055.1, corresponding to Gene ID: 100520746, "Predicted: origin recognition complex subunit I like isoformX1 [Sus scrofa]", dated Sep. 26, 2013, and to Applicant's knowledge, the indicated reference sequence was indexed on BLAST at least as of Apr. 2012, In 2 pages.
Genbank: EHB00695.1, "Origin recognition complex subunit 1 [Heterocephalus glaber]" submitted Jul. 11, 2011, in 2 pages.
Genbank: Q58DC8.2, "RecName: Full=Origin recognition complex subunit 1" submitted Feb. 2007, in 4 pages.
NCBI Reference Sequence: NP_001014918.1, corresponding to Gene ID: 513523, "origin recognition complex subunit 1 [Bos taurus]" dated Apr. 11, 2005; in 3 pages.
Genbank: E0609806.1, "hypothetical protein AURANDRAFT_71324 [Aureococcus anophagefferens]" submitted in Aug. 26, 2010, in 2 pages.
Genbank: EFY98846,1, "Ankyrin repeatcontaining domain protein [Metarhiziurn robertsii ARSEF 23]", this item lists a reference date of 2011, in 3 pages.
Genbank: EFY85297.1, "ankyrin repeat protein [Metarhizium acridurn CQMa 102]" submitted in May 10, 2010, in 2 pages.
Genbank: CBY09431.1, "unnamed protein product [Oikopleura dioica]" submitted in Dec. 10, 2009, in 1 page.
NCBI Reference sequence Reference sequence YP_584917, corresponding to Gene ID: 4039601, "Rmet_2775 PepSY-associated TM helix [ Cupriavielus rnetallidurans CH34 ]" submitted Jun. 7, 2011, 2 pages.
NCBI Reference sequence YP_005416505, corresponding to Gene ID: 12209565, "hppA pyrophosphate-energized proton pump [Rhodospirillum photornetricum DSM 122 ]", submitted Feb. 2, 2012, in 2 pages.
Office Action dated Aug. 26, 2016 in Australian Application No. 2014317884.
Office Action dated Aug. 31, 2018 in Chinese Application No. 201480061392.0.
Office Action dated Aug. 7, 2018 in Japanese Application No. 2016-54047.

(56) References Cited

OTHER PUBLICATIONS

Summons to Attend Oral Proceedings for European Patent Application No. 14771713.6 dated Nov. 5, 2018 in 5 pages.
Office Action dated Mar. 21, 2019 in Chinese Application No. 201480061392.0 with English Translation.
"Cellular and Molecular Basis of Cancer", http://www.merckmanuals.com/professional/print/hematology_and_oncology/overview_of . . . , pp. 1-5, accessed Nov. 7, 2012.
Farkona et al., "Cancer immunotherapy: the beginning of the end of cancer?", BMC Medicine, vol. 14, No. 73, pp. 1-18, 2016.
Jeanbart et al., "Engineering opportunities in cancer immunotherapy", PNAS, vol. 112, No. 47, pp. 14467-14472, Nov. 24, 2015.
Kiesler, E., "Why a New Immunotherapy for Lung Cancer Works for Only Some People", https://www.mskcc.org/blog/why-new-immunotherapy-lung-works-only-some-people, pp. 1-4, Apr. 16, 2015.
Oiseth et al., "Cancer immunotherapy: a brief review of the history, possibilities, and challenges ahead", J Cancer Metastasis Treat, vol. 3, pp. 250-261, 2017.
Sahin et al., Immunotherapy in pancreatic ductal adenocarcinoma: an emerging entity?, Annals of Oncology, vol. 28, pp. 2950-2961, 2017.
Office Action dated Apr. 4, 2019 in European Application No. 16711069.1.
Office Action dated Mar. 9, 2018 in U.S. Appl. No. 15/488,283.
Office Action dated Aug. 28, 2018 in U.S. Appl. No. 15/488,283.
Notice of Allowance dated Jan. 4, 2019 in U.S. Appl. No. 15/488,283.
Office Action dated Sep. 23, 2019 in Chinese Application No. 201480061392.0 with English Translation.
NCBI Protein Information Resource: S07455, "Ig kappa chain V region (hybridoma G8 Ca 1.7)—mouse", dated May 9, 1997, in 1 page.
Office Action dated Jun. 4, 2019 in Japanese Application No. 2016-54047.
Office Action dated Dec. 13, 2019 in Korean Application No. 10-201 6-7008914.
Extended European Search Report in European Patent Application No. 19204654.8 dated Apr. 3, 2020.
Office Action in Korean Patent Application No. 10-2016-7008914 dated Apr. 10, 2020.

\* cited by examiner

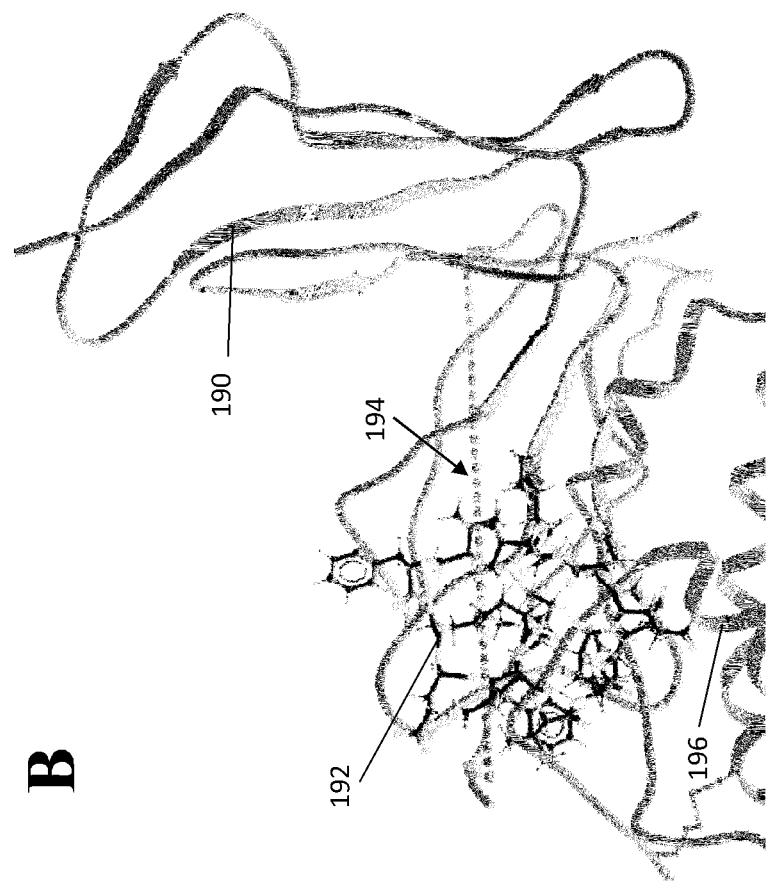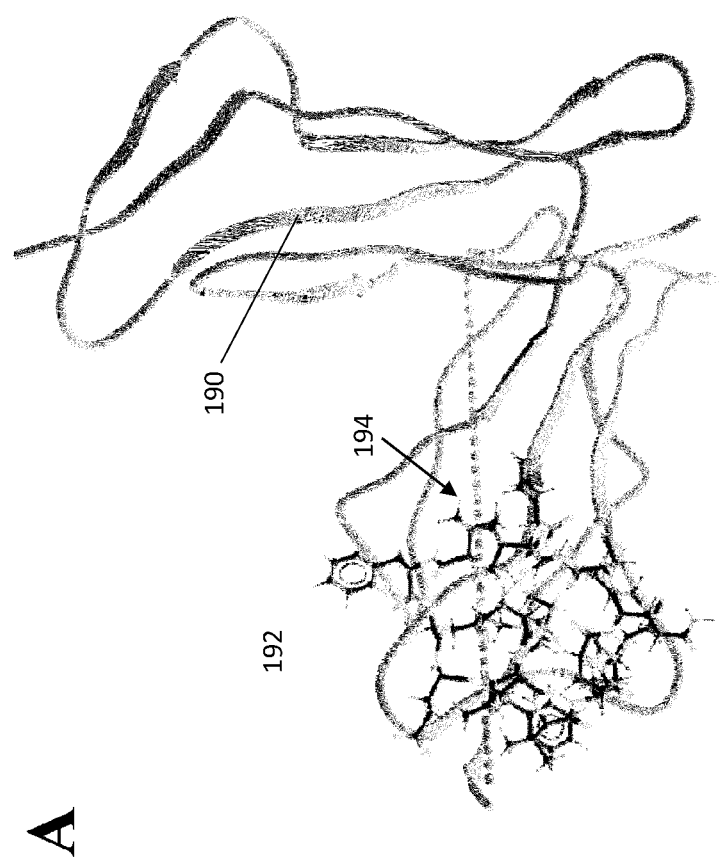
FIG. 19

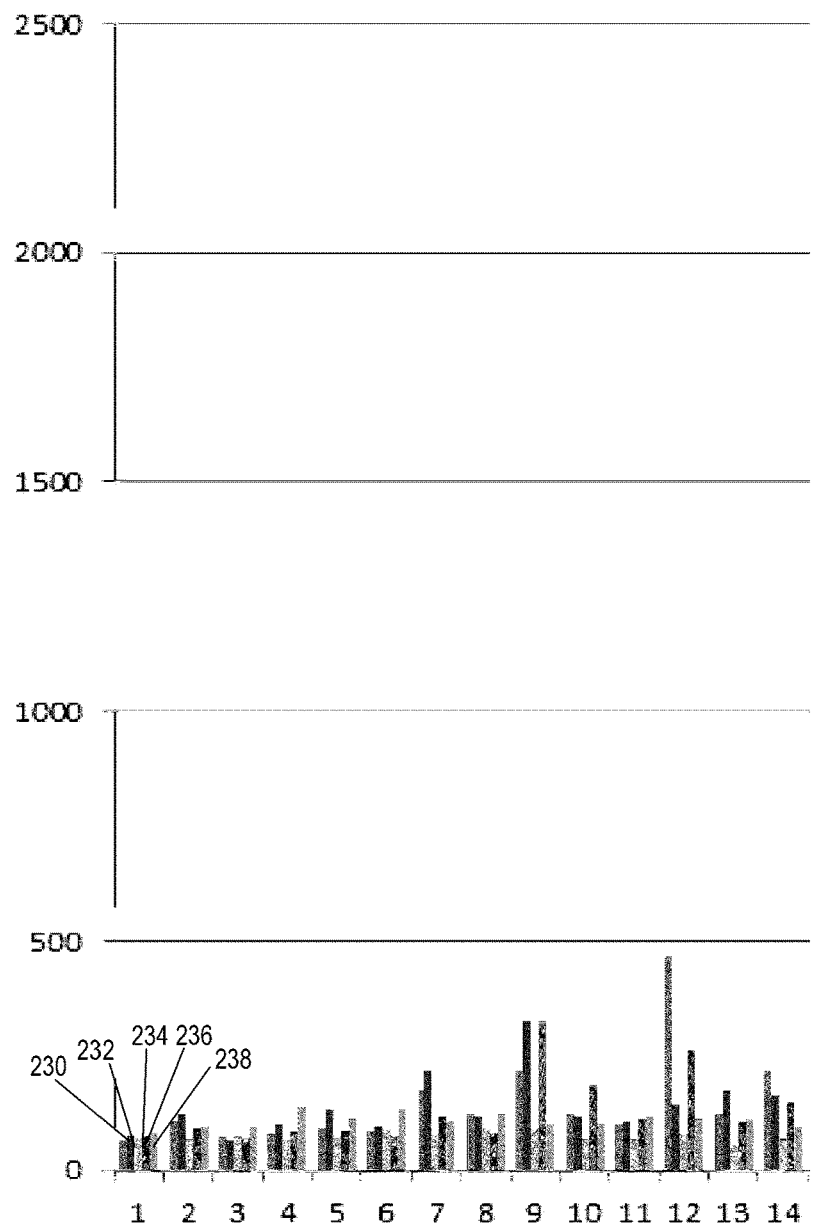

230 — Test : 16-2-2011 PGE73 10 ug/ml+anti-his(1/1000) no peptide added assay in PBS-buffer Rampo 1/1000

232 — Test : 17-2-2011 PGE73 10 ug/ml+anti-his(1/1000) also added: SCF027 (0,5 mg/ml) assay in PBS-buffer Rampo 1/1000

234 — Test : 18-2-2011 PGE73 10 ug/ml+anti-his(1/1000) also added: SCF029 (0,5 mg/ml) assay in PBS-buffer+10% DMSO Rampo 1/1000

236 — Test : 22-2-2011 PGE73 10 ug/ml+anti-his(1/1000) no peptide added assay in PBS-buffer+10% DMSO Rampo 1/1000

238 — Test : 23-2-2011 PGE73 10 ug/ml+anti-his(1/1000) also added: SCF028 (0,5 mg/ml) assay in PBS-buffer+10% DMSO Rampo 1/1000

FIG. 23A

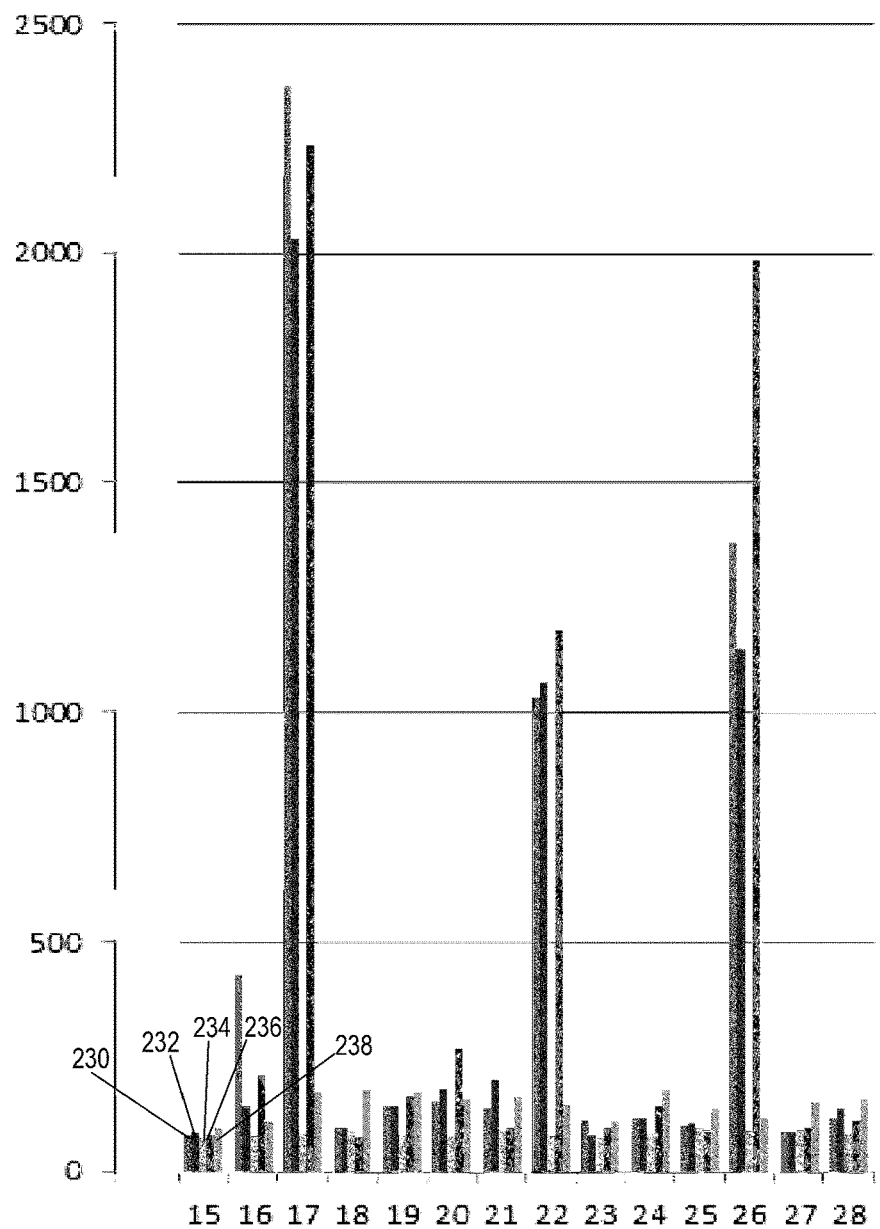

230 — Test : 16-2-2011 PGE73 10 ug/ml+anti-his(1/1000) no peptide added assay in PBS-buffer Rampo 1/1000

232 — Test : 17-2-2011 PGE73 10 ug/ml+anti-his(1/1000) also added: SCF027 (0,5 mg/ml) assay in PBS-buffer Rampo 1/1000

234 — Test : 18-2-2011 PGE73 10 ug/ml+anti-his(1/1000) also added: SCF029 (0,5 mg/ml) assay in PBS-buffer+10% DMSO Rampo 1/1000

236 — Test : 22-2-2011 PGE73 10 ug/ml+anti-his(1/1000) no peptide added assay in PBS-buffer+10% DMSO Rampo 1/1000

238 — Test : 23-2-2011 PGE73 10 ug/ml+anti-his(1/1000) also added: SCF028 (0,5 mg/ml) assay in PBS-buffer+10% DMSO Rampo 1/1000

FIG. 23B

All substitutions with rampo value over 500:

```
Substitutions >500    KKLDTFFVKLSLFTER
                      R-G-QAM--VQQMN--      (largest)
                        E   VS   MVQP
                             V   TMHR
                             T   H N
                             L     P
                                   S
                                   G
                                   A
                                   R         (lowest)
```

FIG. 28

```
CIG3028      VFDEFKPLVEEPQNLIK
             ||*|***||*  **|
KKL15        KKLDTFFKKLSLFTE
```

| = Favorable electrostatic interaction
\* = Favorable hydrophobic interaction

SEQUENCE LISTING

<160> NUMBER OF SEQ ID NOS: 596

<210> SEQ ID NO 1
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 1

Lys Lys Leu Asp Thr Phe Phe Lys Leu Ser Leu Phe Thr Glu
1               5                   10                  15

<210> SEQ ID NO 2
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 2

Lys Lys Leu Asp Thr Phe Phe Val Lys Leu Ser Leu Phe Thr Glu Arg
1               5                   10                  15

<210> SEQ ID NO 3
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 3

Arg Lys Leu Asp Thr Phe Phe Val Lys Leu Ser Leu Phe Thr Glu Arg
1               5                   10                  15

<210> SEQ ID NO 4
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 4

Lys Lys Gly Asp Thr Phe Phe Val Lys Leu Ser Leu Phe Thr Glu Arg
1               5                   10                  15

<210> SEQ ID NO 5
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 5

Lys Lys Glu Asp Thr Phe Phe Val Lys Leu Ser Leu Phe Thr Glu Arg
1               5                   10                  15

<210> SEQ ID NO 6
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 6

Lys Lys Leu Asp Gln Phe Phe Val Lys Leu Ser Leu Phe Thr Glu Arg
1               5                   10                  15

<210> SEQ ID NO 7
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 7

```
Lys Lys Leu Asp Thr Ala Phe Val Lys Leu Ser Leu Phe Thr Glu Arg
1               5                   10                  15
```

<210> SEQ ID NO 8
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 8

```
Lys Lys Leu Asp Thr Val Phe Val Lys Leu Ser Leu Phe Thr Glu Arg
1               5                   10                  15
```

<210> SEQ ID NO 9
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 9

```
Lys Lys Leu Asp Thr Phe Met Val Lys Leu Ser Leu Phe Thr Glu Arg
1               5                   10                  15
```

<210> SEQ ID NO 10
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 10

```
Lys Lys Leu Asp Thr Phe Ser Val Lys Leu Ser Leu Phe Thr Glu Arg
1               5                   10                  15
```

<210> SEQ ID NO 11
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 11

```
Lys Lys Leu Asp Thr Phe Val Val Lys Leu Ser Leu Phe Thr Glu Arg
1               5                   10                  15
```

<210> SEQ ID NO 12
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 12

```
Lys Lys Leu Asp Thr Phe Thr Val Lys Leu Ser Leu Phe Thr Glu Arg
1               5                   10                  15
```

<210> SEQ ID NO 13
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 13

```
Lys Lys Leu Asp Thr Phe Leu Val Lys Leu Ser Leu Phe Thr Glu Arg
```

```
1               5                   10                  15

<210> SEQ ID NO 14
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 14

Lys Lys Leu Asp Thr Phe Phe Val Lys Val Ser Leu Phe Thr Glu Arg
1               5                   10                  15

<210> SEQ ID NO 15
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 15

Lys Lys Leu Asp Thr Phe Phe Val Lys Leu Gln Leu Phe Thr Glu Arg
1               5                   10                  15

<210> SEQ ID NO 16
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 16

Lys Lys Leu Asp Thr Phe Phe Val Lys Leu Met Leu Phe Thr Glu Arg
1               5                   10                  15

<210> SEQ ID NO 17
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 17

Lys Lys Leu Asp Thr Phe Phe Val Lys Leu Thr Leu Phe Thr Glu Arg
1               5                   10                  15

<210> SEQ ID NO 18
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 18

Lys Lys Leu Asp Thr Phe Phe Val Lys Leu His Leu Phe Thr Glu Arg
1               5                   10                  15

<210> SEQ ID NO 19
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 19

Lys Lys Leu Asp Thr Phe Phe Val Lys Leu Ser Gln Phe Thr Glu Arg
1               5                   10                  15
```

<210> SEQ ID NO 20
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 20

Lys Lys Leu Asp Thr Phe Phe Val Lys Leu Ser Val Phe Thr Glu Arg
1               5                   10                  15

<210> SEQ ID NO 21
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 21

Lys Lys Leu Asp Thr Phe Phe Val Lys Leu Ser Met Phe Thr Glu Arg
1               5                   10                  15

<210> SEQ ID NO 22
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 22

Lys Lys Leu Asp Thr Phe Phe Val Lys Leu Ser Leu Met Thr Glu Arg
1               5                   10                  15

<210> SEQ ID NO 23
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 23

Lys Lys Leu Asp Thr Phe Phe Val Lys Leu Ser Leu Gln Thr Glu Arg
1               5                   10                  15

<210> SEQ ID NO 24
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 24

Lys Lys Leu Asp Thr Phe Phe Val Lys Leu Ser Leu His Thr Glu Arg
1               5                   10                  15

<210> SEQ ID NO 25
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 25

Lys Lys Leu Asp Thr Phe Phe Val Lys Leu Ser Leu Asn Thr Glu Arg
1               5                   10                  15

<210> SEQ ID NO 26
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 26

```
Lys Lys Leu Asp Thr Phe Phe Val Lys Leu Ser Leu Pro Thr Glu Arg
1               5                   10                  15
```

<210> SEQ ID NO 27
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 27

```
Lys Lys Leu Asp Thr Phe Phe Val Lys Leu Ser Leu Ser Thr Glu Arg
1               5                   10                  15
```

<210> SEQ ID NO 28
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 28

```
Lys Lys Leu Asp Thr Phe Phe Val Lys Leu Ser Leu Gly Thr Glu Arg
1               5                   10                  15
```

<210> SEQ ID NO 29
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 29

```
Lys Lys Leu Asp Thr Phe Phe Val Lys Leu Ser Leu Ala Thr Glu Arg
1               5                   10                  15
```

<210> SEQ ID NO 30
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 30

```
Lys Lys Leu Asp Thr Phe Phe Val Lys Leu Ser Leu Arg Thr Glu Arg
1               5                   10                  15
```

<210> SEQ ID NO 31
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 31

```
Lys Lys Leu Asp Thr Phe Phe Val Lys Leu Ser Leu Phe Asn Glu Arg
1               5                   10                  15
```

<210> SEQ ID NO 32
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 32

Lys Lys Leu Asp Thr Phe Phe Val Lys Leu Ser Leu Phe Pro Glu Arg
1               5                   10                  15

<210> SEQ ID NO 33
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 33

Lys Lys Leu Asp Thr Phe Phe Val Lys Leu Ser Leu Phe Arg Glu Arg
1               5                   10                  15

<210> SEQ ID NO 34
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 34

Lys Lys Leu Asp Thr Phe Phe Val Lys Leu Ser Leu Phe Thr Glu
1               5                   10                  15

<210> SEQ ID NO 35
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 35

Lys Lys Leu Asp Thr Phe Phe Val Lys Leu Ser Leu Phe Thr
1               5                   10

<210> SEQ ID NO 36
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 36

Lys Lys Leu Asp Thr Phe Phe Val Lys Leu Ser Leu Phe
1               5                   10

<210> SEQ ID NO 37
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 37

Lys Lys Leu Asp Thr Phe Phe Val Lys Leu Ser Leu
1               5                   10

<210> SEQ ID NO 38

```
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 38

Lys Lys Leu Asp Thr Phe Phe Val Lys Leu Ser
1               5                   10

<210> SEQ ID NO 39
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 39

Lys Lys Leu Asp Thr Phe Phe Val Lys Leu
1               5                   10

<210> SEQ ID NO 40
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 40

Lys Lys Leu Asp Thr Phe Phe Val Lys
1               5

<210> SEQ ID NO 41
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 41

Lys Lys Leu Asp Thr Phe Phe Val
1               5

<210> SEQ ID NO 42
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 42

Lys Lys Leu Asp Thr Phe Phe
1               5

<210> SEQ ID NO 43
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 43

Lys Lys Leu Asp Thr Phe
1               5

<210> SEQ ID NO 44
<211> LENGTH: 5
```

```
<212> TYPE: PRT
<213> ORGANISM: Artificial Sequence
<220> FEATURE:
<223> OTHER INFORMATION: Synthetic polypeptide

<400> SEQUENCE: 44

Lys Lys Leu Asp Thr
1               5

<210> SEQ ID NO 45
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 45

Lys Lys Leu Asp
1

<210> SEQ ID NO 46
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 46

Lys Leu Asp Thr Phe Phe Val Lys Leu Ser Leu Phe Thr Glu Arg
1               5                   10                  15

<210> SEQ ID NO 47
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 47

Leu Asp Thr Phe Phe Val Lys Leu Ser Leu Phe Thr Glu Arg
1               5                   10

<210> SEQ ID NO 48
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 48

Asp Thr Phe Phe Val Lys Leu Ser Leu Phe Thr Glu Arg
1               5                   10

<210> SEQ ID NO 49
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 49

Thr Phe Phe Val Lys Leu Ser Leu Phe Thr Glu Arg
1               5                   10

<210> SEQ ID NO 50
<211> LENGTH: 11
<212> TYPE: PRT
```

```
<213> ORGANISM: Artificial Sequence
<220> FEATURE:
<223> OTHER INFORMATION: Synthetic polypeptide

<400> SEQUENCE: 50

Phe Phe Val Lys Leu Ser Leu Phe Thr Glu Arg
1               5                   10

<210> SEQ ID NO 51
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 51

Phe Val Lys Leu Ser Leu Phe Thr Glu Arg
1               5                   10

<210> SEQ ID NO 52
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 52

Val Lys Leu Ser Leu Phe Thr Glu Arg
1               5

<210> SEQ ID NO 53
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 53

Lys Leu Ser Leu Phe Thr Glu Arg
1               5

<210> SEQ ID NO 54
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 54

Leu Ser Leu Phe Thr Glu Arg
1               5

<210> SEQ ID NO 55
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 55

Ser Leu Phe Thr Glu Arg
1               5

<210> SEQ ID NO 56
<211> LENGTH: 5
<212> TYPE: PRT
<213> ORGANISM: Artificial Sequence
```

```
<220> FEATURE:
<223> OTHER INFORMATION: Synthetic polypeptide

<400> SEQUENCE: 56

Leu Phe Thr Glu Arg
1               5

<210> SEQ ID NO 57
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 57

Phe Thr Glu Arg
1

<210> SEQ ID NO 58
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 58

Lys Leu Asp Thr Phe Phe Val Lys Leu Ser Leu Phe Thr Glu
1               5                   10

<210> SEQ ID NO 59
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 59

Leu Asp Thr Phe Phe Val Lys Leu Ser Leu Phe Thr
1               5                   10

<210> SEQ ID NO 60
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 60

Asp Thr Phe Phe Val Lys Leu Ser Leu Phe
1               5                   10

<210> SEQ ID NO 61
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 61

Thr Phe Phe Val Lys Leu Ser Leu
1               5

<210> SEQ ID NO 62
<211> LENGTH: 6
<212> TYPE: PRT
<213> ORGANISM: Artificial Sequence
<220> FEATURE:
```

<223> OTHER INFORMATION: Synthetic polypeptide

<400> SEQUENCE: 62

Phe Phe Val Lys Leu Ser
1               5

<210> SEQ ID NO 63
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 63

Phe Val Lys Leu
1

<210> SEQ ID NO 64
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 64

Lys Lys Leu Thr Phe Phe Val Lys Leu Ser Leu Phe Thr Glu Arg
1               5                   10                  15

<210> SEQ ID NO 65
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 65

Lys Lys Leu Asp Thr Phe Val Lys Leu Ser Leu Phe Thr Glu Arg
1               5                   10                  15

<210> SEQ ID NO 66
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 66

Lys Lys Leu Asp Thr Phe Phe Lys Leu Ser Leu Phe Thr Glu Arg
1               5                   10                  15

<210> SEQ ID NO 67
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 67

Lys Lys Leu Asp Thr Phe Phe Val Lys Ser Leu Phe Thr Glu Arg
1               5                   10                  15

<210> SEQ ID NO 68
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 68

Lys Lys Leu Asp Thr Phe Phe Val Lys Leu Ser Phe Thr Glu Arg
1               5                   10                  15

<210> SEQ ID NO 69
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 69

Lys Leu Asp Thr Phe Phe Val Lys Leu Ser Leu Phe Glu Arg
1               5                   10

<210> SEQ ID NO 70
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 70

Lys Lys Thr Phe Phe Val Lys Leu Ser Leu Phe Thr Glu Arg
1               5                   10

<210> SEQ ID NO 71
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 71

Lys Lys Leu Asp Phe Val Lys Leu Ser Leu Phe Thr Glu Arg
1               5                   10

<210> SEQ ID NO 72
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 72

Lys Lys Leu Asp Thr Glu Lys Leu Ser Leu Phe Thr Glu Arg
1               5                   10

<210> SEQ ID NO 73
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 73

Lys Lys Leu Asp Thr Phe Phe Val Ser Leu Phe Thr Glu Arg
1               5                   10

<210> SEQ ID NO 74
<211> LENGTH: 14
<212> TYPE: PRT
<213> ORGANISM: Artificial Sequence
<220> FEATURE:
<223> OTHER INFORMATION: Synthetic polypeptide

```
<400> SEQUENCE: 74

Lys Lys Leu Asp Thr Phe Phe Val Lys Leu Phe Thr Glu Arg
1               5                   10

<210> SEQ ID NO 75
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 75

Lys Lys Leu Asp Thr Phe Phe Val Lys Leu Ser Leu Glu Arg
1               5                   10

<210> SEQ ID NO 76
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 76

Lys Lys Phe Phe Val Lys Leu Ser Leu Phe Thr Glu Arg
1               5                   10

<210> SEQ ID NO 77
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 77

Lys Lys Leu Asp Val Lys Leu Ser Leu Phe Thr Glu Arg
1               5                   10

<210> SEQ ID NO 78
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 78

Lys Lys Leu Asp Thr Phe Leu Ser Leu Phe Thr Glu Arg
1               5                   10

<210> SEQ ID NO 79
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 79

Lys Lys Leu Asp Thr Phe Phe Val Leu Phe Thr Glu Arg
1               5                   10

<210> SEQ ID NO 80
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 80
```

```
Lys Lys Leu Asp Thr Phe Phe Val Lys Leu Thr Glu Arg
1               5                   10
```

<210> SEQ ID NO 81
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 81

```
Lys Lys Leu Asp Thr Phe Phe Val Lys Leu Ser Leu Arg
1               5                   10
```

<210> SEQ ID NO 82
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 82

```
Lys Phe Phe Val Lys Leu Ser Leu Phe Thr Glu Arg
1               5                   10
```

<210> SEQ ID NO 83
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 83

```
Lys Lys Leu Val Lys Leu Ser Leu Phe Thr Glu Arg
1               5                   10
```

<210> SEQ ID NO 84
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 84

```
Lys Lys Leu Asp Thr Leu Ser Leu Phe Thr Glu Arg
1               5                   10
```

<210> SEQ ID NO 85
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 85

```
Lys Lys Leu Asp Thr Phe Phe Leu Phe Thr Glu Arg
1               5                   10
```

<210> SEQ ID NO 86
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 86

```
Lys Lys Leu Asp Thr Phe Phe Val Lys Thr Glu Arg
1               5                   10
```

<210> SEQ ID NO 87
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 87

```
Lys Lys Leu Asp Thr Phe Phe Val Lys Leu Ser Arg
1               5                   10
```

<210> SEQ ID NO 88
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 88

```
Lys Phe Val Lys Leu Ser Leu Phe Thr Glu Arg
1               5                   10
```

<210> SEQ ID NO 89
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 89

```
Lys Lys Leu Lys Leu Ser Leu Phe Thr Glu Arg
1               5                   10
```

<210> SEQ ID NO 90
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 90

```
Lys Lys Leu Asp Thr Ser Leu Phe Thr Glu Arg
1               5                   10
```

<210> SEQ ID NO 91
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 91

```
Lys Lys Leu Asp Thr Phe Phe Phe Thr Glu Arg
1               5                   10
```

<210> SEQ ID NO 92
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 92

```
Lys Lys Leu Asp Thr Phe Phe Val Lys Glu Arg
```

<210> SEQ ID NO 93
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 93

Gly Lys Leu Asp Thr Phe Phe Val Lys Leu Ser Leu Phe Thr Glu Arg
1               5                   10                  15

<210> SEQ ID NO 94
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 94

Lys Lys Gly Asp Thr Phe Phe Val Lys Leu Ser Leu Phe Thr Glu Arg
1               5                   10                  15

<210> SEQ ID NO 95
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 95

Lys Lys Leu Asp Gly Phe Phe Val Lys Leu Ser Leu Phe Thr Glu Arg
1               5                   10                  15

<210> SEQ ID NO 96
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 96

Lys Lys Leu Asp Thr Phe Gly Val Lys Leu Ser Leu Phe Thr Glu Arg
1               5                   10                  15

<210> SEQ ID NO 97
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 97

Lys Lys Leu Asp Thr Phe Phe Val Gly Leu Ser Leu Phe Thr Glu Arg
1               5                   10                  15

<210> SEQ ID NO 98
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 98

Lys Lys Leu Asp Thr Phe Phe Val Gly Leu Ser Leu Phe Thr Glu Arg
1               5                   10                  15

<210> SEQ ID NO 99
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 99

```
Lys Lys Leu Asp Thr Phe Phe Val Lys Leu Gly Leu Phe Thr Glu Arg
1               5                   10                  15
```

<210> SEQ ID NO 100
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 100

```
Lys Lys Leu Asp Thr Phe Phe Val Lys Leu Ser Leu Gly Thr Glu Arg
1               5                   10                  15
```

<210> SEQ ID NO 101
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 101

```
Lys Lys Leu Asp Thr Phe Phe Val Lys Leu Ser Leu Phe Thr Gly Arg
1               5                   10                  15
```

<210> SEQ ID NO 102
<211> LENGTH: 48
<212> TYPE: DNA
<213> ORGANISM: Artificial Sequence
<220> FEATURE:
<223> OTHER INFORMATION: Consensus polynucleotide encoding P28R (SEQ ID
      NO:2)
<220> FEATURE:
<221> NAME/KEY: misc_feature
<222> LOCATION: 9,15,24,30,33,36,42,48
<223> OTHER INFORMATION: N=A,G,C,or T

<400> SEQUENCE: 102
aaraarytng ayacnttytt ygtnaarytn wsnytnttya cngarmgn            48

<210> SEQ ID NO 103
<211> LENGTH: 48
<212> TYPE: DNA
<213> ORGANISM: Artificial Sequence
<220> FEATURE:
<223> OTHER INFORMATION: Exemplary polynucleotide encoding P28R (SEQ ID
      NO:2)

<400> SEQUENCE: 103
aaaaaactgg atacctttt tgtgaaactg agcctgttta ccgaacgc             48

<210> SEQ ID NO 104
<211> LENGTH: 48
<212> TYPE: DNA
<213> ORGANISM: Artificial Sequence
<220> FEATURE:
<223> OTHER INFORMATION: Consensus polynucleotide encoding SEQ ID NO:3
<220> FEATURE:
<221> NAME/KEY: misc_feature

```
<222> LOCATION: 3,9,15,24,30,33,36,42,48
<223> OTHER INFORMATION: N=A,G,C,or T

<400> SEQUENCE: 104
mgnaarytng ayacnttytt ygtnaarytn wsnytnttya cngarmgn        48

<210> SEQ ID NO 105
<211> LENGTH: 48
<212> TYPE: DNA
<213> ORGANISM: Artificial Sequence
<220> FEATURE:
<223> OTHER INFORMATION: Exemplary NT encoding SEQ ID NO: 3

<400> SEQUENCE: 105
cgcaaactgg atacctttt tgtgaaactg agcctgttta ccgaacgc          48

<210> SEQ ID NO 106
<211> LENGTH: 48
<212> TYPE: DNA
<213> ORGANISM: Artificial Sequence
<220> FEATURE:
<223> OTHER INFORMATION: Consensus polynucleotide encoding SEQ ID NO:4
<220> FEATURE:
<221> NAME/KEY: misc_feature
<222> LOCATION: 9,15,24,30,33,36,42,48
<223> OTHER INFORMATION: N=A,G,C,or T

<400> SEQUENCE: 106
aaraarggng ayacnttytt ygtnaarytn wsnytnttya cngarmgn        48

<210> SEQ ID NO 107
<211> LENGTH: 48
<212> TYPE: DNA
<213> ORGANISM: Artificial Sequence
<220> FEATURE:
<223> OTHER INFORMATION: Exemplary NT encoding  SEQ ID NO: 4

<400> SEQUENCE: 107
aaaaaaggcg atacctttt tgtgaaactg agcctgttta ccgaacgc          48

<210> SEQ ID NO 108
<211> LENGTH: 48
<212> TYPE: DNA
<213> ORGANISM: Artificial Sequence
<220> FEATURE:
<223> OTHER INFORMATION: Consensus polynucleotide encoding SEQ ID NO:5
<220> FEATURE:
<221> NAME/KEY: misc_feature
<222> LOCATION: 15,24,30,33,36,42,48
<223> OTHER INFORMATION: N=A,G,C,or T

<400> SEQUENCE: 108
aaraargarg ayacnttytt ygtnaarytn wsnytnttya cngarmgn        48

<210> SEQ ID NO 109
<211> LENGTH: 48
<212> TYPE: DNA
<213> ORGANISM: Artificial Sequence
<220> FEATURE:
<223> OTHER INFORMATION: Exemplary NT encoding SEQ ID NO: 5

<400> SEQUENCE: 109
aaaaaagaag atacctttt tgtgaaactg agcctgttta ccgaacgc          48

<210> SEQ ID NO 110
<211> LENGTH: 48
<212> TYPE: DNA
```

-continued

```
<213> ORGANISM: Artificial Sequence
<220> FEATURE:
<223> OTHER INFORMATION: Consensus polynucleotide encoding SEQ ID NO:6
<220> FEATURE:
<221> NAME/KEY: misc_feature
<222> LOCATION: 9,24,30,33,36,42,48
<223> OTHER INFORMATION: N=A,G,C,or T

<400> SEQUENCE: 110
aaraarytng aycarttytt ygtnaarytn wsnytnttya cngarmgn            48

<210> SEQ ID NO 111
<211> LENGTH: 48
<212> TYPE: DNA
<213> ORGANISM: Artificial Sequence
<220> FEATURE:
<223> OTHER INFORMATION: Exemplary NT encoding SEQ ID NO: 6

<400> SEQUENCE: 111
aaaaaactgg atcagttttt tgtgaaactg agcctgttta ccgaacgc            48

<210> SEQ ID NO 112
<211> LENGTH: 48
<212> TYPE: DNA
<213> ORGANISM: Artificial Sequence
<220> FEATURE:
<223> OTHER INFORMATION: Consensus polynucleotide encoding SEQ ID NO:7
<220> FEATURE:
<221> NAME/KEY: misc_feature
<222> LOCATION: 9, 15, 18, 24, 30, 33, 36, 42, 48
<223> OTHER INFORMATION: N=A,G,C,or T

<400> SEQUENCE: 112
aaraarytng ayacngcntt ygtnaarytn wsnytnttya cngarmgn            48

<210> SEQ ID NO 113
<211> LENGTH: 48
<212> TYPE: DNA
<213> ORGANISM: Artificial Sequence
<220> FEATURE:
<223> OTHER INFORMATION: Exemplary NT encoding SEQ ID NO: 7

<400> SEQUENCE: 113
aaaaaactgg ataccgcgtt tgtgaaactg agcctgttta ccgaacgc            48

<210> SEQ ID NO 114
<211> LENGTH: 48
<212> TYPE: DNA
<213> ORGANISM: Artificial Sequence
<220> FEATURE:
<223> OTHER INFORMATION: Consensus polynucleotide encoding SEQ ID NO:8
<220> FEATURE:
<221> NAME/KEY: misc_feature
<222> LOCATION: 9, 15, 18, 24, 30, 33, 36, 42, 48
<223> OTHER INFORMATION: N=A,G,C,or T

<400> SEQUENCE: 114
aaraarytng ayacngtntt ygtnaarytn wsnytnttya cngarmgn            48

<210> SEQ ID NO 115
<211> LENGTH: 48
<212> TYPE: DNA
<213> ORGANISM: Artificial Sequence
<220> FEATURE:
<223> OTHER INFORMATION: Exemplary NT encoding SEQ ID NO: 8

<400> SEQUENCE: 115
aaaaaactgg ataccgtgtt tgtgaaactg agcctgttta ccgaacgc            48
```

<210> SEQ ID NO 116
<211> LENGTH: 48
<212> TYPE: DNA
<213> ORGANISM: Artificial Sequence
<220> FEATURE:
<223> OTHER INFORMATION: Consensus polynucleotide encoding SEQ ID NO:9
<220> FEATURE:
<221> NAME/KEY: misc_feature
<222> LOCATION: 9, 15, 24, 30, 33, 36, 42, 48
<223> OTHER INFORMATION: N=A,G,C,or T

<400> SEQUENCE: 116
aaraarytng ayacnttyat ggtnaarytn wsnytnttya cngarmgn              48

<210> SEQ ID NO 117
<211> LENGTH: 48
<212> TYPE: DNA
<213> ORGANISM: Artificial Sequence
<220> FEATURE:
<223> OTHER INFORMATION: Exemplary NT encoding SEQ ID NO: 9

<400> SEQUENCE: 117
aaaaaactgg atacctttat ggtgaaactg agcctgttta ccgaacgc              48

<210> SEQ ID NO 118
<211> LENGTH: 48
<212> TYPE: DNA
<213> ORGANISM: Artificial Sequence
<220> FEATURE:
<223> OTHER INFORMATION: Consensus polynucleotide encoding SEQ ID NO:10
<220> FEATURE:
<221> NAME/KEY: misc_feature
<222> LOCATION: 9 15, 21, 24, 30, 33, 36, 42, 48
<223> OTHER INFORMATION: N=A,G,C,or T

<400> SEQUENCE: 118
aaraarytng ayacnttyws ngtnaarytn wsnytnttya cngarmgn              48

<210> SEQ ID NO 119
<211> LENGTH: 48
<212> TYPE: DNA
<213> ORGANISM: Artificial Sequence
<220> FEATURE:
<223> OTHER INFORMATION: Exemplary NT encoding SEQ ID NO: 10

<400> SEQUENCE: 119
aaaaaactgg atacctttag cgtgaaactg agcctgttta ccgaacgc              48

<210> SEQ ID NO 120
<211> LENGTH: 48
<212> TYPE: DNA
<213> ORGANISM: Artificial Sequence
<220> FEATURE:
<223> OTHER INFORMATION: Consensus polynucleotide encoding  SEQ ID NO:
      11

<400> SEQUENCE: 120
aaaaaactgg atacctttgt ggtgaaactg agcctgttta ccgaacgc              48

<210> SEQ ID NO 121
<211> LENGTH: 48
<212> TYPE: DNA
<213> ORGANISM: Artificial Sequence
<220> FEATURE:
<223> OTHER INFORMATION: Exemplary NT encoding SEQ ID NO:11
<220> FEATURE:
<221> NAME/KEY: misc_feature

```
<222> LOCATION: 9, 15, 21, 24, 30, 33, 36, 42, 48
<223> OTHER INFORMATION: N=A,G,C,or T

<400> SEQUENCE: 121
aaraarytng ayacnttygt ngtnaarytn wsnytnttya cngarmgn          48

<210> SEQ ID NO 122
<211> LENGTH: 48
<212> TYPE: DNA
<213> ORGANISM: Artificial Sequence
<220> FEATURE:
<223> OTHER INFORMATION: Consensus polynucleotide encoding SEQ ID NO:12
<220> FEATURE:
<221> NAME/KEY: misc_feature
<222> LOCATION: 9, 15, 21, 24, 30, 33, 36, 42, 48
<223> OTHER INFORMATION: N=A,G,C,or T

<400> SEQUENCE: 122
aaraarytng ayacnttyac ngtnaarytn wsnytnttya cngarmgn          48

<210> SEQ ID NO 123
<211> LENGTH: 48
<212> TYPE: DNA
<213> ORGANISM: Artificial Sequence
<220> FEATURE:
<223> OTHER INFORMATION: Exemplary NT encoding SEQ ID NO: 12

<400> SEQUENCE: 123
aaaaaactgg atacctttac cgtgaaactg agcctgttta ccgaacgc          48

<210> SEQ ID NO 124
<211> LENGTH: 48
<212> TYPE: DNA
<213> ORGANISM: Artificial Sequence
<220> FEATURE:
<223> OTHER INFORMATION: Consensus polynucleotide encoding SEQ ID NO:13
<220> FEATURE:
<221> NAME/KEY: misc_feature
<222> LOCATION: 9, 15, 21, 24, 30, 33, 36, 42, 48
<223> OTHER INFORMATION: N=A,G,C,or T

<400> SEQUENCE: 124
aaraarytng ayacnttyyt ngtnaarytn wsnytnttya cngarmgn          48

<210> SEQ ID NO 125
<211> LENGTH: 48
<212> TYPE: DNA
<213> ORGANISM: Artificial Sequence
<220> FEATURE:
<223> OTHER INFORMATION: Exemplary NT encoding SEQ ID NO: 13

<400> SEQUENCE: 125
aaaaaactgg atacctttct ggtgaaactg agcctgttta ccgaacgc          48

<210> SEQ ID NO 126
<211> LENGTH: 48
<212> TYPE: DNA
<213> ORGANISM: Artificial Sequence
<220> FEATURE:
<223> OTHER INFORMATION: Consensus polynucleotide encoding SEQ ID NO:14
<220> FEATURE:
<221> NAME/KEY: misc_feature
<222> LOCATION: 9, 15, 24, 30, 33, 36, 42, 48
<223> OTHER INFORMATION: N=A,G,C,or T

<400> SEQUENCE: 126
aaraarytng ayacnttytt ygtnaargtn wsnytnttya cngarmgn          48
```

<210> SEQ ID NO 127
<211> LENGTH: 48
<212> TYPE: DNA
<213> ORGANISM: Artificial Sequence
<220> FEATURE:
<223> OTHER INFORMATION: Exemplary NT encoding SEQ ID NO: 14

<400> SEQUENCE: 127
aaaaaactgg atacctttt tgtgaaagtg agcctgttta ccgaacgc      48

<210> SEQ ID NO 128
<211> LENGTH: 48
<212> TYPE: DNA
<213> ORGANISM: Artificial Sequence
<220> FEATURE:
<223> OTHER INFORMATION: Consensus polynucleotide encoding SEQ ID NO:15
<220> FEATURE:
<221> NAME/KEY: misc_feature
<222> LOCATION: 9, 15, 24, 30, 36, 42, 48
<223> OTHER INFORMATION: N=A,G,C,or T

<400> SEQUENCE: 128
aaraarytng ayacnttytt ygtnaarytn carytnttya cngarmgn      48

<210> SEQ ID NO 129
<211> LENGTH: 48
<212> TYPE: DNA
<213> ORGANISM: Artificial Sequence
<220> FEATURE:
<223> OTHER INFORMATION: Exemplary NT encoding SEQ ID NO: 15

<400> SEQUENCE: 129
aaaaaactgg atacctttt tgtgaaactg cagctgttta ccgaacgc      48

<210> SEQ ID NO 130
<211> LENGTH: 48
<212> TYPE: DNA
<213> ORGANISM: Artificial Sequence
<220> FEATURE:
<223> OTHER INFORMATION: Consensus polynucleotide encoding SEQ ID NO:16
<220> FEATURE:
<221> NAME/KEY: misc_feature
<222> LOCATION: 9, 15, 24, 30, 36, 42, 48
<223> OTHER INFORMATION: N=A,G,C,or T

<400> SEQUENCE: 130
aaraarytng ayacnttytt ygtnaarytn atgytnttya cngarmgn      48

<210> SEQ ID NO 131
<211> LENGTH: 48
<212> TYPE: DNA
<213> ORGANISM: Artificial Sequence
<220> FEATURE:
<223> OTHER INFORMATION: Exemplary NT encoding SEQ ID NO: 16

<400> SEQUENCE: 131
aaaaaactgg atacctttt tgtgaaactg atgctgttta ccgaacgc      48

<210> SEQ ID NO 132
<211> LENGTH: 48
<212> TYPE: DNA
<213> ORGANISM: Artificial Sequence
<220> FEATURE:
<223> OTHER INFORMATION: Consensus polynucleotide encoding SEQ ID NO:17
<220> FEATURE:
<221> NAME/KEY: misc_feature
<222> LOCATION: 9, 15, 24, 30, 33, 36, 42, 48
<223> OTHER INFORMATION: N=A,G,C,or T

<400> SEQUENCE: 132
aaraarytng ayacnttytt ygtnaarytn acnytnttya cngarmgn                48

<210> SEQ ID NO 133
<211> LENGTH: 48
<212> TYPE: DNA
<213> ORGANISM: Artificial Sequence
<220> FEATURE:
<223> OTHER INFORMATION: Exemplary NT encoding SEQ ID NO: 17

<400> SEQUENCE: 133
aaaaaactgg atccttttt tgtgaaactg accctgttta ccgaacgc                 48

<210> SEQ ID NO 134
<211> LENGTH: 48
<212> TYPE: DNA
<213> ORGANISM: Artificial Sequence
<220> FEATURE:
<223> OTHER INFORMATION: Consensus polynucleotide encoding SEQ ID NO:18
<220> FEATURE:
<221> NAME/KEY: misc_feature
<222> LOCATION: 9, 15, 24, 30, 33, 36, 42, 48
<223> OTHER INFORMATION: N=A,G,C,or T

<400> SEQUENCE: 134
aaraarytng ayacnttytt ygtnaarytn cayytnttya cngarmgn                48

<210> SEQ ID NO 135
<211> LENGTH: 48
<212> TYPE: DNA
<213> ORGANISM: Artificial Sequence
<220> FEATURE:
<223> OTHER INFORMATION: Exemplary NT encoding SEQ ID NO: 18

<400> SEQUENCE: 135
aaaaaactgg atccttttt tgtgaaactg catctgttta ccgaacgc                 48

<210> SEQ ID NO 136
<211> LENGTH: 48
<212> TYPE: DNA
<213> ORGANISM: Artificial Sequence
<220> FEATURE:
<223> OTHER INFORMATION: Consensus polynucleotide encoding SEQ ID NO:19
<220> FEATURE:
<221> NAME/KEY: misc_feature
<222> LOCATION: 9, 15, 24, 30, 33, 42, 48
<223> OTHER INFORMATION: N=A,G,C,or T

<400> SEQUENCE: 136
aaraarytng ayacnttytt ygtnaarytn wsncarttya cngarmgn                48

<210> SEQ ID NO 137
<211> LENGTH: 48
<212> TYPE: DNA
<213> ORGANISM: Artificial Sequence
<220> FEATURE:
<223> OTHER INFORMATION: Exemplary NT encoding SEQ ID NO: 19

<400> SEQUENCE: 137
aaaaaactgg atccttttt tgtgaaactg agccagttta ccgaacgc                 48

<210> SEQ ID NO 138
<211> LENGTH: 48
<212> TYPE: DNA
<213> ORGANISM: Artificial Sequence
<220> FEATURE:

<223> OTHER INFORMATION: Consensus polynucleotide encoding SEQ ID NO:20
<220> FEATURE:
<221> NAME/KEY: misc_feature
<222> LOCATION: 9, 15, 24, 30, 33, 36, 42, 48
<223> OTHER INFORMATION: N=A,G,C,or T

<400> SEQUENCE: 138
aaraarytng ayacnttytt ygtnaarytn wsngtnttya cngarmgn                48

<210> SEQ ID NO 139
<211> LENGTH: 48
<212> TYPE: DNA
<213> ORGANISM: Artificial Sequence
<220> FEATURE:
<223> OTHER INFORMATION: Exemplary NT encoding SEQ ID NO: 20

<400> SEQUENCE: 139
aaaaaactgg atacctttt tgtgaaactg agcgtgttta ccgaacgc                 48

<210> SEQ ID NO 140
<211> LENGTH: 48
<212> TYPE: DNA
<213> ORGANISM: Artificial Sequence
<220> FEATURE:
<223> OTHER INFORMATION: Consensus polynucleotide encoding SEQ ID NO:21
<220> FEATURE:
<221> NAME/KEY: misc_feature
<222> LOCATION: 9, 15, 24, 30, 33, 42, 48
<223> OTHER INFORMATION: N=A,G,C,or T

<400> SEQUENCE: 140
aaraarytng ayacnttytt ygtnaarytn wsnatgttya cngarmgn                48

<210> SEQ ID NO 141
<211> LENGTH: 48
<212> TYPE: DNA
<213> ORGANISM: Artificial Sequence
<220> FEATURE:
<223> OTHER INFORMATION: Exemplary NT encoding SEQ ID NO: 21

<400> SEQUENCE: 141
aaaaaactgg atacctttt tgtgaaactg agcatgttta ccgaacgc                 48

<210> SEQ ID NO 142
<211> LENGTH: 48
<212> TYPE: DNA
<213> ORGANISM: Artificial Sequence
<220> FEATURE:
<223> OTHER INFORMATION: Consensus polynucleotide encoding SEQ ID NO:22
<220> FEATURE:
<221> NAME/KEY: misc_feature
<222> LOCATION: 9, 15, 24, 30, 33, 36, 42, 48
<223> OTHER INFORMATION: N=A,G,C,or T

<400> SEQUENCE: 142
aaraarytng ayacnttytt ygtnaarytn wsnytnatga cngarmgn                48

<210> SEQ ID NO 143
<211> LENGTH: 48
<212> TYPE: DNA
<213> ORGANISM: Artificial Sequence
<220> FEATURE:
<223> OTHER INFORMATION: Exemplary NT encoding SEQ ID NO: 22

<400> SEQUENCE: 143
aaaaaactgg atacctttt tgtgaaactg agcctgatga ccgaacgc                 48

```
<210> SEQ ID NO 144
<211> LENGTH: 48
<212> TYPE: DNA
<213> ORGANISM: Artificial Sequence
<220> FEATURE:
<223> OTHER INFORMATION: Consensus polynucleotide encoding SEQ ID NO:23
<220> FEATURE:
<221> NAME/KEY: misc_feature
<222> LOCATION: 9, 15, 24, 30, 33, 36, 42, 48
<223> OTHER INFORMATION: N=A,G,C,or T

<400> SEQUENCE: 144
aaraarytng ayacnttytt ygtnaarytn wsnytncara cngarmgn                48

<210> SEQ ID NO 145
<211> LENGTH: 48
<212> TYPE: DNA
<213> ORGANISM: Artificial Sequence
<220> FEATURE:
<223> OTHER INFORMATION: Exemplary NT encoding SEQ ID NO: 23

<400> SEQUENCE: 145
aaaaaactgg atacctttt tgtgaaactg agcctgcaga ccgaacgc                 48

<210> SEQ ID NO 146
<211> LENGTH: 48
<212> TYPE: DNA
<213> ORGANISM: Artificial Sequence
<220> FEATURE:
<223> OTHER INFORMATION: Consensus polynucleotide encoding SEQ ID NO:24
<220> FEATURE:
<221> NAME/KEY: misc_feature
<222> LOCATION: 9, 15, 24, 30, 33, 36, 42, 48
<223> OTHER INFORMATION: N=A,G,C,or T

<400> SEQUENCE: 146
aaraarytng ayacnttytt ygtnaarytn wsnytncaya cngarmgn                48

<210> SEQ ID NO 147
<211> LENGTH: 48
<212> TYPE: DNA
<213> ORGANISM: Artificial Sequence
<220> FEATURE:
<223> OTHER INFORMATION: Exemplary NT encoding  SEQ ID NO: 24

<400> SEQUENCE: 147
aaaaaactgg atacctttt tgtgaaactg agcctgcata ccgaacgc                 48

<210> SEQ ID NO 148
<211> LENGTH: 48
<212> TYPE: DNA
<213> ORGANISM: Artificial Sequence
<220> FEATURE:
<223> OTHER INFORMATION: Consensus polynucleotide encoding SEQ ID NO:25
<220> FEATURE:
<221> NAME/KEY: misc_feature
<222> LOCATION: 9, 15, 24, 30, 33, 36, 42, 48
<223> OTHER INFORMATION: N=A,G,C,or T

<400> SEQUENCE: 148
aaraarytng ayacnttytt ygtnaarytn wsnytnaaya cngarmgn                48

<210> SEQ ID NO 149
<211> LENGTH: 48
<212> TYPE: DNA
<213> ORGANISM: Artificial Sequence
<220> FEATURE:
<223> OTHER INFORMATION: Exemplary NT encoding SEQ ID NO: 25
```

```
<400> SEQUENCE: 149
aaaaaactgg atacctttt tgtgaaactg agcctgaaca ccgaacgc          48

<210> SEQ ID NO 150
<211> LENGTH: 48
<212> TYPE: DNA
<213> ORGANISM: Artificial Sequence
<220> FEATURE:
<223> OTHER INFORMATION: Consensus polynucleotide encoding SEQ ID NO:26
<220> FEATURE:
<221> NAME/KEY: misc_feature
<222> LOCATION: 9, 15, 24, 30, 33, 36, 39, 42, 48
<223> OTHER INFORMATION: N=A,G,C,or T

<400> SEQUENCE: 150
aaraarytng ayacnttytt ygtnaarytn wsnytnccna cngarmgn          48

<210> SEQ ID NO 151
<211> LENGTH: 48
<212> TYPE: DNA
<213> ORGANISM: Artificial Sequence
<220> FEATURE:
<223> OTHER INFORMATION: Exemplary NT encoding SEQ ID NO: 26

<400> SEQUENCE: 151
aaaaaactgg atacctttt tgtgaaactg agcctgccga ccgaacgc          48

<210> SEQ ID NO 152
<211> LENGTH: 48
<212> TYPE: DNA
<213> ORGANISM: Artificial Sequence
<220> FEATURE:
<223> OTHER INFORMATION: Consensus polynucleotide encoding SEQ ID NO:27
<220> FEATURE:
<221> NAME/KEY: misc_feature
<222> LOCATION: 9, 15, 24, 30, 33, 36, 39, 42, 48
<223> OTHER INFORMATION: N=A,G,C,or T

<400> SEQUENCE: 152
aaraarytng ayacnttytt ygtnaarytn wsnytnwsna cngarmgn          48

<210> SEQ ID NO 153
<211> LENGTH: 48
<212> TYPE: DNA
<213> ORGANISM: Artificial Sequence
<220> FEATURE:
<223> OTHER INFORMATION: Exemplary NT encoding SEQ ID NO: 27

<400> SEQUENCE: 153
aaaaaactgg atacctttt tgtgaaactg agcctgagca ccgaacgc          48

<210> SEQ ID NO 154
<211> LENGTH: 48
<212> TYPE: DNA
<213> ORGANISM: Artificial Sequence
<220> FEATURE:
<223> OTHER INFORMATION: Consensus polynucleotide encoding SEQ ID NO:28
<220> FEATURE:
<221> NAME/KEY: misc_feature
<222> LOCATION: 9, 15, 24, 30, 33, 36, 39, 42, 48
<223> OTHER INFORMATION: N=A,G,C,or T

<400> SEQUENCE: 154
aaraarytng ayacnttytt ygtnaarytn wsnytnggna cngarmgn          48

<210> SEQ ID NO 155
<211> LENGTH: 48
```

```
<212> TYPE: DNA
<213> ORGANISM: Artificial Sequence
<220> FEATURE:
<223> OTHER INFORMATION: Exemplary NT encoding SEQ ID NO: 28

<400> SEQUENCE: 155
aaaaaactgg atacctttt tgtgaaactg agcctgggca ccgaacgc                48

<210> SEQ ID NO 156
<211> LENGTH: 48
<212> TYPE: DNA
<213> ORGANISM: Artificial Sequence
<220> FEATURE:
<223> OTHER INFORMATION: Consensus polynucleotide encoding SEQ ID NO:29
<220> FEATURE:
<221> NAME/KEY: misc_feature
<222> LOCATION: 9, 15, 24, 30, 33, 36, 39, 42, 48
<223> OTHER INFORMATION: N=A,G,C,or T

<400> SEQUENCE: 156
aaraarytng ayacnttytt ygtnaarytn wsnytngcna cngarmgn                48

<210> SEQ ID NO 157
<211> LENGTH: 48
<212> TYPE: DNA
<213> ORGANISM: Artificial Sequence
<220> FEATURE:
<223> OTHER INFORMATION: Exemplary NT encoding SEQ ID NO: 29

<400> SEQUENCE: 157
aaaaaactgg atacctttt tgtgaaactg agcctggcga ccgaacgc                48

<210> SEQ ID NO 158
<211> LENGTH: 48
<212> TYPE: DNA
<213> ORGANISM: Artificial Sequence
<220> FEATURE:
<223> OTHER INFORMATION: Consensus polynucleotide encoding SEQ ID NO:30
<220> FEATURE:
<221> NAME/KEY: misc_feature
<222> LOCATION: 9, 15, 24, 30, 33, 36, 39, 42, 48
<223> OTHER INFORMATION: N=A,G,C,or T

<400> SEQUENCE: 158
aaraarytng ayacnttytt ygtnaarytn wsnytnmgna cngarmgn                48

<210> SEQ ID NO 159
<211> LENGTH: 48
<212> TYPE: DNA
<213> ORGANISM: Artificial Sequence
<220> FEATURE:
<223> OTHER INFORMATION: Exemplary NT encoding SEQ ID NO: 30

<400> SEQUENCE: 159
aaaaaactgg atacctttt tgtgaaactg agcctgcgca ccgaacgc                48

<210> SEQ ID NO 160
<211> LENGTH: 48
<212> TYPE: DNA
<213> ORGANISM: Artificial Sequence
<220> FEATURE:
<223> OTHER INFORMATION: Consensus polynucleotide encoding SEQ ID NO:31
<220> FEATURE:
<221> NAME/KEY: misc_feature
<222> LOCATION: 9, 15, 24, 30, 33, 36, 48
<223> OTHER INFORMATION: N=A,G,C,or T

<400> SEQUENCE: 160
```

```
aaaaaactgg atacctttt tgtgaaactg agcctgttta acgaacgc                    48

<210> SEQ ID NO 161
<211> LENGTH: 48
<212> TYPE: DNA
<213> ORGANISM: Artificial Sequence
<220> FEATURE:
<223> OTHER INFORMATION: Exemplary NT encoding SEQ ID NO: 31

<400> SEQUENCE: 161
aaaaaactgg atacctttt tgtgaaactg agcctgttta acgaacgc                    48

<210> SEQ ID NO 162
<211> LENGTH: 48
<212> TYPE: DNA
<213> ORGANISM: Artificial Sequence
<220> FEATURE:
<223> OTHER INFORMATION: Consensus polynucleotide encoding SEQ ID NO:32
<220> FEATURE:
<221> NAME/KEY: misc_feature
<222> LOCATION: 9, 15, 24, 30, 33, 36, 42, 48
<223> OTHER INFORMATION: N=A,G,C,or T

<400> SEQUENCE: 162
aaraarytng ayacnttytt ygtnaarytn wsnytnttyc cngarmgn                   48

<210> SEQ ID NO 163
<211> LENGTH: 48
<212> TYPE: DNA
<213> ORGANISM: Artificial Sequence
<220> FEATURE:
<223> OTHER INFORMATION: Exemplary NT encoding SEQ ID NO: 32

<400> SEQUENCE: 163
aaaaaactgg atacctttt tgtgaaactg agcctgtttc cggaacgc                    48

<210> SEQ ID NO 164
<211> LENGTH: 48
<212> TYPE: DNA
<213> ORGANISM: Artificial Sequence
<220> FEATURE:
<223> OTHER INFORMATION: Consensus polynucleotide encoding SEQ ID NO:33
<220> FEATURE:
<221> NAME/KEY: misc_feature
<222> LOCATION: 9, 15, 24, 30, 33, 36, 42, 48
<223> OTHER INFORMATION: N=A,G,C,or T

<400> SEQUENCE: 164
aaraarytng ayacnttytt ygtnaarytn wsnytnttym gngarmgn                   48

<210> SEQ ID NO 165
<211> LENGTH: 48
<212> TYPE: DNA
<213> ORGANISM: Artificial Sequence
<220> FEATURE:
<223> OTHER INFORMATION: Exemplary NT encoding SEQ ID NO: 33

<400> SEQUENCE: 165
aaaaaactgg atacctttt tgtgaaactg agcctgtttc gcgaacgc                    48

<210> SEQ ID NO 166
<211> LENGTH: 16
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
```

```
<222> LOCATION: 1-5
<223> OTHER INFORMATION: Variable length region= KKLDT RKLDT, KKGDT,
      KKEDT, KKLDQ, KKGDQ, KKEDQ, RKLDQ, RKGDQ, RKEDQ, RKGTD,
      RKEDT, KLDT, KGDT, KEDT, KLDQ, KGDQ, KEDQ, LDT,
      LDQ, GDT, GDQ, EDT, EDQ, DT, DQ, T, Q,
<220> FEATURE:
<221> NAME/KEY: VARIANT
<222> LOCATION: 1-5
<223> OTHER INFORMATION: Variable length region= or no amino acid
<220> FEATURE:
<221> NAME/KEY: VARIANT
<222> LOCATION: 6-7
<223> OTHER INFORMATION: Xaa Xaa= FF, FM, FS, FV, FT, FL, AF, AM, AS,
      AV, AT, AL, VF, VM, VS, VV, VT, or VL
<220> FEATURE:
<221> NAME/KEY: VARIANT
<222> LOCATION: 10-11
<223> OTHER INFORMATION: Xaa Xaa= LS, LQ, LM, LT, LH, VS, VQ, VM, VT, or
      VH
<220> FEATURE:
<221> NAME/KEY: VARIANT
<222> LOCATION: 12-14
<223> OTHER INFORMATION: Xaa Xaa Xaa=LFT, LMT, LQT, LHT, LNT, LPT, LST,
      LGT, LAT, LRT, QFT, QMT, QQT, QHT, QNT, QPT, QST,
      QGT, QAT, QRT, VFT, VMT, VQT, VHT, VNT, VPT, VST,
      VGT, VAT, VRT, MFT, MMT, MQT, MHT, MNT, MPT, MST,
<220> FEATURE:
<221> NAME/KEY: VARIANT
<222> LOCATION: (12)...(14)
<223> OTHER INFORMATION: Xaa Xaa Xaa=MGT, MAT, MRT, LFN, LMN, LQN, LHN,
      LNN, LPN, LSN, LGN, LAN, LRN, QFN, QMN, QQN, QHN,
      QNN, QPN, QSN, QGN, QAN, QRN, VFN, VMN, VQN, VHN,
      VNN, VPN, VSN, VGN, VAN, VRN, MFN, MMN, MQN, MHN,
<220> FEATURE:
<221> NAME/KEY: VARIANT
<222> LOCATION: (12)...(14)
<223> OTHER INFORMATION: Xaa Xaa Xaa=MNN, MPN, MSN, MGN, MAN, MRN, LFP,
      LMP, LQP, LHP, LNP, LPP, LSP, LGP, LAP, LRP, QFP,
      QMP, QQP, QHP, QNP, QPP, QSP, QGP, QAP, QRP, VFP,
      VMP, VQP, VHP, VNP, VPP, VSP, VGP, VAP, VRP, MFP,
<220> FEATURE:
<221> NAME/KEY: VARIANT
<222> LOCATION: (12)...(14)
<223> OTHER INFORMATION: Xaa Xaa Xaa=MMP, MQP, MHP, MNP, MPP, MSP, MGP,
      MAP, MRPR, LFR, LMR, LQR, LHR, LNR, LPR, LSR, LGR,
      LAR, LRR, QFR, QMR, QQR, QHR, QNR, QPR, QSR, QGR,
      QAR, QRR, VFR, VMR, VQR, VHR, VNR, VPR, VSR, VGR,
<220> FEATURE:
<221> NAME/KEY: VARIANT
<222> LOCATION: (12)...(14)
<223> OTHER INFORMATION: Xaa Xaa Xaa=VAR, VRR, MFR, MMR, MQR, MHR, MNR,
      MPR, MSR, MGR, MAR, or MRR
<220> FEATURE:
<221> NAME/KEY: VARIANT
<222> LOCATION: (15)...(16)
<223> OTHER INFORMATION: Variable length region=ER, R, or no amino acid

<400> SEQUENCE: 166

Xaa Xaa Xaa Xaa Xaa Xaa Xaa Val Lys Xaa Xaa Xaa Xaa Xaa Xaa Xaa
1               5                   10                  15

<210> SEQ ID NO 167
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 167

Lys Lys Leu Asp Thr
1               5

<210> SEQ ID NO 168
<211> LENGTH: 5
<212> TYPE: PRT
```

<213> ORGANISM: Artificial Sequence
<220> FEATURE:
<223> OTHER INFORMATION: Synthetic polypeptide

<400> SEQUENCE: 168

Arg Lys Leu Asp Thr
1               5

<210> SEQ ID NO 169
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 169

Lys Lys Gly Asp Thr
1               5

<210> SEQ ID NO 170
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 170

Lys Lys Glu Asp Thr
1               5

<210> SEQ ID NO 171
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 171

Lys Lys Leu Asp Gln
1               5

<210> SEQ ID NO 172
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 172

Lys Leu Asp Thr
1

<210> SEQ ID NO 173
<211> LENGTH: 16
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 1-4
<223> OTHER INFORMATION: Variable length region=KKLD, RKLD, KKGD, KKED,
      KLD, KGD, KED, LD, GD, ED, D, or no amino acid
<220> FEATURE:
<221> NAME/KEY: VARIANT
<222> LOCATION: 12-14
<223> OTHER INFORMATION: Xaa Xaa Xaa= LFT, LMT, LQT, LHT, LNT, LPT, LST,
      LGT, LAT, LRT, QFT, QMT, QQT, QHT, QNT, QPT, QST,
      QGT, QAT, QRT, VFT, VMT, VQT, VHT, VNT, VPT, VST,

```
        VGT, VAT, VRT, MFT, MMT, MQT, MHT, MNT, MPT, MST,
<220> FEATURE:
<221> NAME/KEY: VARIANT
<222> LOCATION: 12-14
<223> OTHER INFORMATION: Xaa Xaa Xaa= MGT, MAT, MRT, LFN, LMN, LQN, LHN,
        LNN, LPN, LSN, LGN, LAN, LRN, QFN, QMN, QQN, QHN,
        QNN, QPN, QSN, QGN, QAN, QRN, VFN, VMN, VQN, VHN,
        VNN, VPN, VSN, VGN, VAN, VRN, MFN, MMN, MQN, MHN,
<220> FEATURE:
<221> NAME/KEY: VARIANT
<222> LOCATION: 12-14
<223> OTHER INFORMATION: Xaa Xaa Xaa= MNN, MPN, MSN, MGN, MAN, MRN, LFP,
        LMP, LQP, LHP, LNP, LPP, LSP, LGP, LAP, LRP, QFP,
        QMP, QQP, QHP, QNP, QPP, QSP, QGP, QAP, QRP, VFP,
        VMP, VQP, VHP, VNP, VPP, VSP, VGP, VAP, VRP, MFP,
<220> FEATURE:
<221> NAME/KEY: VARIANT
<222> LOCATION: 12-14
<223> OTHER INFORMATION: Xaa Xaa Xaa= MMP, MQP, MHP, MNP, MPP, MSP, MGP,
        MAP, MRPR, LFR, LMR, LQR, LHR, LNR, LPR, LSR, LGR,
        LAR, LRR, QFR, QMR, QQR, QHR, QNR, QPR, QSR, QGR,
        QAR, QRR, VFR, VMR, VQR, VHR, VNR, VPR, VSR, VGR,
<220> FEATURE:
<221> NAME/KEY: VARIANT
<222> LOCATION: (12)...(14)
<223> OTHER INFORMATION: Xaa Xaa Xaa= VAR, VRR, MFR, MMR, MQR, MHR, MNR,
        MPR, MSR, MGR, MAR, MRR, or no amino acid
<220> FEATURE:
<221> NAME/KEY: VARIANT
<222> LOCATION: (15)...(16)
<223> OTHER INFORMATION: Variable length region=ER, R, or no amino acid

<400> SEQUENCE: 173

Xaa Xaa Xaa Xaa Thr Phe Phe Val Lys Leu Ser Xaa Xaa Xaa Xaa Xaa
1               5                   10                  15

<210> SEQ ID NO 174
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 174

Lys Lys Leu Asp
1

<210> SEQ ID NO 175
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 175

Arg Lys Leu Asp
1

<210> SEQ ID NO 176
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 176

Lys Lys Gly Asp
1

<210> SEQ ID NO 177
<211> LENGTH: 4
```

```
<212> TYPE: PRT
<213> ORGANISM: Artificial Sequence
<220> FEATURE:
<223> OTHER INFORMATION: Synthetic polypeptide

<400> SEQUENCE: 177

Lys Lys Glu Asp
1

<210> SEQ ID NO 178
<211> LENGTH: 16
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 1-6
<223> OTHER INFORMATION: The sequence may be deleted at the N terminus
      by 1, 2, 3, 4, 5, or 6 amino acids
<220> FEATURE:
<221> NAME/KEY: VARIANT
<222> LOCATION: 7
<223> OTHER INFORMATION: Xaa= F, S, M, V, T, L, or no amino acid
<220> FEATURE:
<221> NAME/KEY: VARIANT
<222> LOCATION: 11
<223> OTHER INFORMATION: Xaa= S, Q, M, T, or H
<220> FEATURE:
<221> NAME/KEY: VARIANT
<222> LOCATION: 13
<223> OTHER INFORMATION: Xaa= F, M, Q, H, N, P, S, G, A, or R
<220> FEATURE:
<221> NAME/KEY: VARIANT
<222> LOCATION: 16
<223> OTHER INFORMATION: Xaa= R, or no amino acid

<400> SEQUENCE: 178

Lys Lys Leu Asp Thr Phe Xaa Val Lys Leu Xaa Leu Xaa Thr Glu Xaa
1               5                   10                  15

<210> SEQ ID NO 179
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 179

Lys Lys Leu Asp Thr Phe
1               5

<210> SEQ ID NO 180
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 180

Lys Leu Asp Thr Phe
1               5

<210> SEQ ID NO 181
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 181
```

Leu Asp Thr Phe
1

<210> SEQ ID NO 182
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 182

Phe Phe Val Lys
1

<210> SEQ ID NO 183
<211> LENGTH: 23
<212> TYPE: PRT
<213> ORGANISM: Homo sapiens

<400> SEQUENCE: 183

Asn Glu Glu Thr Phe Leu Lys Lys Tyr Leu Tyr Glu Ile Ala Arg Arg
1               5                   10                  15

His Pro Tyr Phe Tyr Ala Pro
            20

<210> SEQ ID NO 184
<211> LENGTH: 18
<212> TYPE: PRT
<213> ORGANISM: Homo sapiens

<400> SEQUENCE: 184

Glu Leu Phe Glu Gln Leu Gly Glu Tyr Lys Phe Gln Asn Ala Leu Leu
1               5                   10                  15

Val Arg

<210> SEQ ID NO 185
<211> LENGTH: 17
<212> TYPE: PRT
<213> ORGANISM: Homo sapiens

<400> SEQUENCE: 185

Val Phe Asp Glu Phe Lys Pro Leu Val Glu Glu Pro Gln Asn Leu Ile
1               5                   10                  15

Lys

<210> SEQ ID NO 186
<211> LENGTH: 10
<212> TYPE: PRT
<213> ORGANISM: Homo sapiens

<400> SEQUENCE: 186

Val Phe Asp Glu Phe Lys Pro Leu Val Glu
1               5                   10

<210> SEQ ID NO 187
<211> LENGTH: 7
<212> TYPE: PRT
<213> ORGANISM: Homo sapiens

<400> SEQUENCE: 187

Glu Pro Gln Asn Leu Ile Lys
1               5

```
<210> SEQ ID NO 188
<211> LENGTH: 15
<212> TYPE: PRT
<213> ORGANISM: Homo sapiens

<400> SEQUENCE: 188

Lys Val Pro Gln Val Ser Thr Pro Thr Leu Val Glu Val Ser Arg
1               5                   10                  15

<210> SEQ ID NO 189
<211> LENGTH: 12
<212> TYPE: PRT
<213> ORGANISM: Homo sapiens

<400> SEQUENCE: 189

Lys Leu Val Asn Glu Val Thr Glu Phe Ala Lys Thr
1               5                   10

<210> SEQ ID NO 190
<211> LENGTH: 12
<212> TYPE: PRT
<213> ORGANISM: Homo sapiens

<400> SEQUENCE: 190

Asn Glu Glu Thr Phe Leu Lys Lys Tyr Leu Tyr Glu
1               5                   10

<210> SEQ ID NO 191
<211> LENGTH: 11
<212> TYPE: PRT
<213> ORGANISM: Homo sapiens

<400> SEQUENCE: 191

Leu Asp Glu Leu Arg Asp Glu Gly Lys Ala Ser
1               5                   10

<210> SEQ ID NO 192
<211> LENGTH: 12
<212> TYPE: PRT
<213> ORGANISM: Homo sapiens

<400> SEQUENCE: 192

Glu Met Ala Asp Cys Cys Ala Lys Gln Glu Pro Glu
1               5                   10

<210> SEQ ID NO 193
<211> LENGTH: 11
<212> TYPE: PRT
<213> ORGANISM: Homo sapiens

<400> SEQUENCE: 193

Glu Leu Phe Glu Gln Leu Gly Glu Tyr Lys Phe
1               5                   10

<210> SEQ ID NO 194
<211> LENGTH: 8
<212> TYPE: PRT
<213> ORGANISM: Homo sapiens

<400> SEQUENCE: 194

Lys Tyr Leu Tyr Glu Ile Ala Arg
1               5

<210> SEQ ID NO 195
```

-continued

```
<211> LENGTH: 15
<212> TYPE: PRT
<213> ORGANISM: Homo sapiens

<400> SEQUENCE: 195

Lys Val Pro Gln Val Ser Thr Pro Thr Leu Val Glu Val Ser Arg
1               5                   10                  15

<210> SEQ ID NO 196
<211> LENGTH: 17
<212> TYPE: PRT
<213> ORGANISM: Homo sapiens

<400> SEQUENCE: 196

Val Phe Asp Glu Phe Lys Pro Leu Val Glu Glu Pro Gln Asn Leu Ile
1               5                   10                  15

Lys

<210> SEQ ID NO 197
<211> LENGTH: 14
<212> TYPE: PRT
<213> ORGANISM: Homo sapiens

<400> SEQUENCE: 197

Val Pro Gln Val Ser Thr Pro Thr Leu Val Glu Val Ser Arg
1               5                   10

<210> SEQ ID NO 198
<211> LENGTH: 16
<212> TYPE: PRT
<213> ORGANISM: Homo sapiens

<400> SEQUENCE: 198

Arg Pro Cys Phe Ser Ala Leu Glu Val Asp Glu Thr Tyr Val Pro Lys
1               5                   10                  15

<210> SEQ ID NO 199
<211> LENGTH: 8
<212> TYPE: PRT
<213> ORGANISM: Homo sapiens

<400> SEQUENCE: 199

Phe Gln Asn Ala Leu Leu Val Arg
1               5

<210> SEQ ID NO 200
<211> LENGTH: 9
<212> TYPE: PRT
<213> ORGANISM: Homo sapiens

<400> SEQUENCE: 200

Ser Leu His Thr Leu Phe Gly Asp Lys
1               5

<210> SEQ ID NO 201
<211> LENGTH: 12
<212> TYPE: PRT
<213> ORGANISM: Homo sapiens

<400> SEQUENCE: 201

Leu Lys Glu Cys Cys Glu Lys Pro Leu Leu Glu Lys
1               5                   10

<210> SEQ ID NO 202
```

```
<211> LENGTH: 8
<212> TYPE: PRT
<213> ORGANISM: Homo sapiens

<400> SEQUENCE: 202

Leu Cys Thr Val Ala Thr Leu Arg
1               5

<210> SEQ ID NO 203
<211> LENGTH: 7
<212> TYPE: PRT
<213> ORGANISM: Homo sapiens

<400> SEQUENCE: 203

Tyr Leu Tyr Glu Ile Ala Arg
1               5

<210> SEQ ID NO 204
<211> LENGTH: 13
<212> TYPE: PRT
<213> ORGANISM: Homo sapiens

<400> SEQUENCE: 204

Cys Cys Ala Ala Ala Asp Pro His Glu Cys Tyr Ala Lys
1               5                   10

<210> SEQ ID NO 205
<211> LENGTH: 12
<212> TYPE: PRT
<213> ORGANISM: Homo sapiens

<400> SEQUENCE: 205

Ala Ala Phe Thr Glu Cys Cys Gln Ala Ala Asp Lys
1               5                   10

<210> SEQ ID NO 206
<211> LENGTH: 9
<212> TYPE: PRT
<213> ORGANISM: Homo sapiens

<400> SEQUENCE: 206

Cys Cys Thr Glu Ser Leu Val Asn Arg
1               5

<210> SEQ ID NO 207
<211> LENGTH: 13
<212> TYPE: PRT
<213> ORGANISM: Homo sapiens

<400> SEQUENCE: 207

Gln Glu Pro Glu Arg Asn Glu Cys Phe Leu Gln His Lys
1               5                   10

<210> SEQ ID NO 208
<211> LENGTH: 12
<212> TYPE: PRT
<213> ORGANISM: Homo sapiens

<400> SEQUENCE: 208

Ala Val Met Asp Asp Phe Ala Ala Phe Val Glu Lys
1               5                   10

<210> SEQ ID NO 209
<211> LENGTH: 8
<212> TYPE: PRT
```

```
<213> ORGANISM: Homo sapiens

<400> SEQUENCE: 209

Asn Glu Cys Phe Leu Gln His Lys
1               5

<210> SEQ ID NO 210
<211> LENGTH: 13
<212> TYPE: PRT
<213> ORGANISM: Homo sapiens

<400> SEQUENCE: 210

Gln Asn Cys Glu Leu Phe Glu Gln Leu Gly Glu Tyr Lys
1               5                   10

<210> SEQ ID NO 211
<211> LENGTH: 13
<212> TYPE: PRT
<213> ORGANISM: Homo sapiens

<400> SEQUENCE: 211

Gln Glu Pro Glu Arg Asn Glu Cys Phe Leu Gln His Lys
1               5                   10

<210> SEQ ID NO 212
<211> LENGTH: 17
<212> TYPE: PRT
<213> ORGANISM: Homo sapiens

<400> SEQUENCE: 212

Val His Thr Glu Cys Cys His Gly Asp Leu Leu Glu Cys Ala Asp Asp
1               5                   10                  15

Arg

<210> SEQ ID NO 213
<211> LENGTH: 10
<212> TYPE: PRT
<213> ORGANISM: Homo sapiens

<400> SEQUENCE: 213

Phe Lys Asp Leu Gly Glu Glu Asn Phe Lys
1               5                   10

<210> SEQ ID NO 214
<211> LENGTH: 12
<212> TYPE: PRT
<213> ORGANISM: Homo sapiens

<400> SEQUENCE: 214

Tyr Ile Cys Glu Asn Gln Asp Ser Ile Ser Ser Lys
1               5                   10

<210> SEQ ID NO 215
<211> LENGTH: 9
<212> TYPE: PRT
<213> ORGANISM: Homo sapiens

<400> SEQUENCE: 215

Leu Asp Glu Leu Arg Asp Glu Gly Lys
1               5

<210> SEQ ID NO 216
<211> LENGTH: 8
<212> TYPE: PRT
```

<213> ORGANISM: Homo sapiens

<400> SEQUENCE: 216

Asp Asp Asn Pro Asn Leu Pro Arg
1               5

<210> SEQ ID NO 217
<211> LENGTH: 18
<212> TYPE: PRT
<213> ORGANISM: Homo sapiens

<400> SEQUENCE: 217

Asp His Val Lys Leu Val Asn Glu Val Thr Glu Phe Ala Lys Thr Cys
1               5                   10                  15

Val Ala

<210> SEQ ID NO 218
<211> LENGTH: 24
<212> TYPE: PRT
<213> ORGANISM: Homo sapiens

<400> SEQUENCE: 218

Asp Asp Lys Glu Thr Cys Phe Ala Glu Glu Gly Lys Lys Leu Val Ala
1               5                   10                  15

Ala Ser Gln Ala Ala Leu Gly Leu
            20

<210> SEQ ID NO 219
<211> LENGTH: 23
<212> TYPE: PRT
<213> ORGANISM: Homo sapiens

<400> SEQUENCE: 219

Asp Arg Val Thr Lys Cys Cys Thr Glu Ser Leu Val Asn Arg Arg Pro
1               5                   10                  15

Cys Phe Ser Ala Leu Glu Val
            20

<210> SEQ ID NO 220
<211> LENGTH: 17
<212> TYPE: PRT
<213> ORGANISM: Homo sapiens

<400> SEQUENCE: 220

Asp Glu Thr Tyr Val Pro Lys Glu Phe Asn Ala Glu Thr Phe Thr His
1               5                   10                  15

Ala

<210> SEQ ID NO 221
<211> LENGTH: 27
<212> TYPE: PRT
<213> ORGANISM: Homo sapiens

<400> SEQUENCE: 221

Asp Ser Ile Ser Ser Lys Leu Lys Glu Cys Cys Glu Lys Pro Leu Leu
1               5                   10                  15

Glu Lys Ser His Cys Ile Ala Glu Val Glu Asn
            20                  25

<210> SEQ ID NO 222
<211> LENGTH: 16
<212> TYPE: PRT

<213> ORGANISM: Homo sapiens

<400> SEQUENCE: 222

Asp Lys Leu Cys Thr Val Ala Thr Leu Arg Glu Thr Tyr Gly Glu Met
1               5                   10                  15

<210> SEQ ID NO 223
<211> LENGTH: 34
<212> TYPE: PRT
<213> ORGANISM: Homo sapiens

<400> SEQUENCE: 223

Tyr Ser Val Val Leu Leu Leu Arg Leu Ala Lys Thr Tyr Glu Thr Thr
1               5                   10                  15

Leu Glu Lys Cys Cys Ala Ala Ala Asp Pro His Glu Cys Tyr Ala Lys
                20                  25                  30

Val Phe

<210> SEQ ID NO 224
<211> LENGTH: 34
<212> TYPE: PRT
<213> ORGANISM: Homo sapiens

<400> SEQUENCE: 224

Lys Leu Cys Thr Val Ala Thr Leu Arg Glu Thr Tyr Gly Glu Met Ala
1               5                   10                  15

Asp Cys Cys Ala Lys Gln Glu Pro Glu Arg Asn Glu Cys Phe Leu Gln
                20                  25                  30

His Lys

<210> SEQ ID NO 225
<211> LENGTH: 36
<212> TYPE: PRT
<213> ORGANISM: Homo sapiens

<400> SEQUENCE: 225

Ile Cys Thr Leu Ser Glu Lys Glu Arg Gln Ile Lys Lys Gln Thr Ala
1               5                   10                  15

Leu Val Glu Leu Val Lys His Lys Pro Lys Ala Thr Lys Glu Gln Leu
                20                  25                  30

Lys Ala Val Met
        35

<210> SEQ ID NO 226
<211> LENGTH: 35
<212> TYPE: PRT
<213> ORGANISM: Homo sapiens

<400> SEQUENCE: 226

Leu Ala Lys Tyr Ile Cys Glu Asn Gln Asp Ser Ile Ser Ser Lys Leu
1               5                   10                  15

Lys Glu Cys Cys Glu Lys Pro Leu Leu Glu Lys His Cys Ile Ala Glu
                20                  25                  30

Val Glu Asn
        35

<210> SEQ ID NO 227
<211> LENGTH: 40
<212> TYPE: PRT
<213> ORGANISM: Homo sapiens

<400> SEQUENCE: 227

```
Val Phe Leu Gly Met Phe Leu Tyr Glu Tyr Ala Arg Arg His Pro Asp
1               5                   10                  15
Tyr Ser Val Val Leu Leu Leu Arg Leu Ala Lys Thr Tyr Glu Thr Thr
            20                  25                  30
Leu Glu Lys Cys Cys Ala Ala Ala
        35                  40
```

<210> SEQ ID NO 228
<211> LENGTH: 42
<212> TYPE: PRT
<213> ORGANISM: Homo sapiens

<400> SEQUENCE: 228

```
Leu Gly Glu Glu Asn Phe Lys Ala Leu Val Leu Ile Ala Phe Ala Gln
1               5                   10                  15
Tyr Leu Gln Gln Cys Pro Phe Glu Asp His Val Lys Leu Val Asn Glu
            20                  25                  30
Val Thr Glu Phe Ala Lys Thr Cys Val Ala
        35                  40
```

<210> SEQ ID NO 229
<211> LENGTH: 40
<212> TYPE: PRT
<213> ORGANISM: Homo sapiens

<400> SEQUENCE: 229

```
Arg Val Thr Lys Cys Cys Thr Glu Ser Leu Val Asn Arg Arg Pro Cys
1               5                   10                  15
Phe Ser Ala Leu Glu Val Asp Glu Thr Tyr Val Pro Lys Glu Phe Asn
            20                  25                  30
Ala Glu Thr Phe Thr Phe His Ala
        35                  40
```

<210> SEQ ID NO 230
<211> LENGTH: 42
<212> TYPE: PRT
<213> ORGANISM: Homo sapiens

<400> SEQUENCE: 230

```
Tyr Leu Ser Val Val Leu Asn Gln Leu Cys Val Leu His Glu Lys Thr
1               5                   10                  15
Pro Val Ser Asp Arg Val Thr Lys Cys Cys Cys Thr Glu Ser Leu Val
            20                  25                  30
Asn Arg Arg Pro Phe Ser Ala Leu Glu Val
        35                  40
```

<210> SEQ ID NO 231
<211> LENGTH: 10
<212> TYPE: PRT
<213> ORGANISM: Homo sapiens

<400> SEQUENCE: 231

```
Leu Val Asn Glu Val Thr Glu Phe Ala Lys
1               5                   10
```

<210> SEQ ID NO 232
<211> LENGTH: 9
<212> TYPE: PRT
<213> ORGANISM: Homo sapiens

```
<400> SEQUENCE: 232

Ser Leu His Thr Leu Phe Gly Asp Lys
1               5

<210> SEQ ID NO 233
<211> LENGTH: 8
<212> TYPE: PRT
<213> ORGANISM: Homo sapiens

<400> SEQUENCE: 233

Leu Cys Thr Val Ala Thr Leu Arg
1               5

<210> SEQ ID NO 234
<211> LENGTH: 12
<212> TYPE: PRT
<213> ORGANISM: Artificial Sequence
<220> FEATURE:
<223> OTHER INFORMATION: P28R truncation

<400> SEQUENCE: 234

Glu Thr Tyr Gly Glu Met Ala Asp Cys Cys Ala Lys
1               5                   10

<210> SEQ ID NO 235
<211> LENGTH: 7
<212> TYPE: PRT
<213> ORGANISM: Artificial Sequence
<220> FEATURE:
<223> OTHER INFORMATION: P28R truncation

<400> SEQUENCE: 235

Tyr Leu Tyr Glu Ile Ala Arg
1               5

<210> SEQ ID NO 236
<211> LENGTH: 9
<212> TYPE: PRT
<213> ORGANISM: Homo sapiens

<400> SEQUENCE: 236

Leu Asp Glu Leu Arg Asp Glu Gly Lys
1               5

<210> SEQ ID NO 237
<211> LENGTH: 12
<212> TYPE: PRT
<213> ORGANISM: Homo sapiens

<400> SEQUENCE: 237

Tyr Ile Cys Glu Asn Gln Asp Ser Ile Ser Ser Lys
1               5                   10

<210> SEQ ID NO 238
<211> LENGTH: 12
<212> TYPE: PRT
<213> ORGANISM: Homo sapiens

<400> SEQUENCE: 238

Leu Lys Glu Cys Cys Glu Lys Pro Leu Leu Glu Lys
1               5                   10

<210> SEQ ID NO 239
<211> LENGTH: 11
<212> TYPE: PRT
```

<213> ORGANISM: Homo sapiens

<400> SEQUENCE: 239

His Pro Asp Tyr Ser Val Val Leu Leu Arg
1               5                   10

<210> SEQ ID NO 240
<211> LENGTH: 13
<212> TYPE: PRT
<213> ORGANISM: Homo sapiens

<400> SEQUENCE: 240

Cys Cys Ala Ala Ala Asp Pro His Glu Cys Tyr Ala Lys
1               5                   10

<210> SEQ ID NO 241
<211> LENGTH: 13
<212> TYPE: PRT
<213> ORGANISM: Homo sapiens

<400> SEQUENCE: 241

Gln Asn Cys Glu Leu Phe Glu Gln Leu Gly Glu Tyr Lys
1               5                   10

<210> SEQ ID NO 242
<211> LENGTH: 8
<212> TYPE: PRT
<213> ORGANISM: Homo sapiens

<400> SEQUENCE: 242

Phe Gln Asn Ala Leu Leu Val Arg
1               5

<210> SEQ ID NO 243
<211> LENGTH: 9
<212> TYPE: PRT
<213> ORGANISM: Homo sapiens

<400> SEQUENCE: 243

Cys Cys Thr Glu Ser Leu Val Asn Arg
1               5

<210> SEQ ID NO 244
<211> LENGTH: 12
<212> TYPE: PRT
<213> ORGANISM: Homo sapiens

<400> SEQUENCE: 244

Ala Val Met Asp Asp Phe Ala Ala Phe Val Glu Lys
1               5                   10

<210> SEQ ID NO 245
<211> LENGTH: 7
<212> TYPE: PRT
<213> ORGANISM: Homo sapiens

<400> SEQUENCE: 245

Leu Ser Gln Arg Phe Pro Lys
1               5

<210> SEQ ID NO 246
<211> LENGTH: 8
<212> TYPE: PRT
<213> ORGANISM: Homo sapiens

<400> SEQUENCE: 246

Asp Asp Asn Pro Asn Leu Pro Arg
1               5

<210> SEQ ID NO 247
<211> LENGTH: 272
<212> TYPE: PRT
<213> ORGANISM: Homo sapiens

<400> SEQUENCE: 247

Met Asp Ser Tyr Leu Leu Met Trp Gly Leu Thr Phe Ile Met Val
1               5                   10                  15

Pro Gly Cys Gln Ala Glu Leu Cys Asp Asp Pro Pro Glu Ile Pro
                20                  25                  30

His Ala Thr Phe Lys Ala Met Ala Tyr Lys Glu Gly Thr Met Leu Asn
            35                  40                  45

Cys Glu Cys Lys Arg Gly Phe Arg Arg Ile Lys Ser Gly Ser Leu Tyr
        50                  55                  60

Met Leu Cys Thr Gly Asn Ser Ser His Ser Ser Trp Asp Asn Gln Cys
65                  70                  75                  80

Gln Cys Thr Ser Ser Ala Thr Arg Asn Thr Thr Lys Gln Val Thr Pro
                85                  90                  95

Gln Pro Glu Glu Gln Lys Glu Arg Lys Thr Thr Glu Met Gln Ser Pro
            100                 105                 110

Met Gln Pro Val Asp Gln Ala Ser Leu Pro Gly His Cys Arg Glu Pro
        115                 120                 125

Pro Pro Trp Glu Asn Glu Ala Thr Glu Arg Ile Tyr His Phe Val Val
        130                 135                 140

Gly Gln Met Val Tyr Tyr Gln Cys Val Gln Gly Tyr Arg Ala Leu His
145                 150                 155                 160

Arg Gly Pro Ala Glu Ser Val Cys Lys Met Thr His Gly Lys Thr Arg
                165                 170                 175

Trp Thr Gln Pro Gln Leu Ile Cys Thr Gly Glu Met Glu Thr Ser Gln
            180                 185                 190

Phe Pro Gly Glu Glu Lys Pro Gln Ala Ser Pro Glu Gly Arg Pro Glu
        195                 200                 205

Ser Glu Thr Ser Cys Leu Val Thr Thr Thr Asp Phe Gln Ile Gln Thr
    210                 215                 220

Glu Met Ala Ala Thr Met Glu Thr Ser Ile Phe Thr Thr Glu Tyr Gln
225                 230                 235                 240

Val Ala Val Ala Gly Cys Val Phe Leu Leu Ile Ser Val Leu Leu Leu
                245                 250                 255

Ser Gly Leu Thr Trp Gln Arg Arg Gln Arg Lys Ser Arg Arg Thr Ile
            260                 265                 270

<210> SEQ ID NO 248
<211> LENGTH: 1170
<212> TYPE: PRT
<213> ORGANISM: Homo sapiens

<400> SEQUENCE: 248

Met Lys Asp Ser Cys Ile Thr Val Met Ala Met Ala Leu Leu Ser Gly
1               5                   10                  15

Phe Phe Phe Phe Ala Pro Ala Ser Ser Tyr Asn Leu Asp Val Arg Gly
                20                  25                  30

Ala Arg Ser Phe Ser Pro Pro Arg Ala Gly Arg His Phe Gly Tyr Arg

```
                35                  40                  45
Val Leu Gln Val Gly Asn Gly Val Ile Val Gly Ala Pro Gly Glu Gly
 50                  55                  60

Asn Ser Thr Gly Ser Leu Tyr Gln Cys Gln Ser Gly Thr Gly His Cys
 65                  70                  75                  80

Leu Pro Val Thr Leu Arg Gly Ser Asn Tyr Thr Ser Lys Tyr Leu Gly
                 85                  90                  95

Met Thr Leu Ala Thr Asp Pro Thr Asp Gly Ser Ile Leu Ala Cys Asp
                100                 105                 110

Pro Gly Leu Ser Arg Thr Cys Asp Gln Asn Thr Tyr Leu Ser Gly Leu
                115                 120                 125

Cys Tyr Leu Phe Arg Gln Asn Leu Gln Gly Pro Met Leu Gln Gly Arg
                130                 135                 140

Pro Gly Phe Gln Glu Cys Ile Lys Gly Asn Val Asp Leu Val Phe Leu
145                 150                 155                 160

Phe Asp Gly Ser Met Ser Leu Gln Pro Asp Glu Phe Gln Lys Ile Leu
                165                 170                 175

Asp Phe Met Lys Asp Val Met Lys Lys Leu Ser Asn Thr Ser Tyr Gln
                180                 185                 190

Phe Ala Ala Val Gln Phe Ser Thr Ser Tyr Lys Thr Glu Phe Asp Phe
                195                 200                 205

Ser Asp Tyr Val Lys Arg Lys Asp Pro Asp Ala Leu Leu Lys His Val
                210                 215                 220

Lys His Met Leu Leu Leu Thr Asn Thr Phe Gly Ala Ile Asn Tyr Val
225                 230                 235                 240

Ala Thr Glu Val Phe Arg Glu Glu Leu Gly Ala Arg Pro Asp Ala Thr
                245                 250                 255

Lys Val Leu Ile Ile Ile Thr Asp Gly Glu Ala Thr Asp Ser Gly Asn
                260                 265                 270

Ile Asp Ala Ala Lys Asp Ile Ile Arg Tyr Ile Ile Gly Ile Gly Lys
                275                 280                 285

His Phe Gln Thr Lys Glu Ser Gln Glu Thr Leu His Lys Phe Ala Ser
                290                 295                 300

Lys Pro Ala Ser Glu Phe Val Lys Ile Leu Asp Thr Phe Glu Lys Leu
305                 310                 315                 320

Lys Asp Leu Phe Thr Glu Leu Gln Lys Lys Ile Tyr Val Ile Glu Gly
                325                 330                 335

Thr Ser Lys Gln Asp Leu Thr Ser Phe Asn Met Glu Leu Ser Ser Ser
                340                 345                 350

Gly Ile Ser Ala Asp Leu Ser Arg Gly His Ala Val Val Gly Ala Val
                355                 360                 365

Gly Ala Lys Asp Trp Ala Gly Gly Phe Leu Asp Leu Lys Ala Asp Leu
                370                 375                 380

Gln Asp Asp Thr Phe Ile Gly Asn Glu Pro Leu Thr Pro Glu Val Arg
385                 390                 395                 400

Ala Gly Tyr Leu Gly Tyr Thr Val Thr Trp Leu Pro Ser Arg Gln Lys
                405                 410                 415

Thr Ser Leu Leu Ala Ser Gly Ala Pro Arg Tyr Gln His Met Gly Arg
                420                 425                 430

Val Leu Leu Phe Gln Glu Pro Gln Gly Gly Gly His Trp Ser Gln Val
                435                 440                 445

Gln Thr Ile His Gly Thr Gln Ile Gly Ser Tyr Phe Gly Gly Glu Leu
                450                 455                 460
```

```
Cys Gly Val Asp Val Asp Gln Asp Gly Glu Thr Glu Leu Leu Leu Ile
465                 470                 475                 480

Gly Ala Pro Leu Phe Tyr Gly Glu Gln Arg Gly Arg Val Phe Ile
            485                 490                 495

Tyr Gln Arg Arg Gln Leu Gly Phe Glu Glu Val Ser Glu Leu Gln Gly
                500                 505                 510

Asp Pro Gly Tyr Pro Leu Gly Arg Phe Gly Glu Ala Ile Thr Ala Leu
            515                 520                 525

Thr Asp Ile Asn Gly Asp Gly Leu Val Asp Val Ala Val Gly Ala Pro
530                 535                 540

Leu Glu Glu Gln Gly Ala Val Tyr Ile Phe Asn Gly Arg His Gly Gly
545                 550                 555                 560

Leu Ser Pro Gln Pro Ser Gln Arg Ile Glu Gly Thr Gln Val Leu Ser
            565                 570                 575

Gly Ile Gln Trp Phe Gly Arg Ser Ile His Gly Val Lys Asp Leu Glu
            580                 585                 590

Gly Asp Gly Leu Ala Asp Val Ala Val Gly Ala Glu Ser Gln Met Ile
        595                 600                 605

Val Leu Ser Ser Arg Pro Val Val Asp Met Val Thr Leu Met Ser Phe
610                 615                 620

Ser Pro Ala Glu Ile Pro Val His Glu Val Glu Cys Ser Tyr Ser Thr
625                 630                 635                 640

Ser Asn Lys Met Lys Glu Gly Val Asn Ile Thr Ile Cys Phe Gln Ile
                645                 650                 655

Lys Ser Leu Ile Pro Gln Phe Gln Gly Arg Leu Val Ala Asn Leu Thr
            660                 665                 670

Tyr Thr Leu Gln Leu Asp Gly His Arg Thr Arg Arg Arg Gly Leu Phe
            675                 680                 685

Pro Gly Gly Arg His Glu Leu Arg Arg Asn Ile Ala Val Thr Thr Ser
690                 695                 700

Met Ser Cys Thr Asp Phe Ser Phe His Phe Pro Val Cys Val Gln Asp
705                 710                 715                 720

Leu Ile Ser Pro Ile Asn Val Ser Leu Asn Phe Ser Leu Trp Glu Glu
            725                 730                 735

Glu Gly Thr Pro Arg Asp Gln Arg Ala Gln Gly Lys Asp Ile Pro Pro
            740                 745                 750

Ile Leu Arg Pro Ser Leu His Ser Glu Thr Trp Glu Ile Pro Phe Glu
            755                 760                 765

Lys Asn Cys Gly Glu Asp Lys Lys Cys Glu Ala Asn Leu Arg Val Ser
            770                 775                 780

Phe Ser Pro Ala Arg Ser Arg Ala Leu Arg Leu Thr Ala Phe Ala Ser
785                 790                 795                 800

Leu Ser Val Glu Leu Ser Leu Ser Asn Leu Glu Glu Asp Ala Tyr Trp
                805                 810                 815

Val Gln Leu Asp Leu His Phe Pro Pro Gly Leu Ser Phe Arg Lys Val
            820                 825                 830

Glu Met Leu Lys Pro His Ser Gln Ile Pro Val Ser Cys Glu Glu Leu
            835                 840                 845

Pro Glu Glu Ser Arg Leu Leu Ser Arg Ala Leu Ser Cys Asn Val Ser
            850                 855                 860

Ser Pro Ile Phe Lys Ala Gly His Ser Val Ala Leu Gln Met Met Phe
865                 870                 875                 880
```

```
Asn Thr Leu Val Asn Ser Ser Trp Gly Asp Ser Val Glu Leu His Ala
                885                 890                 895

Asn Val Thr Cys Asn Asn Glu Asp Ser Asp Leu Leu Glu Asp Asn Ser
            900                 905                 910

Ala Thr Thr Ile Ile Pro Ile Leu Tyr Pro Ile Asn Ile Leu Ile Gln
            915                 920                 925

Asp Gln Glu Asp Ser Thr Leu Tyr Val Ser Phe Thr Pro Lys Gly Pro
        930                 935                 940

Lys Ile His Gln Val Lys His Met Tyr Gln Val Arg Ile Gln Pro Ser
945                 950                 955                 960

Ile His Asp His Asn Ile Pro Thr Leu Glu Ala Val Val Gly Val Pro
                965                 970                 975

Gln Pro Pro Ser Glu Gly Pro Ile Thr His Gln Trp Ser Val Gln Met
            980                 985                 990

Glu Pro Pro Val Pro Cys His Tyr Glu Asp Leu Glu Arg Leu Pro Asp
        995                 1000                1005

Ala Ala Glu Pro Cys Leu Pro Gly Ala Leu Phe Arg Cys Pro Val Val
    1010                1015                1020

Phe Arg Gln Glu Ile Leu Val Gln Val Ile Gly Thr Leu Glu Leu Val
1025                1030                1035                1040

Gly Glu Ile Glu Ala Ser Ser Met Phe Ser Leu Cys Ser Ser Leu Ser
                1045                1050                1055

Ile Ser Phe Asn Ser Ser Lys His Phe His Leu Tyr Gly Ser Asn Ala
            1060                1065                1070

Ser Leu Ala Gln Val Val Met Lys Val Asp Val Val Tyr Glu Lys Gln
        1075                1080                1085

Met Leu Tyr Leu Tyr Val Leu Ser Gly Ile Gly Gly Leu Leu Leu Leu
    1090                1095                1100

Leu Leu Ile Phe Ile Val Leu Tyr Lys Val Gly Phe Phe Lys Arg Asn
1105                1110                1115                1120

Leu Lys Glu Lys Met Glu Ala Gly Arg Gly Val Pro Asn Gly Ile Pro
                1125                1130                1135

Ala Glu Asp Ser Glu Gln Leu Ala Ser Gly Gln Glu Ala Gly Asp Pro
            1140                1145                1150

Gly Cys Leu Lys Pro Leu His Glu Lys Asp Ser Glu Ser Gly Gly Gly
        1155                1160                1165

Lys Asp
   1170

<210> SEQ ID NO 249
<211> LENGTH: 600
<212> TYPE: PRT
<213> ORGANISM: Homo sapiens

<400> SEQUENCE: 249

Met Leu Gly Leu Arg Pro Pro Leu Leu Ala Leu Val Gly Leu Leu Ser
1               5                   10                  15

Leu Gly Cys Val Leu Ser Gln Glu Cys Thr Lys Phe Lys Val Ser Ser
            20                  25                  30

Cys Arg Glu Cys Ile Glu Ser Gly Pro Gly Cys Thr Trp Cys Gln Lys
        35                  40                  45

Leu Asn Phe Thr Gly Pro Gly Asp Pro Asp Ser Ile Arg Cys Asp Thr
    50                  55                  60

Arg Pro Gln Leu Leu Met Arg Gly Cys Ala Ala Asp Asp Ile Met Asp
65                  70                  75                  80
```

```
Pro Thr Ser Leu Ala Glu Thr Gln Glu Asp His Asn Gly Gly Gln Lys
                85                  90                  95

Gln Leu Ser Pro Gln Lys Val Thr Leu Tyr Leu Arg Pro Gly Gln Ala
            100                 105                 110

Ala Ala Phe Asn Val Thr Phe Arg Arg Ala Lys Gly Tyr Pro Ile Asp
        115                 120                 125

Leu Tyr Tyr Leu Met Asp Leu Ser Tyr Ser Met Leu Asp Asp Leu Arg
    130                 135                 140

Asn Val Lys Lys Leu Gly Gly Asp Leu Leu Arg Ala Leu Asn Glu Ile
145                 150                 155                 160

Thr Glu Ser Gly Arg Ile Gly Phe Gly Ser Phe Val Asp Lys Thr Val
                165                 170                 175

Leu Pro Phe Val Asn Thr His Pro Asp Lys Leu Arg Asn Pro Cys Pro
            180                 185                 190

Asn Lys Glu Lys Glu Cys Gln Pro Pro Phe Ala Phe Arg His Val Leu
        195                 200                 205

Lys Leu Thr Asn Asn Ser Asn Gln Phe Gln Thr Glu Val Gly Lys Gln
    210                 215                 220

Leu Ile Ser Gly Asn Leu Asp Ala Pro Glu Gly Gly Leu Asp Ala Met
225                 230                 235                 240

Met Gln Val Ala Ala Cys Pro Glu Glu Ile Gly Trp Arg Asn Val Thr
                245                 250                 255

Arg Leu Leu Val Phe Ala Thr Asp Asp Gly Phe His Phe Ala Gly Asp
            260                 265                 270

Gly Lys Leu Gly Ala Ile Leu Thr Pro Asn Asp Gly Arg Cys His Leu
        275                 280                 285

Glu Asp Asn Leu Tyr Lys Arg Ser Asn Glu Phe Asp Tyr Pro Ser Val
    290                 295                 300

Gly Gln Leu Ala His Lys Leu Ala Glu Asn Asn Ile Gln Pro Ile Phe
305                 310                 315                 320

Ala Val Thr Ser Arg Met Val Lys Thr Tyr Glu Lys Leu Thr Glu Ile
                325                 330                 335

Ile Pro Lys Ser Ala Val Gly Glu Leu Ser Glu Asp Ser Ser Asn Val
            340                 345                 350

Val His Leu Ile Lys Asn Ala Tyr Asn Lys Leu Ser Ser Arg Val Phe
        355                 360                 365

Leu Asp His Asn Ala Leu Pro Asp Thr Leu Lys Val Thr Tyr Asp Ser
    370                 375                 380

Phe Cys Ser Asn Gly Val Thr His Arg Asn Gln Pro Arg Gly Asp Cys
385                 390                 395                 400

Asp Gly Val Gln Ile Asn Val Pro Ile Thr Phe Gln Val Lys Val Thr
                405                 410                 415

Ala Thr Glu Cys Ile Gln Glu Gln Ser Phe Val Ile Arg Ala Leu Gly
            420                 425                 430

Phe Thr Asp Ile Val Thr Val Gln Val Leu Pro Gln Cys Glu Cys Arg
        435                 440                 445

Cys Arg Asp Gln Ser Arg Asp Arg Ser Leu Cys His Gly Lys Gly Phe
    450                 455                 460

Leu Glu Cys Gly Ile Cys Arg Cys Asp Thr Gly Tyr Ile Gly Lys Asn
465                 470                 475                 480

Cys Glu Cys Gln Thr Gln Gly Arg Ser Ser Gln Glu Leu Glu Gly Ser
                485                 490                 495
```

```
Cys Arg Lys Asp Asn Asn Ser Ile Ile Cys Ser Gly Leu Gly Asp Cys
            500                 505                 510

Val Cys Gly Gln Cys Leu Cys His Thr Ser Asp Val Pro Gly Lys Leu
        515                 520                 525

Ile Tyr Gly Gln Tyr Cys Glu Cys Asp Thr Ile Asn Cys Glu Arg Tyr
            530                 535                 540

Asn Gly Gln Val Cys Gly Pro Gly Arg Gly Leu Cys Phe Cys Gly
545                 550                 555                 560

Lys Cys Arg Cys His Pro Gly Phe Glu Gly Ser Ala Cys Gln Cys Glu
                565                 570                 575

Arg Thr Thr Glu Gly Cys Leu Asn Pro Arg Arg Val Glu Cys Ser Gly
            580                 585                 590

Arg Gly Arg Cys Arg Cys Asn Val
            595                 600

<210> SEQ ID NO 250
<211> LENGTH: 12
<212> TYPE: PRT
<213> ORGANISM: Artificial Sequence
<220> FEATURE:
<223> OTHER INFORMATION: P28R truncation

<400> SEQUENCE: 250

Thr Phe Phe Val Lys Leu Ser Leu Phe Thr Glu Arg
1               5                   10

<210> SEQ ID NO 251
<211> LENGTH: 8
<212> TYPE: PRT
<213> ORGANISM: Artificial Sequence
<220> FEATURE:
<223> OTHER INFORMATION: P28R truncation

<400> SEQUENCE: 251

Val Lys Leu Ser Leu Phe Thr Glu
1               5

<210> SEQ ID NO 252
<211> LENGTH: 5
<212> TYPE: PRT
<213> ORGANISM: Artificial Sequence
<220> FEATURE:
<223> OTHER INFORMATION: Synthetic peptide

<400> SEQUENCE: 252

Lys Lys Gly Asp Gln
1               5

<210> SEQ ID NO 253
<211> LENGTH: 5
<212> TYPE: PRT
<213> ORGANISM: Artificial Sequence
<220> FEATURE:
<223> OTHER INFORMATION: Synthetic peptide

<400> SEQUENCE: 253

Lys Lys Glu Asp Gln
1               5

<210> SEQ ID NO 254
<211> LENGTH: 5
<212> TYPE: PRT
<213> ORGANISM: Artificial Sequence
<220> FEATURE:
```

<223> OTHER INFORMATION: Synthetic peptide

<400> SEQUENCE: 254

Arg Lys Leu Asp Gln
1               5

<210> SEQ ID NO 255
<211> LENGTH: 5
<212> TYPE: PRT
<213> ORGANISM: Artificial Sequence
<220> FEATURE:
<223> OTHER INFORMATION: Synthetic peptide

<400> SEQUENCE: 255

Arg Lys Gly Asp Gln
1               5

<210> SEQ ID NO 256
<211> LENGTH: 5
<212> TYPE: PRT
<213> ORGANISM: Artificial Sequence
<220> FEATURE:
<223> OTHER INFORMATION: Synthetic peptide

<400> SEQUENCE: 256

Arg Lys Glu Asp Gln
1               5

<210> SEQ ID NO 257
<211> LENGTH: 5
<212> TYPE: PRT
<213> ORGANISM: Artificial Sequence
<220> FEATURE:
<223> OTHER INFORMATION: Synthetic peptide

<400> SEQUENCE: 257

Arg Lys Gly Thr Asp
1               5

<210> SEQ ID NO 258
<211> LENGTH: 5
<212> TYPE: PRT
<213> ORGANISM: Artificial Sequence
<220> FEATURE:
<223> OTHER INFORMATION: Synthetic peptide

<400> SEQUENCE: 258

Arg Lys Glu Asp Thr
1               5

<210> SEQ ID NO 259
<211> LENGTH: 4
<212> TYPE: PRT
<213> ORGANISM: Artificial Sequence
<220> FEATURE:
<223> OTHER INFORMATION: Synthetic peptide

<400> SEQUENCE: 259

Lys Gly Asp Thr
1

<210> SEQ ID NO 260
<211> LENGTH: 4
<212> TYPE: PRT
<213> ORGANISM: Artificial Sequence
<220> FEATURE:
<223> OTHER INFORMATION: Synthetic peptide

<400> SEQUENCE: 260

Lys Glu Asp Thr
1

<210> SEQ ID NO 261
<211> LENGTH: 4
<212> TYPE: PRT
<213> ORGANISM: Artificial Sequence
<220> FEATURE:
<223> OTHER INFORMATION: Synthetic peptide

<400> SEQUENCE: 261

Lys Leu Asp Gln
1

<210> SEQ ID NO 262
<211> LENGTH: 4
<212> TYPE: PRT
<213> ORGANISM: Artificial Sequence
<220> FEATURE:
<223> OTHER INFORMATION: Synthetic peptide

<400> SEQUENCE: 262

Lys Gly Asp Gln
1

<210> SEQ ID NO 263
<211> LENGTH: 4
<212> TYPE: PRT
<213> ORGANISM: Artificial Sequence
<220> FEATURE:
<223> OTHER INFORMATION: Synthetic peptide

<400> SEQUENCE: 263

Lys Glu Asp Gln
1

<210> SEQ ID NO 264
<211> LENGTH: 16
<212> TYPE: PRT
<213> ORGANISM: Artificial Sequence
<220> FEATURE:
<223> OTHER INFORMATION: Synthetic peptide

<400> SEQUENCE: 264

Lys Lys Leu Asp Thr Phe Phe Lys Lys Leu Ser Leu Phe Thr Glu Arg
1               5                   10                  15

<210> SEQ ID NO 265
<211> LENGTH: 9
<212> TYPE: PRT
<213> ORGANISM: Artificial Sequence
<220> FEATURE:
<223> OTHER INFORMATION: Synthetic peptide

<400> SEQUENCE: 265

Cys Leu Ala Leu Asn Val Met Cys Gly
1               5

<210> SEQ ID NO 266
<211> LENGTH: 9
<212> TYPE: PRT
<213> ORGANISM: Artificial Sequence
<220> FEATURE:
<223> OTHER INFORMATION: Synthetic peptide

```
<400> SEQUENCE: 266

Cys Leu Arg Leu Asn Val Phe Cys Gly
1               5

<210> SEQ ID NO 267
<211> LENGTH: 9
<212> TYPE: PRT
<213> ORGANISM: Artificial Sequence
<220> FEATURE:
<223> OTHER INFORMATION: Synthetic peptide

<400> SEQUENCE: 267

Cys Leu Arg Leu Ile Val Met Cys Gly
1               5

<210> SEQ ID NO 268
<211> LENGTH: 16
<212> TYPE: PRT
<213> ORGANISM: Artificial Sequence
<220> FEATURE:
<223> OTHER INFORMATION: Synthetic peptide

<400> SEQUENCE: 268

Ala Lys Leu Asp Thr Phe Phe Val Lys Leu Ser Leu Phe Thr Glu Arg
1               5                   10                  15

<210> SEQ ID NO 269
<211> LENGTH: 16
<212> TYPE: PRT
<213> ORGANISM: Artificial Sequence
<220> FEATURE:
<223> OTHER INFORMATION: Synthetic peptide

<400> SEQUENCE: 269

Asp Lys Leu Asp Thr Phe Phe Val Lys Leu Ser Leu Phe Thr Glu Arg
1               5                   10                  15

<210> SEQ ID NO 270
<211> LENGTH: 16
<212> TYPE: PRT
<213> ORGANISM: Artificial Sequence
<220> FEATURE:
<223> OTHER INFORMATION: Synthetic peptide

<400> SEQUENCE: 270

Glu Lys Leu Asp Thr Phe Phe Val Lys Leu Ser Leu Phe Thr Glu Arg
1               5                   10                  15

<210> SEQ ID NO 271
<211> LENGTH: 16
<212> TYPE: PRT
<213> ORGANISM: Artificial Sequence
<220> FEATURE:
<223> OTHER INFORMATION: Synthetic peptide

<400> SEQUENCE: 271

Gly Lys Leu Asp Thr Phe Phe Val Lys Leu Ser Leu Phe Thr Glu Arg
1               5                   10                  15

<210> SEQ ID NO 272
<211> LENGTH: 16
<212> TYPE: PRT
<213> ORGANISM: Artificial Sequence
<220> FEATURE:
<223> OTHER INFORMATION: Synthetic peptide

<400> SEQUENCE: 272
```

```
His Lys Leu Asp Thr Phe Phe Val Lys Leu Ser Leu Phe Thr Glu Arg
1               5                   10                  15

<210> SEQ ID NO 273
<211> LENGTH: 16
<212> TYPE: PRT
<213> ORGANISM: Artificial Sequence
<220> FEATURE:
<223> OTHER INFORMATION: Synthetic peptide

<400> SEQUENCE: 273

Ile Lys Leu Asp Thr Phe Phe Val Lys Leu Ser Leu Phe Thr Glu Arg
1               5                   10                  15

<210> SEQ ID NO 274
<211> LENGTH: 16
<212> TYPE: PRT
<213> ORGANISM: Artificial Sequence
<220> FEATURE:
<223> OTHER INFORMATION: Synthetic peptide

<400> SEQUENCE: 274

Leu Lys Leu Asp Thr Phe Phe Val Lys Leu Ser Leu Phe Thr Glu Arg
1               5                   10                  15

<210> SEQ ID NO 275
<211> LENGTH: 16
<212> TYPE: PRT
<213> ORGANISM: Artificial Sequence
<220> FEATURE:
<223> OTHER INFORMATION: Synthetic peptide

<400> SEQUENCE: 275

Met Lys Leu Asp Thr Phe Phe Val Lys Leu Ser Leu Phe Thr Glu Arg
1               5                   10                  15

<210> SEQ ID NO 276
<211> LENGTH: 16
<212> TYPE: PRT
<213> ORGANISM: Artificial Sequence
<220> FEATURE:
<223> OTHER INFORMATION: Synthetic peptide

<400> SEQUENCE: 276

Asn Lys Leu Asp Thr Phe Phe Val Lys Leu Ser Leu Phe Thr Glu Arg
1               5                   10                  15

<210> SEQ ID NO 277
<211> LENGTH: 16
<212> TYPE: PRT
<213> ORGANISM: Artificial Sequence
<220> FEATURE:
<223> OTHER INFORMATION: Synthetic peptide

<400> SEQUENCE: 277

Pro Lys Leu Asp Thr Phe Phe Val Lys Leu Ser Leu Phe Thr Glu Arg
1               5                   10                  15

<210> SEQ ID NO 278
<211> LENGTH: 16
<212> TYPE: PRT
<213> ORGANISM: Artificial Sequence
<220> FEATURE:
<223> OTHER INFORMATION: Synthetic peptide

<400> SEQUENCE: 278
```

Gln Lys Leu Asp Thr Phe Phe Val Lys Leu Ser Leu Phe Thr Glu Arg
1               5                   10                  15

<210> SEQ ID NO 279
<211> LENGTH: 16
<212> TYPE: PRT
<213> ORGANISM: Artificial Sequence
<220> FEATURE:
<223> OTHER INFORMATION: Synthetic peptide

<400> SEQUENCE: 279

Arg Lys Leu Asp Thr Phe Phe Val Lys Leu Ser Leu Phe Thr Glu Arg
1               5                   10                  15

<210> SEQ ID NO 280
<211> LENGTH: 16
<212> TYPE: PRT
<213> ORGANISM: Artificial Sequence
<220> FEATURE:
<223> OTHER INFORMATION: Synthetic peptide

<400> SEQUENCE: 280

Thr Lys Leu Asp Thr Phe Phe Val Lys Leu Ser Leu Phe Thr Glu Arg
1               5                   10                  15

<210> SEQ ID NO 281
<211> LENGTH: 16
<212> TYPE: PRT
<213> ORGANISM: Artificial Sequence
<220> FEATURE:
<223> OTHER INFORMATION: Synthetic peptide

<400> SEQUENCE: 281

Val Lys Leu Asp Thr Phe Phe Val Lys Leu Ser Leu Phe Thr Glu Arg
1               5                   10                  15

<210> SEQ ID NO 282
<211> LENGTH: 16
<212> TYPE: PRT
<213> ORGANISM: Artificial Sequence
<220> FEATURE:
<223> OTHER INFORMATION: Synthetic peptide

<400> SEQUENCE: 282

Lys Lys Ala Asp Thr Phe Phe Val Lys Leu Ser Leu Phe Thr Glu Arg
1               5                   10                  15

<210> SEQ ID NO 283
<211> LENGTH: 16
<212> TYPE: PRT
<213> ORGANISM: Artificial Sequence
<220> FEATURE:
<223> OTHER INFORMATION: Synthetic peptide

<400> SEQUENCE: 283

Lys Lys Cys Asp Thr Phe Phe Val Lys Leu Ser Leu Phe Thr Glu Arg
1               5                   10                  15

<210> SEQ ID NO 284
<211> LENGTH: 16
<212> TYPE: PRT
<213> ORGANISM: Artificial Sequence
<220> FEATURE:
<223> OTHER INFORMATION: Synthetic peptide

<400> SEQUENCE: 284

Lys Lys Asp Asp Thr Phe Phe Val Lys Leu Ser Leu Phe Thr Glu Arg

<210> SEQ ID NO 285
<211> LENGTH: 16
<212> TYPE: PRT
<213> ORGANISM: Artificial Sequence
<220> FEATURE:
<223> OTHER INFORMATION: Synthetic peptide

<400> SEQUENCE: 285

Lys Lys Glu Asp Thr Phe Phe Val Lys Leu Ser Leu Phe Thr Glu Arg
1               5                   10                  15

<210> SEQ ID NO 286
<211> LENGTH: 16
<212> TYPE: PRT
<213> ORGANISM: Artificial Sequence
<220> FEATURE:
<223> OTHER INFORMATION: Synthetic peptide

<400> SEQUENCE: 286

Lys Lys Phe Asp Thr Phe Phe Val Lys Leu Ser Leu Phe Thr Glu Arg
1               5                   10                  15

<210> SEQ ID NO 287
<211> LENGTH: 16
<212> TYPE: PRT
<213> ORGANISM: Artificial Sequence
<220> FEATURE:
<223> OTHER INFORMATION: Synthetic peptide

<400> SEQUENCE: 287

Lys Lys Gly Asp Thr Phe Phe Val Lys Leu Ser Leu Phe Thr Glu Arg
1               5                   10                  15

<210> SEQ ID NO 288
<211> LENGTH: 16
<212> TYPE: PRT
<213> ORGANISM: Artificial Sequence
<220> FEATURE:
<223> OTHER INFORMATION: Synthetic peptide

<400> SEQUENCE: 288

Lys Lys His Asp Thr Phe Phe Val Lys Leu Ser Leu Phe Thr Glu Arg
1               5                   10                  15

<210> SEQ ID NO 289
<211> LENGTH: 16
<212> TYPE: PRT
<213> ORGANISM: Artificial Sequence
<220> FEATURE:
<223> OTHER INFORMATION: Synthetic peptide

<400> SEQUENCE: 289

Lys Lys Ile Asp Thr Phe Phe Val Lys Leu Ser Leu Phe Thr Glu Arg
1               5                   10                  15

<210> SEQ ID NO 290
<211> LENGTH: 16
<212> TYPE: PRT
<213> ORGANISM: Artificial Sequence
<220> FEATURE:
<223> OTHER INFORMATION: Synthetic peptide

<400> SEQUENCE: 290

Lys Lys Lys Asp Thr Phe Phe Val Lys Leu Ser Leu Phe Thr Glu Arg
1               5                   10                  15

<210> SEQ ID NO 291
<211> LENGTH: 16
<212> TYPE: PRT
<213> ORGANISM: Artificial Sequence
<220> FEATURE:
<223> OTHER INFORMATION: Synthetic peptide

<400> SEQUENCE: 291

Lys Lys Met Asp Thr Phe Phe Val Lys Leu Ser Leu Phe Thr Glu Arg
1               5                   10                  15

<210> SEQ ID NO 292
<211> LENGTH: 16
<212> TYPE: PRT
<213> ORGANISM: Artificial Sequence
<220> FEATURE:
<223> OTHER INFORMATION: Synthetic peptide

<400> SEQUENCE: 292

Lys Lys Asn Asp Thr Phe Phe Val Lys Leu Ser Leu Phe Thr Glu Arg
1               5                   10                  15

<210> SEQ ID NO 293
<211> LENGTH: 16
<212> TYPE: PRT
<213> ORGANISM: Artificial Sequence
<220> FEATURE:
<223> OTHER INFORMATION: Synthetic peptide

<400> SEQUENCE: 293

Lys Lys Gln Asp Thr Phe Phe Val Lys Leu Ser Leu Phe Thr Glu Arg
1               5                   10                  15

<210> SEQ ID NO 294
<211> LENGTH: 16
<212> TYPE: PRT
<213> ORGANISM: Artificial Sequence
<220> FEATURE:
<223> OTHER INFORMATION: Synthetic peptide

<400> SEQUENCE: 294

Lys Lys Arg Asp Thr Phe Phe Val Lys Leu Ser Leu Phe Thr Glu Arg
1               5                   10                  15

<210> SEQ ID NO 295
<211> LENGTH: 16
<212> TYPE: PRT
<213> ORGANISM: Artificial Sequence
<220> FEATURE:
<223> OTHER INFORMATION: Synthetic peptide

<400> SEQUENCE: 295

Lys Lys Ser Asp Thr Phe Phe Val Lys Leu Ser Leu Phe Thr Glu Arg
1               5                   10                  15

<210> SEQ ID NO 296
<211> LENGTH: 16
<212> TYPE: PRT
<213> ORGANISM: Artificial Sequence
<220> FEATURE:
<223> OTHER INFORMATION: Synthetic peptide

<400> SEQUENCE: 296

Lys Lys Thr Asp Thr Phe Phe Val Lys Leu Ser Leu Phe Thr Glu Arg
1               5                   10                  15

```
<210> SEQ ID NO 297
<211> LENGTH: 16
<212> TYPE: PRT
<213> ORGANISM: Artificial Sequence
<220> FEATURE:
<223> OTHER INFORMATION: Synthetic peptide

<400> SEQUENCE: 297

Lys Lys Val Asp Thr Phe Phe Val Lys Leu Ser Leu Phe Thr Glu Arg
1               5                   10                  15

<210> SEQ ID NO 298
<211> LENGTH: 16
<212> TYPE: PRT
<213> ORGANISM: Artificial Sequence
<220> FEATURE:
<223> OTHER INFORMATION: Synthetic peptide

<400> SEQUENCE: 298

Lys Lys Leu Ala Thr Phe Phe Val Lys Leu Ser Leu Phe Thr Glu Arg
1               5                   10                  15

<210> SEQ ID NO 299
<211> LENGTH: 16
<212> TYPE: PRT
<213> ORGANISM: Artificial Sequence
<220> FEATURE:
<223> OTHER INFORMATION: Synthetic peptide

<400> SEQUENCE: 299

Lys Lys Leu Glu Thr Phe Phe Val Lys Leu Ser Leu Phe Thr Glu Arg
1               5                   10                  15

<210> SEQ ID NO 300
<211> LENGTH: 16
<212> TYPE: PRT
<213> ORGANISM: Artificial Sequence
<220> FEATURE:
<223> OTHER INFORMATION: Synthetic peptide

<400> SEQUENCE: 300

Lys Lys Leu Ile Thr Phe Phe Val Lys Leu Ser Leu Phe Thr Glu Arg
1               5                   10                  15

<210> SEQ ID NO 301
<211> LENGTH: 16
<212> TYPE: PRT
<213> ORGANISM: Artificial Sequence
<220> FEATURE:
<223> OTHER INFORMATION: Synthetic peptide

<400> SEQUENCE: 301

Lys Lys Leu Val Thr Phe Phe Val Lys Leu Ser Leu Phe Thr Glu Arg
1               5                   10                  15

<210> SEQ ID NO 302
<211> LENGTH: 16
<212> TYPE: PRT
<213> ORGANISM: Artificial Sequence
<220> FEATURE:
<223> OTHER INFORMATION: Synthetic peptide

<400> SEQUENCE: 302

Lys Lys Leu Trp Thr Phe Phe Val Lys Leu Ser Leu Phe Thr Glu Arg
1               5                   10                  15
```

```
<210> SEQ ID NO 303
<211> LENGTH: 16
<212> TYPE: PRT
<213> ORGANISM: Artificial Sequence
<220> FEATURE:
<223> OTHER INFORMATION: Synthetic peptide

<400> SEQUENCE: 303

Lys Lys Leu Tyr Thr Phe Phe Val Lys Leu Ser Leu Phe Thr Glu Arg
1               5                   10                  15

<210> SEQ ID NO 304
<211> LENGTH: 16
<212> TYPE: PRT
<213> ORGANISM: Artificial Sequence
<220> FEATURE:
<223> OTHER INFORMATION: Synthetic peptide

<400> SEQUENCE: 304

Lys Lys Leu Asp Cys Phe Phe Val Lys Leu Ser Leu Phe Thr Glu Arg
1               5                   10                  15

<210> SEQ ID NO 305
<211> LENGTH: 16
<212> TYPE: PRT
<213> ORGANISM: Artificial Sequence
<220> FEATURE:
<223> OTHER INFORMATION: Synthetic peptide

<400> SEQUENCE: 305

Lys Lys Leu Asp Met Phe Phe Val Lys Leu Ser Leu Phe Thr Glu Arg
1               5                   10                  15

<210> SEQ ID NO 306
<211> LENGTH: 16
<212> TYPE: PRT
<213> ORGANISM: Artificial Sequence
<220> FEATURE:
<223> OTHER INFORMATION: Synthetic peptide

<400> SEQUENCE: 306

Lys Lys Leu Asp Asn Phe Phe Val Lys Leu Ser Leu Phe Thr Glu Arg
1               5                   10                  15

<210> SEQ ID NO 307
<211> LENGTH: 16
<212> TYPE: PRT
<213> ORGANISM: Artificial Sequence
<220> FEATURE:
<223> OTHER INFORMATION: Synthetic peptide

<400> SEQUENCE: 307

Lys Lys Leu Asp Pro Phe Phe Val Lys Leu Ser Leu Phe Thr Glu Arg
1               5                   10                  15

<210> SEQ ID NO 308
<211> LENGTH: 16
<212> TYPE: PRT
<213> ORGANISM: Artificial Sequence
<220> FEATURE:
<223> OTHER INFORMATION: Synthetic peptide

<400> SEQUENCE: 308

Lys Lys Leu Asp Gln Phe Phe Val Lys Leu Ser Leu Phe Thr Glu Arg
1               5                   10                  15

<210> SEQ ID NO 309
```

```
<211> LENGTH: 16
<212> TYPE: PRT
<213> ORGANISM: Artificial Sequence
<220> FEATURE:
<223> OTHER INFORMATION: Synthetic peptide

<400> SEQUENCE: 309

Lys Lys Leu Asp Arg Phe Phe Val Lys Leu Ser Leu Phe Thr Glu Arg
1               5                   10                  15

<210> SEQ ID NO 310
<211> LENGTH: 16
<212> TYPE: PRT
<213> ORGANISM: Artificial Sequence
<220> FEATURE:
<223> OTHER INFORMATION: Synthetic peptide

<400> SEQUENCE: 310

Lys Lys Leu Asp Ser Phe Phe Val Lys Leu Ser Leu Phe Thr Glu Arg
1               5                   10                  15

<210> SEQ ID NO 311
<211> LENGTH: 16
<212> TYPE: PRT
<213> ORGANISM: Artificial Sequence
<220> FEATURE:
<223> OTHER INFORMATION: Synthetic peptide

<400> SEQUENCE: 311

Lys Lys Leu Asp Trp Phe Phe Val Lys Leu Ser Leu Phe Thr Glu Arg
1               5                   10                  15

<210> SEQ ID NO 312
<211> LENGTH: 16
<212> TYPE: PRT
<213> ORGANISM: Artificial Sequence
<220> FEATURE:
<223> OTHER INFORMATION: Synthetic peptide

<400> SEQUENCE: 312

Lys Lys Leu Asp Tyr Phe Phe Val Lys Leu Ser Leu Phe Thr Glu Arg
1               5                   10                  15

<210> SEQ ID NO 313
<211> LENGTH: 16
<212> TYPE: PRT
<213> ORGANISM: Artificial Sequence
<220> FEATURE:
<223> OTHER INFORMATION: Synthetic peptide

<400> SEQUENCE: 313

Lys Lys Leu Asp Thr Ala Phe Val Lys Leu Ser Leu Phe Thr Glu Arg
1               5                   10                  15

<210> SEQ ID NO 314
<211> LENGTH: 16
<212> TYPE: PRT
<213> ORGANISM: Artificial Sequence
<220> FEATURE:
<223> OTHER INFORMATION: Synthetic peptide

<400> SEQUENCE: 314

Lys Lys Leu Asp Thr Ile Phe Val Lys Leu Ser Leu Phe Thr Glu Arg
1               5                   10                  15

<210> SEQ ID NO 315
<211> LENGTH: 16
```

```
<212> TYPE: PRT
<213> ORGANISM: Artificial Sequence
<220> FEATURE:
<223> OTHER INFORMATION: Synthetic peptide

<400> SEQUENCE: 315

Lys Lys Leu Asp Thr Met Phe Val Lys Leu Ser Leu Phe Thr Glu Arg
1               5                   10                  15

<210> SEQ ID NO 316
<211> LENGTH: 16
<212> TYPE: PRT
<213> ORGANISM: Artificial Sequence
<220> FEATURE:
<223> OTHER INFORMATION: Synthetic peptide

<400> SEQUENCE: 316

Lys Lys Leu Asp Thr Asn Phe Val Lys Leu Ser Leu Phe Thr Glu Arg
1               5                   10                  15

<210> SEQ ID NO 317
<211> LENGTH: 16
<212> TYPE: PRT
<213> ORGANISM: Artificial Sequence
<220> FEATURE:
<223> OTHER INFORMATION: Synthetic peptide

<400> SEQUENCE: 317

Lys Lys Leu Asp Thr Pro Phe Val Lys Leu Ser Leu Phe Thr Glu Arg
1               5                   10                  15

<210> SEQ ID NO 318
<211> LENGTH: 16
<212> TYPE: PRT
<213> ORGANISM: Artificial Sequence
<220> FEATURE:
<223> OTHER INFORMATION: Synthetic peptide

<400> SEQUENCE: 318

Lys Lys Leu Asp Thr Thr Phe Val Lys Leu Ser Leu Phe Thr Glu Arg
1               5                   10                  15

<210> SEQ ID NO 319
<211> LENGTH: 16
<212> TYPE: PRT
<213> ORGANISM: Artificial Sequence
<220> FEATURE:
<223> OTHER INFORMATION: Synthetic peptide

<400> SEQUENCE: 319

Lys Lys Leu Asp Thr Val Phe Val Lys Leu Ser Leu Phe Thr Glu Arg
1               5                   10                  15

<210> SEQ ID NO 320
<211> LENGTH: 16
<212> TYPE: PRT
<213> ORGANISM: Artificial Sequence
<220> FEATURE:
<223> OTHER INFORMATION: Synthetic peptide

<400> SEQUENCE: 320

Lys Lys Leu Asp Thr Phe Leu Val Lys Leu Ser Leu Phe Thr Glu Arg
1               5                   10                  15

<210> SEQ ID NO 321
<211> LENGTH: 16
<212> TYPE: PRT
```

<213> ORGANISM: Artificial Sequence
<220> FEATURE:
<223> OTHER INFORMATION: Synthetic peptide

<400> SEQUENCE: 321

Lys Lys Leu Asp Thr Phe Met Val Lys Leu Ser Leu Phe Thr Glu Arg
1               5                   10                  15

<210> SEQ ID NO 322
<211> LENGTH: 16
<212> TYPE: PRT
<213> ORGANISM: Artificial Sequence
<220> FEATURE:
<223> OTHER INFORMATION: Synthetic peptide

<400> SEQUENCE: 322

Lys Lys Leu Asp Thr Phe Gln Val Lys Leu Ser Leu Phe Thr Glu Arg
1               5                   10                  15

<210> SEQ ID NO 323
<211> LENGTH: 16
<212> TYPE: PRT
<213> ORGANISM: Artificial Sequence
<220> FEATURE:
<223> OTHER INFORMATION: Synthetic peptide

<400> SEQUENCE: 323

Lys Lys Leu Asp Thr Phe Ser Val Lys Leu Ser Leu Phe Thr Glu Arg
1               5                   10                  15

<210> SEQ ID NO 324
<211> LENGTH: 16
<212> TYPE: PRT
<213> ORGANISM: Artificial Sequence
<220> FEATURE:
<223> OTHER INFORMATION: Synthetic peptide

<400> SEQUENCE: 324

Lys Lys Leu Asp Thr Phe Thr Val Lys Leu Ser Leu Phe Thr Glu Arg
1               5                   10                  15

<210> SEQ ID NO 325
<211> LENGTH: 16
<212> TYPE: PRT
<213> ORGANISM: Artificial Sequence
<220> FEATURE:
<223> OTHER INFORMATION: Synthetic peptide

<400> SEQUENCE: 325

Lys Lys Leu Asp Thr Phe Val Val Lys Leu Ser Leu Phe Thr Glu Arg
1               5                   10                  15

<210> SEQ ID NO 326
<211> LENGTH: 16
<212> TYPE: PRT
<213> ORGANISM: Artificial Sequence
<220> FEATURE:
<223> OTHER INFORMATION: Synthetic peptide

<400> SEQUENCE: 326

Lys Lys Leu Asp Thr Phe Phe Phe Lys Leu Ser Leu Phe Thr Glu Arg
1               5                   10                  15

<210> SEQ ID NO 327
<211> LENGTH: 16
<212> TYPE: PRT
<213> ORGANISM: Artificial Sequence
<220> FEATURE:
<223> OTHER INFORMATION: Synthetic peptide

<400> SEQUENCE: 327

Lys Lys Leu Asp Thr Phe Phe Gly Lys Leu Ser Leu Phe Thr Glu Arg
1               5                   10                  15

<210> SEQ ID NO 328
<211> LENGTH: 16
<212> TYPE: PRT
<213> ORGANISM: Artificial Sequence
<220> FEATURE:
<223> OTHER INFORMATION: Synthetic peptide

<400> SEQUENCE: 328

Lys Lys Leu Asp Thr Phe Phe Leu Lys Leu Ser Leu Phe Thr Glu Arg
1               5                   10                  15

<210> SEQ ID NO 329
<211> LENGTH: 16
<212> TYPE: PRT
<213> ORGANISM: Artificial Sequence
<220> FEATURE:
<223> OTHER INFORMATION: Synthetic peptide

<400> SEQUENCE: 329

Lys Lys Leu Asp Thr Phe Phe Pro Lys Leu Ser Leu Phe Thr Glu Arg
1               5                   10                  15

<210> SEQ ID NO 330
<211> LENGTH: 16
<212> TYPE: PRT
<213> ORGANISM: Artificial Sequence
<220> FEATURE:
<223> OTHER INFORMATION: Synthetic peptide

<400> SEQUENCE: 330

Lys Lys Leu Asp Thr Phe Phe Arg Lys Leu Ser Leu Phe Thr Glu Arg
1               5                   10                  15

<210> SEQ ID NO 331
<211> LENGTH: 16
<212> TYPE: PRT
<213> ORGANISM: Artificial Sequence
<220> FEATURE:
<223> OTHER INFORMATION: Synthetic peptide

<400> SEQUENCE: 331

Lys Lys Leu Asp Thr Phe Phe Val Arg Leu Ser Leu Phe Thr Glu Arg
1               5                   10                  15

<210> SEQ ID NO 332
<211> LENGTH: 16
<212> TYPE: PRT
<213> ORGANISM: Artificial Sequence
<220> FEATURE:
<223> OTHER INFORMATION: Synthetic peptide

<400> SEQUENCE: 332

Lys Lys Leu Asp Thr Phe Phe Val Lys Ala Ser Leu Phe Thr Glu Arg
1               5                   10                  15

<210> SEQ ID NO 333
<211> LENGTH: 16
<212> TYPE: PRT
<213> ORGANISM: Artificial Sequence
<220> FEATURE:

```
<223> OTHER INFORMATION: Synthetic peptide

<400> SEQUENCE: 333

Lys Lys Leu Asp Thr Phe Phe Val Lys Phe Ser Leu Phe Thr Glu Arg
1               5                   10                  15

<210> SEQ ID NO 334
<211> LENGTH: 16
<212> TYPE: PRT
<213> ORGANISM: Artificial Sequence
<220> FEATURE:
<223> OTHER INFORMATION: Synthetic peptide

<400> SEQUENCE: 334

Lys Lys Leu Asp Thr Phe Phe Val Lys Gly Ser Leu Phe Thr Glu Arg
1               5                   10                  15

<210> SEQ ID NO 335
<211> LENGTH: 16
<212> TYPE: PRT
<213> ORGANISM: Artificial Sequence
<220> FEATURE:
<223> OTHER INFORMATION: Synthetic peptide

<400> SEQUENCE: 335

Lys Lys Leu Asp Thr Phe Phe Val Lys Ile Ser Leu Phe Thr Glu Arg
1               5                   10                  15

<210> SEQ ID NO 336
<211> LENGTH: 16
<212> TYPE: PRT
<213> ORGANISM: Artificial Sequence
<220> FEATURE:
<223> OTHER INFORMATION: Synthetic peptide

<400> SEQUENCE: 336

Lys Lys Leu Asp Thr Phe Phe Val Lys Met Ser Leu Phe Thr Glu Arg
1               5                   10                  15

<210> SEQ ID NO 337
<211> LENGTH: 16
<212> TYPE: PRT
<213> ORGANISM: Artificial Sequence
<220> FEATURE:
<223> OTHER INFORMATION: Synthetic peptide

<400> SEQUENCE: 337

Lys Lys Leu Asp Thr Phe Phe Val Lys Asn Ser Leu Phe Thr Glu Arg
1               5                   10                  15

<210> SEQ ID NO 338
<211> LENGTH: 16
<212> TYPE: PRT
<213> ORGANISM: Artificial Sequence
<220> FEATURE:
<223> OTHER INFORMATION: Synthetic peptide

<400> SEQUENCE: 338

Lys Lys Leu Asp Thr Phe Phe Val Lys Pro Ser Leu Phe Thr Glu Arg
1               5                   10                  15

<210> SEQ ID NO 339
<211> LENGTH: 16
<212> TYPE: PRT
<213> ORGANISM: Artificial Sequence
<220> FEATURE:
<223> OTHER INFORMATION: Synthetic peptide
```

<400> SEQUENCE: 339

Lys Lys Leu Asp Thr Phe Phe Val Lys Gln Ser Leu Phe Thr Glu Arg
1               5                   10                  15

<210> SEQ ID NO 340
<211> LENGTH: 16
<212> TYPE: PRT
<213> ORGANISM: Artificial Sequence
<220> FEATURE:
<223> OTHER INFORMATION: Synthetic peptide

<400> SEQUENCE: 340

Lys Lys Leu Asp Thr Phe Phe Val Lys Arg Ser Leu Phe Thr Glu Arg
1               5                   10                  15

<210> SEQ ID NO 341
<211> LENGTH: 16
<212> TYPE: PRT
<213> ORGANISM: Artificial Sequence
<220> FEATURE:
<223> OTHER INFORMATION: Synthetic peptide

<400> SEQUENCE: 341

Lys Lys Leu Asp Thr Phe Phe Val Lys Ser Ser Leu Phe Thr Glu Arg
1               5                   10                  15

<210> SEQ ID NO 342
<211> LENGTH: 16
<212> TYPE: PRT
<213> ORGANISM: Artificial Sequence
<220> FEATURE:
<223> OTHER INFORMATION: Synthetic peptide

<400> SEQUENCE: 342

Lys Lys Leu Asp Thr Phe Phe Val Lys Thr Ser Leu Phe Thr Glu Arg
1               5                   10                  15

<210> SEQ ID NO 343
<211> LENGTH: 16
<212> TYPE: PRT
<213> ORGANISM: Artificial Sequence
<220> FEATURE:
<223> OTHER INFORMATION: Synthetic peptide

<400> SEQUENCE: 343

Lys Lys Leu Asp Thr Phe Phe Val Lys Val Ser Leu Phe Thr Glu Arg
1               5                   10                  15

<210> SEQ ID NO 344
<211> LENGTH: 16
<212> TYPE: PRT
<213> ORGANISM: Artificial Sequence
<220> FEATURE:
<223> OTHER INFORMATION: Synthetic peptide

<400> SEQUENCE: 344

Lys Lys Leu Asp Thr Phe Phe Val Lys Tyr Ser Leu Phe Thr Glu Arg
1               5                   10                  15

<210> SEQ ID NO 345
<211> LENGTH: 16
<212> TYPE: PRT
<213> ORGANISM: Artificial Sequence
<220> FEATURE:
<223> OTHER INFORMATION: Synthetic peptide

```
<400> SEQUENCE: 345

Lys Lys Leu Asp Thr Phe Phe Val Lys Leu His Leu Phe Thr Glu Arg
1               5                   10                  15

<210> SEQ ID NO 346
<211> LENGTH: 16
<212> TYPE: PRT
<213> ORGANISM: Artificial Sequence
<220> FEATURE:
<223> OTHER INFORMATION: Synthetic peptide

<400> SEQUENCE: 346

Lys Lys Leu Asp Thr Phe Phe Val Lys Leu Met Leu Phe Thr Glu Arg
1               5                   10                  15

<210> SEQ ID NO 347
<211> LENGTH: 16
<212> TYPE: PRT
<213> ORGANISM: Artificial Sequence
<220> FEATURE:
<223> OTHER INFORMATION: Synthetic peptide

<400> SEQUENCE: 347

Lys Lys Leu Asp Thr Phe Phe Val Lys Leu Asn Leu Phe Thr Glu Arg
1               5                   10                  15

<210> SEQ ID NO 348
<211> LENGTH: 16
<212> TYPE: PRT
<213> ORGANISM: Artificial Sequence
<220> FEATURE:
<223> OTHER INFORMATION: Synthetic peptide

<400> SEQUENCE: 348

Lys Lys Leu Asp Thr Phe Phe Val Lys Leu Gln Leu Phe Thr Glu Arg
1               5                   10                  15

<210> SEQ ID NO 349
<211> LENGTH: 16
<212> TYPE: PRT
<213> ORGANISM: Artificial Sequence
<220> FEATURE:
<223> OTHER INFORMATION: Synthetic peptide

<400> SEQUENCE: 349

Lys Lys Leu Asp Thr Phe Phe Val Lys Leu Thr Leu Phe Thr Glu Arg
1               5                   10                  15

<210> SEQ ID NO 350
<211> LENGTH: 16
<212> TYPE: PRT
<213> ORGANISM: Artificial Sequence
<220> FEATURE:
<223> OTHER INFORMATION: Synthetic peptide

<400> SEQUENCE: 350

Lys Lys Leu Asp Thr Phe Phe Val Lys Leu Ser Ala Phe Thr Glu Arg
1               5                   10                  15

<210> SEQ ID NO 351
<211> LENGTH: 16
<212> TYPE: PRT
<213> ORGANISM: Artificial Sequence
<220> FEATURE:
<223> OTHER INFORMATION: Synthetic peptide

<400> SEQUENCE: 351
```

Lys Lys Leu Asp Thr Phe Phe Val Lys Leu Ser His Phe Thr Glu Arg
1               5                   10                  15

<210> SEQ ID NO 352
<211> LENGTH: 16
<212> TYPE: PRT
<213> ORGANISM: Artificial Sequence
<220> FEATURE:
<223> OTHER INFORMATION: Synthetic peptide

<400> SEQUENCE: 352

Lys Lys Leu Asp Thr Phe Phe Val Lys Leu Ser Ile Phe Thr Glu Arg
1               5                   10                  15

<210> SEQ ID NO 353
<211> LENGTH: 16
<212> TYPE: PRT
<213> ORGANISM: Artificial Sequence
<220> FEATURE:
<223> OTHER INFORMATION: Synthetic peptide

<400> SEQUENCE: 353

Lys Lys Leu Asp Thr Phe Phe Val Lys Leu Ser Met Phe Thr Glu Arg
1               5                   10                  15

<210> SEQ ID NO 354
<211> LENGTH: 16
<212> TYPE: PRT
<213> ORGANISM: Artificial Sequence
<220> FEATURE:
<223> OTHER INFORMATION: Synthetic peptide

<400> SEQUENCE: 354

Lys Lys Leu Asp Thr Phe Phe Val Lys Leu Ser Asn Phe Thr Glu Arg
1               5                   10                  15

<210> SEQ ID NO 355
<211> LENGTH: 16
<212> TYPE: PRT
<213> ORGANISM: Artificial Sequence
<220> FEATURE:
<223> OTHER INFORMATION: Synthetic peptide

<400> SEQUENCE: 355

Lys Lys Leu Asp Thr Phe Phe Val Lys Leu Ser Gln Phe Thr Glu Arg
1               5                   10                  15

<210> SEQ ID NO 356
<211> LENGTH: 16
<212> TYPE: PRT
<213> ORGANISM: Artificial Sequence
<220> FEATURE:
<223> OTHER INFORMATION: Synthetic peptide

<400> SEQUENCE: 356

Lys Lys Leu Asp Thr Phe Phe Val Lys Leu Ser Arg Phe Thr Glu Arg
1               5                   10                  15

<210> SEQ ID NO 357
<211> LENGTH: 16
<212> TYPE: PRT
<213> ORGANISM: Artificial Sequence
<220> FEATURE:
<223> OTHER INFORMATION: Synthetic peptide

<400> SEQUENCE: 357

Lys Lys Leu Asp Thr Phe Phe Val Lys Leu Ser Ser Phe Thr Glu Arg
1               5                   10                  15

<210> SEQ ID NO 358
<211> LENGTH: 16
<212> TYPE: PRT
<213> ORGANISM: Artificial Sequence
<220> FEATURE:
<223> OTHER INFORMATION: Synthetic peptide

<400> SEQUENCE: 358

Lys Lys Leu Asp Thr Phe Phe Val Lys Leu Ser Thr Phe Thr Glu Arg
1               5                   10                  15

<210> SEQ ID NO 359
<211> LENGTH: 16
<212> TYPE: PRT
<213> ORGANISM: Artificial Sequence
<220> FEATURE:
<223> OTHER INFORMATION: Synthetic peptide

<400> SEQUENCE: 359

Lys Lys Leu Asp Thr Phe Phe Val Lys Leu Ser Val Phe Thr Glu Arg
1               5                   10                  15

<210> SEQ ID NO 360
<211> LENGTH: 16
<212> TYPE: PRT
<213> ORGANISM: Artificial Sequence
<220> FEATURE:
<223> OTHER INFORMATION: Synthetic peptide

<400> SEQUENCE: 360

Lys Lys Leu Asp Thr Phe Phe Val Lys Leu Ser Trp Phe Thr Glu Arg
1               5                   10                  15

<210> SEQ ID NO 361
<211> LENGTH: 16
<212> TYPE: PRT
<213> ORGANISM: Artificial Sequence
<220> FEATURE:
<223> OTHER INFORMATION: Synthetic peptide

<400> SEQUENCE: 361

Lys Lys Leu Asp Thr Phe Phe Val Lys Leu Ser Leu Ala Thr Glu Arg
1               5                   10                  15

<210> SEQ ID NO 362
<211> LENGTH: 16
<212> TYPE: PRT
<213> ORGANISM: Artificial Sequence
<220> FEATURE:
<223> OTHER INFORMATION: Synthetic peptide

<400> SEQUENCE: 362

Lys Lys Leu Asp Thr Phe Phe Val Lys Leu Ser Leu Cys Thr Glu Arg
1               5                   10                  15

<210> SEQ ID NO 363
<211> LENGTH: 16
<212> TYPE: PRT
<213> ORGANISM: Artificial Sequence
<220> FEATURE:
<223> OTHER INFORMATION: Synthetic peptide

<400> SEQUENCE: 363

Lys Lys Leu Asp Thr Phe Phe Val Lys Leu Ser Leu Gly Thr Glu Arg

```
1               5               10              15
```

<210> SEQ ID NO 364
<211> LENGTH: 16
<212> TYPE: PRT
<213> ORGANISM: Artificial Sequence
<220> FEATURE:
<223> OTHER INFORMATION: Synthetic peptide

<400> SEQUENCE: 364

```
Lys Lys Leu Asp Thr Phe Phe Val Lys Leu Ser Leu His Thr Glu Arg
1               5                   10                  15
```

<210> SEQ ID NO 365
<211> LENGTH: 16
<212> TYPE: PRT
<213> ORGANISM: Artificial Sequence
<220> FEATURE:
<223> OTHER INFORMATION: Synthetic peptide

<400> SEQUENCE: 365

```
Lys Lys Leu Asp Thr Phe Phe Val Lys Leu Ser Leu Ile Thr Glu Arg
1               5                   10                  15
```

<210> SEQ ID NO 366
<211> LENGTH: 16
<212> TYPE: PRT
<213> ORGANISM: Artificial Sequence
<220> FEATURE:
<223> OTHER INFORMATION: Synthetic peptide

<400> SEQUENCE: 366

```
Lys Lys Leu Asp Thr Phe Phe Val Lys Leu Ser Leu Leu Thr Glu Arg
1               5                   10                  15
```

<210> SEQ ID NO 367
<211> LENGTH: 16
<212> TYPE: PRT
<213> ORGANISM: Artificial Sequence
<220> FEATURE:
<223> OTHER INFORMATION: Synthetic peptide

<400> SEQUENCE: 367

```
Lys Lys Leu Asp Thr Phe Phe Val Lys Leu Ser Leu Met Thr Glu Arg
1               5                   10                  15
```

<210> SEQ ID NO 368
<211> LENGTH: 16
<212> TYPE: PRT
<213> ORGANISM: Artificial Sequence
<220> FEATURE:
<223> OTHER INFORMATION: Synthetic peptide

<400> SEQUENCE: 368

```
Lys Lys Leu Asp Thr Phe Phe Val Lys Leu Ser Leu Asn Thr Glu Arg
1               5                   10                  15
```

<210> SEQ ID NO 369
<211> LENGTH: 16
<212> TYPE: PRT
<213> ORGANISM: Artificial Sequence
<220> FEATURE:
<223> OTHER INFORMATION: Synthetic peptide

<400> SEQUENCE: 369

```
Lys Lys Leu Asp Thr Phe Phe Val Lys Leu Ser Leu Pro Thr Glu Arg
1               5                   10                  15
```

<210> SEQ ID NO 370
<211> LENGTH: 16
<212> TYPE: PRT
<213> ORGANISM: Artificial Sequence
<220> FEATURE:
<223> OTHER INFORMATION: Synthetic peptide

<400> SEQUENCE: 370

Lys Lys Leu Asp Thr Phe Phe Val Lys Leu Ser Leu Gln Thr Glu Arg
1               5                   10                  15

<210> SEQ ID NO 371
<211> LENGTH: 16
<212> TYPE: PRT
<213> ORGANISM: Artificial Sequence
<220> FEATURE:
<223> OTHER INFORMATION: Synthetic peptide

<400> SEQUENCE: 371

Lys Lys Leu Asp Thr Phe Phe Val Lys Leu Ser Leu Arg Thr Glu Arg
1               5                   10                  15

<210> SEQ ID NO 372
<211> LENGTH: 16
<212> TYPE: PRT
<213> ORGANISM: Artificial Sequence
<220> FEATURE:
<223> OTHER INFORMATION: Synthetic peptide

<400> SEQUENCE: 372

Lys Lys Leu Asp Thr Phe Phe Val Lys Leu Ser Leu Ser Thr Glu Arg
1               5                   10                  15

<210> SEQ ID NO 373
<211> LENGTH: 16
<212> TYPE: PRT
<213> ORGANISM: Artificial Sequence
<220> FEATURE:
<223> OTHER INFORMATION: Synthetic peptide

<400> SEQUENCE: 373

Lys Lys Leu Asp Thr Phe Phe Val Lys Leu Ser Leu Thr Thr Glu Arg
1               5                   10                  15

<210> SEQ ID NO 374
<211> LENGTH: 16
<212> TYPE: PRT
<213> ORGANISM: Artificial Sequence
<220> FEATURE:
<223> OTHER INFORMATION: Synthetic peptide

<400> SEQUENCE: 374

Lys Lys Leu Asp Thr Phe Phe Val Lys Leu Ser Leu Val Thr Glu Arg
1               5                   10                  15

<210> SEQ ID NO 375
<211> LENGTH: 16
<212> TYPE: PRT
<213> ORGANISM: Artificial Sequence
<220> FEATURE:
<223> OTHER INFORMATION: Synthetic peptide

<400> SEQUENCE: 375

Lys Lys Leu Asp Thr Phe Phe Val Lys Leu Ser Leu Trp Thr Glu Arg
1               5                   10                  15

```
<210> SEQ ID NO 376
<211> LENGTH: 16
<212> TYPE: PRT
<213> ORGANISM: Artificial Sequence
<220> FEATURE:
<223> OTHER INFORMATION: Synthetic peptide

<400> SEQUENCE: 376

Lys Lys Leu Asp Thr Phe Phe Val Lys Leu Ser Leu Phe Phe Glu Arg
1               5                   10                  15

<210> SEQ ID NO 377
<211> LENGTH: 16
<212> TYPE: PRT
<213> ORGANISM: Artificial Sequence
<220> FEATURE:
<223> OTHER INFORMATION: Synthetic peptide

<400> SEQUENCE: 377

Lys Lys Leu Asp Thr Phe Phe Val Lys Leu Ser Leu Phe Gly Glu Arg
1               5                   10                  15

<210> SEQ ID NO 378
<211> LENGTH: 16
<212> TYPE: PRT
<213> ORGANISM: Artificial Sequence
<220> FEATURE:
<223> OTHER INFORMATION: Synthetic peptide

<400> SEQUENCE: 378

Lys Lys Leu Asp Thr Phe Phe Val Lys Leu Ser Leu Phe His Glu Arg
1               5                   10                  15

<210> SEQ ID NO 379
<211> LENGTH: 16
<212> TYPE: PRT
<213> ORGANISM: Artificial Sequence
<220> FEATURE:
<223> OTHER INFORMATION: Synthetic peptide

<400> SEQUENCE: 379

Lys Lys Leu Asp Thr Phe Phe Val Lys Leu Ser Leu Phe Ile Glu Arg
1               5                   10                  15

<210> SEQ ID NO 380
<211> LENGTH: 16
<212> TYPE: PRT
<213> ORGANISM: Artificial Sequence
<220> FEATURE:
<223> OTHER INFORMATION: Synthetic peptide

<400> SEQUENCE: 380

Lys Lys Leu Asp Thr Phe Phe Val Lys Leu Ser Leu Phe Leu Glu Arg
1               5                   10                  15

<210> SEQ ID NO 381
<211> LENGTH: 16
<212> TYPE: PRT
<213> ORGANISM: Artificial Sequence
<220> FEATURE:
<223> OTHER INFORMATION: Synthetic peptide

<400> SEQUENCE: 381

Lys Lys Leu Asp Thr Phe Phe Val Lys Leu Ser Leu Phe Met Glu Arg
1               5                   10                  15
```

-continued

```
<210> SEQ ID NO 382
<211> LENGTH: 16
<212> TYPE: PRT
<213> ORGANISM: Artificial Sequence
<220> FEATURE:
<223> OTHER INFORMATION: Synthetic peptide

<400> SEQUENCE: 382

Lys Lys Leu Asp Thr Phe Phe Val Lys Leu Ser Leu Phe Asn Glu Arg
1               5                   10                  15

<210> SEQ ID NO 383
<211> LENGTH: 16
<212> TYPE: PRT
<213> ORGANISM: Artificial Sequence
<220> FEATURE:
<223> OTHER INFORMATION: Synthetic peptide

<400> SEQUENCE: 383

Lys Lys Leu Asp Thr Phe Phe Val Lys Leu Ser Leu Phe Pro Glu Arg
1               5                   10                  15

<210> SEQ ID NO 384
<211> LENGTH: 16
<212> TYPE: PRT
<213> ORGANISM: Artificial Sequence
<220> FEATURE:
<223> OTHER INFORMATION: Synthetic peptide

<400> SEQUENCE: 384

Lys Lys Leu Asp Thr Phe Phe Val Lys Leu Ser Leu Phe Ser Glu Arg
1               5                   10                  15

<210> SEQ ID NO 385
<211> LENGTH: 16
<212> TYPE: PRT
<213> ORGANISM: Artificial Sequence
<220> FEATURE:
<223> OTHER INFORMATION: Synthetic peptide

<400> SEQUENCE: 385

Lys Lys Leu Asp Thr Phe Phe Val Lys Leu Ser Leu Phe Val Glu Arg
1               5                   10                  15

<210> SEQ ID NO 386
<211> LENGTH: 16
<212> TYPE: PRT
<213> ORGANISM: Artificial Sequence
<220> FEATURE:
<223> OTHER INFORMATION: Synthetic peptide

<400> SEQUENCE: 386

Lys Lys Leu Asp Thr Phe Phe Val Lys Leu Ser Leu Phe Trp Glu Arg
1               5                   10                  15

<210> SEQ ID NO 387
<211> LENGTH: 16
<212> TYPE: PRT
<213> ORGANISM: Artificial Sequence
<220> FEATURE:
<223> OTHER INFORMATION: Synthetic peptide

<400> SEQUENCE: 387

Lys Lys Leu Asp Thr Phe Phe Val Lys Leu Ser Leu Phe Thr Asp Arg
1               5                   10                  15

<210> SEQ ID NO 388
```

```
<211> LENGTH: 16
<212> TYPE: PRT
<213> ORGANISM: Artificial Sequence
<220> FEATURE:
<223> OTHER INFORMATION: Synthetic peptide

<400> SEQUENCE: 388

Lys Lys Leu Asp Thr Phe Phe Val Lys Leu Ser Leu Phe Thr Glu Phe
1               5                   10                  15

<210> SEQ ID NO 389
<211> LENGTH: 16
<212> TYPE: PRT
<213> ORGANISM: Artificial Sequence
<220> FEATURE:
<223> OTHER INFORMATION: Synthetic peptide

<400> SEQUENCE: 389

Lys Lys Leu Asp Thr Phe Phe Val Lys Leu Ser Leu Phe Thr Glu Lys
1               5                   10                  15

<210> SEQ ID NO 390
<211> LENGTH: 16
<212> TYPE: PRT
<213> ORGANISM: Artificial Sequence
<220> FEATURE:
<223> OTHER INFORMATION: Synthetic peptide

<400> SEQUENCE: 390

Lys Lys Leu Asp Thr Phe Phe Val Lys Leu Ser Leu Phe Thr Glu Asn
1               5                   10                  15

<210> SEQ ID NO 391
<211> LENGTH: 16
<212> TYPE: PRT
<213> ORGANISM: Artificial Sequence
<220> FEATURE:
<223> OTHER INFORMATION: Synthetic peptide

<400> SEQUENCE: 391

Lys Lys Leu Asp Thr Phe Phe Val Lys Leu Ser Leu Phe Thr Glu Arg
1               5                   10                  15

<210> SEQ ID NO 392
<211> LENGTH: 16
<212> TYPE: PRT
<213> ORGANISM: Artificial Sequence
<220> FEATURE:
<223> OTHER INFORMATION: Synthetic peptide

<400> SEQUENCE: 392

Lys Lys Leu Asp Thr Phe Phe Val Lys Leu Ser Leu Phe Thr Glu Thr
1               5                   10                  15

<210> SEQ ID NO 393
<211> LENGTH: 16
<212> TYPE: PRT
<213> ORGANISM: Artificial Sequence
<220> FEATURE:
<223> OTHER INFORMATION: Synthetic peptide

<400> SEQUENCE: 393

Lys Lys Leu Asp Thr Phe Phe Val Lys Leu Ser Leu Phe Thr Glu Tyr
1               5                   10                  15

<210> SEQ ID NO 394
<211> LENGTH: 16
```

```
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 1
<223> OTHER INFORMATION: Xaa = K, A, D, E, G, H, I, L, M, N, P, Q, R, T,
      V, or absent
<220> FEATURE:
<221> NAME/KEY: VARIANT
<222> LOCATION: 3
<223> OTHER INFORMATION: Xaa = L, A, C, D, E, F, G, H, I, K, M, N, Q, R,
      S, T, V, or absent
<220> FEATURE:
<221> NAME/KEY: VARIANT
<222> LOCATION: 4
<223> OTHER INFORMATION: Xaa = D, A, E, I, V, W, Y, or absent
<220> FEATURE:
<221> NAME/KEY: VARIANT
<222> LOCATION: 5
<223> OTHER INFORMATION: Xaa = T, C, M, N, P, Q, R, S, W, Y, or absent
<220> FEATURE:
<221> NAME/KEY: VARIANT
<222> LOCATION: 6
<223> OTHER INFORMATION: Xaa = F, A, I, M, N, P, T, V, or absent
<220> FEATURE:
<221> NAME/KEY: VARIANT
<222> LOCATION: (7)...(7)
<223> OTHER INFORMATION: Xaa = F, L, M, Q, S, T, V, or absent
<220> FEATURE:
<221> NAME/KEY: VARIANT
<222> LOCATION: (8)...(8)
<223> OTHER INFORMATION: Xaa = V, F, G, L, P, R, or absent
<220> FEATURE:
<221> NAME/KEY: VARIANT
<222> LOCATION: (10)...(10)
<223> OTHER INFORMATION: Xaa =  L,A,F,G,I,M,N,P,Q,R,S,T,V,Y, or absent
<220> FEATURE:
<221> NAME/KEY: VARIANT
<222> LOCATION: (11)...(11)
<223> OTHER INFORMATION: Xaa = S, H, M, N, Q, T, or absent
<220> FEATURE:
<221> NAME/KEY: VARIANT
<222> LOCATION: (12)...(12)
<223> OTHER INFORMATION: Xaa = L, A, H, I, M, N, Q, R, S, T, V, W, or
      absent
<220> FEATURE:
<221> NAME/KEY: VARIANT
<222> LOCATION: (13)...(13)
<223> OTHER INFORMATION: XAa = F, A, C, G, H, I, L, M, N, P, Q, R, S, T,
      V, W, or absent
<220> FEATURE:
<221> NAME/KEY: VARIANT
<222> LOCATION: (14)...(14)
<223> OTHER INFORMATION: Xaa = T, F, G, H, I, L, M, N, P, S, V, W or
      absent
<220> FEATURE:
<221> NAME/KEY: VARIANT
<222> LOCATION: (16)...(16)
<223> OTHER INFORMATION: Xaa = R, F, K, N, R, T, Y or absent

<400> SEQUENCE: 394

Xaa Lys Xaa Xaa Xaa Xaa Xaa Xaa Lys Xaa Xaa Xaa Xaa Xaa Glu Xaa
1               5                   10                  15

<210> SEQ ID NO 395
<211> LENGTH: 7
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 1
<223> OTHER INFORMATION: Xaa = K, A, D, E, G, H, I, L, M, N, P, Q, R, T,
      V, or absent
```

-continued

```
<220> FEATURE:
<221> NAME/KEY: VARIANT
<222> LOCATION: 3
<223> OTHER INFORMATION: Xaa = LDTFFV, GDTFFV, EDTFFV, LDQFFV, LDTAFV,
      LDTVFV, LDTFMV, LDTFSV, LDTFVV, LDTFTV, LDTFLV,
      LDGFFV, LDTFGV, LDTFFK, ADTFFV, CDTFFV, DDTFFV,
      FDTFFV, HDTFFV, IDTFFV, KDTFFV, MDTFFV, NDTFFV,
<220> FEATURE:
<221> NAME/KEY: VARIANT
<222> LOCATION: 3
<223> OTHER INFORMATION: Xaa = QDTFFV, RDTFFV, SDTFFV, TDTFFV, VDTFFV,
      LATFFV, LETFFV, LITFFV, LVTFFV, LWTFFV, LYTFFV,
      LDCFFV, LDMFFV, LDNFFV, LDPFFV, LDRFFV, LDSFFV,
      LDWFFV, LDYFFV, LDTIFV, LDTMFV, LDTNFV, LDTPFV,
<220> FEATURE:
<221> NAME/KEY: VARIANT
<222> LOCATION: 3
<223> OTHER INFORMATION: Xaa = LDTTFV, LDTFQV, LDTFFF, LDTFFG, LDTFFL,
      LDTFFP, LDTFFR, LDTFIV, LDTSFV, LDTFAV, LDTFCV,
      LDTQFV, LDTLFV, LTTFFV, LDTFFI, LDHFFV, LMTFFV,
      LDTFEV, LDTFWV, LFTFFV, LDVFFV, LDTFRV, LDTFHV,
<220> FEATURE:
<221> NAME/KEY: VARIANT
<222> LOCATION: 3
<223> OTHER INFORMATION: Xaa = LDTYFV, LPTFFV, PDTFFV, LDTFPV, LDTFNV,
      LDTWFV, LDTGFV, LDAFFV, LQTFFV, LCTFFV, LSTFFV,
      YDTFFV, LDEFFV, WDTFFV, LDTKFV, LDTCFV, LDTFYV,
      LDTHFV, LHTFFV, LRTFFV, LDLFFV, LDTRFV, LLTFFV,
<220> FEATURE:
<221> NAME/KEY: VARIANT
<222> LOCATION: (3)...(3)
<223> OTHER INFORMATION: Xaa = LDTFDV, LDTFFA, LDTFFT, LNTFFV, LDDFFV,
      LDIFFV, LDFFFV, LKTFFV, LDTFFQ, LGTFFV, LDTFFC,
      LDKFFV, LDTFKV, LDTEFV, LDTFFW, LDTFFM, LDTFFS,
      LDTFFH, LDTFFY, LDTFFN, LDTDFV, LDTFFE, LDTFFD,
<220> FEATURE:
<221> NAME/KEY: VARIANT
<222> LOCATION: (3)...(3)
<223> OTHER INFORMATION: Xaa = LTFFV, LDTFF, TFFV, LDF, LDTE, FFV, LDV,
      LV, L, or absent
<220> FEATURE:
<221> NAME/KEY: VARIANT
<222> LOCATION: (5)...(5)
<223> OTHER INFORMATION: Xaa = LSLFT, VSLFT, LQLFT, LMLFT, LTLFT, LHLFT,
      LSQFT, LSVFT, LSMFT, LSLMT, LSLQT, LSLHT, LSLNT,
      LSLPT, LSLST, LSLGT, LSLAT, LSLRT, LSLFN, LSLFP,
      LSLFR, LGLFT, ASLFT, FSLFT, GSLFT, ISLFT, MSLFT,
<220> FEATURE:
<221> NAME/KEY: VARIANT
<222> LOCATION: (5)...(5)
<223> OTHER INFORMATION: Xaa = NSLFT, PSLFT, QSLFT, RSLFT, SSLFT, TSLFT,
      YSLFT, LNLFT, LSAFT, LSHFT, LSIFT, LSNFT, LSRFT,
      LSSFT, LSTFT, LSWFT, LSLCT, LSLIT, LSLLT, LSLTT,
      LSLVT, LSLWT, LSLFF, LSLFG, LSLFH, LSLFI, LSLFL,
<220> FEATURE:
<221> NAME/KEY: VARIANT
<222> LOCATION: (5)...(5)
<223> OTHER INFORMATION: Xaa = LSLFM, LSLFS, LSLFV, LSLFW, LYLFT, LVLFT,
      LSFFT, LSGFT, LSKFT, LSCFT, LCLFT, LRLFT, LPLFT,
      LWLFT, LKLFT, LDLFT, LSYFT, LALFT, WSLFT, LSLFA,
      LSLFQ, LSPFT, HSLFT, LSLYT, LILFT, KSLFT, CSLFT,
<220> FEATURE:
<221> NAME/KEY: VARIANT
<222> LOCATION: (5)...(5)
<223> OTHER INFORMATION: Xaa = LSLFY, LSLFK, LSLFC, LFLFT, LELFT, LSLKT,
      LLLFT, LSLFD, LSLDT, LSLFE, DSLFT, LSLET, LSDFT,
      LSEFT, ESLFT, SLFT, LSFT, LFT, LSL, LT, T, or
      absent
<220> FEATURE:
<221> NAME/KEY: VARIANT
<222> LOCATION: (7)...(7)
<223> OTHER INFORMATION: Xaa = R, F, K, N, R, T, Y, or absent

<400> SEQUENCE: 395

Xaa Lys Xaa Lys Xaa Glu Xaa
1               5
```

```
<210> SEQ ID NO 396
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 396

Lys Lys Leu Asp Thr Phe Phe Val Lys Leu Ser Leu Phe Thr Glu Arg
1               5                   10                  15

<210> SEQ ID NO 397
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 397

Lys Lys Leu Asp Thr Phe Ile Val Lys Leu Ser Leu Phe Thr Glu Arg
1               5                   10                  15

<210> SEQ ID NO 398
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 398

Lys Lys Leu Asp Thr Phe Phe Val Lys Leu Ser Leu Phe Thr Glu Arg
1               5                   10                  15

<210> SEQ ID NO 399
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 399

Lys Lys Leu Asp Thr Phe Phe Val Lys Leu Ser Leu Phe Thr Glu Arg
1               5                   10                  15

<210> SEQ ID NO 400
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 400

Lys Lys Leu Asp Thr Phe Phe Val Lys Leu Ser Leu Phe Thr Glu Arg
1               5                   10                  15

<210> SEQ ID NO 401
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 401

Lys Lys Leu Asp Thr Ser Phe Val Lys Leu Ser Leu Phe Thr Glu Arg
1               5                   10                  15

<210> SEQ ID NO 402
```

```
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 402

Lys Asn Leu Asp Thr Phe Phe Val Lys Leu Ser Leu Phe Thr Glu Arg
1               5                   10                  15

<210> SEQ ID NO 403
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 403

Lys Lys Leu Asp Thr Phe Phe Val Lys Leu Ser Leu Phe Thr Glu Arg
1               5                   10                  15

<210> SEQ ID NO 404
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 404

Lys Lys Leu Asp Thr Phe Ala Val Lys Leu Ser Leu Phe Thr Glu Arg
1               5                   10                  15

<210> SEQ ID NO 405
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 405

Lys Pro Leu Asp Thr Phe Phe Val Lys Leu Ser Leu Phe Thr Glu Arg
1               5                   10                  15

<210> SEQ ID NO 406
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 406

Lys Lys Leu Asp Thr Phe Phe Val Lys Leu Ser Leu Phe Thr Glu Arg
1               5                   10                  15

<210> SEQ ID NO 407
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 407

Lys Arg Leu Asp Thr Phe Phe Val Lys Leu Ser Leu Phe Thr Glu Arg
1               5                   10                  15

<210> SEQ ID NO 408
<211> LENGTH: 16
```

<212> TYPE: PRT
<213> ORGANISM: Artificial Sequence
<220> FEATURE:
<223> OTHER INFORMATION: Synthetic polypeptide

<400> SEQUENCE: 408

Lys Lys Leu Asp Thr Phe Phe Val Lys Leu Ser Leu Phe Thr Glu Arg
1               5                   10                  15

<210> SEQ ID NO 409
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 409

Lys Lys Leu Asp Thr Phe Cys Val Lys Leu Ser Leu Phe Thr Glu Arg
1               5                   10                  15

<210> SEQ ID NO 410
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 410

Lys Lys Leu Asp Thr Gln Phe Val Lys Leu Ser Leu Phe Thr Glu Arg
1               5                   10                  15

<210> SEQ ID NO 411
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 411

Lys Lys Leu Asp Thr Leu Phe Val Lys Leu Ser Leu Phe Thr Glu Arg
1               5                   10                  15

<210> SEQ ID NO 412
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 412

Lys Gly Leu Asp Thr Phe Phe Val Lys Leu Ser Leu Phe Thr Glu Arg
1               5                   10                  15

<210> SEQ ID NO 413
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 413

Lys Lys Leu Thr Thr Phe Phe Val Lys Leu Ser Leu Phe Thr Glu Arg
1               5                   10                  15

<210> SEQ ID NO 414
<211> LENGTH: 16
<212> TYPE: PRT

<213> ORGANISM: Artificial Sequence
<220> FEATURE:
<223> OTHER INFORMATION: Synthetic polypeptide

<400> SEQUENCE: 414

Lys Lys Leu Asp Thr Phe Phe Val Lys Leu Ser Leu Phe Thr Glu Arg
1               5                   10                  15

<210> SEQ ID NO 415
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 415

Lys Lys Leu Asp Thr Phe Phe Val Lys Leu Tyr Leu Phe Thr Glu Arg
1               5                   10                  15

<210> SEQ ID NO 416
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 416

Lys Lys Leu Asp Thr Phe Phe Ile Lys Leu Ser Leu Phe Thr Glu Arg
1               5                   10                  15

<210> SEQ ID NO 417
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 417

Lys Met Leu Asp Thr Phe Phe Val Lys Leu Ser Leu Phe Thr Glu Arg
1               5                   10                  15

<210> SEQ ID NO 418
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 418

Lys His Leu Asp Thr Phe Phe Val Lys Leu Ser Leu Phe Thr Glu Arg
1               5                   10                  15

<210> SEQ ID NO 419
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 419

Lys Lys Leu Asp Thr Phe Phe Val Lys Leu Val Leu Phe Thr Glu Arg
1               5                   10                  15

<210> SEQ ID NO 420
<211> LENGTH: 16
<212> TYPE: PRT
<213> ORGANISM: Artificial Sequence

```
<220> FEATURE:
<223> OTHER INFORMATION: Synthetic polypeptide

<400> SEQUENCE: 420

Lys Lys Leu Asp His Phe Phe Val Lys Leu Ser Leu Phe Thr Glu Arg
1               5                   10                  15

<210> SEQ ID NO 421
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 421

Lys Phe Leu Asp Thr Phe Phe Val Lys Leu Ser Leu Phe Thr Glu Arg
1               5                   10                  15

<210> SEQ ID NO 422
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 422

Lys Lys Leu Asp Thr Phe Phe Val Lys Leu Ser Phe Phe Thr Glu Arg
1               5                   10                  15

<210> SEQ ID NO 423
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 423

Lys Lys Leu Met Thr Phe Phe Val Lys Leu Ser Leu Phe Thr Glu Arg
1               5                   10                  15

<210> SEQ ID NO 424
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 424

Lys Lys Leu Asp Thr Phe Glu Val Lys Leu Ser Leu Phe Thr Glu Arg
1               5                   10                  15

<210> SEQ ID NO 425
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 425

Lys Lys Leu Asp Thr Phe Trp Val Lys Leu Ser Leu Phe Thr Glu Arg
1               5                   10                  15

<210> SEQ ID NO 426
<211> LENGTH: 16
<212> TYPE: PRT
<213> ORGANISM: Artificial Sequence
<220> FEATURE:
```

<223> OTHER INFORMATION: Synthetic polypeptide

<400> SEQUENCE: 426

Lys Lys Leu Phe Thr Phe Phe Val Lys Leu Ser Leu Phe Thr Glu Arg
1               5                   10                  15

<210> SEQ ID NO 427
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 427

Lys Lys Leu Asp Thr Phe Phe Val Lys Leu Ser Leu Phe Thr Glu Arg
1               5                   10                  15

<210> SEQ ID NO 428
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 428

Lys Lys Leu Asp Thr Phe Phe Val Lys Leu Ser Leu Phe Thr Glu Arg
1               5                   10                  15

<210> SEQ ID NO 429
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 429

Lys Lys Leu Asp Val Phe Phe Val Lys Leu Ser Leu Phe Thr Glu Arg
1               5                   10                  15

<210> SEQ ID NO 430
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 430

Lys Lys Leu Asp Thr Phe Phe Val Lys Leu Ser Leu Phe Thr Glu Arg
1               5                   10                  15

<210> SEQ ID NO 431
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 431

Lys Lys Leu Asp Thr Phe Phe Val Lys Leu Ser Gly Phe Thr Glu Arg
1               5                   10                  15

<210> SEQ ID NO 432
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 432

Lys Lys Leu Asp Thr Phe Arg Val Lys Leu Ser Leu Phe Thr Glu Arg
1               5                   10                  15

<210> SEQ ID NO 433
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 433

Lys Lys Leu Asp Thr Phe His Val Lys Leu Ser Leu Phe Thr Glu Arg
1               5                   10                  15

<210> SEQ ID NO 434
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 434

Lys Lys Leu Asp Thr Tyr Phe Val Lys Leu Ser Leu Phe Thr Glu Arg
1               5                   10                  15

<210> SEQ ID NO 435
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 435

Lys Lys Leu Pro Thr Phe Phe Val Lys Leu Ser Leu Phe Thr Glu Arg
1               5                   10                  15

<210> SEQ ID NO 436
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 436

Lys Lys Pro Asp Thr Phe Phe Val Lys Leu Ser Leu Phe Thr Glu Arg
1               5                   10                  15

<210> SEQ ID NO 437
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 437

Lys Lys Leu Asp Thr Phe Pro Val Lys Leu Ser Leu Phe Thr Glu Arg
1               5                   10                  15

<210> SEQ ID NO 438
<211> LENGTH: 16
<212> TYPE: PRT
<213> ORGANISM: Artificial Sequence
<220> FEATURE:
<223> OTHER INFORMATION: Synthetic polypeptide -continued

<400> SEQUENCE: 438

Lys Lys Leu Asp Thr Phe Phe Val Lys Leu Ser Lys Phe Thr Glu Arg
1               5                   10                  15

<210> SEQ ID NO 439
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 439

Lys Lys Leu Asp Thr Phe Phe Val Lys Leu Ser Leu Phe Thr Pro Arg
1               5                   10                  15

<210> SEQ ID NO 440
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 440

Lys Gln Leu Asp Thr Phe Phe Val Lys Leu Ser Leu Phe Thr Glu Arg
1               5                   10                  15

<210> SEQ ID NO 441
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 441

Lys Glu Leu Asp Thr Phe Phe Val Lys Leu Ser Leu Phe Thr Glu Arg
1               5                   10                  15

<210> SEQ ID NO 442
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 442

Lys Lys Leu Asp Thr Phe Phe Val Lys Leu Ser Leu Phe Thr Glu Arg
1               5                   10                  15

<210> SEQ ID NO 443
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 443

Lys Lys Leu Asp Thr Phe Asn Val Lys Leu Ser Leu Phe Thr Glu Arg
1               5                   10                  15

<210> SEQ ID NO 444
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 444

```
Lys Lys Leu Asp Thr Trp Phe Val Lys Leu Ser Leu Phe Thr Glu Arg
1               5                   10                  15

<210> SEQ ID NO 445
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 445

Lys Lys Leu Asp Thr Phe Phe Val Thr Leu Ser Leu Phe Thr Glu Arg
1               5                   10                  15

<210> SEQ ID NO 446
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 446

Lys Lys Leu Asp Thr Gly Phe Val Lys Leu Ser Leu Phe Thr Glu Arg
1               5                   10                  15

<210> SEQ ID NO 447
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 447

Lys Lys Leu Asp Ala Phe Phe Val Lys Leu Ser Leu Phe Thr Glu Arg
1               5                   10                  15

<210> SEQ ID NO 448
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 448

Lys Lys Leu Gln Thr Phe Phe Val Lys Leu Ser Leu Phe Thr Glu Arg
1               5                   10                  15

<210> SEQ ID NO 449
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 449

Lys Lys Leu Cys Thr Phe Phe Val Lys Leu Ser Leu Phe Thr Glu Arg
1               5                   10                  15

<210> SEQ ID NO 450
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 450
```

Lys Lys Leu Asp Thr Phe Phe Val Lys Leu Ser Leu Phe Thr Gln Arg
1               5                   10                  15

<210> SEQ ID NO 451
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 451

Lys Lys Leu Ser Thr Phe Phe Val Lys Leu Ser Leu Phe Thr Glu Arg
1               5                   10                  15

<210> SEQ ID NO 452
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 452

Lys Lys Tyr Asp Thr Phe Phe Val Lys Leu Ser Leu Phe Thr Glu Arg
1               5                   10                  15

<210> SEQ ID NO 453
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 453

Ser Lys Leu Asp Thr Phe Phe Val Lys Leu Ser Leu Phe Thr Glu Arg
1               5                   10                  15

<210> SEQ ID NO 454
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 454

Lys Leu Leu Asp Thr Phe Phe Val Lys Leu Ser Leu Phe Thr Glu Arg
1               5                   10                  15

<210> SEQ ID NO 455
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 455

Lys Lys Leu Asp Thr Phe Phe Val Lys Leu Ser Cys Phe Thr Glu Arg
1               5                   10                  15

<210> SEQ ID NO 456
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 456

Lys Lys Leu Asp Glu Phe Phe Val Lys Leu Ser Leu Phe Thr Glu Arg

```
<210> SEQ ID NO 457
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 457

Lys Lys Leu Asp Thr Phe Phe Val Lys Leu Cys Leu Phe Thr Glu Arg
1               5                   10                  15

<210> SEQ ID NO 458
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 458

Lys Lys Trp Asp Thr Phe Phe Val Lys Leu Ser Leu Phe Thr Glu Arg
1               5                   10                  15

<210> SEQ ID NO 459
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 459

Lys Lys Leu Asp Thr Phe Phe Val Lys Leu Ser Leu Phe Thr Tyr Arg
1               5                   10                  15

<210> SEQ ID NO 460
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 460

Lys Lys Leu Asp Thr Lys Phe Val Lys Leu Ser Leu Phe Thr Glu Arg
1               5                   10                  15

<210> SEQ ID NO 461
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 461

Lys Asp Leu Asp Thr Phe Phe Val Lys Leu Ser Leu Phe Thr Glu Arg
1               5                   10                  15

<210> SEQ ID NO 462
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 462

Lys Lys Leu Asp Thr Cys Phe Val Lys Leu Ser Leu Phe Thr Glu Arg
1               5                   10                  15
```

<210> SEQ ID NO 463
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 463

Lys Lys Leu Asp Thr Phe Tyr Val Lys Leu Ser Leu Phe Thr Glu Arg
1               5                   10                  15

<210> SEQ ID NO 464
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 464

Lys Lys Leu Asp Thr Phe Phe Val Lys Leu Arg Leu Phe Thr Glu Arg
1               5                   10                  15

<210> SEQ ID NO 465
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 465

Phe Lys Leu Asp Thr Phe Phe Val Lys Leu Ser Leu Phe Thr Glu Arg
1               5                   10                  15

<210> SEQ ID NO 466
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 466

Lys Lys Leu Asp Thr His Phe Val Lys Leu Ser Leu Phe Thr Glu Arg
1               5                   10                  15

<210> SEQ ID NO 467
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 467

Lys Ile Leu Asp Thr Phe Phe Val Lys Leu Ser Leu Phe Thr Glu Arg
1               5                   10                  15

<210> SEQ ID NO 468
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 468

Lys Thr Leu Asp Thr Phe Phe Val Lys Leu Ser Leu Phe Thr Glu Arg
1               5                   10                  15

<210> SEQ ID NO 469
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 469

Lys Lys Leu Asp Thr Phe Phe Val Gln Leu Ser Leu Phe Thr Glu Arg
1               5                   10                  15

<210> SEQ ID NO 470
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 470

Lys Lys Leu Asp Thr Phe Phe Val Lys Leu Pro Leu Phe Thr Glu Arg
1               5                   10                  15

<210> SEQ ID NO 471
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 471

Lys Lys Leu Asp Thr Phe Phe Val Lys Leu Ser Leu Phe Thr Lys Arg
1               5                   10                  15

<210> SEQ ID NO 472
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 472

Lys Lys Leu Asp Thr Phe Phe Val Lys Leu Trp Leu Phe Thr Glu Arg
1               5                   10                  15

<210> SEQ ID NO 473
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 473

Lys Lys Leu Asp Thr Phe Phe Val Lys Leu Lys Leu Phe Thr Glu Arg
1               5                   10                  15

<210> SEQ ID NO 474
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 474

Lys Lys Leu Asp Thr Phe Phe Val Lys Leu Asp Leu Phe Thr Glu Arg
1               5                   10                  15

```
<210> SEQ ID NO 475
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 475

Lys Lys Leu Asp Thr Phe Phe Val Lys Leu Ser Tyr Phe Thr Glu Arg
1               5                   10                  15

<210> SEQ ID NO 476
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 476

Lys Lys Leu Asp Thr Phe Phe Val Lys Leu Ser Leu Phe Thr Glu Arg
1               5                   10                  15

<210> SEQ ID NO 477
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 477

Lys Lys Leu Asp Thr Phe Phe Val Lys Leu Ala Leu Phe Thr Glu Arg
1               5                   10                  15

<210> SEQ ID NO 478
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 478

Lys Lys Leu Asp Thr Phe Phe Val Lys Leu Ser Leu Phe Thr His Arg
1               5                   10                  15

<210> SEQ ID NO 479
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 479

Lys Lys Leu His Thr Phe Phe Val Lys Leu Ser Leu Phe Thr Glu Arg
1               5                   10                  15

<210> SEQ ID NO 480
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 480

Lys Lys Leu Arg Thr Phe Phe Val Lys Leu Ser Leu Phe Thr Glu Arg
1               5                   10                  15

<210> SEQ ID NO 481
```

```
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 481

Lys Val Leu Asp Thr Phe Phe Val Lys Leu Ser Leu Phe Thr Glu Arg
1               5                   10                  15

<210> SEQ ID NO 482
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 482

Lys Lys Leu Asp Thr Phe Phe Val Lys Trp Ser Leu Phe Thr Glu Arg
1               5                   10                  15

<210> SEQ ID NO 483
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 483

Tyr Lys Leu Asp Thr Phe Phe Val Lys Leu Ser Leu Phe Thr Glu Arg
1               5                   10                  15

<210> SEQ ID NO 484
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 484

Lys Lys Leu Asp Leu Phe Phe Val Lys Leu Ser Leu Phe Thr Glu Arg
1               5                   10                  15

<210> SEQ ID NO 485
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 485

Lys Ala Leu Asp Thr Phe Phe Val Lys Leu Ser Leu Phe Thr Glu Arg
1               5                   10                  15

<210> SEQ ID NO 486
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 486

Lys Lys Leu Asp Thr Arg Phe Val Lys Leu Ser Leu Phe Thr Glu Arg
1               5                   10                  15

<210> SEQ ID NO 487
<211> LENGTH: 16
```

```
<212> TYPE: PRT
<213> ORGANISM: Artificial Sequence
<220> FEATURE:
<223> OTHER INFORMATION: Synthetic polypeptide

<400> SEQUENCE: 487

Lys Lys Leu Asp Thr Phe Phe Val Lys Leu Ser Leu Phe Thr Glu Arg
1               5                   10                  15

<210> SEQ ID NO 488
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 488

Lys Lys Leu Asp Thr Phe Phe Val His Leu Ser Leu Phe Thr Glu Arg
1               5                   10                  15

<210> SEQ ID NO 489
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 489

Lys Lys Leu Asp Thr Phe Phe Val Lys Leu Ser Leu Phe Ala Glu Arg
1               5                   10                  15

<210> SEQ ID NO 490
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 490

Lys Trp Leu Asp Thr Phe Phe Val Lys Leu Ser Leu Phe Thr Glu Arg
1               5                   10                  15

<210> SEQ ID NO 491
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 491

Lys Lys Leu Leu Thr Phe Phe Val Lys Leu Ser Leu Phe Thr Glu Arg
1               5                   10                  15

<210> SEQ ID NO 492
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 492

Lys Lys Leu Asp Thr Phe Asp Val Lys Leu Ser Leu Phe Thr Glu Arg
1               5                   10                  15

<210> SEQ ID NO 493
<211> LENGTH: 16
<212> TYPE: PRT
```

```
<213> ORGANISM: Artificial Sequence
<220> FEATURE:
<223> OTHER INFORMATION: Synthetic polypeptide

<400> SEQUENCE: 493

Lys Lys Leu Asp Thr Phe Phe Val Lys Leu Ser Leu Phe Gln Glu Arg
1               5                   10                  15

<210> SEQ ID NO 494
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 494

Lys Tyr Leu Asp Thr Phe Phe Val Lys Leu Ser Leu Phe Thr Glu Arg
1               5                   10                  15

<210> SEQ ID NO 495
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 495

Lys Lys Leu Asp Thr Phe Phe Ala Lys Leu Ser Leu Phe Thr Glu Arg
1               5                   10                  15

<210> SEQ ID NO 496
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 496

Lys Lys Leu Asp Thr Phe Phe Thr Lys Leu Ser Leu Phe Thr Glu Arg
1               5                   10                  15

<210> SEQ ID NO 497
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 497

Lys Lys Leu Asp Thr Phe Phe Val Lys Leu Ser Pro Phe Thr Glu Arg
1               5                   10                  15

<210> SEQ ID NO 498
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 498

Lys Lys Leu Asn Thr Phe Phe Val Lys Leu Ser Leu Phe Thr Glu Arg
1               5                   10                  15

<210> SEQ ID NO 499
<211> LENGTH: 16
<212> TYPE: PRT
<213> ORGANISM: Artificial Sequence
```

<220> FEATURE:
<223> OTHER INFORMATION: Synthetic polypeptide

<400> SEQUENCE: 499

Lys Cys Leu Asp Thr Phe Phe Val Lys Leu Ser Leu Phe Thr Glu Arg
1               5                   10                  15

<210> SEQ ID NO 500
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 500

Lys Lys Leu Asp Asp Phe Phe Val Lys Leu Ser Leu Phe Thr Glu Arg
1               5                   10                  15

<210> SEQ ID NO 501
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 501

Lys Lys Leu Asp Ile Phe Phe Val Lys Leu Ser Leu Phe Thr Glu Arg
1               5                   10                  15

<210> SEQ ID NO 502
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 502

Lys Lys Leu Asp Thr Phe Phe Val Lys His Ser Leu Phe Thr Glu Arg
1               5                   10                  15

<210> SEQ ID NO 503
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 503

Lys Lys Leu Asp Thr Phe Phe Val Lys Leu Ser Leu Tyr Thr Glu Arg
1               5                   10                  15

<210> SEQ ID NO 504
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 504

Lys Lys Leu Asp Phe Phe Phe Val Lys Leu Ser Leu Phe Thr Glu Arg
1               5                   10                  15

<210> SEQ ID NO 505
<211> LENGTH: 16
<212> TYPE: PRT
<213> ORGANISM: Artificial Sequence
<220> FEATURE:

-continued

```
<223> OTHER INFORMATION: Synthetic polypeptide

<400> SEQUENCE: 505

Lys Lys Leu Asp Thr Phe Phe Val Lys Leu Ile Leu Phe Thr Glu Arg
1               5                   10                  15

<210> SEQ ID NO 506
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 506

Lys Lys Leu Asp Thr Phe Phe Val Lys Lys Ser Leu Phe Thr Glu Arg
1               5                   10                  15

<210> SEQ ID NO 507
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 507

Trp Lys Leu Asp Thr Phe Phe Val Lys Leu Ser Leu Phe Thr Glu Arg
1               5                   10                  15

<210> SEQ ID NO 508
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 508

Lys Lys Leu Asp Thr Phe Phe Val Lys Cys Ser Leu Phe Thr Glu Arg
1               5                   10                  15

<210> SEQ ID NO 509
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 509

Lys Lys Leu Asp Thr Phe Phe Val Met Leu Ser Leu Phe Thr Glu Arg
1               5                   10                  15

<210> SEQ ID NO 510
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 510

Lys Ser Leu Asp Thr Phe Phe Val Lys Leu Ser Leu Phe Thr Glu Arg
1               5                   10                  15

<210> SEQ ID NO 511
<211> LENGTH: 16
<212> TYPE: PRT
<213> ORGANISM: Artificial Sequence
<220> FEATURE:
<223> OTHER INFORMATION: Synthetic polypeptide
```

<400> SEQUENCE: 511

Lys Lys Leu Asp Thr Phe Phe Val Ser Leu Ser Leu Phe Thr Glu Arg
1               5                   10                  15

<210> SEQ ID NO 512
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 512

Lys Lys Leu Lys Thr Phe Phe Val Lys Leu Ser Leu Phe Thr Glu Arg
1               5                   10                  15

<210> SEQ ID NO 513
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 513

Lys Lys Leu Asp Thr Phe Phe Gln Lys Leu Ser Leu Phe Thr Glu Arg
1               5                   10                  15

<210> SEQ ID NO 514
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 514

Lys Lys Leu Asp Thr Phe Phe Val Lys Leu Ser Leu Phe Tyr Glu Arg
1               5                   10                  15

<210> SEQ ID NO 515
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 515

Lys Lys Leu Gly Thr Phe Phe Val Lys Leu Ser Leu Phe Thr Glu Arg
1               5                   10                  15

<210> SEQ ID NO 516
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 516

Lys Lys Leu Asp Thr Phe Phe Val Lys Leu Ser Leu Phe Thr Glu Arg
1               5                   10                  15

<210> SEQ ID NO 517
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 517

Lys Lys Leu Asp Thr Phe Phe Val Lys Leu Ser Leu Phe Lys Glu Arg
1               5                   10                  15

<210> SEQ ID NO 518
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 518

Lys Lys Leu Asp Thr Phe Phe Val Asn Leu Ser Leu Phe Thr Glu Arg
1               5                   10                  15

<210> SEQ ID NO 519
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 519

Lys Lys Leu Asp Thr Phe Phe Cys Lys Leu Ser Leu Phe Thr Glu Arg
1               5                   10                  15

<210> SEQ ID NO 520
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 520

Lys Lys Leu Asp Thr Phe Phe Val Lys Leu Ser Leu Phe Cys Glu Arg
1               5                   10                  15

<210> SEQ ID NO 521
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 521

Lys Lys Leu Asp Thr Phe Phe Val Lys Leu Ser Leu Phe Thr Glu Val
1               5                   10                  15

<210> SEQ ID NO 522
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 522

Lys Lys Leu Asp Thr Phe Phe Val Lys Leu Phe Leu Phe Thr Glu Arg
1               5                   10                  15

<210> SEQ ID NO 523
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 523

Lys Lys Leu Asp Thr Phe Phe Val Val Leu Ser Leu Phe Thr Glu Arg
1               5                   10                  15

<210> SEQ ID NO 524
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 524

Lys Lys Leu Asp Thr Phe Phe Val Lys Leu Ser Leu Phe Thr Met Arg
1               5                   10                  15

<210> SEQ ID NO 525
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 525

Lys Lys Leu Asp Thr Phe Phe Val Lys Leu Ser Leu Phe Thr Leu Arg
1               5                   10                  15

<210> SEQ ID NO 526
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 526

Lys Lys Leu Asp Thr Phe Phe Val Trp Leu Ser Leu Phe Thr Glu Arg
1               5                   10                  15

<210> SEQ ID NO 527
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 527

Lys Lys Leu Asp Thr Phe Phe Val Glu Leu Ser Leu Phe Thr Glu Arg
1               5                   10                  15

<210> SEQ ID NO 528
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 528

Lys Lys Leu Asp Thr Phe Phe Val Lys Leu Ser Leu Phe Thr Glu His
1               5                   10                  15

<210> SEQ ID NO 529
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 529

Lys Lys Leu Asp Thr Phe Phe Val Lys Leu Ser Leu Phe Thr Glu Met
1               5                   10                  15

<210> SEQ ID NO 530
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 530

Lys Lys Leu Asp Lys Phe Phe Val Lys Leu Ser Leu Phe Thr Glu Arg
1               5                   10                  15

<210> SEQ ID NO 531
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 531

Lys Lys Leu Asp Thr Phe Phe Val Lys Leu Ser Leu Phe Thr Arg Arg
1               5                   10                  15

<210> SEQ ID NO 532
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 532

Lys Lys Leu Asp Thr Phe Phe Val Lys Leu Glu Leu Phe Thr Glu Arg
1               5                   10                  15

<210> SEQ ID NO 533
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 533

Lys Lys Leu Asp Thr Phe Phe Val Lys Leu Ser Leu Phe Thr Glu Pro
1               5                   10                  15

<210> SEQ ID NO 534
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 534

Lys Lys Leu Asp Thr Phe Phe Val Pro Leu Ser Leu Phe Thr Glu Arg
1               5                   10                  15

<210> SEQ ID NO 535
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 535

Lys Lys Leu Asp Thr Phe Lys Val Lys Leu Ser Leu Phe Thr Glu Arg

```
1               5                   10                  15
```

<210> SEQ ID NO 536
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 536

```
Lys Lys Leu Asp Thr Glu Phe Val Lys Leu Ser Leu Phe Thr Glu Arg
1               5                   10                  15
```

<210> SEQ ID NO 537
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 537

```
Lys Lys Leu Asp Thr Phe Phe Trp Lys Leu Ser Leu Phe Thr Glu Arg
1               5                   10                  15
```

<210> SEQ ID NO 538
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 538

```
Lys Lys Leu Asp Thr Phe Phe Val Lys Leu Ser Leu Phe Thr Glu Ala
1               5                   10                  15
```

<210> SEQ ID NO 539
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 539

```
Lys Lys Leu Asp Thr Phe Phe Val Lys Leu Ser Leu Phe Thr Trp Arg
1               5                   10                  15
```

<210> SEQ ID NO 540
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 540

```
Lys Lys Leu Asp Thr Phe Phe Met Lys Leu Ser Leu Phe Thr Glu Arg
1               5                   10                  15
```

<210> SEQ ID NO 541
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 541

```
Lys Lys Leu Asp Thr Phe Phe Val Cys Leu Ser Leu Phe Thr Glu Arg
1               5                   10                  15
```

<210> SEQ ID NO 542
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 542

Lys Lys Leu Asp Thr Phe Phe Val Lys Leu Ser Leu Lys Thr Glu Arg
1               5                   10                  15

<210> SEQ ID NO 543
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 543

Lys Lys Leu Asp Thr Phe Phe Val Lys Leu Ser Leu Phe Thr Glu Gly
1               5                   10                  15

<210> SEQ ID NO 544
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 544

Lys Lys Leu Asp Thr Phe Phe Val Lys Leu Ser Leu Phe Thr Glu Leu
1               5                   10                  15

<210> SEQ ID NO 545
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 545

Lys Lys Leu Asp Thr Phe Phe Ser Lys Leu Ser Leu Phe Thr Glu Arg
1               5                   10                  15

<210> SEQ ID NO 546
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 546

Cys Lys Leu Asp Thr Phe Phe Val Lys Leu Ser Leu Phe Thr Glu Arg
1               5                   10                  15

<210> SEQ ID NO 547
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 547

Lys Lys Leu Asp Thr Phe Phe His Lys Leu Ser Leu Phe Thr Glu Arg
1               5                   10                  15

```
<210> SEQ ID NO 548
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 548

Lys Lys Leu Asp Thr Phe Phe Val Lys Leu Leu Leu Phe Thr Glu Arg
1               5                   10                  15

<210> SEQ ID NO 549
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 549

Lys Lys Leu Asp Thr Phe Phe Tyr Lys Leu Ser Leu Phe Thr Glu Arg
1               5                   10                  15

<210> SEQ ID NO 550
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 550

Lys Lys Leu Asp Thr Phe Phe Asn Lys Leu Ser Leu Phe Thr Glu Arg
1               5                   10                  15

<210> SEQ ID NO 551
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 551

Lys Lys Leu Asp Thr Phe Phe Val Lys Leu Ser Leu Phe Thr Glu Trp
1               5                   10                  15

<210> SEQ ID NO 552
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 552

Lys Lys Leu Asp Thr Phe Phe Val Tyr Leu Ser Leu Phe Thr Glu Arg
1               5                   10                  15

<210> SEQ ID NO 553
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 553

Lys Lys Leu Asp Thr Asp Phe Val Lys Leu Ser Leu Phe Thr Glu Arg
1               5                   10                  15
```

-continued

```
<210> SEQ ID NO 554
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 554

Lys Lys Leu Asp Thr Phe Phe Val Ala Leu Ser Leu Phe Thr Glu Arg
1               5                   10                  15

<210> SEQ ID NO 555
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 555

Lys Lys Leu Asp Thr Phe Phe Val Ile Leu Ser Leu Phe Thr Glu Arg
1               5                   10                  15

<210> SEQ ID NO 556
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 556

Lys Lys Leu Asp Thr Phe Phe Val Lys Leu Ser Leu Phe Thr Cys Arg
1               5                   10                  15

<210> SEQ ID NO 557
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 557

Lys Lys Leu Asp Thr Phe Phe Val Lys Leu Ser Leu Phe Thr Glu Ser
1               5                   10                  15

<210> SEQ ID NO 558
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 558

Lys Lys Leu Asp Thr Phe Phe Val Lys Leu Ser Leu Phe Thr Glu Ile
1               5                   10                  15

<210> SEQ ID NO 559
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 559

Lys Lys Leu Asp Thr Phe Phe Val Lys Leu Ser Leu Phe Thr Glu Cys
1               5                   10                  15

<210> SEQ ID NO 560
```

```
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 560

Lys Lys Leu Asp Thr Phe Phe Val Phe Leu Ser Leu Phe Thr Glu Arg
1               5                   10                  15

<210> SEQ ID NO 561
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 561

Lys Lys Leu Asp Thr Phe Phe Val Lys Leu Ser Leu Phe Thr Ala Arg
1               5                   10                  15

<210> SEQ ID NO 562
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 562

Lys Lys Leu Asp Thr Phe Phe Val Leu Leu Ser Leu Phe Thr Glu Arg
1               5                   10                  15

<210> SEQ ID NO 563
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 563

Lys Lys Leu Asp Thr Phe Phe Val Lys Leu Ser Leu Phe Thr Ser Arg
1               5                   10                  15

<210> SEQ ID NO 564
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 564

Lys Lys Leu Asp Thr Phe Phe Val Lys Leu Ser Leu Phe Thr Ile Arg
1               5                   10                  15

<210> SEQ ID NO 565
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 565

Lys Lys Leu Asp Thr Phe Phe Val Lys Leu Ser Leu Phe Thr Val Arg
1               5                   10                  15

<210> SEQ ID NO 566
<211> LENGTH: 16
```

<212> TYPE: PRT
<213> ORGANISM: Artificial Sequence
<220> FEATURE:
<223> OTHER INFORMATION: Synthetic polypeptide

<400> SEQUENCE: 566

Lys Lys Leu Asp Thr Phe Phe Val Lys Leu Ser Leu Phe Thr Asn Arg
1               5                   10                  15

<210> SEQ ID NO 567
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 567

Lys Lys Leu Asp Thr Phe Phe Val Lys Leu Ser Leu Phe Asp Glu Arg
1               5                   10                  15

<210> SEQ ID NO 568
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 568

Lys Lys Leu Asp Thr Phe Phe Val Lys Leu Ser Leu Phe Thr Thr Arg
1               5                   10                  15

<210> SEQ ID NO 569
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 569

Lys Lys Leu Asp Thr Phe Phe Val Asp Leu Ser Leu Phe Thr Glu Arg
1               5                   10                  15

<210> SEQ ID NO 570
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 570

Lys Lys Leu Asp Thr Phe Phe Glu Lys Leu Ser Leu Phe Thr Glu Arg
1               5                   10                  15

<210> SEQ ID NO 571
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 571

Lys Lys Leu Asp Thr Phe Phe Val Lys Leu Ser Leu Phe Thr Phe Arg
1               5                   10                  15

<210> SEQ ID NO 572
<211> LENGTH: 16
<212> TYPE: PRT

```
<213> ORGANISM: Artificial Sequence
<220> FEATURE:
<223> OTHER INFORMATION: Synthetic polypeptide

<400> SEQUENCE: 572

Lys Lys Leu Asp Thr Phe Phe Val Lys Leu Ser Leu Phe Thr Glu Asp
1               5                   10                  15

<210> SEQ ID NO 573
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 573

Lys Lys Leu Asp Thr Phe Phe Val Lys Leu Ser Leu Phe Thr Glu Gln
1               5                   10                  15

<210> SEQ ID NO 574
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 574

Lys Lys Leu Asp Thr Phe Phe Asp Lys Leu Ser Leu Phe Thr Glu Arg
1               5                   10                  15

<210> SEQ ID NO 575
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 575

Lys Lys Leu Asp Thr Phe Phe Val Lys Leu Ser Leu Asp Thr Glu Arg
1               5                   10                  15

<210> SEQ ID NO 576
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 576

Lys Lys Leu Asp Thr Phe Phe Val Lys Leu Ser Leu Phe Glu Glu Arg
1               5                   10                  15

<210> SEQ ID NO 577
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 577

Lys Lys Leu Asp Thr Phe Phe Val Lys Leu Ser Leu Phe Thr Glu Glu
1               5                   10                  15

<210> SEQ ID NO 578
<211> LENGTH: 16
<212> TYPE: PRT
<213> ORGANISM: Artificial Sequence
```

<220> FEATURE:
<223> OTHER INFORMATION: Synthetic polypeptide

<400> SEQUENCE: 578

Lys Lys Leu Asp Thr Phe Phe Val Lys Asp Ser Leu Phe Thr Glu Arg
1               5                   10                  15

<210> SEQ ID NO 579
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 579

Lys Lys Leu Asp Thr Phe Phe Val Lys Leu Ser Leu Glu Thr Glu Arg
1               5                   10                  15

<210> SEQ ID NO 580
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 580

Lys Lys Leu Asp Thr Phe Phe Val Lys Leu Ser Asp Phe Thr Glu Arg
1               5                   10                  15

<210> SEQ ID NO 581
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 581

Lys Lys Leu Asp Thr Phe Phe Val Lys Leu Ser Glu Phe Thr Glu Arg
1               5                   10                  15

<210> SEQ ID NO 582
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 582

Lys Lys Leu Asp Thr Phe Phe Val Lys Glu Ser Leu Phe Thr Glu Arg
1               5                   10                  15

<210> SEQ ID NO 583
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 583

Lys Lys Leu Asp Thr Phe Phe Val Lys Leu Ser Leu Met Thr Glu Arg
1               5                   10                  15

<210> SEQ ID NO 584
<211> LENGTH: 16
<212> TYPE: PRT
<213> ORGANISM: Artificial Sequence
<220> FEATURE:

```
<223> OTHER INFORMATION: Synthetic polypeptide

<400> SEQUENCE: 584

Lys Lys Leu Asp Thr Phe Phe Val Lys Leu Gln Leu Phe Thr Glu Arg
1               5                   10                  15

<210> SEQ ID NO 585
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 585

Lys Lys Leu Asp Thr Val Met Val Lys Leu Gln Leu Met Thr Glu Arg
1               5                   10                  15

<210> SEQ ID NO 586
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 586

Arg Lys Leu Asp Thr Phe Phe Val Lys Leu Ser Leu Phe Thr Glu Arg
1               5                   10                  15

Arg Arg

<210> SEQ ID NO 587
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 587

Lys Ser Leu Asp Thr Phe Phe Val Lys Leu Ser Leu Phe Thr Glu Arg
1               5                   10                  15

<210> SEQ ID NO 588
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 588

Lys Lys Leu Asp Thr Phe Phe Val Lys Leu Ser Leu Phe Thr Phe Arg
1               5                   10                  15

<210> SEQ ID NO 589
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 589

Lys Lys Leu Asp Thr Phe Phe Val Tyr Leu Ser Leu Phe Thr Glu Arg
1               5                   10                  15

<210> SEQ ID NO 590
<211> LENGTH: 16
<212> TYPE: PRT
<213> ORGANISM: Artificial Sequence
```

```
<220> FEATURE:
<223> OTHER INFORMATION: Synthetic polypeptide

<400> SEQUENCE: 590

Lys Lys Leu Asp Thr Phe Phe Val Asn Leu Ser Leu Phe Thr Glu Arg
1               5                   10                  15

<210> SEQ ID NO 591
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 591

Lys Lys Leu Asp Thr Phe Phe Val Asp Leu Ser Leu Phe Thr Glu Arg
1               5                   10                  15

<210> SEQ ID NO 592
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 592

Lys Lys Leu Asp Thr Phe Phe Pro Lys Leu Ser Leu Phe Thr Glu Arg
1               5                   10                  15

<210> SEQ ID NO 593
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 593

Lys Lys Leu Asp Thr Phe Met Val Lys Leu Ser Gln His Thr Glu Arg
1               5                   10                  15

<210> SEQ ID NO 594
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: 17
<223> OTHER INFORMATION: Pegylation

<400> SEQUENCE: 594

Lys Lys Leu Asp Thr Phe Phe Val Lys Leu Ser Leu Phe Thr Glu Arg
1               5                   10                  15
Cys

<210> SEQ ID NO 595
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 595

Lys Lys Leu Asp Gln Phe Phe Val Lys Leu Ser Gln His Asn Glu Arg
1               5                   10                  15
```

```
<210> SEQ ID NO 596
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 596

Gly Pro Gln Gly Ile Ala Gly Gln
1               5
```

IMMUNE SYSTEM MODULATORS AND COMPOSITIONS

RELATED APPLICATIONS

This application is a U.S. National Phase of PCT International App. No. PCT/US2016/020510, filed on Mar. 2, 2016, designating the United States of America and published in the English language, which claims the benefit of U.S. Provisional App. No. 62/129,669 filed Mar. 6, 2015, which is hereby incorporated by reference in its entirety.

SEQUENCE IN ELECTRONIC FORMAT

The present application is being filed along with a Sequence Listing as an ASCII text file via EFS-Web. The Sequence Listing is provided as a file entitled CANIG006NPSEQUENCE.TXT, created and last saved on Aug. 30, 2017, which is 162,442 bytes in size, and updated by a file entitled CANIG006NPREPLACEMENT.TXT, created and last saved Jan. 25, 2018, which is 162,486 bytes in size. The information in the electronic format of the Sequence Listing is incorporated herein by reference in its entirety in accordance with 35 U.S.C. § 1.52(e).

FIELD OF THE INVENTION

Aspects of the present invention generally relate to compositions that interact with molecules, which suppress the immune system. More specifically, embodiments described herein concern the discovery, manufacture, and use of compositions that modulate the immune system.

BACKGROUND OF THE INVENTION

The immune system is finely tuned to detect and eradicate foreign molecules and, at the same time, avoid over reactivity, which could result in destruction of normal tissues resulting in autoimmune or chronic inflammatory diseases. The initiation of a specific immune response is a well-orchestrated chain of events culminating in the activation of effector functions, such as the release of cytokines, production of specific antibodies and/or cellular cytotoxic activity.

The role of the immune system in human cancer has been under debate for several years. It has been puzzling, for example, that an increased incidence of malignant tumors is not observed in immunocompromised animals, such as nude mice. It is, however, now clarified that these animal models were in reality not profoundly immunocompromised, but were still able to mount a significant anti-tumour immune reactivity. When severely immunocompromised transgenic mice of the Stat 1−/−, IFNγR−/−, or RAG2−/− genotypes were studied, the tumor incidence and the immunogenicity of cancers growing in these animals strongly supported the existence of an immune mediated anti-cancer reactivity with the capacity to control cancer development. Based on these results, the immunoediting model was developed (Dunn and Schreiber, Immunity, 21:137-148 (2004)).

Similarly, the modest increase in cancer incidence in therapeutically immunosuppressed, allo-organ transplanted patients seems to be explained by the early appearance of immunosuppression in epithelial cancers (Schüle J, et al., Breast Cancer Res Treat. 2002; 74:33-40; Wolfram R M, et al., Int J Cancer. 2000; 88:239-44, Petersen R P, et al., Cancer. 2006; 107:2866-72). The occurrence of spontaneous immune-mediated tumor regression, the correlation between tumor-infiltrating lymphocytes and prognosis, the occurrence of tumor specific cytotoxic T-lymphocytes and antibodies and the efficacy of immunostimulatory treatment all support a significant role of the immune system in the control or regulation of cancer progression.

These observations are also consistent with the results of Clinchy et al. (Clinchy B, et al., Cancer. 2007; 109:1742-9), showing that dysregulation of the immune system in cancer, with an enhanced capacity to produce IL-6, correlate to poor prognosis in radically resected colorectal cancer patients. Not even in the group of high risk patients with locally advance tumors, T3N1-2, did patients die from their cancer if their immune cells exhibited a normal production of IL-6. Similarly, Galon et al. (Galon J, et al., Science. 2006; 313:1960-4, Mlecnik B, et al., J Clin Oncol. 2011, 29:610-8) have shown that T-cell immune parameters strongly correlate to the prognosis in these patients.

The majority of human cancers of different origin induce immune mediated anti-tumor reactivity, but immunosuppressor mechanisms often appearing at an early stage, compromise the immune system. The existence of regional immunosuppression in the absence of systemic suppression (concomitant immunity), indicates a regional, systemic gradient of immunosuppression (Gorelik E., et al., Adv Cancer Res. 1983; 39:71-120). For instance, the function of immune cells can be more impaired near the tumor than in peripheral blood (Vose B M, et al., Int J Cancer 1977 20:895-902). Several factors may mediate this suppression (Ménétrier-Caux C, et al., Br J Cancer 1999 79: 119-130, Heimdal J H, et al., Scand J Immunol 2000 51: 271-278, Heimdal J H, et al., Scand J Immunol 2001 53: 162-170), but no fundamental mechanism has been identified (Kim R, et al., Cancer Res. 2006 Jun. 1; 66(11):5527-36, Mocellin S, et al., J Immunother 2001 24:392-407). The impact of the hostile intra-tumoral milieu has been described by several groups (Perdrizet G A, et al., J Exp Med. 1990; 171:1205-20, Yu P, et al., J Exp Med. 2005 201:779-91.) Immune reactivity against cancer can be suppressed at various levels, e.g., initiation, recruitment of effector cells to the tumor and migration of these cells within the tumor and their cytotoxic activity. Effector mechanisms present at the tumor site can also provide immune mediated cancer control.

Although data indicate that the immune system is of major importance for cancer control (Dunn G P, et al., Immunity. 2004 21:137-48, Galon J, et al., Science. 2006 313:1960-4, Koebel C M, et al., Nature. 2007 450:903-7, Clinchy B, et al., Cancer. 2007 109:1742-9, Teng M W, et al., J Leukoc Biol. 2008 84:988-93) malignant tumors continue to grow and the efficacy of immunotherapy is rather poor with an objective remission rate of 10-20%. There can be several reasons for this apparent paradox, e.g., tumors avoid recognition by the immune system due to tumor antigens being weak self-antigens, poor antigen presentation due to down-regulation of TAP and MHC I and II) or induction of tolerance or cancer related immunosuppression. The impact of an hostile intra-tumoral milieu is demonstrated by results from animal experiments (Perdrizet G A, et al., J Exp Med. 1990; 171:1205-20, Yu P, et al., J Exp Med. 2005 201:779-91) and human tumors (Gajewski T F, et al., J Immunother. 2006 29:233-40, Whiteside T L, Oncogene. 2008 27:5904-12).

Different types of immunosuppressor cells, regulatory T-cells, immature dendritic cells (iDC), tumor associated macrophages (TAM) and myeloid derived suppressor cells (MDSC), can function substantially in cancer related immunosuppression. The immune balance is generally skewed to a Th2 dominance characterized by cytokines, such as IL-4, IL-10 and PGE2. Additionally, other immunosuppressor mechanisms, such as serum blocking factors, circulating immune complexes, enhanced IL-1Ra production and enhanced intra-tumoral proteolytic activity can function in cancer related immunosuppression.

While investigating mechanisms for induction of interleukin-6 (IL-6) in cancer patients, immunoregulatory peptide sequences derived from serum albumin were found (see e.g., U.S. Pat. Nos. 7,960,126; 8,110,347; and 8,110,347; as well as, US Publication No. 2010/0323370, each of which is hereby expressly incorporated by reference in their entireties. Interleukin-2 (IL-2) plays a major role in initiation and activation of the immune response and its capacity to induce lymphokine activated killer cells (LAK-cells), T-cell proliferation and cytotoxicity. Several reports have shown that peripheral blood mononuclear cells (PBMC) from cancer patients have a diminished capacity to both synthesize (Wanebo H J, et al., Cancer. 1986 57:656-62, Mantovani, G., et al., Diagn. Clin. Immunol. 1987 5: 104-111, Lauerova L, et al., Neoplasma 1999 46: 141-149) and respond to IL-2 (Tsubono M, et al., J Clin Lab Immunol 1990 33:107-115, Pellegrini P, et al., Cancer Immunol Immunother 1996 42:1-8). Soluble products from tumor explants or serum from cancer patients can inhibit cytokine production, inhibit IL-2 receptor expression (Botti C, et al., Intl J Biol Markers 1998 13:51-69, Lauerova L, et al., Neoplasma 1999 46:141-149) and/or reduce the proliferative capacity in normal T lymphocytes (Botti C, et al., Intl J Biol Markers 1998 13:51-69).

Integrins are a superfamily of transmembrane glycoproteins, found predominantly on leukocytes that mediate cell-cell and cell substratum interactions. Integrins play an important role in immune regulation, as well, in particular αLβ2, (Leukocyte Function Associated molecule-1, LFA-1) is of pivotal importance for the initiation and regulation of an immune response, tissue recruitment and migration of inflammatory cells and cytotoxic activity of lymphocytes (Hogg N, et al., J Cell Sci. 2003 116:4695-705, Giblin P A, et al., Curr Pharm Des. 2006 12:2771-95, Evans R, et al., Cell Sci. 2009 122:215-25). In addition, LFA-1 is involved in the proliferative response to interleukin-2 (Vyth-Dreese F A, Eur J Immunol. 1993 12:3292-9) and some fragments of albumin bind to LFA-1 and/or the IL-2 receptor thereby modulating the functional properties mediated through these receptors including immune cell proliferation (see U.S. Publication No. 2011/0262470, which is hereby expressly incorporated by reference in its entirety). Despite these advancements, the need for more compositions to modulate the immune system, especially in individuals that have a compromised immune system and/or cancer, is manifest.

BRIEF SUMMARY OF THE INVENTION

A number of Alternatives are provided herein:

In Alternative 1, a method of treating, inhibiting, or ameliorating a cancer, such as a metastatic cancer is provided, the cancer comprising a first tumor and a second tumor in a subject. The method can comprise administering a composition comprising an isolated peptide comprising the amino acid sequence FFVKLS (SEQ ID NO: 62) to the subject, in which (a) the composition is administered intratumorally or peritumorally to the first tumor, but not the second tumor, or (b) the composition is administered at a site in the subject that is neither intratumoral or peritumoral to either of the first tumor or the second tumor, such as systemically, thus ameliorating, inhibiting, or eliminating the first tumor and ameliorating, inhibiting, or eliminating the second tumor.

Alternative 2 comprises the method of Alternative 1, in which the first tumor comprises a prostate tumor, a melanoma, a lung carcinoma, a colon cancer, an Apocrine gland carcinoma, a testis tumor, a mast cell tumor, a mammary tumor, a mucinous carcinoma, or a histicytoma, and wherein the second tumor is a same or different type of tumor as the first tumor.

Alternative 3 comprises the method of Alternative 2, in which the mammary tumor comprises a malignant mammary tumor, or the mammary tumor comprises a mixed mammary tumor (for example a malignant mixed mammary tumor).

Alternative 4 comprises the method of Alternative 3, in which the mucinous carcinoma comprises a mammary gland mucinous carcinoma.

Alternative 5 comprises the method of any one of Alternatives 1-4, in which, wherein the second tumor is the same type of tumor as the first tumor.

Alternative 6 comprises the method of any one of Alternatives 1-4, in which the second tumor is a different type of tumor from the first tumor.

Alternative 7 comprises the method of Alternative 6, in which the second tumor comprises a prostate tumor, a melanoma, a lung carcinoma, a colon cancer, an Apocrine gland carcinoma, a testis tumor, a mast cell tumor, a mammary tumor, a mucinous carcinoma, or a histicytoma.

Alternative 8 comprises the method of any one of Alternatives 1-7, in which the first tumor is a primary tumor and the second tumor comprises a metastatic tumor tumor.

Alternative 9 comprises the method of any one of Alternatives 1-7, in which the first tumor is a metastatic tumor and the second tumor is a metastatic tumor.

Alternative 10 comprises the method of any one of Alternatives 1-7, in which wherein the first tumor is a primary tumor and the second tumor is a primary tumor.

Alternative 11 comprises the method of any one of Alternatives 1-10, in which (a) said composition is administered intratumorally or peritumorally to the first tumor, but not the second tumor.

Alternative 12 comprises the method of any one of Alternatives 1-10, in which (b) said composition is administered a site in the subject that is neither intratumoral or peritumoral to either of the first tumor or the second tumor.

Alternative 13 comprises the method of Alternative 12, in which said composition is administered systemically to the subject.

Alternative 14 comprises the method of Alternative 13, in which said systemic administration comprises enteral administration or parenteral administration.

Alternative 15 comprises the method of Alternative 13, in which said systemic administration comprises at least one of subcutaneous, intravenous, intraperitoneal, or intramuscular administration.

Alternative 16 comprises the method of any one of Alternatives 1-15, in which the administering further induces regressive changes in the first tumor, thereby ameliorating, inhibiting, or eliminating the first tumor.

Alternative 17 comprises the method of any one of Alternatives 1-16, in which the administering further induces immune cell infiltration of the first tumor, thereby ameliorating, inhibiting, or eliminating the first tumor.

Alternative 18 comprises the method of any one of Alternatives 1-17, in which the administering further induces eradication of cells of the first tumor, thereby ameliorating, inhibiting, or eliminating the first tumor.

Alternative 19 comprises the method of any one of Alternatives 1-18, in which the administering further induces eradication of the first tumor, thereby eliminating the first tumor.

Alternative 20 comprises the method of any one of Alternatives 1-19, in which the administering further induces regressive changes in the second tumor, thereby ameliorating, inhibiting, or eliminating the second tumor.

Alternative 21 comprises the method of any one of Alternatives 1-20, in which the administering further induces immune cell infiltration of the second tumor, thereby ameliorating, inhibiting, or eliminating the second tumor.

Alternative 22 comprises the method of any one of Alternatives 1-21, in which the administering further induces eradication of cells of the second tumor, thereby ameliorating, inhibiting, or eliminating the second tumor.

Alternative 23 comprises the method of any one of Alternatives 1-22, in which the administering further induces eradication of the second tumor, thereby eliminating the second tumor.

Alternative 24 comprises the method of any one of Alternatives 1-23, in which the isolated peptide is administered to the subject at a dose of at least about 1 ng/kg.

Alternative 25 comprises a method of ameliorating, inhibiting, or treating a cancer comprising administering an isolated peptide comprising the amino acid sequence FFVKLS (SEQ ID NO: 62) to a subject having a first tumor, wherein said isolated peptide is administered to a site in the subject other than the first tumor, but is not administered intratumorally to the first tumor and is not administered peritumorally to the first tumor, thereby ameliorating or eliminating the first tumor.

Alternative 26 comprises the method of Alternative 25, in which the subject further comprises a second tumor in a different location than the first tumor and different from the site of administration, and wherein said second tumor is further ameliorated, inhibited, or eliminated.

Alternative 27 comprises the method of Alternative 25, in which the subject further comprises a second tumor in a different location than the first tumor, wherein said second tumor comprises the site of administration, and wherein said second tumor is further ameliorated, inhibited, or eliminated.

Alternative 28 comprises the method of Alternative 25, in which the isolated peptide is administered intratumorally or peritumroally to the second tumor.

Alternative 28 comprises the method of any one of Alternatives 26-28, in which said subject has metastatic cancer, said metastatic cancer comprising said first and second tumors, and wherein said metastatic cancer is ameliorated, inhibited, or eliminated.

Alternative 30 comprises the method of any one of Alternatives 25-27 or 29, in which said isolated peptide is administered systemically to the subject.

Alternative 31 comprises the method of Alternative 30, in which said systemic administration comprises enteral administration or parenteral administration.

Alternative 32 comprises the method of Alternative 60, in which said systemic administration comprises at least one of subcutaneous, intravenous, intraperitoneal, or intramuscular administration.

Alternative 33 comprises the method of any one of Alternatives 25-32, in which the administering further induces regressive changes in the first tumor, thereby ameliorating, inhibiting or eliminating the first tumor.

Alternative 34 comprises the method of any one of Alternatives 25-33, in which the administering further induces immune cell infiltration of the first tumor, thereby ameliorating, inhibiting or eliminating the first tumor.

Alternative 35 comprises the method of any one of Alternatives 25-34, in which the administering further induces eradication of cells of the first tumor, thereby ameliorating, inhibiting or eliminating the first tumor.

Alternative 36 comprises the method of any one of Alternatives 25-35, in which the administering further induces eradication of the first tumor, thereby ameliorating, inhibiting or eliminating the first tumor.

Alternative 37 comprises the method of any one of Alternatives 26-36, in which the administering further induces regressive changes in the second tumor, thereby ameliorating, inhibiting or eliminating the second tumor.

Alternative 38 comprises the method of any one of Alternatives 26-37, in which the administering further induces immune cell infiltration of the second tumor, thereby ameliorating, inhibiting or eliminating the second tumor.

Alternative 39 comprises the method of any one of Alternatives 26-38, in which the administering further induces eradication of cells of the second tumor, thereby eliminating the second tumor.

Alternative 40 comprises the method of any one of Alternatives 26-39, in which the administering further induces eradication of the second tumor, thereby eliminating the second tumor.

Alternative 41 comprises the method of any one of Alternatives 1-40, in which said isolated peptide comprises no more than 30 amino acid residues.

Alternative 42 comprises the method of any one of Alternatives 1-40, in which said isolated peptide comprises no more than 20 amino acid residues.

Alternative 43 comprises the method of any one of Alternatives 1-40, in which said isolated peptide comprises no more than 16 amino acid residues.

Alternative 44 comprises the method of any one of Alternatives 1-40, in which said isolated peptide consists of the amino acid sequence FFVKLS (SEQ ID NO: 62).

Alternative 45 comprises the method of any one of Alternatives 1-40, in which said isolated peptide comprises the amino acid sequence KKLDTFFVKLSLFTER (SEQ ID NO: 2).

Alternative 46 comprises the method of any one of Alternatives 1-40, in which said isolated peptide consists of the amino acid sequence KKLDTFFVKLSLFTER (SEQ ID NO: 2).

Alternative 47 comprises the method of any one of Alternatives 1-42, in which said isolated peptide comprises the amino acid sequence RKLDTFFVKLSLFTERRR (SEQ ID NO: 586).

Alternative 48 comprises the method of any one of Alternatives 1-40, in which said isolated peptide consists of the amino acid sequence RKLDTFFVKLSLFTERRR (SEQ ID NO: 586).

Alternative 49 comprises an isolated peptide for use in treating, inhibiting or ameliorating a cancer, such as metastatic cancer, said cancer comprising a first tumor and a metastatic tumor in a subject, said isolated and said use comprising: (a) intratumoral administration or petitumoral administration of the isolated peptide to the first tumor, but not the metastatic tumor; or (b) administration of the isolated peptide to a site in the subject that is neither intratumoral nor peritumoral to either of the first tumor or the metastatic tumor, such as systemically, thus ameliorating, inhibiting or eliminating the first tumor, and ameliorating or eliminating the metastatic tumor.

Alternative 50 comprises the isolated peptide for use according to Alternative 49, in which the first tumor comprises a prostate tumor, a melanoma, a lung carcinoma, a colon cancer, an Apocrine gland carcinoma, a testis tumor, a mast cell tumor, a mammary tumor, a mucinous carcinoma, or a histicytoma, and wherein the metastatic tumor is a same or different type of tumor as the first tumor.

Alternative 51 comprises the isolated peptide for use according to Alternative 50, in which the mammary tumor comprises a malignant mammary tumor, or the mammary tumor comprises a mixed mammary tumor (for example a malignant mixed mammary tumor), or wherein the mammary tumor comprises a mucinous carcinoma comprising a mammary gland mucinous carcinoma.

Alternative 52 comprises the isolated peptide for use according to any one of Alternatives 49-51, in which the metastatic tumor is the same type of tumor as the first tumor.

Alternative 53 comprises the isolated peptide for use according to any one of Alternatives 49-51, in which the metastatic tumor is a different type of tumor from the first tumor.

Alternative 54 comprises the isolated peptide for use according to Alternative 50, in which the metastatic tumor comprises a prostate tumor, a melanoma, a colon cancer, a lung carcinoma, an Apocrine gland carcinoma, a testis tumor, a mast cell tumor, a mammary tumor, a mucinous carcinoma, or a histicytoma.

Alternative 55 comprises the isolated peptide for use according to any one of Alternatives 49-54, in which said use comprises administering said composition intratumorally or peritumorally to the first tumor.

Alternative 56 comprises the isolated peptide for use according to any one of Alternatives 49-54, in which said use comprises administering the composition to a site in the subject that is neither intratumoral or peritumoral to either of the first tumor or the metastatic tumor Alternative 57 comprises the isolated peptide for use according to any one of Alternatives 49-56, in which said isolated peptide is administered systemically to the subject.

Alternative 58 comprises the isolated peptide for use according to Alternative 57, in which said composition is administered systemically via at least one of subcutaneous, intravenous, intraperitoneal, or intramuscular administration.

Alternative 59 comprises the isolated peptide for use according to any one of Alternatives 49-58, in which the administering further induces regressive changes in the first tumor, thereby ameliorating or eliminating the first tumor.

Alternative 60 comprises the isolated peptide for use according to any one of Alternatives 49-59, in which the administering further induces immune cell infiltration of the first tumor, thereby ameliorating, inhibiting or eliminating the first tumor.

Alternative 61 comprises the isolated peptide for use according to any one of Alternatives 49-60, in which the administering further induces eradication of cells of the first tumor, thereby ameliorating, inhibiting or eliminating the first tumor.

Alternative 62 comprises the isolated peptide for use according to any one of Alternatives 49-61, in which the administering further induces eradication of the first tumor, thereby eliminating the first tumor.

Alternative 63 comprises the isolated peptide for use according to any one of Alternatives 49-62, in which the administering further induces regressive changes in the metastatic tumor, thereby ameliorating, inhibiting or eliminating the metastatic tumor.

Alternative 64 comprises the isolated peptide for use according to any one of Alternatives 49-63, in which the administering further induces immune cell infiltration of the metastatic tumor, thereby ameliorating, inhibiting or eliminating the metastatic tumor.

Alternative 65 comprises the isolated peptide for use according to any one of Alternatives 49-64, in which the administering further induces eradication of cells of the metastatic tumor, thereby ameliorating, inhibiting or eliminating the metastatic tumor.

Alternative 66 comprises the isolated peptide for use according to any one of Alternatives 49-65, in which the administering further induces eradication of the metastatic tumor, thereby eliminating the metastatic tumor.

Alternative 67 comprises the isolated peptide for use according to any one of Alternatives 49-66, in which the first tumor is a primary tumor.

Alternative 68 comprises the isolated peptide for use according to any one of Alternatives 49-66, in which the first tumor is an other metastatic tumor.

Alternative 69 comprises the isolated peptide for use according to any one of Alternatives 49-68, in which said isolated peptide comprises no more than 30 amino acid residues.

Alternative 70 comprises the isolated peptide for use according to any one of Alternatives 49-68, in which said isolated peptide comprises no more than 20 amino acid residues.

Alternative 71 comprises the isolated peptide for use according to any one of Alternatives 49-68, in which said isolated peptide comprises no more than 16 amino acid residues.

Alternative 72 comprises the isolated peptide for use according to any one of Alternatives 49-68, in which said isolated peptide consists of the amino acid sequence FFVKLS (SEQ ID NO: 62).

Alternative 73 comprises the isolated peptide for use according to any one of Alternatives 49-70, in which said isolated peptide comprises the amino acid sequence KKLDTFFVKLSLFTER (SEQ ID NO: 2).

Alternative 74 comprises the isolated peptide for use according to any one of Alternatives 49-68, in which said isolated peptide consists of the amino acid sequence KKLDTFFVKLSLFTER (SEQ ID NO: 2)

Alternative 75 comprises the isolated peptide for use according to any one of Alternatives 49-70, in which said isolated peptide comprises the amino acid sequence RKLDTFFVKLSLFTERRR (SEQ ID NO: 586).

Alternative 76 comprises the isolated peptide for use according to any one of Alternatives 49-68, in which said isolated peptide consists of the amino acid sequence RKLDTFFVKLSLFTERRR (SEQ ID NO: 586).

Alternative 77 comprises the isolated peptide for use according to any one of Alternatives 49-76, in which the composition is for use in administering the isolated peptide to the subject at a dose of at least about 1 ng/kg.

Alternative 78 comprises a composition comprising an isolated peptide comprising the amino acid sequence FFVKLS (SEQ ID NO: 62), and a support, such as a nanoparticle, in which the isolated peptide is immobilized on the nanoparticle.

Alternative 79 comprises the composition of Alternative 78, in which the support comprises the nanoparticle.

Alternative 80 comprises the composition of Alternative 78, in which the support comprises the nanoparticle comprising at least one of: a polymer (such as PLGA, glycerol, chitosan, DNA, a hydrogel, or an acrylamide), a dendrimer (such as PAMAM), a quantum dot (such as CdSe, CuInSe, or CdTe), a gold nanoparticle (such as a sphere, rod, or shell), a silica nanoparticle (such as a sphere, a shell, or a mesoporous structure), a magnetic particle (such as an iron oxide, a cobalt-based material, a magnetic sphere, an aggregate in dextran or silica, or a Dynal® bead), a carbon-based material (such as a carbon nanotube, a buckminsterfullerene, a graphene, or an activated carbon), a carbohydrate, a nucleic acid, a polypeptide (such as an albumin or an albumin fragment), or a lipid.

Alternative 81 comprises the composition of any one of Alternatives 78-80, in which said isolated peptide comprises no more than 30 amino acid residues.

Alternative 82 comprises the composition of any one of Alternatives 78-80, in which said isolated peptide comprises no more than 20 amino acid residues.

Alternative 83 comprises the composition of any one of Alternatives 78-80, in which said isolated peptide comprises no more than 16 amino acid residues.

Alternative 84 comprises the composition of any one of Alternatives 78-80, in which said isolated peptide consists of the amino acid sequence FFVKLS (SEQ ID NO: 62).

Alternative 85 comprises the composition of any one of Alternatives 78-82, in which said isolated peptide comprises the amino acid sequence KKLDTFFVKLSLFTER (SEQ ID NO: 2).

Alternative 86 comprises the composition of any one of Alternatives 78-80, in which said isolated peptide consists of the amino acid sequence KKLDTFFVKLSLFTER (SEQ ID NO: 2)

Alternative 87 comprises the composition of any one of Alternatives 78-82, in which said isolated peptide comprises the amino acid sequence RKLDTFFVKLSLFTERRR (SEQ ID NO: 586).

Alternative 88 comprises the composition of any one of Alternatives 78-80, in which said isolated peptide consists of the amino acid sequence RKLDTFFVKLSLFTERRR (SEQ ID NO: 586).

Alternative 89 comprises the composition of any one of Alternatives 78-88 for use in treating, inhibiting or ameliorating a cancer, such as metastatic cancer, said cancer comprising a first tumor and a metastatic tumor in a subject, in which the use comprises: (a) intratumoral administration or petitumoral administration of the composition to the first tumor, but not the metastatic tumor; or (b) administration of the composition to a site in the subject that is neither intratumoral nor peritumoral to either of the first tumor or the metastatic tumor, such as systemically, thus ameliorating, inhibiting or eliminating the first tumor, and ameliorating or eliminating the metastatic tumor.

Alternative 90 comprises the composition for use according to Alternative 89, in which the first tumor comprises a prostate tumor, a melanoma, a lung carcinoma, a colon cancer, an Apocrine gland carcinoma, a testis tumor, a mast cell tumor, a mammary tumor, a mucinous carcinoma, or a histicytoma, and wherein the metastatic tumor is a same or different type of tumor as the first tumor.

Alternative 91 comprises the composition for use according to Alternative 90, in which the mammary tumor comprises a malignant mammary tumor, or the mammary tumor comprises a mixed mammary tumor (for example a malignant mixed mammary tumor), or wherein the mammary tumor comprises a mucinous carcinoma comprising a mammary gland mucinous carcinoma.

Alternative 92 comprises the composition for use according to any one of Alternatives 89-91, in which the metastatic tumor is the same type of tumor as the first tumor.

Alternative 93 comprises the composition for use according to any one of Alternatives 89-91, in which the metastatic tumor is a different type of tumor from the first tumor.

Alternative 94 comprises the composition for use according to Alternative 93, in which the metastatic tumor comprises a prostate tumor, a melanoma, a colon cancer, a lung carcinoma, an Apocrine gland carcinoma, a testis tumor, a mast cell tumor, a mammary tumor, a mucinous carcinoma, or a histicytoma.

Alternative 95 comprises the composition for use according to any one of Alternatives 89-94, in which said use comprises administering said composition intratumorally or peritumorally to the first tumor.

Alternative 96 comprises the composition for use according to any one of Alternatives 89-94, in which said use comprises administering the composition to a site in the subject that is neither intratumoral or peritumoral to either of the first tumor or the metastatic tumor Alternative 97 comprises the composition for use according to Alternative 96, in which said composition is administered systemically to the subject.

Alternative 98 comprises the composition for use according to Alternative 97, in which said composition is administered systemically via at least one of subcutaneous, intravenous, intraperitoneal, or intramuscular administration.

BRIEF DESCRIPTION OF THE DRAWINGS

FIG. 9A depicts effects for K5 and K6. FIG. 9B depicts effects for K12 and K13.

FIG. 18B is a contrast-enhanced image of FIG. 18A, so as to depict the binding data for non biotinylated IL-2 (triangles;

FIG. 19 illustrates the α-chain of the IL-2 receptor (CD25) binding P3028 (A) at the IL-2 binding site (B).

FIG. 23 illustrates identification of P3028 inhibitors in solution. Based on previous analyses potential binders of P3028 were synthesized on a chip. FIG. 23A illustrates results for assays 1-14. FIG. 23B illustrates results for assays 15-28. FIGS. 23A and 23B represent the left and right sides, respectively, of a single graph that was enlarged to show the text more clearly. The Y axis has been reproduced in FIG. 23B for reference.

FIG. 24 illustrates stimulatory activity of P28R on suppressed proliferative response to IL-2.

FIG. 28 illustrates single amino acid substitutions of peptide P28R having rampo scores greater than 500.

FIG. 30 illustrates rampo scores for binding of P3028 to internal deletion mutants, and single amino acid substitution mutants of peptide P28R.

FIG. 31 illustrates favorable electrostatic interactions and hydrophobic interactions between peptide 3028 and peptide KKL15.

Figure 32:
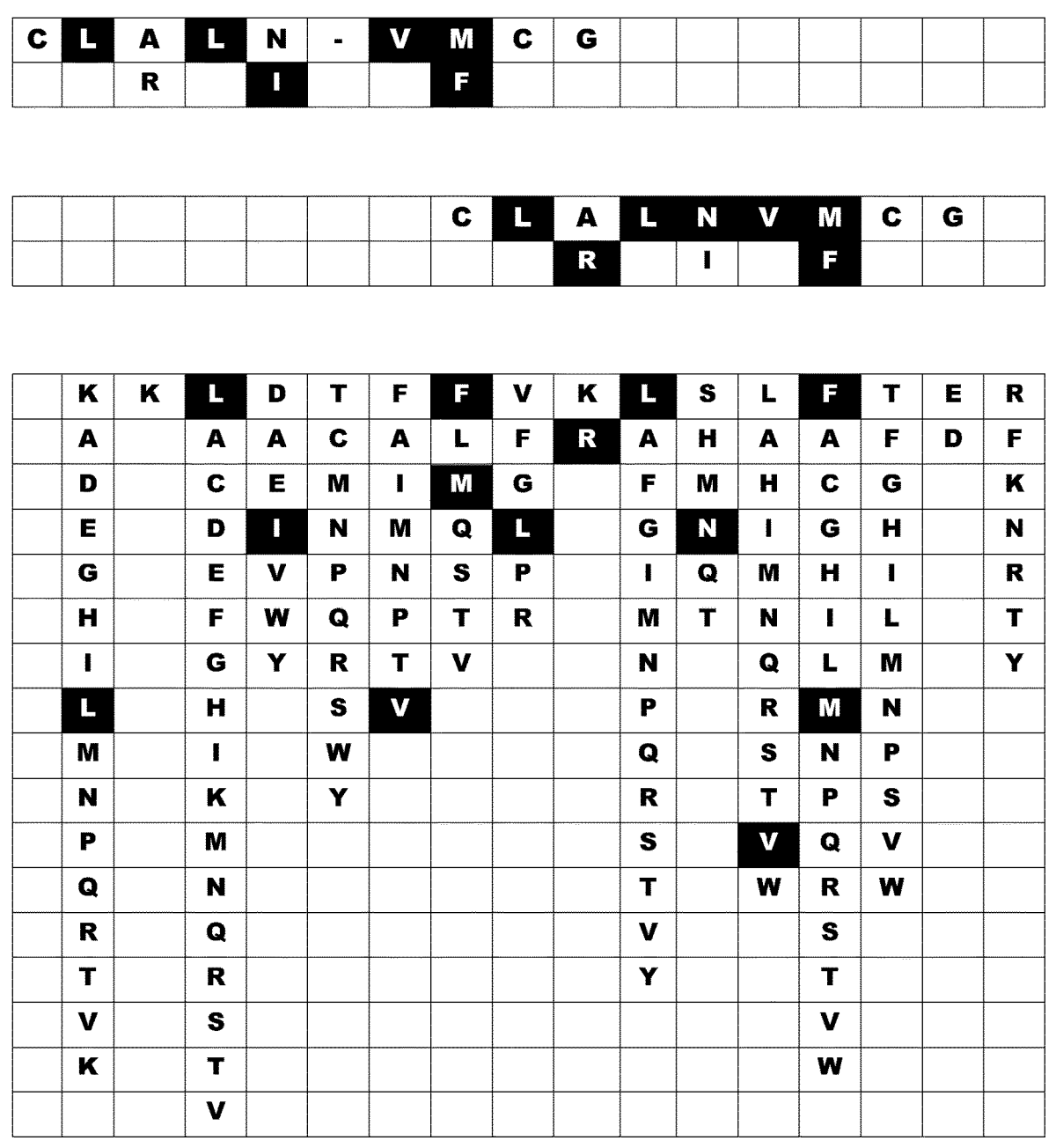

FIG. 32 illustrates alignments of cyclic peptides identified as binding to P3028 in positional scan experiments (SEQ ID NOs: 265-267) and linear peptides identified as binding to P3028 (SEQ ID NOs: 2, and 268-293).

FIG. 41 is a series of graphs illustrating effects of modified peptides on activation of PBMCs from healthy control person. PBMCs were incubated with the peptides (40 µg/mL) for 24 hours in RPMI plus 10% human AB serum. Activation is determined as percentage of cells with enhanced marker CD69 using flow cytometry.

FIG. 42 is a series of graphs illustrating effects of the full length peptide P28R and the 6 amino acid central sequence (32230, FFVKLS, SEQ ID NO: 62) in culture medium containing normal human AB serum. Activation is determined as percentage of cells with enhanced marker CD69 or CD71 using flow cytometry. PBMCs were incubated with the peptides (40 µg/mL) for 24 hours in RPMI plus 10% human AB serum.

FIG. 48 is a series of microscope images illustrating that tumor cells can generate P3028 structures in accordance with some embodiments herein.

FIG. 49 is a series of microscope images illustrating that administration of immunoregulatory peptide inhibitors immobilized on nanoparticles in accordance with some embodiments herein can remove bound dHSA from immune cells.

FIG. 61 is a series of microscope images illustrating H&E staining of dog tumors in accordance with some embodiments herein.

FIG. 62 is a series of microscope images illustrating a dog Apocrine gland carcinoma stained for CD45+ inflammatory cells in accordance with some embodiments herein.

FIG. 63 is a series of microscope images illustrating only few scattered CD3+ or CD8+ cells were found after treatment in this dog tumour in accordance with some embodiments herein. Two images of the tumor.

FIG. 66 is a series of microscope images illustrating biopsies of a dog testis tumor in accordance with some embodiments herein.

FIG. 70 is a series of microscope images illustrating a dog mastocytoma after intra-tumoral treatment with P28R in accordance with some embodiments herein.

FIG. 72 is a series of microscope images illustrating H&E staining of the central slice of the dog breast tumour showing infiltration of inflammatory cells with various degrees of tumour regressive changes from well preserved glandular structures to scattered tumour cells surrounded by inflammatory cells in accordance with some embodiments herein.

FIG. 73 is a series of microscope images illustrating H&E staining of a regional metastatic lesion of dog breast tumor showing infiltration of inflammatory cells with various degrees of tumour regressive changes, from well preserved glandular structures to scattered tumour cells surrounded by inflammatory cells in accordance with some embodiments herein.

FIG. 75 is a series of microscope images illustrating staining of a regional metastatic lesion of a dog breast tumor showing infiltration of CD45+ inflammatory cells in tumour areas with various degrees of regressive changes in accordance with some embodiments herein.

FIG. 77 is a series of microscope images illustrating staining of a regional metastatic lesion showing infiltration of CD45+ inflammatory cells in dog breast tumour areas with various degrees of regressive changes in accordance with some embodiments herein.

FIG. 92A shows an untreated tumour in an untreated control mouse. FIG. 92B shows a tumour treated with 12 microgram P28R, twice weekly for two weeks.

FIG. 93A illustrates a saline control, and FIG. 93B illustrates a mouse injected with oligoclonal rabbit antibody against P3028.

DETAILED DESCRIPTION OF THE INVENTION

Figure 2:
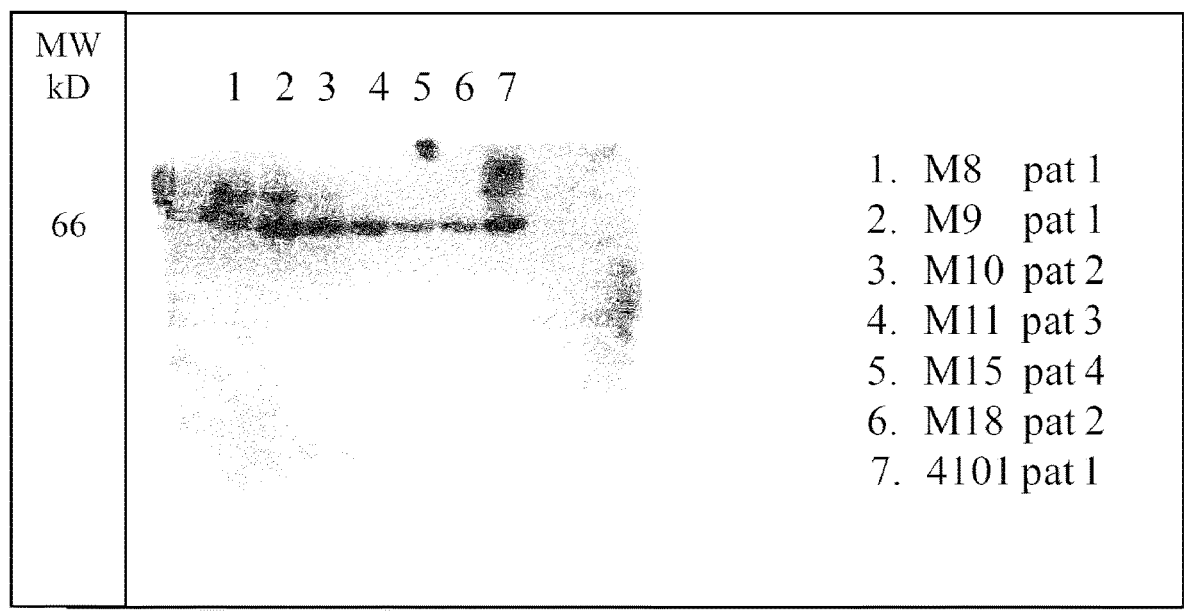
FIG. 2 illustrates Western blot performed on tumor extracts using antibodies directed against the 3028-structure.

Several immunoregulatory peptide inhibitors, which interact with immunoregulatory peptides that cause immunosuppression in a human (e.g., a human having cancer, enduring or chronic infectious or inflammatory disease), have been developed. Preferred immunoregulatory peptide inhibitors bind to proteins or peptides that comprise the P3028 structure and/or the P3028 sequence (SEQ ID NO: 185). With reference to some embodiments and description herein, the P3028 structure refers to polypeptides, such as peptides, proteins, and the like that include the P3028 sequence (SEQ ID NO: 185). The P3028 structure can include macromolecules such as peptides, proteins, and the like that are recognized by antibodies that bind specifically to P3028 structures (see Example 1 and FIG. 2). For example, aggregates of albumin, denatured albumin and other damaged albumins can include the P3028 structure. In some contexts in the present application, the P3028 structure, P3028 sequence, and P3028 are terms used interchangeably. Molecules having the P3028 structure interact with receptors on immune cells, such as the IL-2 receptor and the LFA-1 receptor, causing immunosuppression. As such, it is contemplated herein that peptides, proteins, albumin fragments, damaged albumin (e.g. denature albumin) and albumin aggregates can include the P3028 structure, and can interact with immune cell receptors such as the IL-2 receptor and LFA-1 receptor. Immunosuppression can be characterized by a reduced immune cell proliferation, spreading and migration, as well as, NK-cell cytotoxicity. In the presence of an immunoregulatory peptide inhibitor, as described herein; however, the immunosuppression mediated by the P3028 structure can be altered (e.g., reduced, ameliorated, eliminated, or removed altogether). In some experiments, for example, it was found that an immunoregulatory peptide inhibitor can remove a molecule including a P3028 structure from the LFA-1 receptor thereby altering the immunosuppression mediated by P3028 structure. Accordingly, the description that follows provides details on many different classes of immunoregulatory peptide inhibitors including, but not limited to, antibody or antibody fragment based immunoregulatory peptide inhibitors, peptide based immunoregulatory peptide inhibitors, peptidomimetic immunoregulatory peptide inhibitors, modified immunoregulatory peptide inhibitors (e.g., containing a D amino acid, N-terminal acetyl, or C terminal amide group), cyclic peptides inhibitors, and aptamer based immunoregulatory peptide inhibitors, as well as compositions comprising immunoregulatory inhibitors, for example compositions comprising immunoregulatory peptide inhibitors. Methods of using compositions (as described herein) to reduce immunosuppression or an aspect thereof (e.g., reducing a P3028-mediated inhibition of immune cell proliferation, spreading, migration, or NK-cell cytotoxicity), as well as, approaches to inhibit, reduce, or alter the progression of cancer (e.g. inducing immune cell infiltration of tumors, inducing regressive changes in tumors, and/or inducing eradiation or some or all of a tumor) or inflammatory disease are provided. The composition can comprise, consist of, or consist essentially of an immunoregulatory peptide inhibitor as described herein. Accordingly, compositions comprising immunoregulatory peptide inhibitors as described herein can be useful for ameliorating, reducing the symptoms of, reducing the severity of, and/or treating immunosuppression.

Immunoregulatory peptide inhibitors as described herein interact with or bind to proteins or peptides that comprise at least one of sequence SEQ ID NOs: 183-185 or 188-246. Such peptides can have immunoregulatory properties similar to P3028 sequences and structures (see Examples 17 to 26).

With reference to some embodiments in the following disclosure, amino acids, or amino acid residues can be referred to by either a three-letter or a one-letter code. Twenty amino acids are typically encoded by the genetic code, and can be referred to using the following codes or abbreviations herein: Arginine ("Arg" or "R"), Histidine ("His" or "H"), Lysine ("Lys" or "K"), Aspartic Acid ("Asp"

or "D"), Glutamic Acid ("Glu" or "E"), Serine ("Ser" or "S"), Threonine ("Thr" or "T"), Asparagine ("Asp" or "N"), Glutamine ("Gln" or "Q"), Cysteine ("Cys" or "C"), Glycine ("Gly" or "G"), Proline ("Pro" or "P"), Alanine ("Ala" or "A"), Valine ("Val" or "V"), Isoleucine ("Be" or "I"), Leucine ("Leu" or "L"), Methionine ("Met" or "M"), Phenylalanine ("Phe" or "F"), Tyrosine ("Tyr" or "Y"), Tryptophan ("Trp" or "W").

With reference to some embodiments in the following disclosure by "peptide" is meant a protein and/or a fragment of a protein, which may have several different lengths (e.g., at least or equal to 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 120, 140, 160, 180, 200, 240, 260, 300, 350, 400, 450, 500, 600, 700, 800, or 1000 amino acids or a range defined by any number in between these numbers).

With reference to some embodiments in the following disclosure, amino acids (and their residues) can be categorized according to various characteristics of the side chains of the alpha carbon of the amino acid. It is noted that the twenty naturally occurring amino acids encoded by the genetic code, and also synthetic amino acids are contemplated herein. As used herein "hydrophobic amino acid" (including pluralizations and variations of this root term) refer to naturally occurring or synthetic amino acids having a hydrophobic side chain, for example A, V, I, L, M, F, Y, or W. As used herein, "positively charged amino acid" (including pluralizations and variations of this root term) refer to naturally occurring or synthetic amino acids having a positively charged side chain, for example, R, H, or K. As used herein, "negatively charged amino acid" (including pluralizations and variations of this root term) refer to naturally occurring or synthetic amino acids having a negatively charged side chain, for example, D or E. As used herein, "hydrophobic non-aromatic carbon chain amino acid" (including pluralizations and variations of this root term) refer to naturally occurring or synthetic amino acids having a hydrophobic non-aromatic carbon side chain, for example, A, V, I, or L. As used herein, "polar uncharged amino acid" (including pluralizations and variations of this root term) refer to naturally occurring or synthetic amino acids having a polar uncharged side chain, for example, S, T, N, or Q.

With reference to some embodiments and description herein, the bases of nucleic acids, such as DNA, RNA, and the like can be referred to by either the name of the base or a one letter code. One skilled in the art will appreciate that the genetic code is degenerate, in that for some amino acid residues, two or more three-base codons can encode the same amino acid. Thus, some one letter codes, and described herein, can represent one of two or more bases, for example to describe two or more possible nucleic acids that can encode a single amino acid. One-letter codes used herein include: "A" (adenine), "G" (guanine), "C" (cytosine), "T" (thymine), "R" (one of adenine or guanine), "Y" (one of cytosine or thymine), "M" (one of adenine or cytosine), "K" (one of guanine or thymine), "S" (one of cytosine or guanine), "W" (one of adenine or thymine), "H" (one of adenine, cytosine, or thymine), "B" (one of cytosine, guanine, or thymine), "V" (one of adenine, cytosine, or guanine), "D" (one of adenine, guanine, or thymine), and "N" (one of adenine, guanine, cytosine, or thymine).

The terms "de-blocking" and "unblocking" as used herein (including pluralization and variations of this root term) refers to displacing a bound immunoregulatory peptide or P3028 structure from a receptor. As such, de-blocking or unblocking a receptor shifts the equilibrium between receptor-bound and non-receptor-bound immunoregulatory peptide towards the "non-receptor-bound" category. For example, an LFA-1 receptor or IL-2 receptor can be de-blocked in accordance with embodiments herein by displacing a bound peptide P3028 from the LFA-1 receptor of IL-2 receptor. For example, an LFA-1 receptor or IL-2 receptor can be de-blocked in accordance with embodiments herein by displacing any immunoregulatory peptide comprising one or more sequences for Tables 1-4 from the LFA-1 receptor or IL-2 receptor.

The term "immune cell activation" as used herein, and pluralizations and variations of this root term (including such as "activating an immune cell"), refers to immune cell proliferation, activating or enhancing expression of CD69 and/or CD71, induction of secretion of a signal substance (e.g. IFNγ or IL-12), induction of secretion of a cytolytic molecule (e.g. perforin or granzyme B), enhanced cytotoxicity, cytokine production, cell migration, cell proliferation, or two or more of these listed items. By way of example, immune cell activation in accordance with some embodiments herein can occur if an immune cell proliferates, or if an immune cell begins to express detectable CD69, or if an immune cell increases its expression of CD71, or if an immune cell secretes IFNγ, IL-12, or IFNγ and IL-12.

Available data support a major role of the immune system in cancer control sample. Malignant tumors, however, can exploit a large number of immunoregulatory mechanisms to suppress immune mediated anti-tumor reactivity. Based on the observation that an increased serum concentration of interleukin-6 (IL-6) often is correlated to a poor prognosis in cancer patients of various diagnoses, the origin and induction of this cytokine was explored. It was found that proteolytic fragmentation or denaturation of normal serum albumin generated neo-structures, which exhibit immunoregulatory activity by binding to immune cells. Accordingly, a new class of immunoregulatory substances was discovered.

The existence of albumin sequences having neo-structures that bind to immune cells was identified using a human ex vivo model based on affinity chromatography over an "Artificial Cell Surface Column" (ACS). The effect of different albumin fragments on IL-2 induced proliferation of human immune cells (PBMCs) was analyzed in the ACS system (see Example 9). Briefly, PBMCs were cultured for seven days in the presence of IL-2 and the various synthetically prepared albumin fragments. Proliferation was measured as incorporation of $^3$H thymidine during the final 18 hours. One of the peptides, P3028 (also referred to as "peptide 3028" and having the amino acid sequence VFDEFKPLVEEPQNLIK—SEQ ID NO: 185) regularly inhibited IL-2 induced proliferation, but none of the other peptides identified by their binding to the artificial cell surface showed as much inhibitory activity as the P3028 sequence/structure (see FIG. 6). Accordingly, the immune cell proliferative response induced by LFA-1 or IL-2 could be inhibited by P3028, indicating that P3028 sequence/structure may be acting through at least the LFA-1 or IL-2 receptor.

The enhanced incorporation of $^3$HTdR can be the result of an enhanced specific activity of the intracellular thymidine pools and thereby an enhanced specific activity of DNA, thus, not necessarily mirroring an increase in the number of cells. It was therefore considered of be of importance to explore a different mode of stimulation of lymphocyte proliferation and to measure the response using a different method, the MTS technique (see Example 3). Accordingly, T-cells were stimulated in cultures on plates pre-coated with a monoclonal antibody directed against CD3 and the number of metabolically active cells was determined using MTS staining after 3 to 7 days of culture (see FIG. 8). As shown, P3028 sequence/structure had an inhibitory effect. It can be argued that the reduced MTS staining caused by P3028 sequence/structure might be due to a reduced cell metabolism; however, taken together the results from both models of lymphocyte proliferation, a reduced metabolism should reasonably reduce the endogenous thymidine pools and thereby result in an increased uptake of exogenous thymidine/specific activity of the thymidine pools, which then should be erroneously registered as an enhanced proliferation. The $^3$H-TdR was actually reduced in these experiments, indicating inhibition of proliferation. Accordingly, it was confirmed that peptides comprising the 3028 sequence effectively inhibited IL-2 mediated immune cell proliferation.

Peptide fragments encompassing the C- and N-terminal parts of P3028 were then synthesized and the ability of these peptides (separately and in combination) to inhibit IL-2 induced proliferation of immune cells was analyzed (see Example 6). An N-terminal fragment of P3028 (i.e., P3325 having the amino acid sequence VFDEFKPLVE (SEQ ID NO: 186)) and a C-terminal fragment of P3028 (i.e., P3218 having the amino acid sequence EPQNLIK) (SEQ ID NO: 187)) were synthesized. It was determined that the inhibitory activity of these two fragments of P3028 alone or in combination was weaker than P3028 (see FIG. 12) and the peptide fragments of 3028 do not inhibit the effect of P3028 on IL-2 induced proliferation (see FIG. 13).

It was then determined that peptides comprising the P3028 sequence/structure sequence not only interacted with the IL-2 receptor but also interacted with the LFA-1 receptor. In a first set of experiments, it was found that the P3028 peptide has the capacity to modulate the binding of an LFA-1 specific monoclonal antibody to the LFA-1 receptor on human immune cells (see Example 7). This LFA-1 specific monoclonal antibody is a potent inhibitor of IL-2 induced immune cell proliferation (see Vyth-Dreese et al., Eur. J. Immunol. 12:3292-3299 (1993)). A standard immunohistochemical staining procedure was employed in the presence and absence of the P3028 peptide. Briefly, immune cells (PBMCs) from healthy individuals and cancer patients were compared. The cells were fixed utilizing acetone, blocked with 10% human AB-serum with or without P3028, and incubated with a monoclonal anti-LFA-1 antibody and a secondary antibody followed by color development using Fast Red. As shown in FIG. 16A, a clear membrane staining 3 was found on PBMCs from healthy control samples in contrast to PBMCs from a patient with advanced cancer, which exhibited weak staining 5. However, when the PBMCs from this cancer patient were incubated with an antibody specific for the 3028 structure for 24 hours the membrane staining 3 appeared, indicating that the antibody bound the 3028-structure and thereby unblocked LFA-1 (see FIG. 16C) and the discussion infra.

Since P3028 sequence/structure significantly inhibited the proliferative response of immune cells to IL-2, the effect of P3028 sequence/structure on the binding of IL-2 to CD25 was studied. The fusion protein of CD25 and the Fc-part of IgG was bound to protein G coated micro-plates/ELISA plates and the plates were incubated with biotinylated IL-2 with or without the presence of P3028. Surprisingly, the binding of IL-2 to CD25 was enhanced by the presence of P3028, providing evidence of a three-part interaction between IL-2, CD25 and P3028 (see FIG. 18A-B). Even if the binding of IL-2 to CD25 is enhanced, the proper assembly of the high affinity receptor and/or signal transduction is blocked as the P3028 sequence/structure is a potent inhibitor of IL-2 induced proliferation. Using computer-assisted molecular modeling, it was determined that the P3028 sequence/structure binds to CD25 at the IL-2 binding site (see FIG. 19). These results provide greater evidence that the P3028 sequence/structure has at least a dual immunoregulatory capacity since it binds to both the LFA-1 receptor and the IL-2 receptor.

The ability of specific albumin fragments to impact NK-cell cytotoxicity was also evaluated. In these experiments, synthetic peptides corresponding to albumin fragments (P3028, P3026, and P3027) (SEQ ID NOs: 185, 183, and 184, respectively) were prepared and the amount of lysis of K562 target cells was assessed (see Example 4). Inhibition was not seen in the presence of the control sample peptide P3027 but P3028 and to a lesser degree P3026 caused a reduction in NK-cell cytotoxicity (see FIGS. 9A-B). Accordingly, peptides having the sequence of P3028 effectively inhibit NK-cell cytotoxicity.

The ability of specific albumin fragments to inhibit leukocyte spreading and immune cell migration was also analyzed. Briefly, buffy coat cells were prepared from heparinized blood by Dextran assisted sedimentation. These cells were then washed twice in PBS and transferred to clean slides. The cells strongly adhered to the glass surface and spread out; however, pre-treatment of these cells with P3028 at a concentration of 10 μg/ml for 15 minutes efficiently inhibited the immune cell spreading (see Example 5). Similarly, the impact of P3028 on PBMC migration was studied using the Boyden chamber technique (see Example 5). As shown in FIG. 11, P3028 is a potent inhibitor of immune cell migration ($p<0.002$).

Antibodies specific for proteins having the P3028 sequence/structure were prepared, purified, and characterized (see Example 9). Polyclonal antibodies specific for P3028 were generated in rabbits or goats. Briefly, rabbits were immunized with P3028 and specific antibodies were affinity purified using P3028. These antibodies were found to bind to P3325 (the N-terminal fragment SEQ ID NO: 186) but not P3218 (the C-terminal fragment (SEQ ID NO: 187) of P3028.

In a next series of experiments, the expression of P3028 in malignant tumors (e.g., malignant melanoma, renal cell carcinoma, and colorectal cancer) was identified by immunohistochemical staining using affinity purified rabbit anti-3028 antibodies (see Example 9). The immunohistochemical staining of malignant melanoma, renal cell carcinoma, and colorectal cancer tissue slices showed that the P3028 sequence containing molecules are widely expressed and/or localized on cancer cells. These results were further supported by the demonstration of 3028-structures in tumor extracts prepared from malignant melanoma metastases using a Western technique (see Example 1). Appreciable 3028 structures (approximately, slightly larger than 66 kD) were identified by the Western blot but the 3028 sequence was also detected in full size albumin and larger molecules (see FIG. 2). These results provide evidence that molecules comprising the 3028 structure are generated not only by proteolytic fragmentation but also by denaturation. Accordingly, it was determined that P3028 sequence and/or molecules that comprise this sequence are present in and/or localized to tumor tissue.

An ELISA technique was then used to confirm that proteins and peptides comprising the 3028 sequence were present in human serum. Briefly, a sandwich assay was employed, wherein affinity purified anti-3028 antibodies were coated onto high protein binding ELISA microwells (capture antibody), and a 1% solution of heat-inactivated serum, spiked with increasing concentrations of P3028, was then added to the wells. After washing, a biotinylated mouse anti-human albumin monoclonal antibody was added and the amount of bound antibody was detected with HRP-conjugated streptavidin and TMB chromogen substrate (see Example 1). The serum concentration was found to be in the range of 1.2-1.6 µg/ml P3028 equivalents in one serum pool from 5 healthy control samples, 1 healthy control sample serum and 2 sera obtained from cancer patients. The amount of 3028 containing molecules was determined as the amount of P3028, which inhibits 50% of the binding of 3028 structures in the serum to the capture antibody (directed against the 3028 epitope) in the sandwich ELISA (see FIG. 3). The amount of these 3028-substances in serum may be considerably more as the molecular weight of albumin is about 35 times more than that of P3028, but their epitope specific reactivity is accurately determined using the method described above.

Experiments were then performed using a first class of inhibitors that are specific for the P3028 sequence/structure. The proliferative response of human immune cells from healthy individuals and cancer patients after IL-2 induction were analyzed in the presence and absence of antibodies specific for the P3028 sequence/structure (see Example 9). That is, the proliferative response of PBMCs from a patient having renal cell carcinoma and a patient having malignant melanoma were compared to the proliferative response of PBMCs obtained from a healthy individual in the presence and absence of antibodies specific for the P3028 sequence/structure. It was determined that in the presence of the antibodies that are specific for the P3028 sequence/structure, enhanced proliferation of the PBMCs after IL-2 induction was seen. That is, the antibody inhibitor for the P3028 sequence/structure was able to remove the blockade on IL-2-induce proliferation of the immune cells mediated by the P3028 sequence/structure. These results demonstrate that a binding partner for the P3028 sequence/structure (e.g., an antibody or binding fragment thereof specific for P3028), can reduce the immune suppression mediated by the P3028 sequence/structure.

The P3028 sequence/structure is a potent physiological inhibitor of the immune system, and is a possible a target for therapeutic compositions that can modulate immune activity. Antibodies directed against the P3028 sequence/structure reversed cancer-related immunosuppression, which was modeled as reduced proliferative response of PBMCs to IL-2 in a human ex vivo model (see Example 9). Moreover, the outcome in this model correlated to over-all survival of the cancer patients (see Example 2). Therefore, it was contemplated that additional binding partners for the P3028 sequence/structure (e.g., peptides, cyclic peptides, peptidomimetics, antibodies and portions thereof) may be useful for inhibiting the P3028 sequence/structure-mediated immune suppression.

Three peptide-based binding partners for the P3028 sequence/structure were initially developed and the binding capacity of these inhibitors with P3028 in solution was tested, as shown in FIG. 23 (see Example 10). Only one molecule, SCF28, had a solubility sufficient to allow testing in biological human ex vivo models. Based on this structure, a first drug candidate, P28R (SEQ ID NO: 2), was developed.

Since P28R strongly bound to P3028, the ability of P28R to inhibit the function of the P3028 sequence/structure was tested. As described above, the β2-integrins plays a major role in the normal function of the immune system. However, the binding of the P3028 sequence/structure, to the β2-integrin LFA-1 has a substantial immunosuppressive effect. As demonstrated above (see Example 7), in assays staining for LFA-1, the membrane staining of PBMCs from cancer patients is markedly decreased compared to normal control samples. The exposure of LFA-1 could, however, be enhanced by incubating PBMCs from cancer patients with an antibody directed against the inhibitory P3028 sequence/structure (see Example 7 and FIG. 16C).

Figures 26A, 26B:
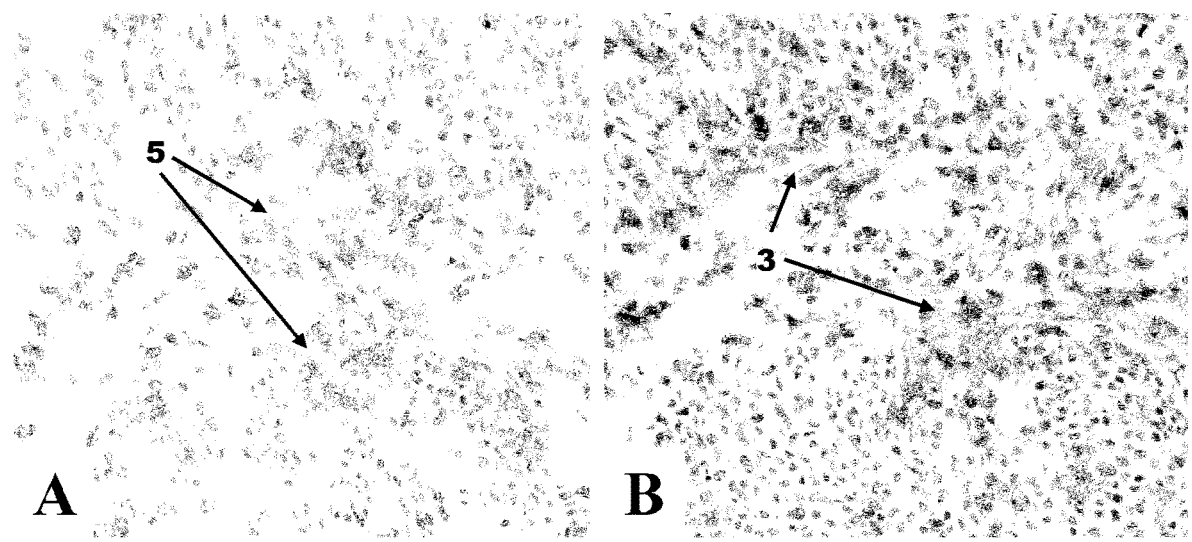
FIG. 26 illustrates breast cancer tissue incubated with buffer (FIG. 26A) or P28R (FIG. 26B) stained by an antibody directed against LFA-1.

Without being limited by any theory, the occurrence of tumour infiltrating lymphocytes in primary tumours generally indicates good prognosis. However, in many tumors, tumor-infiltrating lymphocytes can have reduced function or a lack of function, and rather than migrate into nodules of tumour cells, can "get stuck" in the stromal areas of the tumour. It is observed that incubation of fresh frozen tumour sections with peptide P28R (SEQ ID NO: 2) de-blocks LFA-1 of tumour infiltrating lymphocytes (i.e. displaces a bound immunoregulatory peptides or P3028 structures from the LFA-1 receptors), resulting in an enhanced binding of the anti-CD11a antibody (FIG. 26). These results showed that the LFA-1 receptor was unblocked by removal of the P3028 structure by the antibody. To test the ability of P28R to inhibit the P3028 structure, fresh frozen tumor sections without fixation were incubated for 4-20 hours in the presence of the drug candidate, P28R before staining for LFA-1 (see Example 15). For comparison, tumor sections were incubated with phosphate buffered saline only. As shown in FIG. 26, P28R effectively unblocked the LFA-1 receptor (e.g. displaced bound immunoregulatory peptides or 3028 structures from the LFA-1 receptor) and thereby markedly enhanced the functional expression of LFA-1 enabling migration and cytotoxic activity of these cells. Accordingly, P28R decreases the binding of P3028 to LFA-1 and effectively inhibits the immune suppression mediated by P3028. It is contemplated that incubation with P28 core (SEQ ID NO: 62) in accordance with some embodiments herein also de-blocks LFA-1 (e.g. displaces bound immunoregulatory peptides or 3028 structures from the LFA-1 receptor).

As such, the receptors of P3028 include LFA-1 and the alpha chain of the IL-2 receptor (CD25). Binding of a monoclonal antibody to CD11a (the alpha chain of LFA-1) was used to study the possible occurrence of a physiological blocker of LFA-1 and the de-blocking activity of P28R and antibodies directed to P3028. Accordingly, it is further contemplated that, similar to the LFA-1 receptor, the IL-2 receptor can be de-blocked by immunoregulatory peptide inhibitors as described herein (e.g. bound immunoregulatory peptides or 3028 structures can be displaced from the IL-2 receptor). As such, in some embodiments, an immunoregulatory peptide inhibitor as described herein deblocks an IL-2 receptor, for example an IL-2 receptor that has been blocked by any one or more of the peptides listed in Tables 1-4 (e.g. a peptide comprising SEQ ID NO: 185).

Figure 15:
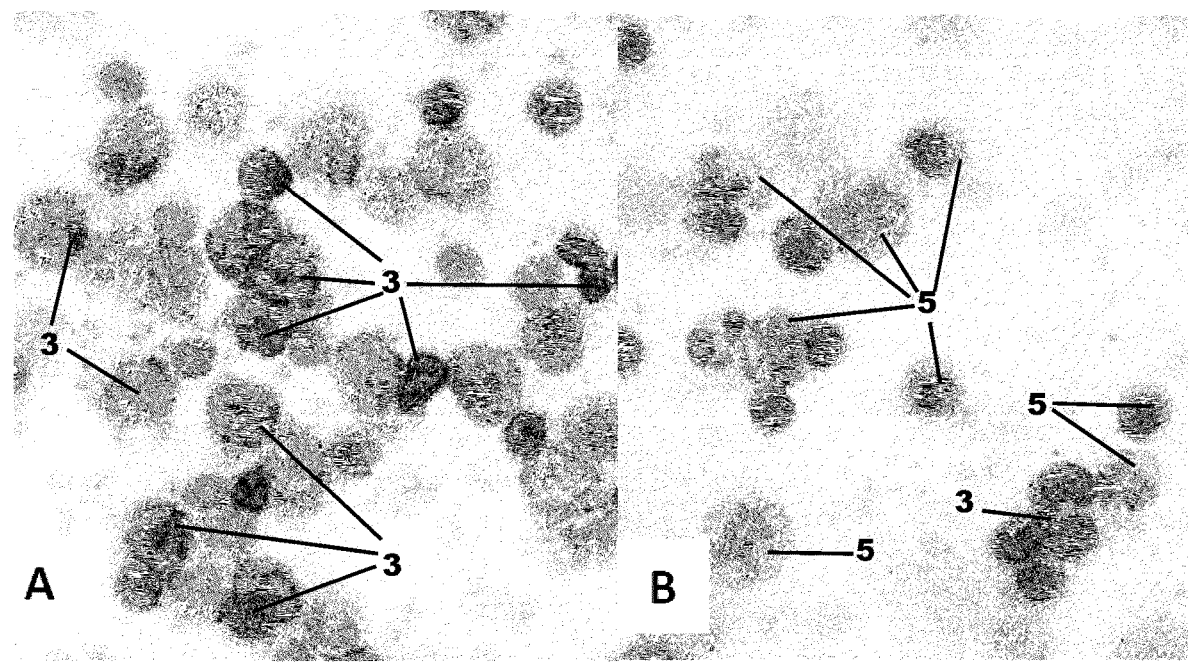
FIG. 15 illustrates inhibition of the binding of an anti-LFA-1, mAb, to mononuclear blood cells by P3028.
Figure 16:
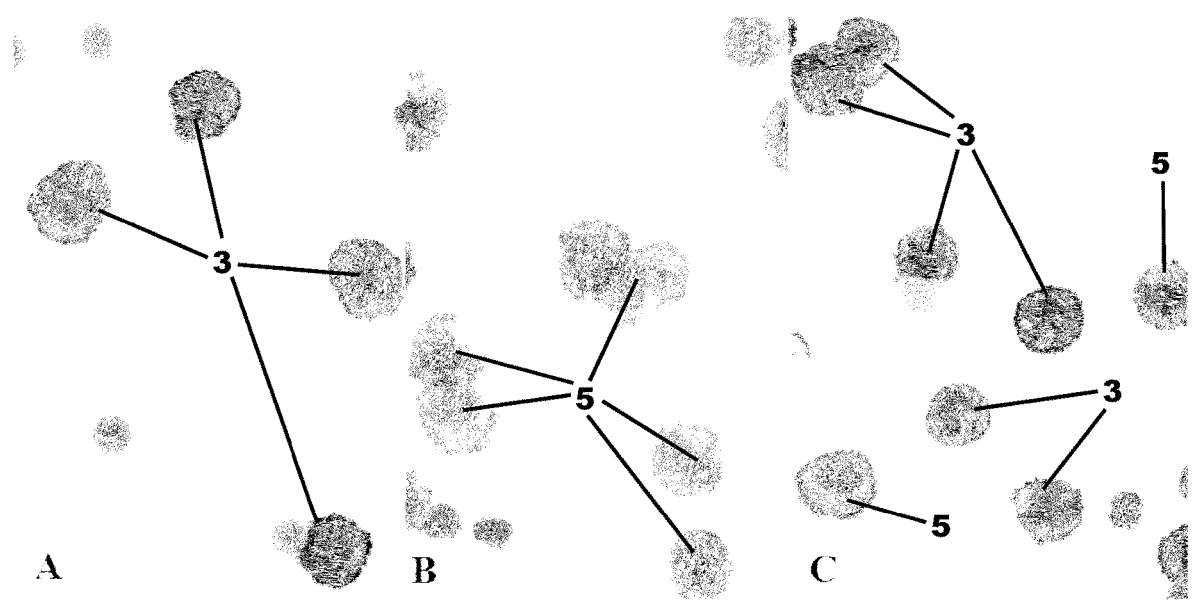
FIG. 16 illustrates staining of LFA-1 on PBMCs from a healthy control sample (A), and a cancer patient before (B) and after (C) treatment with an antibody directed against the inhibitory P3028.

Incubation of PBMCs from healthy controls with P3028 (FIGS. 15 and 17) or cancer patient sera (FIG. 17) blocks the binding of the anti-CD11a antibody to LFA-1. Furthermore, incubation of PBMCs from advanced cancer patients with an antibody directed against P3028 restitutes the binding of the anti-CD11a antibody to LFA-1 (FIG. 16). P3028 can bind to PBMCs (see FIG. 15A depicting no peptide added, and FIG. 15B, depicting preincubation with peptide 3028; anti-LFA-1 mAb HIM was inhibited by preincubation with peptide 3028, indicating binding to mononuclear blood cells by peptide 3028).

Figure 24A:
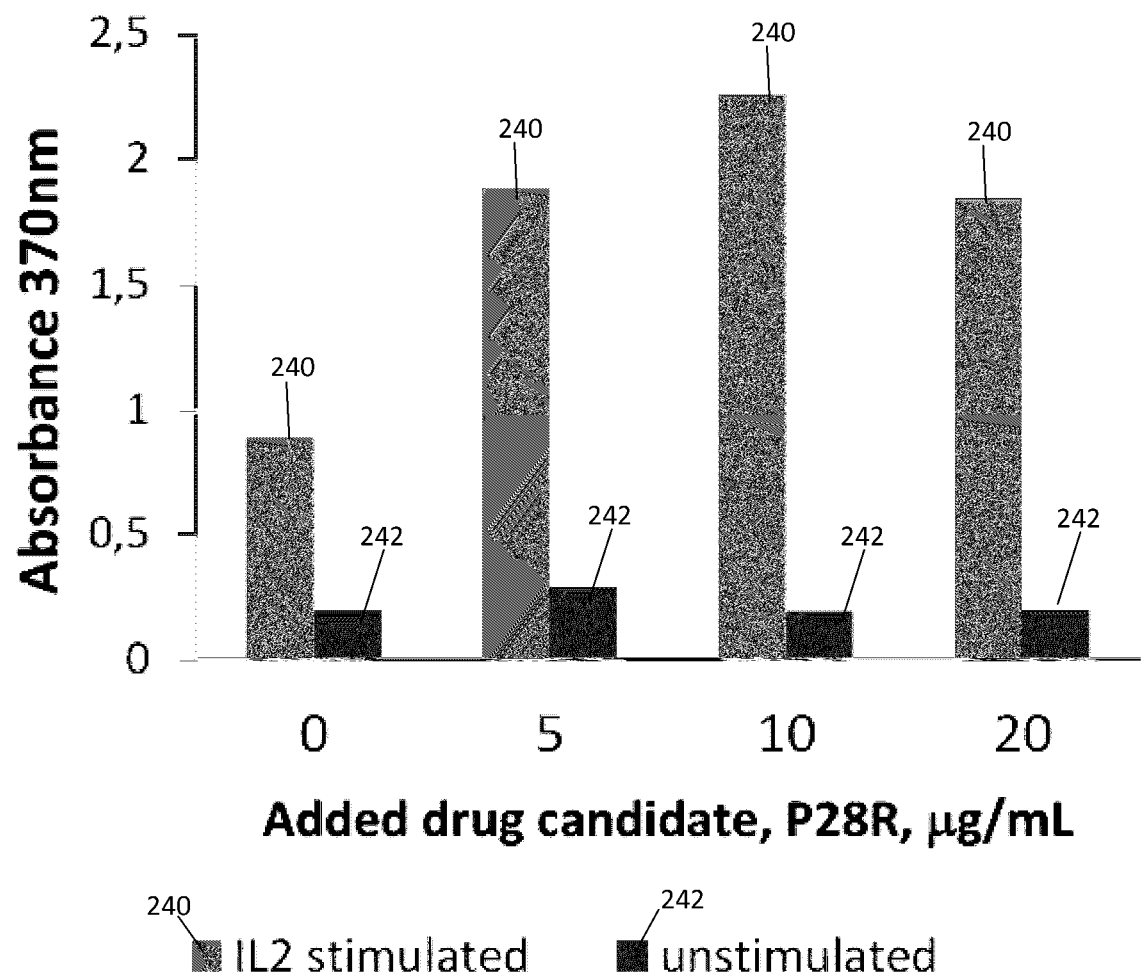
FIGS. 24A, 24B, 24C, and 24D respectively illustrate stimulatory activity for four different cancer patients.
Figure 24B:
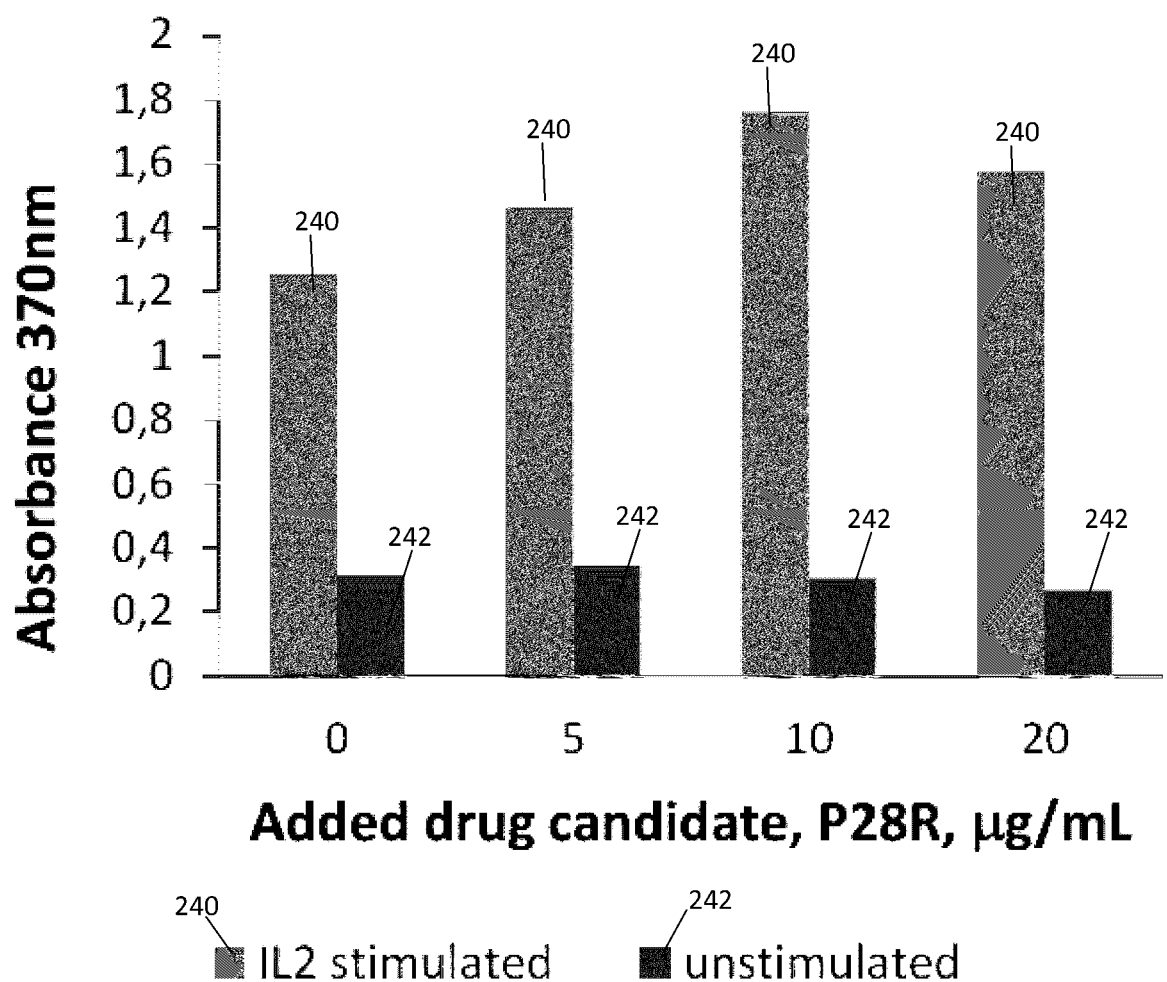
Figure 24C:
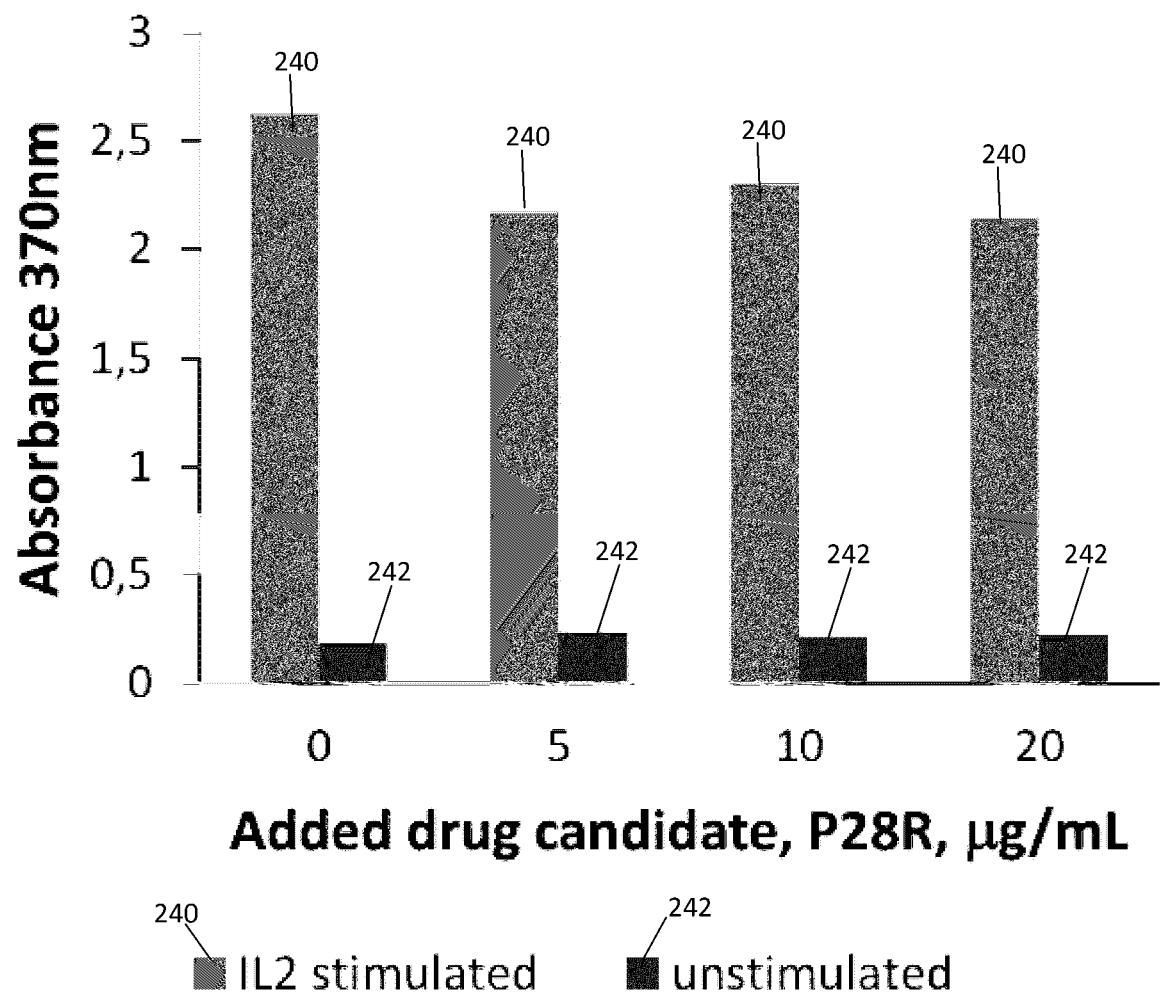
Figure 24D:
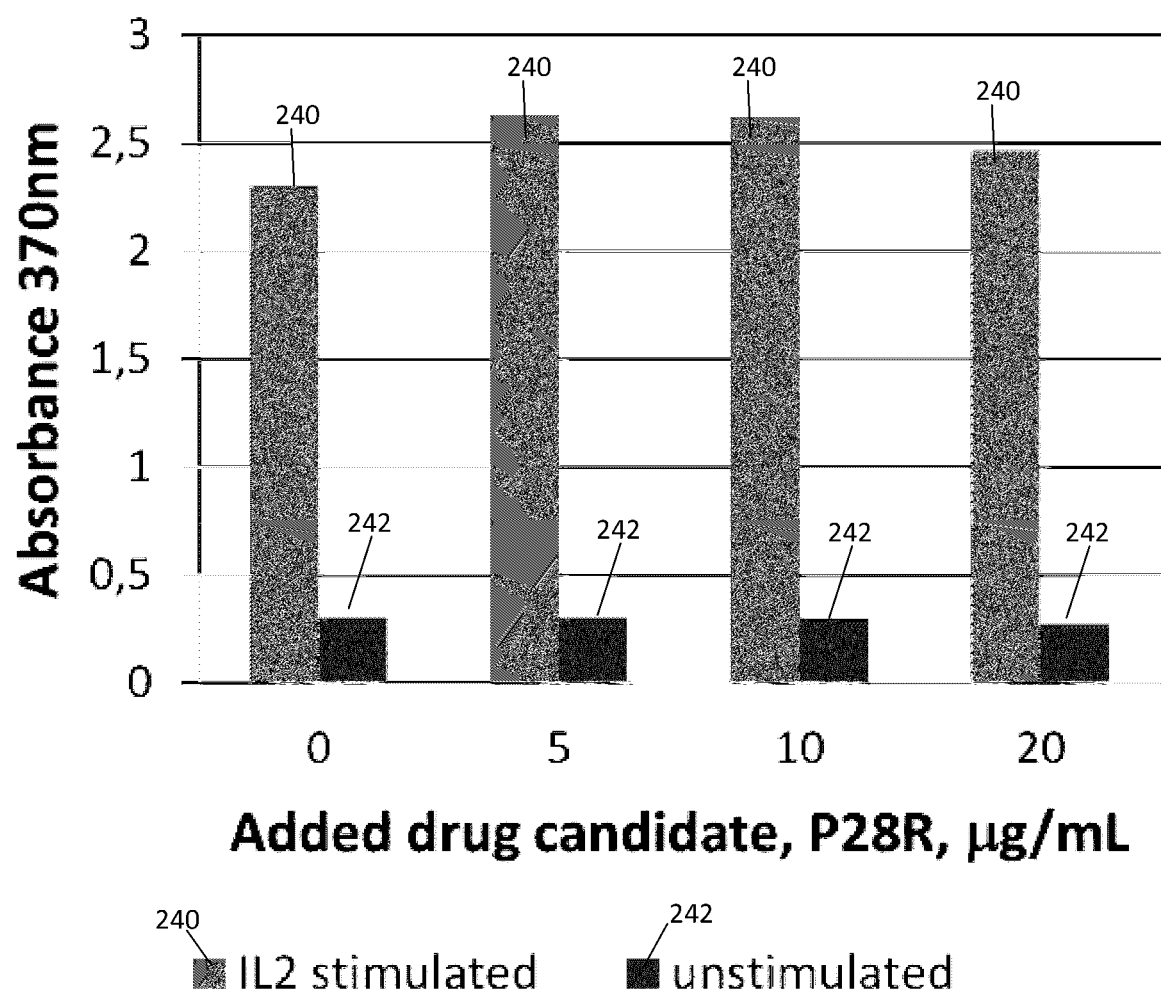

Since P28R unblocks LFA-1 receptors that are suppressed by the P3028 sequence/structure (e.g. displaces bound immunoregulatory peptides or 3028 structures from the LFA-1 receptor), the ability of P28R to enhance immune stimulation was tested in human ex vivo models. The stimulatory activity of P28R on PBMCs was measured using the MTS or CFSE techniques in 7 healthy control samples and 7 cancer patients of various diagnoses (see Example 13). Even in the absence of other types of stimulation, P28R has a significant stimulatory activity in 6 out of 7 cancer patients; whereas PBMCs from control samples showed only weak or no stimulation (see Example 13). Similar to the studies on the efficacy of antibodies directed against P3028 to reverse cancer related immunosuppression above (see Example 9; see FIG. 22), the ability of the P28R inhibitor to unblock the IL-2 receptor and thereby induce immune cell proliferation was investigated. Cultures of PBMCs from four different treatment naïve patients were each treated with P28R, and proliferation of PBMCs was measured. While PBMCs that had high proliferative activity before P28R treatment were largely unaffected by the drug (see FIG. 24C and FIG. 24D), PBMCs with a low initial proliferation were markedly stimulated (see FIG. 24A and FIG. 23B; see Example 13). Thus, the P28R inhibitor effectively induces immune cell proliferation when the immune cells are bound and suppressed by the P3028 sequence/structure, even in the absence of additional stimulation.

Since cancer cells have been shown to be enriched for P3028 structures (see Example 1 and FIGS. 1-2), the ability of P28R to specifically bind cancer cells was investigated. The binding of biotinylated P28R to tumors was studied. Three breast cancers, two renal cell carcinomas and four malignant melanomas were analyzed. Notably, all of the different types of tumors analyzed in the experiments bound P28R. The stained breast cancer section, shown in FIG. 25, for example, exhibits a strong positive signal, indicating the presence of the inhibitory P3028-structure in this tumor, and ability of P28R to bind to this tumor (see Example 14).

Since the P3028-structure inhibits lymphocyte migration, as well as, cytotoxic activity (see Examples 4 and 5), an immune system mediated attack against positively-staining tumor areas is expected to be efficiently suppressed so long as the a P3028-containing structure is present and not sequestered by a binding partner for the P3028 sequence/structure (e.g., an antibody, binding fragment thereof, and/or an inhibitory peptide, such as P28R, or a peptidomimetic corresponding to the P28R structure). Consistent with the observation that P3028 strongly binds the LFA-1 receptor, lymphocytes were not stained by this procedure since the P3028 structure was blocked by binding to LFA-1 on these cells.

Figure 27:
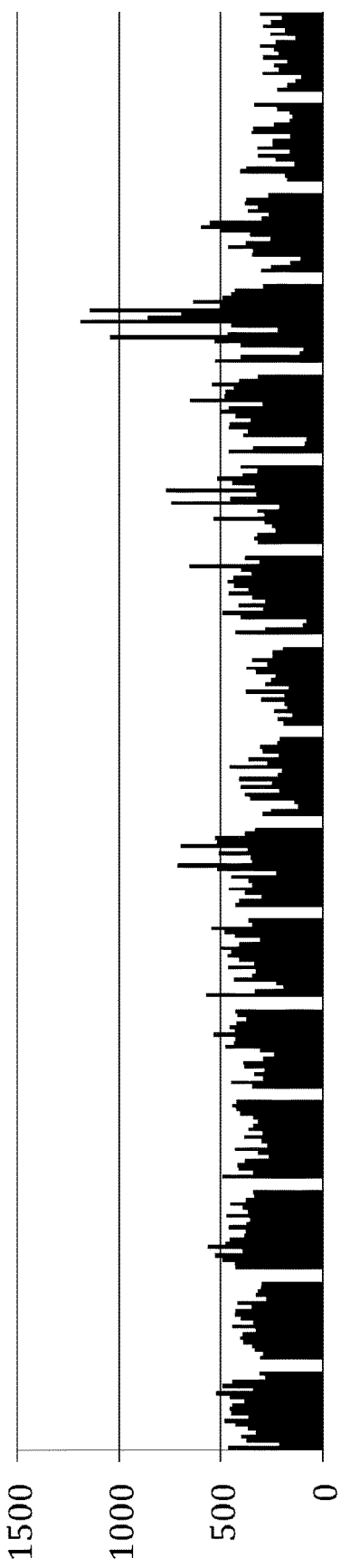
FIG. 27 illustrates rampo scores for binding of P3028 to peptides having single amino acid substitutions of each position of P28R.

Based on the ability of P28R to bind the P3028 sequence/ structure, unblock the LFA-1 receptor, and ameliorate the P3028 sequence/structure-dependent immunosuppression, P28R was used as a template compound to identify additional compounds that bind to and sequester P3028. Variants of the P28R structure were synthesized, and tested for the ability to bind P3028 using PEPSCAN technology (see Example 12). A library of peptides that include each genetically-coded amino acid substitution at each amino acid position of P28R (i.e., 19 substitutions for each position) was synthesized. Each peptide was affixed to a support pin, and the peptide library was incubated with P3028. The binding of the candidate inhibitors to P3028 was detected by a sandwich ELISA, where a rabbit anti-mouse peroxidase (rampo) secondary antibody was employed (see Example 12). The binding of each peptide was then assigned a rampo score (see FIG. 27). Peptide P28R had rampo values ranging between about 262 and 460 with a mean value of 370. In some embodiments, the immunoregulatory peptide inhibitor as disclosed herein, is selected for a desired P3028 binding rampo score. In some embodiments, the desired P3028 binding rampo score is greater than or equal to the rampo score of P28R. It is also contemplated that some peptides that bind to P3028 with less affinity than P28R have therapeutic application. Some peptides with binding affinities that are less than P28R, for example, may modulate signal transduction events differently than P28R by virtue of the fact that the affinity to P3028 is less. Accordingly, embodiments also include any peptide that binds to P3028, wherein said peptides have a rampo score that is less than that exhibited by P28R. Accordingly, contemplated embodiments include peptides that bind with any affinity to P3028 (e.g., any one or more of the peptides provided in Table 5.1, preferably peptides that modulate the immune system (e.g., modulate, upregulate or down regulate a marker of the immune system or immunosuppression, such as reducing a P3028-mediated inhibition of immune cell proliferation, spreading, migration, or NK-cell cytotoxicity).

A total of 31 substitutions of peptide P28R (SEQ ID NOs: 3-33) had rampo values greater than 500 (see FIG. 28), indicating that these 31 peptides (strong binding partners for P3028) can be used to efficiently bind and sequester P3028 and thereby reduce P3028-mediated immunosuppression. Table 6.1 lists these 31 peptides that were evaluated in assays and shown to have appreciable binding to P3028. Additionally, the binding strength of substituted peptides at each position (based on rampo score) was compared to the binding strength of a P28R (SEQ ID NO: 2) control sample for the same position (see Example 12). Peptides that bound with a rampo score substantially equal to or greater than that of the P28R control sample (i.e., at peptides that bound to P3028 with at least 98% of the rampo score of the P28R control sample) were identified (SEQ ID NOs: 268-393). Table 6.2 lists these 126 peptides that were shown to have appreciable binding to P3028. It is noted that these 126 peptides include the 31 peptides of Table 6.1. Accordingly, 126 different binding partners for P3028 were identified by this initial screen and these molecules or variants thereof (e.g., variants having D amino acids, N-terminal amides, and/or C terminal acetyl groups or peptidomimetics or aptamers corresponding to these binding partners) can be used to inhibit the binding of the P3028 sequence/structure to an immune cell and thereby alleviate, or reduce P3028-dependent immunosuppression. One variant of P28R, Peptide KKL15 (SEQ ID NO: 1), which lacks only a C-terminal arginine, is thought to bind to the P3028 sequence/structure through both charged and hydrophobic interactions. As shown in FIG. 31, positively charged amino acids of KKL15 interact with negatively charged amino acids on P3028 and hydrophobic amino acids generate hydrophobic contacts enhancing the interaction.

To further map the P3028 binding domain of P28R, deletions, and truncations of P28R were synthesized, and tested for binding to P3028 using the PEPSCAN assay. This approach led to the development of many more binding partners for P3028. While deletion of residues 6-9 ("FFVK"—SEQ ID NO: 182) and the C-terminal amino acids tended to reduce the binding of peptides to P3028 based on rampo score (see Example 12 and FIG. 30), several deletions and truncations of peptide P28R have a rampo score comparable to, or higher than peptide P28R (see, e.g., SEQ ID NOs: 34, 64-66, 68, and 76). Additionally, peptides deleted up to at least 8 amino acids from the N-terminus of P28R (see, e.g., SEQ ID NOs: 46-53) retained a high affinity to P3028, as measured by rampo score, providing evidence that inhibitors that are smaller than P28R can be useful for binding to and sequestering P3028, preventing the interaction of P3028 with immune cell receptors, such as the IL-2 or LFA-1 receptors, thereby reducing P3028-induced immunosuppression.

Because P28R was shown to have a modulatory effect on IL-2 stimulation of immune cell proliferation (see Example 2), it was further investigated whether P28R would have a modulatory effect on other aspects of IL-2 stimulation of immune cells. PBMCs from eight healthy control samples and nine cancer patients with various diagnoses were cultured in a modified version of the ex vivo model of Example 2 for seven days in the presence of various doses of P28R (either "no P28R" control samples, or 5 μg/mL, 10 μg/ml, or 20 μg/ml of P28R). A dose dependent stimulation of the mitochondrial metabolism measured as conversion of MTS was observed in 5/8 (see FIG. 33A) control samples and 9/9 cancer patients (see FIG. 33B). Similar results were obtained when the PBMCs were cultured for only three days (see Example 28).

To identify the effectiveness of other inhibitors of immunomodulatory peptides, the effect of P28R (SEQ ID NO: 2) on mitochondrial metabolism based on MTS conversion was compared to the effect of a closely related peptide P27. P27 has the sequence KKLDTFFKKLSLFTER (SEQ ID NO: 264), and is a variant of P28R that differs in that V8 of P28R is substituted to K8 in P27. P28R binds to P3028 more efficiently than P27 (P27 binds P3028 with a rampo score of 253, while a P28R control sample binds P3028 with a rampo score of 308; see Example 12). The concentrations were either untreated control samples, 5 μg/mL ("SCF28-R5" and "SCF275"), 10 μg/ml ("SCF28-R10" and "SCF2710"), 20 μg/ml ("SCF28-R20" and "SCF2720"), or 40 μg/ml ("SCF28-R40" and "SCF2740"). The results are shown in FIG. 34. While P28R stimulated the cells of cancer patients in a dose-dependent manner, P27 had no effect (see Example 29).

The effect of P28R (SEQ ID NO: 2) on IL-2 induced proliferation was also measured in a BrdU incorporation assay. PBMCs from six healthy control samples and ten cancer were harvested in a modified version of the ex vivo model. Four out of six control samples had a high proliferative response to IL-2 compared to four out of ten cancer patient samples (see FIG. 35). These differences in proliferative response to IL-2 in PBMCs demonstrated the difference existence of high and low responders to IL-2 stimulation (see Example 30).

The response of high responders and low responders to various doses of P28R was compared. Cells from either high responders or low responders were cultured with various doses of P28R (see FIGS. 36A and 36B). IL-2-induced proliferation was measured as BrdU incorporation. While P28R had no stimulatory effect in cells from patients with a high response to IL-2 (N=4) (see FIG. 36A), P28R had a stimulatory effect on cells from patients with a low response to IL-2 (N=6) (see FIG. 36B). Accordingly effects of P28R on binding to and blocking immunoinhibitory activity of P3028 were demonstrated in in the ex vivo model, as addition of P28R to the cultures had no effect on proliferation when added to PBMCs from healthy controls and cancer patients with a normal proliferative rate, but the proliferation of PBMCs from immunosuppressed cancer patients were significantly stimulated by P28R. Without being limited by any theory, in some embodiments P28R (SEQ ID NO: 2) or P28 core (SEQ ID NO: 62) binds to a blocker of immune cell proliferation, and induces immune cell proliferation.

The effect of P27 (SEQ ID NO: 264) was then compared to the effect of P28R (SEQ ID NO: 2) on IL-2 induced proliferation as measured by BrdU Incorporation. PBMCs from low responder cancer patients were with various concentrations of either P28R of P27, ranging from no peptide ("untreated cells"), to 5 μg/mL, 10 μg/ml, or 20 μg/ml. As shown in FIG. 37, both P28R and P27 enhanced the proliferative rate of PBMCs induced by IL-2 as measured by BrdU incorporation. When comparing the results shown in FIG. 37 to those of FIG. 34, P27 was observed to enhance IL-2 stimulation of cell proliferation as measured by BrdU incorporation, but not mitochondrial metabolism as measured by MTS conversion. On the other hand, P28R was observed to enhance both MTS conversion and BrdU incorporation in response to IL-2 stimulation (see Example 31).

The different effects of different inhibitors of immunoregulatory peptides on BrdU incorporation and MTS conversion were further investigated. The effects of P28R on IL-2 stimulation of immune cell proliferation differed significantly, depending on which assay was used (see FIG. 38). Peptide P28R had a stimulatory activity of MTS conversion in seven day cultures of PBMCs in 100% of cancer patients examined (N=9) and in 63% of healthy control samples examined (N=8). In contrast, P28R stimulated incorporation of BrdU in seven day cultures of PBMCs from only 17% (N=6) and 20% of (N=10) patients. P28R stimulated IL-2 induced proliferation, measured as incorporation of BrdU, in PBMC cultures from cancer patients with a low proliferative response to IL-2. On the other hand, PBMCs from 67% of healthy control samples examined (N=3) and 50% of cancer patients (N=4) were not stimulated by IL-2 when the effect was measured as MTS conversion (see Example 32 and FIG. 38). However, PBMCs from all these persons ("non-responders") who did not respond when measured with MTS were significantly stimulated by IL-2 when the effect was measured as incorporation of BrdU (see FIG. 38). In two patients, the response to IL-2, measured as BrdU incorporation, was enhanced by P28R (see FIGS. 38A and 38C), but this effect of P28R was only observed in one of these patients when MTS conversion was used (see FIG. 38B). Thus, while in one patient (see FIGS. 38A and 38B) the stimulatory activity of IL-2 was registered using both BrdU and MTS, in the other patient, the stimulatory activity of IL-2 was registered using BrDU only (see FIG. 38C) (see Example 32). Based on these observations, it was contemplated that effects on the metabolic activity measured as MTS conversion does not always correlate with DNA synthesis measured as incorporation of BrdU, and different populations of patients can respond differently to inhibitors of immunoregulatory peptides.

It was contemplated that other molecules that bind to P3028 could be identified. These additional binding molecules could also potentially block P3028. Looped 6-mere peptides were synthesized, and 6-meres that demonstrated appreciable binding to P3028 were identified (see Table 12, SEQ ID NOs: 265-267) (see Example 19). It was observed that two of the 6-meres with the strongest binding to P3028 based on rampo score possessed homology to linear peptides that bind 3028 (see FIG. 32).

In addition to P3028, several other albumin fragments and synthetic peptides were found to bind to the immune cells. Some of these fragments can have immunomodulatory activity similar to P3028, can bind to immune cells similar to P3028, and/or can bind to immunomodulatory antibodies that recognized P3028. In a first set of experiments, albumin fragments were generated by trypsin digestion and the tryptic fragments were found to bind to immune cells in the ACS system described herein (see Example 17). Table 1 provides a listing of trypsin-generated fragments of albumin, which bind to immune cells in the ACS system, as detected by MALDI-TOF analysis.

TABLE 1

Trypsin-generated albumin fragments that bind to ACS

| SEQ ID NO: | Percent Absorbed | Sequence | Albumin Positions |
|---|---|---|---|
| 194 | 71% | KYLYEIAR | 161-168 |
| 195 | 64% | KVPQVSTPTLVEVSR | 438-452 |
| 196 | 60% | VFDEFKPLVEEPQNLIK | 397-413 |
| 197 | 59% | VPQVSTPTLVEVSR | 439-452 |
| 198 | 42% | RPCFSALEVDETYVPK | 509-524 |
| 199 | 41% | FQNALLVR | 427-434 |
| 200 | 36% | SLHTLFGDK | 89-97 |
| 201 | 36% | LKECCEKPLLEK | 299-310 |
| 202 | 35% | LCTVATLR | 98-105 |
| 203 | 34% | YLYEIAR | 162-168 |
| 204 | 32% | CCAAADPHECYAK | 384-396 |
| 205 | 29% | AAFTECCQAADK | 187-198 |
| 206 | 26% | CCTESLVNR | 500-508 |
| 207 | 25% | QEPERNECFLQHK | 118-130 |
| 208 | 23% | AVMDDFAAFVEK | 570-581 |
| 209 | 22% | NECFLQHK | 123-130 |
| 210 | 20% | ONCELFEQLGEYK | 414-426 |
| 211 | 18% | QEPERNECFLQHK | 118-130 |
| 212 | 13% | VHTECCHGDLLECADDR | 265-281 |
| 213 | 8% | FKDLGEENFK | 35-44 |
| 214 | 3% | YICENQDSISSK | 287-298 |
| 215 | 2% | LDELRDEGK | 206-214 |
| 216 | 1% | DDNPNLPR | 131-138 |

In a second set of experiments, denatured human serum albumin was degraded by asparaginase (ASN-N), and the ability of these proteolytic fragments to bind with immune cells was evaluated in the ACS system. Again, the immune cell binding peptides were identified by comparing adsorbed and unadsorbed peptide solutions using the MALDI TOF technique. These peptides are shown in Table 2.

TABLE 2

Asp-N-generated albumin fragments that bind to ACS

| SEQ ID NO: | Percent Absorbed | Sequence | Albumin Positions |
|---|---|---|---|
| 217 | 100% | DHVKLVNEVTEFAKTCVA | 62-79 |
| 218 | 100% | DDKETCFAEEGKKLVAASQAALGL | 586-609 |
| 219 | 87% | DRVTKCCTESLVNRRPCFSALEV | 495-517 |
| 220 | 86% | DETYVPKEFNAETFTHA | 518-535 |
| 221 | 65% | DSISSKLKECCEKPLLEKSHCIAEVEN | 293-319 |
| 222 | 65% | DKLCTVATLRETYGEM | 96-112 |
| 223 | 100% | YSVVLLLRLAKTYETTLEKCCAAADPHEC YAKVF | 364-398 |
| 224 | 100% | KLCTVATLRETYGEMADCCAKQEPERNEC FLQHK | 96-130 |
| 225 | 100% | ICTLSEKERQIKKQTALVELVKHKPKATK EQLKAVM | 536-572 |
| 226 | 100% | LAKYICENQDSISSKLKECCEKPLLEKHC IAEVEN | 283-319 |
| 227 | 100% | VFLGMFLYEYARRHPDYSVVLLLRLAKT YETT LEKCCAAA | 348-388 |
| 228 | 100% | LGEENFKALVLIAFAQYLQQCPFEDHVKL VNEVTEFAKTCVA | 37-79 |
| 229 | 100% | RVTKCCTESLVNRRPCFSALEVDETYVPK EFNAETFTHA | 495-535 |
| 230 | 37% | YLSVVLNQLCVLHEKTPVSDRVTKCCCTE SLVNRRPFSALEV | 475-517 |

Additionally, several synthetic peptides were synthesized, as shown in Table 3, and the binding of these molecules to immune cells using the ACS system was evaluated.

TABLE 3

Synthetic albumin peptides

| SEQ ID NO: | Peptide Name | Sequence | Albumin Positions |
|---|---|---|---|
| 183 | 3026 | NEETFLKKYLYEIARRHPYFYAP | 153-176 |
| 184 | 3027 | ELFEQLGEYKFQNALLVR | 417-434 |
| 188 | 3029 | KVPQVSTPTLVEVSR | 438-452 |
| 189 | 2604 | KLVNEVTEFAKT | 65-76 |
| 190 | 2605 | NEETFLKKYLYE | 153-168 |
| 191 | 2606 | LDELRDEGKAS | 205-217 |
| 192 | 2607 | EMADCCAKQEPE | 110-122 |
| 193 | 2608 | ELFEQLGEYKF | 417-427 |

Additionally, several albumin fragment peptides bind specifically to an dHSA-specific antibody with immunomodulatory effects (mAb A) (see Example 18). These peptides are shown in Table 4.

TABLE 4

Albumin peptides that bind to monoclonal antibody mAb A

| SEQ ID NO: | Sequence | Albumin Positions |
|---|---|---|
| 231 | LVNEVTEFAK | 066-075 |
| 232 | SLHTLFGDK | 089-097 |
| 233 | LCTVATLR | 098-105 |
| 234 | ETYGEMADCCAK | 106-117 |
| 235 | YLYEIAR | 162-168 |
| 236 | LDELRDEGK | 206-214 |
| 237 | YICENQDSISSK | 287-298 |
| 238 | LKECCEKPLLEK | 299-310 |
| 239 | HPDYSVVLLLR | 362-372 |
| 240 | CCAAADPHECYAK | 384-396 |
| 241 | QNCELFEQLGEYK | 414-426 |
| 242 | FQNALLVR | 427-434 |
| 243 | CCTESLVNR | 500-508 |
| 244 | AVMDDFAAFVEK | 570-581 |
| 245 | LSQRFPK | 243-249 |
| 246 | DDNPNLPR | 131-138 |

It is contemplated that inhibitors to any one or more of the peptides listed in Tables 1-4 can be generated in much the same way that inhibitors to P3028 were generated. In brief, polyclonal and monoclonal antibodies that are specific for any one or more of the peptides in Tables 1-4 can be easily generated using conventional techniques in immunology. Antibody binding fragments can also be prepared and isolated using conventional techniques in immunology. These antibodies or antibody fragments can be human, or humanized, as described herein. Using an approach similar to that described supra and in Examples 9 and 10, these peptide inhibitors can be evaluated on a chip based assay and biochemical assays, such as immune cell proliferation in the presence and absence of the peptide inhibitors, can be evaluated. The section below provides more information on the development of immunoregulatory peptide inhibitors, preferably inhibitors of P3028.

It is contemplated that inhibitors of any one or more of the peptides listed in Tables 1-4 can comprise modifications of the P28R (SEQ ID NO: 2) or P28 core (SEQ ID NO: 62) sequence, and further can be useful for reducing inhibition of the LFA-1 receptor, or for stimulating immune cells. To identify modification to inhibitor peptides in accordance with some embodiments herein, positional scan data was used to study the influence of substitution of different types of amino acids in each position of P28R (SEQ ID NO: 2) on the binding of P3028 (SEQ ID NO: 185). Each amino acid in the peptide sequence of P28R (SEQ ID NO: 2) was exchanged with all of the naturally occurring amino acids, and binding of P3028 (SEQ ID NO: 185) to each peptide on a solid phase chip was assessed (see, e.g. Example 36). A number of optional modifications to P28R in accordance with embodiments herein are summarized in Tables 5.3, 5.4, 5.5, 5.6, and 13. Optionally, an inhibitor peptide in accordance with some embodiments herein can comprise one or more of the modifications of Table 5.3 or Table 13. Optionally, an inhibitor peptide comprises a central core of positions 2, 5-11, and 15 as provided in Table 5.3, and the remaining position are omitted or substituted with substantially any amino acid. Optionally, an inhibitor peptide comprises a central core of positions K2, T5-S11, and E15 of SEQ ID NO: 2, and the remaining position are omitted or substituted with substantially any amino acid.

From the positional scan data it is also noted that a "core peptide" can be identified, FFVKLS (SEQ ID NO: 62) (referred to herein as "P28 core"). In some embodiments, a peptide comprising, consisting of, or consisting essentially of P28 core (SEQ ID NO: 62) is provided. The peptide can comprise no more than about 30 amino acid residues, for example no more than about 30, 29, 28, 27, 26, 25, 24, 23, 22, 21, 20, 19, 18, 17, 16, 15, 14, 13, 12, 11, 10, 9, 8, 7, or 6 amino acid residues. In some embodiments, the core peptide de-blocks an LFA-1 receptor (e.g. displaces bound immunoregulatory peptides or 3028 structures from the LFA-1 receptor) that has been bound by one or more immunoregulatory peptides of Tables 1-4.

Based on the positional scan data, it is contemplated that substitutions of SEQ ID NO: 2 can be useful in accordance with some embodiments herein for binding P3028, de-blocking the LFA-1 receptor from P3028-mediated inhibition (e.g. displacing bound P3028 peptide and P3028-structure containing molecules from the LFA-1 receptor), and/or stimulating immune cells. The activity of peptide P28R (SEQ ID NO: 2) and modifications of P28R was studied in a human ex vivo model using PBMCs from a healthy control human in short term cultures, and with PBMC activation measured as a percentage of cells with enhanced CD69 (see Example 37). It was observed that P28R (SEQ ID NO: 2) and peptide 31135 (KKLDTFFVYLSLFTER)(SEQ ID NO: 589) directly stimulate healthy PBMCs in this ex vivo model, but peptides 30677 (KKLDTFFVKLSLMTER) (SEQ ID NO: 583), 30678 (KKLDTFFVKLQLFTER)(SEQ ID NO: 584), 30680 (KKLDTVMVKLQLMTER)(SEQ ID NO: 585), 30864 (KSLDTFFVKLSLFTER)(SEQ ID NO: 587); 30685 (KKLDTFFVKLSLFTFR)(SEQ ID NO: 588); and 31136 (KKLDTFFVNLSLFTER)(SEQ ID NO: 590), and 31138 (KKLDTFFVDLSLFTER)(SEQ ID NO: 591) did not stimulate the healthy PBMCs in this ex vivo model (see FIGS. 41A and 41B). As such, in some embodiments, a composition comprising, consisting essentially of, or consisting of P28R (SEQ ID NO: 2), peptide 31135 (SEQ ID NO: 589), or a combination of P28R and peptide 31135 is provided to directly stimulate immune cells. As such, in some embodiments, a composition comprising, consisting essentially of a peptide of SEQ ID NO: 2, SEQ ID NO: 62, or any of SEQ ID NOs: 583-586 or 587-595, or a combination of these peptides is provided.

It is noted that peptide 31135 comprises a Y at the position corresponding to position 9 of SEQ ID NO: 2 and position 4 of SEQ ID NO: 62. (see Tables 5.3 and 5.5). In some embodiments, a composition comprising, consisting essentially of, or consisting of a modified peptide comprising a modification of P28R comprising a Y at position 9 of SEQ ID NO: 2 is provided. Optionally, the immune cells can comprise healthy immune cells. Optionally, the immune cells can comprise immune cells in cancer patient serum, for example cancer patient immune cells. In some embodiments, a composition comprising, consisting essentially of, or consisting of a modified peptide comprising a modification of P28 core comprising a Y at position 4 of SEQ ID NO: 62 is provided. Optionally, the immune cells can comprise healthy immune cells. Optionally, the immune cells can comprise immune cells in cancer patient serum, for example cancer patient immune cells.

Figure 42A:
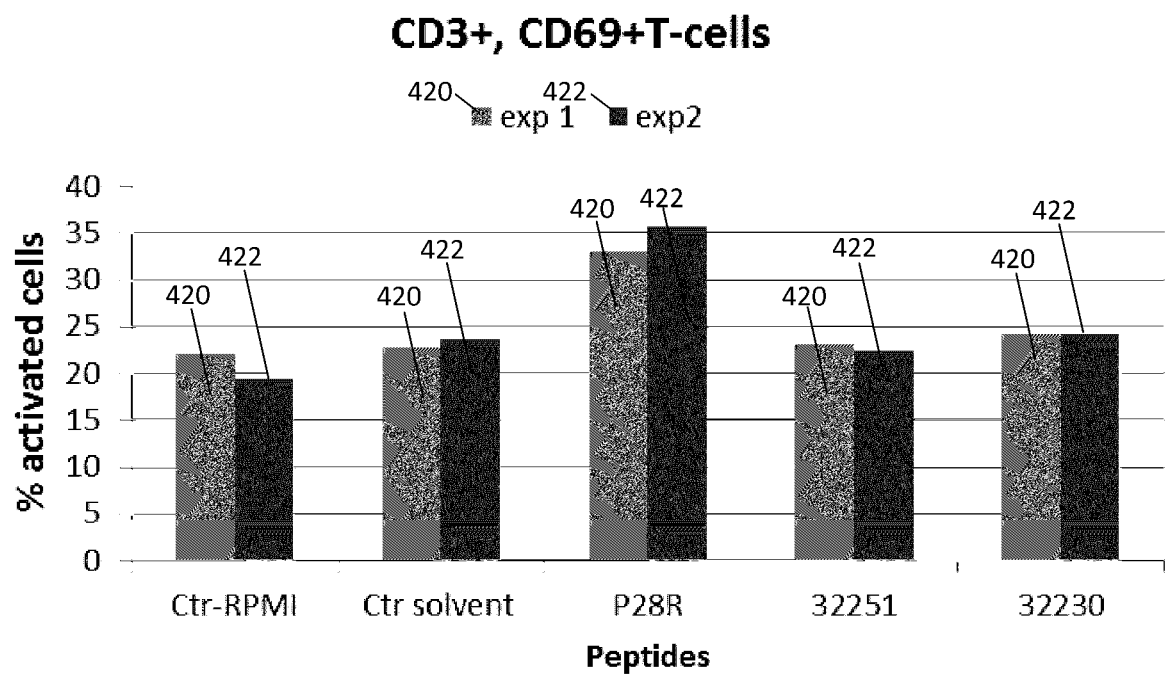
FIG. 42A illustrates the results of two experiments (420 and 422) performed for each peptide.
Figure 42B:
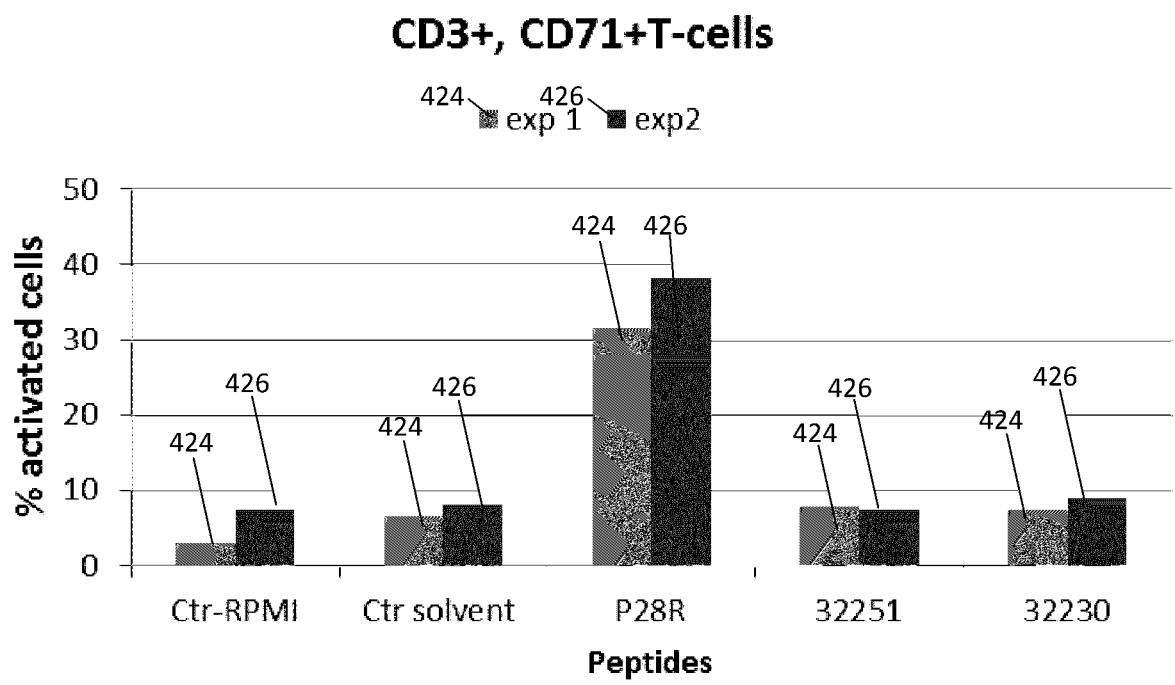
FIG. 42B illustrates the results of two experiments (424 and 426) performed for each peptide.

As P28R (SEQ ID NO: 2) can bind to P3028 and stimulate PBMCs from healthy controls in short term cultures, for example when in a culture medium comprising RPMI plus 10% normal human AB serum (see Example 37), it is contemplated that truncations of P28R in accordance with some embodiments herein can be useful for binding to inhibitors of any one or more of the peptides listed in Tables 1-4. Truncations of P28R were assessed for their ability to activate PBMCs (see Example 38). PBMCs were incubated with the peptides (40 μg/mL) for 24 hours in RPMI plus 10% human AB serum. PBMC activation was measured as percent cells with enhanced expression of either CD69 (FIG. 42A) or CD71 (FIG. 42B) using flow cytometry. As shown in FIGS. 42A and 42B, peptide P28R (SEQ ID NO: 2) effectively activated healthy PBMCs in this ex vivo model, but peptide 32251 (SEQ ID NO: 592) and peptide 32230 ("P28 core")(FFVKLS)(SEQ ID NO: 62) did not. However, PBMCs were also incubated with the peptides in cancer sera from dogs, or in cancer sera from human cancer patients (see FIG. 43). It was observed that full length peptide P28R (SEQ ID NO: 2) and the P28 core peptide (peptide 32230)(SEQ ID NO: 62) activated PBMCs in the presence of cancer serum. As such, it is contemplated that in accordance with some embodiments herein, P28R, P28 core, or combinations of these peptides are useful for stimulating immune cells in the serum of a subject that has cancer.

In some embodiments, a peptide comprising, consisting of, or consisting essentially of P28 core (SEQ ID NO: 62) is provided. Optionally, the peptide comprising, consisting of, or consisting essentially of P28 core (SEQ ID NO: 62) can bind to P3028 peptide. It was observed that P28 core peptide (SEQ ID NO: 62) can bind the 3028 peptide as efficiently as the full length peptide P28R, and can induce activation (e.g. proliferation, enhanced expression of CD69 and/or CD71, secretion of IL-12 or IFNγ, or secretion of perforin or granzyme B, enhanced cytotoxicity, cell migration, or cytokine production) of PBMCs in cancer serum (see Example 38 and FIG. 43), but that in an ex vivo model comprising short term cultures of PBMCs, the P28 core peptide (SEQ ID NO: 62) not stimulate PBMC activation (CD69 and CD71) as the P28R peptide does (see FIGS. 42A and 42B). Accordingly, in some embodiments, a peptide comprising, consisting of, or consisting essentially of P28 core (SEQ ID NO: 62) binds to P3028 peptide as efficiently or substantially as efficiently as P28R (SEQ ID NO: 2). In some embodiments, P28R (SEQ ID NO: 2 is provided to bind to P3028 and de-block cellular receptors (e.g. displaces bound immunoregulatory peptides or 3028 structures from the cellular receptors). Optionally P28R can further have a direct stimulatory activity on immune cells. In some embodiments, P28 core (SEQ ID NO: 62) is provided to bind to P3028 and de-block cellular receptors (e.g. displaces bound P3028 peptides or 3028 structures from the cellular receptors).

It has also been observed that, biotinylated P28R has been shown to bind directly to PBMCs as demonstrated by immunocytochemistry or rosetting of P28R coated beads (binding of beads to the cells). Accordingly, in some embodiments, P28R is provided to bind directly to PBMCs. In some embodiments, P28R comprising a detectable moiety is provided to bind to PBMCs. In some embodiments, P28R comprising a toxin is provided to bind to PBMCs. In some embodiments, peptide 31135 comprising a toxin or a detectable moiety is provided.

The effect of P28R (SEQ ID NO:2) on cancer cells was further studied in in vivo models in nude and immunocompetent mice. P28R was injected intra-tumorally into human pancreas cancer in a xenograft model in nude mice, and induced tumor cell apoptosis after one day (see Example 39). P28R induced Caspase 3, a marker of ongoing apoptosis, while treatment of tumors with the drug solvent only did not induce Caspase 3 (see FIGS. 44A and 44B). In some embodiments, P28R (SEQ ID NO: 2) has a direct cytotoxic action on tumor cells, for example, prostate cancer cells. In some embodiments, a peptide of Table 5.3, or a modified P28R peptide comprising at least one modification of Table 5.2 has a direct cytotoxic action on tumor cells, for example prostate cancer cells.

Figure 45A:
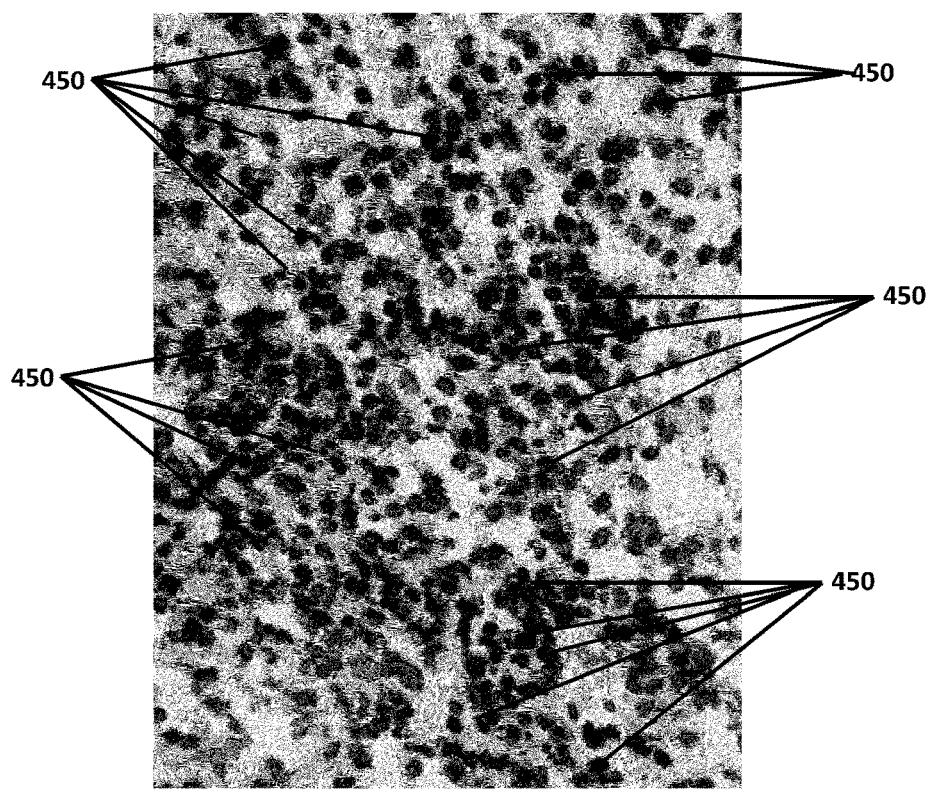
FIG. 45 is a series of microscope images illustrating intra-tumoral treatment of B16 melanoma with P28R. The inflammatory infiltrate was demonstrated after 3 days of treatment using a polyclonal rabbit antibody directed against CD45 (FIG. 45A), and control sections were incubated with rabbit IgG at the same concentration (FIG. 45B). Staining 450 and an absence of staining 452 are depicted.
Figure 45B:
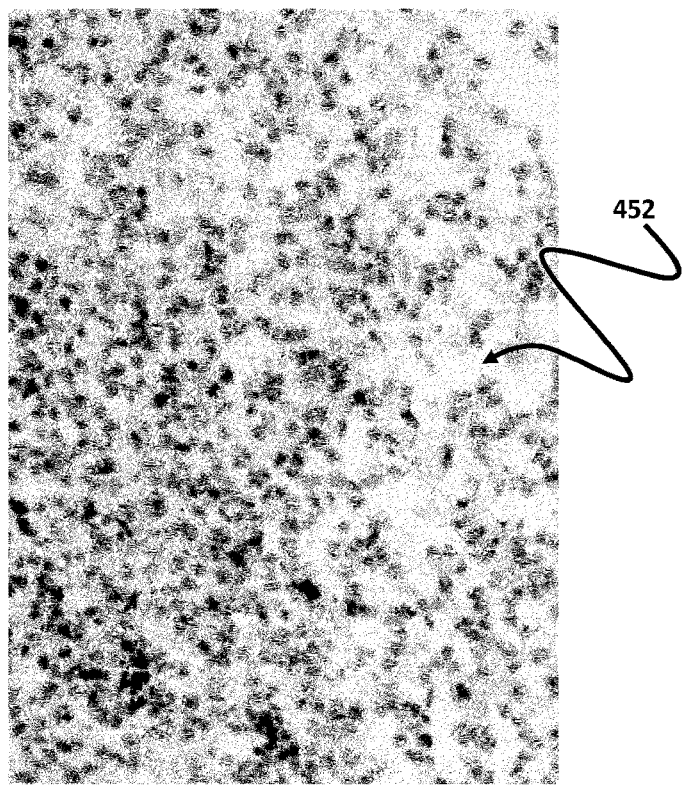

As it was observed that P28R has an immunostimulatory effect (see, e.g. Example 37), the capacity of P28R (SEQ ID NO: 2) to activate the immune system was also evaluated. P28R, 40 microgram in 100 microliter was injected intratumorally into B16 melanoma in B16 melanoma-inoculated immunocompetent mice, C57B1 (see Example 40). Tumors were taken out after 3 days, and sections were immunohistochemically stained using a polyclonal rabbit anti-CD45 antibody. The dominating cells in the tumors after P28R treatment were inflammatory cells, as indicated by CD45 immunostaining 450 (see FIG. 45A). The staining was not observed 452 in a control tumor section incubated with rabbit IgG at the same concentration (FIG. 45B). It is contemplated that in some embodiments P28R (SEQ ID NO: 2), P28 core (SEQ ID NO: 62), a peptide of SEQ ID NO: 586 or 589, or a modified P28R peptide comprising at least one modification of Table 5.2 can activate the immune system, for example to direct an immune response against tumor cells. In some embodiments, one or more of the listed peptides is administered at or near a tumor. In some embodiments, one or more of the listed peptides is administered peri-tumorally. In some embodiments, one or more of the listed peptides is administered systemically.

Figure 46A:
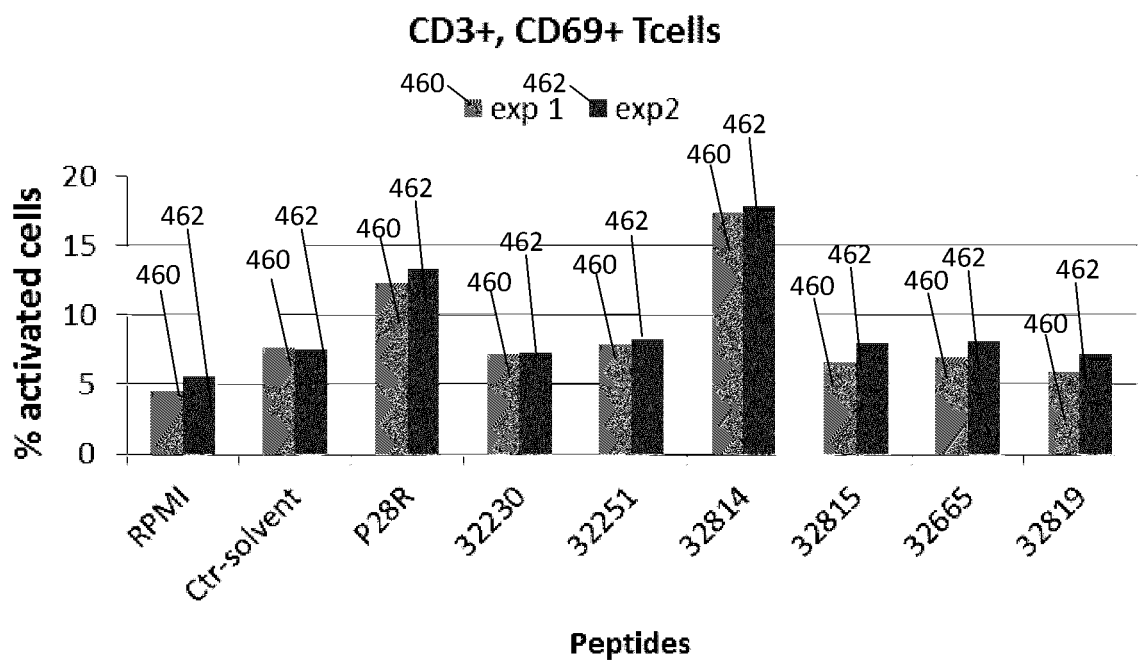
FIG. 46 is a series of graphs illustrating Effect of modified peptides on activation of PBMCs from healthy control person. Activation is determined as percentage of cells with enhanced marker CD69 (FIG. 46A, showing results of two experiments, exp 1 460 and exp 2 462) or CD71 (FIG. 46B, showing results of two experiments, exp 1 464 and exp 2 466) using flow cytometry. PBMCs were incubated with the peptides (40 µg/mL) for 48 hours in RPMI plus 10% human AB serum.
Figure 46B:
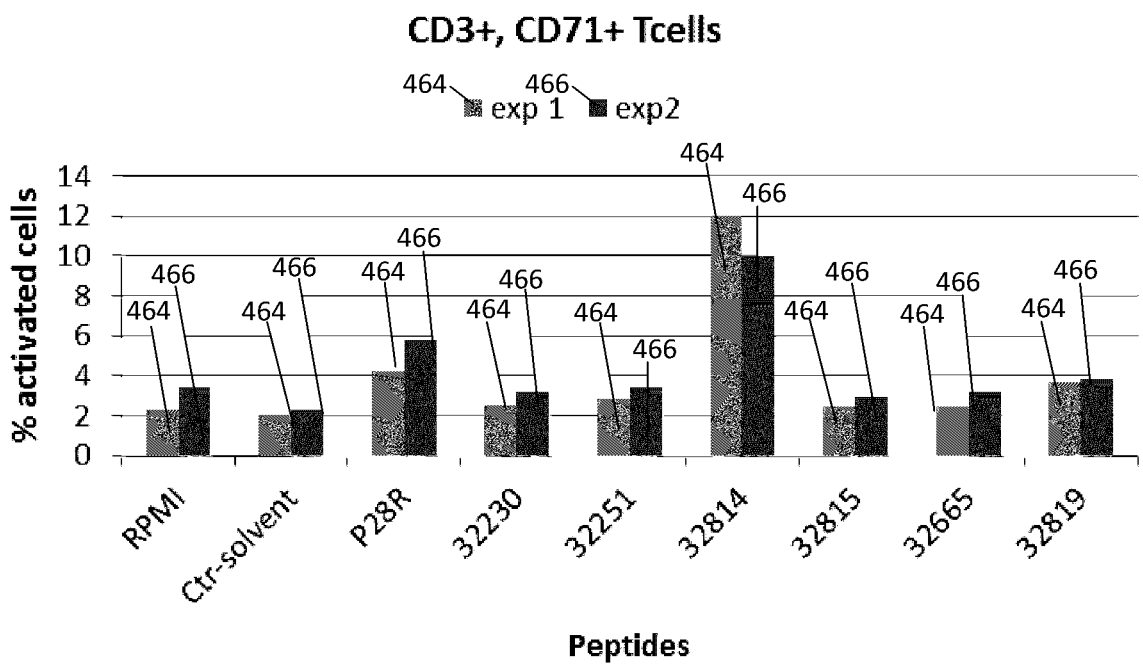

As it is contemplated that modifications of P28R can be useful for immune cell stimulation, the influence of various amino acid substitutions and additions to P28R on the immunostimulatory effect was further studied. Effects of modified peptides on the activation of PBMCs from a healthy control person were assessed (see Example 41). PBMCs were incubated with the peptides (40 μg/mL) for 48 hours in RPMI plus 10% human AB serum, and PBMC activation was determined by flow cytometry based on the percentage of cells with enhanced marker CD69 or CD71. Peptides P28R (SEQ ID NO: 2), P28 core (peptide 32230) (SEQ ID NO: 62), 32251 (KKLDTFFPKLSLFTER)(SEQ ID NO: 592), 32814 (RKLDTFFVKLSLFTERRR)(SEQ ID NO: 586), 32815 (KKLDQFFVKLSQHNER)(SEQ ID NO: 595), 32665 (KKLDTFMVKLSQHTER)(SEQ ID NO: 593), and 32819 (KKLDTFFVKLSLFTER(C(PEG24))) (SEQ ID NO: 594) were tested. As shown in FIG. 46, peptide 32814 (SEQ ID NO: 586), had a stimulatory effect in short term cultures similar to that of P28R (SEQ ID NO: 2) (batch CS8040) for both CD69 enhancement (see FIG. 46A) and CD71 enhancement (see FIG. 46B). Accordingly, it is contemplated herein that In addition to therapeutic applications, diagnostic applications of P28R and truncations and modifications thereof were also contemplated. For example, information about patients systemic and local (intra-tumoural) immune status can be obtained using reagents comprising P28R, or a truncation or modification thereof.

Figure 47A:
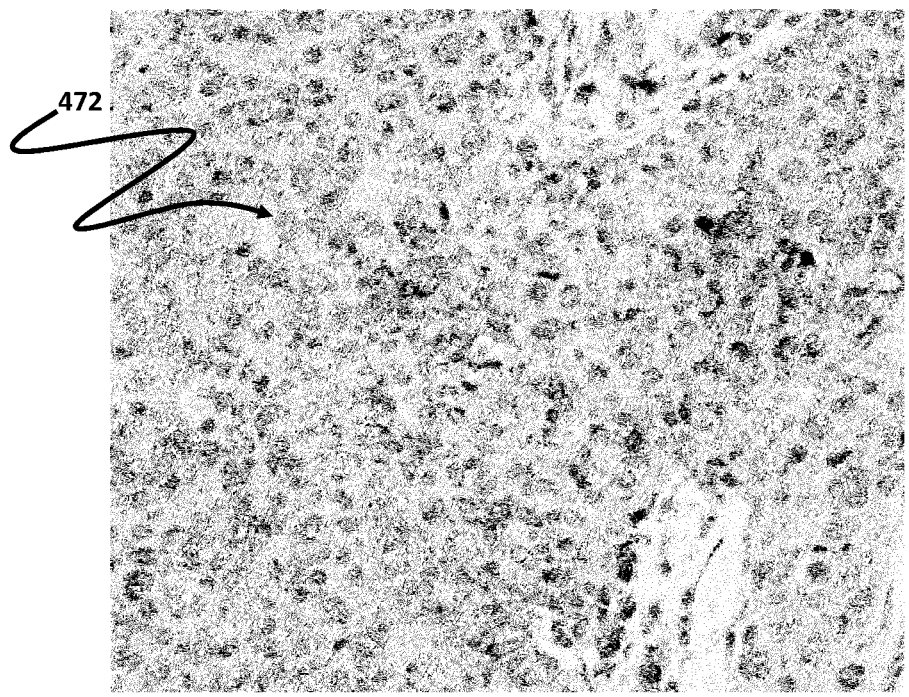
FIG. 47 is a series of microscope images illustrating occurrence of the immunoinhibitory 3028 structure in two areas (FIG. 47A and FIG. 47B, respectively) of a human breast cancer. Immunohistochemical staining (470) using biotinylated P28R is depicted. An absence of staining 472 is observed in FIG. 47A.
Figure 47B:
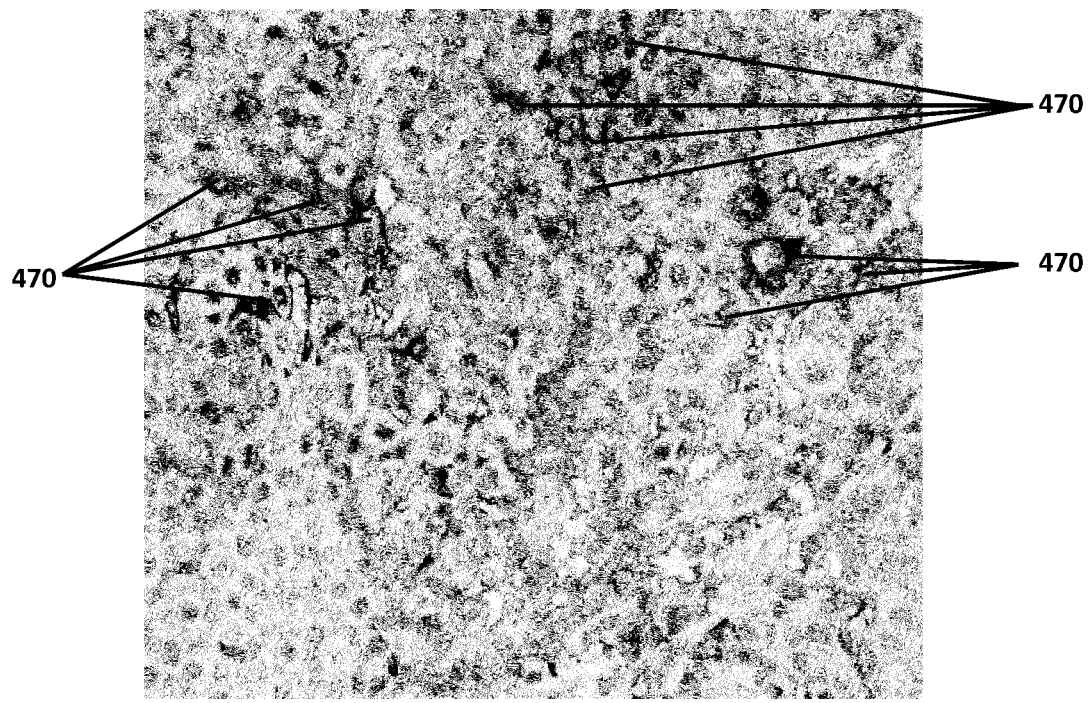

It is contemplated that the occurrence of immunoinhibitory 3028-structures in tumors can be identified by immunohistochemical staining using either an antibody directed against P3028 or using labeled P28R (SEQ ID NO: 2) or P28 core (SEQ ID NO: 62), for example biotinylated P28R or P28 core. FIG. 47 shows two areas of a human breast cancer stained using biotinylated P28R. Staining 470 is observed in FIG. 47B. Staining is not observed in FIG. 47A. An absence of staining is indicated 472.

As such, areas of tumors comprising P3028 structures (as well as areas not comprising these structures) can be identified using labeled peptides in accordance with embodiments herein. In some embodiments, a peptide of SEQ ID NO: 2, SEQ ID NO: 62, SEQ ID NO: 584, a peptide listed in Table 5.4, or a modified P28R or P28 core peptide comprising one or more modifications listed in Table 5.3 or Table 13 is provided, and further comprises a detectable moiety. The peptide comprising the detectable moiety can bind to one or more immunoregulatory peptides of Tables 1-4, for example P3028 (SEQ ID NO: 185).

Figure 48A:
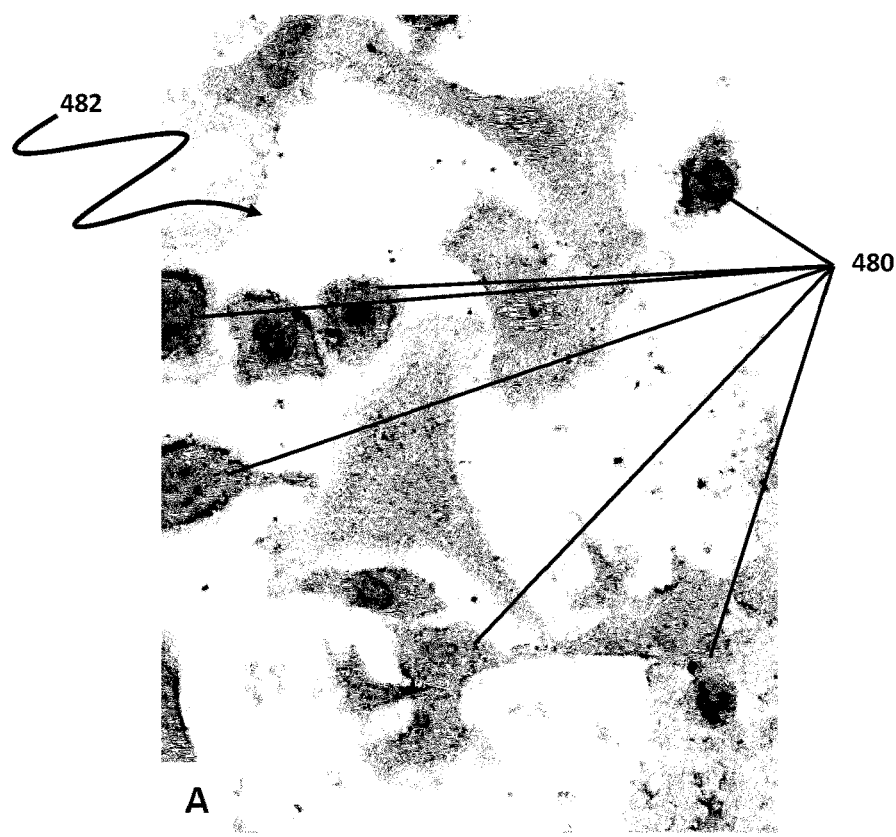
FIG. 48A depicts human prostate cells cultured in the absence of serum proteins, and immunostained with rabbit antibodies against P3028 structures (depicted as 480). Substantially low levels of staining are noted as 482.
Figure 48B:
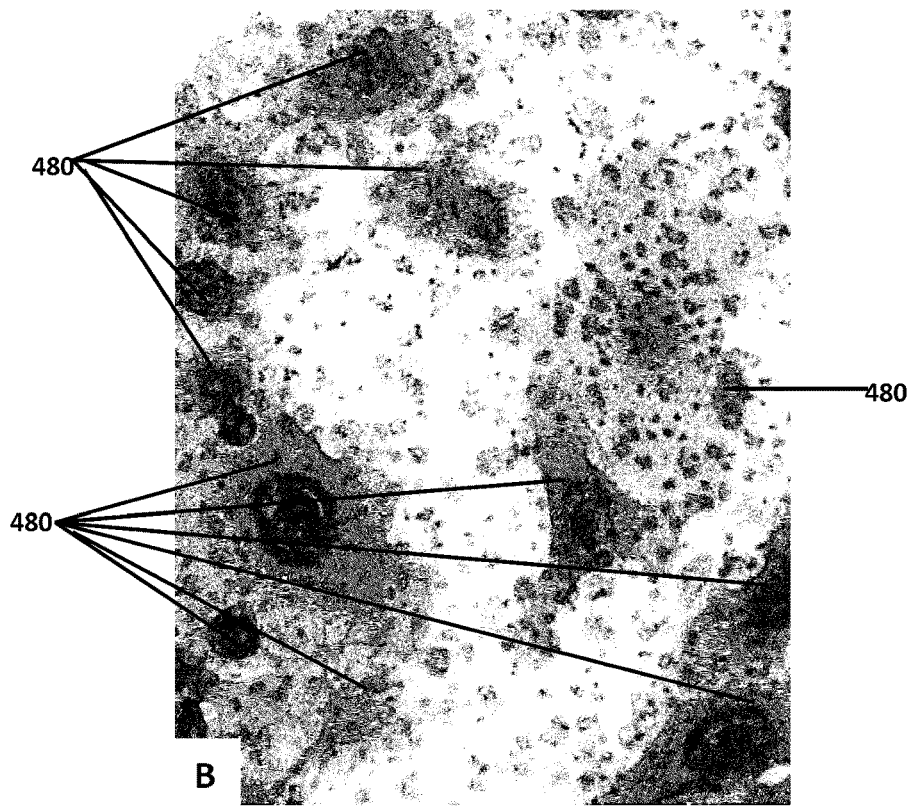
FIG. 48B depicts human prostate cells fed human serum albumin for 2 hours, and immunostained with rabbit antibodies against P3028 structures. Substantial staining 480 is observed.

Additionally, human prostate cancer cells were cultured in the absence of serum proteins, and exhibited minimal immunostaining for P3028 structures, based on detection by rabbit antibodies (FIG. 48A). However, when human prostate cancer cells were fed human serum albumin for 2 hours, and were stained for the presence of P3028 structures using rabbit antibodies, substantial immunostaining was observed (FIG. 48B). Accordingly it is contemplated that tumors can generate P3028 structures. Moreover, it is contemplated that immunoregulatory peptides inhibitors in accordance with some embodiments herein can be administered to tumor cells to counteract immunoinhibitory effects of P3028 structures. In some embodiments, a composition comprising a peptide of SEQ ID NO: 2, SEQ ID NO: 62, SEQ ID NO: 584, a peptide listed in Table 5.4, or a modified P28R or P28 core peptide comprising one or more modifications listed in Table 5.3 or Table 13, is administered to a tumor cell, and can bind to one or more P3028 structures so as to de-block an LFA-1 and/or IL-2 receptor and enhance immune cell stimulation.

Figure 49A:
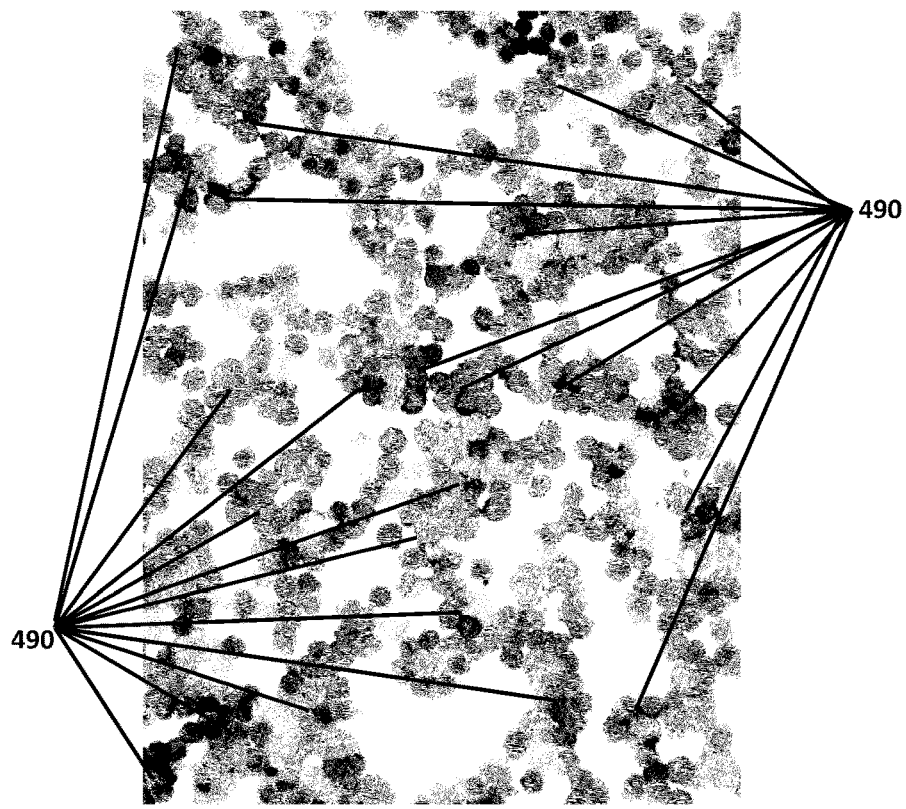
FIG. 49A depicts control PBMCs immunostained for dHSA (shown as 490).
Figure 49B:
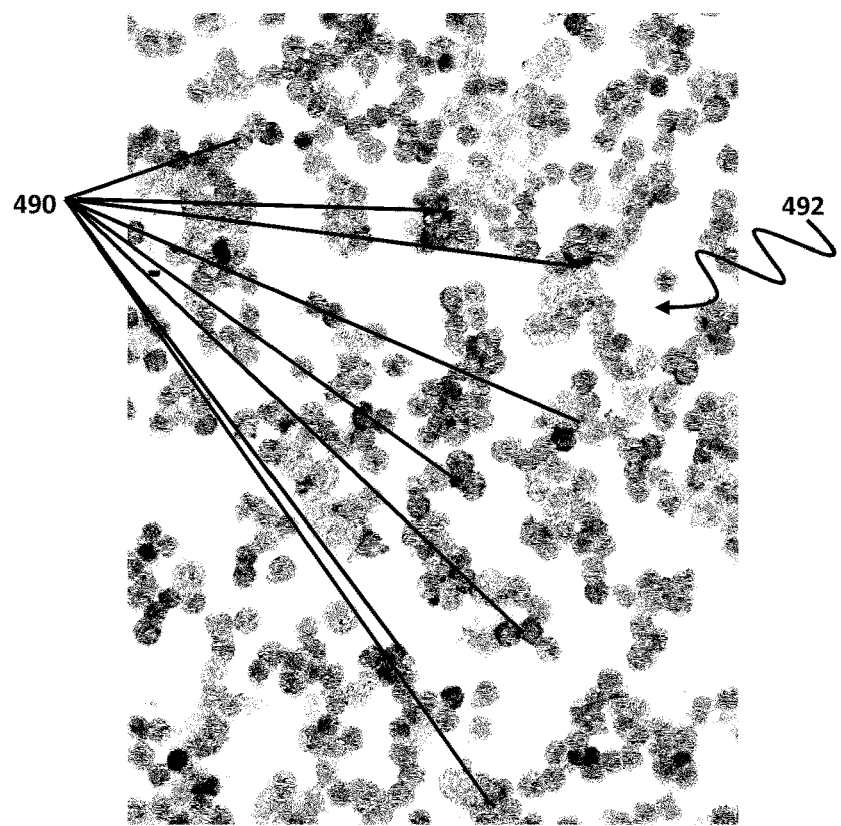
FIG. 49B depicts PBMCs incubated with magnetic Dynabead® beads bound to P28 core peptide (SEQ ID NO: 62), and immunostained for dHSA (shown as 490). Levels bound dHSA are substantially lower in the cells incubated with Dynabead® beads bound to P28 core peptide (shown as 492).

It was observed that compositions comprising immunoregulatory peptide inhibitors immobilized on nanoparticles in accordance with some embodiments herein can displace bound dHSA from immune cells. Magnetic Dynabead® beads were bound to P28 core peptide (FFVKLS)(SEQ ID NO: 62). As shown in FIG. 49A, control PBMCs cultured with dHSA exhibited substantial levels of bound dHSA. However, as shown in FIG. 49B, PBMCs cultured with dHSA and incubated for 24 hours with the Dynabead® bead-P28 core peptide composition exhibited substantially lower levels of bound dHSA. Accordingly, it is contemplated that compositions comprising immunoregulatory peptide inhibitors immobilized on nanoparticles in accordance with some embodiments herein can be useful for enhancing immune cell stimulation, for example by providing immunoregulatory peptide inhibitors to immune cells (e.g. lymphocyte, monocyte, macrophage, or NK-cell) bound to P3028. In some embodiments, a composition comprising a peptide of SEQ ID NO: 2, SEQ ID NO: 62, SEQ ID NO: 584, a peptide listed in Table 5.4, or a modified P28R or P28 core peptide comprising one or more modifications listed in Table 5.3 or Table 13 is provided. The composition can comprise a nanoparticle, and the immunoregulatory peptide inhibitor (e.g. a peptide of SEQ ID NO: 62) can be immobilized on the nanoparticle. Optionally, the composition can be administered to a patient in need of immune cell stimulation. Optionally, stimulation of immune cells of the subject can be detected, for example, as enhanced expression of CD69 and/or CD71, secretion of IL-12 or IFNγ, or secretion of perforin or granzyme B, enhanced cytotoxicity, cytokine production, cell migration, and/or cell proliferation. Optionally, the patient in need of immune cell stimulation is suffering from a tumor, for example a prostate tumor, a melanoma, a colon cancer, a lung carcinoma, an Apocrine gland carcinoma, a testis tumor, a mast cell tumor, a mammary tumor (e.g. a benign mammary tumor or a malignant mammary tumor, for example a mixed mammary tumor such as a benign mixed mammary tumor or a malignant mixed mammary tumor), a mucinous carcinoma (e.g. a mammary gland mucinous carcinoma), or a histicytoma. Optionally, administration of the composition to the patient induces regressive changes in the tumor, and/or eradicates or contributes to the eradication of the tumor.

Figure 57A:
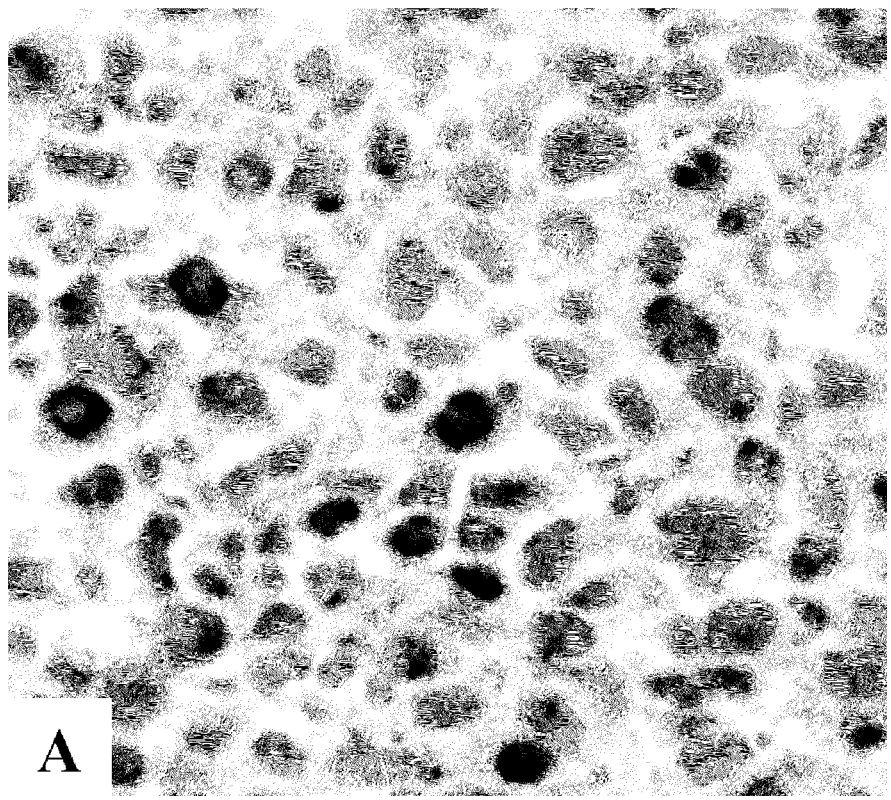
FIG. 57 is a series of microscope images illustrating injection of P28R into the tumours resulted in extensive tumour regressive changes in a Lewis lung carcinoma in accordance with some embodiments herein. The Lewis lung carcinoma was treated intratumorally with P28R (FIG. 57A) in accordance with some embodiments herein. A similar anti-tumour effect is seen also in contralateral untreated tumours (FIG. 57B).
Figure 57B:
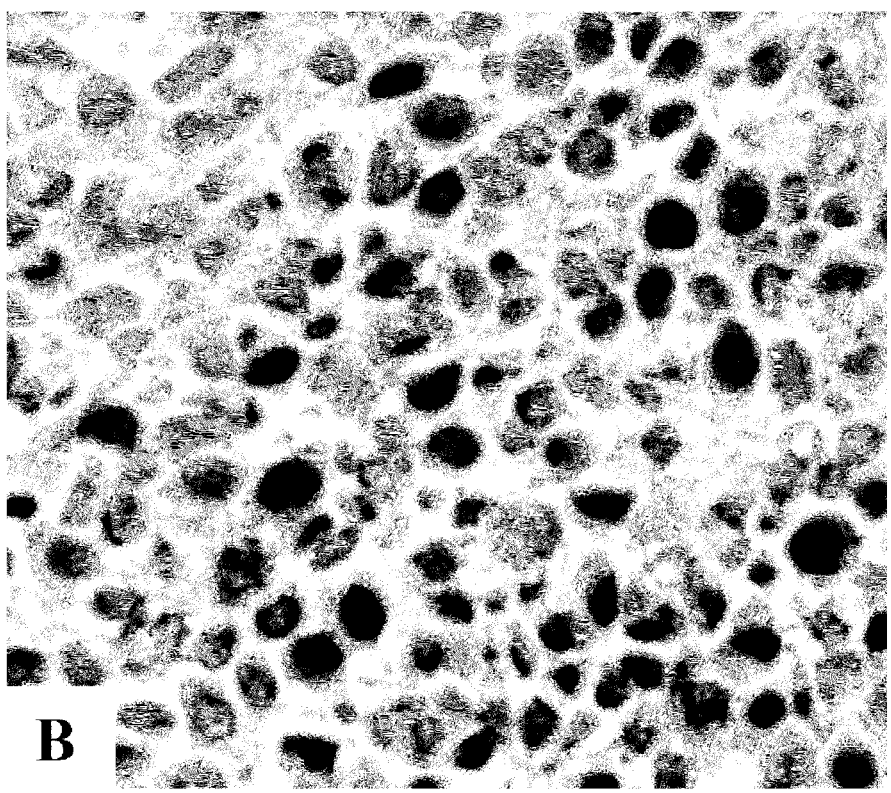
Figure 58A:
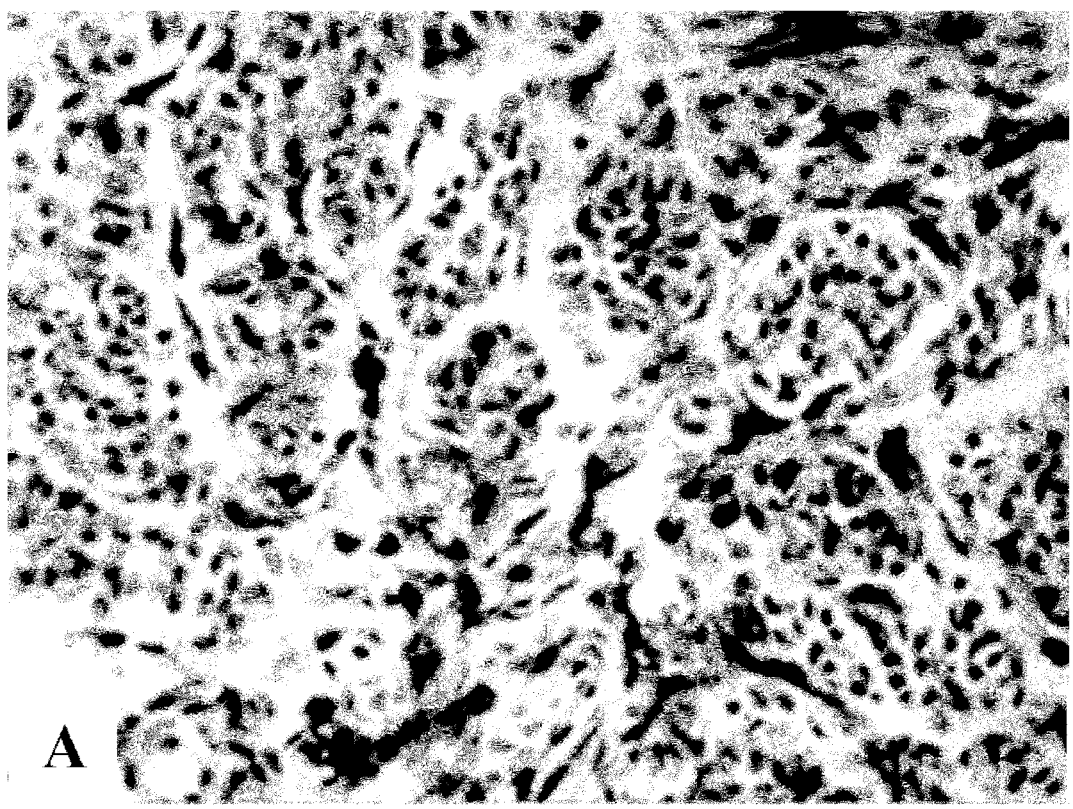
FIG. 58 is a series of microscope images illustrating spontaneous breast tumour in a dog staining of a regional metastatic lesion showing infiltration of CD45+ inflammatory cells in tumour areas with various degrees of regressive changes in accordance with some embodiments herein. Four different images of the tumor (FIG. 58A, FIG. 58B, FIG. 58C, FIG. 58D) are shown.
Figure 58B:
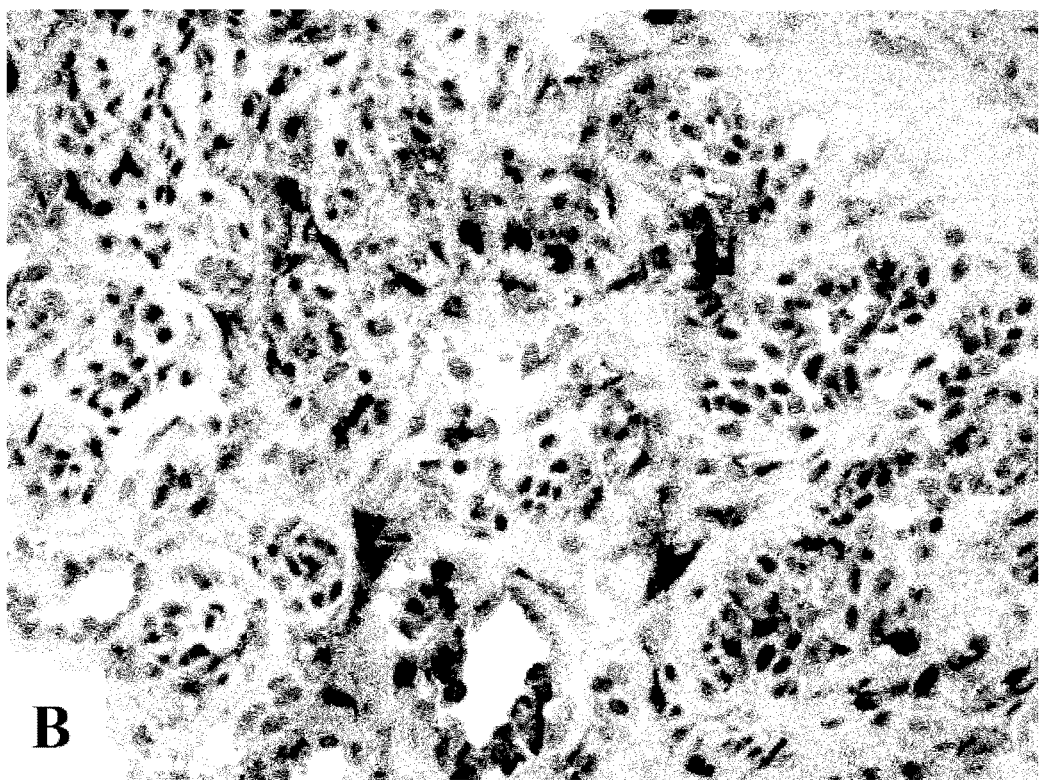
Figure 58C:
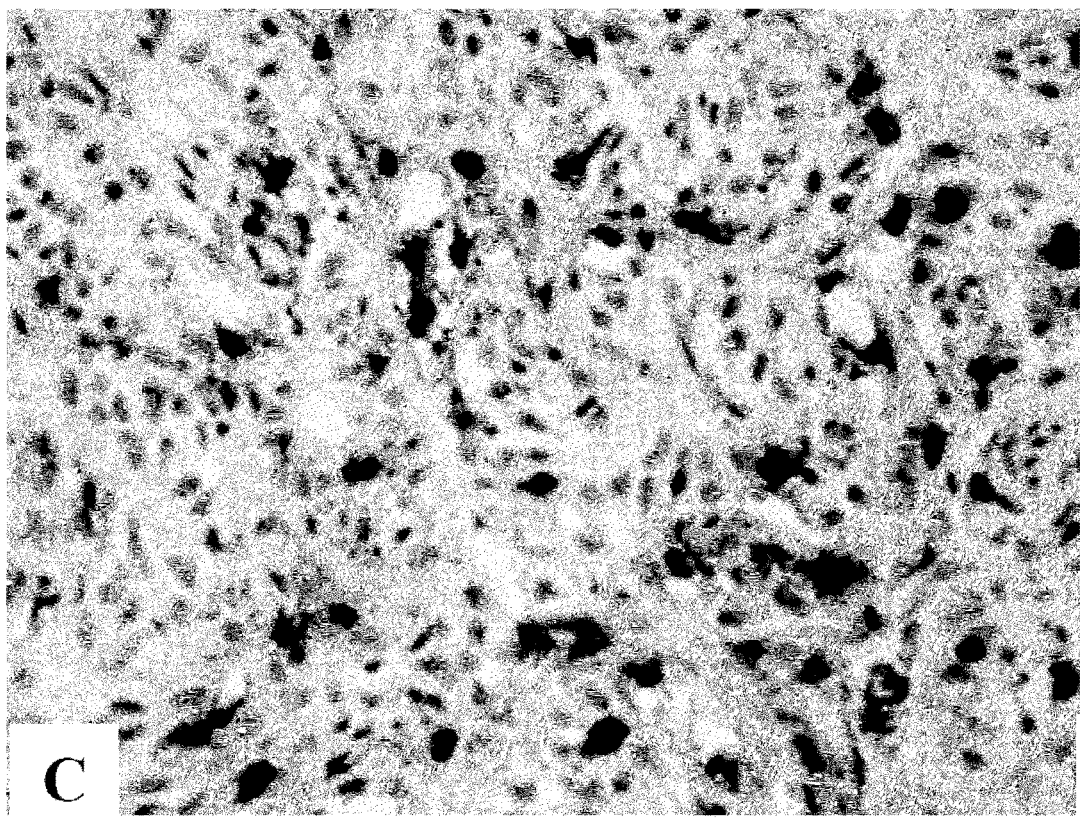
Figure 58D:
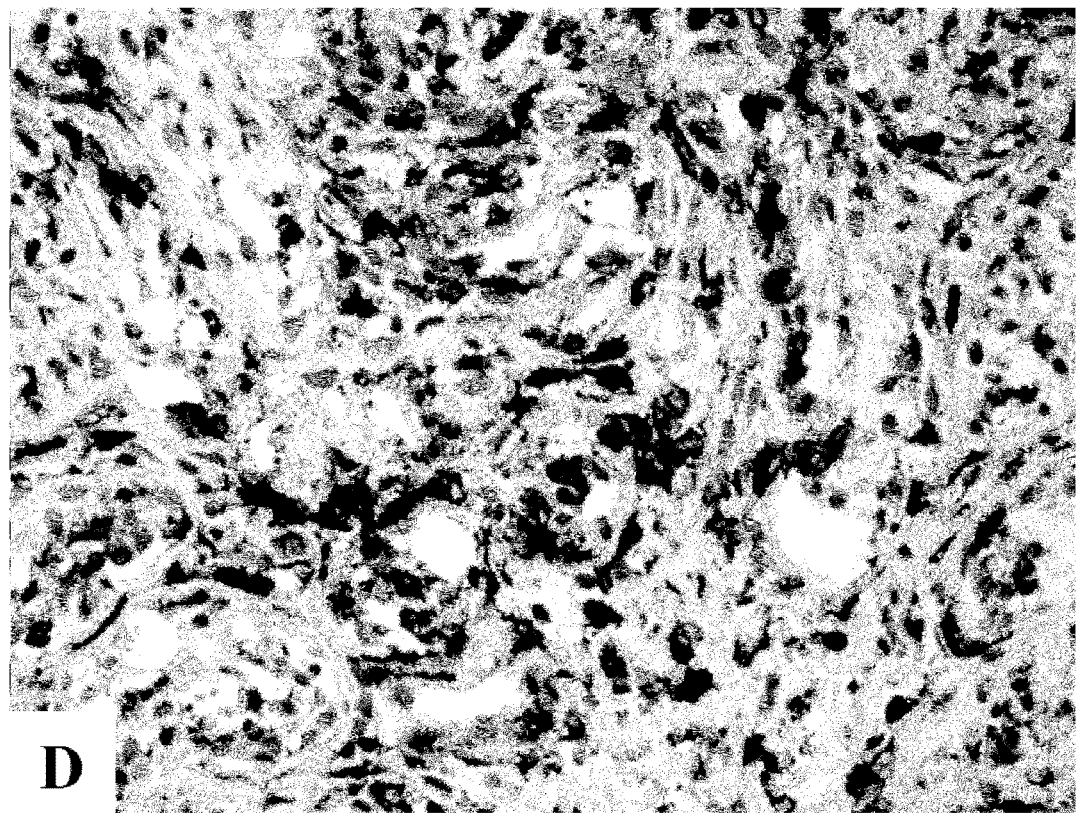
Figure 62A:
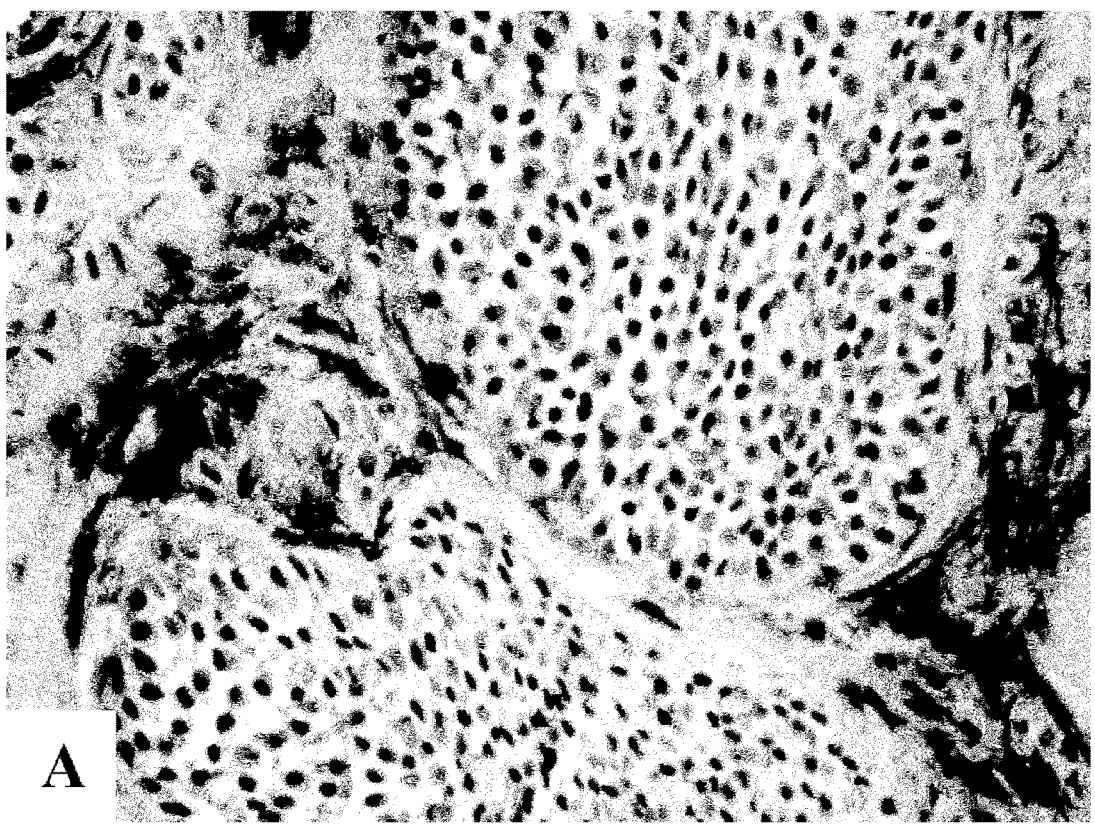
FIG. 62A shows CD45+ inflammatory cells surrounding tumour nodules.
Figure 62B:
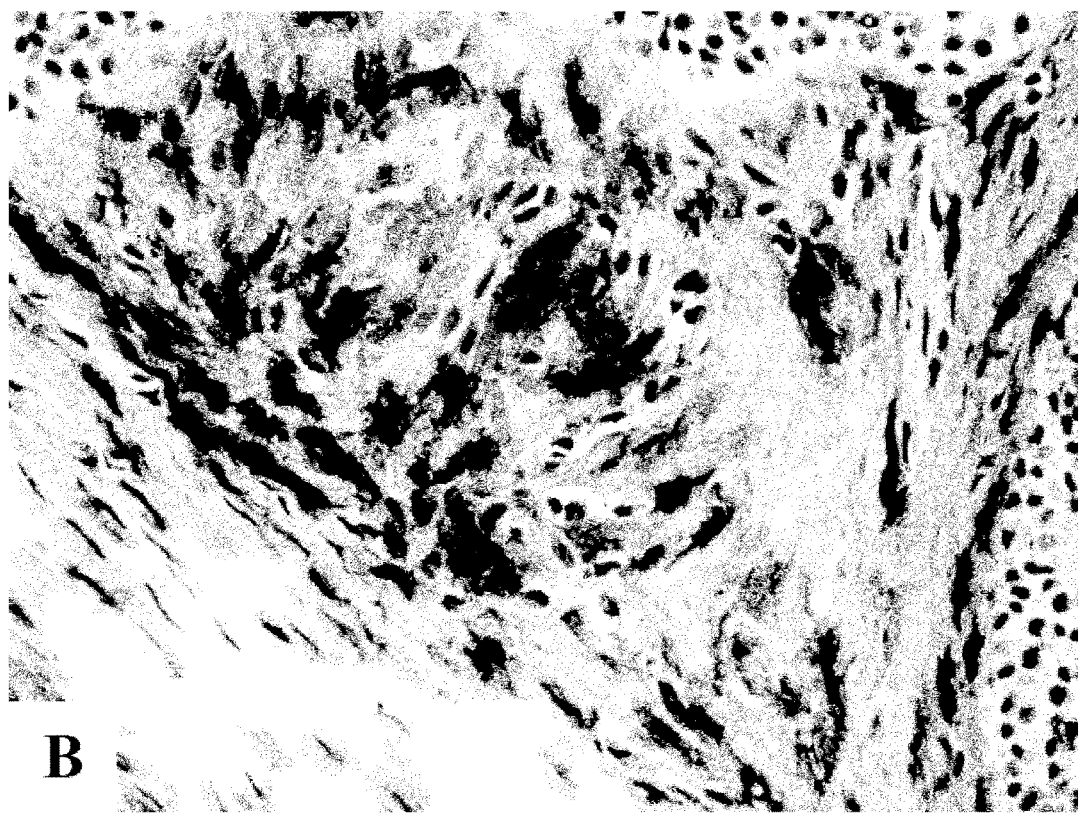
FIG. 62B shows CD45+ inflammatory cells infiltrating a thin lesion.
Figure 66A:
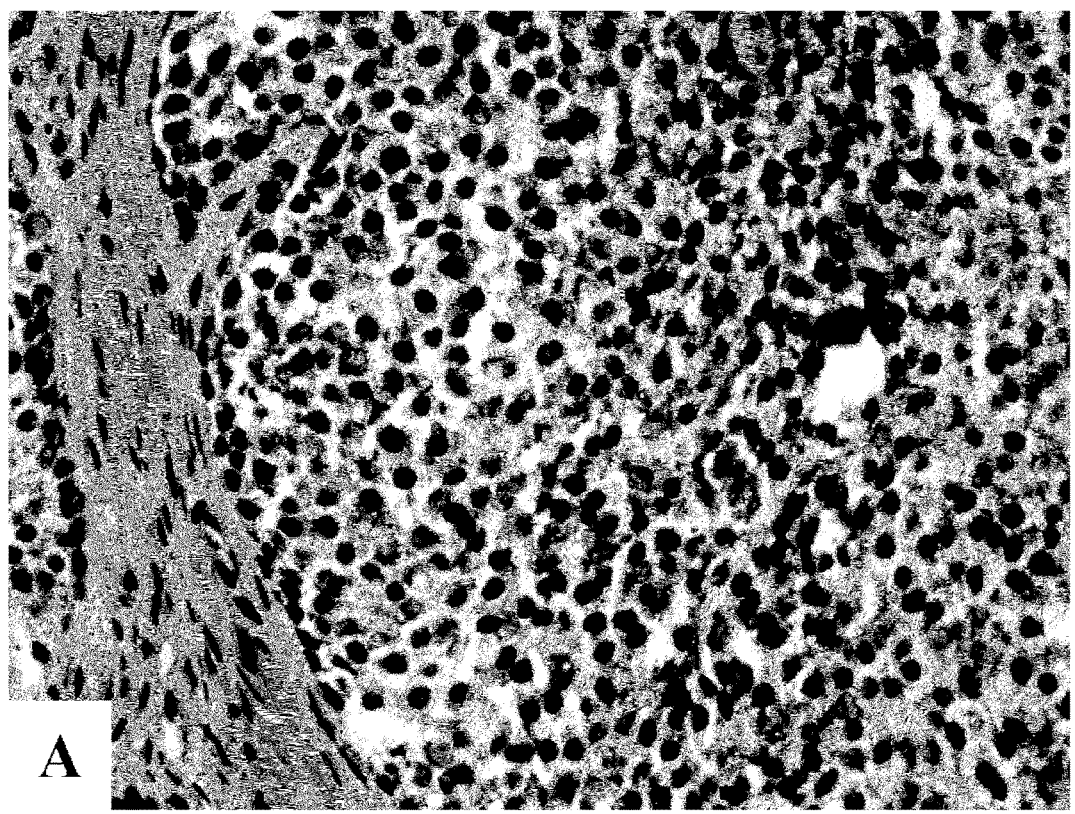
FIG. 66A illustrates H&E stained section showing the ordinary histopathological picture of a testis tumour.
Figure 66B:
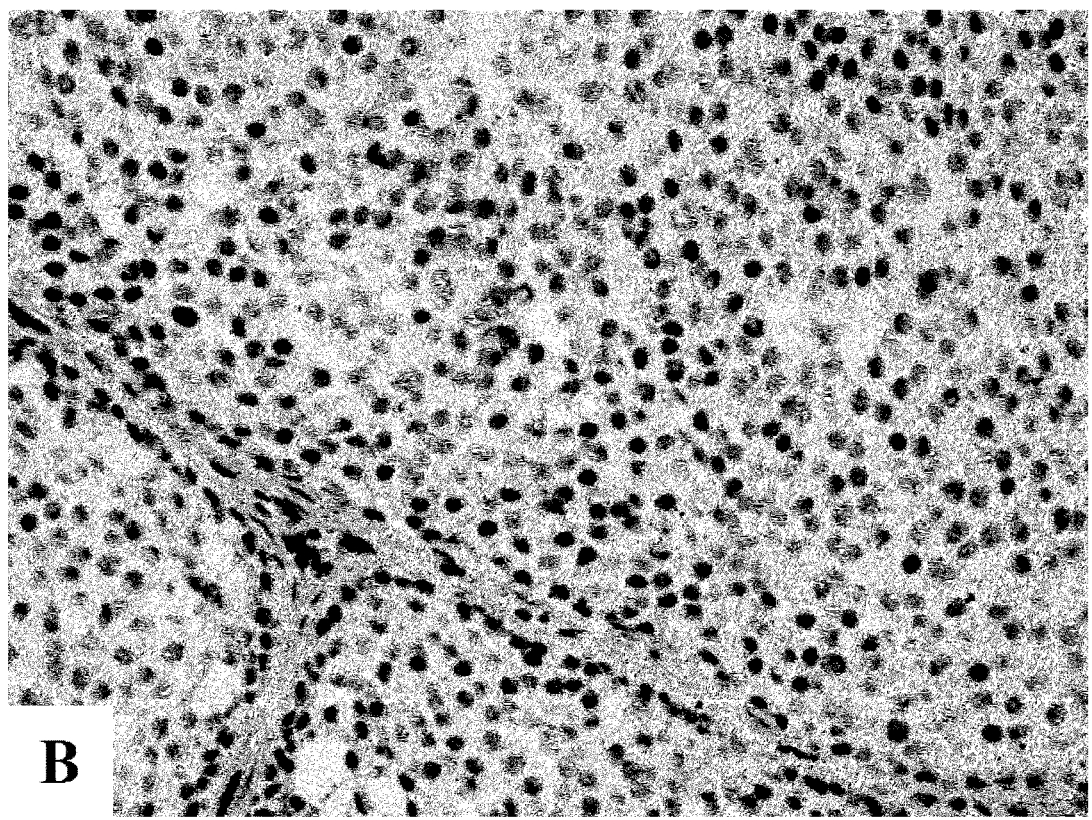
FIG. 66B illustrates the low degree of infiltration of inflammatory cells was demonstrated by IHC staining for CD45.
Figure 71A:
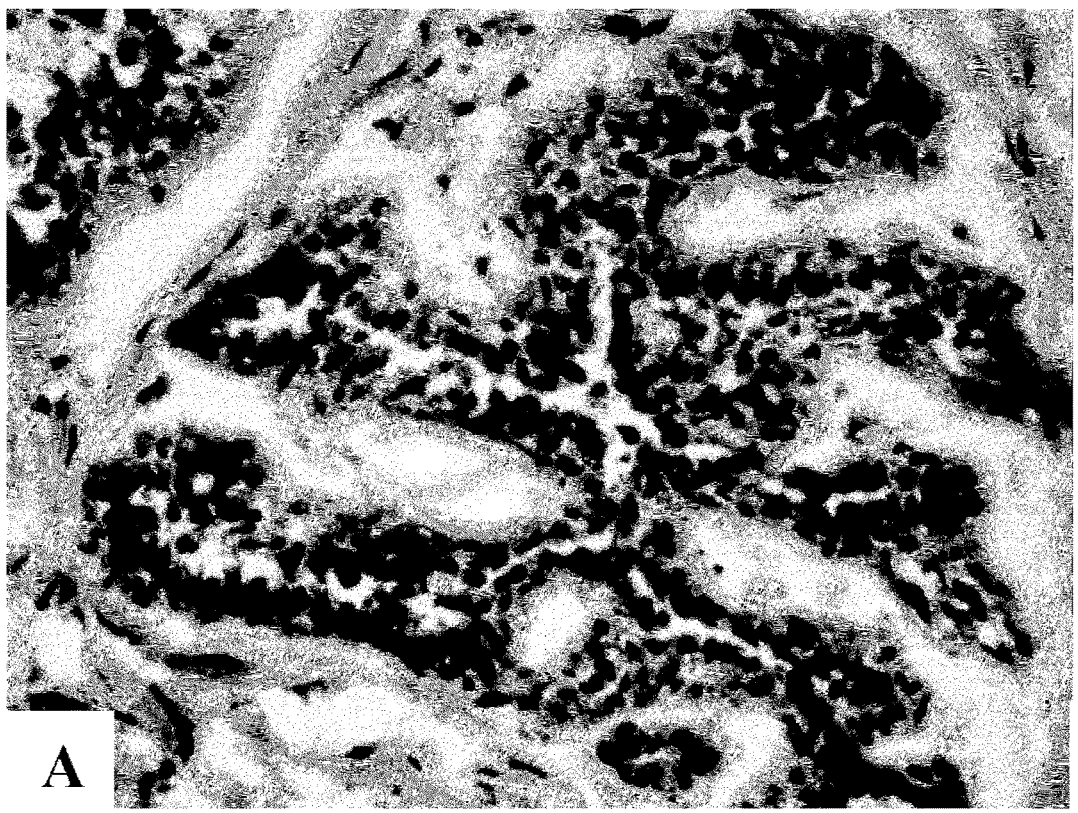
FIG. 71 is a series of microscope images illustrating H&E stained dog breast tumor sections indicating regressive changes at the injection site in accordance with some embodiments herein, presumably with some toxic effects. Two different sites of injection are shown (FIG. 71A and FIG. 71B).
Figure 71B:
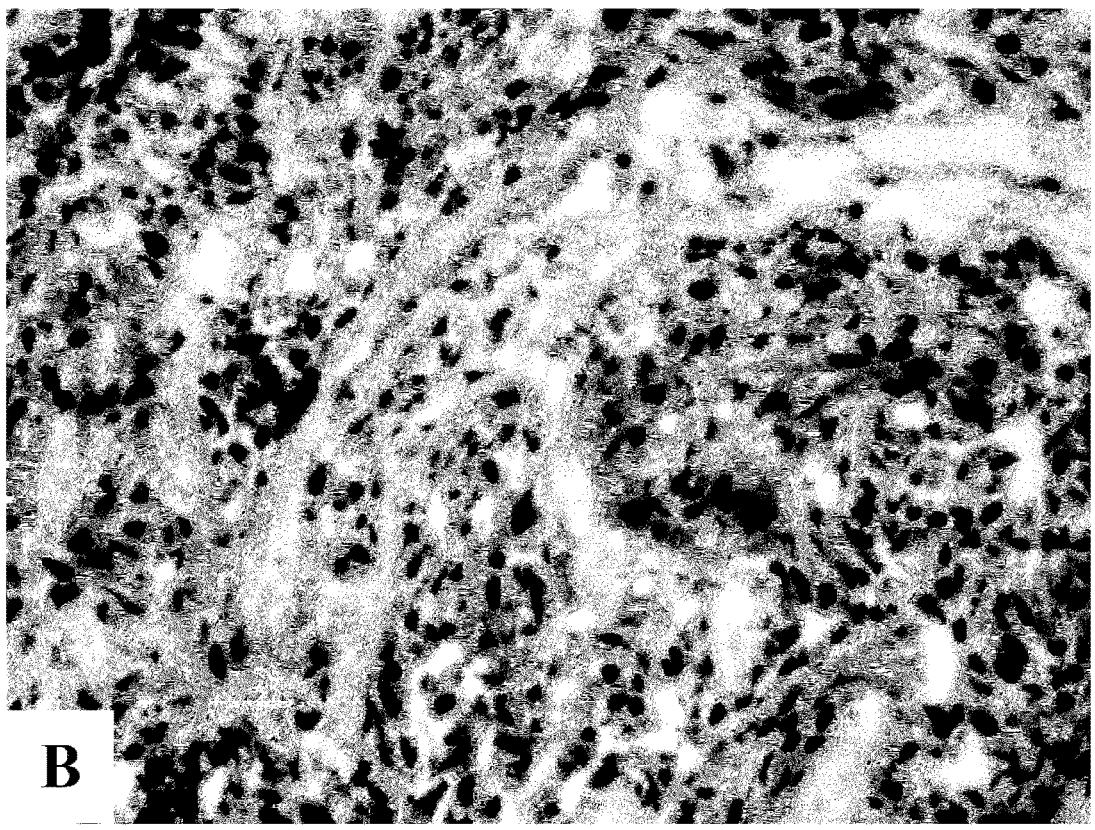
Figure 72A:
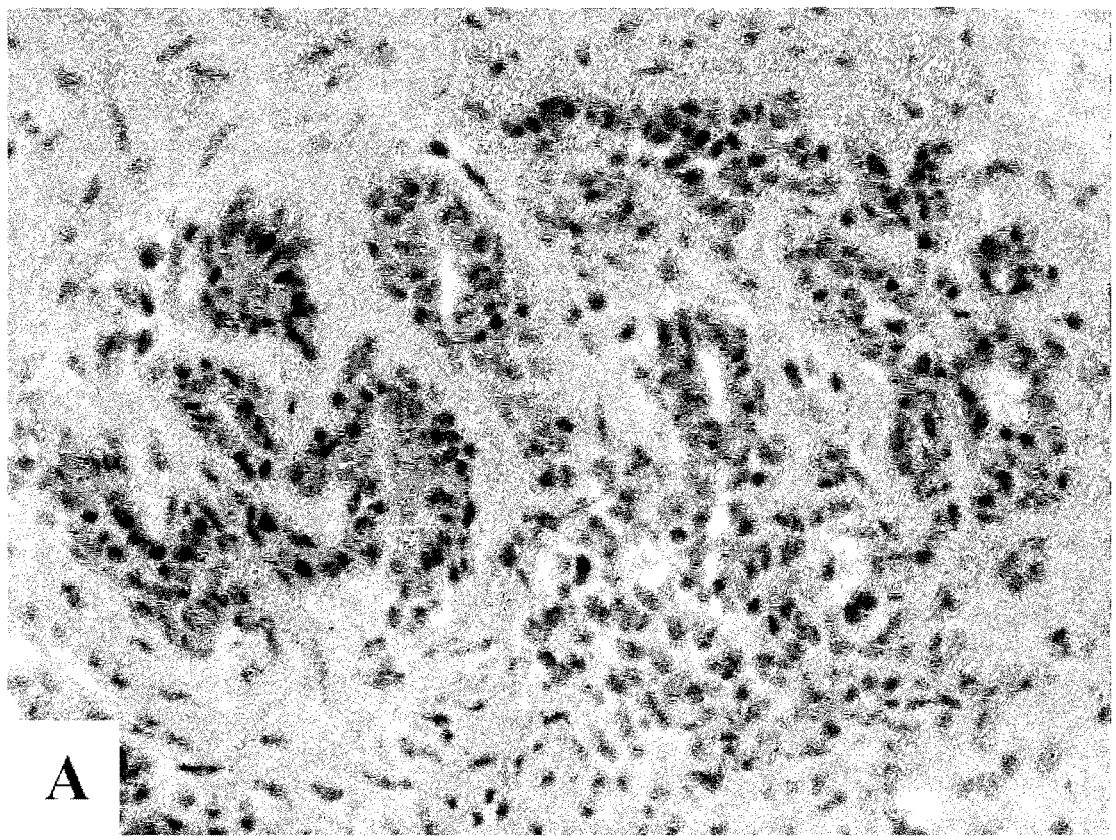
FIG. 72A, FIG. 72B, FIG. 72C, and FIG. 72D are images from the lesion showing various degrees of tumour regressive changes.
Figure 72B:
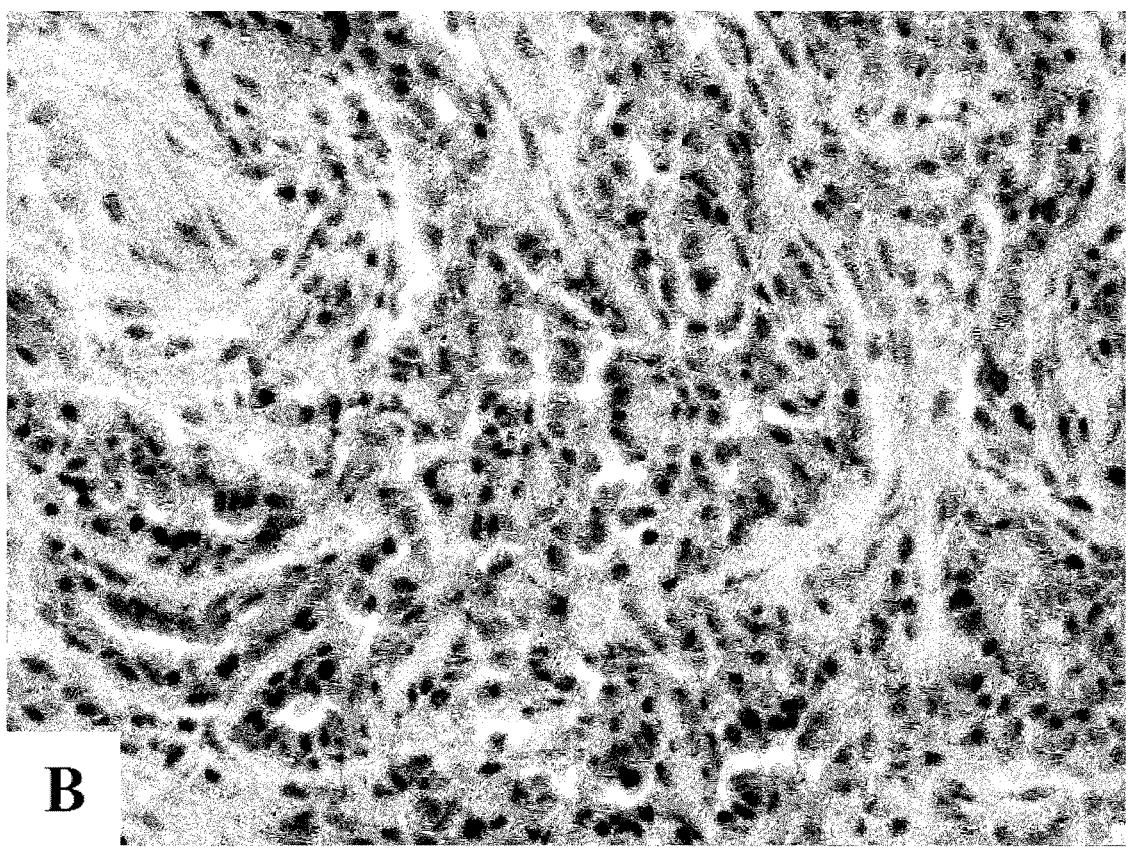
Figure 72C:
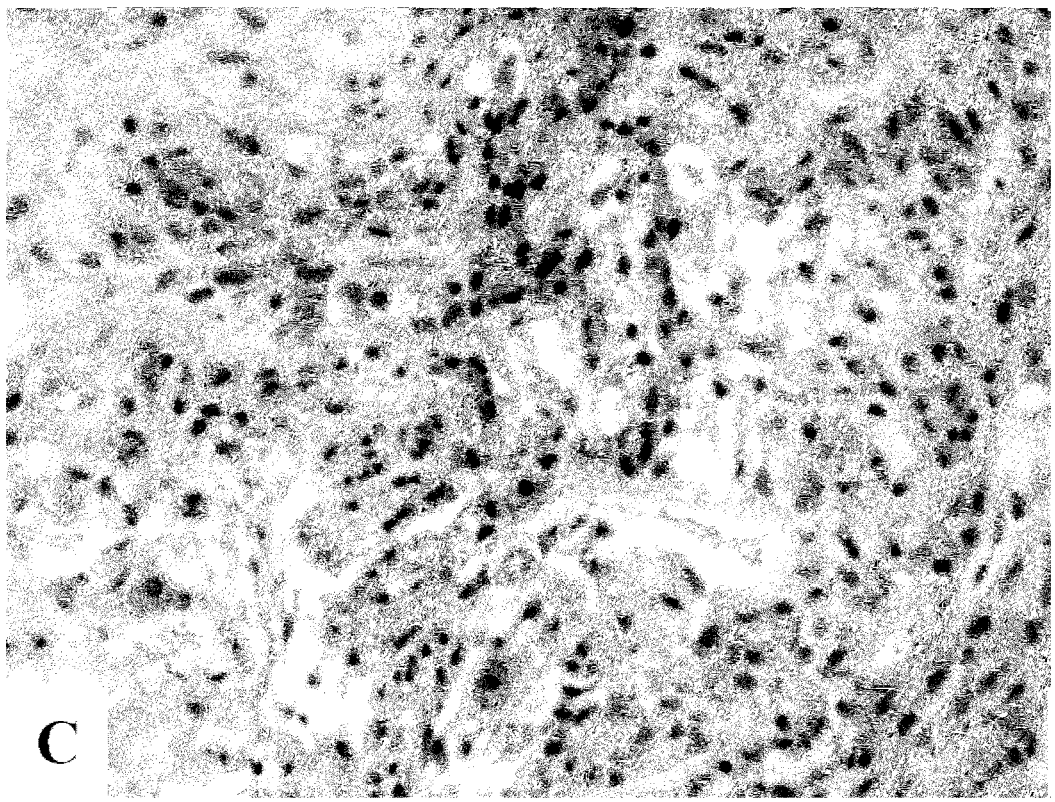
Figure 72D:
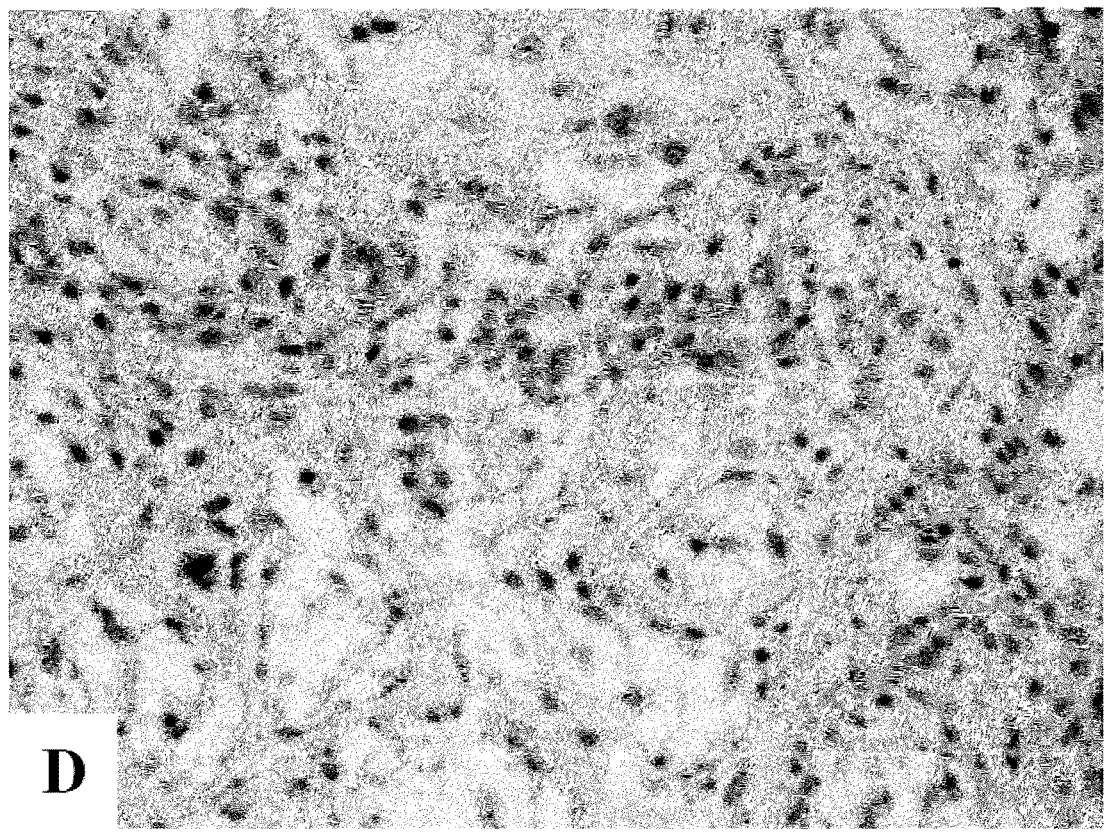
Figure 73A:
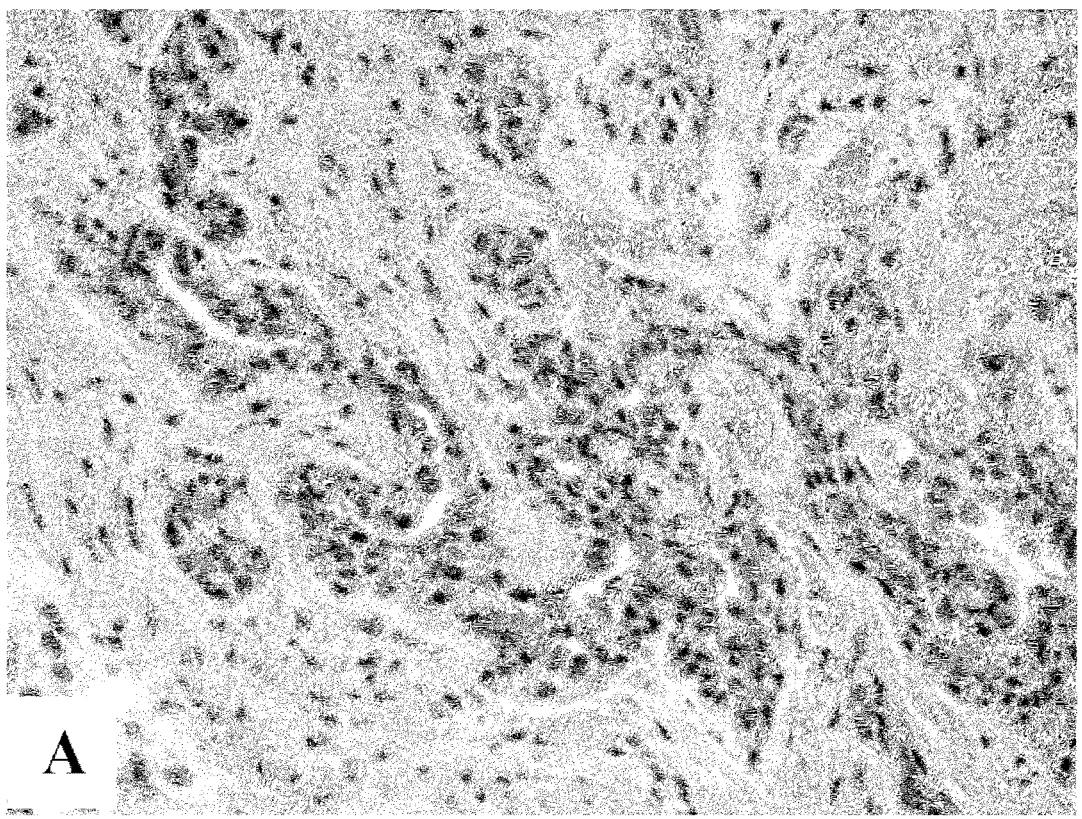
FIG. 73A, FIG. 73B, FIG. 73C, and FIG. 73D are images from the lesion showing various degrees of tumour regressive changes.
Figure 73B:
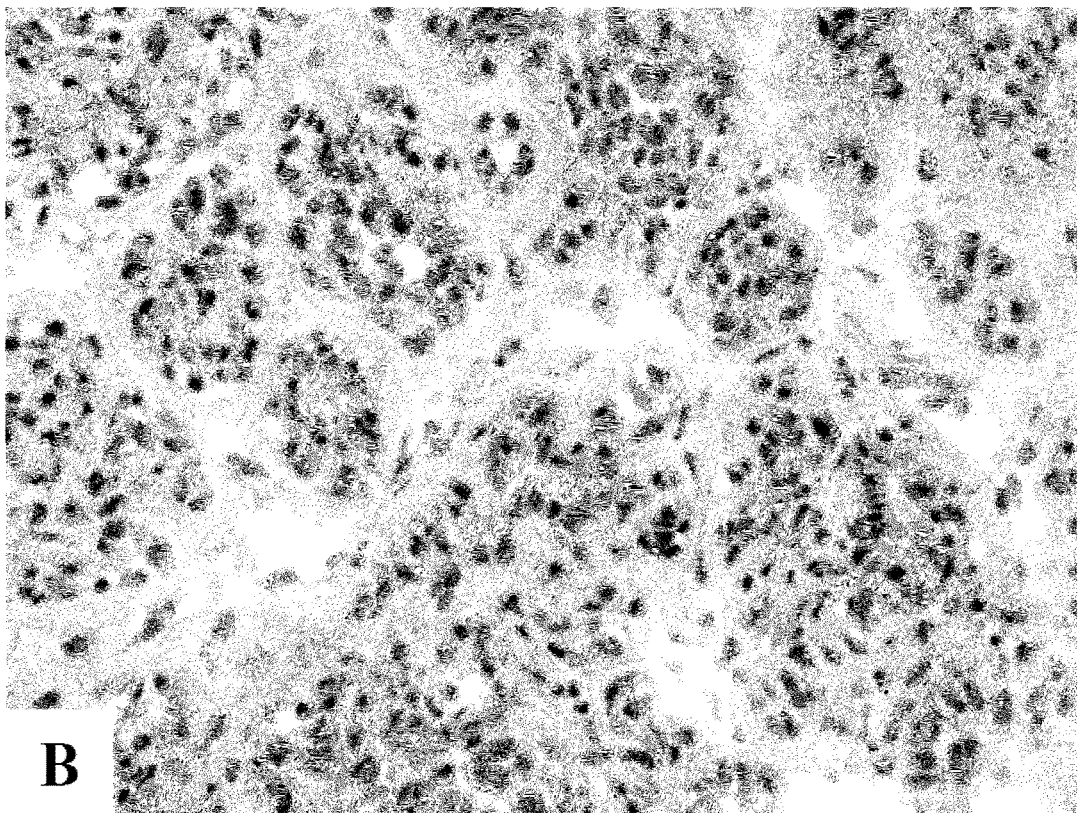
Figure 73C:
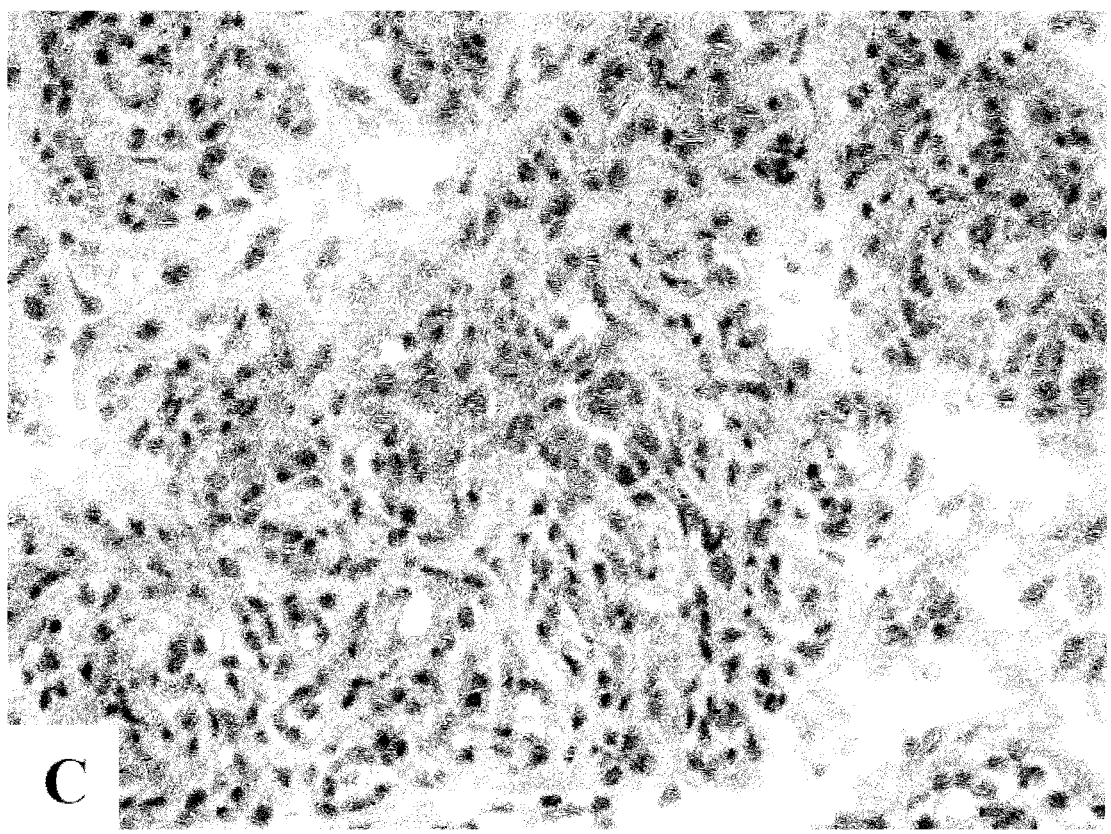
Figure 73D:
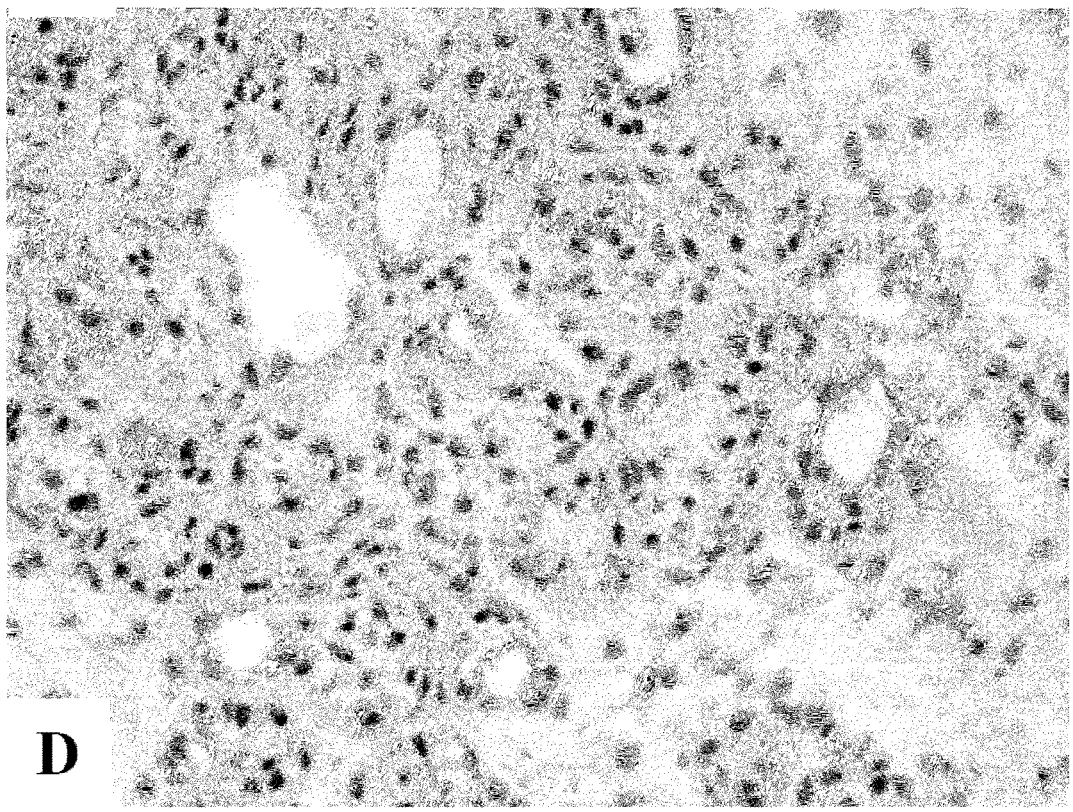
Figure 74A:
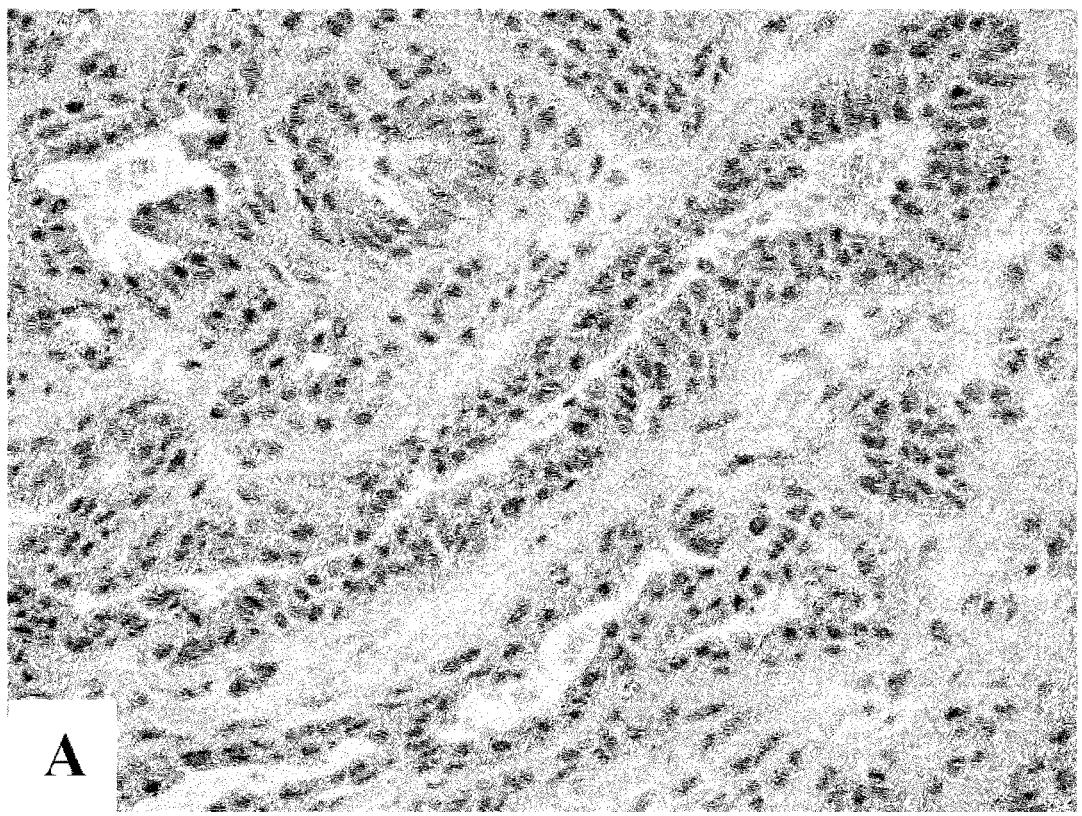
FIG. 74A and FIG. 74B are is a series of microscope images illustrating H&E staining of a distant metastasis/new primary tumour of a dog breast tumor showing infiltration of inflammatory cells with various degrees of tumour regressive changes from well preserved glandular structures to scattered tumour cells surrounded by inflammatory cells in accordance with some embodiments herein.
Figure 74B:
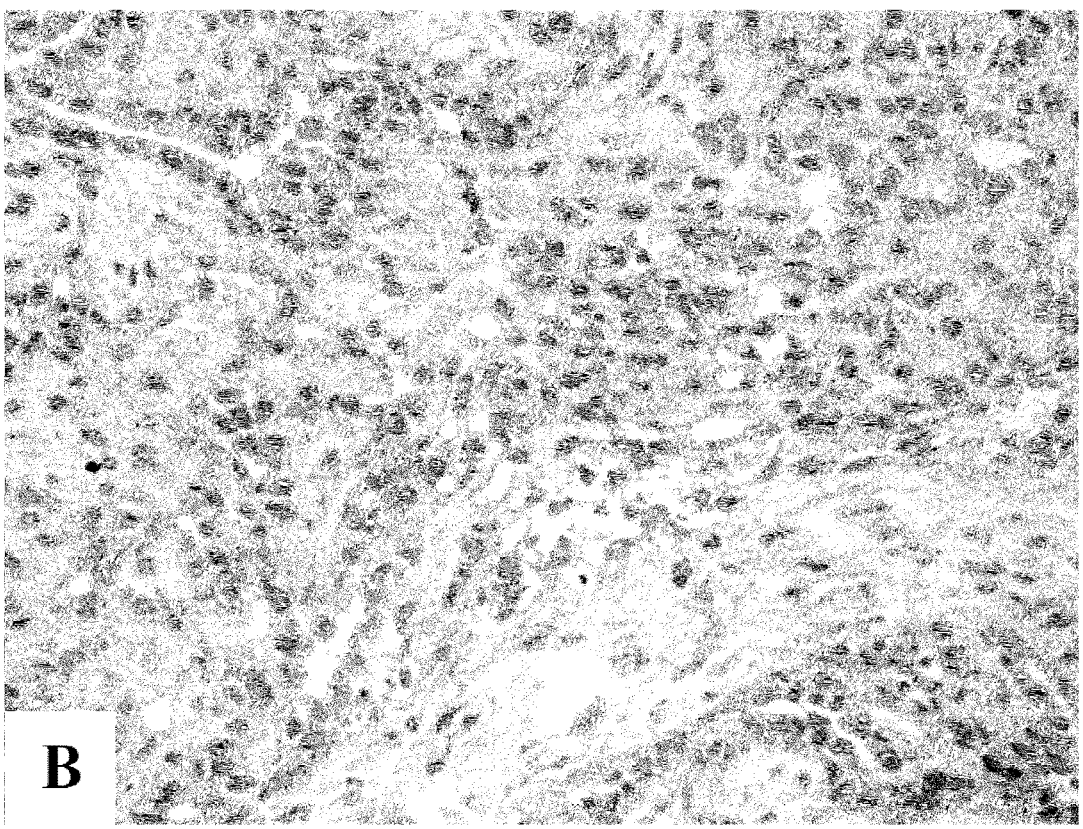
Figure 75A:
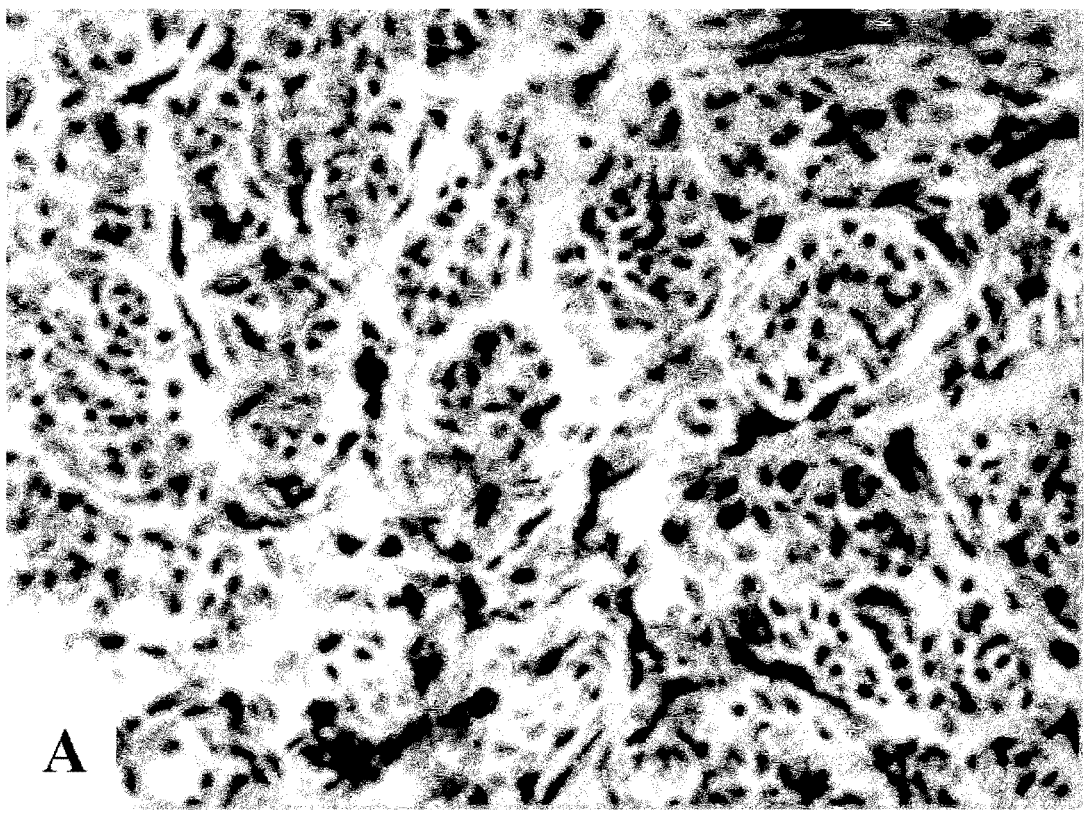
FIG. 75A, FIG. 75B, FIG. 75C, and FIG. 75D are images from the lesion showing various degrees of tumour regressive changes.
Figure 75B:
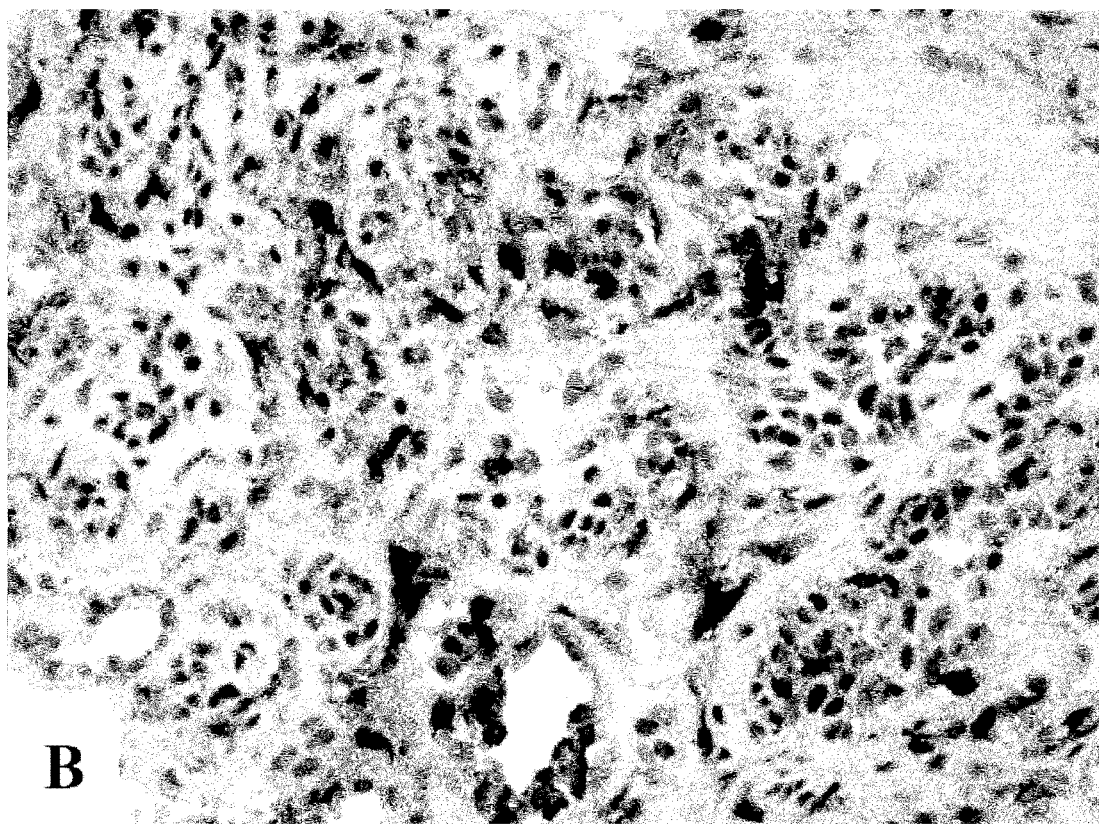
Figure 75C:
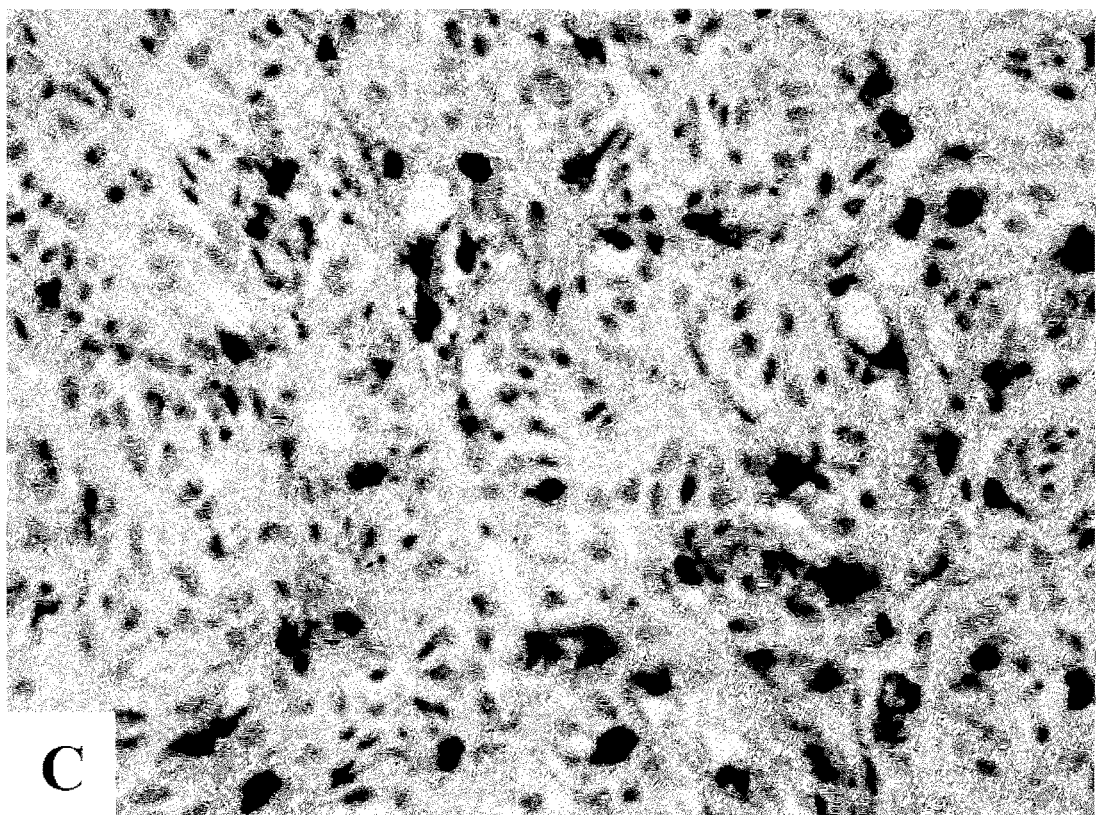
Figure 75D:
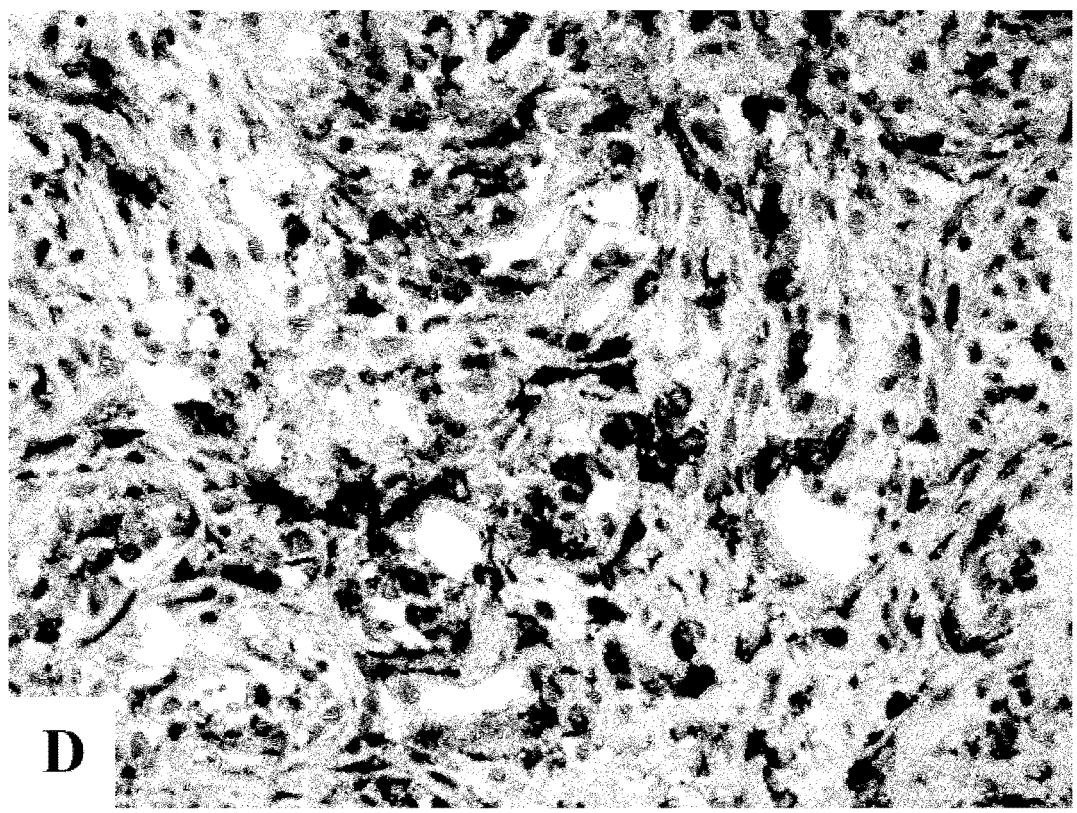
Figure 79A:
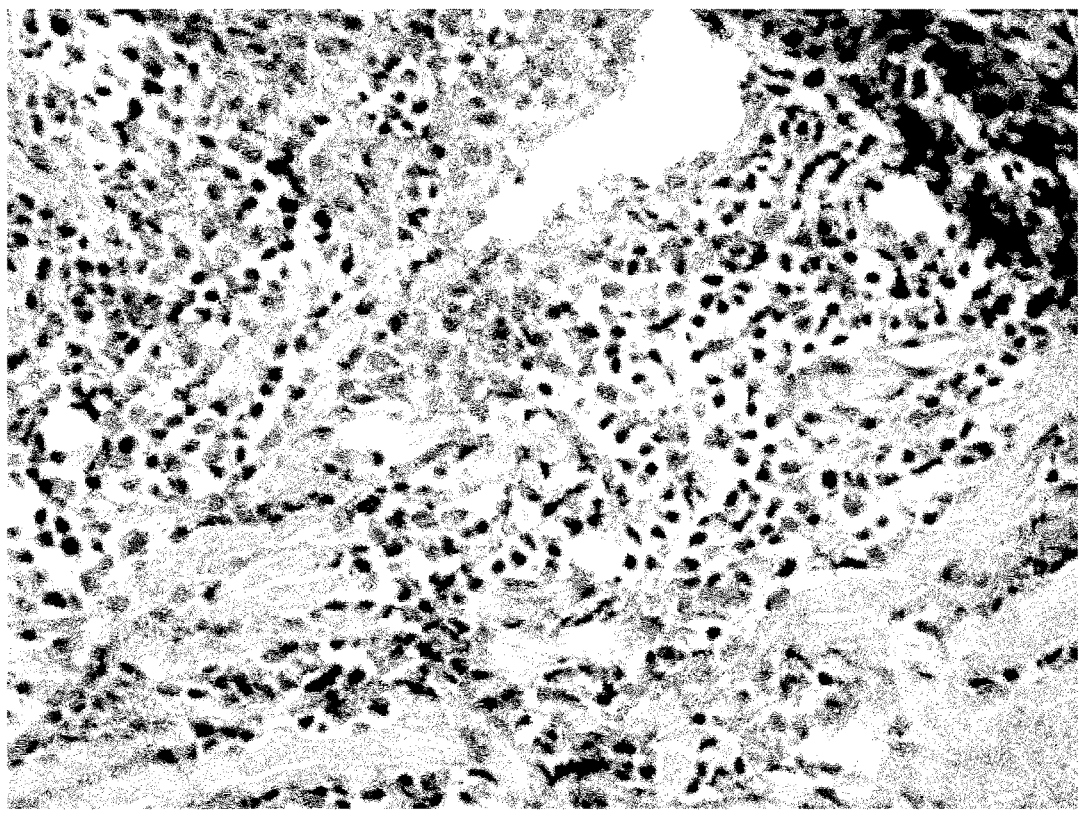
FIG. 79A and FIG. 79B are a series of microscope images illustrating hematoxylin stained sections of histiocytoma after intra-tumoral treatment with P28R in accordance with some embodiments herein. Extensive regressive changes of the tumour were observed.
Figure 79B:
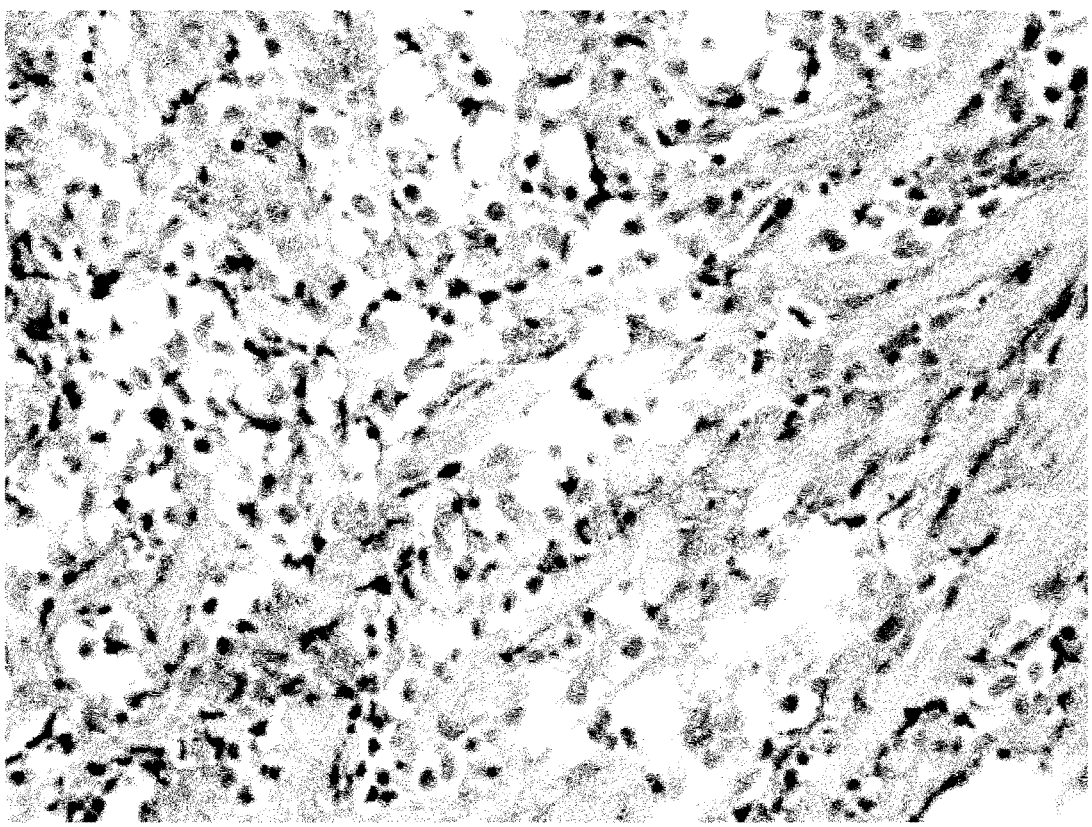
Figure 80A:
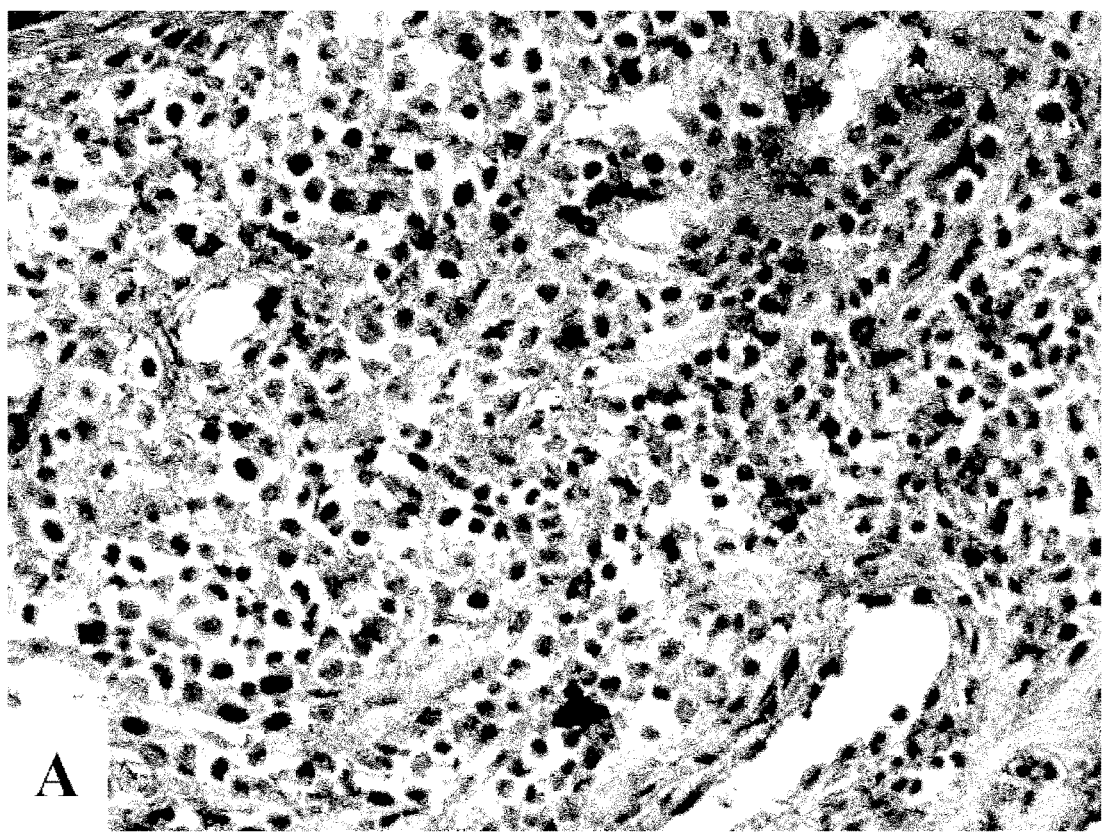
FIG. 80 is a series of microscope images illustrating infiltration of CD56+ cells (FIG. 80A) and NCR1+(FIG. 80B) cells in a histiocytoma with extensive tumour cell destruction in accordance with some embodiments herein.
Figure 80B:
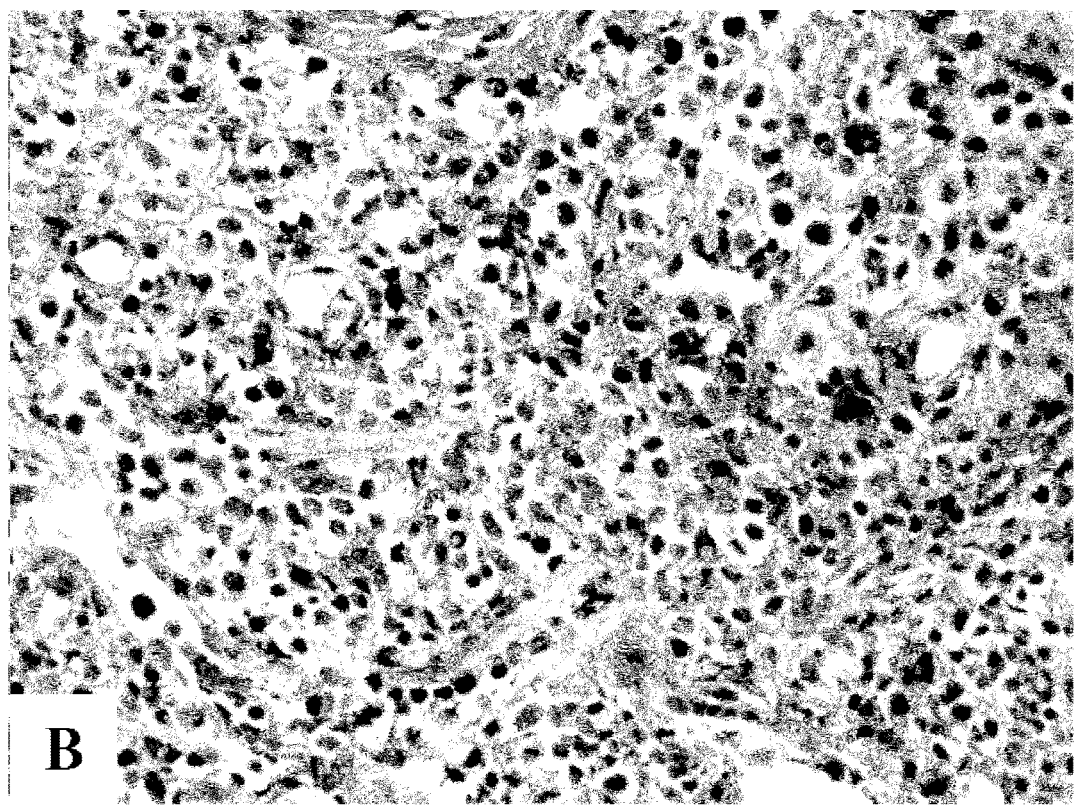
Figure 84A:
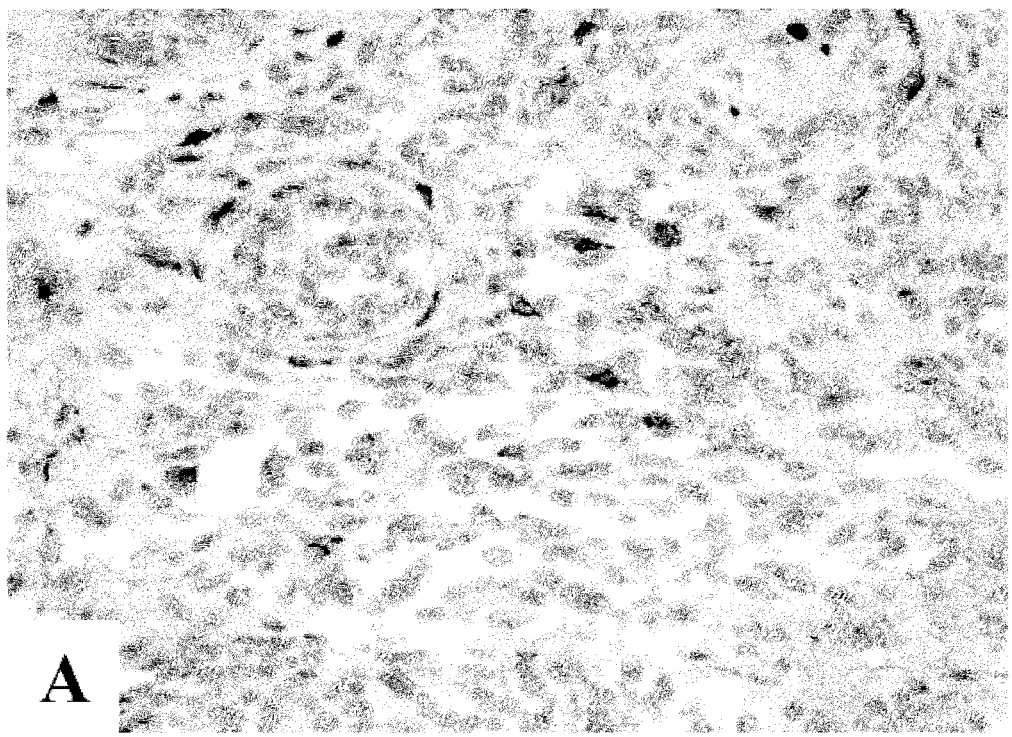
FIGS. 84A-B are a series of microscope images illustrating one canine breast tumour treated with 40 nmol P28R in accordance with some embodiments herein. The inflammatory infiltrate was evaluated after 5 days treatment by staining of parallel sections for CD3+ cells with standard antibody concentration, diluted 1:50 (FIG. 84A) or an increased concentration, diluted 1:25 (FIG. 84B). The large differences in expression of CD3 are observed, as a large number of lymphocytes are completely negative when stained with a "standard" antibody concentration but are actually found to express this marker when an increased" concentration of the antibody is used.
Figure 84B:
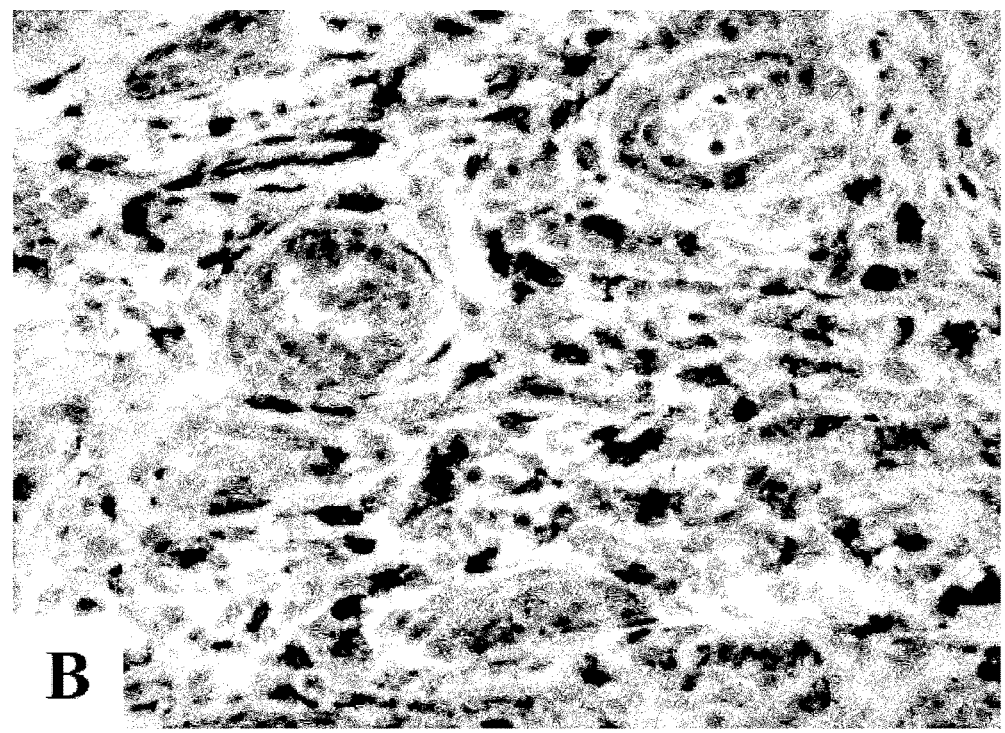
Figure 85:
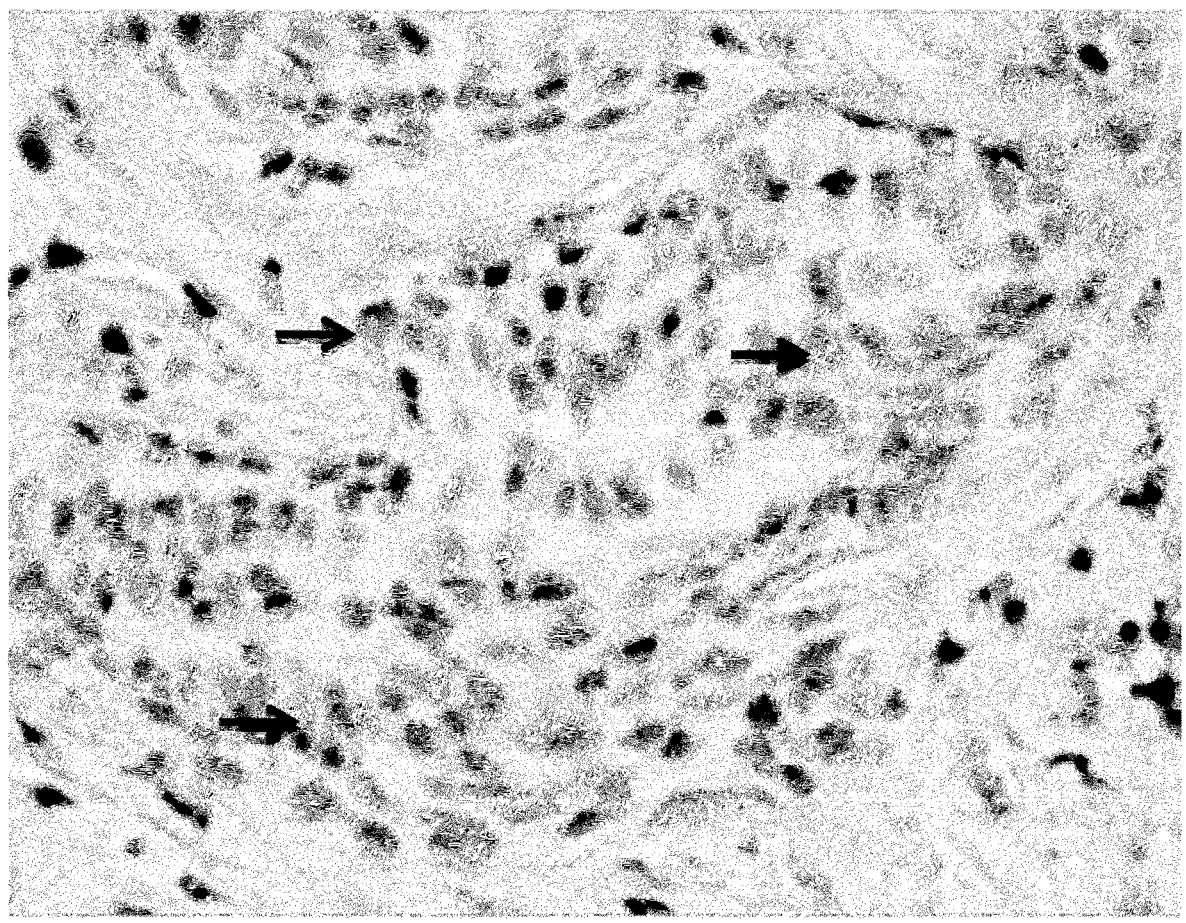
FIG. 85 is a microscope image illustrating Canine breast tumour treated with 40 nmol P28R intra-tumourally in accordance with some embodiments herein. Regressive changes of a large number of tumour cells are demonstrated as cells with irregular shaped nuclei and often disrupted nuclear membrane, positive in TUNEL staining (arrows). This section is counterstained using methylgreen pyronin.

It has been observed that compositions comprising immunoregulatory peptide inhibitors in accordance with some embodiments herein can induce immune cell infiltration of tumors in mammal models. For example, administration of a composition comprising P28R (SEQ ID NO: 2) directly to a B16 melanoma in C57B1 mice induced regressive changes in the tumor and permeation of the tumour by CD45+ inflammatory cells, and it was observed that a systemic immune activation against the tumor was achieved (see FIGS. 53A-53B). Moreover, contralateral tumors of the mouse that did not receive the direct administration of the P28R composition also underwent regressive changes, and were also infiltrated by immune cells (FIGS. 55A-D). It was further observed that direct injection of P28R composition into a Lewis lung carcinoma model in B7B1 mice induced regressive changes in both the tumor that received the P28R composition, and in contralateral tumors that were not directly injected (FIGS. 57A and 57B). It was further observed that intra-tumoral administration of a composition comprising P28R to a breast tumor of a dog induced regressive changes in the tumor and infiltration of the tumor by CD45+ inflammatory cells (see FIG. 58A-D). It was further observed that intra-tumoral injection of a composition comprising P28R to an apocrine gland carcinoma of a dog induced infiltration of the tumor by CD45+ inflammatory cells (FIG. 62A-B) and NK cells (e.g. CD56+ cells and/or NCR1+ cells)(FIGS. 64*a*-B and 65A-B), and also induced regressive changed in the tumor. It was further observed that intra-tumoral injection of a control composition (vehicle that did not comprise P28R) to a testis tumor of a dog did not induce infiltration by immune cells (FIGS. 66A-B). It was further observed that intra-tumoral injection of a composition comprising P28R to a mast cell tumor of a dog induced massive tumor destruction and infiltration by CD45+ inflammatory cells (see FIG. 69) and extensive infiltration by CD56+ inflammatory cells (see FIG. 70A-D). It was further observed that intra-tumoral injection of a composition comprising P28R to a benign mixed mammary tumor of a dog induced regressive changes at the injection site (FIG. 71A-B) and infiltration of the tumor by inflammatory cells (FIG. 72A-D, FIG. 73A-D, and FIG. 74A-B), for example CD45+ cells (FIG. 75A-D). Distant metastases of the tumor were also infiltrated by CD45+ cells (FIG. 76 and FIG. 77A-D). It was further observed that intra-tumoral injection of a composition comprising P28R to a mammary gland mucous carcinoma of a dog induced infiltration of the tumor by CD45+ inflammatory cells (FIG. 78A-B) and extensive regressive changes of the tumor. It was further observed that intra-tumoral injection of a composition comprising P28R to a histiocytoma of a dog induced extensive regressive changes of the tumor (FIG. 79A-B) and infiltration of the tumor by CD56+ cells (FIG. 80A) and NCR1+ cells (FIG. 80B). It was further observed that intra-tumoral injection of a composition comprising P28R to a intraductal papillary adenoma of a dog induced intense inflammatory infiltration of the tumor (FIG. 81 and FIG. 82A-D), and extensive eradication of the tumor cells. It was further observed that of CD3 (T cells), CD8 (T cells), and CD45 (leukocytes) were down-regulated or lost when inflammatory cells infiltrated into the tumour-cell-areas, so that a number of lymphocytes infiltrating tumor cell areas appear to have lower staining intensity compared to the stroma (see FIG. 83). The use or morphological criteria, however, confirmed that a number of lymphocytes close to the tumour cells were present, but unstained. The presence of lymphocytes with reduced CD3, CD8 and CD45 was further confirmed using more intense immunostaining, which yielded increased background staining, but did not yield any more specific staining (see FIG. 84). Tumor cells in dogs treated with P28R also exhibited faintly-stained, often irregularly-shaped nuclei and disruption of the nuclear membrane, and were confirmed to be apoptotic, as demonstrated by TUNEL staining (FIG. 85). Accordingly, administration of immunoregulatory peptide inhibitor comprising, consisting of, or consisting essentially of SEQ ID NO: 2, SEQ ID NO: 62, SEQ ID NO: 584, a peptide listed in Table 5.4, or a modified P28R or P28 core peptide comprising one or more modifications listed in Table 5.3 or Table 13 to a subject with a tumor in accordance with some embodiments herein can induce apoptosis of the tumor cells. The ratio between normal and "damaged" tumour cells was observed, and treatment with P28R was confirmed to result in a significantly lower density of tumour cells in treated tumours (see FIG. 86B) compared with tumours from untreated control dogs (see FIG. 86A and FIGS. 87A-D). The inflammatory infiltrate in tissues of was further quantified and compared with total tumor cell number in breast tumors for both P28R-treated dogs and untreated dogs. It was observed that treated tumours contained more than a 3-fold higher ratio between inflammatory cells and tumour cells compared with untreated tumours (see FIG. 88). In addition, as a control, the inflammatory infiltrate was evaluated in ten formalin fixed and paraffin embedded ("FFPE") tumours, and generally the infiltration of inflammatory cells was very low (see FIG. 89). Accordingly, administration of immunoregulatory peptide inhibitor comprising, consisting of, or consisting essentially of SEQ ID NO: 2, SEQ ID NO: 62, SEQ ID NO: 584, a peptide listed in Table 5.4, or a modified P28R or P28 core peptide comprising one or more modifications listed in Table 5.3 or Table 13 in accordance with some embodiments herein induces infiltration of tumour cells by inflammatory cells, and decreases the number of tumour cells relative to inflammatory cells.

The effects of P28R on tumors at locations other than the site of administration were evaluated. In P28R-treated dogs, tumours that were not directly injected with P28R exhibited regressive changes, providing strong evidence of treatment of these uninjected, remote, or peripheral tumours. Enhanced inflammatory infiltrate and an enhanced amount of "damaged" tumour cells were observed in large remote or peripheral tumours after injection of only 200 μL of P28R, indicating a distant effect of P28R (see FIGS. 91B and 91D). Accordingly, this experiment provides strong evidence that administration of an immunoregulatory peptide inhibitor comprising, consisting of, or consisting essentially of SEQ ID NO: 2, SEQ ID NO: 62, SEQ ID NO: 584, a peptide listed in Table 5.4, P28R or a modified P28R or P28 core peptide comprising one or more modifications listed in Table 5.3 or Table 13 is effective for inhibiting, ameliorating, or treating cancer cells and/or tumors that are distant from a primary tumor, such as metastasis. In another experiment, mice with inoculate CT26 colon cancer were treated with 12 microgram P28R, twice weekly for two weeks. Apoptosis, identified using the TUNEL staining technique, was induced in the majority of tumour cells (see FIGS. 92A-B). In another experiment, P28R was administered subcutaneously twice weekly to two weeks to BALBc mice with inoculate CT26 colon cancer cells. Two dose levels, 4 (D10) or 12 mg (D30) per injection were compared with injection of the vehicle, and apoptotic tumour cells were identified by staining using the TUNEL staining technique. The systemic administration of P28R decreased the number of viable tumour cells, and increased the number of apoptotic tumour cells at both D10 and D30 (see Table 16). Accordingly, both low and high doses of P28R, administered systemically in accordance with some embodiments herein (e.g. enterally, or example orally; or parenterally, for example subcutaneously, intravenously, intraperitoneally, or via implantation), systemically induces apoptosis in cancer cells and tumours. In some embodiments, an immunoregulatory peptide inhibitor as described herein (or a composition comprising the immunoregulatory peptide inhibitor) is administered intra-tumorally or peri-tumorally to a subset of tumors in a subject having multiple tumors (for example, metastatic cancer), so as to treat, inhibit, or ameliorate cancer cells, tumors, and/or metastasis, even those cancer cells and tumors that did not intra-tumorally or peri-tumorally receive the immunoregulatory peptide inhibitor. In some embodiments, an immunoregulatory peptide inhibitor as described herein is administered intra-tumorally or peri-tumorally to one tumor in a subject having metastatic cancer, but is not administered intra-tumorally or peri-tumorally to another tumor in the subject, so as to treat, ameliorate, destroy, and/or eliminate both tumors and/or cancer cells that originated from said primary tumor, such as in the case of metastasis.

Figure 93A:
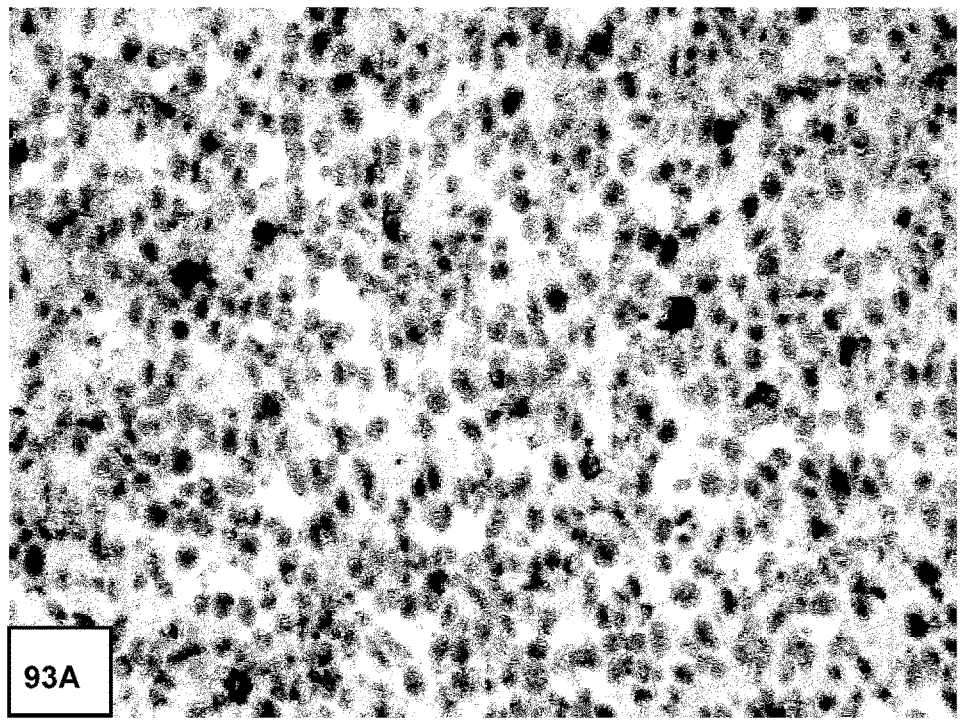
FIGS. 93A-B are a series of microscope images illustrating show haematoxylin staining of uninjected tumours on the contralateral side of tumours that were injected in CT26 colon cancers in Balb/c mice.
Figure 93B:
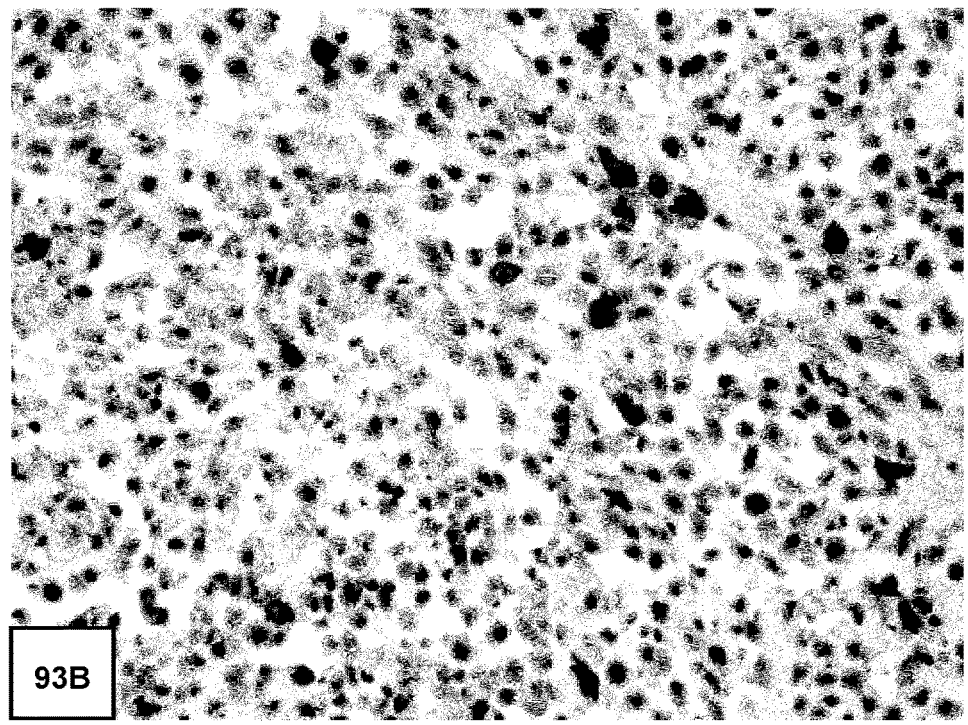

Systemic effects of immunoregulatory peptide inhibitors were also observed in CT26 colon cancers in Balb/c mice. The Balb/c mice were injected with an oligoclonal rabbit antibody (oligoclonal antibody "R") against the human albumin fragment P3028. The oligoclonal rabbit antibody was 100 micrograms in 100 microliters, or with the same volume of saline as a control ("A"), and eradication of the tumor cells was observed in the antibody-injected mice after five days. The number of tumour cells was substantially reduced in the oligoclonal antibody-injected mice (see FIG. 93B) compared to saline controls (FIG. 93A). As shown in FIG. 93B, and summarized numerically in Table 17, the tumour cell density is reduced by antibody treatment. Thus, an abscopal and/or systemic effect in an uninjected tumour is observed in a mouse treated with an immunoregulatory peptide inhibitor. As such, systemic effects of immunoregulatory peptide inhibitors are contemplated in accordance with some embodiments herein. In some embodiments, an immunoregulatory peptide inhibitor is administered intratumorally to a tumor, or peritumorally to a tumor in a subject having multiple tumors, so as to ameliorate, inhibit or eliminate at least one tumor that did not intratumorally or peritumorally receive the immunoregulatory peptide inhibitor. In some embodiments, the immunoregulatory peptide inhibitor comprises an antibody against any of the peptides of SEQ ID NOs: 183-185 or 188-246, for example P3028 (SEQ ID NO: 185). Optionally, the antibody binds specifically to P3028 (SEQ ID NO: 185). Optionally, the antibody comprises a polyclonal antibody. Optionally, the antibody comprises an oliogoclonal antibody. Optionally, the antibody comprises a monoclonal antibody. Optionally, the antibody comprises a full-length monoclonal antibody.

Optionally, the antibody comprises a binding fragment of a monoclonal antibody. In some embodiments, immunoregulatory peptide inhibitor induces regressive changes in the tumor(s) that did not intratumorally or peritumorally receive the immunoregulatory peptide inhibitor. In some embodiments, immunoregulatory peptide inhibitor induces immune cell infiltration in the tumor(s) that did not intratumorally or peritumorally receive the immunoregulatory peptide inhibitor.

is contemplated that compositions comprising immunoregulatory peptide inhibitors as described herein can treat, ameliorate, eliminate, inhibit, and/or eradicate multiple tumors or cancer cells in a subject, even if the compositions are not directly administered intratumorally or peri-tumorally to each of the tumors or cancer cells. Moreover, it is contemplated that compositions comprising immunoregulatory peptide inhibitors as described herein can treat, ameliorate, inhibit, eliminate, and/or eradicate metastatic cancer without being intratumorally or peri-tumorally administered to each any every tumor of the metastatic cancer. As such, in some embodiments a composition comprising an immunoregulatory peptide inhibitor comprising, consisting of, or consisting essentially of SEQ ID NO: 2, SEQ ID NO: 62, SEQ ID NO: 584, a peptide listed in Table 5.4, P28R, or a modified P28R or P28 core peptide comprising one or more modifications listed in Table 5.3 or Table 13 is administered systemically (e.g., enterally, or example orally; or parenterally, for example subcutaneously, intravenously, intraperitoneally, or via implantation), and induces apoptosis of tumour and/or cancer cells throughout the subject including in a subject having metastasis. In some embodiments, the composition comprising the immunoregulatory peptide inhibitor is administered intratumorally or peritumorally to some, but not all, of the tumors and/or cancer cells in a metastatic cancer in a subject having metastasis, for example at least 1, 2, 3, 4, 5, 6, 7, 8, 9, 10, 11, 12, 13, 14, 15, 16, 17, 18, 19, or 20 tumors of the subject (including ranges between any two of the listed values), for use in treating, inhibiting, or ameliorating the metastatic tumors and/or cancer cells of the subject (e.g., the composition is for treating or inhibiting at least one more tumor than the number of tumors that receives an intratumoral or peritumoral administration of the aforementioned compositions).

Accordingly, it is contemplated that in some embodiments, a composition comprising an immunoregulatory peptide inhibitor of SEQ ID NO: 2, SEQ ID NO: 62, SEQ ID NO: 584, a peptide listed in Table 5.4, or a modified P28R or P28 core peptide comprising one or more modifications listed in Table 5.3 or Table 13 is provided. The composition can comprise a nanoparticle, and the immunoregulatory peptide inhibitor (e.g. SEQ ID NO: 2, SEQ ID NO: 62, SEQ ID NO: 584, a peptide listed in Table 5.4, or a modified P28R or P28 core peptide comprising one or more modifications listed in Table 5.3 or Table 13) can be immobilized on the nanoparticle. Optionally, the composition is for use in direct administration to a tumor, or is directly administered to a tumor. Optionally, the tumor can be part of a metastatic cancer. Optionally, the composition induces regressive changes of the tumor. Optionally, the composition induces eradication of some or all of the tumor or inhibits proliferation of tumor cells and/or metastasis. Optionally, the composition is for use in treating, ameliorating, inducing regressive changes in, inducing eradiation of some of, or inducing eradication of all of a prostate tumor, a melanoma, a colon cancer, a lung carcinoma, an Apocrine gland carcinoma, a testis tumor, a mast cell tumor, a mammary tumor (e.g. a benign mammary tumor or a malignant mammary tumor, for example a mixed mammary tumor such as a benign mixed mammary tumor or a malignant mixed mammary tumor), a mucinous carcinoma (e.g. a mammary gland mucinous carcinoma), a histicytoma, or an adenoma (e.g. an intraductal papillary adenoma) or inhibits proliferation of cells and/or metastasis associated with the aforementioned cancers. As such, the composition can be administered to a subject having a cancer or tumor or at subject at risk for metastasis, for example prostate tumor, a melanoma, a colon cancer, a lung carcinoma, an Apocrine gland carcinoma, a testis tumor, a mast cell tumor, a mammary tumor (e.g. a benign mammary tumor or a malignant mammary tumor, for example a mixed mammary tumor such as a benign mixed mammary tumor or a malignant mixed mammary tumor), a mucinous carcinoma (e.g. a mammary gland mucinous carcinoma), a histicytoma, or an adenoma (e.g. an intraductal papillary adenoma). The subject can be in need of treatment of the cancer or tumor. Optionally, the composition induces immune cell infiltration of the tumor to which the composition was directly administered, for example infiltration by CD45+ and/or NK cells. Optionally, the composition induces immune cell infiltration of a tumor of the subject that it was not directly administered, such as a metastatic tumor or a contralateral tumor (e.g. a second, metastatic tumor and/or contralateral tumor, if the composition is directly administered to a first tumor). Optionally, the composition induces a systemic immune response.

Ameliorating Immunosuppression

As the inhibitors of immunoregulatory peptides described herein can be useful for removing immunosuppression, some embodiments herein comprise methods of ameliorating, reducing the symptoms of, reducing, or treating immunosuppression. In some embodiments a subject suffering from immunosuppression is identified. The subject can comprise a human, or a non-human mammal. A composition comprising at least one of the inhibitors of immunoregulatory peptides described herein can be administered to the patient. The composition can comprise at least one peptide comprising, consisting of, or consisting essentially of any one of SEQ ID NOs: 1-33, 34, 46-53, 62, 64-66, 68, 76, 94-96, 98, 265-393, 583-586, 587-595, or a modified P28R or P28 core peptide comprising one or more of the modifications of Table 5.3 or Table 13. The peptide can have length is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids or a length defined by a range between any two of these numbers. Optionally, the composition can further comprise a buffer as described herein, for example, Trizma, Bicine, Tricine, MOPS, MOPSO, MOBS, Tris, Hepes, HEPBS, MES, phosphate, carbonate, acetate, citrate, glycolate, lactate, borate, ACES, ADA, tartrate, AMP, AMPD, AMPSO, BES, CABS, cacodylate, CHES, DIPSO, EPPS, ethanolamine, glycine, HEPPSO, imidazole, imidazolelactic acid, PIPES, SSC, SSPE, POPSO, TAPS, TABS, TAPSO or TES. Optionally, the composition can further comprise a degradable particle as described herein. The composition can be administered to the subject via a variety of routes, for example, systemically, at the site of immunosuppression (e.g. if there is local immunosuppression by a tumor), or near the site of immunosuppression, for example within 10 cm 9 cm, 8 cm, 7 cm, 6 cm, 5 cm, 4 cm, 3 cm, 2 cm, 1 cm, or 0.5 cm of the site of immunosuppression. Optionally a second therapeutic agent can be administered in addition to the composition, for example prior to, concurrently with, or subsequent to the administration of the composition. For example, the second therapeutic agent can comprise an immunostimulatory agent. Optionally, activation of immune cells (e.g. enhanced expression of CD69 and/or CD71, secretion of IL-12 or IFNγ, or secretion of perforin or granzyme B, enhanced cytotoxicity, cytokine production, cell migration, and/or cell proliferation) of the subject can be detected. For example, activation of immune cells can be detected as enhanced expression of one or more markers of immune cells, for example CD69, CD71, and the like. Activation of immune cells (e.g. enhanced expression of CD69 and/or CD71, secretion of IL-12 or IFNγ, or secretion of perforin or granzyme B, enhanced cytotoxicity, cytokine production, cell migration, and/or cell proliferation) can be detected by a number of techniques known to the skilled artisan, for example flow cytometry, immunohistochemistry, ELISA, western blotting, immunoblotting, quantitative PCR, detection of BUdR incorporation to measure proliferation, and the like. Without being limited by any theory, different types of immunosuppressor cells, regulatory T-cells, immature dendritic cells (iDC), tumor associated macrophages (TAM) and myeloid derived suppressor cells (MDSC), can function immunosuppression, and further, other immunosuppressor mechanisms, such as serum blocking factors, circulating immune complexes, enhanced IL-1Ra production and enhanced intra-tumoral proteolytic activity can function in cancer related immunosuppression. As such, in some embodiments, treatment, amelioration, reduction, or reduction of the symptoms of immunosuppression can be determined by a change in activity, phenotype, or proliferation of an immunosuppressive cell, or a change in expression level or localization of an immunosuppressive factor.

Inhibitors of Immunoregulatory Peptides

Some embodiments include inhibitors of immunoregulatory peptides such as P3028 and/or one or more of the immunoregulatory peptides listed in Tables 1-4 (SEQ ID NOs: 183-184, and 188-246), also referred to as blockers of albumin derived immunoregulatory peptides, binding partners for immunoregulatory peptides, or immunoregulatory peptide inhibitors. The immunoregulatory peptide inhibitors can include, but are not limited to: peptides, cyclic peptides, peptidomimetics, proteins, nucleic acids, antibodies; antibody fragments, nucleic acid aptamers; peptide aptamers; and small molecules. The following section provides more details on antibody or antibody fragment-based immunoregulatory peptide inhibitors.

Antibody or Antibody Fragment-Based Immunoregulatory Peptide Inhibitors

Some embodiments include antibody or antibody fragment based immunoregulatory peptide inhibitors. Methods that use these immunoregulatory peptide inhibitors to inhibit immunosuppression in a subject (e.g., a subject having cancer or a pathogenic infection such as a bacterial or viral infection) are also contemplated. The core antibody structural unit is known to comprise a tetramer. Each tetramer is composed of two identical pairs of polypeptide chains, each pair having one "light" chain (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Heavy chains are classified as mu, delta, gamma, alpha, or epsilon, and define the antibody's isotype as IgM, IgD, IgG, IgA, and IgE, respectively. An additional isotope, IgY is found in avian hosts. The chains all exhibit the same general structure of relatively conserved framework regions (FR) joined by three hyper variable regions, also called complementarity determining regions or CDRs. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat, Sequences of Proteins of Immunological Interest (National Institutes of Health, Bethesda, Md. (1987 and 1991)), or Chothia & Lesk J. Mol. Biol. 196:901-917 (1987); Chothia et al., Nature 342:878-883 (1989).

Accordingly, some embodiments include a composition that comprises, consists of, or consists essentially of an immunoregulatory peptide inhibitor that comprises an antibody or antibody fragment comprising a domain, which binds to one or more regions of an immunoregulatory peptide, such as P3028 or one or more of the immunoregulatory peptides provided in Tables 1-4 (SEQ ID NOs: 183-184 and 188-246). In some embodiments, the antibody or antibody fragment is from a mouse, rabbit, rat, hamster, guinea pig, goat, donkey, bovine, horse, camel, cow, chicken, or human host. In some embodiments, the antibody or fragment is of isotype IgG, IgM, IgA, IgD, IgE, or IgY. In some embodiments, the antibody or fragment is part of a collection of polyclonal antibodies. In some embodiments, the antibody is monoclonal. In some embodiments, the antibody or fragment is chimeric. In some embodiments, the antibody or fragment includes at least one region form a human host, which can be at least one of the following Fc; Fab; light chain variable region; light chain CDR1, CDR2, or CDR3; heavy chain variable region; heavy chain CDR1, CDR2, or CDR3; light chain framework region; light chain FR1, FR2, FR3, or FR4; heavy chain framework region; heavy chain FR1, FR2, FR3, or FR4. In some embodiments, the antibody includes at least one CDR or FR of a non-human host. In some embodiments, the antibody regions are in accordance with the definition of Kabat. In some embodiments, the antibody regions are in accordance with the definition of Chothia. In some embodiments, the antibody regions are in accordance with a combination of the definition of Kabat and Chothia. In some embodiments, the antibody or antibody fragment mimics one or more of the peptides described in Table 5.1, Table 5.4, Table 5.5, or Table 5.6.

Antibodies can be readily produced using conventional techniques in immunology, for example techniques described in US Pat Nos (U.S. Pat. Nos. 8,142,784 and 7,628,986). Antibodies generated in non-human hosts can be humanized, for example by substituting at least one variable region of the antibody of the non-human host into a human antibody. Moreover, human antibodies can be generated, for example in a transgenic host animal. Transgenic animals (e.g., mouse, such as XENOMOUSE) can be engineered, upon immunization, to produce a full repertoire of human antibodies in the absence of endogenous immunoglobulin production (Jakobovits et al. (1993) Proc. Natl. Acad. Sci. USA, 90:2551; Jakobovits et al. (1993) Nature 362:255-258;

Bruggermann et al. (1993) Year in Immuno. 7:33; and U.S. Pat. Nos. 5,591,669; 5,589,369; 5,545,807). Moreover, phage display technology (McCafferty et al. (1990) Nature 348:552-553) can be used to produce human antibodies and antibody fragments in vitro, from immunoglobulin variable (V) domain gene repertoires from unimmunized donors (Johnson, Kevin S. and Chiswell, David J. (1993) Current Opinion in Structural Biology 3:564-571). A repertoire of V genes from unimmunized human donors can be constructed and antibodies to a diverse array of antigens (including self-antigens) can be isolated essentially (Marks et al. (1991) J. Mol. Biol. 222:581-597; Griffith et al. (1993) EMBO J. 12:725-734; U.S. Pat. Nos. 5,565,332; 5,573,905). Many phage display libraries are known, or can be generated, for example those of (U.S. Pat. No. 7,985,840). Human antibodies may also be generated by in vitro activated B cells (U.S. Pat. Nos. 5,567,610; 5,229,275). Thus, some embodiments include generating antibodies that bind to P3028 (SEQ ID NO: 185) and/or the peptides of Tables 1-4 (SEQ ID NOs: 183-184 and 188-246). In some embodiments, the antibodies are humanized antibodies that include at least one variable region of a non-human host antibody. In some embodiments, the antibodies are human antibodies generated in a non-human host, for example a transgenic animal. In some embodiments, the transgenic animal is a transgenic mouse. In some embodiments, the antibodies are generated in vitro. In some embodiments, the antibodies are generated using phage display technology. In some embodiments, the antibodies are generated in activated B cells in vitro.

Antibodies and antibody fragments can be configured to deliver cytotoxic compounds to a target site. Thus, some embodiments include antibodies and/or antibody fragments bound to cytotoxic compounds as described herein. In some embodiments, the antibodies or antibody fragments are bound to the cytotoxic compounds via a cleavable linker as described herein.

Some embodiments include a composition that comprises, consists of, or consists essentially of an immunoregulatory peptide inhibitor that comprises antibodies or a binding fragment thereof, which specifically binds to P3028 (SEQ ID NO: 185). Some embodiments include antibodies or fragments thereof, which specifically bind to a fragment of P3028 (SEQ ID NOs: 186 and 187). Exemplary antibodies that bind to P3028 are described in Example 9.

In some embodiments, the antibody or fragment thereof described above can be used to inhibit or sequester P3028. In some embodiments, the antibody or fragment thereof specific for P3028 can be administered to a patient having at least one immune cell bound to P3028 so as to unblock at least one of the patient's LFA-1 or IL-2 receptors. In some embodiments, the antibody or fragment thereof can be administered to a patient in need of treatment immunosuppression, as described herein, thereby stimulating or enhancing an immune response of said patient. For example, the antibody or fragment thereof can be provided to a patient in need of an inhibition of immunosuppression (e.g., a subject that has cancer or a pathogenic infection such as a bacterial or viral infection). After providing the antibody or fragment thereof the patient can be evaluated for an inhibition of immunosupression, which can be accomplished by determining immune cell infiltration of a tumor or a reduction in a bacterial or viral infection, for example, or an improved immune response by the PBMCs of said subject.

In other embodiments, the antibody or fragment thereof can be used to detect the presence of P3028, for example, in a biological sample. The antibody or fragment thereof can be used to detect the formation of a complex, for example when an immunoregulatory peptide inhibitor (e.g., a peptide SEQ ID NOs: 1-33, 34, 46-53, 64-66, 68, 76, 94-96, 98 or 264-393) is attached to a support, and the antibody is used as a primary antibody or fragment thereof is used to detect the presence of P3028 bound to the inhibitor.

Some embodiments include an antibody or fragment thereof that specifically binds to an immunoregulatory peptide inhibitor of P3028 (e.g., an antibody or fragment thereof that mimics or has at least 70%, 75%, 80%, 85%, 90%, 95%, or 98% identity to one or more of the peptides of Table 5.1). The antibody or fragment thereof can specifically bind to a peptide that includes at least one of SEQ ID NOs: 1-33, 34, 46-53, 64-66, 68, 76, 94-96, 98 or 264-393. In some embodiments, the antibody or fragment thereof specific for an immunoregulatory peptide inhibitor of P3028 can be used to detect the presence of an immunoregulatory peptide inhibitor of P3028 in a biological sample. The antibody or fragment thereof specific for an immunoregulatory peptide inhibitor of P3028 can also be used to detect the formation of a complex, for example, if P3028 is attached to a support, and the antibody or fragment thereof is used as a primary antibody to detect the presence of an immunoregulatory peptide inhibitor bound to P3028.

In some embodiments, the antibody or fragment thereof specific for an immunoregulatory peptide inhibitor of P3028 can be used to isolate or identify the presence of an inhibitor of P3028. For example, the antibody or fragment thereof can be used to purify an inhibitor to be used for stimulating an immune cell of a human, and/or for binding to the cancer cell of a human. For example, the antibody or fragment thereof, such as a binding fragment, can be used to purify an inhibitor to be used for stimulating an immune cell of a non-human mammal, and/or for binding to the cancer cell of a non-human mammal.

In some embodiments, the antibody or fragment thereof specific for an immunoregulatory peptide inhibitor of P3028 can be used to detect the presence of P3028. For example, the antibody or fragment thereof specific for an immunoregulatory peptide inhibitor of P3028 can be used for immunohistochemical staining of a biological sample to detect the presence of a cancer cell that has been contacted with an immunoregulatory peptide inhibitor. For example, the antibody specific for an immunoregulatory peptide inhibitor of P3028 can be used in flow cytometry to detect and/or isolate immune or cancer cells that are bound to an immunoregulatory peptide inhibitor. The following section provides more details on peptide-based immunoregulatory peptide inhibitors.

Peptide-Based Immunoregulatory Peptide Inhibitors

In some embodiments, an isolated peptide that comprises a domain, which binds to one or more regions of an immunoregulatory peptide, such as P3028, is provided. The term "isolated" requires that the material be removed from its original environment (e.g., the natural environment if it is naturally occurring). For example, a naturally-occurring polynucleotide present in a living animal is not isolated, but the same polynucleotide, separated from some or all of the coexisting materials in the natural system, is isolated. It is also advantageous that the sequences be in purified form. The term "purified" does not require absolute purity; rather, it is intended as a relative definition. Isolated proteins have been conventionally purified to electrophoretic homogeneity by Coomassie staining, for example. Purification of starting material or natural material to at least one order of magnitude, preferably two or three orders, and more preferably four or five orders of magnitude is expressly contemplated. An isolated peptide can exist, for example, in a substantially salt form, crystal form, lyophilized form, in solution (for example aqueous solution which can include buffer), and/or in a pharmaceutically carrier or diluent. An isolated peptide can exist in a substantially pure form, for example a composition that includes at least or equal to about 1% of the peptide by weight, for example at least or equal to about 1%, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 98.5, 99, 99.5, 99.9, 99.99, or 99.999% peptide by weight.

In some embodiments, the isolated immunoregulatory peptide inhibitors described herein (e.g., a peptide comprising, consisting of, or consisting essentially of any one of SEQ ID NOs: 1-33, 34, 46-53, 62, 64-66, 68, 76, 94-96, 98, 265-393, 583-586, 587-595, or a modified P28R or P28 core peptide comprising one or more of the modifications of Table 5.3 or Table 13 have lengths that are less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values. For example, an immunoregulatory peptide inhibitor consisting of the sequence (FVKL) can bind to P3028 with a comparable rampo score to immunoregulatory peptide inhibitors, which comprise FVKL, that are 6 to 16 amino acids in length (see FIG. 29 and Example 12). Additionally, amino acids sequences near an N terminal, C terminal, or exposed loop of a peptide are more likely to be accessible to potential binding targets rather than incorporated into a higher-order peptide structure, thus permitting a peptide of 1100 amino acids or less to bind P3028. Therefore, some embodiments of the invention concern compositions and methods of use thereof (e.g., a method of binding P3028 or a method of reducing P3028-mediated immunosuppression), which comprise, consist of, or consist essentially of any one or more of immunoregulatory peptide inhibitors described herein (e.g., any one or more of the peptides provided in Table 5.1, 5.4, 5.5, or 5.6). Desirably these peptides (e.g., any one or more of the peptides of Table 5.1, 5.4, 5.5, or 5.6) have lengths that are less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

TABLE 5.1

Sequences and Corresponding Rampo Scores

| SEQ ID | Sequence | RAMPO Score |
|---|---|---|
| 367 | KKLDTFFVKLSLMTER | 1190 |
| 22 | KKLDTFFVKLSLMTER | 1190 |
| 370 | KKLDTFFVKLSLQTER | 1144 |
| 23 | KKLDTFFVKLSLQTER | 1144 |
| 364 | KKLDTFFVKLSLHTER | 1046 |
| 24 | KKLDTFFVKLSLHTER | 1046 |
| 368 | KKLDTFFVKLSLNTER | 862 |
| 25 | KKLDTFFVKLSLNTER | 862 |
| 348 | KKLDTFFVKLQLFTER | 768 |
| 15 | KKLDTFFVKLQLFTER | 768 |
| 346 | KKLDTFFVKLMLFTER | 744 |
| 16 | KKLDTFFVKLMLFTER | 744 |
| 321 | KKLDTFMVKLSLFTER | 712 |
| 9 | KKLDTFMVKLSLFTER | 712 |
| 323 | KKLDTFSVKLSLFTER | 700 |
| 10 | KKLDTFSVKLSLFTER | 700 |
| 369 | KKLDTFFVKLSLPTER | 696 |
| 26 | KKLDTFFVKLSLPTER | 696 |
| 343 | KKLDTFFVKVSLFTER | 658 |
| 14 | KKLDTFFVKVSLFTER | 658 |
| 355 | KKLDTFFVKLSQFTER | 651 |
| 19 | KKLDTFFVKLSQFTER | 651 |
| 372 | KKLDTFFVKLSLSTER | 635 |
| 27 | KKLDTFFVKLSLSTER | 635 |
| 382 | KKLDTFFVKLSLFNER | 599 |
| 31 | KKLDTFFVKLSLFNER | 599 |
| 313 | KKLDTAFVKLSLFTER | 575 |
| 7 | KKLDTAFVKLSLFTER | 575 |
| 287 | KKGDTFFVKLSLFTER | 563 |
| 94 | KKGDTFFVKLSLFTER | 563 |
| 4 | KKGDTFFVKLSLFTER | 563 |
| 383 | KKLDTFFVKLSLFPER | 551 |
| 32 | KKLDTFFVKLSLFPER | 551 |
| 319 | KKLDTVFVKLSLFTER | 547 |
| 8 | KKLDTVFVKLSLFTER | 547 |

TABLE 5.1-continued

Sequences and Corresponding Rampo Scores

| SEQ ID | Sequence | RAMPO Score |
|---|---|---|
| 359 | KKLDTFFVKLSVFTER | 545 |
| 20 | KKLDTFFVKLSVFTER | 545 |
| 345 | KKLDTFFVKLHLFTER | 535 |
| 308 | KKLDQFFVKLSLFTER | 535 |
| 18 | KKLDTFFVKLHLFTER | 535 |
| 6 | KKLDQFFVKLSLFTER | 535 |
| 363 | KKLDTFFVKLSLGTER | 531 |
| 100 | KKLDTFFVKLSLGTER | 531 |
| 28 | KKLDTFFVKLSLGTER | 531 |
| 285 | KKEDTFFVKLSLFTER | 528 |
| 5 | KKEDTFFVKLSLFTER | 528 |
| 325 | KKLDTFVVKLSLFTER | 527 |
| 11 | KKLDTFVVKLSLFTER | 527 |
| 361 | KKLDTFFVKLSLATER | 525 |
| 29 | KKLDTFFVKLSLATER | 525 |
| 279 | RKLDTFFVKLSLFTER | 523 |
| 3 | RKLDTFFVKLSLFTER | 523 |
| 349 | KKLDTFFVKLTLFTER | 520 |
| 17 | KKLDTFFVKLTLFTER | 520 |
| 324 | KKLDTFTVKLSLFTER | 517 |
| 320 | KKLDTFLVKLSLFTER | 517 |
| 13 | KKLDTFLVKLSLFTER | 517 |
| 12 | KKLDTFTVKLSLFTER | 517 |
| 322 | KKLDTFQVKLSLFTER | 511 |
| 371 | KKLDTFFVKLSLRTER | 502 |
| 30 | KKLDTFFVKLSLRTER | 502 |
| 381 | KKLDTFFVKLSLFMER | 501 |
| 353 | KKLDTFFVKLSMFTER | 499 |
| 21 | KKLDTFFVKLSMFTER | 499 |
| 317 | KKLDTPFVKLSLFTER | 497 |
| 334 | KKLDTFFVKGSLFTER | 495 |
| 373 | KKLDTFFVKLSLTTER | 494 |
| 298 | KKLATFFVKLSLFTER | 494 |
| 280 | TKLDTFFVKLSLFTER | 493 |
| 284 | KKDDTFFVKLSLFTER | 492 |
| 356 | KKLDTFFVKLSRFTER | 483 |
| 273 | IKLDTFFVKLSLFTER | 483 |
| 318 | KKLDTTFVKLSLFTER | 481 |
| 357 | KKLDTFFVKLSSFTER | 478 |
| 288 | KKHDTFFVKLSLFTER | 477 |
| 305 | KKLDMFFVKLSLFTER | 475 |
| 293 | KKQDTFFVKLSLFTER | 473 |
| 339 | KKLDTFFVKQSLFTER | 470 |
| 365 | KKLDTFFVKLSLITER | 468 |
| 315 | KKLDTMFVKLSLFTER | 467 |
| 314 | KKLDTIFVKLSLFTER | 466 |
| 268 | AKLDTFFVKLSLFTER | 466 |
| 378 | KKLDTFFVKLSLFHER | 463 |
| 354 | KKLDTFFVKLSNFTER | 462 |
| 350 | KKLDTFFVKLSAFTER | 462 |
| 396 | KKLDTFFVKLSLFTER | 460 |
| 351 | KKLDTFFVKLSHFTER | 460 |
| 336 | KKLDTFFVKMSLFTER | 460 |
| 291 | KKMDTFFVKLSLFTER | 460 |
| 310 | KKLDSFFVKLSLFTER | 458 |
| 275 | MKLDTFFVKLSLFTER | 457 |
| 352 | KKLDTFFVKLSIFTER | 456 |
| 329 | KKLDTFFPKLSLFTER | 456 |
| 278 | QKLDTFFVKLSLFTER | 455 |
| 289 | KKIDTFFVKLSLFTER | 454 |
| 347 | KKLDTFFVKLNLFTER | 451 |
| 296 | KKTDTFFVKLSLFTER | 451 |
| 304 | KKLDCFFVKLSLFTER | 449 |
| 274 | LKLDTFFVKLSLFTER | 449 |
| 366 | KKLDTFFVKLSLLTER | 448 |
| 397 | KKLDTFIVKLSLFTER | 446 |
| 374 | KKLDTFFVKLSLVTER | 446 |
| 316 | KKLDTNFVKLSLFTER | 446 |
| 398 | KKLDTFFVKLSLFTER | 445 |
| 276 | NKLDTFFVKLSLFTER | 445 |
| 302 | KKLWTFFVKLSLFTER | 443 |
| 399 | KKLDTFFVKLSLFTER | 442 |
| 281 | VKLDTFFVKLSLFTER | 442 |
| 340 | KKLDTFFVKRSLFTER | 439 |
| 400 | KKLDTFFVKLSLFTER | 437 |

TABLE 5.1-continued

Sequences and Corresponding Rampo Scores

| SEQ ID | Sequence | RAMPO Score |
|---|---|---|
| 358 | KKLDTFFVKLSTFTER | 437 |
| 338 | KKLDTFFVKPSLFTER | 436 |
| 306 | KKLDNFFVKLSLFTER | 436 |
| 401 | KKLDTSFVKLSLFTER | 432 |
| 402 | KNLDTFFVKLSLFTER | 432 |
| 283 | KKCDTFFVKLSLFTER | 432 |
| 375 | KKLDTFFVKLSLWTER | 430 |
| 309 | KKLDRFFVKLSLFTER | 430 |
| 300 | KKLITFFVKLSLFTER | 430 |
| 403 | KKLDTFFVKLSLFTER | 428 |
| 272 | HKLDTFFVKLSLFTER | 428 |
| 307 | KKLDPFFVKLSLFTER | 427 |
| 282 | KKADTFFVKLSLFTER | 427 |
| 404 | KKLDTFAVKLSLFTER | 426 |
| 332 | KKLDTFFVKASLFTER | 426 |
| 405 | KPLDTFFVKLSLFTER | 425 |
| 312 | KKLDYFFVKLSLFTER | 425 |
| 406 | KKLDTFFVKLSLFTER | 424 |
| 303 | KKLYTFFVKLSLFTER | 422 |
| 311 | KKLDWFFVKLSLFTER | 418 |
| 407 | KRLDTFFVKLSLFTER | 417 |
| 299 | KKLETFFVKLSLFTER | 417 |
| 335 | KKLDTFFVKISLFTER | 415 |
| 408 | KKLDTFFVKLSLFTER | 414 |
| 409 | KKLDTFCVKLSLFTER | 411 |
| 328 | KKLDTFFLKLSLFTER | 411 |
| 410 | KKLDTQFVKLSLFTER | 410 |
| 360 | KKLDTFFVKLSWFTER | 409 |
| 411 | KKLDTLFVKLSLFTER | 408 |
| 412 | KGLDTFFVKLSLFTER | 405 |
| 413 | KKLTTFFVKLSLFTER | 405 |
| 387 | KKLDTFFVKLSLFTDR | 404 |
| 333 | KKLDTFFVKFSLFTER | 403 |
| 414 | KKLDTFFVKLSLFTER | 402 |
| 415 | KKLDTFFVKLYLFTER | 402 |
| 416 | KKLDTFFIKLSLFTER | 401 |
| 417 | KMLDTFFVKLSLFTER | 400 |
| 362 | KKLDTFFVKLSLCTER | 400 |
| 342 | KKLDTFFVKTSLFTER | 399 |
| 270 | EKLDTFFVKLSLFTER | 396 |
| 418 | KHLDTFFVKLSLFTER | 394 |
| 295 | KKSDTFFVKLSLFTER | 393 |
| 286 | KKFDTFFVKLSLFTER | 393 |
| 419 | KKLDTFFVKLVLFTER | 392 |
| 420 | KKLDHFFVKLSLFTER | 391 |
| 421 | KFLDTFFVKLSLFTER | 390 |
| 422 | KKLDTFFVKLSFFTER | 389 |
| 277 | PKLDTFFVKLSLFTER | 387 |
| 290 | KKKDTFFVKLSLFTER | 386 |
| 95 | KKLDGFFVKLSLFTER | 386 |
| 423 | KKLMTFFVKLSLFTER | 384 |
| 344 | KKLDTFFVKYSLFTER | 382 |
| 424 | KKLDTFEVKLSLFTER | 381 |
| 425 | KKLDTFWVKLSLFTER | 380 |
| 426 | KKLFTFFVKLSLFTER | 380 |
| 385 | KKLDTFFVKLSLFVER | 380 |
| 327 | KKLDTFFGKLSLFTER | 379 |
| 427 | KKLDTFFVKLSLFTER | 377 |
| 297 | KKVDTFFVKLSLFTER | 377 |
| 428 | KKLDTFFVKLSLFTER | 375 |
| 379 | KKLDTFFVKLSLFIER | 375 |
| 429 | KKLDVFFVKLSLFTER | 374 |
| 386 | KKLDTFFVKLSLFWER | 374 |
| 331 | KKLDTFFVRLSLFTER | 374 |
| 292 | KKNDTFFVKLSLFTER | 374 |
| 269 | DKLDTFFVKLSLFTER | 373 |
| 430 | KKLDTFFVKLSLFTER | 371 |
| 431 | KKLDTFFVKLSGFTER | 370 |
| 294 | KKRDTFFVKLSLFTER | 370 |
| 432 | KKLDTFRVKLSLFTER | 369 |
| 384 | KKLDTFFVKLSLFSER | 369 |
| 271 | GKLDTFFVKLSLFTER | 367 |
| 93 | GKLDTFFVKLSLFTER | 367 |
| 391 | KKLDTFFVKLSLFTER | 366 |
| 337 | KKLDTFFVKNSLFTER | 365 |

TABLE 5.1-continued

Sequences and Corresponding Rampo Scores

| SEQ ID | Sequence | RAMPO Score |
|---|---|---|
| 330 | KKLDTFFRKLSLFTER | 365 |
| 433 | KKLDTFHVKLSLFTER | 364 |
| 434 | KKLDTYFVKLSLFTER | 364 |
| 435 | KKLPTFFVKLSLFTER | 364 |
| 436 | KKPDTFFVKLSLFTER | 361 |
| 380 | KKLDTFFVKLSLFLER | 360 |
| 326 | KKLDTFFFKLSLFTER | 358 |
| 437 | KKLDTFPVKLSLFTER | 356 |
| 438 | KKLDTFFVKLSKFTER | 355 |
| 439 | KKLDTFFVKLSLFTPR | 351 |
| 341 | KKLDTFFVKSSLFTER | 351 |
| 440 | KQLDTFFVKLSLFTER | 350 |
| 441 | KELDTFFVKLSLFTER | 349 |
| 442 | KKLDTFFVKLSLFTER | 348 |
| 443 | KKLDTFNVKLSLFTER | 348 |
| 444 | KKLDTWFVKLSLFTER | 348 |
| 376 | KKLDTFFVKLSLFFER | 348 |
| 445 | KKLDTFFVTLSLFTER | 347 |
| 446 | KKLDTGFVKLSLFTER | 347 |
| 96 | KKLDTFGVKLSLFTER | 347 |
| 447 | KKLDAFFVKLSLFTER | 346 |
| 448 | KKLQTFFVKLSLFTER | 345 |
| 449 | KKLCTFFVKLSLFTER | 344 |
| 450 | KKLDTFFVKLSLFTQR | 344 |
| 451 | KKLSTFFVKLSLFTER | 344 |
| 452 | KKYDTFFVKLSLFTER | 344 |
| 453 | SKLDTFFVKLSLFTER | 344 |
| 454 | KLLDTFFVKLSLFTER | 343 |
| 377 | KKLDTFFVKLSLFGER | 343 |
| 455 | KKLDTFFVKLSCFTER | 342 |
| 456 | KKLDEFFVKLSLFTER | 341 |
| 457 | KKLDTFFVKLCLFTER | 341 |
| 458 | KKWDTFFVKLSLFTER | 341 |
| 459 | KKLDTFFVKLSLFTYR | 340 |
| 460 | KKLDTKFVKLSLFTER | 337 |
| 461 | KDLDTFFVKLSLFTER | 335 |
| 462 | KKLDTCFVKLSLFTER | 335 |
| 463 | KKLDTFYVKLSLFTER | 334 |
| 464 | KKLDTFFVKLRLFTER | 333 |
| 465 | FKLDTFFVKLSLFTER | 332 |
| 466 | KKLDTHFVKLSLFTER | 332 |
| 467 | KILDTFFVKLSLFTER | 331 |
| 468 | KTLDTFFVKLSLFTER | 331 |
| 469 | KKLDTFFVQLSLFTER | 330 |
| 470 | KKLDTFFVKLPLFTER | 328 |
| 471 | KKLDTFFVKLSLFTKR | 324 |
| 472 | KKLDTFFVKLWLFTER | 324 |
| 473 | KKLDTFFVKLKLFTER | 323 |
| 474 | KKLDTFFVKLDLFTER | 322 |
| 475 | KKLDTFFVKLSYFTER | 320 |
| 476 | KKLDTFFVKLSLFTER | 319 |
| 477 | KKLDTFFVKLALFTER | 318 |
| 478 | KKLDTFFVKLSLFTHR | 318 |
| 479 | KKLHTFFVKLSLFTER | 317 |
| 480 | KKLRTFFVKLSLFTER | 317 |
| 481 | KVLDTFFVKLSLFTER | 317 |
| 482 | KKLDTFFVKWSLFTER | 316 |
| 483 | YKLDTFFVKLSLFTER | 315 |
| 484 | KKLDLFFVKLSLFTER | 311 |
| 393 | KKLDTFFVKLSLFTEY | 311 |
| 390 | KKLDTFFVKLSLFTEN | 311 |
| 485 | KALDTFFVKLSLFTER | 309 |
| 486 | KKLDTRFVKLSLFTER | 309 |
| 487 | KKLDTFFVKLSLFTER | 308 |
| 488 | KKLDTFFVHLSLFTER | 306 |
| 489 | KKLDTFFVKLSLFAER | 305 |
| 490 | KWLDTFFVKLSLFTER | 304 |
| 491 | KKLLTFFVKLSLFTER | 303 |
| 492 | KKLDTFDVKLSLFTER | 301 |
| 493 | KKLDTFFVKLSLFQER | 301 |
| 494 | KYLDTFFVKLSLFTER | 301 |
| 495 | KKLDTFFAKLSLFTER | 299 |
| 496 | KKLDTFFTKLSLFTER | 298 |
| 497 | KKLDTFFVKLSPFTER | 297 |
| 388 | KKLDTFFVKLSLFTEF | 297 |

TABLE 5.1-continued

Sequences and Corresponding Rampo Scores

| SEQ ID | Sequence | RAMPO Score |
|---|---|---|
| 498 | KKLNTFFVKLSLFTER | 296 |
| 499 | KCLDTFFVKLSLFTER | 295 |
| 500 | KKLDDFFVKLSLFTER | 295 |
| 501 | KKLDIFFVKLSLFTER | 293 |
| 502 | KKLDTFFVKHSLFTER | 293 |
| 392 | KKLDTFFVKLSLFTET | 292 |
| 503 | KKLDTFFVKLSLYTER | 291 |
| 389 | KKLDTFFVKLSLFTEK | 291 |
| 504 | KKLDFFFVKLSLFTER | 290 |
| 505 | KKLDTFFVKLILFTER | 289 |
| 99 | KKLDTFFVKLGLFTER | 288 |
| 506 | KKLDTFFVKKSLFTER | 285 |
| 507 | WKLDTFFVKLSLFTER | 284 |
| 508 | KKLDTFFVKCSLFTER | 283 |
| 509 | KKLDTFFVMLSLFTER | 283 |
| 510 | KSLDTFFVKLSLFTER | 281 |
| 511 | KKLDTFFVSLSLFTER | 274 |
| 512 | KKLKTFFVKLSLFTER | 274 |
| 513 | KKLDTFFQKLSLFTER | 271 |
| 514 | KKLDTFFVKLSLFYER | 270 |
| 515 | KKLGTFFVKLSLFTER | 264 |
| 33 | KKLDTFFVKLSLFRER | 264 |
| 516 | KKLDTFFVKLSLFTER | 260 |
| 517 | KKLDTFFVKLSLFKER | 259 |
| 518 | KKLDTFFVNLSLFTER | 256 |
| 519 | KKLDTFFCKLSLFTER | 254 |
| 520 | KKLDTFFVKLSLFCER | 254 |
| 521 | KKLDTFFVKLSLFTEV | 254 |
| 264 | KKLDTFFKKLSLFTER | 253 |
| 522 | KKLDTFFVKLFLFTER | 250 |
| 523 | KKLDTFFVVLSLFTER | 248 |
| 524 | KKLDTFFVKLSLFTMR | 247 |
| 525 | KKLDTFFVKLSLFTLR | 246 |
| 526 | KKLDTFFVWLSLFTER | 245 |
| 527 | KKLDTFFVELSLFTER | 240 |
| 528 | KKLDTFFVKLSLFTEH | 239 |
| 529 | KKLDTFFVKLSLFTEM | 238 |
| 530 | KKLDKFFVKLSLFTER | 237 |
| 531 | KKLDTFFVKLSLFTRR | 237 |
| 532 | KKLDTFFVKLELFTER | 234 |
| 533 | KKLDTFFVKLSLFTEP | 234 |
| 534 | KKLDTFFVPLSLFTER | 233 |
| 101 | KKLDTFFVKLSLFTGR | 233 |
| 535 | KKLDTFKVKLSLFTER | 232 |
| 536 | KKLDTEFVKLSLFTER | 229 |
| 537 | KKLDTFWKLSLFTER | 228 |
| 538 | KKLDTFFVKLSLFTEA | 226 |
| 539 | KKLDTFFVKLSLFTWR | 226 |
| 540 | KKLDTFFMKLSLFTER | 221 |
| 541 | KKLDTFFVCLSLFTER | 220 |
| 542 | KKLDTFFVKLSLKTER | 220 |
| 543 | KKLDTFFVKLSLFTEG | 218 |
| 544 | KKLDTFFVKLSLFTEL | 217 |
| 545 | KKLDTFFSKLSLFTER | 216 |
| 546 | CKLDTFFVKLSLFTER | 215 |
| 547 | KKLDTFFHKLSLFTER | 213 |
| 548 | KKLDTFFVKLLLFTER | 213 |
| 549 | KKLDTFFYKLSLFTER | 211 |
| 550 | KKLDTFFNKLSLFTER | 203 |
| 551 | KKLDTFFVKLSLFTEW | 202 |
| 552 | KKLDTFFVYLSLFTER | 198 |
| 553 | KKLDTDFVKLSLFTER | 193 |
| 554 | KKLDTFFVALSLFTER | 191 |
| 555 | KKLDTFFVILSLFTER | 190 |
| 98 | KKLDTFFVGLSLFTER | 188 |
| 97 | KKLDTFFVGLSLFTER | 188 |
| 556 | KKLDTFFVKLSLFTCR | 185 |
| 557 | KKLDTFFVKLSLFTES | 184 |
| 558 | KKLDTFFVKLSLFTEI | 176 |
| 559 | KKLDTFFVKLSLFTEC | 175 |
| 560 | KKLDTFFVFLSLFTER | 174 |
| 561 | KKLDTFFVKLSLFTAR | 174 |
| 562 | KKLDTFFVLLSLFTER | 166 |
| 563 | KKLDTFFVKLSLFTSR | 165 |
| 564 | KKLDTFFVKLSLFTIR | 163 |
| 565 | KKLDTFFVKLSLFTVR | 163 |

TABLE 5.1-continued

Sequences and Corresponding Rampo Scores

| SEQ ID | Sequence | RAMPO Score |
|---|---|---|
| 566 | KKLDTFFVKLSLFTNR | 161 |
| 567 | KKLDTFFVKLSLFDER | 159 |
| 568 | KKLDTFFVKLSLFTTR | 152 |
| 569 | KKLDTFFVDLSLFTER | 149 |
| 570 | KKLDTFFEKLSLFTER | 139 |
| 571 | KKLDTFFVKLSLFTFR | 137 |
| 572 | KKLDTFFVKLSLFTED | 133 |
| 573 | KKLDTFFVKLSLFTEQ | 133 |
| 574 | KKLDTFFDKLSLFTER | 122 |
| 575 | KKLDTFFVKLSLDTER | 112 |
| 576 | KKLDTFFVKLSLFEER | 110 |
| 577 | KKLDTFFVKLSLFTEE | 107 |
| 578 | KKLDTFFVKDSLFTER | 102 |
| 579 | KKLDTFFVKLSLETER | 98 |
| 580 | KKLDTFFVKLSDFTER | 89 |
| 581 | KKLDTFFVKLSEFTER | 82 |
| 582 | KKLDTFFVKESLFTER | 81 |

As shown in Example 12, at least 31 single amino acid substitutions of P28R shown in Table 6.1 (SEQ ID NOs: 3-34) bind to P3028 with a higher rampo score than P28R. Additionally at least 4 single substitutions of glycine residues for residues of P28R (SEQ ID NOs: 94-96 and 98) bind to P3028 with a rampo scores at least comparable to P28R, for example a rampo score greater than about 500. Additionally at least 129 single amino acid substitutions bind to P3028 with a rampo score at least substantially equal to (i.e., at least 98% of) P28R, as shown in Table 6.2 (SEQ ID NOs: 268-393). Additionally, truncations of at least the N terminal arginine of P28R (SEQ ID NO: 34), and up to the first 8 C terminal amino acids of P28R (SEQ ID NOs: 46-53) provide peptides with rampo scores at least comparable to P28R. Additionally, at least some internal amino acid residue deletions of P28 (SEQ ID NOs: 64-66, 68, 76) provide peptides with ramp scores at least comparable to P28R. Thus, contemplated herein are peptides that include substitutions of P28R that include combinations of two or more of the substitutions of SEQ ID NOs: 3-34. Moreover, contemplated herein are peptides that include at least one deletion of P28R as in SEQ ID NOs: 34, 46-53, 64-66, 68, and/or 74, and at least one substitution (of a non-deleted residue) of P28R as in SEQ ID NOs: 3-34, 94-96, 98 and/or 268-393.

Accordingly, some embodiments concern compositions that comprise, consist of, or consist essentially of an immunoregulatory peptide inhibitor that comprises, consists of, or consists essentially of Formula (I):

Formula (I):
(SEQ ID NO: 166)
$XX_1VKX_2X_3X_4$.

wherein X is an optional sequence, and can be KKLDT (SEQ ID NO: 167), RKLDT (SEQ ID NO: 168), KKGDT (SEQ ID NO: 169), KKEDT (SEQ ID NO: 170), KKLDQ (SEQ ID NO: 171), KKGDQ (SEQ ID NO: 252), KKEDQ (SEQ ID NO: 253), RKLDQ (SEQ ID NO: 254), RKGDQ (SEQ ID NO: 255), RKEDQ (SEQ ID NO: 256), RKGTD (SEQ ID NO: 257), RKEDT (SEQ ID NO: 258), KLDT (SEQ ID NO: 172), KGDT (SEQ ID NO: 259), KEDT (SEQ ID NO: 260), KLDQ (SEQ ID NO: 261), KGDQ (SEQ ID NO: 262), KEDQ (SEQ ID NO: 263), LDT, LDQ, GDT, GDQ, EDT, EDQ, DT, DQ, T, or Q, or absent.

$X_1$ can be one of FF, FM, FS, FV, FT, FL, AF, AM, AS, AV, AT, AL, VF, VM, VS, VV, VT, or VL.

$X_2$ can be one of LS, LQ, LM, LT, LH, VS, VQ, VM, VT, or VH.

$X_3$ can be one of LFT, LMT, LQT, LHT, LNT, LPT, LST, LGT, LAT, LRT, QFT, QMT, QQT, QHT, QNT, QPT, QST, QGT, QAT, QRT, VFT, VMT, VQT, VHT, VNT, VPT, VST, VGT, VAT, VRT, MFT, MMT, MQT, MHT, MNT, MPT, MST, MGT, MAT, MRT, LFN, LMN, LQN, LHN, LNN, LPN, LSN, LGN, LAN, LRN, QFN, QMN, QQN, QHN, QNN, QPN, QSN, QGN, QAN, QRN, VFN, VMN, VQN, VHN, VNN, VPN, VSN, VGN, VAN, VRN, MFN, MMN, MQN, MHN, MNN, MPN, MSN, MGN, MAN, MRN, LFP, LMP, LQP, LHP, LNP, LPP, LSP, LGP, LAP, LRP, QFP, QMP, QQP, QHP, QNP, QPP, QSP, QGP, QAP, QRP, VFP, VMP, VQP, VHP, VNP, VPP, VSP, VGP, VAP, VRP, MFP, MMP, MQP, MHP, MNP, MPP, MSP, MGP, MAP, MRPR, LFR, LMR, LQR, LHR, LNR, LPR, LSR, LGR, LAR, LRR, QFR, QMR, QQR, QHR, QNR, QPR, QSR, QGR, QAR, QRR, VFR, VMR, VQR, VHR, VNR, VPR, VSR, VGR, VAR, VRR, MFR, MMR, MQR, MHR, MNR, MPR, MSR, MGR, MAR, or MRR.

$X_4$ is an optional sequence, and can be ER, or E, or absent.

In some embodiments, if X is absent, $X_1$ is FF, and $X_2$ is LS.

In some embodiments, the isolated peptide comprising Formula (I) has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Some embodiments concern compositions that comprise, consist of, or consist essentially of an immunoregulatory peptide inhibitor that comprises, consists of, or consists essentially of Formula (II):

Formula (II):
(SEQ ID NO: 173)
$X_{20}TFFVKLSX_{21}X_{22}$ wherein $X_{20}$ is an optional sequence, and can be KKLD (SEQ ID NO: 174), RKLD (SEQ ID NO: 175), KKGD (SEQ ID NO: 176), KKED (SEQ ID NO: 177), KLD, LD, or D, or absent.

$X_{21}$ is an optional sequence, and can be LFT, LMT, LQT, LHT, LNT, LPT, LST, LGT, LAT, LRT, QFT, QMT, QQT, QHT, QNT, QPT, QST, QGT, QAT, QRT, VFT, VMT, VQT, VHT, VNT, VPT, VST, VGT, VAT, VRT, MFT, MMT, MQT, MHT, MNT, MPT, MST, MGT, MAT, MRT, LFN, LMN, LQN, LHN, LNN, LPN, LSN, LGN, LAN, LRN, QFN, QMN, QQN, QHN, QNN, QPN, QSN, QGN, QAN, QRN, VFN, VMN, VQN, VHN, VNN, VPN, VSN, VGN, VAN, VRN, MFN, MMN, MQN, MHN, MNN, MPN, MSN, MGN, MAN, MRN, LFP, LMP, LQP, LHP, LNP, LPP, LSP, LGP, LAP, LRP, QFP, QMP, QQP, QHP, QNP, QPP, QSP, QGP, QAP, QRP, VFP, VMP, VQP, VHP, VNP, VPP, VSP, VGP, VAP, VRP, MFP, MMP, MQP, MHP, MNP, MPP, MSP, MGP, MAP, MRPR, LFR, LMR, LQR, LHR, LNR, LPR, LSR, LGR, LAR, LRR, QFR, QMR, QQR, QHR, QNR, QPR, QSR, QGR, QAR, QRR, VFR, VMR, VQR, VHR, VNR, VPR, VSR, VGR, VAR, VRR, MFR, MMR, MQR, MHR, MNR, MPR, MSR, MGR, MAR, or MRR, or absent.

$X_{22}$ is an optional sequence, and can be ER, or E, or absent.

In some embodiments, the isolated peptide comprising Formula (II) has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Some embodiments concern compositions that comprise, consist of, or consist essentially of an immunoregulatory peptide inhibitor that comprises, consists of, or consists essentially of Formula (III):

Formula (III):
(SEQ ID NO: 178)
$X_{30}X_{31}VKLX_{32}LX_{33}TEX_{34}$ wherein $X_{30}$ is an optional sequence, and can be KKLDTF (SEQ ID NO: 179), KLDTF (SEQ ID NO: 180), LDTF (SEQ ID NO: 181), DTF, TF, or F, or absent.

$X_{31}$ is an optional sequence, and can be F, S, M, V, T, or L, or absent.

In some embodiments, $X_{31}$ is F.

$X_{32}$ can be S, Q, M, T, or H. In some embodiments, $X_{32}$ is S.

$X_{33}$ can be F, M, Q, H, N, P, S, G, A, or R. In some embodiments, $X_{34}$ is F.

$X_{34}$ is an optional sequence, and can be R, or absent.

In some embodiments, the isolated peptide comprising Formula (III) has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Some embodiments concern compositions that comprise, consist of, or consist essentially of an immunoregulatory peptide inhibitor that comprises, consists of, or consists essentially of Formula (VII):

Formula (VII):
(SEQ ID NO: 394)
$X_{700}K\ X_{701}X_{702}X_{703}\ X_{704}X_{705}X_{706}K\ X_{707}\ X_{708}\ X_{709}$
$X_{710}\ X_{711}E\ X_{712}$, wherein $X_{700}$ is an optional sequence, and can be K,A,D,E,G,H,I,L,M,N,P,Q,R,T, or V, or absent.

$X_{701}$ is an optional sequence, and can be L,A,C,D,E,F,G,H,I,K,M,N,Q,R,S,T, or V, or absent.

$X_{702}$ is an optional sequence, and can be D,A,E,I,V,W, or Y, or absent.

$X_{703}$ is an optional sequence, and can be T,C,M,N,P,Q,R,S,W, orY, or absent.

$X_{704}$ is an optional sequence, and can be F,A,I,M,N,P,T, or V, or absent.

$X_{705}$ is an optional sequence, and can be F,L,M,Q,S,T or V, or absent.

$X_{706}$ is an optional sequence, and can be V,F,G,L,P, or R, or absent.

$X_{707}$ is an optional sequence, and can be L,A,F,G,I,M,N,P,Q,R,S,T,V, or Y, or absent.

$X_{708}$ is an optional sequence, and can be S,H,M,N,Q, or T, or absent.

$X_{709}$ is an optional sequence, and can be L,A,H,I,M,N,Q,R,S,T,V, or W, or absent.

$X_{710}$ is an optional sequence, and can be F,A,C,G,H,I,L,M,N,P,Q,R,S,T,V, or W, or absent.

$X_{711}$ is an optional sequence, and can be T,F,G,H,I,L,M,N,P,S,V, or W, or absent.

$X_{712}$ is an optional sequence, and can be R,F,K,N,R,T, orY, or absent.

In some embodiments, the isolated peptide comprising Formula (VII) has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Some embodiments concern compositions that comprise, consist of, or consist essentially of an immunoregulatory peptide inhibitor that comprises, consists of, or consists essentially of Formula (VIII):

Formula (VIII):

(SEQ ID NO: 395)

$X_{800}K\ X_{801}K\ X_{802}E\ X_{803}$ $X_{801}$ is LDTFFV, GDTFFV, EDTFFV, LDQFFV, LDTAFV, LDTVFV, LDTFMV, LDTFSV, LDTFVV, LDTFTV, LDTFLV, LDGFFV, LDTFGV, LDTFFK, ADTFFV, CDTFFV, DDTFFV, FDTFFV, HDTFFV, IDTFFV, KDTFFV, MDTFFV, NDTFFV, QDTFFV, RDTFFV, SDTFFV, TDTFFV, VDTFFV, LATFFV, LETFFV, LITFFV, LVTFFV, LWTFFV, LYTFFV, LDCFFV, LDMFFV, LDNFFV, LDPFFV, LDRFFV, LDSFFV, LDWFFV, LDYFFV, LDTIFV, LDTMFV, LDTNFV, LDTPFV, LDTTFV, LDTFQV, LDTFFF, LDTFFG, LDTFFL, LDTFFP, LDTFFR, LDTFIV, LDTSFV, LDTFAV, LDTFCV, LDTQFV, LDTLFV, LTTFFV, LDTFFI, LDHFFV, LMTFFV, LDTFEV, LDTFWV, LFTFFV, LDVFFV, LDTFRV, LDTFHV, LDTYFV, LPTFFV, PDTFFV, LDTFPV, LDTFNV, LDTWFV, LDTGFV, LDAFFV, LQTFFV, LCTFFV, LSTFFV, YDTFFV, LDEFFV, WDTFFV, LDTKFV, LDTCFV, LDTFYV, LDTHFV, LHTFFV, LRTFFV, LDLFFV, LDTRFV, LLTFFV, LDTFDV, LDTFFA, LDTFFT, LNTFFV, LDDFFV, LDIFFV, LDFFFV, LKTFFV, LDTFFQ, LGTFFV, LDTFFC, LDKFFV, LDTFKV, LDTEFV, LDTFFW, LDTFFM, LDTFFS, LDTFFH, LDTFFY, LDTFFN, LDTDFV, LDTFFE, LDTFFD, LTFFV, LDTFF, TFFV, LDF, LDTE, FFV, LDV, LV, or L, or absent;

wherein $X_{802}$ is LSLFT, VSLFT, LQLFT, LMLFT, LTLFT, LHLFT, LSQFT, LSVFT, LSMFT, LSLMT, LSLQT, LSLHT, LSLNT, LSLPT, LSLST, LSLGT, LSLAT, LSLRT, LSLFN, LSLFP, LSLFR, LGLFT, ASLFT, FSLFT, GSLFT, ISLFT, MSLFT, NSLFT, PSLFT, QSLFT, RSLFT, SSLFT, TSLFT, YSLFT, LNLFT, LSAFT, LSHFT, LSIFT, LSNFT, LSRFT, LSSFT, LSTFT, LSWFT, LSLCT, LSLIT, LSLLT, LSLTT, LSLVT, LSLWT, LSLFF, LSLFG, LSLFH, LSLFI, LSLFL, LSLFM, LSLFS, LSLFV, LSLFW, LYLFT, LVLFT, LSFFT, LSGFT, LSKFT, LSCFT, LCLFT, LRLFT, LPLFT, LWLFT, LKLFT, LDLFT, LSYFT, LALFT, WSLFT, LSLFA, LSLFQ, LSPFT, HSLFT, LSLYT, LILFT, KSLFT, CSLFT, LSLFY, LSLFK, LSLFC, LFLFT, LELFT, LSLKT, LLLFT, LSLFD, LSLDT, LSLFE, DSLFT, LSLET, LSDFT, LSEFT, ESLFT, SLFT, LSFT, LFT, LSL, LT, or T, or absent; and wherein $X_{803}$ is R, F, K, N, R, T, or Y, or absent.

In some embodiments, the isolated peptide comprising Formula (VIII) has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Some embodiments concern compositions that comprise, consist of, or consist essentially of an immunoregulatory peptide inhibitor that comprises, consists of, or consists essentially of any one or more of the peptides set forth in Table 5.1. In some embodiments, the isolated peptide from Table 5.1 used in these compositions has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

In some embodiments, the peptide comprises one of SEQ ID NOs: 1-33, 34, 46-53, 64-66, 68, 76, 94-96 or 98. Again, this isolated peptide can have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Embodiments of the invention also include immunoregulatory peptide inhibitors that have a specific affinity to P3028 sequences or structures. In some embodiments, the immunoregulatory peptide inhibitors have specific affinity to P3028 sequences or structures as measured by a rampo assay in which the immunoregulatory peptide inhibitors are affixed to a solid phase, P3028 is added, and the enzymatic activity of a rampo secondary antibody is measured so as to detect binding (see Example 12). In some embodiments, the immunoregulatory peptide inhibitors bind to P3028 structures or sequences with a rampo score that is at least substantially equal to the rampo score of P28R (see Example 12, Table 6.2). Preferably, the immunoregulatory peptide inhibitors have a specific affinity to P3028 by this rampo assay of at least or equal to about 300 rampo units, for example, at least or equal to about 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 820, 840, 860, 880, 900, 920, 940, 960, 980, 1000, 1020, or 1040 rampo units, including ranges between any two of the listed values. In some embodiments, the immunoregulatory peptide inhibitors bind to P3028 structures or sequences with a rampo score of at 500 (see Example 12, Table 6.1). Exemplary peptides with affinity to P3028 are provided in Example 12 (see Tables 6.1, 6.2, and FIGS. 29-30).

Similarly, embodiments include isolated immunoregulatory peptide inhibitors that have an affinity to any one or more of the immunoregulatory peptides listed in Tables 1-4 (SEQ ID NOs: 183-184 and 188-246). In some embodiments, the immunoregulatory peptide inhibitors have specific affinity to any one or more of the immunoregulatory peptides listed in Tables 1-4 (SEQ ID NOs: 183-184 and 188-246), as measured by a rampo assay in which the immunoregulatory peptide inhibitors are affixed to a solid phase, any one or more of the immunoregulatory peptides listed in Tables 1-4 (SEQ ID NOs: 183-184 and 188-246) is added, and the enzymatic activity of a rampo secondary antibody is measured so as to detect binding. For example, aspects of the invention include any peptide provided in Table 5.1 and any of the methods described herein can be practiced using one or more of the peptides described in Table 5.1. Preferably, the immunoregulatory peptide inhibitors have a specific affinity to any one or more of the immunoregulatory peptides listed in Tables 1-4 (SEQ ID NOs: 183-184 and 188-246) by this rampo assay of at least or equal to about 300 rampo units, for example, at least or equal to about 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 820, 840, 860, 880, 900, 920, 940, 960, 980, 1000, 1020, or 1040 rampo units, including ranges between any two of the listed values.

Peptide Sequence Variations

A number of sequence variations to the immunoregulatory peptide inhibitor P28R (KKLDTFFVKLSLFTER; SEQ ID NO: 2) have been shown to have immunostimulatory activity and/or cytotoxicity to tumor cells (see Examples 37-40). Without being limited by any theory, SEQ ID NO: 2 and variations of SEQ ID NO: 2 as described in Table 5.3 for example, one or more of the peptides of Table 5.4 can be useful for binding peptide 3028 (SEQ ID NO: 185), binding a peptide or albumin fragment that comprises SEQ ID NO: 185, binding any one or more of the peptides listed in Tables 1-4, directly stimulating immune cells, and/or killing tumor cells in accordance with some embodiments herein (see Examples 36-40). As such, in some embodiments, a immunoregulatory peptide inhibitor peptide comprises, consists of, or consists essentially of an amino acid sequence with one or more of the modifications to SEQ ID NO: 2 as shown in Table 5.3, for example, 1, 2, 3, 4, 5, 6, 7, 8, 9, or 10 modifications, for example, 1-2, 1-3, 1-4, 1-5, 1-6, 1-7, 1-8, 1-9, 1-10, 2-3, 2-4, 2-5, 2-6, 2-7, 2-8, 2-9, 2-10, 3-4, 3-5, 3-6, 3-7, 3-8, 3-9, 3-10, 4-5, 4-6, 4-7, 4-8, 4-9, 4-10, 5-6, 5-7, 5-8, 5-9, 5-10, 6-7, 6-8, 6-9, 6-10, 7-8, 7-9, 7-10, 8-9, 8-10, or 9-10 variations. The inhibitor peptide can further comprise a further variation at one or more of positions 1, 3-4, 12-14, or 16 in SEQ ID NO: 2, wherein the further variation comprises any amino acid or the absence of an amino acid, for example, 1, 2, 3, 4, 5, 6, or 7 further variations:

TABLE 5.3

| Position in KKLDTFFVKLSLFTER (SEQ ID NO: 2) | Type of Variation | Exemplary Amino Acids for Variations |
|---|---|---|
| K1 | Any type of amino acid | Any amino acid or absent |
| K2 | Positive charged amino acid | R, H, K |
| L3 | Any type of amino acid | Any amino acid or absent |
| D4 | Any type of amino acid | Any amino acid or absent |
| T5 | Polar uncharged amino acid | S, T, N, Q |
| F6 | Hydrophobic or uncharged polar amino acid | A, V, I, L, F, Y, W, S, T, N, Q |
| F7 | Hydrophobic or uncharged polar amino acid | A, V, I, L, F, Y, W, S, T, N, Q |
| V8 | Hydrophobic, non-aromatic carbon chain amino acids that are not M | A, V, I, L |
| K9 | Positively charged amino acids, T, Q, or Y | R, H, K, T, Q, Y |
| L10 | Any type of amino acid except negatively charged | R, H, K, S, T, N, Q, C, U, G, P, A, V, I, L, M, F, Y, W |
| S11 | Polar uncharged amino acids | S, T, N, Q |
| L12 | Any type of amino acid except negatively charged | R, H, K, S, T, N, Q, C, U, G, P, A, V, I, L, M, F, Y, W |
| F13 | Any type of amino acid except negatively charged | R, H, K, S, T, N, Q, C, U, G, P, A, V, I, L, M, F, Y, W |
| T14 | Any type of amino acid except negatively charged | R, H, K, S, T, N, Q, C, U, G, P, A, V, I, L, M, F, Y, W |
| E15 | Negatively charged amino acids | D, E |

In some embodiments, the varied peptide does not comprise a M at position 8. In some embodiments, the varied peptide does not comprise a M at position 9. In some embodiments, the varied peptide does not comprise a M at position 15. In some embodiments, the modified peptide does not comprise a M at any of positions 8, 9, or 15.

Accordingly, in some embodiments, the peptide inhibitor comprising a variation of P28R comprises, consists essentially of, or consists of a peptide of Formula (IX):

Formula (IX)

$X_{901}X_{902}X_{903}X_{904}X_{905}X_{906}X_{907}X_{908}X_{909}X_{910}X_{911}X_{912}$ $X_{913}X_{914}X_{915}X_{916}X_{917}$, wherein $X_{901}$ is any amino acid or absent, $X_{902}$ is a positively charged amino acid, F, or N, $X_{903}$ is any amino acid, $X_{904}$ is any amino acid, $X_{905}$ is a polar uncharged amino acid, R, Y, or W, $X_{906}$ is a hydrophobic or uncharged polar amino acid, $X_{907}$ is a hydrophobic or uncharged polar amino acid, $X_{908}$ is a hydrophobic, non-aromatic carbon chain amino acid that is not M or F, $X_{909}$ is a positively charged amino acid, T, Q, or Y, $X_{910}$ is any amino acid that is not negatively charged, $X_{911}$ is a polar uncharged amino acid or H, $X_{912}$ is any amino acid that is not negatively charged, $X_{913}$ is any amino acid that is not negatively charged, $X_{914}$ is any amino acid that is not negatively charged, $X_{915}$ is a negatively charged amino acid, Y, or Q, $X_{916}$ is any amino acid that is not negatively charged, and $X_{917}$ is one or more positively charged amino acids or is absent.

Optionally, $X_{901}$ comprises a positively charged amino acid. Optionally, $X_{901}$ is an R or K. Optional, $X_{917}$ comprises or consists of RR.

A number of peptide inhibitors based on variation of peptides described herein have been shown to stimulate immune cells (see Example 36). Exemplary varied peptides are shown in Table 5.4. Accordingly, in some embodiments, the peptide inhibitor comprises, consists of, or consists essentially of a peptide of Table 5.4. Additional exemplary varied peptides shown to have low binding to P3028 (see Example 36) or low stimulation of healthy PBMCs in healthy serum (see Example 37) are shown in Tables 5.5 and 5.6. In some embodiments, a peptide comprising, consisting of, or consisting essentially of a peptide of Table 5.4, 5.5, or 5.6 is provided.

TABLE 5.4

Peptides with "high" binding to P3028 based on positional scans

| SEQ ID NO: | Amino Acid Sequence (variation(s) to SEQ ID NO: 2 are underlined) | May also be referred to as: |
|---|---|---|
| 583 | KKLDTFFVKLSLMTER | 30677 |
| 584 | KKLDTFFVKLQLFTER | 30678 |
| 585 | KKLDTVMVKLQLMTER | 30680 |
| 586 | RKLDTFFVKLSLFTERRR | 32814 |

TABLE 5.5

Peptides with "low" binding to P3028 based on positional scans

| SEQ ID NO: | Amino Acid Sequence (variation(s) to SEQ ID NO: 2 are underlined) | May also be referred to as: |
|---|---|---|
| 587 | KSLDTFFVKLSLFTER | 30684 |
| 588 | KKLDTFFVKLSLFTFR | 30685 |
| 589 | KKLDTFFVYLSLFTER | 31135 |
| 590 | KKLDTFFVNLSLFTER | 31136 |
| 591 | KKLDTFFVDLSLFTER | 31138 |

TABLE 5.6

Additional modification of P28R

| SEQ ID NO: | Amino Acid Sequence (variation(s) to SEQ ID NO: 2 are underlined) | May also be referred to as: |
|---|---|---|
| 592 | KKLDTFFPKLSLFTER | 32251 |
| 593 | KKLDTFMVKLSQHTER | 32665 |
| 594 | KKLDTFFVKLSLFTER(C(PEG24)) | 32819 |
| 595 | KKLDQFFVKLSQHNER | 32815 |

Embodiments of the invention also include peptides and proteins with identity to an isolated immunoregulatory peptide inhibitor described herein. The term "identity" is meant to include nucleic acid or protein sequence homology or three-dimensional homology. Several techniques exist to determine nucleic acid or peptide sequence homology and/or three-dimensional homology to peptides. These methods are routinely employed to discover the extent of identity that one sequence, domain, or model has to a target sequence, domain, or model. A vast range of functional immunoregulatory peptide inhibitors (e.g., an immunoregulatory peptide inhibitor for P3028 sequence or structures) can incorporate features of peptide inhibitors disclosed herein, thus providing for a vast degree of identity to the immunoregulatory peptide inhibitors of SEQ ID NOs: 1-33, 34, 46-53, 64-66, 68, 76, 94-96, 98, 264-393, 583-586, or 589. For example, a fusion protein having a small region of an inhibitor can exhibit a low degree of overall identity to an immunoregulatory peptide inhibitor of SEQ ID NOs: 1-33, 34, 46-53, 64-66, 68, 76, 94-96, 98, 264-393, 583-586, or 589, yet retain the ability to function as inhibitor (e.g., an inhibitor of P3028, such as a molecule that binds to P3028), or to enhance immune cell stimulation via the LFA-1 and/or IL-2 receptor (e.g., modulate, upregulate or down regulate a marker of the immune system or immunosuppression, such as reducing a P3028-mediated inhibition of immune cell proliferation, spreading, migration, or NK-cell cytotoxicity), or to enhance immune cell stimulation. Thus, embodiments of the invention can have from 1% identity to 100% identity to the sequences of SEQ ID NOs: 1-33, 34, 46-53, 62, 64-66, 68, 76, 94-96, 98, 264-393, 583-586, or 589. That is, embodiments can have at least or equal to about, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to any one of SEQ ID NOs: 1-33, 34, 46-53, 64-66, 68, 76, 94-96, 98, 264-393, 583-586, or 589. Preferably, these peptides or modified peptides also retain the ability to modulate the immune system (e.g., modulate, upregulate or down regulate a marker of the immune system or immunosuppression, such as reducing a P3028-mediated inhibition of immune cell proliferation, spreading, migration, or NK-cell cytotoxicity).

Embodiments also include compositions that comprise multimers of isolated immunoregulatory peptide inhibitors and/or isolated immunoregulatory peptide inhibitors bound to a support. Some embodiments include compositions that comprise multimers of immunoregulatory peptide inhibitors that include multiple copies of a single immunoregulatory peptide inhibitor. Some embodiments include compositions that comprise multimers that include two or more different immunoregulatory peptide inhibitors. Some multimers include at least or equal to two immunoregulatory peptide inhibitors, for example 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80, 85, 90, 95, 99, 100, or 101 immunoregulatory peptide inhibitors. In some embodiments, the multimers are of the same immunoregulatory peptide inhibitor and in other embodiments, the multimers are of different immunoregulatory peptide inhibitors. Accordingly, some embodiments concern compositions that comprise one or more immunoregulatory peptide inhibitors and in some embodiments, the one or more immunoregulatory peptide inhibitor are multimers of the same molecule.

Methods of Making Peptide-Based Immunoregulatory Peptide Inhibitors

Many methods of making peptides are known in the art. Examples of methods of making peptides can be found in U.S. Pat. No. 6,495,674, hereby expressly incorporated by reference in its entirety. In some embodiments, peptide inhibitors are chemically synthesized. Chemical synthesis of peptides is also well-known. For example, solid phase chemical synthesis can be used to produce peptides of up to at least about 100 amino acids in length. Accordingly, in some embodiments, the immunoregulatory peptide inhibitor is a synthetic peptide.

In other embodiments, immunoregulatory peptide inhibitors are prepared by recombinant DNA technology using techniques well known in the art. Such methods can be used to construct expression vectors containing nucleotide sequences encoding an immunoregulatory peptide inhibitor, for example, and appropriate transcriptional and translational control signals. These methods can include, for example, in vitro recombinant DNA techniques, synthetic techniques, and in vivo genetic recombination. Alternatively, RNA capable of encoding a peptide inhibitor can be chemically synthesized using, for example, synthesizers. See, for example, the techniques described in Oligonucleotide Synthesis, 1984, Gait, M. J. ed., IRL Press, Oxford, which is incorporated by reference herein in its entirety. Alternatively, a DNA or RNA encoding a peptide or protein substantially longer that the peptide inhibitor can be provided, in which the peptide inhibitor is flanked by protease target sites, thus producing the peptide inhibitor from a larger peptide or protein. Exemplary proteases include thrombin, trypsin, chymotrypsin, LysC, GluC, and AspN. Alternatively, a DNA or RNA encoding two or more copies of the peptide inhibitor can be provided, in which the peptide inhibitors are flanked by protease target sites, thus producing the peptide inhibitor from a larger peptide or protein. Thus, in some embodiments, the peptide inhibitor of P3028 is produced by a ribosome.

In several embodiments, the immunoregulatory peptide inhibitors are expressed in a cell line. For example, some cells are provided a nucleic acid encoding one or more immunoregulatory peptide inhibitors, said cells are made to express the peptides of SEQ ID NOs: 1-33, 34, 46-53, 64-66, 68, 76, 94-96, 98, 264-393, 583-586, or 589 or any one or more of the peptides provided in Table 5.1 and the immunoregulatory peptide inhibitors are isolated and/or purified. Exemplary nucleic acids are listed in Table 5.2, SEQ ID NOs: 102-165.

A variety of host-expression vector systems can be utilized to express inhibitor peptides of some embodiments of the invention. Where the immunoregulatory peptide inhibitor is a soluble peptide, it can be recovered from the culture, i.e., from the host cell in cases where the peptide or polypeptide is not secreted, and from the culture media in cases where the peptide or polypeptide is secreted by the cells. However, the expression systems also encompass engineered host cells that express the peptide or functional equivalents in situ, i.e., anchored in the cell membrane. Purification or enrichment of the peptide from such expression systems can be accomplished using appropriate detergents and lipid micelles and methods well known to those skilled in the art. However, such engineered host cells themselves can be used in situations where it is important not only to retain the structural and functional characteristics of the peptide, but to assess biological activity, e.g., in drug screening assays.

The expression systems that can be used for purposes of the invention include, but are not limited to, microorganisms such as bacteria (e.g., *E. coli* or *B. subtilis*) transformed with recombinant bacteriophage DNA, plasmid DNA or cosmid DNA expression vectors containing nucleotide sequences encoding inhibitor peptides; yeast (e.g., *Saccharomyces, Pichia*) transformed with recombinant yeast expression vectors containing the nucleotide sequences encoding inhibitor peptides; insect cell systems infected with recombinant virus expression vectors (e.g., baculovirus) containing sequences encoding inhibitor peptides; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing nucleotide sequences encoding inhibitor peptides; mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter); or cell-free expression systems, which can include cell lysates or fractions thereof, and nucleic acids encoding the inhibitor peptides.

In bacterial systems, a number of expression vectors can be advantageously selected depending upon the use intended for the peptide being produced. For example, when a large quantity of such a peptide is to be produced, for the generation of pharmaceutical compositions or for raising antibodies to the peptide, for example, vectors which direct the expression of high levels of fusion protein products that are readily purified can be desirable. Such vectors include, but are not limited, to the *E. coli* expression vector pUR278 (Ruther et al., EMBO J., 2:1791 (1983), in which the inhibitor peptide coding sequence can be ligated individually into the vector in frame with the lacZ coding region so that a fusion protein is produced; pIN vectors (Inouye & Inouye, Nucleic Acids Res., 13:3101-3109 (1985); Van Heeke & Schuster, J. Biol. Chem., 264:5503-5509 (1989)); and the like. pGEX vectors can also be used to express foreign polypeptides as fusion proteins with glutathione S-transferase (GST). In general, such fusion proteins are soluble and can be purified from lysed cells by adsorption to glutathione-agarose beads followed by elution in the presence of free glutathione. The PGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The peptide coding sequence can be cloned individually into non-essential regions (for example the polyhedrin gene) of the virus and placed under control of an AcNPV promoter (for example the polyhedrin promoter). Successful insertion of peptide coding sequence will result in inactivation of the polyhedrin gene and production of non-occluded recombinant virus, (i.e., virus lacking the proteinaceous coat coded for by the polyhedrin gene). These recombinant viruses are then used to infect *Spodoptera frugiperda* cells in which the inserted gene is expressed. (E.g., see Smith et al., J. Virol. 46: 584 (1983); and Smith, U.S. Pat. No. 4,215,051).

In mammalian host cells, a number of viral-based expression systems can be utilized. In cases where an adenovirus is used as an expression vector, the nucleotide sequence of interest can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) will result in a recombinant virus that is viable and capable of expressing the peptide in infected hosts. (E.g., see Logan & Shenk, Proc. Natl. Acad. Sci. USA 81:3655-3659 (1984)). Specific initiation signals can also be required for efficient translation of inserted nucleotide sequences encoding peptides. These signals include the ATG initiation codon and adjacent sequences.

In cell free systems, cellular extracts, or fractions thereof are provided for the translation of nucleic acids into polypeptides in vitro. Cell free systems can include, for example *E. coli* extracts, yeast extracts. The extracts can be lysates. The extracts can be purified, for example, to enrich for ribosomes and/or to remove undesired materials such as debris or host genomic DNA. Nucleic acids encoding immunoregulatory peptide inhibitors in cell-free systems can include plasmid DNA, linear DNA, or RNA.

In some embodiments, immunoregulatory peptide inhibitors are isolated or purified after expression. Isolation or purification can include affinity purification. In some embodiments, the peptide product of the expression system includes an affinity tag, for example GST separated by a cleavable linker, for example a thrombin or factor Xa protease cleavage site. After affinity purification, the affinity tag can be cleaved, producing a substantially pure peptide that does not have an affinity tag or cleavage site. In some embodiments, purification results in a composition that is at least or equal to about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 98.5, 99, 99.5, 99.9, 99.99, or 99.999% peptide by weight. The section below provides more information on pharmaceutically acceptable carriers and diluents that can be used with the embodiments described herein.

D Amino Acids and Non-Natural Amino Acids

Some embodiments include compositions that comprise, consist, or consist essentially of one or more immunoregulatory peptide inhibitors that include at least one D amino acid. With the exception of glycine, the chiral carbon of an amino acid can exist as the D or the L isomer. Typically, amino acids synthesized by ribosomes are in the L configuration. However, peptides that include D amino acids, or a combination of D and L amino acids can have activity, for example as ligands or inhibitors. For example, a peptide including at least one D amino acid can bind to the P3028 sequence/structure and inhibit the ability of the P3028 sequence/structure to bind to the LFA-1 receptor and/or the IL-2 receptor.

Accordingly, some embodiments include immunoregulatory peptide inhibitors that comprise at least one non-natural amino acid. Non-natural amino acids include amino acids having R groups other than the R group of the 20 amino acids encoded by the standard genetic code. Non-natural amino acids can exist in the L or D configuration. Thus, some embodiments include peptides having non-natural amino acids in the D configuration and/or the L configuration. Exemplary non-natural amino acids are described in U.S. Pat. Nos. 8,153,758, 7,888,533, 6,344,483, each of which is expressly incorporated by reference in its entirety herein. Some embodiments concern a composition that comprises, consists of, or consists essentially of one or more of the immunoregulatory peptide inhibitors described herein (e.g., an immunoregulatory peptide inhibitor of the P3028 sequence/structure, such as one or more of the immunoregulatory peptide inhibitors provided by of SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13, wherein said immunoregulatory peptide inhibitor comprises at least one D amino acid. Similarly, some embodiments concern a composition comprising immunoregulatory peptide inhibitor of the P3028 sequence/structure, wherein said immunoregulatory peptide inhibitors (e.g., any one or more of the immunoregulatory peptide inhibitors provided by of SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13 comprises at least one non-natural amino acid. Further embodiments include a composition comprising an immunoregulatory peptide inhibitor (e.g., any one or more of the immunoregulatory peptide inhibitors provided by SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13, wherein each non-glycine amino acid of the immunoregulatory peptide inhibitor is a D amino acid.

The crystal structure of the IL-2 receptor (CD25) has been solved, and computer modeling of P3028 binding to the IL-2 binding site of the IL-2 receptor has been performed (see FIG. 19). Moreover, the crystal structure of the ligand binding domain of IL-2 is known (see Qu, A and Leahy, D J, Proc. Natl. Acad. Sci. USA 1995, 92: 10277-10281, which is expressly incorporated by reference in its entirety). Moreover, favorable interactions between P3028 and at least one immunoregulatory peptide inhibitor can facilitate the selection of additional amino acid residues, D amino acid residues, and/or non-natural amino acid residues to maintain favorable interactions.

In some embodiments, at least some of these immunoregulatory peptide inhibitors include D amino acids positions that are selected using rational design or P3028 sequence/structure inhibitors. As noted in U.S. Pat. No. 7,957,912, rational design of peptides can start with a protein backbone structure and designs the amino acid sequence to modify the protein's properties, while maintaining its three dimensional folding properties. In some embodiments, large numbers of sequences can be manipulated using computer modeling, allowing for the design of protein structures (sequences, subsequences, etc.). Aspects of rational design are described in a number of publications, including, e.g., Malakauskas and Mayo (1998) "Design, Structure and Stability of a Hyperthermophilic Protein Variant" Nature Struc. Biol. 5:470; Dahiyat and Mayo (1997) "De Novo Protein Design: Fully Automated Sequence Selection" Science, 278, 82-87. DeGrado, (1997) "Proteins from Scratch" Science, 278:80-81; Dahiyat, Sarisky and Mayo (1997) "De Novo Protein Design: Towards Fully Automated Sequence Selection" J. Mol. Biol. 273:789-796; Dahiyat and Mayo (1997) "Probing the Role of Pachng Specificity in Protein Design" Proc. Natl. Acad. Sci. USA, 94:10172-10177; Hellinga (1997) "Rational Protein Design—Combining Theory and Experiment" Proc. Natl. Acad. Sci. USA, 94: 10015-10017; Su and Mayo (1997 j "Coupling Backbone Flexibility and Amino Acid Sequence Selection in Protein Design" Prot. Sci. 6:1701-1707; Dahiyat, Gordon and Mayo (1997) "Automated Design of the Surface Positions of Protein Helices" Prot. Sci., 6:1333-1337; Dahiyat and Mayo (1996) "Protein Design Automation" Prot. Sci., 5:895-903.

In some embodiments, a library of variant of immunoregulatory peptide inhibitors of the P3028 sequence/structure containing one or more D amino acids and/or non-natural amino acids is screened for binding to the P3028 sequence/structure. In some embodiments, the library is screened for binding to P3028 (see Examples 10 and 12). In some embodiments, the library is screened for inhibiting binding of the P3028 sequence/structure to the LFA-1 receptor (see Example 15).

In some embodiments, a lead molecule is used as a template for directed drug design. A lead peptide, for example, can include, but is not limited to one or more of the exemplary immunoregulatory peptide inhibitors that bind to the P3028 sequence/structure provided herein, such as in Example 12, (e.g., any one or more of the immunoregulatory peptide inhibitors provided by SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13). The lead peptide can be synthesized to include at least one D amino acid and/or at least one non-natural amino acid. In some embodiments, the binding activity of the first generation artificial immunoregulatory peptide inhibitor is then detected, for example by evaluating the binding affinity for the P3028 sequence/structure, as described herein. Additionally, the immunostimulatory activity of the first generation artificial immunoregulatory peptide inhibitor can be detected, for example by evaluating the stimulation of an LFA-1 and/or IL-2 dependent response in a cell having a LFA-1 receptor or IL-2 receptor, which can be inhibited by the P3028 sequence/structure. Once the binding and/or immunostimulatory activity of the first generation artificial immunoregulatory peptide inhibitor is obtained, at least one additional modification is made to the lead peptide and this second generation immunoregulatory peptide inhibitor is evaluated for binding to the P3028 sequence/structure and immunostimulatory activity. The additional modification can include, but is not limited to the addition or substitution, of at least one additional D amino acid and/or a non-natural amino acid. By iteratively conducting this screening and modification procedure, more immunoregulatory peptide inhibitors can be made.

Additionally, any one or more of the immunoregulatory peptide inhibitors described herein (e.g., any one or more of the immunoregulatory peptide inhibitors provided by SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13 can comprise an N-terminal acetyl group and/or a C-terminal amide group. Furthermore, any one or more of the immunoregulatory peptide inhibitors described herein that comprise at least one D amino acid and/or at least one non-natural amino acid (e.g., any one or more of the immunoregulatory peptide inhibitors provided by SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13 can be prepared to comprise an N-terminal acetyl group and/or a C-terminal amide group).

Peptidomimetics

Some embodiments include compositions that comprise, consist of, or consist essentially of peptidomimetic-based immunoregulatory peptide inhibitors. Peptidomimetics can include, but are not limited to small-molecule compounds having at least one biochemical interaction that a peptide also has. Some peptidomimetics can include a small molecule backbone. Some peptidomimetics can include at least one R group of a naturally-occurring amino acid covalently bonded to a small molecule backbone. Some peptidomimetics are substituted into at least one position of a known peptide sequence. Accordingly, some embodiments include a composition that comprises, consists of, or consists essentially of one or more of the exemplary immunoregulatory peptide inhibitors that bind to the P3028 sequence/structure provided herein (e.g., any one or more of the immunoregulatory peptide inhibitors provided by SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13), wherein said immunoregulatory peptide inhibitor comprises at least one peptidomimetic substitution (e.g., a non-peptide bond, a small molecule backbone, or an artificial peptide linkage).

Some embodiments include a composition that comprises, consists of, or consists essentially of one or more of the exemplary isolated immunoregulatory peptide inhibitors that bind to the P3028 sequence/structure provided herein (e.g., any one or more of the immunoregulatory peptide inhibitors provided by SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13, wherein said immunoregulatory inhibitors comprise a peptidomimetic substitution, which includes two or more monomers, wherein each monomer comprises a small molecule backbone covalently bound to at least one R group. More embodiments, include a composition that comprises, consists of, or consists essentially of one or more of the exemplary immunoregulatory peptide inhibitors that bind to the P3028 sequence/structure provided herein (e.g., any one or more of the immunoregulatory peptide inhibitors provided by SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13, wherein said immunoregulatory inhibitors comprise at least one peptidomimetic small molecule backbone, wherein each backbone molecule includes one of an aryl group, for example a benzene, pyrrole, furan, thiophene, imidazole, oxazole, thiazole, triazole, pyrazole, pyridine, pyrazine, pyridazine and pyrimidine, and the like; a cycloalkane or heterocycloalkane; a cycloalkene or heterocycloalkene; or a combination of two or more of the listed molecules. Each R group can be the R group of a naturally occurring amino acid, or optionally can be a synthetic molecule. Each R group can be different, but two or more R groups can be the same. Some peptidomimetics include a first monomer that binds to a first position of P3028, for example, and a second monomer that binds to a second position of P3028, in which the first and second monomers are covalently bonded (see, for example, the approach of Chen et al., ACS Chemical Biology 2009; 4(9): 769-81, hereby expressly incorporated by reference in its entirety). The peptidomimetic backbone that is incorporated into one or more of the exemplary immunoregulatory peptide inhibitors that bind to the P3028 sequence/structure provided herein (e.g., any one or more of the immunoregulatory peptide inhibitors provided by SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13, can include a derivative of a (3-turn peptidomimetic cyclic compound of formula (W), as taught by U.S. Pat. No. 6,881,719, hereby expressly incorporated by reference in its entirety:

Formula (IV)

In some embodiments, R1 and R3 of the above Formula (IV) include R groups of natural and/or synthetic amino acids. Some embodiments include a composition that comprises, consists of, or consists essentially of one or more of the exemplary immunoregulatory peptide inhibitors that bind to the P3028 sequence/structure provided herein (e.g., any one or more of the immunoregulatory peptide inhibitors provided by SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13), wherein said immunoregulatory inhibitors comprise a peptidomimetic substitution that includes a polymer of two or more derivatives of Formula (IV). In some embodiments, individual peptidomimetic monomers or dimers derived from Formula (IV) are selected for their ability to bind the P3028 sequence/structure, and are then assembled into polymers, thus producing a peptidomimetic polymer that specifically binds the P3028 sequence/structure.

As described in U.S. Pat. No. 7,816,324, peptidomimetics of either Formula (V) or Formula (VI) can be modified to mimic alpha-helix motifs that bind to peptides.

Formula (V)

Formula (VI)

Accordingly, aspects of the invention include a composition that comprises, consists of, or consists essentially of one or more of the exemplary immunoregulatory peptide inhibitors that bind to the P3028 sequence/structure provided herein (e.g., any one or more of the immunoregulatory peptide inhibitors provided by SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13), wherein said immunoregulatory inhibitors comprise a peptidomimetic substitution that incorporates the scaffold of formula V or formula VI, which provide a rigid structure and places and orients substituents as an alpha-helix does. Substitution on the rigid tris-benzamide, for instance, can allow placement of three functional groups ($R_1$-$R_3$) corresponding to the side chains of amino acids found at the i, i+4, and i+7 positions of an ideal alpha-helix, bound by the peptide. As shown in FIG. 19, P3028 is modeled to bind to alpha helix-containing regions of the IL-2 receptor. Thus, some embodiments include a composition that comprises, consists of, or consists essentially of one or more of the exemplary immunoregulatory peptide inhibitors that bind to P3028 provided herein (e.g., any one or more of the immunoregulatory peptide inhibitors provided by SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13), wherein said immunoregulatory inhibitors comprise a peptidomimetic substitution that incorporates a peptidomimetic of formula V or formula VI, wherein $R_1$-$R_3$ are selected from positions on a known binding partner of P3028, for example the alpha subunit of the IL-2 receptor (CD25) (SEQ ID NO: 247), the LFA-1 receptor (CD 11a—SEQ ID NO: 248 and CD18—SEQ ID NO: 249), or a peptide of SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13.

Embodiments also include a library of peptidomimetics. In some embodiments, the library of peptidomimetics is selected and/or synthesized using a rational design approach. As disclosed in U.S. Pat. No. 7,816,324, hereby expressly incorporated by reference in its entirety, a peptidomimetic library can be developed based on based on a structural knowledge of the interface of protein complexes. Thus, in some embodiments, peptidomimetic compounds are based on the structure of P3028, and its interactions with known binding partners, for example the IL-2 receptor for which the crystal structure is known (see FIG. 19), the LFA-1 receptor, for which the crystal structure is known, the KKL15 peptide (see Example 11), and known inhibitors of the P3028 sequence/structure (e.g., SEQ ID NOs: 1-33, 34, 46-53, 64-66, 68, 76, 94-96, 98, or 264-393 or any one or more of the peptides provided in Table 5.1). In some embodiments, alpha.-helix mimetics may be used to modulate protein-protein or protein-peptide interaction. Thus, synthetic scaffolds that mimic key elements found in the interface between the P3028 sequence/structure and its binding partners is contemplated for the development of small molecule immunoregulatory protein inhibitors. In some embodiments, the molecules of the peptidomimetic library are attached to a support, chip, surface, or substrate, for example a microarray, as in U.S. Pat. No. 7,153,68, hereby expressly incorporated by reference in its entirety. The section below provides more details on aptamer-based immunoregulatory peptide inhibitors.

Cyclic Peptides

Some embodiments include at least one cyclic peptide immunoregulatory peptide inhibitor. Cyclic peptides, sometimes referred to as "looped peptides" are known in the art, and can be chemically synthesized (see, e.g., U.S. Pat. No. 7,589,170, hereby expressly incorporated by reference in its entirety herein), or synthesized in vivo (see, e.g., U.S. Pat. No. 7,252,952, hereby expressly incorporated by reference in its entirety herein). As taught in U.S. Pat. No. 7,589,170, cyclisation can be accomplished, for example by disulfide bond formation between two side chain functional groups, amide or ester bond formation between one side chain functional group and the backbone alpha-amino or carboxyl function, amide or ester bond formation between two side chain functional groups, amide bond formation between the backbone alpha-amino and carboxyl functions, or via a linker connecting two or more positions of the peptide.

A portion of a peptide can be cyclized, or optionally, the entire peptide can be cyclized, thereby forming a cyclic peptide. Thus, in some embodiments, the N terminus of the peptide is bonded to the C terminus of the peptide, thereby cyclizing the entire peptide. In some embodiments, the N terminus is bonded to the C terminus via an alpha-amide linkage. In some embodiments, the N terminus is bonded to the C terminus via a non-alpha-amide linkage, for example a bond between the side chain of a Ser (S) or Thr(T) and the C-terminal carboxyl group, a disulfide bond between two Cys (C) residues, or a thioether between a Trp (W) and Cys (C) residue, or a synthetic linker molecule. In some embodiments, the C terminus is bonded to an internal amino acid via a non-alpha-amide linkage, for example, a bond between the side chain of a Ser (S) or Thr(T) and the C-terminal carboxyl group, or a synthetic linker molecule. In some embodiments, the N terminus or the C terminus is bonded to an internal amino acid, or two internal amino acids are bonded to each other via a non-alpha-amide linkage, for example a disulfide bond between two Cys (C) residues, or a thioether between a Trp (W) and Cys (C) residue.

In some embodiments, a cyclic peptide immunoregulatory peptide inhibitor includes a single cyclic polypeptide structure. In some embodiments, a cyclic peptide immunoregulatory peptide inhibitor includes two or more cyclic polypeptide structures, for example 2, 3, 4, 5, 6, 7, 8, 9, 10, 11, or 12 cyclic polypeptide structures. Each cyclic polypeptide structure can include at least two amino acid residues, for example, about 2, 3, 4, 5, 6, 7, 8, 9, 10, 11, 12, 13, 14, 15, 16, 17, 18, 19, 20, 25, 26, 27, 28, 29, 30, 35, or 40 amino acid residues or a range that is defined by any two of these numbers.

In some embodiments, a library of cyclic peptides is screened for cyclic peptides that bind to albumin-derived immunoregulatory peptides, for example, the peptides of Tables 1-4 or 5.4 (SEQ ID NOs: 183-184, 188-246). Screening of cyclic peptides libraries is described in PCT Publication WO 95/09344, hereby incorporated by reference in its entirety. In some embodiments, a library of cyclic peptides is synthesized. In some embodiments, each looped peptide in the library has the same length, for example 5-meres, 6-meres, 7-meres, 8-meres, 9-meres, 10-meres, 11-meres, or 12-meres. In some embodiments, the library includes cyclic peptides of two or more lengths. As shown in Example 12, a library of 6-meres was synthesized and was screened for peptides that bind to P3038. Positional scans (i.e., single amino acid substitutions at each position) of a lead cyclic peptide (SEQ ID NO: 265) identified as exhibiting appreciable binding to P3028 were performed to identify additional cyclic 6-meres that bind to P3028. It was observed that the two 6-meres that bound to P3028 with the highest affinity (SEQ ID NOs: 266-267) had homology to linear peptides that bind to P3028 (see FIG. 32). Thus, it is contemplated herein that aspects of linear peptides that bind to albumin-derived immunoregulatory peptides can be incorporated into cyclic peptides, thus producing cyclic peptides that bind albumin-derived immunoregulatory peptides.

In some embodiments, inhibitors of albumin-derived immunoregulatory peptides or structures, or a portion thereof is cyclized. In some embodiments, a peptide of any of SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13, or a portion thereof is modified to facilitate cyclization. In some embodiments, amino residues containing side chains that can for cyclic structures, for example Cysteine, are added to the N terminus, C terminus, and/or internal positions of any of the peptide of SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13.

Aptamers

Aptamers are small molecules that specifically bind to a target molecule. Aptamers can include oligonucleotide aptamers, for example DNA, RNA, or synthetic oligonucleotides. In some embodiments, oligonucleotide aptamers include oligonucleotides with a synthetic backbone, for example morpholinos. Aptamers can also include peptide aptamers. Aspects of the invention include a composition that comprises, consists of, or consists essentially of an aptamer (e.g., nucleic acid based or peptide based), wherein said aptamer corresponds or mimics one or more of the exemplary immunoregulatory peptide inhibitors that bind to the P3028 sequence/structure provided herein (e.g., any one or more of the immunoregulatory peptide inhibitors provided by of SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13). Some embodiments of the invention include aptamers that bind specifically to the P3028 sequence/structure.

Some embodiments include a library of oligonucleotide aptamers. Oligonucleotide aptamers that bind to the P3028 sequence/structure can be readily developed given the teachings described herein. As described in U.S. Pat. No. 7,745,607, which is hereby expressly incorporated by reference in its entirety herein, an aptamer that binds specifically to a target, for example the P3028 sequence/structure can be identified by interacting an antisense oligonucleotide with a library oligonucleotide having a complementary antisense binding domain to form a double stranded duplex, said library oligonucleotide further having a random nucleotide domain; ii) immobilizing the duplex structure on a solid support; iii) incubating the duplex structure in the presence of the P3028 sequence/structure; and iv) collecting library oligonucleotides that dissociate from the duplex structure and bind to the P3028 sequence/structure. Alternatively, a library of oligonucleotides can be provided in which the library oligonucleotide is hybridized to a biotinylated antisense oligonucleotide to form a duplex molecule. The duplex molecules are immobilized on a surface, for example avidin-coated beads. A target, such as P3028 is provided and contacted with the oligonucleotides. Oligonucleotides which have bound to the target, are collected and amplified. Similar screening approaches can be used to identify peptide-based aptamers that bind to the P3028 sequence/structure. Peptide based aptamers that bind to the P3028 sequence/structure, can mimic the immunoregulatory peptide inhibitors described herein (e.g., any one or more of SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13), and variants thereof. The section below discusses many of the modifications that can be incorporated in an immunoregulatory peptide inhibitor described herein.

Modifications

Embodiments described herein also include a composition that comprises, consists of, or consists essentially of one or more of the exemplary isolated immunoregulatory peptide inhibitors that bind to the P3028 sequence/structure provided herein (e.g., any one or more of the immunoregulatory peptide inhibitors provided by (SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13), wherein said immunoregulatory inhibitors comprise at least one modification (e.g., glycosylation, nitrosylation, a cytotoxin, a detectable moiety, or a radionuclide). Glycosylation can include the addition of polyethylene glycol (PEG). The addition of PEG can increase the solubility of one or more of the immunoregulatory peptide inhibitors described herein in aqueous solution, protect the molecule from attack by a host's immune system, and/or increase the half-life of the molecule in the host.

In some embodiments, the immunoregulatory peptide inhibitors are directly bound to a cytotoxin. In some embodiments, a peptide consisting of, consisting essentially of, or comprising one of SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13 is covalently bound to a cytotoxin. In some embodiments, the immunoregulatory peptide inhibitor is attached to the toxin via a linker. In some embodiments, a peptide consisting of, consisting essentially of, or comprising one of SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13 is attached to a cytotoxin via a linker. A wide array of linker technologies can be employed. Linkers can be cleavable or non-cleavable. It is known that in many cases, the full cytotoxic potential of a drug can be observed when the cytotoxic molecules are released from a conjugates, for example an inhibitor of an immunoregulatory peptide, in unmodified form at the target site. One of the cleavable linkers that has been employed for the preparation of cytotoxin conjugates is an acid-labile linker based on cis-aconitic acid that takes advantage of the acidic environment of different intracellular compartments such as the endosomes encountered during receptor mediated endocytosis and the lysosomes. Shen and Ryser introduced this method for the preparation of conjugates of daunorubicin with macromolecular carriers (Biochem. Biophys. Res. Commun. 102:1048-1054 (1981)). Yang and Reisfeld used the same technique to conjugate daunorubicin to an anti-melanoma antibody (J. Natl. Canc. Inst. 80:1154-

1159 (1988)). Recently, Dillman et al. also used an acid-labile linker in a similar fashion to prepare conjugates of daunorubicin with an anti-T cell antibody (Cancer Res. 48:6097-6102 (1988)). An alternative approach, explored by Trouet et al. involved linking daunorubicin to a targeting molecule via a peptide spacer arm (Proc. Natl. Acad. Sci. 79:626-629 (1982)). This was done under the premise that free drug could be released from such a conjugate by the action of lysosomal peptidases. One skilled in the art will appreciate that cleavable linker approaches employed for conjugating cytotoxins to antibodies can also be employed to conjugate a peptide, for example one of SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13 to a cytotoxin.

Exemplary cytotoxins that can be incorporated into one or more of the exemplary immunoregulatory peptide inhibitors that bind to the P3028 sequence/structure provided herein (e.g., any one or more of the immunoregulatory peptide inhibitors provided by SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13) include: radiotoxins, monomethylauristatin-E, monomethylauristatin-F, aplidin, azaribine, anastrozole, azacytidine, bleomycin, bortezomib, bryostatin-1, busulfan, calicheamycin, camptothecin, 10-hydroxycamptothecin, carmustine, celebrex, chlorambucil, cisplatin, irinotecan (CPT-11), SN-38, carboplatin, cladribine, cyclophosphamide, cytarabine, dacarbazine, docetaxel, dactinomycin, daunomycin glucuronide, daunorubicin, dexamethasone, diethylstilbestrol, doxorubicin, doxorubicin glucuronide, epirubicin glucuronide, ethinyl estradiol, estramustine, etoposide, etoposide glucuronide, etoposide phosphate, floxuridine (FUdR), 3',5'-O-dioleoyl-FudR (FUdR-dO), fludarabine, flutamide, fluorouracil, fluoxymesterone, gemcitabine, hydroxyprogesterone caproate, hydroxyurea, idarubicin, ifosfamide, L-asparaginase, leucovorin, lomustine, mechlorethamine, medroprogesterone acetate, megestrol acetate, melphalan, mercaptopurine, 6-mercaptopurine, methotrexate, mitoxantrone, mithramycin, mitomycin, mitotane, phenyl butyrate, prednisone, procarbazine, paclitaxel, pentostatin, PSI-341, saporin, semustine streptozocin, tamoxifen, taxanes, testosterone propionate, thalidomide, thioguanine, thiotepa, teniposide, topotecan, uracil mustard, velcade, vinblastine, vinorelbine, vincristine, ricin, for example ricin A chain, abrin, ribonuclease, onconase, rapLR1, DNase I, Staphylococcal enterotoxin-A, pokeweed antiviral protein, gelonin, diphtheria toxin, Pseudomonas exotoxin, and Pseudomonas endotoxin. Optionally, the cytotoxin is conjugated to the immunoregulatory peptide inhibitor via a linker (e.g. a cleavable or non-cleavable linker) or non-covalent immobilization as described herein. Optionally, a composition comprising the immunoregulatory peptide inhibitor immobilized on a nanoparticle is provided as described herein, and the cytotoxin is immobilized on the nanoparticle (e.g. each of the immunoregulatory peptide inhibitor immobilized and cytotoxin can be immobilized on the nanoparticle, but not necessarily connected to each other). Optionally, the immunoregulatory peptide inhibitor immobilized on the nanoparticle by a first linker, and the cytotoxin is immobilized on the nanoparticle via a second linker that can be the same as or different from the first linker.

Exemplary detectable moieties (which may also be referred to herein as "detectable labels" that can be incorporated into one or more of the exemplary immunoregulatory peptide inhibitors that bind to the P3028 sequence/structure provided herein (e.g., any one or more of the immunoregulatory peptide inhibitors provided by SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13) or to an antibody that binds specifically to P3028 include: a radiolabel, a fluorophore, biotin, a fluorescent protein, colloidal gold, and/or a coenzyme. Radiolabels can include $^3$H and $^4$C. Fluorophores can include Alexa-Fluor dyes, Pacific Blue, Pacific Orange, Cascade Blue, Cascade Yellow and R-phycoerythrin, fluorescein (FITC), rhodamine, Texas red, BODIPY family dyes, Cy2, Cy3, C5, and Cy7. Fluorescent proteins can include Blue, Cyan, Green, Yellow, and Red fluorescent proteins. In some embodiments, fluorescent labels include a FRET pair. For example, a single peptide can be attached to a FRET donor and FRET acceptor, which are configured so that the FRET acceptor is substantially within a FRET radius of the FRET donor when the peptide is in a first configuration (for example, bound to target), but not when the peptide is in a second configuration (for example, unbound to target). For example, a first peptide can be attached to a FRET acceptor, and a second peptide can be attached to a FRET donor, so that the FRET acceptor is substantially within a FRET radius of the FRET donor when the first peptide and second peptide are each bound to a target, for example a target cell, but not when at least one peptide is unbound to the target. In some embodiments, fluorescent label includes a fluorophore and a quencher. The fluorophore and quencher can each be attached to the peptide so that the quench absorbs electromagnetic radiation emitted by the fluorophore when the peptide is in a first configuration (for example, bound to target), but not when the peptide is in a second configuration (for example, unbound to target). Coenzymes can include vitamins such as biotin.

Exemplary radionuclides that can be incorporated into one or more of the exemplary immunoregulatory peptide inhibitors that bind to the P3028 sequence/structure provided herein (e.g., any one or more of the immunoregulatory peptide inhibitors provided by SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13) or an antibody that binds specifically to P3028 include: $^{111}$I, $^{131}$I, $^{90}$Y, $^{67}$Cu, $^{186}$Re, $^{188}$Re, $^{212}$Bi or $^{211}$At. Preferable radiolabeled immunoregulatory peptide inhibitors are able to deliver more than 6000 rads to a tumor, for example, and have sufficient affinity so that the patient's bone marrow is not exposed to more than 300 rads. The section that follows describes in greater detail some of the embodiments, which encompass protein complexes comprising an immunoregulatory peptide inhibitor described herein.

In some embodiments, a diagnostic kit is provided. The kit can include any one or more of the immunoregulatory peptide inhibitors provided by SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13 or an antibody that binds specifically to any of the peptides of SEQ ID NOs: 183-185 or 188-246, for example P3028 (SEQ ID NO: 185). The kit can also include a detectable moiety as described herein. In some embodiments, the peptide inhibitor or antibody of the kit is biotinylated.

Carrier Molecules

Some embodiments include a carrier molecule. Carrier molecules, can for example, increase the stability or half-life, increase the solubility, increase the absorption, target the peptide to an appropriate cell, organ or tissue, and/or minimize an immune response against a therapeutic molecule.

Exemplary carrier molecules include human serum albumin; a polymer having a plurality of acid moieties (see PCT Pub. No. WO 01/93911); anionic group-containing amphiphilic block copolymers that, when used as a drug carrier for a cationic therapeutic molecule can improve stability of that molecule (see PCT Pub. No. WO 03/00778); cyclodextrin and acids for improving the properties of basic therapeutic molecules (European Pat. No. 0 681 481); lipids as carriers for hydrophobic therapeutic molecules (see PCT Pub. No. WO 04/064731); immunoglobulins; and Fc fragments as carriers for improving half-life and minimizing immune response (see U.S. Pat. No. 7,736,653). In some embodiments, an immunoregulatory peptide inhibitor (e.g., a peptide comprising, consisting of, or consisting essentially of SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13) includes or is joined to a carrier. In some embodiments, an immunoregulatory peptide inhibitor (e.g. a peptide comprising, consisting of, or consisting essentially of SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13) includes two or more carriers.

In some embodiments, an immunoregulatory peptide inhibitor is provided with a degradable particle. Without being limited by any theory, it is contemplated that a degradable particle can permit an immunoregulatory particle to be soluble and exert its activity for a controlled period of time in the systemic circulation. Accordingly, in some embodiments, a degradable particle comprising an immunoregulatory peptide inhibitor (for example, a peptide comprising, consisting of, or consisting essentially of SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13) is provided. In some embodiments the degradable particle comprising the immunoregulatory peptide inhibitor is administered to a subject in need. Optionally, the degradable particle can be administered systemically. Optionally, the degradable particle can be administered locally, for example at or near a site of immunosuppression (e.g. within 10 cm, 9 cm, 8 cm 7 cm, 6c, 5 cm, 4 cm, 3 cm, 2 cm, 1 cm, or 0.5 cm of the site of immunosuppression or a range defined by any two of these numbers). In some embodiments, the subject suffers from LFA-1 receptor blockage by an immunoregulatory peptide sequence of any of Tables 1-4. Optionally, the degradable particle can be coadministered with one or more additional therapeutic agents. For example, if a the immunoregulatory peptide inhibitor is useful for de-blocking an LFA-1 receptor (e.g. displaces bound immunoregulatory peptides or P3028 structures from the LFA-1 receptor), a therapeutic agent that stimulates an immune response, for example via an LFA-1 receptor can be useful for co-administering with the immunoregulatory peptide inhibitor and degradable particle. In some embodiments, the additional therapeutic agent is administered at the same time as the immunoregulatory peptide inhibitor, for example as part of the degradable particle. In some embodiments, the additional therapeutic agent is administered after the immunoregulatory peptide inhibitor, for example at least about 1, 2, 3, 4, 5, 6, 7, 8, 9, 10, 11, 12, 13, 14, 15, 16, 17, 18, 19, 20, 21, 22, 23, 24 hours afterwards, or about 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days afterwards or a range defined by any two of aforementioned times. A variety of suitable degradable particles can be used in accordance with embodiments herein. In some embodiments, the degradable particle comprises a sphere, for example a microsphere. In some embodiments, the degradable particle comprises a nanoparticle. In some embodiments, the degradable particle comprises a starch or sugar. In some embodiments, the degradable particle comprises an organic polymer or a combination of organic polymers, for example, polyesters, polyphosphate esters, polyphosphazenes, polyorthoesters, polyanhydrides, polycarbonates, polyamides, poly-lactic acid, a poly-glycoloyic acid, or a combination of two or more polymers, for example two or more of the listed polymers.

Protein Complexes

Some embodiments include a composition comprising an isolated protein complex that comprises an immunoregulatory peptide inhibitor. The isolated protein complex can include an immunoregulatory peptide, for example P3028 (SEQ ID NO: 185) or any one or more of the immunoregulatory peptides described in Tables 1-4 (SEQ ID NOs: 183-184 and 188-246) and at least one immunoregulatory peptide inhibitor (e.g., any one or more of the peptides provided in Table 5.1). In some embodiments, the isolated protein complex includes peptide 3028 (SEQ ID NO: 185) and an inhibitor peptide that includes the sequence of SEQ ID NOs: 1-33, 34, 46-53, 64-66, 68, 76, 94-96 or 98 or any one or more of the peptides provided in Table 5.1. Exemplary protein complexes that include each of the peptides SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13 bound to the P3028 sequence/structure are provided in Examples 10, 11 and 12 and Table 5.1. The protein complex can include at least one favorable electrostatic interaction between an amino acid residue of P3028 or a variant thereof, and an amino acid of an inhibitor peptide or peptide mimetic. The protein complex can include at least one favorable hydrophobic interaction between an amino acid residue of P3028 or a variant thereof, and an amino acid of an inhibitor peptide or peptide mimetic (see Example 11). In some embodiments, the protein complex includes a variant of P3028 having at least about 80% identity to P3028, for example greater than or equal to about 80%, 81%, 82%, 83%, 84%, 85%, 86%, 87%, 88%, 89%, 90%, 91%, 92%, 93%, 94%, 95%, 96%, 97%, 98%, or 99% identity to P3028. The protein complex can further include at least one protein bound to a cancer cell, for example a surface protein. Thus, in some embodiments, the isolated protein complex can localize to the surface of a cancer cell.

Accordingly, some embodiments include a method of making a protein complex that comprises one or more of the immunoregulatory peptide inhibitors described herein. The methods can be practiced, for example, by binding an immunoregulatory peptide inhibitor, as described herein to P3028, or a variant or fragment thereof. The method can optionally include detecting the presence of the complex, which can be accomplished by rampo studies, as described herein.

Some embodiments include methods of binding a peptide comprising, consisting or, or consisting essentially of SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13 to a molecule that comprises the P3028 sequence/structure (SEQ ID NO: 185). Some embodiments include methods of binding a peptide comprising, consisting of, or consisting essentially of at least one of SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13 to a molecule comprising a variant of the P3028 sequence/structure (SEQ ID NO: 185). Some embodiments include methods of binding a peptide including at least one of SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13 to a protein that comprises the P3028 sequence/structure or a fragment of P3028 (SEQ ID NO: 185), wherein the fragment of P3028 has a length of at least about 10 amino acids, more preferably 11 amino acids, more preferable 12 amino acids, more preferably 13 amino acids, more preferably 14 amino acids, more preferably 15 amino acids, more preferably 16 amino acids, or more preferably 17 amino acids. In some embodiments, the binding includes favorable hydrophilic and/or electrostatic interactions between members of the protein complex. In some embodiments, the binding includes covalent bonds between members of the protein complex, for example through crosslinking. Crosslinking can be induced chemically, and/or via electromagnetic radiation, for example electromagnetic radiation in the ultraviolet spectrum.

In some embodiments, the peptide comprises at least one of SEQ ID NOs: 1-33, 34, 46-53, 64-66, 68, 76, 94-96, 98, 583-586, or 589 or any one or more of the peptides provided in Table 5.1, 5.4, 5.5, 5.6, or any variation or combination of variations of P28R or P28 core as provided in Tables 5.3 and 13. Exemplary supports include a pin, bead, surface, matrix, artificial cell surface, or cell surface. For example, the peptide can be affixed via an affinity tag to a support. In some embodiments, P3028, or a variant or fragment thereof is affixed to a support. In some embodiments, the peptide including at least one of SEQ ID NOs: 1-33, 34, 46-53, 64-66, 68, 76, 94-96, 98, 583-586, or 589 or any one or more of the peptides provided in Table 5.1, 5.4, 5.5, 5.6, or any variation or combination of variations of P28R or P28 core as provided in Tables 5.3 and 13 is affixed to a support, and P3028 or a variant or fragment thereof is dissolved in a solvent. In some embodiments, the peptide including at least one of SEQ ID NOs: 1-33, 34, 46-53, 64-66, 68, 76, 94-96, 98, 583-586, or 589 or any one or more of the peptides provided in Table 5.1, 5.4, 5.5, 5.6, or any variation or combination of variations of P28R or P28 core as provided in Tables 5.3 and 13 is dissolved in a solvent, and P3028, or a variant or fragment thereof is affixed to a support. In some embodiments, the peptide including at least one of SEQ ID NOs: 1-33, 34, 46-53, 64-66, 68, 76, 94-96, 98, 583-586, or 589 or any one or more of the peptides provided in Table 5.1, 5.4, 5.5, 5.6, or any variation or combination of variations of P28R or P28 core as provided in Tables 5.3 and 13 and P3028 are each dissolved in a solvent, for example serum.

In some embodiments, the binding occurs in an organism, for example in extracellular matrix, and/or serum or in a biological sample obtained from an organism, such as a human or a non-human mammal. Biological samples can include at least one cell, tissue, or extracellular composition of an organism, include extracts, purified extracts, and/or fractions thereof. Exemplary biological samples include whole blood, serum, bone marrow, isolated immune cells, and tumor biopsies. Isolated immune cells can include leukocytes, and peripheral blood mononuclear cells (PBMCs), for example lymphocytes, monocytes, or macrophages. The method can include delivering at least one member of the complex, for example a peptide including at least one of SEQ ID NOs: 1-33, 34, 46-53, 64-66, 68, 76, 94-96, 98, 583-586, or 589 or any one or more of the peptides provided in Table 5.1, 5.4, 5.5, 5.6, or any variation or combination of variations of P28R or P28 core as provided in Tables 5.3 and 13, to the organism. In some embodiments, the binding occurs in vitro, for example in a buffer solution or in a biological sample. The method can include adding at least one member of the complex, for example a peptide including at least one of SEQ ID NOs: 1-33, 34, 46-53, 64-66, 68, 76, 94-96, 98, 583-586, or 589 or any one or more of the peptides provided in Table 5.1, 5.4, 5.5, 5.6, or any variation or combination of variations of P28R or P28 core as provided in Tables 5.3 and 13, to a solution that contains the remaining members of the complex. Alternatively, the method can include adding two or more members of the complex to a solution for example a peptide including at least one of SEQ ID NOs: 1-33, 34, 46-53, 64-66, 68, 76, 94-96, 98, 583-586, or 589 or any one or more of the peptides provided in Table 5.1, 5.4, 5.5, 5.6, or any variation or combination of variations of P28R or P28 core as provided in Tables 5.3 and 13 and P3028 or a fragment or variant thereof. In some embodiments, a peptide including at least one of SEQ ID NOs: 1-33, 34, 46-53, 64-66, 68, 76, 94-96, 98, 583-586, or 589 or any one or more of the peptides provided in Table 5.1, 5.4, 5.5, 5.6, or any variation or combination of variations of P28R or P28 core as provided in Tables 5.3 and 13 is added to a biological sample.

Some embodiments include detecting the presence of the complex. Some embodiments include detecting the presence of the P3028 sequence/structure bound to a peptide that is affixed to a support (see Example 12), for example by ELISA. Some embodiments include detecting the presence of a complex by FRET. For example a FRET donor fluorophore can be attached to a first member of the complex, and a FRET acceptor fluorophore can be attached to a second member of the complex, so that FRET transfer occurs only when the complex is formed. Some embodiments include detecting the presence of a complex by cessation of quenching. For example a member of the complex can be attached to a fluorophore and a quencher for electromagnetic radiation emitted by the fluorophore, so that when the complex member is unbound, the fluorophore is substantially within the quencher radius, and the quencher absorbs electromagnetic radiation emitted by the fluorophore (e.g., a quencher can be attached to the N terminal and a fluorophore attached to the C terminal, or a quencher can be attached to the C terminal, and a fluorophore attached to the N terminal). Upon complex formation, the fluorophore can be outside of the quencher radius, thus permitting detection of electromagnetic radiation emitted by the fluorophore.

Some embodiments include detecting the presence of the complex by detecting of complex function. For example, an immune cell in which peptide 3028 is bound to the LFA-1 and/or IL-2 receptor can exhibit reduced IL-2-induced proliferation, T cell receptor stimulation, leukocyte spreading, immune cell migration, and/or NK cell cytotoxicity (see Examples 2-6). Direct or indirect detection of increased IL-2-induced proliferation, T cell receptor stimulation, leukocyte spreading, immune cell migration, and/or NK cell cytotoxicity, for example increase in comparison to an untreated control sample in which at least one member of the complex was not added, can detect complex formation. For example, as shown in Example 13, the formation of a complex between the P3028 sequence/structure and an immunoregulatory peptide inhibitor can increase lymphocyte stimulation. For example, as shown in Example 1, the formation of a complex can unblock the LFA-1 receptor. Thus, some embodiments include detecting complex formation indirectly by, for example, detecting increased lymphocyte stimulation, detecting unblocked LFA-1 receptor, and/or detecting immune cell stimulation via an unblock LFA-1 receptor, as compared to a control sample that is known to lack complex formation.

Some embodiments include detecting the presence of the complex by detecting localization of complex members. In some embodiments, detecting the presence of the complex includes detecting the presence of an immunoregulatory peptide inhibitor including at least one of SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13, or a peptidomimetic that binds specifically to the P3028 sequence/structure on tumor cells. As shown in Example 1, the P3028 sequence/structure can bind to tumor cells. As shown in Example 14, an inhibitor of the P3028 sequence/structure can bind to tumor cells, for example by binding to the P3028 sequence/structure. Thus, in some embodiments, the presence of an inhibitor of the P3028 sequence/structure, for example, at least one of SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13 on a tumor cell can indicate complex formation. Thus, complex formation can be detected by colocalization of an inhibitor with at least one marker of a tumor cell. Colocalization can be detected, for example by immunohistochemistry or flow cytometry. In some embodiments, the inhibitor is labeled, for example with a fluorophore or radiolabel. In some embodiments, the inhibitor is detected, for example with a primary antibody that specifically binds to the inhibitor. The section that follows describes in greater detail some of the nucleic acid embodiments, which encode an immunoregulatory peptide inhibitor.

Nucleic Acids Encoding Inhibitor Peptides

Some embodiments include isolated nucleic acids encoding an immunoregulatory peptide inhibitor. One skilled in the art will appreciate that for a given peptide sequence, a nucleic acid sequence encoding that peptide sequence can readily be determined, and due to the degeneracy of the genetic code, more than one nucleic acid sequence can encode any one peptide. A nucleic acid sequence encoding a peptide can be incorporated into an expression vector using known techniques, as well. Expression vectors can be used to produce the peptide in an expression system, for example a host cell, a host organism, a cell-free expression system, and the like. Expression vectors can also be used to produce a peptide in an organism, for example a patient in need of blocking of immunosuppression, as described herein. Exemplary expression vectors include plasmid DNA, such as a pVAX construct, bacteriophage DNA, cosmid DNA, artificial chromosomes such as BACs and YACs, retrovirus systems, for example lentivirus, DNA virus systems, for example adenovirus or vaccinia virus (e.g., MVA). For peptides that do not have an N-terminal amino acid that corresponds to a translation start codon (typically Met corresponding to ATG), expression vectors can include an in-frame translation start codon. Such an amino acid can be separated from the N-terminal of the peptide by a cleavable linker, for example a peptide sequence that is cleaved by a protease. Expression vectors can include transcriptional regulatory sequences, for example core promoters, transcriptional enhancers, and/or insulator sequences. Such sequences can facilitate the assembly of transcriptional machinery (for example RNA Polymerase III), and the subsequent production of a transcript encoding the peptide (for example, by facilitating a heterochromatic environment that is favorable to transcription).

In some embodiments, an expression vector encodes two or more copies of a peptide, and/or two or more unique peptides. In some embodiments, an expression vector encodes two or more peptides, and each peptide is under the control of a unique transcription unit (e.g., promoter, transcriptional enhancers, and/or transcription terminator). In some embodiments, a nucleic acid encoding two or more peptides is under the control of a single transcription unit. In such embodiments, a sequence encoding an individual peptide can be under the control of an individual translation start site, for example an Internal Ribosome Entry Site (IRES). In such embodiments, a single nucleic acid can encode a protein or polypeptide encoding two or more peptides, which are separated by at least one protease target site.

One skilled in the art will appreciate that polynucleotides encoding peptides, such as peptide inhibitors, can be readily constructed based upon the sequence of the peptide. Exemplary polynucleotides encoding the sequences of immunoregulatory peptide inhibitor peptides of (SEQ ID NOs: 2-33) are provided in Table 5.2. One skilled in the art will appreciate that due to the degeneracy of the genetic code, a given polypeptide can be encoded by more than one polynucleotide may encode. Thus, provided herein, for example in Table 5.2, are consensus polynucleotides that account for typical degeneracy of the genetic code, as well as exemplary polynucleotides. The polynucleotides of Table 5.2 are provided by way of example, and include SEQ ID NOs: 102-165. On skilled in the art will further appreciate that additional polynucleotides can encode peptide inhibitors such as the peptide inhibitors disclosed herein (e.g., polynucleotides encoding any one or more of the peptides provided in Table 5.1 are embodiments). For example, polynucleotides can be modified post-transcriptionally, for example by alternative splicing, and/or by enzymes such as RNA-specific adenosine deaminase (ADAR) that can modify the bases of polynucleotides.

TABLE 5.2

Polynucleotides encoding peptide inhibitors of the P3028 sequence/structure

| Seq ID NO | Description |
|---|---|
| 102 | Consensus polynucleotide encoding P28R (SEQ ID NO: 2) |
| 103 | Exemplary NT encoding P28R (SEQ ID NO: 2) |
| 104 | Consensus polynucleotide encoding SEQ ID NO: 3 |
| 105 | Exemplary NT encoding SEQ ID NO: 3 |
| 106 | Consensus polynucleotide encoding SEQ ID NO: 4 |
| 107 | Exemplary NT encoding SEQ ID NO: 4 |
| 108 | Consensus polynucleotide encoding SEQ ID NO: 5 |
| 109 | Exemplary NT encoding SEQ ID NO: 5 |
| 110 | Consensus polynucleotide encoding SEQ ID NO: 6 |
| 111 | Exemplary NT encoding SEQ ID NO: 6 |
| 112 | Consensus polynucleotide encoding SEQ ID NO: 7 |
| 113 | Exemplary NT encoding SEQ ID NO: 7 |
| 114 | Consensus polynucleotide encoding SEQ ID NO: 8 |
| 115 | Exemplary NT encoding SEQ ID NO: 8 |
| 116 | Consensus polynucleotide encoding SEQ ID NO: 9 |
| 117 | Exemplary NT encoding SEQ ID NO: 9 |
| 118 | Consensus polynucleotide encoding SEQ ID NO: 10 |
| 119 | Exemplary NT encoding SEQ ID NO: 10 |
| 120 | Consensus polynucleotide encoding SEQ ID NO: 11 |
| 121 | Exemplary NT encoding SEQ ID NO: 11 |
| 122 | Consensus polynucleotide encoding SEQ ID NO: 12 |
| 123 | Exemplary NT encoding SEQ ID NO: 12 |
| 124 | Consensus polynucleotide encoding SEQ ID NO: 13 |
| 125 | Exemplary NT encoding SEQ ID NO: 13 |
| 126 | Consensus polynucleotide encoding SEQ ID NO: 14 |
| 127 | Exemplary NT encoding SEQ ID NO: 14 |
| 128 | Consensus polynucleotide encoding SEQ ID NO: 15 |
| 129 | Exemplary NT encoding SEQ ID NO: 15 |
| 130 | Consensus polynucleotide encoding SEQ ID NO: 16 |
| 131 | Exemplary NT encoding SEQ ID NO: 16 |
| 132 | Consensus polynucleotide encoding SEQ ID NO: 17 |
| 133 | Exemplary NT encoding SEQ ID NO: 17 |
| 134 | Consensus polynucleotide encoding SEQ ID NO: 18 |
| 135 | Exemplary NT encoding SEQ ID NO: 18 |
| 136 | Consensus polynucleotide encoding SEQ ID NO: 19 |
| 137 | Exemplary NT encoding SEQ ID NO: 19 |
| 138 | Consensus polynucleotide encoding SEQ ID NO: 20 |
| 139 | Exemplary NT encoding SEQ ID NO: 20 |
| 140 | Consensus polynucleotide encoding SEQ ID NO: 21 |
| 141 | Exemplary NT encoding SEQ ID NO: 21 |
| 142 | Consensus polynucleotide encoding SEQ ID NO: 22 |
| 143 | Exemplary NT encoding SEQ ID NO: 22 |
| 144 | Consensus polynucleotide encoding SEQ ID NO: 23 |
| 145 | Exemplary NT encoding SEQ ID NO: 23 |
| 146 | Consensus polynucleotide encoding SEQ ID NO: 24 |
| 147 | Exemplary NT encoding SEQ ID NO: 24 |
| 148 | Consensus polynucleotide encoding SEQ ID NO: 25 |
| 149 | Exemplary NT encoding SEQ ID NO: 25 |
| 150 | Consensus polynucleotide encoding SEQ ID NO: 26 |
| 151 | Exemplary NT encoding SEQ ID NO: 26 |
| 152 | Consensus polynucleotide encoding SEQ ID NO: 27 |
| 153 | Exemplary NT encoding SEQ ID NO: 27 |
| 154 | Consensus polynucleotide encoding SEQ ID NO: 28 |
| 155 | Exemplary NT encoding SEQ ID NO: 28 |
| 156 | Consensus polynucleotide encoding SEQ ID NO: 29 |
| 157 | Exemplary NT encoding SEQ ID NO: 29 |
| 158 | Consensus polynucleotide encoding SEQ ID NO: 30 |
| 159 | Exemplary NT encoding SEQ ID NO: 30 |
| 160 | Consensus polynucleotide encoding SEQ ID NO: 31 |
| 161 | Exemplary NT encoding SEQ ID NO: 31 |
| 162 | Consensus polynucleotide encoding SEQ ID NO: 32 |
| 163 | Exemplary NT encoding SEQ ID NO: 32 |
| 164 | Consensus polynucleotide encoding SEQ ID NO: 33 |
| 165 | Exemplary NT encoding SEQ ID NO: 33 |

Accordingly, embodiments described herein also include a composition that comprises, consists of, or consists essentially of an isolated nucleic acid or polynucleotide that encodes one or more of the exemplary immunoregulatory peptide inhibitors that bind to the P3028 sequence/structure provided herein (e.g., any one or more of the immunoregulatory peptide inhibitors provided by SEQ ID NOs: 1-33, 34, 46-53, 64-66, 68, 76, 94-96 or 98 or any one or more of the peptides provided in Table 5.1). Vectors, constructs, and plasmids comprising the aforementioned nucleic acids or polynucleotides are also embodiments. The following section discusses additional components that may be included in one or more of the compositions described herein.

Pharmaceutical Compositions

In some embodiments, a pharmaceutical composition comprising, consisting essentially of or consisting of a peptide inhibitor (e.g., any one or more of the peptides provided in Table 5.1) is provided. The pharmaceutical composition can include a peptide inhibitor as described herein and a pharmaceutically acceptable ingredient as described herein. Exemplary pharmaceutically acceptable ingredients include diluents, carriers, excipients and/or buffers. In some embodiments, the peptide inhibitor comprises, consists of, or consists essentially of a peptide inhibitor as described herein. For example, a composition can comprise, consist of, or consist essentially of a peptide inhibitor that comprises, consists of, or consists essentially of the peptide of Formula (I), $XX_1VKX_2X_3X_4$ (SEQ ID NO: 166). In some embodiments, X is an optional sequence, and can be KKLDT (SEQ ID NO: 167), RKLDT (SEQ ID NO: 168), KKGDT (SEQ ID NO: 169), KKEDT (SEQ ID NO: 170), KKLDQ (SEQ ID NO: 171), KKGDQ (SEQ ID NO: 252), KKEDQ (SEQ ID NO: 253), RKLDQ (SEQ ID NO: 254), RKGDQ (SEQ ID NO: 255), RKEDQ (SEQ ID NO: 256), RKGTD (SEQ ID NO: 257), RKEDT (SEQ ID NO: 258), KLDT (SEQ ID NO: 172), KGDT (SEQ ID NO: 259), KEDT (SEQ ID NO: 260), KLDQ (SEQ ID NO: 261), KGDQ (SEQ ID NO: 262), KEDQ (SEQ ID NO: 263), LDT, LDQ, GDT, GDQ, EDT, EDQ, DT, DQ, T, or Q, or absent. In some embodiments, $X_1$ is one of FF, FM, FS, FV, FT, FL, AF, AM, AS, AV, AT, AL, VF, VM, VS, VV, VT, or VL. In some embodiments, $X_2$ is one of LS, LQ, LM, LT, LH, VS, VQ, VM, VT, or VH. In some embodiments, $X_3$ is one of LFT, LMT, LQT, LHT, LNT, LPT, LST, LGT, LAT, LRT, QFT, QMT, QQT, QHT, QNT, QPT, QST, QGT, QAT, QRT, VFT, VMT, VQT, VHT, VNT, VPT, VST, VGT, VAT, VRT, MFT, MMT, MQT, MHT, MNT, MPT, MST, MGT, MAT, MRT, LFN, LMN, LQN, LHN, LNN, LPN, LSN, LGN, LAN, LRN, QFN, QMN, QQN, QHN, QNN, QPN, QSN, QGN, QAN, QRN, VFN, VMN, VQN, VHN, VNN, VPN, VSN, VGN, VAN, VRN, MFN, MMN, MQN, MHN, MNN, MPN, MSN, MGN, MAN, MRN, LFP, LMP, LQP, LHP, LNP, LPP, LSP, LGP, LAP, LRP, QFP, QMP, QQP, QHP, QNP, QPP, QSP, QGP, QAP, QRP, VFP, VMP, VQP, VHP, VNP, VPP, VSP, VGP, VAP, VRP, MFP, MMP, MQP, MHP, MNP, MPP, MSP, MGP, MAP, MRPR, LFR, LMR, LQR, LHR, LNR, LPR, LSR, LGR, LAR, LRR, QFR, QMR, QQR, QHR, QNR, QPR, QSR, QGR, QAR, QRR, VFR, VMR, VQR, VHR, VNR, VPR, VSR, VGR, VAR, VRR, MFR, MMR, MQR, MHR, MNR, MPR, MSR, MGR, MAR, or MRR. In some embodiments, $X_4$ is an optional sequence, and can be ER, or E, or absent. In some embodiments, if X is absent, $X_1$ is FF, and $X_2$ is LS. In some embodiments, the isolated peptides comprising Formula (I). have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, a composition can comprise, consist of, or consist essentially of a peptide inhibitor that comprises, consists of, or consists essentially of a peptide of Formula (II) $X_{20}TFFVKLSX_{21}X_{22}$, (SEQ ID NO: 173). In some embodiments, $X_{20}$ is an optional sequence, and can be KKLD (SEQ ID NO: 174), RKLD (SEQ ID NO: 175), KKGD (SEQ ID NO: 176), KKED (SEQ ID NO: 177), KLD, LD, or D, or absent. $X_{21}$ is an optional sequence, and can be LFT, LMT, LQT, LHT, LNT, LPT, LST, LGT, LAT, LRT, QFT, QMT, QQT, QHT, QNT, QPT, QST, QGT, QAT, QRT, VFT, VMT, VQT, VHT, VNT, VPT, VST, VGT, VAT, VRT, MFT, MMT, MQT, MHT, MNT, MPT, MST, MGT, MAT, MRT, LFN, LMN, LQN, LHN, LNN, LPN, LSN, LGN, LAN, LRN, QFN, QMN, QQN, QHN, QNN, QPN, QSN, QGN, QAN, QRN, VFN, VMN, VQN, VHN, VNN, VPN, VSN, VGN, VAN, VRN, MFN, MMN, MQN, MHN, MNN, MPN, MSN, MGN, MAN, MRN, LFP, LMP, LQP, LHP, LNP, LPP, LSP, LGP, LAP, LRP, QFP, QMP, QQP, QHP, QNP, QPP, QSP, QGP, QAP, QRP, VFP, VMP, VQP, VHP, VNP, VPP, VSP, VGP, VAP, VRP, MFP, MMP, MQP, MHP, MNP, MPP, MSP, MGP, MAP, MRPR, LFR, LMR, LQR, LHR, LNR, LPR, LSR, LGR, LAR, LRR, QFR, QMR, QQR, QHR, QNR, QPR, QSR, QGR, QAR, QRR, VFR, VMR, VQR, VHR, VNR, VPR, VSR, VGR, VAR, VRR, MFR, MMR, MQR, MHR, MNR, MPR, MSR, MGR, MAR, or MRR, or absent. In some embodiments, $X_{22}$ is an optional sequence, and can be ER, or E, or absent. In some embodiments, the isolated peptides comprising Formula (II) have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, a composition can comprise, consist of, or consist essentially of a peptide inhibitor that comprises, consists of, or consists essentially of a peptide of Formula (III) $X_{30}X_{31}VKLX_{32}LX_{33}TEX_{34}$ (SEQ ID NO: 178), or of SEQ ID NOs: 1-33, 34, 46-53, 64-66, 68, 76, 94-96 or 98. In some embodiments, $X_{31}$ is an optional sequence, and can be F, S, M, V, T, or L, or absent. In some embodiments, $X_{31}$ is F. In some embodiments, $X_{32}$ can be S, Q, M, T, or H. In some embodiments, $X_{32}$ is S. $X_{33}$ can be F, M, Q, H, N, P, S, G, A, or R. In some embodiments, $X_{34}$ is F. $X_{34}$ is an optional sequence, and can be R, or absent. In some embodiments, $X_{30}$ is an optional sequence, and can be KKLDTF (SEQ ID NO: 179), KLDTF (SEQ ID NO: 180), LDTF (SEQ ID NO: 181), DTF, TF, or F, or absent. In some embodiments, the isolated peptides comprising Formula (III) have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, a composition can comprise, consist of, or consist essentially of a peptide inhibitor that comprises, consists of, or consists essentially of a peptide of Formula (VII), $X_{700}K\ X_{701}X_{702}X_{703}\ X_{704}X_{705}X_{706}K\ X_{707}\ X_{708}\ X_{709}\ X_{710}\ X_{711}E\ X_{712}$ (SEQ ID NO: 394), as described herein. In some embodiments, $X_{700}$ is an optional sequence, and can be K,A,D,E,G,H,I,L,M,N,P,Q,R,T, or V, or absent. In some embodiments, $X_{701}$ is an optional sequence, and can be L,A,C,D,E,F,G,H,I,K,M,N,Q,R,S,T, or V, or absent. In some embodiments, $X_{702}$ is an optional sequence, and can be D,A,E,I,V,W, or Y, or absent. In some embodiments, $X_{703}$ is an optional sequence, and can be T,C,M,N,P,Q,R,S,W, or Y, or absent. In some embodiments, $X_{704}$ is an optional sequence, and can be F,A,I,M,N,P,T, or V, or absent. In some embodiments, $X_{705}$ is an optional sequence, and can be F,L,M,Q,S,T or V, or absent. In some embodiments, $X_{706}$ is an optional sequence, and can be V,F,G,L,P, or R, or absent. In some embodiments, $X_{707}$ is an optional sequence, and can be L,A,F,G,I,M,N,P,Q,R,S,T,V, or Y, or absent. In some embodiments, $X_{708}$ is an optional sequence, and can be S,H,M,N,Q, or T, or absent. In some embodiments, $X_{709}$ is an optional sequence, and can be L,A,H,I,M,N,Q,R,S,T,V, or W, or absent. In some embodiments, $X_{710}$ is an optional sequence, and can be F,A,C,G,H,I,L,M,N,P,Q,R,S,T,V, or W, or absent. In some embodiments, $X_{711}$ is an optional sequence, and can be T,F,G,H,I,L,M,N,P,S,V, or W, or absent. In some embodiments, $X_{712}$ is an optional sequence, and can be R,F,K,N,R,T, or Y, or absent. In some embodiments, the isolated peptide comprising Formula (VII) has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, a composition can comprise, consist of, or consist essentially of a peptide inhibitor that comprises, consists of, or consists essentially of a peptide of Formula (VIII), $X_{800}K\ X_{801}K\ X_{802}E\ X_{803}$ (SEQ ID NO: 395), as described herein. In some embodiments, $X_{800}$ is an optional sequence, and can be K, A, D, E, G, H, I, L, M, N, P, Q, R, T, V, or K, or absent. In some embodiments, $X_{801}$ is an optional sequence, and can be LDTFFV, GDTFFV, EDTFFV, LDQFFV, LDTAFV, LDTVFV, LDTFMV, LDTFSV, LDTFVV, LDTFTV, LDTFLV, LDGFFV, LDTFGV, LDTFFK, ADTFFV, CDTFFV, DDTFFV, FDTFFV, HDTFFV, IDTFFV, KDTFFV, MDTFFV, NDTFFV, QDTFFV, RDTFFV, SDTFFV, TDTFFV, VDTFFV, LATFFV, LETFFV, LITFFV, LVTFFV, LWTFFV, LYTFFV, LDCFFV, LDMFFV, LDNFFV, LDPFFV, LDRFFV, LDSFFV, LDWFFV, LDYFFV, LDTIFV, LDTMFV, LDTNFV, LDTPFV, LDTTFV, LDTFQV, LDTFFF, LDTFFG, LDTFFL, LDTFFP, LDTFFR, LDTFIV, LDTSFV, LDTFAV, LDTFCV, LDTQFV, LDTLFV, LTTFFV, LDTFFI, LDHFFV, LMTFFV, LDTFEV, LDTFWV, LFTFFV, LDVFFV, LDTFRV, LDTFHV, LDTYFV, LPTFFV, PDTFFV, LDTFPV, LDTFNV, LDTWFV, LDTGFV, LDAFFV, LQTFFV, LCTFFV, LSTFFV, YDTFFV, LDEFFV, WDTFFV, LDTKFV, LDTCFV, LDTFYV, LDTHFV, LHTFFV, LRTFFV, LDLFFV, LDTRFV, LLTFFV, LDTFDV, LDTFFA, LDTFFT, LNTFFV, LDDFFV, LDIFFV, LDFFFV, LKTFFV, LDTFFQ, LGTFFV, LDTFFC, LDKFFV, LDTFKV, LDTEFV, LDTFFW, LDTFFM, LDTFFS, LDTFFH, LDTFFY, LDTFFN, LDTDFV, LDTFFE, LDTFFD, LTFFV, LDTFF, TFFV, LDF, LDTE, FFV, LDV, LV, or L, or absent. In some embodiments, $X_{802}$ is an optional sequence, and can be LSLFT, VSLFT, LQLFT, LMLFT, LTLFT, LHLFT, LSQFT, LSVFT, LSMFT, LSLMT, LSLQT, LSLHT, LSLNT, LSLPT, LSLST, LSLGT, LSLAT, LSLRT, LSLFN, LSLFP, LSLFR, LGLFT, ASLFT, FSLFT, GSLFT, ISLFT, MSLFT, NSLFT, PSLFT, QSLFT, RSLFT, SSLFT, TSLFT, YSLFT, LNLFT, LSAFT, LSHFT, LSIFT, LSNFT, LSRFT, LSSFT, LSTFT, LSWFT, LSLCT, LSLIT, LSLLT, LSLTT, LSLVT, LSLWT, LSLFF, LSLFG, LSLFH, LSLFI, LSLFL, LSLFM, LSLFS, LSLFV, LSLFW, LYLFT, LVLFT, LSFFT, LSGFT, LSKFT, LSCFT, LCLFT, LRLFT, LPLFT, LWLFT, LKLFT, LDLFT, LSYFT, LALFT, WSLFT, LSLFA, LSLFQ, LSPFT, HSLFT, LSLYT, LILFT, KSLFT, CSLFT, LSLFY, LSLFK, LSLFC, LFLFT, LELFT, LSLKT, LLLFT, LSLFD, LSLDT, LSLFE, DSLFT, LSLET, LSDFT, LSEFT, ESLFT, SLFT, LSFT, LFT, LSL, LT, or T, or absent. In some embodiments, $X_{803}$ is an optional sequence, and can be R, F, K, N, R, T, or Y, or absent. In some embodiments, the isolated peptide comprising Formula (VIII) has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values. Additionally, a composition can comprise, consist of, or consist essentially of a peptide inhibitor that comprises, consists of, or consists essentially of any one or more of the peptides set forth in Table 5.1. In some embodiments, the isolated peptide from Table 5.1 used in these compositions has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

The pharmaceutical composition can comprise one or more other pharmaceutical acceptable pharmaceutical ingredients, such as a pharmaceutically acceptable diluent, carrier, excipient and/or buffer. "Pharmaceutically acceptable" means a non-toxic compound that does not decrease the effectiveness of the biological activity of the active ingredients. Such pharmaceutically acceptable additives, diluents buffers, carriers or excipients are well-known in the art (see Remington's Pharmaceutical Sciences, 18th edition, A. R Gennaro, Ed., Mack Publishing Company (1990) and handbook of Pharmaceutical Excipients, 3rd edition, A. Kibbe, Ed., Pharmaceutical Press (2000).

The pharmaceutical composition can include a buffer. The term "buffer" is intended to refer to an aqueous solution containing an acid-base mixture with the purpose of stabilizing pH. Examples of buffering agents are magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations. Other examples of buffers are Trizma, Bicine, Tricine, MOPS, MOPSO, MOBS, Tris, Hepes, HEPBS, MES, phosphate, carbonate, acetate, citrate, glycolate, lactate, borate, ACES, ADA, tartrate, AMP, AMPD, AMPSO, BES, CABS, cacodylate, CHES, DIPSO, EPPS, ethanolamine, glycine, HEPPSO, imidazole, imidazolelactic acid, PIPES, SSC, SSPE, POPSO, TAPS, TABS, TAPSO and TES.

The pharmaceutical composition can include a diluent. The term "diluent" is intended to refer to an aqueous or non-aqueous solution with the purpose of diluting the compounds in the pharmaceutical preparation. The diluent may be one or more of saline, water, polyethylene glycol, propylene glycol or ethanol.

The pharmaceutical composition can include an excipient. The excipient can be one or more of carbohydrates, surfactants, polymers, lipids and minerals. Examples of carbohydrates include lactose, sucrose, mannitol, and cyclodextrines, which are added to the composition, e.g., for facilitating lyophilisation. Examples of polymers are starch, cellulose ethers, cellulose carboxymethylcellulose, hydroxypropylmethyl cellulose, hydroxyethyl cellulose, ethylhydroxyethyl cellulose, alginates, carageenans, hyaluronic acid and derivatives thereof, polyacrylic acid, polysulphonate, polyethylenglycol/polyethylene oxide, polyethyleneoxide/polypropylene oxide copolymers, polyvinylalcohol/polyvinylacetate of different degree of hydrolysis, and polyvinylpyrrolidone, all of different molecular weight, which are added to the composition, e.g., for viscosity control, for achieving bioadhesion, or for protecting the lipid from chemical and proteolytic degradation. Examples of lipids are fatty acids, phospholipids, mono-, di-, and triglycerides, ceramides, sphingolipids and glycolipids, all of different acyl chain length and saturation, egg lecithin, soy lecithin, hydrogenated egg and soy lecithin, which are added to the composition for reasons similar to those for polymers. Examples of minerals are talc, magnesium oxide, zinc oxide and titanium oxide, which are added to the composition to obtain benefits such as reduction of liquid accumulation or advantageous pigment properties.

The pharmaceutical composition can include a carrier. In some embodiments, the carrier is a non-aqueous carrier. Examples of suitable aqueous and nonaqueous carriers which can be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions can contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

The pharmaceutical composition can be formulated for a extended release. In some embodiments, the pharmaceutical composition is formulated as a gel or gel-like substance for extended release. The gel or gel-like substance can remain stable under physiological conditions for about 3 days, 4, 5, 6, 7, 8, 9, 10, 11, 12, 13, or 14 days, 3-4 days, 3-5, 3-6, 3-7, 3-8, 3-9, 3-10, 3-11, 3-12, 3-13, 3-14, 4-5, 4-6, 4-7, 4-8, 4-9, 4-10, 4-11, 4-12, 4-13, 4-14, 5-6, 5-7, 5-8, 5-9, 5-10, 5-11, 5-12, 5-13, 5-14, 6-7, 6-8, 6-9, 6-10, 6-11, 6-12, 6-13, 6-14, 7-8, 7-9, 7-10, 7-11, 7-12, 7-13, 7-14, 8-14, 9-14, or 10-14 days. In some embodiments, the gel comprises an inhibitor peptide comprising, consisting of, or consisting essentially of any of SEQ ID NOs: 1-33, 34, 46-53, 64-66, 68, 76, 94-96, 98, 264-393, or 583-586, in which the inhibitor peptide is not water soluble and a buffer or adjuvant selected to formulate a gel when combined with the inhibitor peptide. Without being limited by any theory, in accordance with some embodiments herein, gels can be suitable for slow release of the inhibitor peptide.

The pharmaceutical composition can be formulated for solubility in aqueous solution. By way of example, an inhibitor peptide consisting of or consisting essentially of SEQ ID NO: 589 has been shown to be soluble in aqueous solution. As such, in some embodiments, a pharmaceutical composition comprises an inhibitor peptide consisting of or consisting essentially of SEQ ID NO: 589 solubilized or partially solubilized in an aqueous solution. Optionally, the aqueous solution can be provided as an adjuvant.

Compositions Comprising Nanoparticles

It is contemplated that nanoparticles can be useful in formulations comprising immunoregulatory peptide inhibitors in accordance with some embodiments herein. Without being limited by any theory, nanoparticles can be useful in solubilizing immunoregulatory peptide inhibitors, minimizing aggregates of immunoregulatory peptide inhibitors, and/or delivering immunoregulatory peptide inhibitors to tumors in accordance with some embodiments herein. For example, nanoparticles have been observed to exhibit enhanced permeation (EPR) effects, and it is contemplated that EPR's can be useful for facilitating permeation of tumors by immunoregulatory peptide inhibitors in accordance with some embodiments herein.

As used herein, "nanoparticle" refers to a particle having a diameter of 0.1 to 9000 nm, for example at least or equal to 0.1 nm, 1 nm, 5 nm, 10 nm, 20 nm, 50 nm, 90 nm, 100 nm, 200 nm, 300 nm 500 nm, 900 nm, 1000 nm, 2000 nm, 3000 nm, 4000 nm, 5000 nm, and/or, for example, less than or equal to 9000 nm, 5000 nm, 2000 nm, 1000 nm, 500 nm, 300 nm, 200 nm, 100 nm, 90 nm, 50 nm, 30 nm, 20 nm, 10 nm, 5 nm, 1 nm, or within a range defined by any two of the aforementioned diameters, for example, 0.1 nm to 10 nm, 0.1 nm to 20 nm, 0.1 nm to 50 nm, 0.1 nm to 90 nm, 0.1 nm to 100 nm, 0.1 nm to 200 nm, 0.1 nm to 300 nm, 0.1 nm to 500 nm, 0.1 nm to 900 nm, 0.1 nm to 1000 nm, 0.1 nm to 1500 nm, 0.1 nm to 2000 nm, 0.1 nm to 3000 nm, 0.1 nm to 5000 nm, 0.1 nm to 9000 nm, 1 nm to 10 nm, 1 nm to 20 nm, 1 nm to 50 nm, 1 nm to 90 nm, 1 nm to 100 nm, 1 nm to 200 nm, 1 nm to 300 nm, 1 nm to 500 nm, 1 nm to 900 nm, 1 nm to 1000 nm, 1 nm to 1500 nm, 1 nm to 2000 nm, 1 nm to 3000 nm, 1 nm to 5000 nm, 1 nm to 9000 nm, 5 nm to 10 nm, 5 nm to 20 nm, 5 nm to 50 nm, 5 nm to 90 nm, 5 nm to 100 nm, 5 nm to 200 nm, 5 nm to 300 nm, 5 nm to 500 nm, 5 nm to 900 nm, 5 nm to 1000 nm, 5 nm to 1500 nm, 5 nm to 2000 nm, 5 nm to 3000 nm, 5 nm to 5000 nm, 5 nm to 9000 nm, 10 nm to 20 nm, 10 nm to 50 nm, 10 nm to 90 nm, 10 nm to 100 nm, 10 nm to 200 nm, 10 nm to 300 nm, 10 nm to 500 nm, 10 nm to 900 nm, 10 nm to 1000 nm, 10 nm to 1500 nm, 10 nm to 2000 nm, 10 nm to 3000 nm, 10 nm to 5000 nm, 10 nm to 9000 nm, 20 nm to 50 nm, 20 nm to 90 nm, 20 nm to 100 nm, 20 nm to 200 nm, 20 nm to 300 nm, 20 nm to 500 nm, 20 nm to 900 nm, 20 nm to 1000 nm, 20 nm to 1500 nm, 20 nm to 2000 nm, 20 nm to 3000 nm, 20 nm to 5000 nm, 20 nm to 9000 nm, 50 nm to 90 nm, 50 nm to 100 nm, 50 nm to 200 nm, 50 nm to 300 nm, 50 nm to 500 nm, 50 nm to 900 nm, 50 nm to 1000 nm, 50 nm to 1500 nm, 50 nm to 2000 nm, 50 nm to 3000 nm, 50 nm to 5000 nm, 50 nm to 9000 nm, 100 nm to 200 nm, 100 nm to 300 nm, 100 nm to 500 nm, 100 nm to 900 nm, 100 nm to 1000 nm, 100 nm to 1500 nm, 100 nm to 2000 nm, 100 nm to 3000 nm, 100 nm to 5000 nm, 100 nm to 9000 nm, 500 nm to 1000 nm, 500 nm to 2000 nm, 500 nm to 3000 nm, 500 nm to 5000 nm, or 500 nm to 9000 nm, 1000 nm to 2000 nm, 1000 nm to 3000 nm, 1000 nm to 5000 nm, or 1000 nm to 9000 nm or within a range defined by any two of the aforementioned diameters. Optionally, the nanoparticle comprises a degradable particle and/or a non-degradable particle. Optionally, the nanoparticle comprises a non-degradable particle. Optionally, the nanoparticle consists of or consists essentially of a non-degradable particle. Optionally, the nanoparticle comprises a degradable particle. Optionally, the nanoparticle consists of or consists essentially of a degradable particle.

A number of nanoparticle materials are suitable for nanoparticles in compositions, uses, and methods in accordance with some embodiments herein. The nanoparticles can comprise various properties, for example biocompatibility, ability to carry hydrophobic cargo, and the like. Examples of materials for suitable nanoparticles in accordance with some embodiments herein include semiconductors (e.g. quantum dots) (Gao, X. H. et al., (2004). "In vivo cancer targeting and imaging with semiconductor quantum dots". Nat. Biotechnol. 22, 969-976; Medintz, I. L., et al. (2005). "Quantum dot bioconjugates for imaging, labelling and sensing". Nat. Mater. 4, 435-446; Michalet, X., et al. (2005). "Quantum dots for live cells, in vivo imaging, and diagnostics". Science 307, 538-544; Park et al. (2011). "CuInSe/ZnS Core/Shell NIR quantum dots for biomedical imaging". Small 7, 3148-3152; Chen et al., (2012) "Pharmacokinetics, dosimetry and comparative efficacy of Re-188-liposome and 5-FU in a CT26-luclung-metastatic mice model". Nucl. Med. Biol. 39, 35-43; Petryayeva et al., (2013), "Quantum dots in bioanalysis: a review of applications across various platforms for fluorescence spectroscopy and imaging". Appl. Spectrosc. 67, 215-252), each of which is hereby incorporated by reference in its entirety. Examples of materials for suitable nanoparticles in accordance with some embodiments herein include silica (Vanblaaderen et al., (1992) "Synthesis and characterization of colloidal dispersions of fluorescent, monodispersesilicaspheres". Langmuir 8, 2921-2931; Giri, S., et al. (2007). "Mesoporous silica nanomaterial-based biotechnological and biomedical delivery systems". Nanomedicine 2; Giri et al., (2005) "Stimuli-responsive controlled-release delivery system based on mesoporous silica nanorods capped with magnetic nanoparticles". Angew. Chem. Int. Ed. Engl. 44, 5038-504; Burns et al., (2006) "Fluorescent core-shell silica nanoparticles: towards "LabonaParticle" architectures for nanobiotechnology". Chem. Soc. Rev. 35, 1028-1042), each of which is hereby incorporated by reference in its entirety. Examples of materials for suitable nanoparticles in accordance with some embodiments herein include gold (e.g. gold spheres, gold rods, gold shells)(Boisselier E., et al. (2009) "Gold nanoparticles in nanomedicine: preparations, imaging, diagnostics, therapies and toxicity". Chem. Soc. Rev. 38, 1759-1782; Arvizo et al., (2010), "Gold nanoparticles: opportunities and challenges in nanomedicine". Expert Opin. Drug Deliv. 7, 753-763), each of which is hereby incorporated by reference in its entirety. Examples of materials for suitable nanoparticles in accordance with some embodiments herein include magnetic materials (e.g. magnetic Dynabead® (Invitrogen®)) (Arruebo et al., (2007) "Magnetic nanoparticles for drug delivery". Nano Today 2, 22-32; Banerjee et al., (2010) "Nanomedicine: magnetic nanoparticles and their biomedical applications". Curr. Med. Chem. 17, 3120-3141; Haun et al., (2010) "Magnetic nanoparticle biosensors". Wiley Interdiscip. Rev. Nanome. Nanobiotechnol. 2, 291-304), each of which is hereby incorporated by reference in its entirety. Examples of materials for suitable nanoparticles in accordance with some embodiments herein include carbon-based materials (e.g. a carbon nanotube, an activated carbon, buckminsterfullerene, or graphene) (Prato et al., (2008) "Functionalized carbon nanotubes in drug design and discovery". Acc. Chem. Res. 41, 60-68; Jain, (2012) "Advances in use of functionalized carbon nanotubes for drug design and discovery". Expert Opin. Drug Discov. 7, 1029-1037; Ye et al., (2015) "Targeted delivery of docetaxel to the metastatic lymph nodes: A comparison study between nanoliposomes and activated carbon nanoparticles". Asian Journal of Pharmaceutical Sciences 10: pp. 64-72), each of which is hereby expressly incorporated by reference in its entirety.

In some embodiments, a composition (or method or use thereof) comprising an immunoregulatory peptide inhibitor comprises a nanoparticle comprising at least one of a polymer (e.g. PLGA, glycerol, chitosan, DNA, a hydrogel, an acrylamide, and the like), a dendrimer (e.g. PAMAM and the like), a quantum dot (e.g. CdSe, CuInSe, CdTe, and the like), a gold nanoparticle (e.g. a sphere, rod, or shell), a silica nanoparticle (e.g. a sphere, shell, mesoporous structure, and the like), a magnetic particle (e.g. iron oxide, cobalt-based material, a magnetic sphere, an aggregate in dextran or silica, a Dynal® bead, and the like), a carbon-based material (e.g. a carbon nanotube, buckminsterfullerene, graphene, or an activated carbon), a carbohydrate, a nucleic acid, a polypeptide (e.g. an albumin or albumin fragment), or a lipid. Optionally, the nanoparticle comprises two or more of the listed substances. Optionally, the nanoparticle is PEGylated. Optionally, the nanoparticle is coated with PEGylated lipid.

It is contemplated that in accordance with compositions, uses, and methods in accordance with embodiments herein, the shape of a nanoparticle can be tuned, for example to affect solubility, delivery, or release of an immunoregulatory peptide inhibitor. Examples of nanoparticles suitable for use in accordance with some embodiments herein include beads, tubes, spheres, shells, rods, mesoporous structures, hydrogels, aggregates, carbon-based materials, polymers, fullerenes, and the like. In some embodiments, the nanoparticle comprises a cage that can contain (and subsequently release, or make accessible) the immunoregulatory peptide, for example an albumin or nucleic acid cage (see, e.g. Andersen, et al (2009). Nature. 459: 73-6, hereby incorporated by reference in its entirety), or a porous metal nanocage such as gold (see, e.g. Yavuz, et al. (2009), Nat Mater. 8:935-9, hereby incorporated by reference in its entirety). It is contemplated that engineered viruses or portions thereof, such as engineered plant viruses (e.g. cowpea mosaic virus) can provide nanoparticles with readily scalable production. In some embodiments, the nanoparticle comprises a viral capsid, or portion thereof (see, e.g. Steinmetz (2013). Mol Pharm. 10: 1-2, hereby incorporated by reference in its entirety). In some embodiments, the nanoparticle comprises a lipid capsule or liposome. It is contemplated that that lipid capsules such as liposomes can permit a relatively high level of inhibitory peptide-to-carrier ratio, and minimize escape of inhibitor peptide during circulation. It is contemplated that polymers, such as polyacrylamide or chitosan, can faciliatate sustained release (e.g. slow release) of the immunoregulatory peptide inhibitors (see, e.g., Kashyap et al., Hydrogels for Pharmaceutical and Biomedical Applications, (2005) Critical Reviewsin Therapeutic Drug Carrier Systems, 22(2):107-150, hereby incorporated by reference in its entirety). It is contemplated that active carbon supports, for example activated carbon nanoparticles can facilitate delivery to lymph nodes, for example delivery of the immunoregulatory to lymph nodes in metastatic cancer (see, e.g. Ye et al., (2015) "Targeted delivery of docetaxel to the metastatic lymph nodes: A comparison study between nanoliposomes and activated carbon nanoparticles". Asian Journal of Pharmaceutical Sciences 10: pp. 64-72, hereby incorporated by reference in its entirety).

In some compositions, methods, and uses in accordance with some embodiments herein, a nanoparticle as described herein is conjugated to an immunoregulatory peptide inhibitor. As used herein "conjugate" (and variations of this root term) of immunoregulatory peptide inhibitors refers broadly to covalent, non-covalent, or a combination of covalent and non-covalent associations between an immunoregulatory peptide inhibitor and another particle, such as a nanoparticle. As such, an immunoregulatory peptide inhibitor can be immobilized on the surface of a nanoparticle by conjugation to the nanoparticle. In some embodiments, the immunoregulatory peptide inhibitor is conjugated to a nanoparticle covalently. Examples of covalent linkers are reviewed in Trail (2013), Antibodies 2: 113-129, hereby incorporated by reference in its entirety. In some embodiments, the immunoregulatory peptide inhibitor is conjugated to a nanoparticle non-covalently, for example via hydrophobic or electrostatic interactions. Without being limited by any theory, it is contemplated that it can be useful for immunoregulatory peptide inhibitors in accordance with some embodiments herein to subsequently dissociate from the nanoparticles. Accordingly, in some embodiments, the immunoregulatory peptide inhibitor is noncovalently conjugated to the nanoparticle, or is covalently conjugated to the nanoparticle via a cleavable or reversible covalent linker, for example a cleavable linker or a pH-sensitive linker.

Examples of non-covalent interactions in accordance with some embodiments herein include van der Waals, steric, hydrogen bonding, hydrophobic and electrostatic interactions. In some embodiments, non-covalent associations between immunoregulatory peptide inhibitors and nanoparticles include hydrophobic interactions, electrostatic interactions, hydrogen bonding, and steric immobilization, or combinations of two or more of these. Examples of hydrophobic interactions between nanoparticles and therapeutic moieties are described in Cheng et al. (2008) J Am Chem Soc. 130: 10643-10647, hereby incorporated by reference in its entirety. Examples of electrostatic interactions between nanoparticles and therapeutic moieties are described in Manju et al. (2011). Langmuir. 27: 14489-14496, hereby incorporated by reference in its entirety. Examples of hydrogen bonding between nanoparticles and therapeutic moieties are described in Kim et al. (2008), ACS Nano. 2: 386-392, hereby incorporated by reference in its entirety. Examples of steric immobilization interactions between nanoparticles and therapeutic moieties are described in Kester et al. (2008), Nano Lett. 8: 4116-4121, hereby incorporated by reference in its entirety. Optionally, an immunoregulatory peptide inhibitor and nanoparticle are associated by one or more non-covalent interaction, and one or more covalent interaction (for example a cleavable linker, or a non-cleavable linker), as described herein.

Examples of cleavable linkers suitable for some embodiments herein include peptides comprising protease target sites, such as targets of cathepsin, matrix metalloproteinases, furin, pepsin, trypsin, and the like. By way of example, it has been observed that some solid tumors express proteases such as matrix metalloproteinases. As such, in some embodiments, a linker comprises a matrix metalloproteinase target site such as MMP-sensitive peptide (GPQGIAGQ, SEQ ID NO: 596).

By way of example, it has been observed that some solid tumors comprise a slightly acidic pH. Accordingly, in some embodiments, the linker comprises a pH-sensitive linker that permits dissociation of the immunoregulatory peptide inhibitor from the nanoparticle at an acidic pH. Example pH-sensitive linkers include acid-labile hydrazones, disulfide, thioethers, silyl linkers and peptide. An example acid-labile hydrazone is provided in Formula (IX) below (with the site of acid-sensitive separation depicted as a dashed line).

Formula (IX)

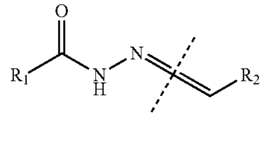

Silyl linkers have also been shown to be cleaved at acidic pH's (see, e.g. Finniss et al. (2014), MedChemComm DOI: 10.1039/c4md00150h). An example acid-labile silyl linker is provided in Formula (X) below:

Formula (X)

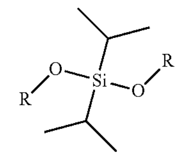

Without being limited by any theory, it is contemplated that some receptors that are un-inhibited (e.g. de-blocked) by immunoregulatory peptide inhibitors in accordance with various embodiments herein can be internalized. For example, the LFA-1 receptor has been shown to undergo internalization (see, Yusuf-Makagiansar et al. (2001), Pharm Res. 18: 329-35). For example, the IL-2 receptor has been shown to undergo internalization (see, Hemar et al. (1994), J. Cell Biology 129: 55-64).

Accordingly, in some embodiments, the cleavable linker is cleaved upon internalization, for example, a citrulline linker (e.g. dipeptide valine-citrulline) or a cathepsin B target site (e.g. Arg-Arg).

In accordance with some embodiments herein, a nanoparticle as described herein is conjugated to a immunoregulatory peptide inhibitor. In some embodiments, the nanoparticle is conjugated to an isolated P28R peptide (SEQ ID NO: 2), or a peptide comprising SEQ ID NO: 2. In some embodiments, the nanoparticle is conjugated to an isolated P28 core peptide (SEQ ID NO: 62) or a peptide comprising SEQ ID NO: 62. Without being limited by any theory, it is contemplated that a composition comprising P28 core peptide (SEQ ID NO: 62) immobilized on a nanoparticle can be useful for facilitating stimulation or activation of immune cells (for example, by removing immunoregulatory peptides from blocking LFA-1 and/or IL-2 receptors), without having a direct immunostimulatory effect itself. In some embodiments, the nanoparticle is conjugated to an isolated peptide comprising Formula VII, wherein Formula VII is:

(SEQ ID NO: 394)

$X_{700}KX_{701}X_{702}X_{703}X_{704}X_{705}X_{706}KX_{707}X_{708}X_{709}X_{710}$ $X_{711}EX_{712}$ wherein $X_{700}$ is K,A,D,E,G,H,I,L,M,N,P,Q,R,T,V, or K, or absent;

wherein $X_{701}$ is L,A,C,D,E,F,G,H,I,K,M,N,Q,R,S,T, or V, or absent;

wherein $X_{702}$ is D,A,E,I,V,W, or Y, or absent;

wherein $X_{703}$ is T,C,M,N,P,Q,R,S,W, or Y, or absent;

wherein $X_{704}$ is F,A,I,M,N,P,T, or V, or absent;

wherein $X_{705}$ is F,L,M,Q,S,T or V, or absent;

wherein $X_{706}$ is V,F,G,L,P, or R, or absent;

wherein $X_{707}$ is L,A,F,G,I,M,N,P,Q,R,S,T,V, or Y, or absent;

wherein $X_{708}$ is S,H,M,N,Q, or T, or absent;

wherein $X_{709}$ is L,A,H,I,M,N,Q,R,S,T,V, or W, or absent;

wherein $X_{710}$ is F,A,C,G,H,I,L,M,NP,Q,R,S,T,V, or W, or absent;

wherein $X_{711}$ is T,F,G,H,I,L,M,N,P,S,V, or W, or absent; and wherein $X_{712}$ is R,F,K,N,R,T, or Y, or absent.

Said formula VII may be one of SEQ ID NO: 1-101, 167-172, 174-177, 179-393, 396-581, or 582.

Some embodiments of the invention include compositions that comprise an isolated peptide comprising Formula VIII, wherein Formula VIII is:

$$X_{800}K\ X_{801}K\ X_{802}E\ X_{803} \quad \text{(SEQ ID NO: 395)}$$

wherein $X_{800}$ is K, A, D, E, G, H, I, L, M, N, P, Q, R, T, V, or K, or absent;

wherein $X_{801}$ is LDTFFV, GDTFFV, EDTFFV, LDQFFV, LDTAFV, LDTVFV, LDTFMV, LDTFSV, LDTFVV, LDTFTV, LDTFLV, LDGFFV, LDTFGV, LDTFFK, ADTFFV, CDTFFV, DDTFFV, FDTFFV, HDTFFV, IDTFFV, KDTFFV, MDTFFV, NDTFFV, QDTFFV, RDTFFV, SDTFFV, TDTFFV, VDTFFV, LATFFV, LETFFV, LITFFV, LVTFFV, LWTFFV, LYTFFV, LDCFFV, LDMFFV, LDNFFV, LDPFFV, LDRFFV, LDSFFV, LDWFFV, LDYFFV, LDTIFV, LDTMFV, LDTNFV, LDTPFV, LDTTFV, LDTFQV, LDTFFF, LDTFFG, LDTFFL, LDTFFP, LDTFFR, LDTFIV, LDTSFV, LDTFAV, LDTFCV, LDTQFV, LDTLFV, LTTFFV, LDTFFI, LDHFFV, LMTFFV, LDTFEV, LDTFWV, LFTFFV, LDVFFV, LDTFRV, LDTFHV, LDTYFV, LPTFFV, PDTFFV, LDTFPV, LDTFNV, LDTWFV, LDTGFV, LDAFFV, LQTFFV, LCTFFV, LSTFFV, YDTFFV, LDEFFV, WDTFFV, LDTKFV, LDTCFV, LDTFYV, LDTHFV, LHTFFV, LRTFFV, LDLFFV, LDTRFV, LLTFFV, LDTFDV, LDTFFA, LDTFFT, LNTFFV, LDDFFV, LDIFFV, LDFFFV, LKTFFV, LDTFFQ, LGTFFV, LDTFFC, LDKFFV, LDTFKV, LDTEFV, LDTFFW, LDTFFM, LDTFFS, LDTFFH, LDTFFY, LDTFFN, LDTDFV, LDTFFE, LDTFFD, LTFFV, LDTFF, TFFV, LDF, LDTE, FFV, LDV, LV, or L, or absent;

wherein $X_{802}$ is LSLFT, VSLFT, LQLFT, LMLFT, LTLFT, LHLFT, LSQFT, LSVFT, LSMFT, LSLMT, LSLQT, LSLHT, LSLNT, LSLPT, LSLST, LSLGT, LSLAT, LSLRT, LSLFN, LSLFP, LSLFR, LGLFT, ASLFT, FSLFT, GSLFT, ISLFT, MSLFT, NSLFT, PSLFT, QSLFT, RSLFT, SSLFT, TSLFT, YSLFT, LNLFT, LSAFT, LSHFT, LSIFT, LSNFT, LSRFT, LSSFT, LSTFT, LSWFT, LSLCT, LSLIT, LSLLT, LSLTT, LSLVT, LSLWT, LSLFF, LSLFG, LSLFH, LSLFI, LSLFL, LSLFM, LSLFS, LSLFV, LSLFW, LYLFT, LVLFT, LSFFT, LSGFT, LSKFT, LSCFT, LCLFT, LRLFT, LPLFT, LWLFT, LKLFT, LDLFT, LSYFT, LALFT, WSLFT, LSLFA, LSLFQ, LSPFT, HSLFT, LSLYT, LILFT, KSLFT, CSLFT, LSLFY, LSLFK, LSLFC, LFLFT, LELFT, LSLKT, LLLFT, LSLFD, LSLDT, LSLFE, DSLFT, LSLET, LSDFT, LSEFT, ESLFT, SLFT, LSFT, LFT, LSL, LT, or T, or absent; and wherein $X_{803}$ is R, F, K, N, R, T, or Y, or absent.

Said formula VIII may be one of SEQ ID NOs: 1-34, 64-68, 70-72, 74-77, 80, 83, 86, 89, 92-96, 99-100, 264, 268-269, 270-386, 388-393, 396-401, 403, 404, 406, 408-411, 413-416, 419-420, 422-438, 442-444, 446-449, 451-453, 455-458, 460, 462-466, 470, 472-477, 479-480, 482-484, 486, 487, 489, 491-493, 495-498, 500-508, 512-517, 519-522, 528-530, 532, 533, 535-538, 540, 542-551, 553, 557-559, 567, 570, 572-581, or 582.

In some embodiments of the invention, the nanoparticle is conjugated to an isolated peptide comprising Formula I, wherein Formula I is:

$$XX_1VKX_2X_3X_4 \quad \text{(SEQ ID NO: 166)}$$

wherein X is KKLDT (SEQ ID NO: 167), RKLDT (SEQ ID NO: 168), KKGDT (SEQ ID NO: 169), KKEDT (SEQ ID NO: 170), KKLDQ (SEQ ID NO: 171), KKGDQ (SEQ ID NO: 252), KKEDQ (SEQ ID NO: 253), RKLDQ (SEQ ID NO: 254), RKGDQ (SEQ ID NO: 255), RKEDQ (SEQ ID NO: 256), RKGTD (SEQ ID NO: 257), RKEDT (SEQ ID NO: 258), KLDT (SEQ ID NO: 172), KGDT (SEQ ID NO: 259), KEDT (SEQ ID NO: 260), KLDQ (SEQ ID NO: 261), KGDQ (SEQ ID NO: 262), KEDQ (SEQ ID NO: 263), LDT, LDQ, GDT, GDQ, EDT, EDQ, DT, DQ, T, Q, or absent.

wherein $X_1$ is FF, FM, FS, FV, FT, FL, AF, AM, AS, AV, AT, AL, VF, VM, VS, VV, VT, or VL, or absent;

wherein $X_2$ is LS, LQ, LM, LT, LH, VS, VQ, VM, VT, or VH, or absent;

wherein $X_3$ is LFT, LMT, LQT, LHT, LNT, LPT, LST, LGT, LAT, LRT, QFT, QMT, QQT, QHT, QNT, QPT, QST, QGT, QAT, QRT, VFT, VMT, VQT, VHT, VNT, VPT, VST, VGT, VAT, VRT, MFT, MMT, MQT, MHT, MNT, MPT, MST, MGT, MAT, MRT, LFN, LMN, LQN, LHN, LNN, LPN, LSN, LGN, LAN, LRN, QFN, QMN, QQN, QHN, QNN, QPN, QSN, QGN, QAN, QRN, VFN, VMN, VQN, VHN, VNN, VPN, VSN, VGN, VAN, VRN, MFN, MMN, MQN, MHN, MNN, MPN, MSN, MGN, MAN, MRN, LFP, LMP, LQP, LHP, LNP, LPP, LSP, LGP, LAP, LRP, QFP, QMP, QQP, QHP, QNP, QPP, QSP, QGP, QAP, QRP, VFP, VMP, VQP, VHP, VNP, VPP, VSP, VGP, VAP, VRP, MFP, MMP, MQP, MHP, MNP, MPP, MSP, MGP, MAP, MRPR, LFR, LMR, LQR, LHR, LNR, LPR, LSR, LGR, LAR, LRR, QFR, QMR, QQR, QHR, QNR, QPR, QSR, QGR, QAR, QRR, VFR, VMR, VQR, VHR, VNR, VPR, VSR, VGR, VAR, VRR, MFR, MMR, MQR, MHR, MNR, MPR, MSR, MGR, MAR, or MRR; and wherein $X_4$ is ER, E, or absent.

Said formula I may be one of SEQ ID NOs: 2-40, 46-52, 58-65, 67-71, 74-77, 80-83, 86-88, 92-96, 99-101, 166, 173, 178, 182, 268-325, 332-392-393, 396-415, 417-444, 446-468, 470-487, 489-494, 497-508, 510, 512, 514-517, 520-522, 524-525, 528-533, 535-536, 538-539, 542-544, 546, 548, 551, 553, 556-559, 561, 563-568, 571-573, 575-581 or 582, such as said formula I may be one of SEQ ID NOs: 2 to 33.

In some embodiments of the invention, the nanoparticle is conjugated to an isolated peptide comprising formula II, wherein formula II is XTFFVKLSX$_1$X$_2$ (SEQ ID NO: 173), wherein X is KKLD (SEQ ID NO: 174), RKLD (SEQ ID NO: 175), KKGD (SEQ ID NO: 176), KKED (SEQ ID NO: 177), KLD, LD, D, or absent wherein $X_1$ is LFT, LMT, LQT, LHT, LNT, LPT, LST, LGT, LAT, LRT, QFT, QMT, QQT, QHT, QNT, QPT, QST, QGT, QAT, QRT, VFT, VMT, VQT, VHT, VNT, VPT, VST, VGT, VAT, VRT, MFT, MMT, MQT, MHT, MNT, MPT, MST, MGT, MAT, MRT, LFN, LMN, LQN, LHN, LNN, LPN, LSN, LGN, LAN, LRN, QFN, QMN, QQN, QHN, QNN, QPN, QSN, QGN, QAN, QRN, VFN, VMN, VQN, VHN, VNN, VPN, VSN, VGN, VAN, VRN, MFN, MMN, MQN, MHN, MNN, MPN, MSN, MGN, MAN, MRN, LFP, LMP, LQP, LHP, LNP, LPP, LSP, LGP, LAP, LRP, QFP, QMP, QQP, QHP, QNP, QPP, QSP, QGP, QAP, QRP, VFP, VMP, VQP, VHP, VNP, VPP, VSP, VGP, VAP, VRP, MFP, MMP, MQP, MHP, MNP, MPP, MSP, MGP, MAP, MRPR, LFR, LMR, LQR, LHR, LNR, LPR, LSR, LGR, LAR, LRR, QFR, QMR, QQR, QHR, QNR, QPR, QSR, QGR, QAR, QRR, VFR, VMR, VQR, VHR, VNR, VPR, VSR, VGR, VAR, VRR, MFR, MMR, MQR, MHR, MNR, MPR, MSR, MGR, MAR, or MRR, or absent; and wherein $X_2$ is ER, or E, or absent, such as said formula II may be one of SEQ ID NO: 2-5, 19-38, 46-49, 58-61, 64, 68-70, 75, 81, 87, 93, 94, 100, 101, 173, 268-303, 350-393, 396, 398, 399, 400, 402, 403, 405, 406-408, 412-414, 417, 418, 421-423, 426-428, 430, 431, 435, 436, 438, 439, 440-442, 448-455, 458, 459, 461, 465, 467, 468, 471, 475, 476, 478-481, 483, 485, 487, 489-491, 493, 494, 497-499, 503, 507, 510, 512, 514-517, 520, 521, 524, 525, 528, 529, 531, 533, 538, 539, 542-, 544, 546, 551, 556-559, 561, 563-568, 571-573, 575-577, 579, 580, or 581. Other examples includes an isolated peptide, wherein X is KKLD (SEQ ID NO: 174) or wherein $X_2$ is ER or wherein said formula is TFFVKLSLFTER (SEQ ID NO: 49) or TFFVKLSLFTE (SEQ ID NO: 250) or wherein said formula is KKLDTFFVKLSLFTER (SEQ ID NO: 2) or KKLDTFFVKLSLFTE (SEQ ID NO: 34).

In some embodiments of the invention, the nanoparticle is conjugated to an isolated peptide comprising Formula III, wherein Formula III is:

$$XX_1VKLX_2LX_3TEX_4 \quad \text{(SEQ ID NO: 178)}$$

wherein X is KKLDTF (SEQ ID NO: 179), KLDTF (SEQ ID NO: 180), LDTF (SEQ ID NO: 181), DTF, TF, or F, or absent;
wherein $X_1$ is F, M, S, V, T, or L, or absent;
wherein $X_2$ is S, Q, M, T, or H, or absent;
wherein $X_3$ is F, M, Q, H, N, P, S, G, A, or R, or absent; and
wherein $X_4$ is R or absent.

Said formula III may be one of SEQ ID NO: 2-13, 15-18, 22-30, 34, 46-52, 58, 64, 65, 70, 71, 76, 77, 82, 83, 88, 93-96, 99, 100, 178, 268-325. Examples includes wherein X is KKLDTF (SEQ ID NO: 178) or wherein $X_4$ is R or wherein said formula is VKLSLFTER (SEQ ID NO: 52) or VKLSLFTE (SEQ ID NO: 251) or wherein said formula is KKLDTFFVKLSLFTER (SEQ ID NO: 2) or KKLDTFFVKLSLFTE (SEQ ID NO: 34).

Other examples includes isolated peptides comprising at least one of SEQ ID NOs: 1-101, 167-172, 174-177, 179-393, 396-581 and 582 or at least one of SEQ ID NOs: 1-32, 34, 64-66, 68, 76, 94-96, 98, and 264-393 or at least one of the sequences of Table 5.1.

The above mentioned isolated peptides conjugated to the nanoparticle, may have at least one amino acid being a D amino acid, artificial amino acid, or chemically modified amino acid and/or comprise an N-terminal acetyl group and/or comprise a C-terminal amide group and/or be glycosylated or nitrosylated.

The above mentioned isolated peptides conjugated to the nanoparticle may be joined to at least one of polyethylene glycol, a fatty acid, or a pharmacokinetic modifier and/or comprises a cyclic peptide.

The above mentioned isolated peptides conjugated to the nanoparticle may comprise at least one modification, for example at least one of a D amino acid and/or a N-terminal acetyl group and/or a C-terminal amide group and/or glycosylation and/or nitrosylation and/or carbonylation and/or oxidation and/or a linked pharmacokinetic modifier and/or a linked polyethylene glycol or any combination thereof.

The above mentioned isolated peptides conjugated to the nanoparticle can be less than or equal to 1100 amino acids in length, such as between 7 amino acids and 20 amino acids in length.

The above mentioned isolated peptides conjugated to the nanoparticle may be multimerized.

The above defined peptides conjugated to the nanoparticle may be less than or equal to 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 16, 15, 14, 13, 12, 11, 10, 9, 8, 7, 6 or 5 amino acids in length or any length in between any of these numbers.

Administration Form

The pharmaceutical formulations described herein (e.g. immunoregulatory peptide inhibitors, and/or immunoregulatory peptide inhibitors immobilized on nanoparticles as described herein) may be administered locally or systemically. Routes of administration include topical, ocular, nasal, pulmonary, buccal, parenteral (intravenous, subcutaneous, and intramuscular), oral, vaginal and rectal. Most commonly used being oral administration.

In some embodiments, for example if immune cell invasion of a tumor, cytotoxicity of a tumor, or deblocking of a an immune cell receptor of a tumor is desired, the pharmaceutical formulation is administered at or near a tumor. For example, the pharmaceutical formulation can be administered peri-tumorally, or within 10 cm of the tumor, for example within 10 cm, 9, 8, 7, 6, 5, 4, 3, 2, 1, or 0.5 cm of the tumor or a range defined by any two of these distances. Optionally, the pharmaceutical formulation is administered directly to a tumor, and induces regressive changes in the tumor. Optionally, the pharmaceutical formulation is administered to a subject, and induces regressive changes of a tumor to which the composition is not directly administered. Optionally, the pharmaceutical formulation is administered directly to a tumor, and induces regressive changes in the tumor, and further induces regressive changes in a second tumor to which the formulation was not directly administered (e.g. a metastatic or contralateral tumor). Optionally, the pharmaceutical formulation is administered directly to a tumor, and induces eradication of the tumor. Optionally, the pharmaceutical formulation is administered to a subject, and induces eradication of a tumor to which the composition is not directly administered. Optionally, the pharmaceutical formulation is administered directly to a tumor, and induces eradication of the tumor, and further induces eradication of a second tumor to which the formulation was not directly administered (e.g. a metastatic or contralateral tumor). Optionally, the pharmaceutical formulation is administered directly to a tumor, and induces immune cell infiltration of the tumor. Optionally, the pharmaceutical formulation is administered directly to a tumor, and induces immune cell infiltration of the tumor, and further induces immune cell infiltration of a second tumor to which the formulation was not directly administered (e.g. a metastatic or contralateral tumor). Optionally, the pharmaceutical formulation is administered to a subject, and induces immune cell infiltration of a tumor to which the composition is not directly administered. Example tumors to which the pharmaceutical composition can be directly or indirect administered include a prostate tumor, a melanoma, a colon cancer, a lung carcinoma, an Apocrine gland carcinoma, a testis tumor, a mast cell tumor, a mammary tumor (e.g. a benign mammary tumor or a malignant mammary tumor, for example a mixed mammary tumor such as a benign mixed mammary tumor or a malignant mixed mammary tumor), a mucinous carcinoma (e g a mammary gland mucinous carcinoma), or a histicytoma The pharmaceutical compositions will be administered to a patient in a therapeutically effective amount or dose. A therapeutically effective amount includes a dose of pharmaceutical composition sufficient to at least partially arrest a symptom of a disorder from which a patient is suffering. The exact dose is dependent on the manner of administration, the nature and severity of the disorder. Depending on the general health, sex, age and body weight of the patient different doses may be needed. The administration of the dose can be carried out both by single administration in the form of an individual dose unit or else several smaller dose units and also by multiple administration of subdivided doses at specific intervals, for example daily intervals (e.g., 1, 2, 3, 4, 5, 6, 7, 8, 9, 10, 11, 12, 13, 14, 15, 16, 17, 19, 20, 21, 22, 23, 24, 25, 26, 27, 28, 29, or 30 days between doses, including ranges between any two of the listed values). Exemplary dosing can comprise doses in the milligram, microgram, or nanogram-range, for example milligrams, micrograms, or nanograms per kg of body weight of the subject. The active compounds or substances may also be administered together or separately depending on the administration form. Exemplary dosing regiments in accordance with some embodiments herein include "prime boost" approaches in which a first dose of compound or substance is administered in a first administration, and second dose of compound or substance is administered in second administration. Optionally, additional subsequent administrations (e.g. third, fourth, fifth, sixth, seventh, eighth, ninth, or tenth) are performed. Optionally, the first dose is greater than a subsequent dose (e.g. the second dose, or if performed, third, fourth, fifth, sixth, seventh, eighth, ninth, or tenth), for example at least 1.1×, 1.2×, 1.5×, 2×, 3×, 4×, 5×, 10×, 20×, 30×, 40×, 50×, 100×, 200×, 500×, 1000×, 2000×, 5000×, or 10000× of the subsequent dose. Optionally, the subsequent dose (e.g. second, third, fourth, fifth, sixth, seventh, eighth, ninth, or tenth) is greater than the first dose, for example at least 1.1×, 1.2×, 1.5×, 2×, 3×, 4×, 5×, 10×, 20×, 30×, 40×, 50×, 100×, 200×, 500×, 1000×, 2000×, 5000×, or 10000× of the first dose. In some embodiments a subsequent dose (e.g. second dose after first dose, third dose after second dose, if performed, fourth dose after fifth dose, if performed) is administered at least one day after the preceding dose, for example, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 60, 90, or 100 days after, including ranges between any two of the listed values.

In some embodiments, the immunoregulatory peptide inhibitor as described herein is administered systemically to the subject (e.g., a subject suffering from a cancer having more than one tumour, such as metastasis) so as to inhibit or prevent cancer (e.g., metastatic cancer) at a does of at least about 1 ng/kg, for example at least about 1 ng/kg, 2 ng/kg, 3 ng/kg, 4 ng/kg, 5 ng/kg, 6 ng/kg, 7 ng/kg, 8 ng/kg, 9 ng/kg, 10 ng/kg, 15 ng/kg, 20 ng/kg, 25 ng/kg 30 ng/kg, 35 ng/kg, 40 ng/kg, 45 ng/kg, 50 ng/kg, 60 ng/kg, 70 ng/kg, 80 ng/kg, 90 ng/kg, 100 ng/kg, 110 ng/kg, 120 ng/kg, 130 ng/kg, 140 ng/kg, 150 ng/kg, 160 ng/kg, 170 ng/kg, 180 ng/kg, 190 ng/kg, 200 ng/kg, 210 ng/kg, 220 ng/kg, 230 ng/kg, 240 ng/kg, 250 ng/kg, 260 ng/kg, 270, ng/kg, 280 ng/kg, 290 ng/kg, 300 ng/kg, 310 ng/kg, 320 ng/kg, 330 ng/kg, 340 ng/kg, 350 ng/kg, 360 ng/kg, 370 ng/kg, 380 ng/kg, 390 ng/kg, 400 ng/kg, 410 ng/kg, 420 ng/kg, 430 ng/kg, 440 ng/kg, 450 ng/kg, 460 ng/kg, 470 ng/kg, 480 ng/kg, 490 ng/kg, 200 ng/kg, 510 ng/kg, 520 ng/kg, 530 ng/kg, 540 ng/kg, 550 ng/kg, 560 ng/kg, 570, ng/kg, 580 ng/kg, 590 ng/kg, 200 ng/kg, 610 ng/kg, 620 ng/kg, 630 ng/kg, 640 ng/kg, 650 ng/kg, 660 ng/kg, 670 ng/kg, 680 ng/kg, 690 ng/kg, 700 ng/kg, 710 ng/kg, 720 ng/kg, 730 ng/kg, 740 ng/kg, 750 ng/kg, 760 ng/kg, 770 ng/kg, 780 ng/kg, 790 ng/kg, 800 ng/kg, 810 ng/kg, 820 ng/kg, 830 ng/kg, 840 ng/kg, 850 ng/kg, 860 ng/kg, 870 ng/kg, 880 ng/kg, 890 ng/kg, 900 ng/kg, 910 ng/kg, 920 ng/kg, 930 ng/kg, 940 ng/kg, 950 ng/kg, 960 ng/kg, 970, ng/kg, 980 ng/kg, 990 ng/kg, 1000 ng/kg, 2 µg/kg, 3 µg/kg, 4 µg/kg, 5 µg/kg, 6 µg/kg, 7 µg/kg, 8 µg/kg, 9 µg/kg, 10 µg/kg, 15 µg/kg, 20 µg/kg, 25 µg/kg, 30 µg/kg, 40 µg/kg, 50 µg/kg, 60 µg/kg, 70 µg/kg, 80 µg/kg, 90 µg/kg, 100 µg/kg, 110 µg/kg, 120 µg/kg, 130 µg/kg, 140 µg/kg, 150 µg/kg, 160 µg/kg, 170 µg/kg, 180 µg/kg, 190 µg/kg, 200 µg/kg, 250 µg/kg, 300 µg/kg, 350 µg/kg, 400 µg/kg, 450 µg/kg, 500 µg/kg, 600 µg/kg, 700 µg/kg, 800 µg/kg, 900 µg/kg, 1000 µg/kg, 2000 µg/kg, 3000 µg/kg, 4000 µg/kg, or 5000 µg/kg, including ranges between any two of the listed values, for example 1 ng/kg-100 ng/kg, 1 ng/kg-200 ng/kg, 1 ng/kg-300 ng/kg, 1 ng/kg-400 ng/kg, 1 ng/kg-500 ng/kg, 1 ng/kg-600 ng/kg, 1 ng/kg-700 ng/kg, 1 ng/kg-800 ng/kg, 1 ng/kg-900 ng/kg, 1 ng/kg-1000 ng/kg, 1 ng/kg-2 µg/kg, 1 ng/kg-3 µg/kg, 1 ng/kg-5 µg/kg, 1 ng/kg-10 µg/kg, 1 ng/kg-20 µg/kg, 1 ng/kg-50 µg/kg, 1 ng/kg-100 µg/kg, 1 ng/kg-200 µg/kg, 1 ng/kg-500 µg/kg, 1 ng/kg-1000 µg/kg, 5 ng/kg-100 ng/kg, 5 ng/kg-200 ng/kg, 5 ng/kg-300 ng/kg, 5 ng/kg-400 ng/kg, 5 ng/kg-500 ng/kg, 5 ng/kg-600 ng/kg, 5 ng/kg-700 ng/kg, 5 ng/kg-800 ng/kg, 5 ng/kg-900 ng/kg, 5 ng/kg-1000 ng/kg, 5 ng/kg-2 µg/kg, 5 ng/kg-3 µg/kg, 5 ng/kg-5 µg/kg, 5 ng/kg-10 µg/kg, 5 ng/kg-20 µg/kg, 5 ng/kg-50 µg/kg, 5 ng/kg-100 µg/kg, 5 ng/kg-200 µg/kg, 5 ng/kg-500 µg/kg, 5 ng/kg-1000 µg/kg, 10 ng/kg-100 ng/kg, 10 ng/kg-200 ng/kg, 10 ng/kg-300 ng/kg, 10 ng/kg-400 ng/kg, 10 ng/kg-500 ng/kg, 10 ng/kg-600 ng/kg, 10 ng/kg-700 ng/kg, 10 ng/kg-800 ng/kg, 10 ng/kg-900 ng/kg, 10 ng/kg-1000 ng/kg, 10 ng/kg-2 µg/kg, 10 ng/kg-3 µg/kg, 10 ng/kg-5 µg/kg, 10 ng/kg-10 µg/kg, 10 ng/kg-20 µg/kg, 10 ng/kg-50 µg/kg, 10 ng/kg-100 µg/kg, 10 ng/kg-200 µg/kg, 10 ng/kg-500 µg/kg, 10 ng/kg-1000 µg/kg, 20 ng/kg-100 ng/kg, 20 ng/kg-200 ng/kg, 20 ng/kg-300 ng/kg, 20 ng/kg-400 ng/kg, 20 ng/kg-500 ng/kg, 20 ng/kg-600 ng/kg, 20 ng/kg-700 ng/kg, 20 ng/kg-800 ng/kg, 20 ng/kg-900 ng/kg, 20 ng/kg-1000 ng/kg, 20 ng/kg-2 µg/kg, 20 ng/kg-3 µg/kg, 20 ng/kg-5 µg/kg, 20 ng/kg-10 µg/kg, 20 ng/kg-20 µg/kg, 20 ng/kg-50 µg/kg, 20 ng/kg-100 µg/kg, 20 ng/kg-200 µg/kg, 20 ng/kg-500 µg/kg, 20 ng/kg-1000 µg/kg, 30 ng/kg-100 ng/kg, 30 ng/kg-200 ng/kg, 30 ng/kg-300 ng/kg, 30 ng/kg-400 ng/kg, 30 ng/kg-500 ng/kg, 30 ng/kg-600 ng/kg, 30 ng/kg-700 ng/kg, 30 ng/kg-800 ng/kg, 30 ng/kg-900 ng/kg, 30 ng/kg-1000 ng/kg, 30 ng/kg-2 µg/kg, 30 ng/kg-3 µg/kg, 30 ng/kg-5 µg/kg, 30 ng/kg-10 µg/kg, 30 ng/kg-20 µg/kg, 30 ng/kg-50 µg/kg, 30 ng/kg-100 µg/kg, 30 ng/kg-200 µg/kg, 30 ng/kg-500 µg/kg, 30 ng/kg-1000 µg/kg, 40 ng/kg-100 ng/kg, 40 ng/kg-200 ng/kg, 40 ng/kg-300 ng/kg, 40 ng/kg-400 ng/kg, 40 ng/kg-500 ng/kg, 40 ng/kg-600 ng/kg, 40 ng/kg-700 ng/kg, 40 ng/kg-800 ng/kg, 40 ng/kg-900 ng/kg, 40 ng/kg-1000 ng/kg, 40 ng/kg-2 µg/kg, 40 ng/kg-3 µg/kg, 40 ng/kg-5 µg/kg, 40 ng/kg-10 µg/kg, 40 ng/kg-20 µg/kg, 40 ng/kg-50 µg/kg, 40 ng/kg-100 µg/kg, 40 ng/kg-200 µg/kg, 40 ng/kg-500 µg/kg, 40 ng/kg-1000 µg/kg, 50 ng/kg-100 ng/kg, 50 ng/kg-200 ng/kg, 50 ng/kg-300 ng/kg, 50 ng/kg-400 ng/kg, 50 ng/kg-500 ng/kg, 50 ng/kg-600 ng/kg, 50 ng/kg-700 ng/kg, 50 ng/kg-800 ng/kg, 50 ng/kg-900 ng/kg, 50 ng/kg-1000 ng/kg, 50 ng/kg-2 µg/kg, 50 ng/kg-3 µg/kg, 50 ng/kg-5 µg/kg, 50 ng/kg-10 µg/kg, 50 ng/kg-20 µg/kg, 50 ng/kg-50 µg/kg, 50 ng/kg-100 µg/kg, 50 ng/kg-200 µg/kg, 50 ng/kg-500 µg/kg, 50 ng/kg-1000 µg/kg, 100 ng/kg-200 ng/kg, 100 ng/kg-300 ng/kg, 100 ng/kg-400 ng/kg, 100 ng/kg-500 ng/kg, 100 ng/kg-600 ng/kg, 100 ng/kg-700 ng/kg, 100 ng/kg-800 ng/kg, 100 ng/kg-900 ng/kg, 100 ng/kg-1000 ng/kg, 100 ng/kg-2 µg/kg, 100 ng/kg-3 µg/kg, 100 ng/kg-5 µg/kg, 100 ng/kg-10 µg/kg, 100 ng/kg-20 µg/kg, 100 ng/kg-50 µg/kg, 100 ng/kg-100 µg/kg, 100 ng/kg-200 µg/kg, 100 ng/kg-500 µg/kg, 100 ng/kg-1000 µg/kg, 200 ng/kg-300 ng/kg, 200 ng/kg-400 ng/kg, 200 ng/kg-500 ng/kg, 200 ng/kg-600 ng/kg, 200 ng/kg-700 ng/kg, 200 ng/kg-800 ng/kg, 200 ng/kg-900 ng/kg, 200 ng/kg-1000 ng/kg, 200 ng/kg-2 µg/kg, 200 ng/kg 3 µg/kg, 200 ng/kg-5 µg/kg, 200 ng/kg-10 µg/kg, 200 ng/kg-20 µg/kg, 200 ng/kg-50 µg/kg, 200 ng/kg-100 µg/kg, 200 ng/kg-200 µg/kg, 200 ng/kg-500 µg/kg, 200 ng/kg-1000 µg/kg, 500 ng/kg-600 ng/kg, 500 ng/kg-700 ng/kg, 500 ng/kg-800 ng/kg, 500 ng/kg-900 ng/kg, 500 ng/kg-1000 ng/kg, 500 ng/kg-2 µg/kg, 500 ng/kg 3 µg/kg, 500 ng/kg-5 µg/kg, 500 ng/kg-10 µg/kg, 500 ng/kg-20 µg/kg, 500 ng/kg-50 µg/kg, 500 ng/kg-100 µg/kg, 500 ng/kg-200 µg/kg, 500 ng/kg-500 µg/kg, or 500 ng/kg-1000 µg/kg. In some embodiments, the dosage is administered in a suitable volume of solution. The exact volume is dependent on the dosage, manner of administration, and the nature and severity of the disorder. For example, suitable volumes can include about 10 µl, 20 µl, 30 µl, 40 µl, 50 µl, 60 µl, 70 µl, 80 µl, 90 µl, 100 µl, 110 µl, 120 µl, 130 µl, 140 µl, 150 µl, 160 µl, 170 µl, 180 µl, 190 µl, 200 µl, 250 µl, 300 µl, 250 µl, 400 µl, 450 µl, 500 µl, 550 µl, 600 µl, 650 µl, 700 µl, 750 µl, 800 µl, 850 µl, 900 µl, 950 µl, 1000 µl, 1100 µl, 1200 µl, 1300 µl, 1400 µl, 1500 µl, 1600 µl, 1700 µl, 1800 µl, 1900 µl, 2000 µl, 2500 µl, 3000 µl, 3500 µl, 4000 µl, 4500 µl, 5000 µl, 6000 µl, 7000 µl, 8000 µl, 9000 µl, and 10000 µl, including ranges between any of two of the listed values, for example, about 10 µl-1000 µl, 10 µl-5000 10 µl-10000 50 µl-1000 50 µl-5000 50 µl-10000 100 µl-1000 100 µl-5000 100 µl-10000 500 µl-5000 or 500 µl-10000 µl. A number of suitable manners of systemic administration are contemplated. For example, the systemic administration can be performed subcutaneously, intravenously, orally, intraperitoneally, or peritumorally or intratumorally (contemplating that the intratumoral administration can also ameliorate and/or eliminate tumors other than the one(s) at or near the site of administration).

Suitable preparation forms are, for example granules, powders, tablets, coated tablets, (micro) capsules, microgranulates effervescent powders or granules, suppositories, injectable solution in ampule form and also preparations with protracted release of active compounds, in whose preparation excipients, diluents or carriers are customarily used as described above. Other preparations may be those which give rise to different release profiles of the active ingredients which are well-known for a person skilled in the art. Examples include sustained-release, sustained-action, extended-release, time-release or timed-release, controlled-release, modified release, or continuous-release. The advantages of sustained-release tablets or capsules are that they can often be taken less frequently than immediate-release formulations of the same drug, and that they keep steadier levels of the drug in the bloodstream. Today, many time-release drugs are formulated so that the active ingredient is embedded in a matrix of insoluble substance(s) (for example some acrylics, or chitin) such that the dissolving drug must find its way out through the holes in the matrix. Some drugs are enclosed in polymer-based tablets with a laser-drilled hole on one side and a porous membrane on the other side. Stomach acids push through the porous membrane, thereby pushing the drug out through the laser-drilled hole. In time, the entire drug dose releases into the system while the polymer container remains intact, to be excreted later through normal digestion. In some formulations, the drug dissolves into the matrix, and the matrix physically swells to form a gel, allowing the drug to exit through the gel's outer surface. Micro-encapsulation is also regarded as a more complete technology to produce complex dissolution profiles. Through coating an active pharmaceutical ingredient around an inert core, and layering it with insoluble substances to form a microsphere it is possible to obtain more consistent and replicable dissolution rates. In some embodiments, the composition comprises at least about at least 0.1% of the immunoregulatory peptide inhibitor by weight, for example, at least 0.1%, 0.2%, 0.5%, 1%, 2%, 3%, 4%, 5%, 6%, 7%, 8%, 9%, 10%, 20%, or 30% of the immunoregulatory peptide inhibitor by weight, including ranges between any two of the listed values. All of those being well-known for a person skilled in the art.

Method of Treating, Preventing, or Inhibiting Multiple Tumors, Such as in Metastatic Cancer Many conditions and diseases are associated with immunosuppression, for example, many types of cancer, infection, and inflammatory disease are associated with immunosuppression. Thus, exemplary conditions associated with immunosuppression that can be treated, prevented, or inhibited using one or more of the immunoregulatory peptide inhibitors described herein include many types of cancer, such as colorectal cancer, colon cancer, renal cancer, breast cancer, skin cancer, ovarian cancer, prostate cancer, pancreatic cancer, lung cancer, or hematopoietic cell cancer. Additional examples include a prostate tumor, a melanoma, a lung carcinoma, an Apocrine gland carcinoma, a testis tumor, a mast cell tumor, a mammary tumor (e.g. a benign mammary tumor or a malignant mammary tumor, for example a mixed mammary tumor such as a benign mixed mammary tumor or a malignant mixed mammary tumor), a mucinous carcinoma (e.g. a mammary gland mucinous carcinoma), or a histicytoma. In particular, it is contemplated that cancers comprising two or more tumors, for example metastatic cancer, or two or more tumors (in which the tumors can be of the same or different type of cancer, for example any of the cancers listed herein, or any two different cancers listed here) can be treated, prevented, inhibited, or ameliorated by the immunoregulatory peptide inhibitors described herein. Optionally, the immunoregulatory peptide inhibitors or compositions comprising the immunoregulatory peptide inhibitors as described herein can be administered to a subset of one or more tumors in a subject (but not all of the tumors), so as to treat, prevent, inhibit, or ameliorate at least one tumor that was not at or near the site of administration. Optionally, the immunoregulatory peptide inhibitors are administered to a primary tumor (but not a remove tumor) of the metastasis so as to treat primary and metastatic tumors. Optionally, the immunoregulatory peptide inhibitors are administered to a metastatic tumor (but not a primary tumor) of the metastasis so as to treat primary and metastatic tumors. Optionally, the immunoregulatory peptide inhibitors are administered to some, but not all primary and metastatic tumors of the metastasis so as to treat primary and metastatic tumors. Optionally, the immunoregulatory peptide inhibitors are administered to primary and metastatic tumors of the metastasis so as to treat these primary and metastatic tumors. Optionally, the immunoregulatory peptide inhibitors or compositions comprising the immunoregulatory peptide inhibitors as described herein can be administered systemically to a subject having two or more tumors, so as to treat, prevent, inhibit, or ameliorate two or more tumors in the subject, even if at least one tumor was not at or near the site of administration. Optionally, the immunoregulatory peptide inhibitors or compositions comprising the immunoregulatory peptide inhibitors can induce regressive changes in, immune cell infiltration of, and/or eradication of the tumor, even if the tumor itself was not at or near the site of administration of the immunoregulatory peptide inhibitor. Exemplary conditions associated with immunosuppression that can be treated, prevented, or inhibited by using one or more of the immunoregulatory peptide inhibitors described herein further include hormonal imbalances, such as increased and/or ectopic cortisol activity.

Accordingly, some embodiments include methods of treating, preventing, or reducing immunosuppression or one or more of the aforementioned infections or diseases in a human, in which the diseases comprise two or more tumors, for example metastatic cancer, or two or more tumors at two or more different sites in the human (in which any two of the tumors can be of the same type of cancer or a different type of cancer). In some embodiments, the method includes identifying a patient having a condition associated with immunosuppression and comprising two or more tumors, for example metastatic cancer, and/or a first tumor at a first site and a metastatic tumor at a second site (in which the first and second tumors can be of the same type of cancer, or of different types of cancer). By way of example, the metastatic cancer can comprise one or more primary tumors, and one or more remote tumors. Such an identification step can be accomplished by clinical evaluation (e.g., CT, MRI, or PET scan) or diagnostic assay. The method further includes administering to the identified or selected patient a composition comprising, consisting of, or consisting essentially of an immunoregulatory peptide inhibitor sequence (for example, a composition comprising an immunoregulatory peptide inhibitor immobilized on a nanoparticle as described herein), or a nucleic acid encoding such a molecule as described herein. For example, the composition comprising, consisting of, or consisting essentially of an immunoregulatory peptide inhibitor can include any one of SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13. In some embodiments, the composition is administered peri-tumorally, or near a tumor, for example within 10, 9, 8, 7, 6, 5, 4, 3, 2, 1, or 0.5 cm of a first tumor in the subject, but is not administered peri-tumorally or near a second tumor in the subject (so that the composition is not administered directly to the second tumor). Both the first and second tumors can undergo regressive changes, so as to treat ameliorate both the first and second tumor. Optionally, the first tumor is a primary tumor, and the second tumor is a metastatic tumor. Optionally, the first tumor is a metastatic tumor, and the second tumor is a primary tumor. Optionally, the first tumor and secondary tumors are both primary tumors. Optionally, the first tumor and secondary tumors are both metastatic tumors. Optionally, the first and second tumor are of the same type of cancer. Optionally, the second tumor is of a different type of cancer than the first tumor. Optionally, the first tumor and second tumor are part of a metastatic cancer. Optionally, the first tumor and second tumor are in different tissues of the subject. Optionally, the first tumor and second tumor are in the same tissue, but the tumors are at least 1 mm apart from each other, for example, at least 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 25 mm, 30 mm, 40 mm, 45 mm, 50 mm 55 mm, 60 mm, 65 mm, 70 mm, 80 mm, 90 mm, 100 mm, 200 mm, 300 mm, 400 mm, or 500 mm apart. Some embodiments include methods of treating, preventing, or reducing immunosuppression or one or more of the aforementioned infections or diseases in a non-human mammal, in which the diseases comprise two or more tumors, for example metastatic cancer, or two or more tumors at two or more different sites in the non-human mammal (in which any two of the tumors can be of the same type of cancer or a different type of cancer).

In some embodiments, the composition is administered systemically. In some embodiments, the composition is administered in conjunction with a second therapeutic agent, for example a therapeutic agent selected to stimulate an immune cell after an LFA-1 receptor of the immune cell has been de-blocked (e.g. bound immunoregulatory peptides or 3028 structures have been displaced from the LFA-1 receptor). In some embodiments, these isolated peptides used in these methods have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values. Optionally, the composition is administered directly to a tumor, and induces regressive changes in the tumor. Optionally, the composition is administered to a subject, and induces regressive changes of a tumor to which the composition is not directly administered. Optionally, the composition is administered directly to a tumor, and induces regressive changes in the tumor, and further induces regressive changes in a second tumor to which the formulation was not directly administered (e.g. a metastatic or contralateral tumor). Optionally, the composition is administered directly to a tumor, and induces eradication of the tumor. Optionally, the composition is administered to a subject, and induces eradication of a tumor to which the composition is not directly administered. Optionally, the composition is administered directly to a tumor, and induces eradication of the tumor, and further induces eradication of a second tumor to which the formulation was not directly administered (e.g. a metastatic or contralateral tumor). Optionally, the composition is administered directly to a tumor, and induces immune cell infiltration of the tumor. Optionally, the composition is administered directly to a tumor, and induces immune cell infiltration of the tumor, and further induces immune cell infiltration of a second tumor to which the formulation was not directly administered (e.g. a metastatic or contralateral tumor). Optionally, the composition is administered to a subject, and induces immune cell infiltration of a tumor to which the composition is not directly administered. Example tumors to which the pharmaceutical composition can be directly or indirect administered include a prostate tumor, a melanoma, a colon cancer, a lung carcinoma, an Apocrine gland carcinoma, a testis tumor, a mast cell tumor, a mammary tumor (e.g. a malignant mammary tumor, for example a mixed mammary tumor such as a malignant mixed mammary tumor), a mucinous carcinoma (e.g. a mammary gland mucinous carcinoma), or a histicytoma. As shown in FIGS. 55-92 and Table 16, administration of compositions comprising immunoregulatory peptide inhibitors as described herein induced regressive changes, immune cell infiltration of, and/or eradication of tumors.

Additionally, the composition comprising, consisting of, or consisting essentially of the immunoregulatory peptide inhibitor used in these methods can comprise, consist of, or consist essentially of a peptide as described herein, or a nucleic acid encoding such a molecule. For example, the peptide inhibitor used in these methods can comprise, consist of, or consist essentially of Formula (I), $XX_1VKX_2X_3X_4$ (SEQ ID NO: 166) as described herein. In some embodiments, X is an optional sequence, and can be KKLDT (SEQ ID NO: 167), RKLDT (SEQ ID NO: 168), KKGDT (SEQ ID NO: 169), KKEDT (SEQ ID NO: 170), KKLDQ (SEQ ID NO: 171), KKGDQ (SEQ ID NO: 252), KKEDQ (SEQ ID NO: 253), RKLDQ (SEQ ID NO: 254), RKGDQ (SEQ ID NO: 255), RKEDQ (SEQ ID NO: 256), RKGTD (SEQ ID NO: 257), RKEDT (SEQ ID NO: 258), KLDT (SEQ ID NO: 172), KGDT (SEQ ID NO: 259), KEDT (SEQ ID NO: 260), KLDQ (SEQ ID NO: 261), KGDQ (SEQ ID NO: 262), KEDQ (SEQ ID NO: 263), LDT, LDQ, GDT, GDQ, EDT, EDQ, DT, DQ, T, or Q, or absent. In some embodiments, $X_1$ is one of FF, FM, FS, FV, FT, FL, AF, AM, AS, AV, AT, AL, VF, VM, VS, VV, VT, or VL. In some embodiments, $X_2$ is one of LS, LQ, LM, LT, LH, VS, VQ, VM, VT, or VH. In some embodiments, $X_3$ is one of LFT, LMT, LQT, LHT, LNT, LPT, LST, LGT, LAT, LRT, QFT, QMT, QQT, QHT, QNT, QPT, QST, QGT, QAT, QRT, VFT, VMT, VQT, VHT, VNT, VPT, VST, VGT, VAT, VRT, MFT, MMT, MQT, MHT, MNT, MPT, MST, MGT, MAT, MRT, LFN, LMN, LQN, LHN, LNN, LPN, LSN, LGN, LAN, LRN, QFN, QMN, QQN, QHN, QNN, QPN, QSN, QGN, QAN, QRN, VFN, VMN, VQN, VHN, VNN, VPN, VSN, VGN, VAN, VRN, MFN, MMN, MQN, MHN, MNN, MPN, MSN, MGN, MAN, MRN, LFP, LMP, LQP, LHP, LNP, LPP, LSP, LGP, LAP, LRP, QFP, QMP, QQP, QHP, QNP, QPP, QSP, QGP, QAP, QRP, VFP, VMP, VQP, VHP, VNP, VPP, VSP, VGP, VAP, VRP, MFP, MMP, MQP, MHP, MNP, MPP, MSP, MGP, MAP, MRPR, LFR, LMR, LQR, LHR, LNR, LPR, LSR, LGR, LAR, LRR, QFR, QMR, QQR, QHR, QNR, QPR, QSR, QGR, QAR, QRR, VFR, VMR, VQR, VHR, VNR, VPR, VSR, VGR, VAR, VRR, MFR, MMR, MQR, MHR, MNR, MPR, MSR, MGR, MAR, or MRR. In some embodiments, $X_4$ is an optional sequence, and can be ER, or E, or absent. In some embodiments, if X is absent, $X_1$ is FF, and $X_2$ is LS. In some embodiments, the isolated peptides that comprise Formula (I) used in these methods have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of Formula (II), $X_{20}TFFVKLSX_{21}X_{22}$ (SEQ ID NO: 173), as described herein. In some embodiments, $X_{20}$ is an optional sequence, and can be KKLD (SEQ ID NO: 174), RKLD (SEQ ID NO: 175), KKGD (SEQ ID NO: 176), KKED (SEQ ID NO: 177), KLD, LD, D, or absent. $X_{21}$ is an optional sequence, and can be LFT, LMT, LQT, LHT, LNT, LPT, LST, LGT, LAT, LRT, QFT, QMT, QQT, QHT, QNT, QPT, QST, QGT, QAT, QRT, VFT, VMT, VQT, VHT, VNT, VPT, VST, VGT, VAT, VRT, MFT, MMT, MQT, MHT, MNT, MPT, MST, MGT, MAT, MRT, LFN, LMN, LQN, LHN, LNN, LPN, LSN, LGN, LAN, LRN, QFN, QMN, QQN, QHN, QNN, QPN, QSN, QGN, QAN, QRN, VFN, VMN, VQN, VHN, VNN, VPN, VSN, VGN, VAN, VRN, MFN, MMN, MQN, MHN, MNN, MPN, MSN, MGN, MAN, MRN, LFP, LMP, LQP, LHP, LNP, LPP, LSP, LGP, LAP, LRP, QFP, QMP, QQP, QHP, QNP, QPP, QSP, QGP, QAP, QRP, VFP, VMP, VQP, VHP, VNP, VPP, VSP, VGP, VAP, VRP, MFP, MMP, MQP, MHP, MNP, MPP, MSP, MGP, MAP, MRPR, LFR, LMR, LQR, LHR, LNR, LPR, LSR, LGR, LAR, LRR, QFR, QMR, QQR, QHR, QNR, QPR, QSR, QGR, QAR, QRR, VFR, VMR, VQR, VHR, VNR, VPR, VSR, VGR, VAR, VRR, MFR, MMR, MQR, MHR, MNR, MPR, MSR, MGR, MAR, or MRR, or absent. In some embodiments, $X_{22}$ is an optional sequence, and can be ER, or E, or absent. In some embodiments, the isolated peptides that comprise Formula (II) used in these methods have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of Formula (III), $X_{30}X_{31}VKLX_{32}LX_{33}TEX_{34}$ (SEQ ID NO: 178). In some embodiments, $X_{30}$ is an optional sequence, and can be KKLDTF (SEQ ID NO: 179), KLDTF (SEQ ID NO: 180), LDTF (SEQ ID NO: 181), DTF, TF, or F, or absent. In some embodiments, $X_{31}$ is an optional sequence, and can be F, S, M, V, T, or L, or absent. In some embodiments, $X_{31}$ is F. In some embodiments, $X_{32}$ can be S, Q, M, T, or H. In some embodiments, $X_{32}$ is S. $X_{33}$ can be F, M, Q, H, N, P, S, G, A, or R. In some embodiments, $X_{34}$ is F. $X_{34}$ is an optional sequence, and can be R or absent. In some embodiments, the isolated peptides that comprise Formula (III) used in these methods have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of Formula (VII), $X_{700}K\ X_{701}X_{702}X_{703}\ X_{704}X_{705}X_{706}K\ X_{707}\ X_{708}\ X_{709}\ X_{710}\ X_{711}E\ X_{712}$ (SEQ ID NO: 394), as described herein. In some embodiments, $X_{700}$ is an optional sequence, and can be K,A,D,E,G,H,I,L,M,N,P,Q,R,T, or V, or absent. In some embodiments, $X_{701}$ is an optional sequence, and can be L,A,C,D,E,F,G,H,I,K,M,N,Q,R,S,T, or V, or absent. In some embodiments, $X_{702}$ is an optional sequence, and can be D,A,E,I,V,W, or Y, or absent. In some embodiments, $X_{703}$ is an optional sequence, and can be T,C,M,N,P,Q,R,S,W, or Y, or absent. In some embodiments, $X_{704}$ is an optional sequence, and can be F,A,I,M,N,P,T, or V, or absent. In some embodiments, $X_{705}$ is an optional sequence, and can be F,L,M,Q,S,T, or V, or absent. In some embodiments, $X_{706}$ is an optional sequence, and can be V,F,G,L,P, or R, or absent. In some embodiments, $X_{707}$ is an optional sequence, and can be L,A,F,G,I,M,N,P,Q,R,S,T,V, or Y, or absent. In some embodiments, $X_{708}$ is an optional sequence, and can be S,H,M,N,Q, or T, or absent. In some embodiments, $X_{709}$ is an optional sequence, and can be L,A,H,I,M,N,Q,R,S,T,V, or W, or absent. In some embodiments, $X_{710}$ is an optional sequence, and can be F,A,C,G,H,I,L,M,N,P,Q,R,S,T,V, or W, or absent. In some embodiments, $X_{711}$ is an optional sequence, and can be T,F,G,H,I,L,M,N,P,S,V, or W, or absent. In some embodiments, $X_{712}$ is an optional sequence, and can be R,F,K,N,R,T, or Y, or absent. In some embodiments, the isolated peptide comprising Formula (VII) has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of Formula (VIII), $X_{800}K\ X_{801}K\ X_{802}E\ X_{803}$ (SEQ ID NO: 395), as described herein. In some embodiments, $X_{800}$ is an optional sequence, and can be K, A, D, E, G, H, I, L, M, N, P, Q, R, T, V, or K, or absent. In some embodiments, $X_{801}$ is an optional sequence, and can be LDTFFV, GDTFFV, EDTFFV, LDQFFV, LDTAFV, LDTVFV, LDTFMV, LDTFSV, LDTFVV, LDTFTV, LDTFLV, LDGFFV, LDTFGV, LDTFFK, ADTFFV, CDTFFV, DDTFFV, FDTFFV, HDTFFV, IDTFFV, KDTFFV, MDTFFV, NDTFFV, QDTFFV, RDTFFV, SDTFFV, TDTFFV, VDTFFV, LATFFV, LETFFV, LITFFV, LVTFFV, LWTFFV, LYTFFV, LDCFFV, LDMFFV, LDNFFV, LDPFFV, LDRFFV, LDSFFV, LDWFFV, LDYFFV, LDTIFV, LDTMFV, LDTNFV, LDTPFV, LDTTFV, LDTFQV, LDTFFF, LDTFFG, LDTFFL, LDTFFP, LDTFFR, LDTFIV, LDTSFV, LDTFAV, LDTFCV, LDTQFV, LDTLFV, LTTFFV, LDTFFI, LDHFFV, LMTFFV, LDTFEV, LDTFWV, LFTFFV, LDVFFV, LDTFRV, LDTFHV, LDTYFV, LPTFFV, PDTFFV, LDTFPV, LDTFNV, LDTWFV, LDTGFV, LDAFFV, LQTFFV, LCTFFV, LSTFFV, YDTFFV, LDEFFV, WDTFFV, LDTKFV, LDTCFV, LDTFYV, LDTHFV, LHTFFV, LRTFFV, LDLFFV, LDTRFV, LLTFFV, LDTFDV, LDTFFA, LDTFFT, LNTFFV, LDDFFV, LDIFFV, LDFFFV, LKTFFV, LDTFFQ, LGTFFV, LDTFFC, LDKFFV, LDTFKV, LDTEFV, LDTFFW, LDTFFM, LDTFFS, LDTFFH, LDTFFY, LDTFFN, LDTDFV, LDTFFE, LDTFFD, LTFFV, LDTFF, TFFV, LDF, LDTE, FFV, LDV, LV, or L, or absent. In some embodiments, $X_{802}$ is an optional sequence, and can be LSLFT, VSLFT, LQLFT, LMLFT, LTLFT, LHLFT, LSQFT, LSVFT, LSMFT, LSLMT, LSLQT, LSLHT, LSLNT, LSLPT, LSLST, LSLGT, LSLAT, LSLRT, LSLFN, LSLFP, LSLFR, LGLFT, ASLFT, FSLFT, GSLFT, ISLFT, MSLFT, NSLFT, PSLFT, QSLFT, RSLFT, SSLFT, TSLFT, YSLFT, LNLFT, LSAFT, LSHFT, LSIFT, LSNFT, LSRFT, LSSFT, LSTFT, LSWFT, LSLCT, LSLIT, LSLLT, LSLTT, LSLVT, LSLWT, LSLFF, LSLFG, LSLFH, LSLFI, LSLFL, LSLFM, LSLFS, LSLFV, LSLFW, LYLFT, LVLFT, LSFFT, LSGFT, LSKFT, LSCFT, LCLFT, LRLFT, LPLFT, LWLFT, LKLFT, LDLFT, LSYFT, LALFT, WSLFT, LSLFA, LSLFQ, LSPFT, HSLFT, LSLYT, LILFT, KSLFT, CSLFT, LSLFY, LSLFK, LSLFC, LFLFT, LELFT, LSLKT, LLLFT, LSLFD, LSLDT, LSLFE, DSLFT, LSLET, LSDFT, LSEFT, ESLFT, SLFT, LSFT, LFT, LSL, LT, or T, or absent. In some embodiments, $X_{803}$ is an optional sequence, and can be R, F, K, N, R, T, or Y, or absent. In some embodiments, the isolated peptide comprising Formula (VIII) has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor can comprise, consist of, or consist essentially of Formula (IX). Accordingly, in some embodiments, the peptide inhibitor comprises a peptide of Formula (IX): $X_{901}X_{902}X_{903}X_{904}X_{905}X_{906}X_{907}X_{908}X_{909}X_{910}X_{911}X_{912}X_{913}X_{914}X_{915}X_{916}X_{917}$, wherein $X_{901}$ is any amino acid or absent; $X_{902}$ is a positively charged amino acid, F, or N; $X_{903}$ is any amino acid; $X_{904}$ is any amino acid; $X_{905}$ is a polar uncharged amino acid, R, Y, or W; $X_{906}$ is a hydrophobic or uncharged polar amino acid; $X_{907}$ is a hydrophobic or uncharged polar amino acid; $X_{908}$ is a hydrophobic, non-aromatic carbon chain amino acid that is not M or F; $X_{909}$ is a positively charged amino acid, T, Q, or Y; $X_{910}$ is any amino acid that is not negatively charged; $X_{911}$ is a polar uncharged amino acid or H; $X_{912}$ is any amino acid that is not negatively charged; $X_{913}$ is any amino acid that is not negatively charged; $X_{914}$ is any amino acid that is not negatively charged; $X_{915}$ is a negatively charged amino acid, Y, or Q; $X_{916}$ is any amino acid that is not negatively charged; and $X_{917}$ is one or more positively charged amino acids or is absent. Optionally, $X_{901}$ comprises a positively charged amino acid. Optionally $X_{901}$ is an R or K. Optionally $X_{917}$ is RR. In some embodiments, the isolated peptide comprising Formula (IX) has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of and/or SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13. In some embodiments, these isolated peptides used in these methods have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of a peptide inhibitor that comprises, consists of, or consists essentially of any one or more of the peptides set forth in SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13. In some embodiments, the isolated peptide used in these methods has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

In some embodiments, a nucleic acid encoding such a peptide inhibitor can be provided, for example a nucleic acid of SEQ ID NOs: 102-165. Preferably, the immunoregulatory peptide inhibitor used in the aforementioned methods is P28R, a derivative thereof, or a nucleic acid encoding such a molecule (e.g., any one or more of the immunoregulatory peptide inhibitors comprise, consist of, or consists essentially of a peptide as described herein. For example, the peptide inhibitor can comprise, consist of, or consist essentially of Formula (I), $XX_1VKX_2X_3X_4$ (SEQ ID NO: 166) as described herein. In some embodiments, X is an optional sequence, and can be KKLDT (SEQ ID NO: 167), RKLDT (SEQ ID NO: 168), KKGDT (SEQ ID NO: 169), KKEDT (SEQ ID NO: 170), KKLDQ (SEQ ID NO: 171), KKGDQ (SEQ ID NO: 252), KKEDQ (SEQ ID NO: 253), RKLDQ (SEQ ID NO: 254), RKGDQ (SEQ ID NO: 255), RKEDQ (SEQ ID NO: 256), RKGTD (SEQ ID NO: 257), RKEDT (SEQ ID NO: 258), KLDT (SEQ ID NO: 172), KGDT (SEQ ID NO: 259), KEDT (SEQ ID NO: 260), KLDQ (SEQ ID NO: 261), KGDQ (SEQ ID NO: 262), KEDQ (SEQ ID NO: 263), LDT, LDQ, GDT, GDQ, EDT, EDQ, DT, DQ, T, or Q, or absent. In some embodiments, $X_1$ is one of FF, FM, FS, FV, FT, FL, AF, AM, AS, AV, AT, AL, VF, VM, VS, VV, VT, or VL. In some embodiments, $X_2$ is one of LS, LQ, LM, LT, LH, VS, VQ, VM, VT, or VH. In some embodiments, $X_3$ is one of LFT, LMT, LQT, LHT, LNT, LPT, LST, LGT, LAT, LRT, QFT, QMT, QQT, QHT, QNT, QPT, QST, QGT, QAT, QRT, VFT, VMT, VQT, VHT, VNT, VPT, VST, VGT, VAT, VRT, MFT, MMT, MQT, MHT, MNT, MPT, MST, MGT, MAT, MRT, LFN, LMN, LQN, LHN, LNN, LPN, LSN, LGN, LAN, LRN, QFN, QMN, QQN, QHN, QNN, QPN, QSN, QGN, QAN, QRN, VFN, VMN, VQN, VHN, VNN, VPN, VSN, VGN, VAN, VRN, MFN, MMN, MQN, MHN, MNN, MPN, MSN, MGN, MAN, MRN, LFP, LMP, LQP, LHP, LNP, LPP, LSP, LGP, LAP, LRP, QFP, QMP, QQP, QHP, QNP, QPP, QSP, QGP, QAP, QRP, VFP, VMP, VQP, VHP, VNP, VPP, VSP, VGP, VAP, VRP, MFP, MMP, MQP, MHP, MNP, MPP, MSP, MGP, MAP, MRPR, LFR, LMR, LQR, LHR, LNR, LPR, LSR, LGR, LAR, LRR, QFR, QMR, QQR, QHR, QNR, QPR, QSR, QGR, QAR, QRR, VFR, VMR, VQR, VHR, VNR, VPR, VSR, VGR, VAR, VRR, MFR, MMR, MQR, MHR, MNR, MPR, MSR, MGR, MAR, or MRR. In some embodiments, $X_4$ is an optional sequence, and can be ER, or E, or absent. In some embodiments, if X is absent, $X_1$ is FF, and $X_2$ is LS. In some embodiments, the isolated peptides that comprise Formula (I) have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor can comprise, consist of, or consist essentially of Formula (II), $X_{20}TFFVKLSX_{21}X_{22}$ (SEQ ID NO: 173). In some embodiments, $X_{20}$ is an optional sequence, and can be KKLD (SEQ ID NO: 174), RKLD (SEQ ID NO: 175), KKGD (SEQ ID NO: 176), KKED (SEQ ID NO: 177), KLD, LD, or D, or absent. $X_{21}$ is an optional sequence, and can be LFT, LMT, LQT, LHT, LNT, LPT, LST, LGT, LAT, LRT, QFT, QMT, QQT, QHT, QNT, QPT, QST, QGT, QAT, QRT, VFT, VMT, VQT, VHT, VNT, VPT, VST, VGT, VAT, VRT, MFT, MMT, MQT, MHT, MNT, MPT, MST, MGT, MAT, MRT, LFN, LMN, LQN, LHN, LNN, LPN, LSN, LGN, LAN, LRN, QFN, QMN, QQN, QHN, QNN, QPN, QSN, QGN, QAN, QRN, VFN, VMN, VQN, VHN, VNN, VPN, VSN, VGN, VAN, VRN, MFN, MMN, MQN, MHN, MNN, MPN, MSN, MGN, MAN, MRN, LFP, LMP, LQP, LHP, LNP, LPP, LSP, LGP, LAP, LRP, QFP, QMP, QQP, QHP, QNP, QPP, QSP, QGP, QAP, QRP, VFP, VMP, VQP, VHP, VNP, VPP, VSP, VGP, VAP, VRP, MFP, MMP, MQP, MHP, MNP, MPP, MSP, MGP, MAP, MRPR, LFR, LMR, LQR, LHR, LNR, LPR, LSR, LGR, LAR, LRR, QFR, QMR, QQR, QHR, QNR, QPR, QSR, QGR, QAR, QRR, VFR, VMR, VQR, VHR, VNR, VPR, VSR, VGR, VAR, VRR, MFR, MMR, MQR, MHR, MNR, MPR, MSR, MGR, MAR, or MRR, or absent. In some embodiments, $X_{22}$ is an optional sequence, and can be ER, or E, or absent. In some embodiments, the isolated peptides that comprise Formula (II) have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor can comprise, consist of, or consist essentially of Formula (III), $X_{30}X_{31}VKLX_{32}LX_{33}TEX_{34}$ (SEQ ID NO: 178). In some embodiments, $X_{30}$ is an optional sequence, and can be KKLDTF (SEQ ID NO: 179), KLDTF (SEQ ID NO: 180), LDTF (SEQ ID NO: 181), DTF, TF, F, or absent. In some embodiments, $X_{31}$ is an optional sequence, and can be F, S, M, V, T, or L, or absent. In some embodiments, $X_{31}$ is F. In some embodiments, $X_{32}$ can be S, Q, M, T, or H. In some embodiments, $X_{32}$ is S. $X_{33}$ can be F, M, Q, H, N, P, S, G, A, or R. In some embodiments, $X_{34}$ is F. $X_{34}$ is an optional sequence, and can be R or absent. In some embodiments, the isolated peptides that comprise Formula (III) have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor can comprise, consist of, or consist essentially of Formula (VII), $X_{700}K$ $X_{701}X_{702}X_{703}$ $X_{704}X_{705}X_{706}K$ $X_{707}$ $X_{708}$ $X_{709}$ $X_{710}$ $X_{71}E$ $X_{712}$ (SEQ ID NO: 394), as described herein. In some embodiments, $X_{700}$ is an optional sequence, and can be K,A,D,E,G,H,I,L,M,N,P,Q,R,T, or V, or absent. In some embodiments, $X_{701}$ is an optional sequence, and can be L,A,C,D,E,F,G,H,I,K,M,N,Q,R,S,T, or V, or absent. In some embodiments, $X_{702}$ is an optional sequence, and can be D,A,E,I,V,W, or Y, or absent. In some embodiments, $X_{703}$ is an optional sequence, and can be T,C,M,N,P,Q,R,S,W, or Y, or absent. In some embodiments, $X_{704}$ is an optional sequence, and can be F,A,I,M,N,P,T, or V, or absent. In some embodiments, $X_{705}$ is an optional sequence, and can be F,L,M,Q,S,TV, or absent. In some embodiments, $X_{706}$ is an optional sequence, and can be V,F,G,L,P, or R, or absent. In some embodiments, $X_{707}$ is an optional sequence, and can be L,A,F,G,I,M,N,P,Q,R,S,T,V, or Y, or absent. In some embodiments, $X_{708}$ is an optional sequence, and can be S,H,M,N,Q, or T, or absent. In some embodiments, $X_{709}$ is an optional sequence, and can be L,A,H,I,M,N,Q,R,S,T,V, or W, or absent. In some embodiments, $X_{710}$ is an optional sequence, and can be F,A,C,G,H,I,L,M,N,P,Q,R,S,T,V, or W, or absent. In some embodiments, $X_{711}$ is an optional sequence, and can be T,F,G,H,I,L,M,N,P,S,V, or W, or absent. In some embodiments, $X_{712}$ is an optional sequence, and can be R,F,K,N,R,T,+ or Y, or absent. In some embodiments, the isolated peptide comprising Formula (VII) has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor can comprise, consist of, or consist essentially of Formula (VIII), $X_{800}K$ $X_{801}K$ $X_{802}E$ $X_{803}$ (SEQ ID NO: 395), as described herein. In some embodiments, $X_{800}$ is an optional sequence, and can be K, A, D, E, G, H, I, L, M, N, P, Q, R, T, V, or K, or absent. In some embodiments, $X_{801}$ is an optional sequence, and can be LDTFFV, GDTFFV, EDTFFV, LDQFFV, LDTAFV, LDTVFV, LDTFMV, LDTFSV, LDTFVV, LDTFTV, LDTFLV, LDGFFV, LDTFGV, LDTFFK, ADTFFV, CDTFFV, DDTFFV, FDTFFV, HDTFFV, IDTFFV, KDTFFV, MDTFFV, NDTFFV, QDTFFV, RDTFFV, SDTFFV, TDTFFV, VDTFFV, LATFFV, LETFFV, LITFFV, LVTFFV, LWTFFV, LYTFFV, LDCFFV, LDMFFV, LDNFFV, LDPFFV, LDRFFV, LDSFFV, LDWFFV, LDYFFV, LDTIFV, LDTMFV, LDTNFV, LDTPFV, LDTTFV, LDTFQV, LDTFFF, LDTFFG, LDTFFL, LDTFFP, LDTFFR, LDTFIV, LDTSFV, LDTFAV, LDTFCV, LDTQFV, LDTLFV, LTTFFV, LDTFFI, LDHFFV, LMTFFV, LDTFEV, LDTFWV, LFTFFV, LDVFFV, LDTFRV, LDTFHV, LDTYFV, LPTFFV, PDTFFV, LDTFPV, LDTFNV, LDTWFV, LDTGFV, LDAFFV, LQTFFV, LCTFFV, LSTFFV, YDTFFV, LDEFFV, WDTFFV, LDTKFV, LDTCFV, LDTFYV, LDTHFV, LHTFFV, LRTFFV, LDLFFV, LDTRFV, LLTFFV, LDTFDV, LDTFFA, LDTFFT, LNTFFV, LDDFFV, LDIFFV, LDFFFV, LKTFFV, LDTFFQ, LGTFFV, LDTFFC, LDKFFV, LDTFKV, LDTEFV, LDTFFW, LDTFFM, LDTFFS, LDTFFH, LDTFFY, LDTFFN, LDTDFV, LDTFFE, LDTFFD, LTFFV, LDTFF, TFFV, LDF, LDTE, FFV, LDV, LV, or L, or absent. In some embodiments, $X_{802}$ is an optional sequence, and can be LSLFT, VSLFT, LQLFT, LMLFT, LTLFT, LHLFT, LSQFT, LSVFT, LSMFT, LSLMT, LSLQT, LSLHT, LSLNT, LSLPT, LSLST, LSLGT, LSLAT, LSLRT, LSLFN, LSLFP, LSLFR, LGLFT, ASLFT, FSLFT, GSLFT, ISLFT, MSLFT, NSLFT, PSLFT, QSLFT, RSLFT, SSLFT, TSLFT, YSLFT, LNLFT, LSAFT, LSHFT, LSIFT, LSNFT, LSRFT, LSSFT, LSTFT, LSWFT, LSLCT, LSLIT, LSLLT, LSLTT, LSLVT, LSLWT, LSLFF, LSLFG, LSLFH, LSLFI, LSLFL, LSLFM, LSLFS, LSLFV, LSLFW, LYLFT, LVLFT, LSFFT, LSGFT, LSKFT, LSCFT, LCLFT, LRLFT, LPLFT, LWLFT, LKLFT, LDLFT, LSYFT, LALFT, WSLFT, LSLFA, LSLFQ, LSPFT, HSLFT, LSLYT, LILFT, KSLFT, CSLFT, LSLFY, LSLFK, LSLFC, LFLFT, LELFT, LSLKT, LLLFT, LSLFD, LSLDT, LSLFE, DSLFT, LSLET, LSDFT, LSEFT, ESLFT, SLFT, LSFT, LFT, LSL, LT, or T, or absent. In some embodiments, $X_{803}$ is an optional sequence, and can be R, F, K, N, R, T, or Y, or absent. In some embodiments, the isolated peptide comprising Formula (VIII) has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor can comprise, consist of, or consist essentially of Formula (IX). Accordingly, in some embodiments, the peptide inhibitor comprises a peptide of Formula (IX): $X_{901}X_{902}X_{903}X_{904}X_{905}X_{906}X_{907}X_{908}X_{909}X_{910}X_{911}X_{912}X_{913}X_{914}X_{915}X_{916}X_{917}$, wherein $X_{901}$ is any amino acid or absent; $X_{902}$ is a positively charged amino acid, F, or N; $X_{903}$ is any amino acid; $X_{904}$ is any amino acid; $X_{905}$ is a polar uncharged amino acid, R, Y, or W; $X_{906}$ is a hydrophobic or uncharged polar amino acid; $X_{907}$ is a hydrophobic or uncharged polar amino acid; $X_{908}$ is a hydrophobic, non-aromatic carbon chain amino acid that is not M or F; $X_{909}$ is a positively charged amino acid, T, Q, or Y; $X_{910}$ is any amino acid that is not negatively charged; $X_{911}$ is a polar uncharged amino acid or H; $X_{912}$ is any amino acid that is not negatively charged; $X_{913}$ is any amino acid that is not negatively charged; $X_{914}$ is any amino acid that is not negatively charged; $X_{915}$ is a negatively charged amino acid, Y, or Q; $X_{916}$ is any amino acid that is not negatively charged; and $X_{917}$ is one or more positively charged amino acids or is absent. Optionally, $X_{901}$ comprises a positively charged amino acid. Optionally $X_{901}$ is an R or K. Optionally $X_{917}$ is RR. In some embodiments, the isolated peptide comprising Formula (IX) has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor can comprise, consist of, or consist essentially of and/or SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13, as described herein. In some embodiments, the isolated peptides have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor can comprise, consist of, or consist essentially of a peptide inhibitor that comprises, consists of, or consists essentially of any one or more of the peptides set forth in Table 5.1, 5.4, 5.5, or 5.6 or any variation or combination of variations of P28R or P28 core as provided in Tables 5.3 and 13 In some embodiments, the isolated peptide from Table 5.1, 5.4, 5.5, or 5.6 or any variation or combination of variations of P28R or P28 core as provided in Tables 5.3 and 13 has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values. For example, a nucleic acid encoding such a peptide inhibitor can be provided, by SEQ ID NOs: 102-165.

The immunoregulatory peptide inhibitors used in the aforementioned methods can comprise at least one D amino acid, at least one non-natural amino acid, an N-terminal acetyl group, or a C terminal amide group and said immunoregulatory peptide inhibitors can be glycosylated or joined to PEG, a cytotoxin, or radionuclide. The peptide can be administered to at least one cell of the patient. The administration can be performed in vivo, for example therapeutically. The administration can be performed ex vivo, for example as a diagnostic tool, or as an ex vivo therapy to stimulate immune cells of the patient before the immune cells are administered to the patient. Administration of an immunoregulatory peptide inhibitor comprising, consisting, or consisting essentially of a peptide inhibitor as described herein, or a nucleic acid encoding such a molecule to human immune cells, and detection of immune cell stimulation is described in Example 13). For example, the peptide inhibitor used in these methods can comprise, consist of, or consist essentially of Formula (I), $XX_1VKX_2X_3X_4$ (SEQ ID NO: 166) as described herein. In some embodiments, X is an optional sequence, and can be KKLDT (SEQ ID NO: 167), RKLDT (SEQ ID NO: 168), KKGDT (SEQ ID NO: 169), KKEDT (SEQ ID NO: 170), KKLDQ (SEQ ID NO: 171), KKGDQ (SEQ ID NO: 252), KKEDQ (SEQ ID NO: 253), RKLDQ (SEQ ID NO: 254), RKGDQ (SEQ ID NO: 255), RKEDQ (SEQ ID NO: 256), RKGTD (SEQ ID NO: 257), RKEDT (SEQ ID NO: 258), KLDT (SEQ ID NO: 172), KGDT (SEQ ID NO: 259), KEDT (SEQ ID NO: 260), KLDQ (SEQ ID NO: 261), KGDQ (SEQ ID NO: 262), KEDQ (SEQ ID NO: 263), LDT, LDQ, GDT, GDQ, EDT, EDQ, DT, DQ, T, or Q, or absent. In some embodiments, $X_1$ is be one of FF, FM, FS, FV, FT, FL, AF, AM, AS, AV, AT, AL, VF, VM, VS, VV, VT, or VL. In some embodiments, $X_2$ is one of LS, LQ, LM, LT, LH, VS, VQ, VM, VT, or VH. In some embodiments, $X_3$ is be one of LFT, LMT, LQT, LHT, LNT, LPT, LST, LGT, LAT, LRT, QFT, QMT, QQT, QHT, QNT, QPT, QST, QGT, QAT, QRT, VFT, VMT, VQT, VHT, VNT, VPT, VST, VGT, VAT, VRT, MFT, MMT, MQT, MHT, MNT, MPT, MST, MGT, MAT, MRT, LFN, LMN, LQN, LHN, LNN, LPN, LSN, LGN, LAN, LRN, QFN, QMN, QQN, QHN, QNN, QPN, QSN, QGN, QAN, QRN, VFN, VMN, VQN, VHN, VNN, VPN, VSN, VGN, VAN, VRN, MFN, MMN, MQN, MHN, MNN, MPN, MSN, MGN, MAN, MRN, LFP, LMP, LQP, LHP, LNP, LPP, LSP, LGP, LAP, LRP, QFP, QMP, QQP, QHP, QNP, QPP, QSP, QGP, QAP, QRP, VFP, VMP, VQP, VHP, VNP, VPP, VSP, VGP, VAP, VRP, MFP, MMP, MQP, MHP, MNP, MPP, MSP, MGP, MAP, MRPR, LFR, LMR, LQR, LHR, LNR, LPR, LSR, LGR, LAR, LRR, QFR, QMR, QQR, QHR, QNR, QPR, QSR, QGR, QAR, QRR, VFR, VMR, VQR, VHR, VNR, VPR, VSR, VGR, VAR, VRR, MFR, MMR, MQR, MHR, MNR, MPR, MSR, MGR, MAR, or MRR. In some embodiments, $X_4$ is an optional sequence, and can be ER, or E, or absent. In some embodiments, if X is absent, $X_1$ is FF, and $X_2$ is LS. In some embodiments, the isolated peptides that comprise Formula (I) used in these methods have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of Formula (II), $X_{20}TFFVKLSX_{21}X_{22}$ (SEQ ID NO: 173). In some embodiments, $X_{20}$ is an optional sequence, and can be KKLD (SEQ ID NO: 174), RKLD (SEQ ID NO: 175), KKGD (SEQ ID NO: 176), KKED (SEQ ID NO: 177), KLD, LD, or D, or absent. $X_{21}$ is an optional sequence, and can be LFT, LMT, LQT, LHT, LNT, LPT, LST, LGT, LAT, LRT, QFT, QMT, QQT, QHT, QNT, QPT, QST, QGT, QAT, QRT, VFT, VMT, VQT, VHT, VNT, VPT, VST, VGT, VAT, VRT, MFT, MMT, MQT, MHT, MNT, MPT, MST, MGT, MAT, MRT, LFN, LMN, LQN, LHN, LNN, LPN, LSN, LGN, LAN, LRN, QFN, QMN, QQN, QHN, QNN, QPN, QSN, QGN, QAN, QRN, VFN, VMN, VQN, VHN, VNN, VPN, VSN, VGN, VAN, VRN, MFN, MMN, MQN, MHN, MNN, MPN, MSN, MGN, MAN, MRN, LFP, LMP, LQP, LHP, LNP, LPP, LSP, LGP, LAP, LRP, QFP, QMP, QQP, QHP, QNP, QPP, QSP, QGP, QAP, QRP, VFP, VMP, VQP, VHP, VNP, VPP, VSP, VGP, VAP, VRP, MFP, MMP, MQP, MHP, MNP, MPP, MSP, MGP, MAP, MRPR, LFR, LMR, LQR, LHR, LNR, LPR, LSR, LGR, LAR, LRR, QFR, QMR, QQR, QHR, QNR, QPR, QSR, QGR, QAR, QRR, VFR, VMR, VQR, VHR, VNR, VPR, VSR, VGR, VAR, VRR, MFR, MMR, MQR, MHR, MNR, MPR, MSR, MGR, MAR, or MRR, or absent. In some embodiments, $X_{22}$ is an optional sequence, and can be ER, or E, or absent. In some embodiments, the isolated peptides that comprise Formula (II) used in these methods have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of Formula (III), $X_{30}X_{31}VKLX_{32}LX_{33}TEX_{34}$ (SEQ ID NO: 178). In some embodiments, $X_{30}$ is an optional sequence, and can be KKLDTF (SEQ ID NO: 179), KLDTF (SEQ ID NO: 180), LDTF (SEQ ID NO: 181), DTF, TF, or F, or absent. In some embodiments, $X_{31}$ is an optional sequence, and can be F, S, M, V, T, or L, or absent. In some embodiments, $X_{31}$ is F. In some embodiments, $X_{32}$ can be S, Q, M, T, or H. In some embodiments, $X_{32}$ is S. $X_{33}$ can be F, M, Q, H, N, P, S, G, A, or R. In some embodiments, $X_{34}$ is F. $X_{34}$ is an optional sequence, and can be R or absent. In some embodiments, the isolated peptides that comprise Formula (III) used in these methods have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of Formula (VII), $X_{700}K\ X_{701}X_{702}X_{703}\ X_{704}X_{705}X_{706}K\ X_{707}\ X_{708}\ X_{709}\ X_{710}\ X_{711}E\ X_{712}$ (SEQ ID NO: 394), as described herein. In some embodiments, $X_{700}$ is an optional sequence, and can be K,A,D,E,G,H,I,L,M,N,P,Q,R,T, or V, or absent. In some embodiments, $X_{701}$ is an optional sequence, and can be L,A,C,D,E,F,G,H,I,K,M,N,Q,R,S,T, or V, or absent. In some embodiments, $X_{702}$ is an optional sequence, and can be D,A,E,I,V,W,Y, or absent. In some embodiments, $X_{703}$ is an optional sequence, and can be T,C,M,N,P,Q,R,S,W,Y, or absent. In some embodiments, $X_{704}$ is an optional sequence, and can be F,A,I,M,N,P,T, or V, or absent. In some embodiments, $X_{705}$ is an optional sequence, and can be F,L,M,Q, S,T, or V, or absent. In some embodiments, $X_{706}$ is an optional sequence, and can be V,F,G,L,P, or R, or absent. In some embodiments, $X_{707}$ is an optional sequence, and can be L,A,F,G,I,M,N,P,Q,R,S,T,V, or Y, or absent. In some embodiments, $X_{708}$ is an optional sequence, and can be S,H,M,N,Q, or T, or absent. In some embodiments, $X_{700}$ is an optional sequence, and can be L,A,H,I,M,N,Q,R,S,T,V, or W, or absent. In some embodiments, $X_{710}$ is an optional sequence, and can be F,A,C,G,H,I,L,M,N,P,Q,R,S,T,V, or W, or absent. In some embodiments, $X_{711}$ is an optional sequence, and can be T,F,G,H,I,L,M,N,P,S,V, or W, or absent. In some embodiments, $X_{712}$ is an optional sequence, and can be R,F,K,N,R,T, or Y, or absent. In some embodiments, the isolated peptide comprising Formula (VII) has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of Formula (VIII), $X_{800}K$ $X_{801}K$ $X_{802}E$ $X_{803}$ (SEQ ID NO: 395), as described herein. In some embodiments, $X_{800}$ is an optional sequence, and can be K, A, D, E, G, H, I, L, M, N, P, Q, R, T, V, or K, or absent. In some embodiments, $X_{801}$ is an optional sequence, and can be LDTFFV, GDTFFV, EDTFFV, LDQFFV, LDTAFV, LDTVFV, LDTFMV, LDTFSV, LDTFVV, LDTFTV, LDTFLV, LDGFFV, LDTFGV, LDTFFK, ADTFFV, CDTFFV, DDTFFV, FDTFFV, HDTFFV, IDTFFV, KDTFFV, MDTFFV, NDTFFV, QDTFFV, RDTFFV, SDTFFV, TDTFFV, VDTFFV, LATFFV, LETFFV, LITFFV, LVTFFV, LWTFFV, LYTFFV, LDCFFV, LDMFFV, LDNFFV, LDPFFV, LDRFFV, LDSFFV, LDWFFV, LDYFFV, LDTIFV, LDTMFV, LDTNFV, LDTPFV, LDTTFV, LDTFQV, LDTFFF, LDTFFG, LDTFFL, LDTFFP, LDTFFR, LDTFIV, LDTSFV, LDTFAV, LDTFCV, LDTQFV, LDTLFV, LTTFFV, LDTFF, LDHFFV, LMTFFV, LDTFEV, LDTFWV, LFTFFV, LDVFFV, LDTFRV, LDTFHV, LDTYFV, LPTFFV, PDTFFV, LDTFPV, LDTFNV, LDTWFV, LDTGFV, LDAFFV, LQTFFV, LCTFFV, LSTFFV, YDTFFV, LDEFFV, WDTFFV, LDTKFV, LDTCFV, LDTFYV, LDTHFV, LHTFFV, LRTFFV, LDLFFV, LDTRFV, LLTFFV, LDTFDV, LDTFFA, LDTFFT, LNTFFV, LDDFFV, LDIFFV, LDFFFV, LKTFFV, LDTFFQ, LGTFFV, LDTFFC, LDKFFV, LDTFKV, LDTEFV, LDTFFW, LDTFFM, LDTFFS, LDTFFH, LDTFFY, LDTFFN, LDDFV, LDTFFE, LDTFFD, LTFFV, LDTFF, TFFV, LDF, LDTE, FFV, LDV, LV, or L, or absent. In some embodiments, $X_{802}$ is an optional sequence, and can be LSLFT, VSLFT, LQLFT, LMLFT, LTLFT, LHLFT, LSQFT, LSVFT, LSMFT, LSLMT, LSLQT, LSLHT, LSLNT, LSLPT, LSLST, LSLGT, LSLAT, LSLRT, LSLFN, LSLFP, LSLFR, LGLFT, ASLFT, FSLFT, GSLFT, ISLFT, MSLFT, NSLFT, PSLFT, QSLFT, RSLFT, SSLFT, TSLFT, YSLFT, LNLFT, LSAFT, LSHFT, LSIFT, LSNFT, LSRFT, LSSFT, LSTFT, LSWFT, LSLCT, LSLIT, LSLLT, LSLTT, LSLVT, LSLWT, LSLFF, LSLFG, LSLFH, LSLFI, LSLFL, LSLFM, LSLFS, LSLFV, LSLFW, LYLFT, LVLFT, LSFFT, LSGFT, LSKFT, LSCFT, LCLFT, LRLFT, LPLFT, LWLFT, LKLFT, LDLFT, LSYFT, LALFT, WSLFT, LSLFA, LSLFQ, LSPFT, HSLFT, LSLYT, LILFT, KSLFT, CSLFT, LSLFY, LSLFK, LSLFC, LFLFT, LELFT, LSLKT, LLLFT, LSLFD, LSLDT, LSLFE, DSLFT, LSLET, LSDFT, LSEFT, ESLFT, SLFT, LSFT, LFT, LSL, LT, or T, or absent. In some embodiments, $X_{803}$ is an optional sequence, and can be R, F, K, N, R, T, or Y, or absent. In some embodiments, the isolated peptide comprising Formula (VIII) has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor can comprise, consist of, or consist essentially of and/or SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13, as described herein. In some embodiments, these isolated peptides used in these methods have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of a peptide inhibitor that comprises, consists of, or consists essentially of any one or more of the peptides set forth in Table 5.1. In some embodiments, the isolated peptide from Table 5.1 used in these methods has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

A nucleic acid encoding such a peptide inhibitor can be provided, for example a nucleic acid of SEQ ID NOs: 102-165. Following administration of the immunoregulatory peptide inhibitor, stimulation of human immune cells of the human can be detected (e.g., an increase in immune cell proliferation, migration of NK cell cytotoxicity). Once the immunoregulatory peptide inhibitor has been administered, these methods can, optionally, include measuring or observing a reduction in immunosuppression in the patient (e.g., an increase in immune cell proliferation, migration, or spreading or NK-cell cytotoxicity can be evaluated or detecting activation or stimulation of an immune cell, as evidenced by an increase in CD69 or CD71 expression, induction of the secretion of a signal substance, as evidenced by interferon gamma or IL-12 production, or stimulation of the release of a cytolytic substance, as evidenced by the release of granzyme B or perforin, enhanced cytotoxicity, cytokine production, cell migration, and/or cell proliferation).

As mentioned above, some embodiments include a step of identifying a patient suffering from immunosuppression. This analysis can include generally determining the immune cell activity of the patient, for example determining the quantity of at least one immune cell type, for example leukocytes, PBMCs, lymphocytes, monocytes, macrophages in a biological sample of the patient. The presence of the P3028 sequence/structure in the serum of a patient, and/or on a cancer cell of a patient (an evaluation that can be accomplished using a labeled immunoregulatory peptide inhibitor) is also indicative of suppression of the immune system of the patient. Accordingly, some embodiments of the invention include detecting the presence of the P3028 sequence/structure in a biological sample of a patient, for example a sample that includes blood, plasma, serum, or a cancer cell biopsy. Examples, methods, and compositions for detecting the presence of Peptide 3028 in a biological sample of a patient can be found in U.S. Pat. Nos. 7,960,126, 8,133,688, 8,110,347, and US Publication Nos. 2010/0323370 and 2011/0262470, each of which is hereby expressly incorporated by reference in its entirety. The P3028 sequence/structure can be detected, for example, by immunoassays, a blotting technique, ELISA, ELISpot, flow cytometry, cytometric bead assay, proteomics, and/or immunohistochemistry of a biological sample, using at least one antibody that binds to the P3028 sequence/structure. The P3028 sequence/structure can also be detected, for example, by mass spectrometry of a biological sample of a patient or a fraction thereof. The P3028 sequence/structure can further be detected by direct detection of a labeled peptide inhibitor of the P3028 sequence/structure as described herein, for example by histological staining, fluorescent microscopy, immunohistochemistry, or colorimetric enzymatic assays (see Example 14). The P3028 sequence/structure can also be detected, for example, functionally, by comparing an immune cell contacted by a patient's serum to an immune cell contacted by control sample serum known not to contain the P3028 sequence/structure. In some embodiments, the serum is denatured. Exemplary immune cells include PBMCs. In some embodiments, the serum is not denatured. The immune cells can be optionally stimulated, for example, by IL-2 or lipopolysaccharide (LPS). In some embodiments, the immune cells are analyzed for IL-6 production.

In some embodiments, a patient suffering from immunosuppression can be identified by diagnosing the patient with cancer, for example metastatic cancer, and/or two or more tumors in different locations. In some embodiments, cancer cells can be identified, and the patient can thus be identified, by detecting the binding of cells of the patient to the P3028 sequence/structure (see Example 7) or an inhibitor of the P3028 sequence/structure (see Example 14). For example, binding of P3028 to cells or tissues from multiple locations in the patient can indicate the presence of multiple tumors, such as primary and remote tumors in metastasis. Exemplary cancers that can be identified, and that are associated with immunosuppression include breast cancer, renal cell carcinoma, and malignant melanoma. Additional examples include a prostate tumor, a melanoma, a colon cancer, a lung carcinoma, an Apocrine gland carcinoma, a testis tumor, a mast cell tumor, a mammary tumor (e.g. a benign mammary tumor or a malignant mammary tumor, for example a mixed mammary tumor such as a benign mixed mammary tumor or a malignant mixed mammary tumor), a mucinous carcinoma (e g a mammary gland mucinous carcinoma), or a histicytoma The administration of the immunoregulatory peptide inhibitor (or a composition comprising the immunoregulatory peptide inhibitor, for example an immunoregulatory peptide inhibitor immobilized on a nanoparticle as described herein) to the patient can be accomplished by a variety of approaches. In some embodiments, the immunoregulatory peptide inhibitor is administered directly to the patient. The immunoregulatory peptide inhibitor can be administered intravenously, intraperitoneally, subcutaneousously, intramuscularly, topically, transdermally, orally, and/or peri-tumorally. In some embodiments, the immunoregulatory peptide inhibitor is administered at the site of a tumor, for example via direct injection. In some embodiments, the immunoregulatory peptide inhibitor is administered near a tumor, for example within 10 cm, 9 cm, 8 cm, 7 cm, 6 cm, 5 cm, 4 cm, 3 cm, 2 cm, 1 cm, or 0.5 cm of the tumor or a range defined by any tow of the aforementioned distances. In some embodiments, the immunoregulatory peptide inhibitor is administered with a pharmaceutically acceptable diluent or carrier, as described herein. In some embodiments, the immunoregulatory peptide inhibitor is administered ex vivo Immune cells of the patient can be isolated from the patient, contacted with the inhibitor, and returned to the patient, for example. Examples 13 and 14 describe contacting immune cells of a patient with an inhibitor of the P3028 sequence/structure. Optionally, the pharmaceutical formulation is administered directly to a tumor, and induces regressive changes in the tumor. Optionally, the pharmaceutical formulation is administered to a subject, and induces regressive changes of a tumor to which the composition is not directly administered. Optionally, the pharmaceutical formulation is administered directly to a tumor, and induces regressive changes in the tumor, and further induces regressive changes in a second tumor to which the formulation was not directly administered (e.g. a metastatic or contralateral tumor). Optionally, the pharmaceutical formulation is administered directly to a tumor, and induces eradication of the tumor. Optionally, the pharmaceutical formulation is administered to a subject, and induces eradication of a tumor to which the composition is not directly administered. Optionally, the pharmaceutical formulation is administered directly to a tumor, and induces eradication of the tumor, and further induces eradication of a second tumor to which the formulation was not directly administered (e.g. a metastatic or contralateral tumor). Optionally, the pharmaceutical formulation is administered directly to a tumor, and induces immune cell infiltration of the tumor. Optionally, the pharmaceutical formulation is administered directly to a tumor, and induces immune cell infiltration of the tumor, and further induces immune cell infiltration of a second tumor to which the formulation was not directly administered (e.g. a metastatic or contralateral tumor). Optionally, the pharmaceutical formulation is administered to a subject, and induces immune cell infiltration of a tumor to which the composition is not directly administered. Example tumors to which the pharmaceutical composition can be directly or indirect administered include a prostate tumor, a melanoma, a colon cancer, a lung carcinoma, an Apocrine gland carcinoma, a testis tumor, a mast cell tumor, a mammary tumor (e.g. a benign mammary tumor or a malignant mammary tumor, for example a mixed mammary tumor such as a benign mixed mammary tumor or a malignant mixed mammary tumor), a mucinous carcinoma (e.g. a mammary gland mucinous carcinoma), or a histicytoma. As shown in FIGS. 55-82, administration of compositions comprising immunoregulatory peptide inhibitors as described herein induced regressive changes, immune cell infiltration of, and/or eradication of tumors.

Any one or more of the immunoregulatory peptide inhibitors described herein can be employed with one or more of the aforementioned methods. In some embodiments, the immunoregulatory peptide inhibitor comprises at least one of SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13. In some embodiments, the immunoregulatory peptide inhibitor includes at least one peptidomimetic inhibitor of the P3028 sequence/structure corresponding to any one or more of SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13. In some embodiments, the immunoregulatory peptide inhibitor is a small molecule inhibitor of Peptide 3028 corresponding to any one or more of SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13. In some embodiments, the immunoregulatory peptide inhibitor includes an antibody or fragment thereof that specifically binds to the P3028 sequence/structure. Antibodies that inhibit the P3028 sequence/structure are described in Example 9.

In some of the aforementioned methods, the immunoregulatory peptide inhibitor of the P3028 sequence/structure comprises a nucleic acid encoding an immunoregulatory peptide inhibitor, such as a peptide described herein. For example, the peptide inhibitor encoded by the nucleic acid can comprise, consist of, or consist essentially of Formula (I), $XX_1VKX_2X_3X_4$ (SEQ ID NO: 166) as described herein. In some embodiments, X is an optional sequence, and can be KKLDT (SEQ ID NO: 167), RKLDT (SEQ ID NO: 168), KKGDT (SEQ ID NO: 169), KKEDT (SEQ ID NO: 170), KKLDQ (SEQ ID NO: 171), KKGDQ (SEQ ID NO: 252), KKEDQ (SEQ ID NO: 253), RKLDQ (SEQ ID NO: 254), RKGDQ (SEQ ID NO: 255), RKEDQ (SEQ ID NO: 256), RKGTD (SEQ ID NO: 257), RKEDT (SEQ ID NO: 258), KLDT (SEQ ID NO: 172), KGDT (SEQ ID NO: 259), KEDT (SEQ ID NO: 260), KLDQ (SEQ ID NO: 261), KGDQ (SEQ ID NO: 262), KEDQ (SEQ ID NO: 263), LDT, LDQ, GDT, GDQ, EDT, EDQ, DT, DQ, T, or Q, or absent. In some embodiments, $X_1$ is one of FF, FM, FS, FV, FT, FL, AF, AM, AS, AV, AT, AL, VF, VM, VS, VV, VT, or VL. In some embodiments, $X_2$ is one of LS, LQ, LM, LT, LH, VS, VQ, VM, VT, or VH. In some embodiments, $X_3$ is one of LFT, LMT, LQT, LHT, LNT, LPT, LST, LGT, LAT, LRT, QFT, QMT, QQT, QHT, QNT, QPT, QST, QGT, QAT, QRT, VFT, VMT, VQT, VHT, VNT, VPT, VST, VGT, VAT, VRT, MFT, MMT, MQT, MHT, MNT, MPT, MST, MGT, MAT, MRT, LFN, LMN, LQN, LHN, LNN, LPN, LSN, LGN, LAN, LRN, QFN, QMN, QQN, QHN, QNN, QPN, QSN, QGN, QAN, QRN, VFN, VMN, VQN, VHN, VNN, VPN, VSN, VGN, VAN, VRN, MFN, MMN, MQN, MHN, MNN, MPN, MSN, MGN, MAN, MRN, LFP, LMP, LQP, LHP, LNP, LPP, LSP, LGP, LAP, LRP, QFP, QMP, QQP, QHP, QNP, QPP, QSP, QGP, QAP, QRP, VFP, VMP, VQP, VHP, VNP, VPP, VSP, VGP, VAP, VRP, MFP, MMP, MQP, MHP, MNP, MPP, MSP, MGP, MAP, MRPR, LFR, LMR, LQR, LHR, LNR, LPR, LSR, LGR, LAR, LRR, QFR, QMR, QQR, QHR, QNR, QPR, QSR, QGR, QAR, QRR, VFR, VMR, VQR, VHR, VNR, VPR, VSR, VGR, VAR, VRR, MFR, MMR, MQR, MHR, MNR, MPR, MSR, MGR, MAR, or MRR. In some embodiments, $X_4$ is an optional sequence, and can be ER, or E, or absent. In some embodiments, if X is absent, $X_1$ is FF, and $X_2$ is LS. In some embodiments, the isolated peptides that comprise Formula (I) encoded by the nucleic acids used in these methods have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor encoded by the nucleic acids can comprise, consist of, or consist essentially of Formula (II), $X_{20}TFFVKLSX_{21}X_{22}$ (SEQ ID NO: 173). In some embodiments, $X_{20}$ is an optional sequence, and can be KKLD (SEQ ID NO: 174), RKLD (SEQ ID NO: 175), KKGD (SEQ ID NO: 176), KKED (SEQ ID NO: 177), KLD, LD, or D, or absent. $X_{21}$ is an optional sequence, and can be LFT, LMT, LQT, LHT, LNT, LPT, LST, LGT, LAT, LRT, QFT, QMT, QQT, QHT, QNT, QPT, QST, QGT, QAT, QRT, VFT, VMT, VQT, VHT, VNT, VPT, VST, VGT, VAT, VRT, MFT, MMT, MQT, MHT, MNT, MPT, MST, MGT, MAT, MRT, LFN, LMN, LQN, LHN, LNN, LPN, LSN, LGN, LAN, LRN, QFN, QMN, QQN, QHN, QNN, QPN, QSN, QGN, QAN, QRN, VFN, VMN, VQN, VHN, VNN, VPN, VSN, VGN, VAN, VRN, MFN, MMN, MQN, MHN, MNN, MPN, MSN, MGN, MAN, MRN, LFP, LMP, LQP, LHP, LNP, LPP, LSP, LGP, LAP, LRP, QFP, QMP, QQP, QHP, QNP, QPP, QSP, QGP, QAP, QRP, VFP, VMP, VQP, VHP, VNP, VPP, VSP, VGP, VAP, VRP, MFP, MMP, MQP, MHP, MNP, MPP, MSP, MGP, MAP, MRPR, LFR, LMR, LQR, LHR, LNR, LPR, LSR, LGR, LAR, LRR, QFR, QMR, QQR, QHR, QNR, QPR, QSR, QGR, QAR, QRR, VFR, VMR, VQR, VHR, VNR, VPR, VSR, VGR, VAR, VRR, MFR, MMR, MQR, MHR, MNR, MPR, MSR, MGR, MAR, or MRR, or absent. In some embodiments, $X_{22}$ is an optional sequence, and can be ER, E, or absent. In some embodiments, the isolated peptides that comprise Formula (II) encoded by the nucleic acids used in these methods have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor encoded by the nucleic acids can comprise, consist of, or consist essentially of Formula (III), $X_{30}X_{31}VKLX_{32}LX_{33}TEX_{34}$ (SEQ ID NO: 178). In some embodiments, $X_{30}$ is an optional sequence, and can be KKLDTF (SEQ ID NO: 179), KLDTF (SEQ ID NO: 180), LDTF (SEQ ID NO: 181), DTF, TF, or F, or absent. In some embodiments, $X_{31}$ is an optional sequence, and can be F, S, M, V, T, or L, or absent. In some embodiments, $X_{31}$ is F. In some embodiments, $X_{32}$ can be S, Q, M, T, or H. In some embodiments, $X_{32}$ is S. $X_{33}$ can be F, M, Q, H, N, P, S, G, A, or R. In some embodiments, $X_{34}$ is F. $X_{34}$ is an optional sequence, can be R or absent. In some embodiments, the isolated peptides that comprise Formula (III) encoded by the nucleic acids used in these methods have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor encoded by the nucleic acids can comprise, consist of, or consist essentially of Formula (VII), $X_{700}K\ X_{701}X_{702}X_{703}\ X_{704}X_{705}X_{706}K\ X_{707}\ X_{708}\ X_{709}\ X_{710}\ X_{711}E\ X_{712}$ (SEQ ID NO: 394), as described herein. In some embodiments, $X_{700}$ is an optional sequence, and can be K,A,D,E,G,H,I,L,M,N,P,Q,R,T, or V, or absent. In some embodiments, $X_{701}$ is an optional sequence, and can be L,A,C,D,E,F,G,H,I,K,M,N,Q,R,S,T, or V, or absent. In some embodiments, $X_{702}$ is an optional sequence, and can be D,A,E,I,V,W, or Y, or absent. In some embodiments, $X_{703}$ is an optional sequence, and can be T,C,M,N,P,Q,R,S,W, or Y, or absent. In some embodiments, $X_{704}$ is an optional sequence, and can be F,A,I,M,N,P,T, or V, or absent. In some embodiments, $X_{705}$ is an optional sequence, and can be F,L,M,Q,S,T, or V, or absent. In some embodiments, $X_{706}$ is an optional sequence, and can be V,F,G,L,P, or R, or absent. In some embodiments, $X_{707}$ is an optional sequence, and can be L,A,F,G,I,M,N,P,Q,R,S,T,V, or Y, or absent. In some embodiments, $X_{708}$ is an optional sequence, and can be S,H,M,N,Q, or T, or absent. In some embodiments, $X_{709}$ is an optional sequence, and can be L,A,H,I,M,N,Q,R,S,T,V, or W, or absent. In some embodiments, $X_{710}$ is an optional sequence, and can be F,A,C,G,H,I,L,M,N,P,Q,R,S,T,V, or W, or absent. In some embodiments, $X_{711}$ is an optional sequence, and can be T,F,G,H,I,L,M,N,P,S,V, or W, or absent. In some embodiments, $X_{712}$ is an optional sequence, and can be R,F,K,N,R,T, or Y, or absent. In some embodiments, the isolated peptide comprising Formula (VII) has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor encoded by the nucleic acids can comprise, consist of, or consist essentially of Formula (VIII), $X_{800}K\ X_{801}K\ X_{802}E\ X_{803}$ (SEQ ID NO: 395), as described herein. In some embodiments, $X_{800}$ is an optional sequence, and can be K, A, D, E, G, H, I, L, M, N, P, Q, R, T, V, or K, or absent. In some embodiments, $X_{801}$ is an optional sequence, and can be LDTFFV, GDTFFV, EDTFFV, LDQFFV, LDTAFV, LDTVFV, LDTFMV, LDTFSV, LDTFVV, LDTFTV, LDTFLV, LDGFFV, LDTFGV, LDTFFK, ADTFFV, CDTFFV, DDTFFV, FDTFFV, HDTFFV, IDTFFV, KDTFFV, MDTFFV, NDTFFV, QDTFFV, RDTFFV, SDTFFV, TDTFFV, VDTFFV, LATFFV, LETFFV, LITFFV, LVTFFV, LWTFFV, LYTFFV, LDCFFV, LDMFFV, LDNFFV, LDPFFV, LDRFFV, LDSFFV, LDWFFV, LDYFFV, LDTIFV, LDTMFV, LDTNFV, LDTPFV, LDTTFV, LDTFQV, LDTFFF, LDTFFG, LDTFFL, LDTFFP, LDTFFR, LDTFIV, LDTSFV, LDTFAV, LDTFCV, LDTQFV, LDTLFV, LTTFFV, LDTFF, LDHFFV, LMTFFV, LDTFEV, LDTFWV, LFTFFV, LDVFFV, LDTFRV, LDTFHV, LDTYFV, LPTFFV, PDTFFV, LDTFPV, LDTFNV, LDTWFV, LDTGFV, LDAFFV, LQTFFV, LCTFFV, LSTFFV, YDTFFV, LDEFFV, WDTFFV, LDTKFV, LDTCFV, LDTFYV, LDTHFV, LHTFFV, LRTFFV, LDLFFV, LDTRFV, LLTFFV, LDTFDV, LDTFFA, LDTFFT, LNTFFV, LDDFFV, LDIFFV, LDFFFV, LKTFFV, LDTFFQ, LGTFFV, LDTFFC, LDKFFV, LDTFKV, LDTEFV, LDTFFW, LDTFFM, LDTFFS, LDTFFH, LDTFFY, LDTFFN, LDTDFV, LDTFFE, LDTFFD, LTFFV, LDTFF, TFFV, LDF, LDTE, FFV, LDV, LV, or L, or absent. In some embodiments, $X_{802}$ is an optional sequence, and can be LSLFT, VSLFT, LQLFT, LMLFT, LTLFT, LHLFT, LSQFT, LSVFT, LSMFT, LSLMT, LSLQT, LSLHT, LSLNT, LSLPT, LSLST, LSLGT, LSLAT, LSLRT, LSLFN, LSLFP, LSLFR, LGLFT, ASLFT, FSLFT, GSLFT, ISLFT, MSLFT, NSLFT, PSLFT, QSLFT, RSLFT, SSLFT, TSLFT, YSLFT, LNLFT, LSAFT, LSHFT, LSIFT, LSNFT, LSRFT, LSSFT, LSTFT, LSWFT, LSLCT, LSLIT, LSLLT, LSLTT, LSLVT, LSLWT, LSLFF, LSLFG, LSLFH, LSLFI, LSLFL, LSLFM, LSLFS, LSLFV, LSLFW, LYLFT, LVLFT, LSFFT, LSGFT, LSKFT, LSCFT, LCLFT, LRLFT, LPLFT, LWLFT, LKLFT, LDLFT, LSYFT, LALFT, WSLFT, LSLFA, LSLFQ, LSPFT, HSLFT, LSLYT, LILFT, KSLFT, CSLFT, LSLFY, LSLFK, LSLFC, LFLFT, LELFT, LSLKT, LLLFT, LSLFD, LSLDT, LSLFE, DSLFT, LSLET, LSDFT, LSEFT, ESLFT, SLFT, LSFT, LFT, LSL, LT, or T, or absent. In some embodiments, $X_{803}$ is an optional sequence, and can be R, F, K, N, R, T, or Y, or absent. In some embodiments, the isolated peptide comprising Formula (VIII) has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor encoded by the nucleic acid used in these methods can comprise, consist of, or consist essentially of Formula (IX). Accordingly, in some embodiments, the peptide inhibitor comprises a peptide of Formula (IX): $X_{901}X_{902}X_{903}X_{904}X_{905}X_{906}X_{907}X_{908}X_{909}X_{910}X_{911}X_{912}X_{913}X_{914}X_{915}X_{916}X_{917}$, wherein $X_{901}$ is any amino acid or absent; $X_{902}$ is a positively charged amino acid, F, or N; $X_{903}$ is any amino acid; $X_{904}$ is any amino acid; $X_{905}$ is a polar uncharged amino acid, R, Y, or W; $X_{906}$ is a hydrophobic or uncharged polar amino acid; $X_{907}$ is a hydrophobic or uncharged polar amino acid; $X_{908}$ is a hydrophobic, non-aromatic carbon chain amino acid that is not M or F; $X_{909}$ is a positively charged amino acid, T, Q, or Y; $X_{910}$ is any amino acid that is not negatively charged; $X_{911}$ is a polar uncharged amino acid or H; $X_{912}$ is any amino acid that is not negatively charged; $X_{913}$ is any amino acid that is not negatively charged; $X_{914}$ is any amino acid that is not negatively charged; $X_{915}$ is a negatively charged amino acid, Y, or Q; $X_{916}$ is any amino acid that is not negatively charged; and $X_{917}$ is one or more positively charged amino acids or is absent. Optionally, $X_{901}$ comprises a positively charged amino acid. Optionally $X_{901}$ is an R or K. Optionally $X_{917}$ is RR. In some embodiments, the isolated peptide comprising Formula (IX) has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor encoded by the nucleic acid used in these methods can comprise, consist of, or consist essentially of and/or SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13, as described herein. In some embodiments, these isolated peptides encoded by the nucleic acids used in these methods have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor encoded by the nucleic acid used in these methods can comprise, consist of, or consist essentially of a peptide inhibitor that comprises, consists of, or consists essentially of any one or more of the peptides set forth in Table 5.1, 5.4, 5.5, 5.6, or any variation or combination of variations of P28R or P28 core as provided in Tables 5.3 and 13. In some embodiments, the isolated peptide from Table 5.1 5.4, 5.5, 5.6, or any variation or combination of variations of P28R or P28 core as provided in Tables 5.3 and 13, which is encoded by the nucleic acid used in these methods has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

For example, a nucleic acid encoding such a peptide inhibitor can be provided, for example a nucleic acid of SEQ ID NOs: 102-165. The nucleic acid can be provided in an expression vector as described herein. The nucleic acid can be provided to the human by directly administering an expression vector comprising the nucleic acid that encodes the immunoregulatory peptide inhibitor to the human, for example via a retroviral or adenoviral vector or expression plasmid used in genetic immunization (e.g., pVAX). The expression vector can be provided to cells of the human ex vivo, and the cells can be returned to the human or in vivo using electroporation technology. Methods of delivering nucleic acids to a host cell via viral vectors are described in U.S. Pat. No. 7,572,906, which is expressly incorporated by reference in its entirety herein. Methods of transducing immune cells with an adenovirus ex vivo and returning them to a patient are described in U.S. Pat. No. 8,012,468, which is expressly incorporated by reference in its entirety herein. In some embodiments, a host cell, is contacted with a vector encoding the immunoregulatory peptide inhibitor of P3028. The vector can replicates in the host cell. In some embodiments, the host cell is also contacted with a "helper-expression vector," i.e., a viral genome that promotes the replication of the vector in an uninfected host. In some embodiments, the inhibitor is administered as in Example 16. In some embodiments, the cell is contacted ex vivo. In some embodiments, the cell is an immune cell. In some embodiments, the cell is one of a lymphocyte, a PBMC, or a leukocyte. In some embodiments, the inhibitor is administered as in Example 13. In some embodiments, the nucleic acid encoding the peptide inhibitor is administered to a non-human mammal, for treatment of immunosuppression or cancer (for example metastatic cancer) in the non-human mammal.

Preferably, a therapeutically effective amount of the immunoregulatory peptide inhibitor is provided. For a patient already suffering from P3028-dependent immunosuppression, a therapeutically effective amount of inhibitor may include a dose of immunoregulatory peptide inhibitor sufficient to at least partially arrest a symptom of immunosuppression (e.g., an amount sufficient to improve proliferation or migration of immune cells). In some embodiments, a therapeutically effective amount includes at least about 1 nanogram of substantially pure immunoregulatory peptide inhibitor, for example, at least or equal to about 1 nanogram, 2, 3, 4, 5, 6, 7, 8, 9, 10, 15, 20, 25, 30, 40, 50, 60, 70, 80, 90, 100, 120, 140, 160, 180, 200, 250, 300, 350, 400, 450, 500, 550, 600, 650, 700, 750, 800, 850, 900, 950, 1000 nanograms, 1 microgram, 2, 3, 4, 5, 6, 7, 8, 9, 10, 15, 20, 25, 30, 40, 50, 60, 70, 80, 90, 100, 120, 140, 160, 180, 200, 250, 300, 350, 400, 450, 500, 550, 600, 650, 700, 750, 800, 850, 900, 950, 1000 micrograms, about 1 milligram, 2, 3, 4, 5, 6, 7, 8, 9, 10, 15, 20, 25, 30, 40, 50, 60, 70, 80, 90, 100, 120, 140, 160, 180, 200, 250, 300, 350, 400, 450, 500, 550, 600, 650, 700, 750, 800, 850, 900, 950, 1000 milligrams, or 1.1 gram, 1.2, 1.3, 1.4, 1.5, 1.6, 1.7, 1.8, 1.9, 2, 2, 3, 3.5, 4, 4.5, 5, 5.5, 6, 6.5, 7, 7.5, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 99, 100, 105, 110, 120, 130, 140, 150, 160, 170, 180, 190, 200, 250, 300, 350, 400, 450, or 500 grams, including ranges between any two of the listed values can be provided to a patient in need.

In some embodiments, a therapeutically effective amount can be provided according to a schedule that includes one, or more than one administration of a therapeutically effective amount of inhibitor, for example at least or equal to about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 99, 100, 105, 110, 120, 130, 140, 150, 160, 170, 180, 190, 200, 250, 300, 350, 400, 450, or 500 administrations. An administration can be provided hourly or less, for example no more than once every 1, 2, 3, 4, 5, 6, 7, 8, 9, 10, 11, 12, 13, 14, 15, 16, 17, 18, 19, 20, 21, 22, 23, 24 hours, or no more than once every 1 day, 1.5, 2, 2.5, 3, 3.5, 4, 4.5, 5, 5.5, 6, 6.5, 7, 7.5, 8, 9, 10, 11, 12, 13, 15, 16, 17, 18, 19, 20, 21, 22, 23, 24, 25, 26, 27, 28, 29, 30, or 31 days.

By some methods, after administration of the immunoregulatory peptide inhibitor, a reduction in immunosuppression is measured, detected, or observed. In some embodiments, a reduction in immunosuppression is detected, measured, or observed by obtaining a biological sample from the patient that received the immunoregulatory peptide inhibitor and detecting a reduction in immune cell receptor binding to P3028 and/or a detecting immune cell proliferation after IL-2 induction of the immune cells present in the biological sample. In some embodiments, the analysis of the biological sample obtained from the patient above is compared to the same analysis (e.g., determining the amount of immune cell receptor binding to the P3028 sequence/structure or IL-2 induced immune cell proliferation) conducted on a control biological sample, for example, a biological sample from the same patient taken prior to administration of the immunoregulatory peptide inhibitor or a biological sample taken from a healthy human. Examples 9 and 13 describe detection of a reduction of immunosuppression in cells contacted by serum as compared to a control sample. In some embodiments, the reduction in immunosuppression is observed as immune cell infiltration of a tumor, regressive changes in a tumor, and/or eradication of a tumor. As shown in FIGS. 55-82, administration of compositions comprising immunoregulatory peptide inhibitors as described herein induced regressive changes, immune cell infiltration of, and/or eradication of tumors.

As mentioned above, a reduction in immunosuppression can be detected as an increase in immune cell stimulation, for example immune cell proliferation or immune cell cytotoxicity. A reduction in P3028-induced immunosuppression, which can be measured in the methods described supra, can include: increased T-Cell receptor stimulation (see Example 3); increased NK-Cell cytotoxicity (see Example 4); increased leukocyte spreading (see Example 5); increased immune cell migration (see Example 5); and/or IL-2 Induced Proliferation (see Example 6). Decreased IL-6 production can also an improvised prognosis for cancer patients, for example cancer patients suffering from immunosuppression (see U.S. Pat. No. 8,110,347, herein expressly incorporated by reference in its entirety). Desirably, a reduction in immunosuppression is detected by an increased proliferative response of PBMCs to IL-2, as shown in Example 9, or by detecting activation or stimulation of an immune cell, as evidenced by an increase in CD69 or CD71 expression, induction of the secretion of a signal substance, as evidenced by interferon gamma or IL-12 production, or stimulation of the release of a cytolytic substance, as evidenced by the release of granzyme B or perforin, enhanced cytotoxicity, cytokine production, cell migration, and/or cell proliferation.

In some embodiments, the reduction in immunosuppression is detected by detecting the presence or quantity of markers from immune cells and/or serum and/or albumin collected from a patient. In some embodiments, the detection includes collecting patient serum, blood, and/or patient albumin, and contacting the patient serum, plasma, blood, or albumin with an immune cell ex vivo. In some embodiments, the immune cell is also contacted with IL-2. The proliferative response of the immune cell to IL-2 can be used to detect a decrease in immunosuppression. The immune cell can be a patient cell, or a cell from another human, or a cell from cell culture. In some embodiments, the reduction in immunosuppression can be detected by detecting effects of increased immune system activity, for example reduction in cancer cell number, a reduction in tumor size, or a reduction or inhibition of cancer cell proliferation. In some embodiments, cancer cells can be identified, and cancer cells can thus be quantified, by detecting cells that bind to the P3028 sequence/structure (see Example 7) or an inhibitor of the P3028 sequence/structure (see Example 14).

Methods of Binding Cancer Cells with an Immunoregulatory Peptide Inhibitor

Embodiments also include methods of binding cancer cells in two or more different tumors with an immunoregulatory peptide inhibitor (e.g., an immunoregulatory peptide inhibitor having a cytotoxin, radionuclide, or detectable label) of two or more tumors, in which an immunoregulatory peptide inhibitor is neither intratumorally nor peri-tumorally administered to at least one of the tumors. For example, for a patient with metastatic cancer, an immunoregulatory peptide inhibitor can bind to both primary tumor cells and remote tumor cells. These methods are practiced by contacting cancer cells (e.g., in vitro or in vivo) with a composition that comprises, consists of, or consists essentially of any one or more of the immunoregulatory peptide inhibitors described herein. For example, the peptide inhibitor used in these methods can comprise, consist of, or consist essentially of Formula (I), $XX_1VKX_2X_3X_4$ (SEQ ID NO: 166) as described herein. In some embodiments, X is an optional sequence, and can be KKLDT (SEQ ID NO: 167), RKLDT (SEQ ID NO: 168), KKGDT (SEQ ID NO: 169), KKEDT (SEQ ID NO: 170), KKLDQ (SEQ ID NO: 171), KKGDQ (SEQ ID NO: 252), KKEDQ (SEQ ID NO: 253), RKLDQ (SEQ ID NO: 254), RKGDQ (SEQ ID NO: 255), RKEDQ (SEQ ID NO: 256), RKGTD (SEQ ID NO: 257), RKEDT (SEQ ID NO: 258), KLDT (SEQ ID NO: 172), KGDT (SEQ ID NO: 259), KEDT (SEQ ID NO: 260), KLDQ (SEQ ID NO: 261), KGDQ (SEQ ID NO: 262), KEDQ (SEQ ID NO: 263), LDT, LDQ, GDT, GDQ, EDT, EDQ, DT, DQ, T, or Q, or absent. In some embodiments, $X_1$ is one of FF, FM, FS, FV, FT, FL, AF, AM, AS, AV, AT, AL, VF, VM, VS, VV, VT, or VL. In some embodiments, $X_2$ is one of LS, LQ, LM, LT, LH, VS, VQ, VM, VT, or VH. In some embodiments, $X_3$ is one of LFT, LMT, LQT, LHT, LNT, LPT, LST, LGT, LAT, LRT, QFT, QMT, QQT, QHT, QNT, QPT, QST, QGT, QAT, QRT, VFT, VMT, VQT, VHT, VNT, VPT, VST, VGT, VAT, VRT, MFT, MMT, MQT, MHT, MNT, MPT, MST, MGT, MAT, MRT, LFN, LMN, LQN, LHN, LNN, LPN, LSN, LGN, LAN, LRN, QFN, QMN, QQN, QHN, QNN, QPN, QSN, QGN, QAN, QRN, VFN, VMN, VQN, VHN, VNN, VPN, VSN, VGN, VAN, VRN, MFN, MMN, MQN, MHN, MNN, MPN, MSN, MGN, MAN, MRN, LFP, LMP, LQP, LHP, LNP, LPP, LSP, LGP, LAP, LRP, QFP, QMP, QQP, QHP, QNP, QPP, QSP, QGP, QAP, QRP, VFP, VMP, VQP, VHP, VNP, VPP, VSP, VGP, VAP, VRP, MFP, MMP, MQP, MHP, MNP, MPP, MSP, MGP, MAP, MRPR, LFR, LMR, LQR, LHR, LNR, LPR, LSR, LGR, LAR, LRR, QFR, QMR, QQR, QHR, QNR, QPR, QSR, QGR, QAR, QRR, VFR, VMR, VQR, VHR, VNR, VPR, VSR, VGR, VAR, VRR, MFR, MMR, MQR, MHR, MNR, MPR, MSR, MGR, MAR, or MRR. In some embodiments, $X_4$ is an optional sequence, and can be ER, or E, or absent. In some embodiments, if X is absent, $X_1$ is FF, and $X_2$ is LS. In some embodiments, the isolated peptides that comprise Formula (I) used in these methods have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of Formula (II), $X_{20}TFFVKLSX_{21}X_{22}$ (SEQ ID NO: 173). In some embodiments, $X_{20}$ is an optional sequence, and can be KKLD (SEQ ID NO: 174), RKLD (SEQ ID NO: 175), KKGD (SEQ ID NO: 176), KKED (SEQ ID NO: 177), KLD, LD, D, or absent. $X_{21}$ is an optional sequence, and can be LFT, LMT, LQT, LHT, LNT, LPT, LST, LGT, LAT, LRT, QFT, QMT, QQT, QHT, QNT, QPT, QST, QGT, QAT, QRT, VFT, VMT, VQT, VHT, VNT, VPT, VST, VGT, VAT, VRT, MFT, MMT, MQT, MHT, MNT, MPT, MST, MGT, MAT, MRT, LFN, LMN, LQN, LHN, LNN, LPN, LSN, LGN, LAN, LRN, QFN, QMN, QQN, QHN, QNN, QPN, QSN, QGN, QAN, QRN, VFN, VMN, VQN, VHN, VNN, VPN, VSN, VGN, VAN, VRN, MFN, MMN, MQN, MHN, MNN, MPN, MSN, MGN, MAN, MRN, LFP, LMP, LQP, LHP, LNP, LPP, LSP, LGP, LAP, LRP, QFP, QMP, QQP, QHP, QNP, QPP, QSP, QGP, QAP, QRP, VFP, VMP, VQP, VHP, VNP, VPP, VSP, VGP, VAP, VRP, MFP, MMP, MQP, MHP, MNP, MPP, MSP, MGP, MAP, MRPR, LFR, LMR, LQR, LHR, LNR, LPR, LSR, LGR, LAR, LRR, QFR, QMR, QQR, QHR, QNR, QPR, QSR, QGR, QAR, QRR, VFR, VMR, VQR, VHR, VNR, VPR, VSR, VGR, VAR, VRR, MFR, MMR, MQR, MHR, MNR, MPR, MSR, MGR, MAR, or MRR, or absent. In some embodiments, $X_{22}$ is an optional sequence, and can be ER, or E, or absent. In some embodiments, the isolated peptides that comprise Formula (II) used in these methods have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of Formula (III), $X_{30}X_{31}VKLX_{32}LX_{33}TEX_{34}$ (SEQ ID NO: 178). In some embodiments, $X_{30}$ is an optional sequence, and can be KKLDTF (SEQ ID NO: 179), KLDTF (SEQ ID NO: 180), LDTF (SEQ ID NO: 181), DTF, TF, or F, or absent. In some embodiments, $X_{31}$ is an optional sequence, and can be F, S, M, V, T, or L, or absent. In some embodiments, $X_{31}$ is F. In some embodiments, $X_{32}$ can be S, Q, M, T, or H. In some embodiments, $X_{32}$ is S. $X_{33}$ can be F, M, Q, H, N, P, S, G, A, or R. In some embodiments, $X_{34}$ is F. $X_{34}$ is an optional sequence, and can be R or absent. In some embodiments, the isolated peptides that comprise Formula (III) used in these methods have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of Formula (VII), $X_{700}K\ X_{701}X_{702}X_{703}\ X_{704}X_{705}X_{706}K\ X_{707}\ X_{708}\ X_{709}\ X_{710}\ X_{711}E\ X_{712}$ (SEQ ID NO: 394), as described herein. In some embodiments, $X_{700}$ is an optional sequence, and can be K,A,D,E,G,H,I,L,M,N,P,Q,R,T, or V, or absent. In some embodiments, $X_{701}$ is an optional sequence, and can be L,A,C,D,E,F,G,H,I,K,M,N,Q,R,S,T, or V, or absent. In some embodiments, $X_{702}$ is an optional sequence, and can be D,A,E,I,V,W, or Y, or absent. In some embodiments, $X_{703}$ is an optional sequence, and can be T,C,M,N,P,Q,R,S,W, or Y, or absent. In some embodiments, $X_{704}$ is an optional sequence, and can be F,A,I,M,N,P,T, or V, or absent. In some embodiments, $X_{705}$ is an optional sequence, and can be F,L,M,Q,S,T, or V, or absent. In some embodiments, $X_{706}$ is an optional sequence, and can be V,F,G,L,P, or R, or absent. In some embodiments, $X_{707}$ is an optional sequence, and can be L,A,F,G,I,M,N,P,Q,R,S,T,V, or Y, or absent. In some embodiments, $X_{708}$ is an optional sequence, and can be S,H,M,N,Q, or T, or absent. In some embodiments, $X_{709}$ is an optional sequence, and can be L,A,H,I,M,N,Q,R,S,T,V, or W, or absent. In some embodiments, $X_{710}$ is an optional sequence, and can be F,A,C,G,H,I,L,M,N,P,Q,R,S,T,V, or W, or absent. In some embodiments, $X_{711}$ is an optional sequence, and can be T,F,G,H,I,L,M,N,P,S,V, or W, or absent. In some embodiments, $X_{712}$ is an optional sequence, and can be R,F,K,N,R,T, or Y, or absent. In some embodiments, the isolated peptide comprising Formula (VII) has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of Formula (VIII), $X_{800}K\ X_{801}K\ X_{802}E\ X_{803}$ (SEQ ID NO: 395), as described herein. In some embodiments, $X_{800}$ is an optional sequence, and can be K, A, D, E, G, H, I, L, M, N, P, Q, R, T, V, or K, or absent. In some embodiments, $X_{801}$ is an optional sequence, and can be LDTFFV, GDTFFV, EDTFFV, LDQFFV, LDTAFV, LDTVFV, LDTFMV, LDTFSV, LDTFVV, LDTFTV, LDTFLV, LDGFFV, LDTFGV, LDTFFK, ADTFFV, CDTFFV, DDTFFV, FDTFFV, HDTFFV, IDTFFV, KDTFFV, MDTFFV, NDTFFV, QDTFFV, RDTFFV, SDTFFV, TDTFFV, VDTFFV, LATFFV, LETFFV, LITFFV, LVTFFV, LWTFFV, LYTFFV, LDCFFV, LDMFFV, LDNFFV, LDPFFV, LDRFFV, LDSFFV, LDWFFV, LDYFFV, LDTIFV, LDTMFV, LDTNFV, LDTPFV, LDTTFV, LDTFQV, LDTFFF, LDTFFG, LDTFFL, LDTFFP, LDTFFR, LDTFIV, LDTSFV, LDTFAV, LDTFCV, LDTQFV, LDTLFV, LTTFFV, LDTFF, LDHFFV, LMTFFV, LDTFEV, LDTFWV, LFTFFV, LDVFFV, LDTFRV, LDTFHV, LDTYFV, LPTFFV, PDTFFV, LDTFPV, LDTFNV, LDTWFV, LDTGFV, LDAFFV, LQTFFV, LCTFFV, LSTFFV, YDTFFV, LDEFFV, WDTFFV, LDTKFV, LDTCFV, LDTFYV, LDTHFV, LHTFFV, LRTFFV, LDLFFV, LDTRFV, LLTFFV, LDTFDV, LDTFFA, LDTFFT, LNTFFV, LDDFFV, LDIFFV, LDFFFV, LKTFFV, LDTFFQ, LGTFFV, LDTFFC, LDKFFV, LDTFKV, LDTEFV, LDTFFW, LDTFFM, LDTFFS, LDTFFH, LDTFFY, LDTFFN, LDTDFV, LDTFFE, LDTFFD, LTFFV, LDTFF, TFFV, LDF, LDTE, FFV, LDV, LV, or L, or absent. In some embodiments, $X_{802}$ is an optional sequence, and can be LSLFT, VSLFT, LQLFT, LMLFT, LTLFT, LHLFT, LSQFT, LSVFT, LSMFT, LSLMT, LSLQT, LSLHT, LSLNT, LSLPT, LSLST, LSLGT, LSLAT, LSLRT, LSLFN, LSLFP, LSLFR, LGLFT, ASLFT, FSLFT, GSLFT, ISLFT, MSLFT, NSLFT, PSLFT, QSLFT, RSLFT, SSLFT, TSLFT, YSLFT, LNLFT, LSAFT, LSHFT, LSIFT, LSNFT, LSRFT, LSSFT, LSTFT, LSWFT, LSLCT, LSLIT, LSLLT, LSLTT, LSLVT, LSLWT, LSLFF, LSLFG, LSLFH, LSLFI, LSLFL, LSLFM, LSLFS, LSLFV, LSLFW, LYLFT, LVLFT, LSFFT, LSGFT, LSKFT, LSCFT, LCLFT, LRLFT, LPLFT, LWLFT, LKLFT, LDLFT, LSYFT, LALFT, WSLFT, LSLFA, LSLFQ, LSPFT, HSLFT, LSLYT, LILFT, KSLFT, CSLFT, LSLFY, LSLFK, LSLFC, LFLFT, LELFT, LSLKT, LLLFT, LSLFD, LSLDT, LSLFE, DSLFT, LSLET, LSDFT, LSEFT, ESLFT, SLFT, LSFT, LFT, LSL, LT, or T, or absent. In some embodiments, $X_{803}$ is an optional sequence, and can be R, F, K, N, R, T, or Y, or absent. In some embodiments, the isolated peptide comprising Formula (VIII) has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of and/or SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13 as described herein. In some embodiments, these isolated peptides used in these methods have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of a peptide inhibitor that comprises, consists of, or consists essentially of any one or more of the peptides set forth in Table 5.1. In some embodiments, the isolated peptide from Table 5.1 used in these methods has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values. Additionally, a nucleic acid encoding such a peptide inhibitor can be provided, for example a nucleic acid of SEQ ID NOs: 102-165.

Preferably, the immunoregulatory peptide inhibitor used in the aforementioned methods is P28R, P28 core, a derivative thereof, or a nucleic acid encoding such a molecule (e.g., any one or more of the immunoregulatory peptide inhibitors provided by SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13, or a nucleic acid encoding such a molecule (e.g., SEQ ID NOs: 102-165)). The immunoregulatory peptide inhibitors used in the aforementioned methods can comprise at least one D amino acid, at least one non-natural amino acid, an N-terminal acetyl group, or a C terminal amide group and said immunoregulatory peptide inhibitors can be glycosylated or joined to PEG, a cytotoxin, or radionuclide.

Once the immunoregulatory peptide inhibitor or antibody that binds specifically to any immunoregulatory peptide of Tables 1-4 is bound to the cancer cell, it can be detected. That is, optionally, the method above includes a detecting step whereby the binding of the immunoregulatory peptide inhibitor is determined directly or indirectly. In some embodiments, the binding of the immunoregulatory peptide inhibitor is directly detected as in Example 14. In some embodiments, the binding of the immunoregulatory peptide inhibitor is indirectly detected. As described herein, the presence of P3028 on cancer cells can locally suppress an immune response. Thus, in some embodiments, detecting the binding of an immunoregulatory peptide inhibitor to a cancer cell can also include a step of detecting a reversal of immunosuppression, as described in Example 13. Reversal of immunosuppression can be determined, for example as a reversal of impaired PBMC proliferation (see Examples 2 and 13), reversal of T cell receptor stimulation (see Example 3), reversal of decreased NK cell cytotoxicity (see Example 4), reversal of decreased leukocyte spreading (see Example 5) or decreased immune cell migration (see Example 6), or increased IL-2 induced proliferation (see Examples 6 and 9). In some embodiments, cancer cells are bound to an immunoregulatory peptide inhibitor in vivo. Example 16 describes delivery of an inhibitor of P3028 to cancer cells in vivo. Example 42 describes detection of an inhibitor of P3028 on cancer cells.

In some embodiments, the detection of an immunoregulatory peptide inhibitor can occur on tissue biopsies obtained from a human. In some embodiments, the tissue biopsies can include putative cancer cells, or the biopsies can be screened for cancer cells. By these methods, the tissue biopsies are contacted with an immunoregulatory peptide inhibitor, as described herein. Preferably, the immunoregulatory peptide inhibitor comprises a detectable label, as described herein. In some embodiments, live cells are contacted with the immunoregulatory peptide inhibitor (see Example 14). In some embodiments, histological sections are bound with the immunoregulatory peptide inhibitor. The detectable label is then detected, thus permitting identification of cancer cells which cannot be attacked by the immune system. The detectable label can be detected through methods known in the art, for example by immunoassays, a blotting technique, ELISA, ELISpot, flow cytometry, cytometric bead assay, proteomics, and/or immunohistochemistry.

Methods of Inhibiting the Proliferation of Cancer Cells

Some embodiments of the invention include methods of inhibiting the proliferation of cancer cells of two or more tumors, in which an immunoregulatory peptide inhibitor is neither intratumorally nor peri-tumorally administered to at least one of the tumors. For example, the two or more tumors can comprise tumors of a metastasis, such as a primary tumor and a remote tumor, and/or two or more primary tumors, and/or two or more remote tumors. The method can include identifying a human cancer patient. The patient can be suffering from one or more cancers, for example colorectal cancer, renal cancer, breast cancer, skin cancer, ovarian cancer, prostate cancer, pancreatic cancer, lung cancer, malignant melanoma, small cell lung cancer, non-small lung cancer (adenocarcinoma), squamous cell carcinoma, bladder cancer, osteosarcoma, bronchial cancer, hematopoietic cell cancer, and/or may have a tumor, for example a prostate tumor, a melanoma, a colon cancer, a lung carcinoma, an Apocrine gland carcinoma, a testis tumor, a mast cell tumor, a mammary tumor (e.g. a benign mammary tumor or a malignant mammary tumor, for example a mixed mammary tumor such as a benign mixed mammary tumor or a malignant mixed mammary tumor), a mucinous carcinoma (e.g. a mammary gland mucinous carcinoma), or a histicytoma. The method can include contacting immune cells of the human by an immunoregulatory peptide inhibitor. In some embodiments, contacting the immune cells comprises intratumoral administration, or administration near a tumor, for example within 10, 9, 8, 7, 6, 5, 4, 3, 2, 1, or 0.5 cm of the tumor. Optionally, the immunoregulatory peptide inhibitor (or a composition comprising the immunoregulatory peptide inhibitor immobilized on a nanoparticle as described herein) is administered directly to a tumor, and induces regressive changes in the tumor. Optionally, the immunoregulatory peptide inhibitor (or a composition comprising the immunoregulatory peptide inhibitor immobilized on a nanoparticle as described herein) is administered to a subject, and induces regressive changes of a tumor to which the composition is not directly administered. Optionally, the immunoregulatory peptide inhibitor (or a composition comprising the immunoregulatory peptide inhibitor immobilized on a nanoparticle as described herein) is administered directly to a tumor, and induces regressive changes in the tumor, and further induces regressive changes in a second tumor to which the formulation was not directly administered (e.g. a metastatic or contralateral tumor). Optionally, the immunoregulatory peptide inhibitor (or a composition comprising the immunoregulatory peptide inhibitor immobilized on a nanoparticle as described herein) is administered directly to a tumor, and induces eradication of the tumor. Optionally, the immunoregulatory peptide inhibitor (or a composition comprising the immunoregulatory peptide inhibitor immobilized on a nanoparticle as described herein) is administered to a subject, and induces eradication of a tumor to which the composition is not directly administered. Optionally, the immunoregulatory peptide inhibitor (or a composition comprising the immunoregulatory peptide inhibitor immobilized on a nanoparticle as described herein) is administered directly to a tumor, and induces eradication of the tumor, and further induces eradication of a second tumor to which the formulation was not directly administered (e.g. a metastatic or contralateral tumor). Optionally, the immunoregulatory peptide inhibitor (or a composition comprising the immunoregulatory peptide inhibitor immobilized on a nanoparticle as described herein) is administered directly to a tumor, and induces immune cell infiltration of the tumor. Optionally, the immunoregulatory peptide inhibitor (or a composition comprising the immunoregulatory peptide inhibitor immobilized on a nanoparticle as described herein) is administered directly to a tumor, and induces immune cell infiltration of the tumor, and further induces immune cell infiltration of a second tumor to which the formulation was not directly administered (e.g. a metastatic or contralateral tumor). Optionally, the immunoregulatory peptide inhibitor (or a composition comprising the immunoregulatory peptide inhibitor immobilized on a nanoparticle as described herein) is administered to a subject, and induces immune cell infiltration of a tumor to which the composition is not directly administered. Example tumors to which the pharmaceutical composition can be directly or indirect administered include a prostate tumor, a melanoma, a colon cancer, a lung carcinoma, an Apocrine gland carcinoma, a testis tumor, a mast cell tumor, a mammary tumor (e.g. a benign mammary tumor or a malignant mammary tumor, for example a mixed mammary tumor such as a benign mixed mammary tumor or a malignant mixed mammary tumor), a mucinous carcinoma (e.g. a mammary gland mucinous carcinoma), or a histicytoma. As shown in FIGS. 55-82, administration of compositions comprising immunoregulatory peptide inhibitors as described herein induced regressive changes, immune cell infiltration of, and/or eradication of tumors. In some embodiments, the method of inhibiting the proliferation of cancer cells of two or more tumors is applied to a non-human mammal.

In some embodiments, the immunoregulatory peptide inhibitor comprises, consists of or consists essentially of a peptide as described herein. For example, the peptide inhibitor used in these methods can comprise, consist of, or consist essentially of Formula (I), $XX_1VKX_2X_3X_4$ (SEQ ID NO: 166) as described herein. In some embodiments, X is an optional sequence, and can be KKLDT (SEQ ID NO: 167), RKLDT (SEQ ID NO: 168), KKGDT (SEQ ID NO: 169), KKEDT (SEQ ID NO: 170), KKLDQ (SEQ ID NO: 171), KKGDQ (SEQ ID NO: 252), KKEDQ (SEQ ID NO: 253), RKLDQ (SEQ ID NO: 254), RKGDQ (SEQ ID NO: 255), RKEDQ (SEQ ID NO: 256), RKGTD (SEQ ID NO: 257), RKEDT (SEQ ID NO: 258), KLDT (SEQ ID NO: 172), KGDT (SEQ ID NO: 259), KEDT (SEQ ID NO: 260), KLDQ (SEQ ID NO: 261), KGDQ (SEQ ID NO: 262), KEDQ (SEQ ID NO: 263), LDT, LDQ, GDT, GDQ, EDT, EDQ, DT, DQ, T, or Q, or absent. In some embodiments, $X_1$ is one of FF, FM, FS, FV, FT, FL, AF, AM, AS, AV, AT, AL, VF, VM, VS, VV, VT, or VL. In some embodiments, $X_2$ is one of LS, LQ, LM, LT, LH, VS, VQ, VM, VT, or VH. In some embodiments, $X_3$ is one of LFT, LMT, LQT, LHT, LNT, LPT, LST, LGT, LAT, LRT, QFT, QMT, QQT, QHT, QNT, QPT, QST, QGT, QAT, QRT, VFT, VMT, VQT, VHT, VNT, VPT, VST, VGT, VAT, VRT, MFT, MMT, MQT, MHT, MNT, MPT, MST, MGT, MAT, MRT, LFN, LMN, LQN, LHN, LNN, LPN, LSN, LGN, LAN, LRN, QFN, QMN, QQN, QHN, QNN, QPN, QSN, QGN, QAN, QRN, VFN, VMN, VQN, VHN, VNN, VPN, VSN, VGN, VAN, VRN, MFN, MMN, MQN, MHN, MNN, MPN, MSN, MGN, MAN, MRN, LFP, LMP, LQP, LHP, LNP, LPP, LSP, LGP, LAP, LRP, QFP, QMP, QQP, QHP, QNP, QPP, QSP, QGP, QAP, QRP, VFP, VMP, VQP, VHP, VNP, VPP, VSP, VGP, VAP, VRP, MFP, MMP, MQP, MHP, MNP, MPP, MSP, MGP, MAP, MRPR, LFR, LMR, LQR, LHR, LNR, LPR, LSR, LGR, LAR, LRR, QFR, QMR, QQR, QHR, QNR, QPR, QSR, QGR, QAR, QRR, VFR, VMR, VQR, VHR, VNR, VPR, VSR, VGR, VAR, VRR, MFR, MMR, MQR, MHR, MNR, MPR, MSR, MGR, MAR, or MRR. In some embodiments, $X_4$ is an optional sequence, and can be ER, or E, or absent. In some embodiments, if X is absent, $X_1$ is FF, and $X_2$ is LS. In some embodiments, the isolated peptides that comprise Formula (I) used in these methods have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of Formula (II), $X_{20}TFFVKLSX_{21}X_{22}$ (SEQ ID NO: 173), as described herein. In some embodiments, $X_{20}$ is an optional sequence, and can be KKLD (SEQ ID NO: 174), RKLD (SEQ ID NO: 175), KKGD (SEQ ID NO: 176), KKED (SEQ ID NO: 177), KLD, LD, or D, or absent. $X_{21}$ is an optional sequence, and can be LFT, LMT, LQT, LHT, LNT, LPT, LST, LGT, LAT, LRT, QFT, QMT, QQT, QHT, QNT, QPT, QST, QGT, QAT, QRT, VFT, VMT, VQT, VHT, VNT, VPT, VST, VGT, VAT, VRT, MFT, MMT, MQT, MHT, MNT, MPT, MST, MGT, MAT, MRT, LFN, LMN, LQN, LHN, LNN, LPN, LSN, LGN, LAN, LRN, QFN, QMN, QQN, QHN, QNN, QPN, QSN, QGN, QAN, QRN, VFN, VMN, VQN, VHN, VNN, VPN, VSN, VGN, VAN, VRN, MFN, MMN, MQN, MHN, MNN, MPN, MSN, MGN, MAN, MRN, LFP, LMP, LQP, LHP, LNP, LPP, LSP, LGP, LAP, LRP, QFP, QMP, QQP, QHP, QNP, QPP, QSP, QGP, QAP, QRP, VFP, VMP, VQP, VHP, VNP, VPP, VSP, VGP, VAP, VRP, MFP, MMP, MQP, MHP, MNP, MPP, MSP, MGP, MAP, MRPR, LFR, LMR, LQR, LHR, LNR, LPR, LSR, LGR, LAR, LRR, QFR, QMR, QQR, QHR, QNR, QPR, QSR, QGR, QAR, QRR, VFR, VMR, VQR, VHR, VNR, VPR, VSR, VGR, VAR, VRR, MFR, MMR, MQR, MHR, MNR, MPR, MSR, MGR, MAR, or MRR, or absent. In some embodiments, $X_{22}$ is an optional sequence, and can be ER, E, or absent. In some embodiments, the isolated peptides that comprise Formula (II) used in these methods have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of Formula (III), $X_{30}X_{31}VKLX_{32}LX_{33}TEX_{34}$ (SEQ ID NO: 178). In some embodiments, $X_{30}$ is an optional sequence, and can be KKLDTF (SEQ ID NO: 179), KLDTF (SEQ ID NO: 180), LDTF (SEQ ID NO: 181), DTF, TF, or F, or absent. In some embodiments, $X_{31}$ is an optional sequence, and can be F, S, M, V, T, or L, or absent. In some embodiments, $X_{31}$ is F. In some embodiments, $X_{32}$ can be S, Q, M, T, or H. In some embodiments, $X_{32}$ is S. $X_{33}$ can be F, M, Q, H, N, P, S, G, A, or R. In some embodiments, $X_{34}$ is F. $X_{34}$ is an optional sequence, and can be R or absent. In some embodiments, the isolated peptides that comprise Formula (III) used in these methods have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of Formula (VII), $X_{700}K\ X_{701}X_{702}X_{703}\ X_{704}X_{705}X_{706}K\ X_{707}\ X_{708}\ X_{709}\ X_{710}\ X_{711}E\ X_{712}$ (SEQ ID NO: 394), as described herein. In some embodiments, $X_{700}$ is an optional sequence, and can be K,A,D,E,G,H,I,L,M,N,P,Q,R,T, or V, or absent. In some embodiments, $X_{701}$ is an optional sequence, and can be L,A,C,D,E,F,G,H,I,K,M,N,Q,R,S,T, or V, or absent. In some embodiments, $X_{702}$ is an optional sequence, and can be D,A,E,I,V,W, or Y, or absent. In some embodiments, $X_{703}$ is an optional sequence, and can be T,C,M,N,P,Q,R,S,W, or Y, or absent. In some embodiments, $X_{704}$ is an optional sequence, and can be F,A,I,M,N,P,T, or V, or absent. In some embodiments, $X_{705}$ is an optional sequence, and can be F,L,M,Q,S,T, or V, or absent. In some embodiments, $X_{706}$ is an optional sequence, and can be V,F,G,L,P, or R, or absent. In some embodiments, $X_{707}$ is an optional sequence, and can be L,A,F,G,I,M,N,P,Q,R,S,T,V, or Y, or absent. In some embodiments, $X_{708}$ is an optional sequence, and can be S,H,M,N,Q, or T, or absent. In some embodiments, $X_{709}$ is an optional sequence, and can be L,A,H,I,M,N,Q,R,S,T,V, or W, or absent. In some embodiments, $X_{710}$ is an optional sequence, and can be F,A,C,G,H,I,L,M,N,P,Q,R,S,T,V, or W, or absent. In some embodiments, $X_{711}$ is an optional sequence, and can be T,F,G,H,I,L,M,N,P,S,V, or W, or absent. In some embodiments, $X_{712}$ is an optional sequence, and can be R,F,K,N,R,T, or Y, or absent. In some embodiments, the isolated peptide comprising Formula (VII) has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of Formula (VIII), $X_{800}K\ X_{801}K\ X_{802}E\ X_{803}$ (SEQ ID NO: 395), as described herein. In some embodiments, $X_{800}$ is an optional sequence, and can be K, A, D, E, G, H, I, L, M, N, P, Q, R, T, V, or K, or absent. In some embodiments, $X_{801}$ is an optional sequence, and can be LDTFFV, GDTFFV, EDTFFV, LDQFFV, LDTAFV, LDTVFV, LDTFMV, LDTFSV, LDTFVV, LDTFTV, LDTFLV, LDGFFV, LDTFGV, LDTFFK, ADTFFV, CDTFFV, DDTFFV, FDTFFV, HDTFFV, IDTFFV, KDTFFV, MDTFFV, NDTFFV, QDTFFV, RDTFFV, SDTFFV, TDTFFV, VDTFFV, LATFFV, LETFFV, LITFFV, LVTFFV, LWTFFV, LYTFFV, LDCFFV, LDMFFV, LDNFFV, LDPFFV, LDRFFV, LDSFFV, LDWFFV, LDYFFV, LDTIFV, LDTMFV, LDTNFV, LDTPFV, LDTTFV, LDTFQV, LDTFFF, LDTFFG, LDTFFL, LDTFFP, LDTFFR, LDTFIV, LDTSFV, LDTFAV, LDTFCV, LDTQFV, LDTLFV, LTTFFV, LDTFFI, LDHFFV, LMTFFV, LDTFEV, LDTFWV, LFTFFV, LDVFFV, LDTFRV, LDTFHV, LDTYFV, LPTFFV, PDTFFV, LDTFPV, LDTFNV, LDTWFV, LDTGFV, LDAFFV, LQTFFV, LCTFFV, LSTFFV, YDTFFV, LDEFFV, WDTFFV, LDTKFV, LDTCFV, LDTFYV, LDTHFV, LHTFFV, LRTFFV, LDLFFV, LDTRFV, LLTFFV, LDTFDV, LDTFFA, LDTFFT, LNTFFV, LDDFFV, LDIFFV, LDFFFV, LKTFFV, LDTFFQ, LGTFFV, LDTFFC, LDKFFV, LDTFKV, LDTEFV, LDTFFW, LDTFFM, LDTFFS, LDTFFH, LDTFFY, LDTFFN, LDTDFV, LDTFFE, LDTFFD, LTFFV, LDTFF, TFFV, LDF, LDTE, FFV, LDV, LV, or L, or absent. In some embodiments, $X_{802}$ is an optional sequence, and can be LSLFT, VSLFT, LQLFT, LMLFT, LTLFT, LHLFT, LSQFT, LSVFT, LSMFT, LSLMT, LSLQT, LSLHT, LSLNT, LSLPT, LSLST, LSLGT, LSLAT, LSLRT, LSLFN, LSLFP, LSLFR, LGLFT, ASLFT, FSLFT, GSLFT, ISLFT, MSLFT, NSLFT, PSLFT, QSLFT, RSLFT, SSLFT, TSLFT, YSLFT, LNLFT, LSAFT, LSHFT, LSIFT, LSNFT, LSRFT, LSSFT, LSTFT, LSWFT, LSLCT, LSLIT, LSLLT, LSLTT, LSLVT, LSLWT, LSLFF, LSLFG, LSLFH, LSLFI, LSLFL, LSLFM, LSLFS, LSLFV, LSLFW, LYLFT, LVLFT, LSFFT, LSGFT, LSKFT, LSCFT, LCLFT, LRLFT, LPLFT, LWLFT, LKLFT, LDLFT, LSYFT, LALFT, WSLFT, LSLFA, LSLFQ, LSPFT, HSLFT, LSLYT, LILFT, KSLFT, CSLFT, LSLFY, LSLFK, LSLFC, LFLFT, LELFT, LSLKT, LLLFT, LSLFD, LSLDT, LSLFE, DSLFT, LSLET, LSDFT, LSEFT, ESLFT, SLFT, LSFT, LFT, LSL, LT, or T, or absent. In some embodiments, $X_{803}$ is an optional sequence, and can be R, F, K, N, R, T, or Y, or absent. In some embodiments, the isolated peptide comprising Formula (VIII) has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of Formula (IX). Accordingly, in some embodiments, the peptide inhibitor comprises a peptide of Formula (IX): $X_{901}X_{902}X_{903}X_{904}X_{905}X_{906}X_{907}X_{908}X_{909}X_{910}X_{911}X_{912}X_{913}X_{914}X_{915}X_{916}X_{917}$, wherein $X_{901}$ is any amino acid or absent; $X_{902}$ is a positively charged amino acid, F, or N; $X_{903}$ is any amino acid; $X_{904}$ is any amino acid; $X_{905}$ is a polar uncharged amino acid, R, Y, or W; $X_{906}$ is a hydrophobic or uncharged polar amino acid; $X_{907}$ is a hydrophobic or uncharged polar amino acid; $X_{908}$ is a hydrophobic, non-aromatic carbon chain amino acid that is not M or F; $X_{909}$ is a positively charged amino acid, T, Q, or Y; $X_{910}$ is any amino acid that is not negatively charged; $X_{911}$ is a polar uncharged amino acid or H; $X_{912}$ is any amino acid that is not negatively charged; $X_{913}$ is any amino acid that is not negatively charged; $X_{914}$ is any amino acid that is not negatively charged; $X_{915}$ is a negatively charged amino acid, Y, or Q; $X_{916}$ is any amino acid that is not negatively charged; and $X_{917}$ is one or more positively charged amino acids or is absent. Optionally, $X_{901}$ comprises a positively charged amino acid. Optionally $X_{901}$ is an R or K. Optionally $X_{917}$ is RR. In some embodiments, the isolated peptide comprising Formula (IX) has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of and/or SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, or any variation or combination of variations of P28R or P28 core as provided in Tables 5.3 and 13 as described herein. In some embodiments, these isolated peptides have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Additionally, the peptide inhibitor used in these methods can comprise, consist of, or consist essentially of a peptide inhibitor that comprises, consists of, or consists essentially of any one or more of the peptides set forth in Table 5.1, 5.4, 5.5, 5.6, or any variation or combination of variations of P28R or P28 core as provided in Tables 5.3 and 13. In some embodiments, the isolated peptide from Table 5.1 used in these methods has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

In some embodiments, the method includes providing to the human a polynucleotide encoding such a peptide inhibitor (e.g., any one or more of the peptides provided in Table 5.1, 5.4, 5.5, 5.6, or any variation or combination of variations of P28R or P28 core as provided in Tables 5.3 and 13). For example, a polynucleotide encoding such a peptide inhibitor can be provided, for example a nucleic acid of SEQ ID NOs: 102-165.

Reduction of cancer-associated immunosuppression can induce and/or enhance an immune response against cancer cells. An immune response against cancer cells can reduce cancer cell proliferation, and/or cause cancer cells to undergo cell death or apoptosis. Thus, the method can include detecting an inhibition in the proliferation of cancer cells of the patient. The method can include detecting an induction of cell death or apoptosis of cancer cells of the patient. The method can include detecting an inhibition in the proliferation of cancer cells of the patient, and an induction of cell death or apoptosis of cancer cells of the patient. Apoptosis can be identified as known in the art, for example by neutral red assay, by trypan blue exclusion of dead cells, by acridine orange staining, by TUNEL staining, and/or by detection of cleaved PARP, and/or cleaved caspases.

Methods of Identifying a Patient in Need

It is contemplated herein that different populations of patients can have different albumin-derived immunoregulatory peptides, and that a given albumin-derived immunoregulatory peptide can have different effects in different individual patients. As shown in Example 30, some cancer patients have immune cells with a high proliferative response to IL-2, while other cancer patients have immune cells with a low proliferative response to IL-2. As shown in Examples 31 and 32, different populations of patients can respond differently to the same inhibitor of immunoregulatory peptides. Additionally, a given inhibitor can modulate the immune system in some patients, but not in other patients. Thus, some embodiments of the invention include methods of identifying a patient in need. A patient in need can include a patient having albumin-derived immunoregulatory peptides bound to at least some of his or her immune cells. A patient in need can include a patient that is likely to respond to an inhibitor of an immunoregulatory peptide. In some embodiments, immune cells of a patient can be isolated. The presence of immunoregulatory structures on the immune cells can be detected. The effect of an inhibitor of an immunoregulatory peptide on the immune cells can be detected. If an immunoregulatory structure is present and/or if immune cell function is modulated by the inhibitor, the patient can be classified as a patient in need. Optionally, an effective dose of the inhibitor can be determined. A therapeutically effective dose of the inhibitor can be administered to the patient in need.

Some embodiments include methods of detecting the presence of immunoregulatory peptides in an in vitro assay. In vitro methods of detecting the presence of albumin-derived immunoregulatory peptides bound to immune cells, immunoregulatory sequences and structures, and in vitro methods of detecting the effects of albumin-derived immunoregulatory peptides on immune cell activity are provided in U.S. Pat. No. 8,182,983, hereby expressly incorporated by reference in its entirety herein; U.S. Pat. No. 7,960,126, hereby expressly incorporated by reference in its entirety herein; U.S. Pat. No. 8,133,688 hereby expressly incorporated by reference in its entirety herein; U.S. Pat. No. 8,110,347, hereby expressly incorporated by reference in its entirety herein; and U.S. Pub. No. 2011/0262470, hereby expressly incorporated by reference in its entirety herein.

Some embodiments include detecting the response of inhibited immune cells to an inhibitor of immunoregulatory peptides. In some embodiments, immune cells are isolated from a patient. In some embodiments, the immune cells include PBMCs. In some embodiments, the immune cells are contacted with an inhibitor of immunoregulatory peptides.

In some embodiments, the immune cells are contacted with an inhibitor that comprises a peptide comprising, consisting of or consisting essentially of at least one peptide of SEQ ID NOs: 1-33, 34, 46-53, 64-66, 68, 76, 94-96, 98, 264-393, 583-586, or 589 or any one or more of the peptides provided in Table 5.1, 5.4, 5.5, 5.6, 6.1, 6.2, or 12 or any variation or combination of variations of P28R or P28 core as provided in Tables 5.3 and 13.

In some embodiments, the immune cells are contacted with an inhibitor that comprises a peptide comprising, consisting of or consisting essentially of Formula (I), XX1VKX2X3X4 (SEQ ID NO: 166). In some embodiments, X is an optional sequence, and can be KKLDT (SEQ ID NO: 167), RKLDT (SEQ ID NO: 168), KKGDT (SEQ ID NO: 169), KKEDT (SEQ ID NO: 170), KKLDQ (SEQ ID NO: 171), KKGDQ (SEQ ID NO: 252), KKEDQ (SEQ ID NO: 253), RKLDQ (SEQ ID NO: 254), RKGDQ (SEQ ID NO: 255), RKEDQ (SEQ ID NO: 256), RKGTD (SEQ ID NO: 257), RKEDT (SEQ ID NO: 258), KLDT (SEQ ID NO: 172), KGDT (SEQ ID NO: 259), KEDT (SEQ ID NO: 260), KLDQ (SEQ ID NO: 261), KGDQ (SEQ ID NO: 262), KEDQ (SEQ ID NO: 263), LDT, LDQ, GDT, GDQ, EDT, EDQ, DT, DQ, T, or Q, or absent. In some embodiments, X1 is one of FF, FM, FS, FV, FT, FL, AF, AM, AS, AV, AT, AL, VF, VM, VS, VV, VT, or VL. In some embodiments, X2 can be one of LS, LQ, LM, LT, LH, VS, VQ, VM, VT, or VH. In some embodiments, X3 can be one of LFT, LMT, LQT, LHT, LNT, LPT, LST, LGT, LAT, LRT, QFT, QMT, QQT, QHT, QNT, QPT, QST, QGT, QAT, QRT, VFT, VMT, VQT, VHT, VNT, VPT, VST, VGT, VAT, VRT, MFT, MMT, MQT, MHT, MNT, MPT, MST, MGT, MAT, MRT, LFN, LMN, LQN, LHN, LNN, LPN, LSN, LGN, LAN, LRN, QFN, QMN, QQN, QHN, QNN, QPN, QSN, QGN, QAN, QRN, VFN, VMN, VQN, VHN, VNN, VPN, VSN, VGN, VAN, VRN, MFN, MMN, MQN, MHN, MNN, MPN, MSN, MGN, MAN, MRN, LFP, LMP, LQP, LHP, LNP, LPP, LSP, LGP, LAP, LRP, QFP, QMP, QQP, QHP, QNP, QPP, QSP, QGP, QAP, QRP, VFP, VMP, VQP, VHP, VNP, VPP, VSP, VGP, VAP, VRP, MFP, MMP, MQP, MHP, MNP, MPP, MSP, MGP, MAP, MRPR, LFR, LMR, LQR, LHR, LNR, LPR, LSR, LGR, LAR, LRR, QFR, QMR, QQR, QHR, QNR, QPR, QSR, QGR, QAR, QRR, VFR, VMR, VQR, VHR, VNR, VPR, VSR, VGR, VAR, VRR, MFR, MMR, MQR, MHR, MNR, MPR, MSR, MGR, MAR, or MRR. In some embodiments, $X_4$ is an optional sequence, and can be ER, or E, or absent. In some embodiments, if X is absent, $X_1$ is FF, and $X_2$ is LS. In some embodiments, the peptide comprises one of SEQ ID NOs: 2-33. In some embodiments, the isolated peptides that comprise Formula (I) have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

In some embodiments, the immune cells are contacted with an inhibitor that comprises a peptide comprising, consisting of or consisting essentially of Formula (II), $X_{20}TFFVKLSX_{21}X_{22}$ (SEQ ID NO: 173). In some embodiments, $X_{20}$ is an optional sequence, and can be KKLD (SEQ ID NO: 174), RKLD (SEQ ID NO: 175), KKGD (SEQ ID NO: 176), KKED (SEQ ID NO: 177), KLD, LD, or D, or absent. $X_{21}$ is an optional sequence, and can be LFT, LMT, LQT, LHT, LNT, LPT, LST, LGT, LAT, LRT, QFT, QMT, QQT, QHT, QNT, QPT, QST, QGT, QAT, QRT, VFT, VMT, VQT, VHT, VNT, VPT, VST, VGT, VAT, VRT, MFT, MMT, MQT, MHT, MNT, MPT, MST, MGT, MAT, MRT, LFN, LMN, LQN, LHN, LNN, LPN, LSN, LGN, LAN, LRN, QFN, QMN, QQN, QHN, QNN, QPN, QSN, QGN, QAN, QRN, VFN, VMN, VQN, VHN, VNN, VPN, VSN, VGN, VAN, VRN, MFN, MMN, MQN, MHN, MNN, MPN, MSN, MGN, MAN, MRN, LFP, LMP, LQP, LHP, LNP, LPP, LSP, LGP, LAP, LRP, QFP, QMP, QQP, QHP, QNP, QPP, QSP, QGP, QAP, QRP, VFP, VMP, VQP, VHP, VNP, VPP, VSP, VGP, VAP, VRP, MFP, MMP, MQP, MHP, MNP, MPP, MSP, MGP, MAP, MRPR, LFR, LMR, LQR, LHR, LNR, LPR, LSR, LGR, LAR, LRR, QFR, QMR, QQR, QHR, QNR, QPR, QSR, QGR, QAR, QRR, VFR, VMR, VQR, VHR, VNR, VPR, VSR, VGR, VAR, VRR, MFR, MMR, MQR, MHR, MNR, MPR, MSR, MGR, MAR, or MRR, or absent. In some embodiments, $X_{22}$ is an optional sequence, and can be ER, or E, or absent. In some embodiments, the isolated peptides that comprise Formula (II) have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

In some embodiments, the immune cells are contacted with an inhibitor that comprises a peptide comprising, consisting of or consisting essentially of Formula (III), $X_{30}X_{31}VKLX_{32}LX_{33}TEX_{34}$ (SEQ ID NO: 178). In some embodiments, $X_{30}$ is an optional sequence, and can be KKLDTF (SEQ ID NO: 179), KLDTF (SEQ ID NO: 180), LDTF (SEQ ID NO: 181), DTF, TF, or F, or absent. In some embodiments, $X_{31}$ is an optional sequence, and can be F, S, M, V, T, or L, or absent. In some embodiments, $X_{31}$ is F. In some embodiments, $X_{32}$ can be S, Q, M, T, or H. In some embodiments, $X_{32}$ is S. $X_{33}$ can be F, M, Q, H, N, P, S, G, A, or R. In some embodiments, $X_{34}$ is F. $X_{34}$ is an optional sequence, and can be R, or absent. In some embodiments, the isolated peptides that comprise Formula (III) used in these methods have a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

In some embodiments, the immune cells are contacted with an inhibitor that comprises a peptide comprising, consisting of or consisting essentially of Formula (VII), $X_{700}K\ X_{701}X_{702}X_{703}\ X_{704}X_{705}X_{706}K\ X_{707}\ X_{708}\ X_{709}\ X_{710}\ X_{711}E\ X_{712}$ (SEQ ID NO: 394), as described herein. In some embodiments, $X_{700}$ is an optional sequence, and can be K,A,D,E,G,H,I,L,M,N,P,Q,R,T, or V, or absent. In some embodiments, $X_{701}$ is an optional sequence, and can be L,A,C,D,E,F,G,H,I,K,M,N,Q,R,S,T, or V, or absent. In some embodiments, $X_{702}$ is an optional sequence, and can be D,A,E,I,V,W, or Y, or absent. In some embodiments, $X_{703}$ is an optional sequence, and can be T,C,M,N,P,Q,R,S,W, or Y, or absent. In some embodiments, $X_{704}$ is an optional sequence, and can be F,A,I,M,N,P,T, or V, or absent. In some embodiments, $X_{705}$ is an optional sequence, and can be F,L,M,Q,S,T, or V, or absent. In some embodiments, $X_{706}$ is an optional sequence, and can be V,F,G,L,P, or R, or absent. In some embodiments, $X_{707}$ is an optional sequence, and can be L,A,F,G,I,M,N,P,Q,R,S,T,V, or Y, or absent. In some embodiments, $X_{708}$ is an optional sequence, and can be S,H,M,N,Q, or T, or absent. In some embodiments, $X_{709}$ is an optional sequence, and can be L,A,H,I,M,N,Q,R,S,T,V, or W, or absent. In some embodiments, $X_{710}$ is an optional sequence, and can be F,A,C,G,H,I,L,M,N,P,Q,R,S,T,V, or W, or absent. In some embodiments, $X_{711}$ is an optional sequence, and can be T,F,G,H,I,L,M,N,P,S,V, or W, or absent. In some embodiments, $X_{712}$ is an optional sequence, and can be R,F,K,N,R,T, or Y, or absent. In some embodiments, the isolated peptide comprising Formula (VII) has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

In some embodiments, the immune cells are contacted with an inhibitor that comprises a peptide comprising, consisting of or consisting essentially of Formula (VIII), $X_{800}K\ X_{801}K\ X_{802}E\ X_{803}$ (SEQ ID NO: 395), as described herein. In some embodiments, $X_{800}$ is an optional sequence, and can be K, A, D, E, G, H, I, L, M, N, P, Q, R, T, V, or K, or absent. In some embodiments, $X_{801}$ is an optional sequence, and can be LDTFFV, GDTFFV, EDTFFV, LDQFFV, LDTAFV, LDTVFV, LDTFMV, LDTFSV, LDTFVV, LDTFTV, LDTFLV, LDGFFV, LDTFGV, LDTFFK, ADTFFV, CDTFFV, DDTFFV, FDTFFV, HDTFFV, IDTFFV, KDTFFV, MDTFFV, NDTFFV, QDTFFV, RDTFFV, SDTFFV, TDTFFV, VDTFFV, LATFFV, LETFFV, LITFFV, LVTFFV, LWTFFV, LYTFFV, LDCFFV, LDMFFV, LDNFFV, LDPFFV, LDRFFV, LDSFFV, LDWFFV, LDYFFV, LDTIFV, LDTMFV, LDTNFV, LDTPFV, LDTTFV, LDTFQV, LDTFFF, LDTFFG, LDTFFL, LDTFFP, LDTFFR, LDTFIV, LDTSFV, LDTFAV, LDTFCV, LDTQFV, LDTLFV, LTTFFV, LDTFFI, LDHFFV, LMTFFV, LDTFEV, LDTFWV, LFTFFV, LDVFFV, LDTFRV, LDTFHV, LDTYFV, LPTFFV, PDTFFV, LDTFPV, LDTFNV, LDTWFV, LDTGFV, LDAFFV, LQTFFV, LCTFFV, LSTFFV, YDTFFV, LDEFFV, WDTFFV, LDTKFV, LDTCFV, LDTFYV, LDTHFV, LHTFFV, LRTFFV, LDLFFV, LDTRFV, LLTFFV, LDTFDV, LDTFFA, LDTFFT, LNTFFV, LDDFFV, LDIFFV, LDFFFV, LKTFFV, LDTFFQ, LGTFFV, LDTFFC, LDKFFV, LDTFKV, LDTEFV, LDTFFW, LDTFFM, LDTFFS, LDTFFH, LDTFFY, LDTFFN, LDTDFV, LDTFFE, LDTFFD, LTFFV, LDTFF, TFFV, LDF, LDTE, FFV, LDV, LV, or L, or absent. In some embodiments, $X_{802}$ is an optional sequence, and can be LSLFT, VSLFT, LQLFT, LMLFT, LTLFT, LHLFT, LSQFT, LSVFT, LSMFT, LSLMT, LSLQT, LSLHT, LSLNT, LSLPT, LSLST, LSLGT, LSLAT, LSLRT, LSLFN, LSLFP, LSLFR, LGLFT, ASLFT, FSLFT, GSLFT, ISLFT, MSLFT, NSLFT, PSLFT, QSLFT, RSLFT, SSLFT, TSLFT, YSLFT, LNLFT, LSAFT, LSHFT, LSIFT, LSNFT, LSRFT, LSSFT, LSTFT, LSWFT, LSLCT, LSLIT, LSLLT, LSLTT, LSLVT, LSLWT, LSLFF, LSLFG, LSLFH, LSLFI, LSLFL, LSLFM, LSLFS, LSLFV, LSLFW, LYLFT, LVLFT, LSFFT, LSGFT, LSKFT, LSCFT, LCLFT, LRLFT, LPLFT, LWLFT, LKLFT, LDLFT, LSYFT, LALFT, WSLFT, LSLFA, LSLFQ, LSPFT, HSLFT, LSLYT, LILFT, KSLFT, CSLFT, LSLFY, LSLFK, LSLFC, LFLFT, LELFT, LSLKT, LLLFT, LSLFD, LSLDT, LSLFE, DSLFT, LSLET, LSDFT, LSEFT, ESLFT, SLFT, LSFT, LFT, LSL, LT, T, or absent. In some embodiments, $X_{803}$ is an optional sequence, and can be R, F, K, N, R, T, or Y, or absent. In some embodiments, the isolated peptide comprising Formula (VIII) has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

In some embodiments, the immune cells are contacted with an inhibitor that comprises a peptide comprising, consisting of or consisting essentially of Formula (IX). Accordingly, in some embodiments, the peptide inhibitor comprises a peptide of Formula (IX): $X_{901}X_{902}X_{903}X_{904}X_{905}X_{906}X_{907}X_{908}X_{909}X_{910}X_{911}X_{912}X_{913}X_{914}X_{915}X_{916}X_{917}$, wherein $X_{901}$ is any amino acid or absent; $X_{902}$ is a positively charged amino acid, F, or N; $X_{903}$ is any amino acid; $X_{904}$ is any amino acid; $X_{905}$ is a polar uncharged amino acid, R, Y, or W; $X_{906}$ is a hydrophobic or uncharged polar amino acid; $X_{907}$ is a hydrophobic or uncharged polar amino acid; $X_{908}$ is a hydrophobic, non-aromatic carbon chain amino acid that is not M or F; $X_{909}$ is a positively charged amino acid, T, Q, or Y; $X_{910}$ is any amino acid that is not negatively charged; $X_{911}$ is a polar uncharged amino acid or H; $X_{912}$ is any amino acid that is not negatively charged; $X_{913}$ is any amino acid that is not negatively charged; $X_{914}$ is any amino acid that is not negatively charged; $X_{915}$ is a negatively charged amino acid, Y, or Q; $X_{916}$ is any amino acid that is not negatively charged; and $X_{917}$ is one or more positively charged amino acids or is absent. Optionally, $X_{901}$ comprises a positively charged amino acid. Optionally $X_{901}$ is an R or K. Optionally $X_{917}$ is RR. In some embodiments, the isolated peptide comprising Formula (IX) has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values.

Figure 33A:
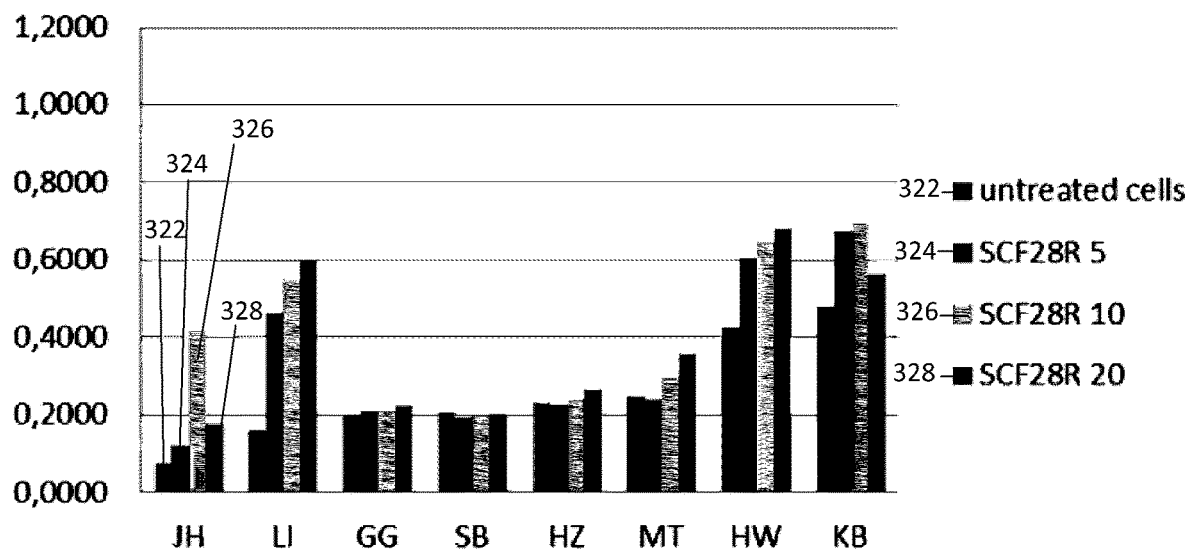
FIGS. 33A and 33B illustrate effects of various concentrations of peptide P28R on MTS bioreduction in (FIG. 33A) PBMCs from healthy control samples, and (FIG. 33B) PBMCs from cancer patients.
Figure 33B:
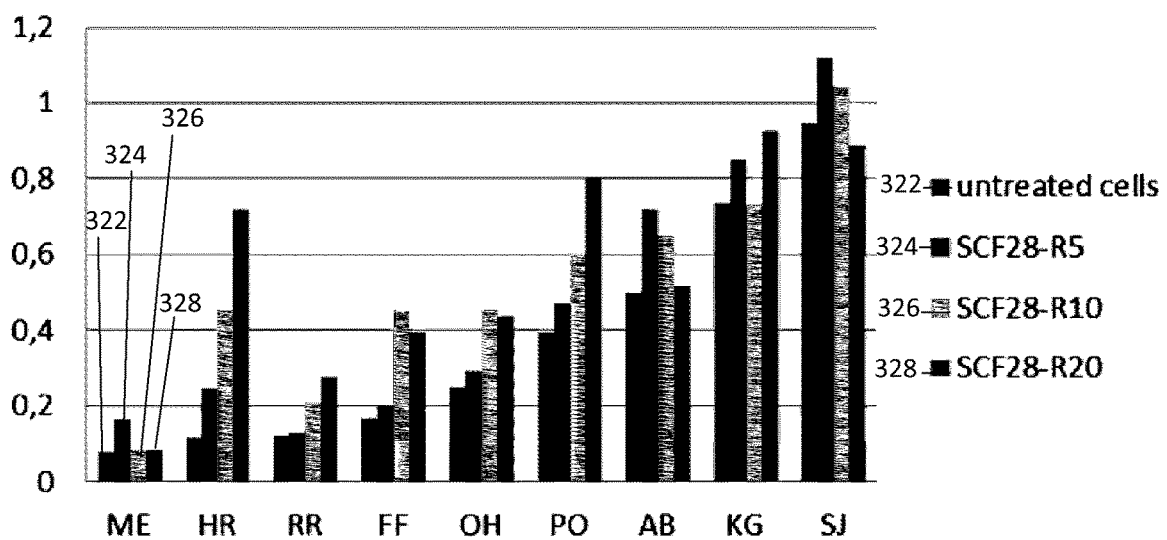
Figure 34:
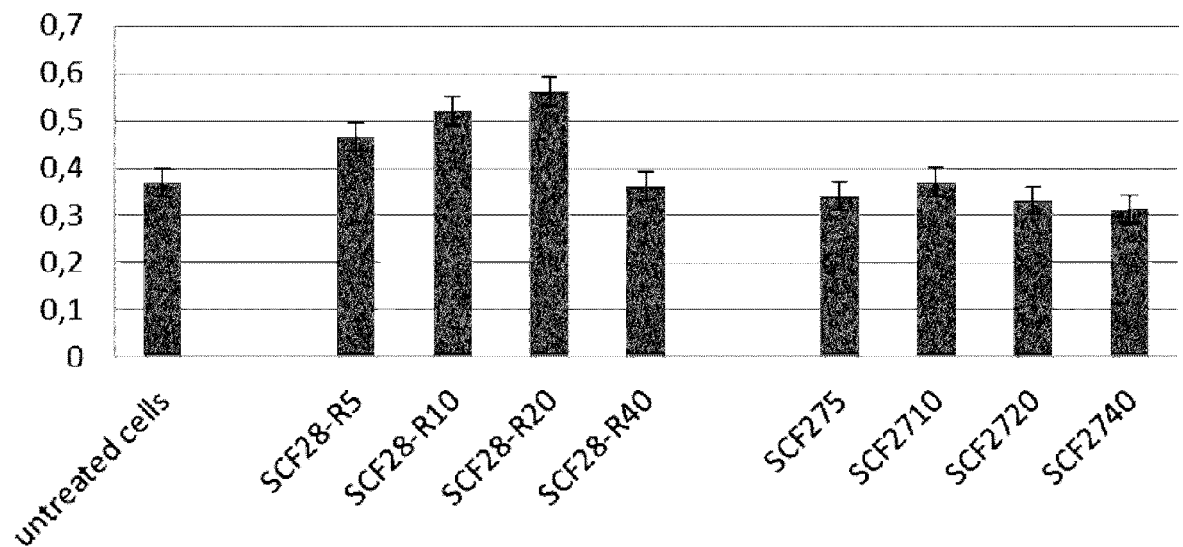
FIG. 34 illustrates effect of P28R (aka "SCF 28W") (N=9) and P27 (aka "SCF 27") (N=8) on PBMCs from cancer patients, MTS measurements, day 7.
Figure 37:
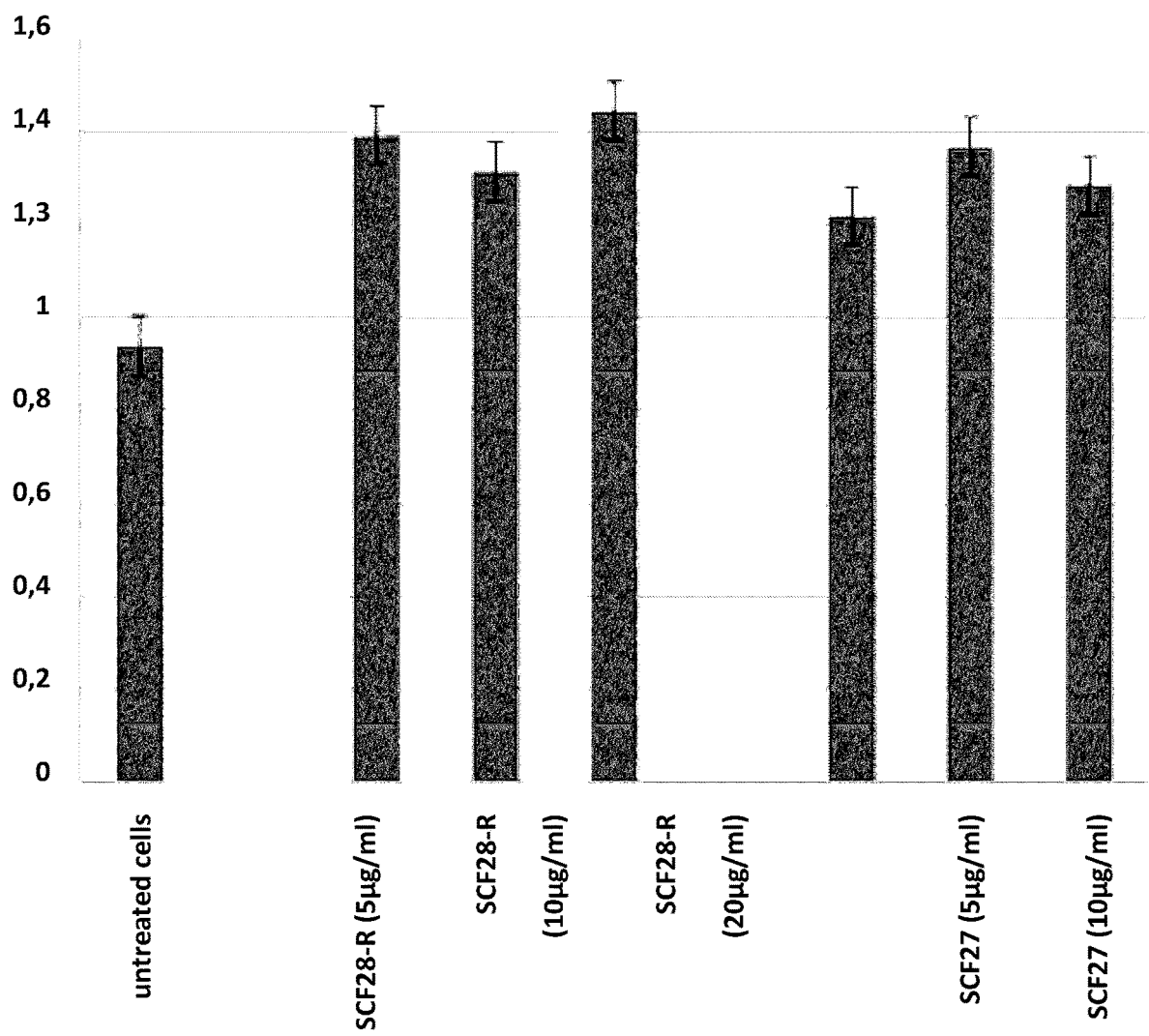
FIG. 37 illustrates effect of P28R (aka "SCF 28R") and P27 (aka "SCF 27") on IL-2 stimulation of PBMCs from cancer patients, based on BrdU incorporation.

In some embodiments, the immune cells are contacted with an inhibitor that comprises, consists of, or consists essentially of a peptide inhibitor that comprises, consists of, or consists essentially of any one or more of the peptides set forth in Table 5.1. In some embodiments, the isolated peptide from Table 5.1 used in these methods has a length that is less than or equal to 1100 amino acids, for example, less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 160, 170, 180, 190, 200, 210, 220, 230, 240, 250, 260, 270, 280, 290, 300, 320, 340, 360, 380, 400, 450, 500, 550, 600, 650, 700, 750, 800, 850, 900, 950, 1000, 1050, or 1100 amino acids, including ranges between any two of the listed values. In some embodiments, the response of the immune cells is detected. In some embodiments, the response to IL-2 stimulation is detected (see Example 2). In some embodiments, T cell stimulation is detected (see Example 3). In some embodiments, NK-Cell cytotoxicity is assayed (see Example 4). In some embodiments, leukocyte spreading is detected (see Example 5). In some embodiments, unblocking of the LFA-1 receptor is detected (see Example 6). In some embodiments, binding of P28R to the tumor can be demonstrated. In some embodiments, binding of P3028 (SEQ ID NO: 185) to the IL-2 receptor is detected (see Example 8). In some embodiments, MTS conversion by the immune cells is detected, for example in response to immune cell stimulation (see Examples 31-32). In some embodiments, BrdU incorporation by the immune cells is detected, for example in response to immune cell stimulation (see Examples 31-32). It is contemplated herein that some patients will exhibit some immune cell responses in response to the inhibitor, but will not exhibit other immune cells responses in response to that same inhibitor (see Example 31-32, and FIGS. 34, 37, and 38, showing, among other results, that P28R enhanced the IL-2 induced stimulation of BrdU uptake and MTS conversion in one patient, but enhanced BrdU updated and not MTS conversion in another patient). Thus, some embodiments include detecting two or more immune cell responses described herein. Detection of two or more immune cell responses can allow the identification of a patient that is likely to elicit a first response, but not a second response, and can be useful in guiding clinical decisions such as which inhibitors or combinations of inhibitors to apply, and whether to apply additional therapies to the patient in need. In some embodiments, detecting activation or stimulation of an immune cell, as evidenced by an increase in CD69 or CD71 expression, induction of the secretion of a signal substance, as evidenced by interferon gamma or IL-12 production, or stimulation of the release of a cytolytic substance, as evidenced by the release of granzyme B or perforin is performed. In some embodiments, detecting activation or stimulation of an immune cell includes detecting one or more of enhanced cytotoxicity, cytokine production, cell migration, and/or cell proliferation In some embodiments, optionally, an effective dose of the inhibitor for the patient in need is determined. In some embodiments, cells of the patient are contacted in vitro with two or more doses of the inhibitor, and an immune response. As shown in FIGS. 33A, 33B, and 34, P28R can have dose-dependent immunomodulatory effects, for example on mitochondrial metabolism (see Example 28 and 29).

As shown in FIG. 34, increasing doses of P28R (SEQ ID NO: 2) were provided to the immune cells of cancer patients in vitro. A dose of 20 µg/ml of P28R resulted in significantly higher MTS conversion than a dose of 40 µg/ml of P28R. Thus, one skilled in the art will appreciate that some embodiments include determining an effective dose of an inhibitor for the cells of a patient in vitro, and then providing an appropriate dose of the inhibitor to the patient.

Additional Alternative Embodiments

Alternative 1001 includes a composition comprising an isolated peptide comprising the amino acid sequence FFVKLS (SEQ ID NO: 62), in which the isolated peptide comprises no more than 30 amino acid residues; and a nanoparticle, in which the isolated peptide is immobilized on the nanoparticle. Alternative 1002 includes the composition of Alternative 1, in which the nanoparticle comprises at least one of: a polymer, a dendrimer, a quantum dot, a gold nanoparticle, a silica nanoparticle, a magnetic particle, a carbon-based material, a carbohydrate, a nucleic acid, a polypeptide, or a lipid. Alternative 1003 includes the composition of Alternative 1001 or Alternative 1002, in which the nanoparticle comprises a polymer comprising at least one of PLGA, glycerol, chitosan, DNA, or a hydrogel. Alternative 1004 includes the composition of any one of Alternatives 1001-1003, in which the nanoparticle comprises a gold nanoparticle comprising at least one of a sphere, rod, or shell. Alternative 1005 includes the composition of any one of alternatives 1001-1004, in which the nanoparticle comprises a dendrimer comprising PAMAM. Alternative 1006 includes the composition of any one Alternatives 1001-1005, in which the nanoparticle comprises a silica nanoparticle comprising at least one of a sphere, shell, or mesoporous structure. Alternative 1007 includes the composition of any one of Alternatives 1001-1006, in which the nanoparticle comprises a quantum dot comprising at least one of CdSe, CuInSe, or CdTe. Alternative 1008 includes the composition of any one of Alternatives 1001-1007, in which the nanoparticle comprises a magnetic particle comprising at least one of iron oxide, cobalt-based material, a magnetic sphere, an aggregate in dextran or silica, or a Dynal® bead. Alternative 1009 includes the composition of any one of Alternatives 1001-1008, in which the nanoparticle comprises a magnetic comprising a carbon-based material comprising at least one of a carbon nanotube, buckminsterfullerene, or graphene. Alternative 1010 includes the composition of any one of Alternatives 1001-1009, in which the nanoparticle comprises a polypeptide comprising an albumin or an albumin fragment. Alternative 1011 includes the composition of any one of Alternatives 1001-1010, in which the nanoparticle comprises a lipid comprising a lipid capsule or liposome. Alternative 1012 includes the composition of any one of Alternatives 1001-1011, in which the nanoparticle is PEGylated. Alternative 1013 includes the composition of any one of Alternatives 1001-1012, in which the nanoparticle comprises a non-degradable particle. Alternative 1014 includes the composition of any one of Alternatives 1001-1012, in which the nanoparticle comprises a degradable particle. Alternative 1015 includes the composition of any one of Alternatives 1001-1014, in which the nanoparticle comprises a structure selected from the group consisting of: a sphere, a rod, a shell, a mesoporous structure, a bead, a hydrogel, an aggregate, a fullerene, a cage, a porous nanocage, a viral capsid, a viral capsid fragment, or a lipid capsule. Alternative 1016 includes the composition of any one of Alternatives 1001-1015, in which the isolated peptide is non-covalently immobilized on the nanoparticle. Alternative 1017 includes the composition of Alternative 1016, in which the nanoparticle is non-covalently immobilized on the nanoparticle by at least one of a van der Waals interaction, steric interaction, hydrogen bonding interaction, hydrophobic interaction or electrostatic interaction. Alternative 1018 includes the composition of any one of Alternatives 1001-1017, in which the isolated peptide is immobilized on the nanoparticle covalently. Alternative 1019 includes the composition of Alternative 1018, in which the isolated peptide is immobilized on the nanoparticle via a cleavable linker or a non-cleavable linker. Alternative 1020 includes the composition of Alternative 1019, in which the cleavable linker comprises one of an acid-labile linker, a matrix metalloproteinase target site, or a cathepsin target site. Alternative 1021 includes the composition of any one of Alternatives 1001-1020, in which the nanoparticle has a diameter of at least 10 nm. Alternative 1022 includes the composition of any one of Alternatives 1001-1021, in which the nanoparticle has a diameter of no more than 5000 nm. Alternative 1023 includes the composition of any one of Alternatives 1001-1022, in which the isolated peptide comprises no more than 16 amino acid residues. Alternative 1024 includes the composition of any one of Alternatives 1001-1022, in which the isolated peptide comprises no more than 8 amino acid residues. Alternative 1025 includes the composition of any one of Alternatives 1001-1022, in which the isolated peptide consists of the amino acid sequence FFVKLS (SEQ ID NO: 62).

Alternative 1026 includes a composition comprising an isolated peptide comprising the amino acid sequence KKLDTFFVKLSLFTER (SEQ ID NO: 2); and a nanoparticle, in which the isolated peptide is immobilized on the nanoparticle. Alternative 1027 includes the composition of Alternative 1026, in which the nanoparticle comprises at least one of: a polymer, a dendrimer, a quantum dot, a gold nanoparticle, a silica nanoparticle, a magnetic particle, a carbon-based material, a carbohydrate, a nucleic acid, a polypeptide, or a lipid. Alternative 1028 includes the composition of Alternative 1026 or Alternative 1027, in which the nanoparticle comprises a polymer comprising at least one of PLGA, glycerol, chitosan, DNA, or a hydrogel. Alternative 1029 includes the composition of any one of Alternatives 1026-1028, in which the nanoparticle comprises a gold nanoparticle comprising at least one of a sphere, rod, or shell. Alternative 1030 includes the composition of any one of Alternatives 1026-1029, in which the nanoparticle comprises a dendrimer comprising PAMAM. Alternative 1031 includes the composition of any one of Alternatives 1026-1030, in which the nanoparticle comprises a silica nanoparticle comprising at least one of a sphere, shell, or mesoporous structure. Alternative 1032 includes the composition of any one of Alternatives 1026-1031, in which the nanoparticle comprises a quantum dot comprising at least one of CdSe, CuInSe, or CdTe. Alternative 1030 includes the composition of any one of Alternatives 1026-1032, in which the nanoparticle comprises a magnetic particle comprising at least one of iron oxide, cobalt-based material, a magnetic sphere, an aggregate in dextran or silica, or a Dynal® bead. Alternative 1002 includes the composition of any one of Alternatives 1026-1033, in which the nanoparticle comprises a magnetic comprising a carbon-based material comprising at least one of a carbon nanotube, buckminsterfullerene, or graphene. Alternative 1035 includes the composition of any one of Alternatives 1026-1034, in which the nanoparticle comprises a polypeptide comprising an albumin or an albumin fragment. Alternative 1036 includes the composition of any one of Alternatives 1026-1035, in which the nanoparticle comprises a lipid comprising a lipid capsule or liposome. Alternative 1037 includes the composition of any one of Alternatives 1026-1036, in which the nanoparticle is PEGylated. Alternative 1038 includes the composition of any one of Alternatives 1026-1037, in which the nanoparticle comprises a non-degradable particle. Alternative 1039 includes the composition of any one of Alternatives 1026-1037, in which the nanoparticle comprises a degradable particle. Alternative 1040 includes the composition of any one of Alternatives 1026-1039, in which the nanoparticle comprises a structure selected from the group consisting of: a sphere, a rod, a shell, a mesoporous structure, a bead, a hydrogel, an aggregate, a fullerene, a cage, a porous nanocage, a viral capsid, a viral capsid fragment, or a lipid capsule. Alternative 1041 includes the composition of any one of Alternatives 1026-1040, in which the isolated peptide is non-covalently immobilized on the nanoparticle. Alternative 1042 includes the composition of Alternative 1041, in which the nanoparticle is non-covalently immobilized on the nanoparticle by at least one of a van der Waals interaction, steric interaction, hydrogen bonding interaction, hydrophobic interaction or electrostatic interaction. Alternative 1043 includes the composition of any one of Alternatives 1026-1042, in which the isolated peptide is immobilized on the nanoparticle covalently. Alternative 1044 includes the composition of Alternative 1043, in which the isolated peptide is immobilized on the nanoparticle via a cleavable linker or a non-cleavable linker. Alternative 1045 includes the composition of Alternative 1044, in which the cleavable linker comprises one of an acid-labile linker, a matrix metalloproteinase target site, or a cathepsin target site. Alternative 1046 includes the composition of any one of Alternatives 1026-1045, in which the nanoparticle has a diameter of at least 10 nm. Alternative 1047 includes the composition of any one of Alternatives 1026-1046, in which the nanoparticle has a diameter of no more than 5000 nm. Alternative 1048 includes the composition of any one of Alternatives 1026-1047, in which the isolated peptide comprises no more than 100 amino acid residues. Alternative 1049 includes the composition of any one of Alternatives 1026-1047, in which the isolated peptide comprises no more than 30 amino acid residues. Alternative 1050 includes the composition of any one of Alternatives 1026-1047, in which the isolated peptide consists of the amino acid sequence of SEQ ID NO: 2.

Alternative 1051 includes a composition comprising an isolated peptide comprising the amino acid sequence RKLDTFFVKLSLFTERRR (SEQ ID NO: 586); and a nanoparticle, in which the isolated peptide is immobilized on the nanoparticle. Alternative 1052 includes the composition of Alternative 1051, in which the nanoparticle comprises at least one of: a polymer, a dendrimer, a quantum dot, a gold nanoparticle, a silica nanoparticle, a magnetic particle, a carbon-based material, a carbohydrate, a nucleic acid, a polypeptide, or a lipid. Alternative 1053 includes the composition of Alternative 1051 or Alternative 1052, in which the nanoparticle comprises a polymer comprising at least one of PLGA, glycerol, chitosan, DNA, or a hydrogel. Alternative 1054 includes the composition of any one of Alternatives 1051-1053, in which the nanoparticle comprises a gold nanoparticle comprising at least one of a sphere, rod, or shell. Alternative 1055 includes the composition of any one of Alternatives 1051-1054, in which the nanoparticle comprises a dendrimer comprising PAMAM. Alternative 1056 includes the composition of any one of Alternatives 1051-1055, in which the nanoparticle comprises a silica nanoparticle comprising at least one of a sphere, shell, or mesoporous structure. Alternative 1057 includes the composition of any one of Alternatives 1051-1056, in which the nanoparticle comprises a quantum dot comprising at least one of CdSe, CuInSe, or CdTe. Alternative 1058 includes the composition of any one of Alternatives 1051-1057, in which the nanoparticle comprises a magnetic particle comprising at least one of iron oxide, cobalt-based material, a magnetic sphere, an aggregate in dextran or silica, or a Dynal® bead. Alternative 1059 includes the composition of any one of Alternatives 1051-1058, in which the nanoparticle comprises a magnetic comprising a carbon-based material comprising at least one of a carbon nanotube, buckminsterfullerene, or graphene. Alternative 1060 includes the composition of any one of Alternatives 1051-1059, in which the nanoparticle comprises a polypeptide comprising an albumin or an albumin fragment. Alternative 1061 includes the composition of any one of Alternatives 1051-1060, in which the nanoparticle comprises a lipid comprising a lipid capsule or liposome. Alternative 1062 includes the composition of any one of Alternatives 1051-1061, in which the nanoparticle is PEGylated. Alternative 1063 includes the composition of any one of Alternatives 1051-1062, in which the nanoparticle comprises a non-degradable particle. Alternative 1064 includes the composition of any one of Alternatives 1051-1062, in which the nanoparticle comprises a degradable particle. Alternative 1065 includes the composition of any one of Alternatives 1051-1054, in which the nanoparticle comprises a structure selected from the group consisting of: a sphere, a rod, a shell, a mesoporous structure, a bead, a hydrogel, an aggregate, a fullerene, a cage, a porous nanocage, a viral capsid, a viral capsid fragment, or a lipid capsule. Alternative 1066 includes the composition of any one of Alternatives 1051-1055, in which the isolated peptide is non-covalently immobilized on the nanoparticle. Alternative 1067 includes the composition of Alternative 1066, in which the nanoparticle is non-covalently immobilized on the nanoparticle by at least one of a van der Waals interaction, steric interaction, hydrogen bonding interaction, hydrophobic interaction or electrostatic interaction. Alternative 1068 includes the composition of any one of Alternatives 1051-1067, in which the isolated peptide is immobilized on the nanoparticle covalently. Alternative 1069 includes the composition of Alternative 1058, in which the isolated peptide is immobilized on the nanoparticle via a cleavable linker or a non-cleavable linker. Alternative 1070 includes the composition of Alternative 1059, in which the cleavable linker comprises one of an acid-labile linker, a matrix metalloproteinase target site, or a cathepsin target site. Alternative 1071 includes the composition of any one of Alternatives 1051-1070, in which the nanoparticle has a diameter of at least 10 nm. Alternative 1072 includes the composition of any one of Alternatives 1051-1071, in which the nanoparticle has a diameter of no more than 5000 nm. Alternative 1073 includes the composition of any one of Alternatives 1051-1072, in which the isolated peptide comprises no more than 16 amino acid residues. Alternative 1074 includes the composition of any one of Alternatives 1051-1073, in which the isolated peptide comprises no more than 100 amino acid residues. Alternative 1075 includes the composition of any one of Alternatives 1051-1074, in which the isolated peptide comprises no more than 30 amino acid residues. Alternative 1076 includes the composition any one of Alternatives 1051-1075, in which the isolated peptide consists of the amino acid sequence of SEQ ID NO: 586.

Alternative 1077 includes a composition comprising: an isolated peptide comprising the formula $X_1X_2X_3X_4X_5X_6X_7X_8X_9X_{10}X_{11}X_{12}X_{13}X_{14}X_{15}X_{16}X_{17}$, in which $X_1$ is any amino acid or is absent; $X_2$ is a positively charged amino acid, F, or N; $X_3$ is any amino acid; $X_4$ is any amino acid; $X_5$ is a polar uncharged amino acid, R, Y, or W; $X_6$ is a hydrophobic or uncharged polar amino acid; $X_7$ is a hydrophobic or uncharged polar amino acid; $X_8$ is a hydrophobic, non-aromatic carbon chain amino acid that is not M or F; $X_9$ is a positively charged amino acid, T, Q, or Y; $X_{10}$ is any amino acid that is not negatively charged; $X_{11}$ is a polar uncharged amino acid or H; $X_{12}$ is any amino acid that is not negatively charged; $X_{13}$ is any amino acid that is not negatively charged; $X_{14}$ is any amino acid that is not negatively charged; $X_{15}$ is a negatively charged amino acid, Y, or Q; $X_{16}$ is any amino acid that is not negatively charged; $X_{17}$ is one or more positively charged amino acids or is absent; and a nanoparticle, in which the isolated peptide is immobilized on the nanoparticle. Alternative 1078 includes the composition of Alternative 1077, in which the nanoparticle comprises at least one of: a polymer, a dendrimer, a quantum dot, a gold nanoparticle, a silica nanoparticle, a magnetic particle, a carbon-based material, a carbohydrate, a nucleic acid, a polypeptide, or a lipid. Alternative 1079 includes the composition of Alternative 1077 or Alternative 1078, in which the nanoparticle comprises a polymer comprising at least one of PLGA, glycerol, chitosan, DNA, or a hydrogel. Alternative 1080 includes the composition of any one of Alternatives 1077-1079, in which the nanoparticle comprises a gold nanoparticle comprising at least one of a sphere, rod, or shell. Alternative 1081 includes the composition of any one of Alternatives 1077-1080, in which the nanoparticle comprises a dendrimer comprising PAMAM. Alternative 1082 includes the composition of any one of Alternatives 1077-1081, in which the nanoparticle comprises a silica nanoparticle comprising at least one of a sphere, shell, or mesoporous structure. Alternative 1083 includes the composition of any one of Alternatives 1077-1082, in which the nanoparticle comprises a quantum dot comprising at least one of CdSe, CuInSe, or CdTe. Alternative 1084 includes the composition of any one of Alternatives 1077-1083, in which the nanoparticle comprises a magnetic particle comprising at least one of iron oxide, cobalt-based material, a magnetic sphere, an aggregate in dextran or silica, or a Dynal® bead. Alternative 1085 includes the composition of any one of Alternatives 1077-1084, in which the nanoparticle comprises a magnetic comprising a carbon-based material comprising at least one of a carbon nanotube, buckminsterfullerene, or graphene. Alternative 1086 includes the composition of any one of Alternatives 1077-1085, in which the nanoparticle comprises a polypeptide comprising an albumin or an albumin fragment. Alternative 1087 includes the composition of any one of Alternatives 1077-1086, in which the nanoparticle comprises a lipid comprising a lipid capsule or liposome. Alternative 1088 includes the composition of any one of Alternatives 1077-1087, in which the nanoparticle is PEGylated. Alternative 1089 includes the composition of any one of Alternatives 1077-1088, in which the nanoparticle comprises a non-degradable particle. Alternative 1090 includes the composition of any one of Alternatives 1077-1088, in which the nanoparticle comprises a degradable particle. Alternative 1091 includes the composition of any one of Alternatives 1077-1090, in which the nanoparticle comprises a structure selected from the group consisting of: a sphere, a rod, a shell, a mesoporous structure, a bead, a hydrogel, an aggregate, a fullerene, a cage, a porous nanocage, a viral capsid, a viral capsid fragment, or a lipid capsule. Alternative 1092 includes the composition of any one of Alternatives 1077-1091, in which the isolated peptide is non-covalently immobilized on the nanoparticle. Alternative 1093 includes the composition of Alternative 1092, in which the nanoparticle is non-covalently immobilized on the nanoparticle by at least one of a van der Waals interaction, steric interaction, hydrogen bonding interaction, hydrophobic interaction or electrostatic interaction. Alternative 1094 includes the composition of any one of Alternatives 1077-1093, in which the isolated peptide is immobilized on the nanoparticle covalently. Alternative 1095 includes the composition of Alternative 1094, in which the isolated peptide is immobilized on the nanoparticle via a cleavable linker or a non-cleavable linker. Alternative 1096 includes the composition of Alternative 1095, in which the cleavable linker comprises one of an acid-labile linker, a matrix metalloproteinase target site, or a cathepsin target site. Alternative 1097 includes the composition of any one of Alternatives 1077-1096, in which the nanoparticle has a diameter of at least 10 nm. Alternative 1098 includes the composition of any one of Alternatives 1077-0197, in which the nanoparticle has a diameter of no more than 5000 nm. Alternative 1099 includes the composition of any one of Alternatives 1077-1098, in which $X_1$ comprises at least one positively charged amino acid. Alternative 1100 includes the composition of any one of Alternatives 1077-1099, in which $X_1$ comprises R and $X_{17}$ comprises RR. Alternative 1101 includes the composition of any one of Alternatives 1077-1100, in which the peptide is soluble in an aqueous solution. Alternative 1102 includes the composition of any one of Alternatives 1077-1101, in which at least one of: $X_1$ is K; $X_2$ is K; $X_3$ is L; $X_4$ is D; $X_5$ is T; $X_6$ is F; $X_7$ is F; $X_8$ is V; $X_9$ is K; $X_{10}$ is L; $X_{11}$ is S; $X_{12}$ is L; $X_{13}$ is F; $X_{14}$ is T; $X_{15}$ is E; or $X_{16}$ is R. Alternative 1103 includes the composition of any one of Alternatives 1077-1102, in which the isolated peptide has a length of 30 amino acid residues or less. Alternative 1104 includes the composition of any one of Alternatives 1077-1102, in which the isolated peptide consists of the formula $X_1X_2X_3X_4X_5X_6X_7X_8X_9X_{10}X_{11}X_{12}X_{13}X_{14}X_{15}X_{16}X_{17}$. Alternative 1105 includes the composition of any one of Alternatives 1077-1104, in which the isolated peptide comprises the amino acid sequence KKLDTFFVKLSLFTER (SEQ ID NO: 2). Alternative 1106 includes the composition of any one of Alternatives 1077-1104, in which the isolated peptide comprises the amino acid sequence RKLDTFFVKLSLFTERR (SEQ ID NO: 586). Alternative 1107 includes a composition comprising: an isolated synthetic peptide consisting of the amino acid sequence FFVKLS (SEQ ID NO: 62); and a nanoparticle, in which the isolated synthetic peptide is immobilized on the nanoparticle. Alternative 1108 includes the composition of Alternative 1107, in which the nanoparticle comprises at least one of: a polymer, a dendrimer, a quantum dot, a gold nanoparticle, a silica nanoparticle, a magnetic particle, a carbon-based material, a carbohydrate, a nucleic acid, a polypeptide, or a lipid. Alternative 1109 includes the composition of Alternative 1107 or Alternative 1108, in which the nanoparticle comprises a polymer comprising at least one of PLGA, glycerol, chitosan, DNA, or a hydrogel. Alternative 1110 includes the composition of any one of Alternatives 1107-1109, in which the nanoparticle comprises a gold nanoparticle comprising at least one of a sphere, rod, or shell. Alternative 1111 includes the composition of any one of Alternatives 1107-1110, in which the nanoparticle comprises a dendrimer comprising PAMAM. Alternative 1112 includes the composition of any one of Alternatives 1107-1111, in which the nanoparticle comprises a silica nanoparticle comprising at least one of a sphere, shell, or mesoporous structure. Alternative 1113 includes the composition of any one of Alternatives 1107-1112, in which the nanoparticle comprises a quantum dot comprising at least one of CdSe, CuInSe, or CdTe. Alternative 1114 includes the composition of any one of Alternatives 1107-1113, in which the nanoparticle comprises a magnetic particle comprising at least one of iron oxide, cobalt-based material, a magnetic sphere, an aggregate in dextran or silica, or a Dynal® bead. Alternative 1115 includes the composition of any one of Alternatives 1107-1114, in which the nanoparticle comprises a magnetic comprising a carbon-based material comprising at least one of a carbon nanotube, buckminsterfullerene, or graphene.

Alternative 1116 includes the composition of any one of Alternatives 1107-1115, in which the nanoparticle comprises a polypeptide comprising an albumin or an albumin fragment. Alternative 1117 includes the composition of any one of Alternatives 1107-1116, in which the nanoparticle comprises a lipid comprising a lipid capsule or liposome. Alternative 1118 includes the composition of any one of Alternatives 1107-1117, in which the nanoparticle is PEGylated. Alternative 1119 includes the composition of any one of Alternatives 1107-1118, in which the nanoparticle comprises a non-degradable particle. Alternative 1120 includes the composition of any one of Alternatives 1107-1118, in which the nanoparticle comprises a degradable particle. Alternative 1121 includes the composition of any one of Alternatives 1107-1120, in which the nanoparticle comprises a structure selected from the group consisting of: a sphere, a rod, a shell, a mesoporous structure, a bead, a hydrogel, an aggregate, a fullerene, a cage, a porous nanocage, a viral capsid, a viral capsid fragment, or a lipid capsule. Alternative 1122 includes the composition of any one of Alternatives 1107-1121, in which the isolated peptide is non-covalently immobilized on the nanoparticle. Alternative 1123 includes the composition of Alternative 1122, in which the nanoparticle is non-covalently immobilized on the nanoparticle by at least one of a van der Waals interaction, steric interaction, hydrogen bonding interaction, hydrophobic interaction or electrostatic interaction. Alternative 1124 includes the composition of any one of Alternatives 1107-1123, in which the isolated peptide is immobilized on the nanoparticle covalently. Alternative 1125 includes the composition of Alternative 1124, in which the isolated peptide is immobilized on the nanoparticle via a cleavable linker or a non-cleavable linker. Alternative 1126 includes the composition of Alternative 1125, in which the cleavable linker comprises one of an acid-labile linker, a matrix metalloproteinase target site, or a cathepsin target site. Alternative 1127 includes the composition of any one of Alternatives 1107-1126, in which the nanoparticle has a diameter of at least 10 nm. Alternative 1128 includes the composition of any one of Alternatives 1107-1127, in which the nanoparticle has a diameter of no more than 5000 nm. Alternative 1129 includes the composition of any one of Alternatives 1001-1128, in which the isolated peptide comprises a modification comprising at least one of a D amino acid, an N-terminal acetyl group, a C-terminal amide group, glycosylation, nitrosylation, carbonylation, oxidation, a linked pharmacokinetic modifier, and a linked polyethylene glycol or any combination thereof. Alternative 1130 includes the composition of any one of Alternatives 1001-1129 in which the isolated peptide activates an immune cell. Alternative 1131 includes the composition of any one of Alternatives 1001-1130 in which the isolated peptide activates an immune cell, if a solution comprising the immune cell comprises a second peptide comprising, consisting essentially of, or consisting of the sequence VFDEFKPLVEEPQNLIK (SEQ ID NO: 185), or if an LFA-1 receptor of the immune cell is bound to the second peptide. Alternative 1132 includes the composition of any one of Alternatives 1001-1131, in which, if the isolated peptide is contacted with a second peptide comprising, consisting essentially of, or consisting of the amino acid sequence VFDEFKPLVEEPQNLIK (SEQ ID NO: 185), the isolated peptide specifically binds to the second peptide. Alternative 1133 includes the composition of any one of Alternatives 1001-1132, in which, if the isolated peptide is contacted with an immune cell comprising an LFA-1 receptor and a second peptide comprising, consisting essentially of, or consisting of the amino acid sequence VFDEFKPLVEEPQNLIK (SEQ ID NO: 185), the isolated peptide inhibits binding of the second peptide to the LFA-1 receptor. Alternative 1134 includes the composition of any one of Alternatives 1001-1133, further comprising a pharmaceutically acceptable carrier or diluent. Alternative 1135 includes the composition of Alternative 1134, in which the pharmaceutically acceptable carrier or diluent comprises a degradable particle. Alternative 1136 includes the composition of any one of Alternatives 1001-1135, in which the composition comprises at least about 10 µg of the isolated peptide. Alternative 1137 includes the composition of any one of Alternatives 1134-1136, comprising a buffer selected from the group consisting of: Trizma, Bicine, Tricine, MOPS, MOPSO, MOBS, Tris, Hepes, HEPBS, MES, phosphate, carbonate, acetate, citrate, glycolate, lactate, borate, ACES, ADA, tartrate, AMP, AMPD, AMPSO, BES, CABS, cacodylate, CHES, DIPSO, EPPS, ethanolamine, glycine, HEPPSO, imidazole, imidazolelactic acid, PIPES, SSC, SSPE, POPSO, TAPS, TABS, TAPSO and TES. Alternative 1138 includes the composition of any one of Alternatives 1001-1137, in which if contacted with a cancer cell, the composition induces cytotoxicity of the cancer cell. Alternative 1139 includes the composition of Alternative 1038, in which the cancer cell comprises a prostate cancer cell. Alternative 1140 includes the composition of any one of Alternatives 1001-1139, in which the composition comprises a gel. Alternative 1141 includes the composition of Alternative 1140 in which the composition will remain in a gel format for at least 72 hours under physiological conditions.

Alternative 1142 includes a method comprising administering to an individual having a cancer, and in need of treatment therefor, an effective amount of the composition of any of Alternatives 1001-1141, thereby inducing at least one of the following: (a) activation of an immune cell; (b) inhibition of binding of a damaged albumin, an aggregate of albumins, an albumin fragment, or a second peptide to an LFA-1 receptor or IL-2 receptor, in which the second peptide or albumin fragment, if present, comprises, consists of, or consists essentially of at least one of SEQ ID NOs: 183-246; or (c) cytotoxicity to the tumor cell. Alternative 1143 includes the method of Alternative 1142, in which (a) and (b) are induced. Alternative 1144 includes the method of Alternative 1142, in which (a), (b), and (c) are induced. Alternative 1145 includes the method of any one of Alternatives 1142-1144, in which the individual having a cancer has a tumor. Alternative 1146 includes the method of Alternative 1145, in which the tumor comprises at least one of a prostate tumor, a melanoma, a colon cancer, a lung carcinoma, an Apocrine gland carcinoma, a testis tumor, a mast cell tumor, a mammary tumor, a mucinous carcinoma, or a histicytoma. Alternative 1147 includes the method of Alternative 1146, in which the mammary tumor comprises a benign mammary tumor or a malignant mammary tumor, or the mammary tumor comprises a mixed mammary tumor (for example a benign mixed mammary tumor, or a malignant mixed mammary tumor). Alternative 1148 includes the method of Alternative 1146, in which the mucinous carcinoma comprises a mammary gland mucinous carcinoma. Alternative 1149 includes the method of any one of Alternatives 1142-1148, in which the administering further induces regressive changes in the cancer. Alternative 1150 includes the method of any one of Alternatives 1145-1149, in which the administering further induces immune cell infiltration of the tumor. Alternative 1151 includes the method of any one of Alternatives 1145-1150, in which the administering further induces eradication of cells of the tumor. Alternative 1152 includes the method of any one of Alternatives 1145-1151, in which the administering further induces eradication of the tumor. Alternative 1153 includes the method of any one of Alternatives 1145-1152, in which the composition is administered directly to the tumor in the subject. Alternative 1154 includes the method of any one of Alternatives 1145-1152, in which the composition induces regressive changes in a tumor to which the composition is not directly administered. Alternative 1155 includes the method of any one of Alternatives 1145-1153, in which the composition induces eradication of a tumor to which the composition is not directly administered. Alternative 1156 includes the method of any one of Alternatives 1154-1155, in which the tumor to which the composition was not administered comprises a contralateral or metastatic tumor different from a tumor to which the composition is directly administered. Alternative 1157 includes the method of any one of Alternatives 1142-1156, in which the albumin fragment or second peptide comprises no more than 100 amino acid residues. Alternative 1158 includes the method of any one of Alternatives 1142-1157, in which the albumin fragment or second peptide comprises SEQ ID NO: 185. Alternative 1159 includes the method of any one of Alternatives 1142-1156 in which the albumin fragment or second peptide consists of or consists essentially of SEQ ID NO: 185. Alternative 1160 includes the method of any one of Alternatives 1142-1159, in which the LFA-1 receptor is available for stimulation following inhibition of binding of the albumin, albumin fragment, or second peptide. Alternative 1161 includes the method of any one of Alternatives 1142-1160, in which the immune cell is stimulated following inhibition of binding of the albumin, albumin fragment, or second peptide. Alternative 1162 includes the method of Alternative 1161, in which the immune cell is stimulated by a second therapeutic agent. Alternative 1163 includes the method of Alternative 1162, in which the second therapeutic agent is administered concurrently with the composition. Alternative 1164 includes the method of Alternative 1162, in which the composition comprises the second therapeutic agent. Alternative 1165 includes the method of Alternative 1162, in which the second therapeutic agent is administered prior to administering the composition. Alternative 1166 includes the method of Alternative 1162, in which the second therapeutic agent is administered subsequent to administering the composition. Alternative 1167 includes the method of any one of Alternatives 1142-1166, in which the peptide of the composition is administered to the individual at a dose of at least about 0.1 mg/kg. Alternative 1168 includes the method of any one of Alternatives 1142-1167, in which the peptide of the composition is administered in at least a first administration and a second administration at least five days after the first administration. Alternative 1169 includes the method of any one of Alternatives 1142-1168, in which the peptide is administered to a tissue within about 10 cm of a tumor of the cancer. Alternative 1170 includes the method of any one of Alternatives 1142-1169, in which the peptide is administered peri-tumorally to a tumor of the cancer. Alternative 1171 includes the method of any one of Alternatives 1142-1170, in which the cancer comprises at least one of colorectal cancer, renal cancer, breast cancer, skin cancer, ovarian cancer, prostate cancer, pancreatic cancer, lung cancer, malignant melanoma, small cell lung cancer, non-small lung cancer (adenocarcinoma), squamous cell carcinoma, bladder cancer, osteosarcoma, bronchial cancer, or hematopoietic cell cancer. Alternative 1172 includes the method of any one of Alternatives 1142-1171, in which the individual comprises serum comprising a damaged albumin, an aggregate of albumins, an albumin fragment, or a second peptide, in which the albumin fragment or second peptide comprises at least one of SEQ ID NOs: 183-246. Alternative 1173 includes the method of Alternative 1172, in which the second peptide or albumin fragment comprises the amino acid sequence VFDEFKPLVEEPQNLIK (SEQ ID NO: 185). Alternative 1174 includes the method of Alternative 1172, in which the second peptide or albumin fragment comprises no more than 100 amino acid residues.

Alternative 1175 includes a method of activating an immune cell in a cancer patient, the method comprising contacting the immune cell with a composition comprising: an isolated peptide comprising the amino acid sequence FFVKLS (SEQ ID NO: 62), in which the peptide consists of about six to thirty amino acids; and a nanoparticle, in which the isolated peptide is immobilized on the nanoparticle. Alternative 1176 includes the method of Alternative 1175, in which the cancer patient has a tumor. Alternative 1177 includes the method of Alternative 1176, in which the tumor comprises at least one of a prostate tumor, a melanoma, a colon cancer, a lung carcinoma, an Apocrine gland carcinoma, a testis tumor, a mast cell tumor, a mammary tumor, a mucinous carcinoma, or a histicytoma. Alternative 1178 includes the method of Alternative 1177, in which the mammary tumor comprises a benign mammary tumor or a malignant mammary tumor, or the mammary tumor comprises a mixed mammary tumor (for example a benign mixed mammary tumor, or a malignant mixed mammary tumor). Alternative 1179 includes the method of Alternative 1177, in which the mucinous carcinoma comprises a mammary gland mucinous carcinoma. Alternative 1180 includes the method of any one of Alternatives 1175-0179, in which the contacting further induces regressive changes in the cancer. Alternative 1181 includes the method of any one of Alternatives 1175-1180, in which the contacting further induces immune cell infiltration of the tumor. Alternative 1182 includes the method of any one of Alternatives 1175-1181, in which the contacting further induces eradication of cells of the tumor. Alternative 1183 includes the method of any one of Alternatives 1175-1182, in which the contacting further induces eradication of the tumor. Alternative 1184 includes the method of any one of Alternatives 1175-1183, in which the composition is administered directly to the tumor in the cancer patient. Alternative 1185 includes the method of any one of Alternatives 1175-1184, in which the composition induces regressive changes in a tumor to which the composition is not directly administered. Alternative 1186 includes the method of any one of Alternatives 1175-1185, in which the composition induces eradication of a tumor to which the composition is not directly administered. Alternative 1187 includes the method of any one of Alternatives 1175-1186, in which the tumor to which the composition is not directly administered comprises a contralateral or metastatic tumor different from a tumor to which the composition is directly administered. Alternative 1188 includes the method of any one of Alternatives 1175-1187, in which the nanoparticle comprises at least one of: a polymer, a dendrimer, a quantum dot, a gold nanoparticle, a silica nanoparticle, a magnetic particle, a carbon-based material, a carbohydrate, a nucleic acid, a polypeptide, or a lipid. Alternative 1189 includes the method of any one of Alternatives 1175-1188, in which the nanoparticle comprises a polymer comprising at least one of PLGA, glycerol, chitosan, DNA, or a hydrogel. Alternative 1190 includes the method of any one of Alternatives 1175-1189, in which the nanoparticle comprises a gold nanoparticle comprising at least one of a sphere, rod, or shell. Alternative 1191 includes the method of any one of Alternatives 1175-1190, in which the nanoparticle comprises a dendrimer comprising PAMAM. Alternative 1192 includes the method of any one of Alternatives 1175-1191, in which the nanoparticle comprises a silica nanoparticle comprising at least one of a sphere, shell, or mesoporous structure. Alternative 1193 includes the method of any one of Alternatives 1175-1192, in which the nanoparticle comprises a quantum dot comprising at least one of CdSe, CuInSe, or CdTe. Alternative 1194 includes the method of any one of Alternatives 1175-1193, in which the nanoparticle comprises a magnetic particle comprising at least one of iron oxide, cobalt-based material, a magnetic sphere, an aggregate in dextran or silica, or a Dynal® bead. Alternative 1195 includes the method of any one of Alternatives 1175-1194, in which the nanoparticle comprises a magnetic comprising a carbon-based material comprising at least one of a carbon nanotube, buckminsterfullerene, or graphene. Alternative 1196 includes the method of any one of Alternatives 1175-1195, in which the nanoparticle comprises a polypeptide comprising an albumin or an albumin fragment. Alternative 1197 includes the method of any one of Alternatives 1175-1196, in which the nanoparticle comprises a lipid comprising a lipid capsule or liposome. Alternative 1198 includes the method of any one of Alternatives 1175-1197, in which the nanoparticle is PEGylated. Alternative 1199 includes the method of any one of Alternatives 1175-1198, in which the nanoparticle comprises a non-degradable particle. Alternative 1200 includes the method of any one of Alternatives 1175-1199, in which the nanoparticle comprises a degradable particle. Alternative 1201 includes the method of any one of Alternatives 1175-1200, in which the nanoparticle comprises a structure selected from the group consisting of: a sphere, a rod, a shell, a mesoporous structure, a bead, a hydrogel, an aggregate, a fullerene, a cage, a porous nanocage, a viral capsid, a viral capsid fragment, or a lipid capsule. Alternative 1202 includes the method of any one of Alternatives 1175-1201, in which the isolated peptide is non-covalently immobilized on the nanoparticle. Alternative 1203 includes the method of Alternative 1202, in which the nanoparticle is non-covalently immobilized on the nanoparticle by at least one of a van der Waals interaction, steric interaction, hydrogen bonding interaction, hydrophobic interaction or electrostatic interaction. Alternative 1204 includes the method of any one of Alternatives 1175-1203, in which the isolated peptide is immobilized on the nanoparticle covalently. Alternative 1205 includes the method of Alternative 1204, in which the isolated peptide is immobilized on the nanoparticle via a cleavable linker or a non-cleavable linker. Alternative 1206 includes the method of Alternative 1205, in which the cleavable linker comprises one of an acid-labile linker, a matrix metalloproteinase target site, or a cathepsin target site. Alternative 1207 includes the method of any one of Alternatives 1175-1206, in which the nanoparticle has a diameter of at least 10 nm. Alternative 1208 includes the method of any one of Alternatives 1175-1207, in which the nanoparticle has a diameter of no more than 5000 nm. Alternative 1209 includes the method of any one of Alternatives 1175-1208, in which the isolated peptide comprises no more than 16 amino acid residues. Alternative 1210 includes the method of any one of Alternatives 1175-1209, in which the isolated peptide comprises no more than 8 amino acid residues. Alternative 1211 includes the method of any one of Alternatives 1175-1210, in which the isolated peptide consists of the amino acid sequence FFVKLS (SEQ ID NO: 62). Alternative 1212 includes the method of any one of Alternatives 1175-1211, in which contacting the immune cell with the composition inhibits binding of a damaged albumin, an aggregate of albumins, an albumin fragment, or a second peptide to an LFA-1 receptor, in which the albumin fragment or second peptide comprises at least one of SEQ ID NOs: 183-246. Alternative 1213 includes the method of Alternative 1212, in which the albumin fragment or second peptide comprises no more than 100 amino acids. Alternative 1214 includes the method of Alternative 1212 or 1213, in which the albumin fragment or second peptide comprises SEQ ID NO: 185. Alternative 1215 includes the method of Alternative 1214, in which the albumin fragment or second peptide consists of or consists essentially of SEQ ID NO: 185. Alternative 1216 includes the method of any one of Alternatives 1212-1215, in which the LFA-1 receptor is available for stimulation following inhibition of binding of the albumin, albumin fragment, or second peptide. Alternative 1217 includes the method of any one of Alternatives 1215-1216, in which the LFA-1 receptor is stimulated following inhibition of binding of the albumin, albumin fragment, or second peptide. Alternative 1218 includes the method of Alternative 1217, in which the immune cells are stimulated by a second therapeutic agent. Alternative 1219 includes the method of Alternative 1218, in which the second therapeutic agent is administered concurrently with the composition. Alternative 1220 includes the method of Alternative 1218, in which the composition comprises the second therapeutic agent. Alternative 1221 includes the method of Alternative 1218, in which the second therapeutic agent is administered prior to administration of the composition. Alternative 1222 includes the method of Alternative 1218, in which the second therapeutic agent is administered subsequent to administration of the composition.

Alternative 1223 includes a method of binding cancer cells with a peptide, the method comprising: contacting a cancer cell with the composition of any one of Alternatives 1001-1141; and detecting the binding of said peptide to said cancer cell. Alternative 1224 includes the method of Alternative 1223, in which the peptide comprises a detectable moiety. Alternative 1225 includes the method of Alternative 1224, in which the detectable moiety comprises a biotinylated label, a radioactive label, a fluorescent label, an enzyme, or a colloidal gold label. Alternative 1226 includes the method of any one of Alternatives 1 1123-1225, in which the cancer cell is a colorectal cancer cell, a renal cancer cell, a breast cancer cell, a skin cancer cell, an ovarian cancer cell, a prostate cancer cell, a pancreatic cancer cell, a lung cancer cell, a malignant melanoma cell, a small cell lung cancer cell, a non-small lung cancer (adenocarcinoma) cell, a squamous cell carcinoma cell, a bladder cancer cell, an osteosarcoma cell, a bronchial cancer cell, or a hematopoietic cell cancer cell. Alternative 1227 includes the method of any one of Alternatives 1223-1226, in which the cancer cell comprises a prostate tumor cell, a melanoma cell, a colon cancer cell, a lung carcinoma cell, an Apocrine gland carcinoma cell, a testis tumor cell, a mast cell tumor cell, a mammary tumor cell, a mucinous carcinoma cell, or a histicytoma cell. Alternative 1228 includes the method of Alternative 1227, in which the mammary tumor comprises a benign mammary tumor or a malignant mammary tumor, or the mammary tumor comprises a mixed mammary tumor (for example a benign mixed mammary tumor, or a malignant mixed mammary tumor). Alternative 1229 includes the method of Alternative 1227, in which the mucinous carcinoma comprises a mammary gland mucinous carcinoma. Alternative 1230 includes the method of any one of Alternatives 1223-1229, in which said peptide comprises an antibody or antibody fragment.

Alternative 1231 includes a method of ameliorating immunosuppression in a subject in need thereof, the method comprising administering to the subject an effective amount of the composition of any of Alternatives 1001-10141, thereby inducing at least one of the following: (a) activation of an immune cell; or (b) inhibition of binding of a damaged albumin, an aggregate of albumins, an albumin fragment, or a second peptide to an LFA-1 receptor, in which the second peptide or albumin fragment, if present, comprises at least one of SEQ ID NOs: 183-246. Alternative 1232 includes the method of Alternative 1231, in which the albumin fragment or second peptide comprises no more than 100 amino acid residues. Alternative 1233 includes the method of Alternative 1231 or 1232, in which the albumin fragment or second peptide comprises SEQ ID NO: 185. Alternative 1234 includes the method of any one of Alternatives 1231-1233, in which the albumin fragment or second peptide consists of or consists essentially of SEQ ID NO: 185. Alternative 1235 includes the method of any one of Alternatives 1231-1234, in which the LFA-1 receptor is available for stimulation following inhibition of binding of the albumin, albumin fragment, or second peptide. Alternative 1236 includes a kit comprising: the composition of any one of Alternatives 1001-1141; and a detectable moiety. Alternative 1237 includes a kit of Alternative 1236, in which the detectable moiety comprises a biotinylated label, a radioactive label, a fluorescent label, an enzyme, or a colloidal gold label. Alternative 1238 includes use of the composition of any one of Alternatives 1001-1141 for the treatment of cancer.

Alternative 1238 includes use of the composition of any one of Alternatives 1001-1141 for stimulating an immune cell in a cancer patient. Alternative 1240 includes the use of any of Alternatives 1238-1239, in which the cancer comprises at least one of colorectal cancer, renal cancer, breast cancer, skin cancer, ovarian cancer, prostate cancer, pancreatic cancer, lung cancer, melanoma, malignant melanoma, small cell lung cancer, non-small lung cancer (adenocarcinoma), lung carcinoma, squamous cell carcinoma, bladder cancer, osteosarcoma, bronchial cancer, hematopoietic cell cancer, mammary tumor, mucinous carcinoma, or histicytoma. Alternative 1241 includes the use of any of Alternatives 1238-1240, in which the cancer comprises a tumor comprising at least one of a prostate tumor, a melanoma, a colon cancer, a lung carcinoma, an Apocrine gland carcinoma, a testis tumor, a mast cell tumor, a mammary tumor, a mucinous carcinoma, or a histicytoma. Alternative 1242 includes the use of Alternative 1241, in which the mammary tumor comprises a benign mammary tumor or a malignant mammary tumor, or the mammary tumor comprises a mixed mammary tumor (for example a benign mixed mammary tumor, or a malignant mixed mammary tumor). Alternative 1243 includes the use of Alternative 1241, in which the mucinous carcinoma comprises a mammary gland mucinous carcinoma. Alternative 1244 includes the use of any of Alternatives 1238-1243, in which the composition is further for use in inducing regressive changes in the cancer. Alternative 1245 includes the use of any of Alternatives 1238-1244, in which the composition is further for use in inducing immune cell infiltration of a tumor of the cancer. Alternative 1246 includes the use of any of Alternatives 1238-1245, in which the composition is further for use in eradicating cells of a tumor of the cancer. Alternative 1247 includes the use of any of Alternatives 1238-1246, in which the composition is further for use in eradicating a tumor of the cancer. Alternative 1248 includes the use of any of Alternatives 1238-1247, in which the composition is for administration directly to a tumor in a cancer patient. Alternative 1249 includes the use of any one of Alternatives 1238-1248, in which the composition is for use in inducing regressive changes in a tumor to which the composition is not directly administered. Alternative 1250 includes the use of any one of Alternatives 1238-1249, in which the composition is for use in eradicating a tumor to which the composition is not directly administered. Alternative 1251 includes the use of any one of Alternatives 1238-1250, in which the composition is for use in direct administration to a first tumor, and is further for use in inducing regressive changes in a second tumor to which the composition was not administered. Alternative 1252 includes the use of Alternative 1251, in which the second tumor comprises a contralateral or metastatic tumor different from the first tumor.

Additional Supporting Information

We have previously noted that immunoregulating neostructures from albumin can be generated by proteolytic fragmentation (see WO03099312A1, hereby incorporated by reference in its entirety herein) or denaturation (see WO06043891A1, hereby incorporated by reference in its entirety herein). In addition to this observation, without being limited by any theory, it is contemplated that tumour cells under stress can have the capacity for albumin uptake via endosomes in order to increase their energy supply and also provide them with amino acids.

It is contemplated that compositions comprising immunoregulatory inhibitors in accordance with some embodiments herein can be administered to subjects with cancers, especially tumors, and can facilitate an immune response (for example, by permitting or enhancing) against the cancer and/or tumor. Without being limited by any theory, it is contemplated that some immunomodulators, for example immunoregulatory inhibitors, in accordance with some embodiments herein can facilitate an immune response against cancer and/or tumors via two modes of action: (1) counteracting P3028 structures, for example by binding and/or displacing P3028 so as to remove P3028-mediated inhibition of immune cells receptors such as the LFA-1 receptor and/or the IL-2 receptor; and (2) immunostimulatory activity of the immunoregulatory inhibitor itself. For example, P28R has been observed to exhibit both modes of action.

As such, in some embodiments, a composition comprising a peptide of SEQ ID NO: 2, SEQ ID NO: 62, SEQ ID NO: 584, a peptide listed in Table 5.4, or a modified P28R or P28 core peptide comprising one or more modifications listed in Table 5.3 or Table 13 is provided. Optionally, the peptide is immobilized on a nanoparticle as described herein. Optionally, the composition has effects in counteracting P3028 structures and immunostimulatory activity. Optionally, the composition has effects in counteracting P3028 structures, but does not have direct immunostimulatory activity. Optionally the composition is administered to, or is for use in administering to, a subject suffering from a cancer and/or a tumor, for example a prostate tumor, a melanoma, a colon cancer, a lung carcinoma, an Apocrine gland carcinoma, a testis tumor, a mast cell tumor, a mammary tumor (e.g. a benign mammary tumor or a malignant mammary tumor, for example a mixed mammary tumor such as a benign mixed mammary tumor or a malignant mixed mammary tumor), a mucinous carcinoma (e.g. a mammary gland mucinous carcinoma), or a histicytoma and/or cancer cells associated therewith. Optionally, the composition is directly administered to the cancer cells/tumor, for example via intra-tumoral injection, implantation of a capsule or infuser comprising the composition, or topically. Optionally, administration of the composition induced immune cell infiltration of the tumor, for example, infiltration by CD45+ inflammatory cells and/or CD56+ NCR1+NK-cells. Optionally, if the composition is administered directly to the cancer cells and/tumor, the composition further induces immune cell infiltration of at least on additional tumor of the subject, for example a contralateral tumor and/or cancer cells at locations that are different or removed from the site of administration.

As outlined in Table 14, without being limited by any theory, it is contemplated that the Beta2-integrin, LFA-1, can be involved in multiple immune functions.

TABLE 14

Involvement of the Beta2-integrin LFA-1 in multiple immune functions

| Function | Comments | Ref, e.g. |
|---|---|---|
| Th1-Th2 balance | Immunostimulation without LFA-1 function results in Th2 polarization and reasonably also in macrophage M2 polarization | Smits et al. J Immunol. 2002 Feb 15; 168(4): 1710-6; Salomon et al., J Immunol. 1998 Nov 15; 161(10): 5138-42; Varga et al., J Invest Dermatol. 2010; 130(4): 1005-12. |
| Initiation of an immune response | LFA-1 plays a pivotal role in the immune synapse between antigen presenting cells and T--cells | Jo et al., J Cell Biochem. 2010; 111(5): 1125-37; Zheng et al., J Biol Chem. 2009; 284(32): 21280-7; Graf et al., J Immunol. 2007; 179(3): 1616-24.; Marwali et al., J Immunol. 2004; 173(5): 2960-7. |
| Recruitment of inflammatory cells to tumours | Binding LFA-1 to ICAM-1 on vascular endothelium is a prerequisite for transmigration of inflammatory cells into tissues/tumours. | Shulman et al., Immunity. 2009; 30(3): 384-96; Borthwick et al., Clin Exp Immunol. 2003; 134(2): 246-52; Ding et al., J Leukoc Biol. 2001; 69(3): 458-66. |
| Cell migration | Migration of inflammatory cells depends on the function of adhesion molecules, LFA-1 plays a major role in this context | Verma et al., J Cell Physiol. 2011; 226(6): 1489-98; Smith et al., Immunol Rev. 2007; 218: 135-46. |
| Cytotoxic activity of T-cells and NK-cells | LFA-1 is required for binding of effector cells to target cells in order to achieve tumour cell lysis | Perez et al., Blood. 2004; 104(4): 1083-93; Suttman et al., Urol Res. 2002; 30(4): 233-9.; Luo et al., J Hepatol. 1999; 31(1): 110-6. |

Table 15, below, summarizes features of modified peptides in accordance with some embodiments herein, for example modifications of P28R. The indicated "changed positions" are with reference to P28R (SEQ ID NO: 2).

TABLE 15

Features of Modified peptides

| Peptide designation (see, e.g. FIG. 41A) | Changed position | Peptide designation (see, e.g. FIG. 41B) | Changed position |
|---|---|---|---|
| 30677 | F13---M13 | 30684 | K2---S2 |
| 30678 | S11---Q11 | 30685 | E15---F15 |
| 30680 | F6---V6 | 31135 | K9---Y9 |
|  | F7---M7 | 31136 | K9---N9 |
|  | S11---Q11 | 31138 | K9---D9 |
|  | F13---M13 |  |  |

Summary of Additional Supporting Information

Five spontaneous tumours have been treated intra-tumorally with P28R in accordance with some embodiments herein. In all of these, a strong inflammatory infiltrate was observed, mainly characterized as CD45+ cells and NK cells stained by antibodies directed against CD56 and NCR1. Extensive tumour regressive changes were found in three of these and in one, the apocrine gland carcinoma, with thick tumour nodules, regressive changes were seen at least in thin lesions and at the periphery of the tumour nodules. The thick tumour nodules were, however, heavily infiltrated by NK-cells. Interestingly, in a breast tumour with regional metastases, also these lesions were heavily infiltrated with inflammatory cells and showed extensive tumour regressive changes. Two tumours were injected with the vehicle, in one of these, a breast tumour, a spontaneous inflammatory infiltrate was found. The other, a testis tumour, did not show any inflammatory reaction.

So far nine dogs have been treated with P28R in accordance with some embodiments herein, 4 in the toxicological study (CiToxLab, Denmark) with 200 nM administered in 1 mL subcutaneously and 5 dogs in the treatment study reported here with 40 nM in 200 microliters intra tumourally. None of these dogs showed any systemic side effects.

A class of immunoregulatory substances is provided in accordance with some embodiments herein.

A general mechanism, whereby this class of immunoregulatory fragments are produced, has been identified in accordance with some embodiments herein.

The enhanced proteolytic activity or enhance capacity to denature proteins in malignant tumours generates neostructures of normally occurring serum proteins such as albumin and immunoglobulin in accordance with some embodiments herein.

Neostructures with both stimulatory and inhibitory immunoregulatory activity have been found in accordance with some embodiments herein.

This class of immunomodulatory substances in accordance with some embodiments herein can comprise targets for immunomodulation in cancer and inflammatory diseases.

A potent inhibitory peptide, P3028, blocking the proliferative response to IL-2, NK-cell cytotoxicity, T-cell receptor stimulation, leukocyte spreading and lymphocyte migration was developed in accordance with some embodiments herein.

The structure of P3028 has been characterized in accordance with some embodiments herein.

P3028 binds to LFA-1 and CD25 in accordance with some embodiments herein.

Affinity purified antibodies to P3028 in accordance with some embodiments herein reverse the suppressed proliferative response to IL-2 in a culture model where the response to IL-2 has been shown to correlate to overall survival.

A low molecular weight immunoregulatory inhibitor peptide of P3028 has been developed, P28R, in accordance with some embodiments herein.

The capacity of the P28R immunoregulatory inhibitor peptide of P3028 to reverse suppressed IL-2 induced proliferation of PBMCs from cancer patients in accordance with some embodiments herein was demonstrated.

The distribution of P3028 and binding of P28R in tumour tissue have been studied in accordance with some embodiments herein.

The capacity of P28R to unblock LFA-1 was demonstrated in accordance with some embodiments herein.

The P28R has a strong immunostimulatory activity in accordance with some embodiments herein as shown, for example, in a human ex vivo model.

In vivo administration of P28R intra-tumorally in immunocompetent mouse models elicits in an extensive inflammatory reaction resulting in tumour cell eradication in accordance with some embodiments herein.

In vivo administration of P28R subcutaneously in immunocompetent mouse models elicits in an extensive inflammatory reaction resulting in tumour cell eradication in accordance with some embodiments herein.

In vivo administration of P28R intra-tumorally in spontaneous tumours in dogs elicits in an extensive inflammatory reaction resulting in tumour cell eradication in accordance with some embodiments herein.

Systemic, SC, administration of P28R, in accordance with some embodiments herein, is as efficient as intra-tumoural administration.

Materials and Methods

Except when stated otherwise, the following materials and or methods were used as appropriate in the Examples provided below.

Human Serum

Human serum was collected in serum collection tubes without additives (Vacutainer®, Becton Dickinson, Franklin Lakes, N.J.) at the same time as blood samples for isolation of PBMC. The sera were heat-inactivated at 56° C. for 30 minutes.

Isolation of PBMCs

To isolate PBMCs, venous blood was drawn from healthy volunteers or from cancer patients in glass vacuum tubes with acid dextrose citrate solution A as anti-coagulant (Vacutainer®, Becton Dickinson, Franklin Lakes, N.J.). Erythrocytes were removed by sedimentation on 2% dextran T500 solution (Amersham® Pharmacia Biotech AB, Uppsala, Sweden) in 0.9% NaCl (this step was omitted for cultures with PHA-stimulation—see below). PBMC were then isolated by Ficoll-Paque® Plus (GE® Healthcare Bio-Sciences AB, Uppsala, Sweden) density gradient centrifugation after which the cells were washed twice in RPMI 1640 Dutch's modification (Gibco®, InVitrogen® AB, Stockholm, Sweden) with 2% human serum albumin (HSA) (Pharmacia & Upjohn®, Stockholm, Sweden) (RPMI/2% HSA). For cell cultures with PHA-stimulation, PBMC were washed in Hank's Balanced Salt Solution (HBSS) with 10% autologous plasma instead of RPMI/2% HSA. Cell viability was assessed by exclusion of 0.05% Trypan Blue and was always above 95%. The cell suspension was stained with Turk's solution and the number of lymphocytes and monocytes in the PBMC preparation were counted in a hemocytometer. PBMCs were suspended in RPMI/2% HSA and the cell concentration adjusted to $5 \times 10^5$ lymphocytes/ml.

IL-2 Induced Proliferation of PBMC in Uncoated and Coated Culture Plates

Pre-coating of culture plates with HSA and HSA/IgG. Round-bottomed, 96-well tissue culture plates (Costar®, Corning® Inc. NY, US) were pre-coated with HSA only or HSA and pooled human IgG for intravenous injection (Gammagard®, Baxter AS, DK). HSA was diluted in RPMI1640 without supplements to a concentration of 10 mg/ml. In some experiments, 1 mg/ml IgG was mixed into a solution of 9 mg/ml HSA in RPMI (HSA/IgG). 200 µl of HSA or HSA/IgG were then added to each well of the plate. The plates were incubated at 4° C. for 30 minutes after which the wells were washed twice with 200 µl of RPMI1640. The coated plates were used immediately.

100 µl of RPMI1640 supplemented with 200 IU/ml penicillin, 200 µl/ml streptomycin, 4 mM L-glutamine (all from Sigma® Chemical Co. MO, US) and 20% heat-inactivated human serum (autologous or from cancer patients) were added to uncoated, HSA or HSA/IgG coated tissue culture microtiter plates. PBMC, isolated from healthy individuals or patients with metastatic renal cell carcinoma, were diluted in RPMI/2% HSA at a concentration of $5 \times 10^5$/ml and 100 µl were added to the microtiter wells. Interleukin-2 (IL-2, Proleukin®, Chiron®, NL), at a final concentration of 120 IU/well, was added to some wells. Cells were cultured for 7 days in a humidified, 5% CO2-atmosphere at 37° C. Proliferation was assayed by incorporation of 1.6 µCi/well of [$^3$H]-thymidine (Amersham® Int., UK) during the last 18 hrs. Mean values of dpm (disintegrations per minute) of triplicates were used for the calculations.

Interleukin-2 (IL-2) Induced Proliferation of PBMC in the Presence of Albumin Peptides Cultures for IL-2 induced proliferation was set up with PBMC from healthy donors and autologous serum as described above with the exception that PBMC were first pre-incubated for 30 min at room temperature with the indicated albumin peptides at a concentration of 10 µg/ml.

Interleukin-2 (IL-2) Induced Proliferation of PBMC in the Presence of Albumin Peptides in Coated and Uncoated Tissue Culture Plates Round-bottomed, 96-well tissue culture plates (Costar®, Corning® Inc. NY, US) were pre-coated with HSA only or HSA and pooled human IgG for intravenous injection (Gammagard®, Baxter AS, DK) as follows; HSA was diluted in RPMI1640 without supplements to a concentration of 10 mg/ml. A mixture of 1 mg/ml IgG in a solution of 9 mg/ml HSA in RPMI (HSA/IgG) was also prepared. 200 µl of HSA or HSA/IgG were then added to each well of the plate. The plates were incubated at 4° C. for 30 minutes after which the wells were washed twice with 200 µl of RPMI1640. The coated plates were used immediately. 100 µl of RPMI1640 supplemented with 200 IU/ml penicillin, 200 µl/ml streptomycin, 4 mM L-glutamine (all from Sigma® Chemical Co. MO, US) and 20% heat-inactivated human serum (autologous) were added to the HSA or HSA/IgG coated tissue culture microtiter wells. PBMC, isolated from healthy individuals, were diluted in RPMI/2% HSA and peptides were added directly to the cell suspension at a concentration of 10 µg/ml. One hundred µl of this cell suspension ($5 \times 10^4$ lymphocytes) was then added per well providing a final concentration of 5 µg/ml peptide per well. IL-2 (Proleukin®, Chiron®, NL), at a final concentration of 120 IU/well, was added to the wells. Cells were cultured for 7 days in a humidified, 5% CO2-atmosphere at 37° C. Proliferation was assayed by incorporation of 1.6 μCi/well of [$^3$H]-thymidine (Amersham® Int., UK) during the last 18 hrs. Mean values of dpm (disintegrations per minute) of triplicates were used for the calculations.

Albumin Peptides

Synthetic albumin peptides were custom prepared by CSBio Co, Menlo Park, Calif. Peptides were >95% pure as confirmed by HPLC. Peptides were kept freeze dried at minus 20° C. Peptides were reconstituted in sterile H2O (Sigma®) for use in ELISA or in RPMI1640 (GIBCO) for use in cell culture experiments. Peptides were sterile filtered through a 0.22 μm syringe filter (Millipore® Co) before use in cell culture experiments.

ELISA for the Detection of Murine Antibodies Binding to Human Albumin

Duplicate wells in Hibinding microtitre plates (Costar® 2592, Corning® Inc, NY, USA) were coated with 100 μl of dHSA diluted in PBS at various concentrations or, alternatively, control albumin sample at the same concentrations. The plates were incubated at room temperature overnight. The wells where then washed with wash buffer consisting of 0.05% Tween-20 in PBS (Sigma®) followed by blocking for 1 h at 25° C. with 200 μl 0.1% gelatin prepared from bovine skin (Sigma®) in PBS followed by washing in wash buffer. Either of two murine monoclonal antibodies (IgG1) with specificity for denatured, human albumin (anti-dAbclh040801 or anti-dAlbclh040809) was added at 1 μg/ml in ELISA reagent diluent (0.01% gelatin (Sigma®) and 0.05% Tween-20 (Sigma®) in 20 mM Tris-buffered saline (TB S, Sigma®)). The antibodies were incubated for 1.5 h at 25° C. followed by washing. Envision-HRP (DakoCytomation® Norden A/S, Glostrup, Denmark) was added diluted 1/5 to 1/10 in ELISA reagent diluent and incubated for 30 min at 25° C. followed by washing. Finally, a substrate solution consisting of H2O2 and tetramethylbenzidine (R&D Systems® Europe, Ltd, Abingdon, UK) was added. The reaction was stopped with 1M H2SO4 and the optical density measured as absorbance (Abs) at dual wavelengths, 450 nm and 570 nm, with a Multiscan® EX microplate reader (Labsystems).

ELISA with Rabbit-Anti 3028 Antiserum

Duplicate wells in Hi-binding microtitre plates (Costar® 2592, Corning® Inc, NY, USA) were coated with 100 μl of P3028 (10 ug/ml), denatured HSA (denHSA, 4.5 ug/ml) or control HSA sample (4.5 ug/ml). All coating reagent were diluted in PBS and incubated at room temperature overnight. The wells where then washed with wash buffer consisting of 0.05% Tween-20 in PBS (Sigma®) followed by blocking for 1 hr at 25° C. with 200 μl 0.5% gelatin prepared from bovine skin (Sigma®) in PBS followed by washing in wash buffer. Rabbit preimmune sera or anti-3028 sera, diluted 1/1000 000 in ELISA reagent diluent (0.01% gelatin and 0.05% Tween-20 in PBS), were added and incubated for 1 h at 25° C. followed by washing. Biotinylated horse anti-rabbit/mouse IgG (Vectastain® ELITE, Vector® Laboratories Inc, CA, USA) diluted 1/5 in ELISA reagent diluent was then added and the plates incubated for 1 h at 25° C. followed by washing. Next, HRP-conjugated streptavidin (R&D Systems® Europe, Ltd, UK) was added. Finally, after washing in wash buffer, substrate solution consisting of $H_2O_2$ and tetramethylbenzidine (R&D Systems®) was added. The reaction was stopped with 1M H2504 and the optical density measured as absorbance (A) at dual wavelengths, 450 nm and 570 nm, with a Multiscan® EX microplate reader (Labsystems).

Statistical Considerations

Comparisons of the means of different patient groups or different test occasions were performed using an unpaired t-test. Time to progression and survival was analyzed using the Kaplan-Meier method and Logrank test.

Comparisons between the proliferative response to PHA in different groups or at different test occasions were done on logarithmated mean values of dpm of triplicates using unpaired t-test. For the determination of the effect of addition of CHL on the proliferative response of PHA-stimulated PBMCs, a modulation index (MI) was calculated according to the following formula: MI=log (dpm PHA+drug/dpm PHA).

Example 1: Serum Peptides with Immune Inhibitory Activities

Identification of Immunoregulatory Peptides

An artificial cell surface (ACS) was prepared by selectively biotinylating cell surface structures of PBMCs and after lysing the cells binding the biotinylated proteins to streptavidin columns (see Example 17 for further description of the ACS). The mixture of peptides obtained after trypsination was adsorbed by ACS and the binding peptides were identified by comparing adsorbed and unadsorbed peptide solutions using the MALDI TOF ms technique. Based on their degree of binding and their spatial relation to previously identified immunoregulatory structures, four new peptides were selected to be synthesized and investigated for their immunoregulatory activity, primarily the effect on the proliferative response to IL-2. One of these peptides, P3028 (SEQ ID NO: 185) was found to have multiple immunoinhibitory activities.

Expression of the P3028 Epitope in Malignant Tumors

Figure 1:
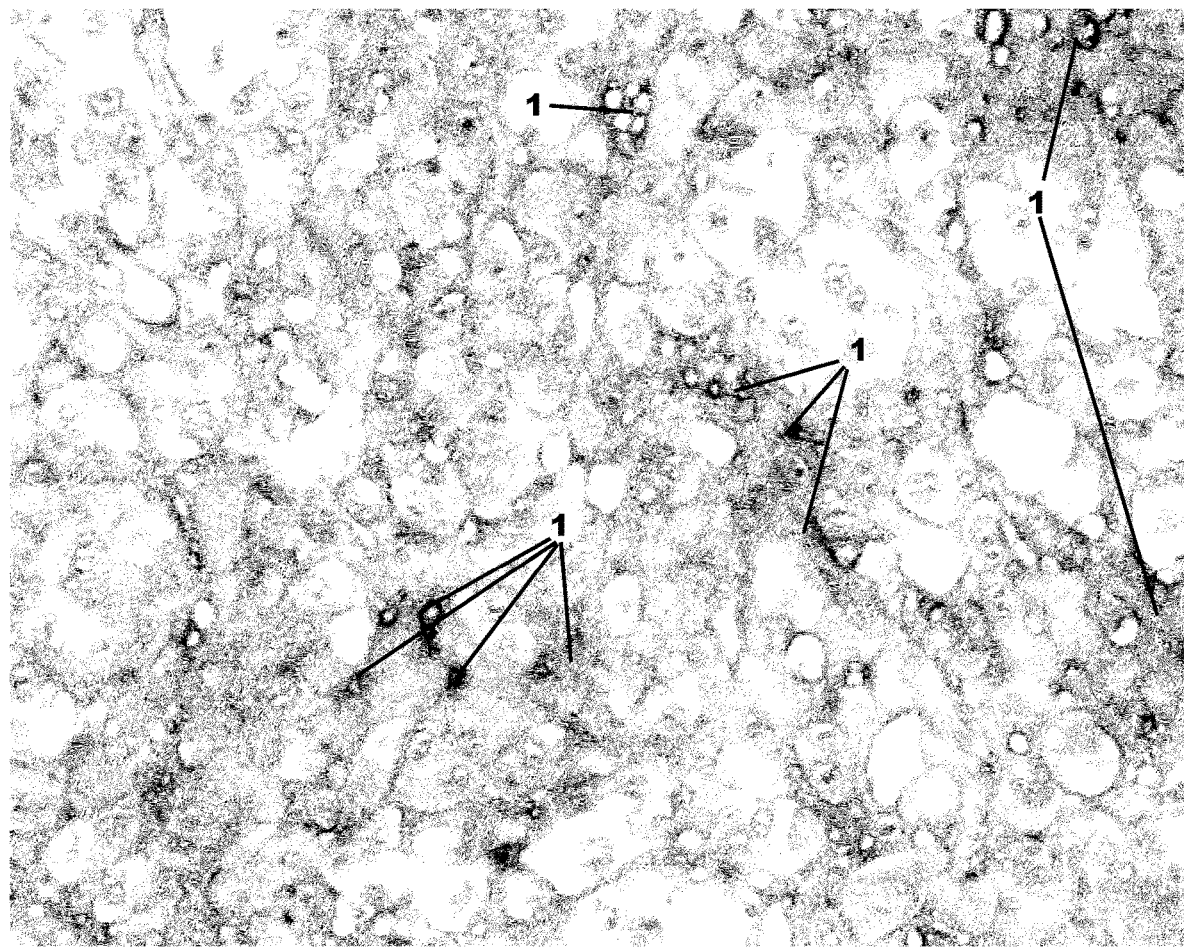
FIG. 1 illustrates immunohistochemical staining of a malignant melanoma metastases using affinity purified rabbit antibodies directed to the P3028 epitope.

Rabbit polyclonal antibodies against P3028 were generated and affinity purified (see Example 9). To determine the localization of P3028 in tumor cells, sections of malignant metastases were immunostained using the anti-P3028 rabbit polyclonal antibodies. Tissue sections were prepared from formalin fixed biopsies from cancer patients. Sections were de-paraffinased and blocked with 10% normal, human AB-serum in Hank's balanced salt solution supplemented with 0.01 M Hepes (BSS, GIBCO BRL) for one hour prior to staining. Sections were then stained with 10 ug/ml affinity purified rabbit anti-P3028 diluted in BSS with 2% AB-serum and 0.1 g/ml saponin for 30 min. After washing in BSS with 0.1 g/ml saponin, Ultravison® One alkaline phosphatase polymer specific for mouse and rabbit Ig (Lab Vision® Co., CA, USA) was added. Excess polymer was then washed from the sections with BSS with 0.1 g/ml saponin. Bound polymer complex was the detected by naphthol phosphate substrate and liquid Fast Red chromogen (Lab Vision® Corp.) The sections were counter stained in Mayer's haematoxylin and mounted in Glycergel®. As shown in FIG. 1, structures 1 to which anti-P3028 antibodies bind are widely expressed in human malignant tumors, e.g., malignant melanoma, renal cell carcinoma and colorectal cancer.

Western blotting was performed on extracts of malignant melanoma metastases to detect the presence of P3028 structures. Western blotting was performed using standard techniques, and P3028 structures were detected using affinity purified Rabbit polyclonal antibodies against P3028 (see Example 9). P3028 structures in tumor extracts from malignant melanoma metastases were identified in the extracts of 7 out of 7 mestases from 4 patients that were screened (see FIG. 2). The P3028 peptide was present in all patients. Additionally, the P3028 structure was present in full-length albumin. In addition this structure was found in larger molecules. These results are compatible with the P3028 structure being generated not only by proteolytic fragmentation but also by denaturation.

Occurrence of P3028 Structures in Serum

Substances exposing the structure of P3028 were determined in human serum by using affinity purified antibodies in a sandwich ELISA. That is, the ability to detect P3028 structures in human serum was confirmed.

A sandwich ELISA was performed to detect albumin exposing the P3028 epitope in serum as follows: An affinity polyclonal purified rabbit antisera, specific for human albumin P3028, was coated onto high protein binding ELISA microwells (capture antibody; see Example 9). A 1% solution of heat-inactivated serum (from a serum pool of 5 healthy control samples, 1 healthy control serum sample and 2 sera obtained from cancer patients), spiked with increasing concentrations of P3028, was then added to the wells. After washing, a biotinylated mouse anti-human albumin monoclonal antibody was added and the amount of bound antibody was detected with HRP-conjugated streptaviddin and TMB chromogen substrate. (One representative experiment out of two is shown FIG. 3).

Figure 3:
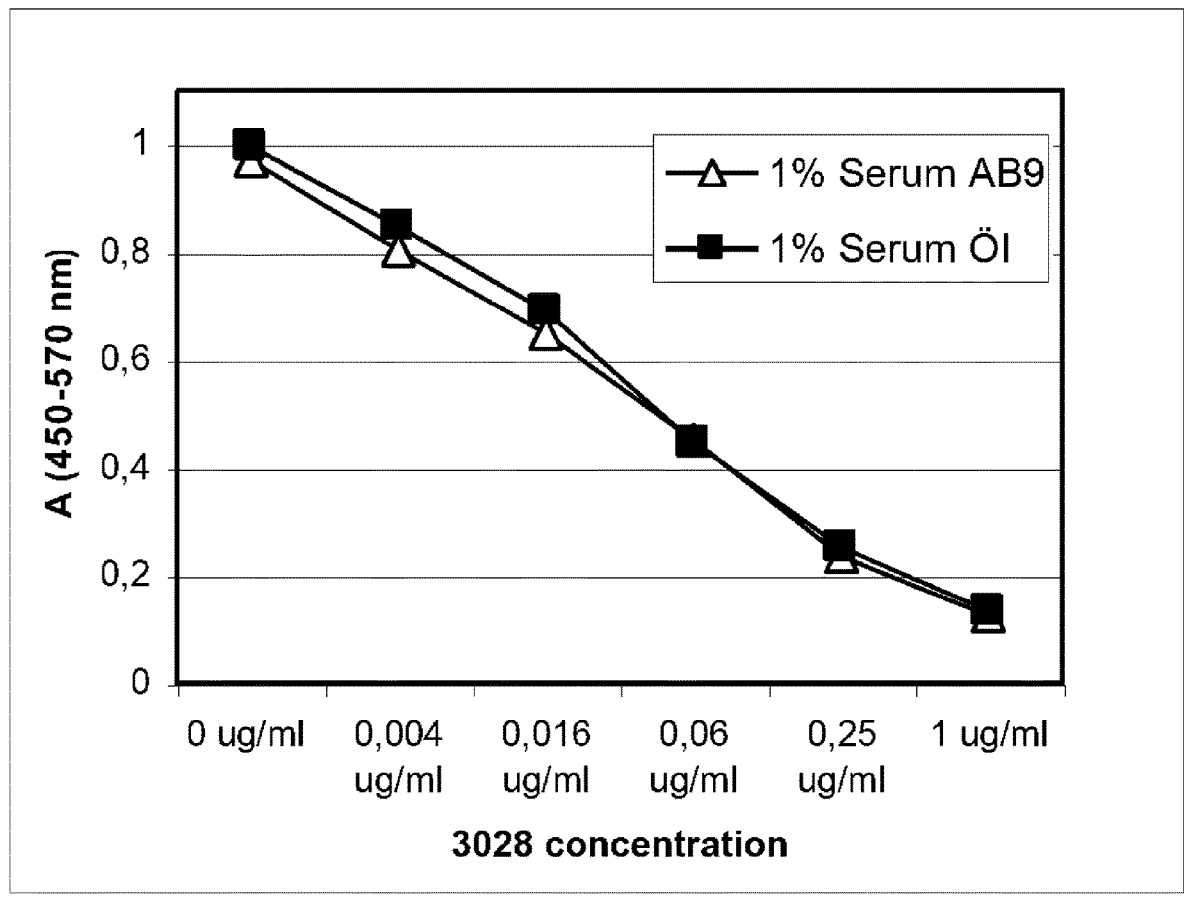
FIG. 3 illustrates Sandwich ELISA detecting albumin exposing the P3028 epitope in serum; competition with the P3028 peptide.

The amount of P3028 structures were determined as the amount of P3028, which inhibits 50% of the binding of P3028 structures in the serum to the capture antibody (see FIG. 3). The serum concentration was determined to be in the range of 1.2-1.6 µg/ml P3028 equivalents in one serum pool from 5 healthy control samples, 1 healthy control serum sample and 2 sera obtained from cancer patients. The amount of these P3028-substances in serum can be considerably more as the molecular weight of albumin is about 35 times more than that of P3028. The epitope specific reactivity of P3028-substances was accurately determined using the methods of this Example.

Example 2: Effect of ACS-Identified Peptides on IL-2 Induced Proliferation

Human Ex Vivo Model for Immunosuppression in Cancer Patients

Interleukin-2 (IL-2) plays a major role in initiation and activation of an immune response and its capacity to induce lymphokine activated killer cells (LAK-cells), T-cell proliferation and cytotoxicity. Accordingly, a human ex vivo model of IL-2 stimulation of immune cells was developed. This model was useful for studying the effects of immune system modulators, such as P3028, and inhibitors thereof.

The model included PBMCs isolated from venous blood samples from healthy blood donors (control samples) or cancer patients. One hundred pl of culture medium (RPMI 1640 Dutch's modification (Gibco®, InVitrogenAB®, Stockholm, Sweden) supplemented with 200 IV/ml penicillin, 200 ug/ml streptomycin, 4 mM L-glutamine (all from Sigma® Chemical Co. MO, US) and 20% heat-inactivated human serum) were added to roundbottomed, 96-well tissue culture plates (Costar®, Corning® Inc. NY, US). One hundred ul of PBMCs in RPMI/2% HSA (5×104 lymphocytes) was then added per well followed by IL-2 (Proleukin®, Chiron®, NL) at a final concentration of 120 IU/well. Control sample wells without IL-2 was set up in parallel. Cells were cultured for 7 days in a humidified, 5% CO2-atmosphere at 37° C. Cell proliferation was assayed by incorporation of 1.6 µCi/well of [$^3$H]-thymidine (Amersham® Int., UK) during the last 18-24 h hrs. Mean values of dpm (disintegrations per minute) of triplicate wells were used for the calculations.

Figure 4:
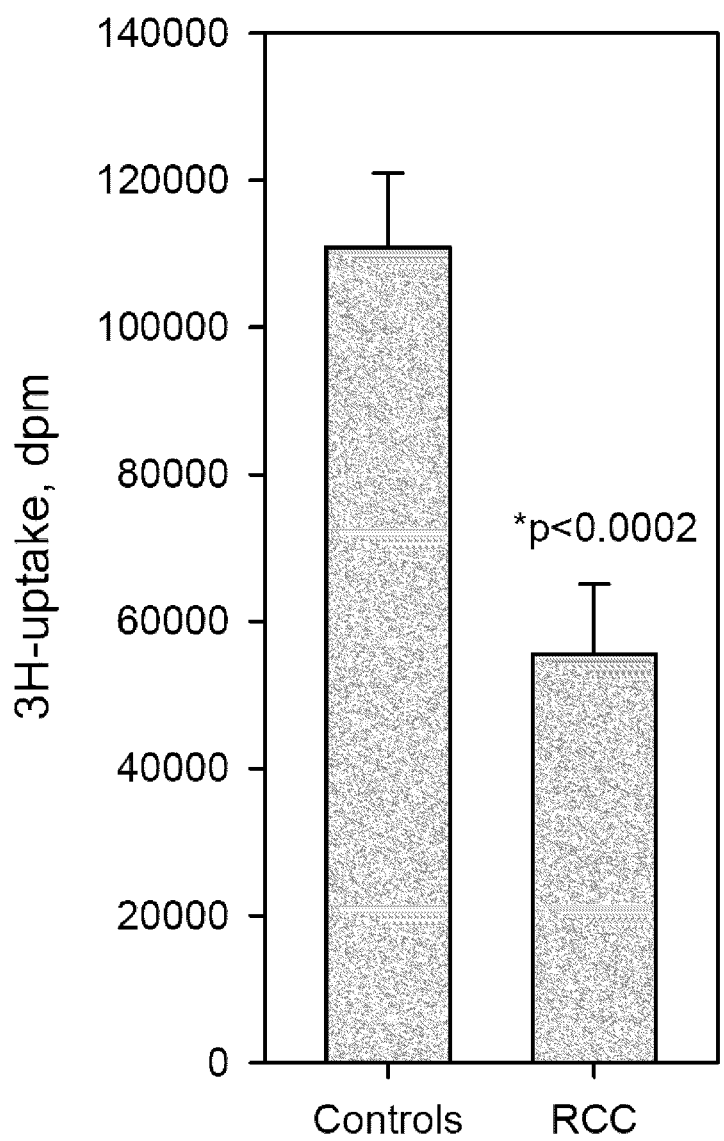
FIG. 4 illustrates IL-2 induced proliferation by PBMCs from healthy control samples and human immune cells (PBMC) from renal cell carcinoma patients (RCC) cultured in 10% autologous sera.

IL-2 induced proliferation by PBMC from healthy control samples and PBMC from renal cell carcinoma patients (RCC) cultured in 10% autologous sera was studied using this model. Results of the study are shown in FIG. 4. IL-2 induced proliferation was significantly reduced (p<0.0002) for PBMCs cultured in serum of a renal carcinoma patient as compared to a healthy control sample.

Correlation Between IL-2 Response in Ex Vivo Model and Overall Survival of Renal Cell Carcinoma Patients The response to IL-2 in this model was demonstrated to correlate to overall survival of renal cell carcinoma patients. Patients, included in the analyses of over-all survival according to proliferative response of PBMCs to interleukin-2, were diagnosed with systemic metastatic renal cell carcinoma. They were previously untreated and scheduled for Interleukin-2 treatment (Proleukin®, Chiron®, NL). Blood samples were taken prior to initiation of treatment. Survival curves were plotted using the method of Kaplan and Meier and time to progression and survival comparisons between subgroups were performed using the log rank test. In addition, the prognostic significance of the level of LPS-stimulated IL-6 production was also calculated using Cox regression.

Figure 5:
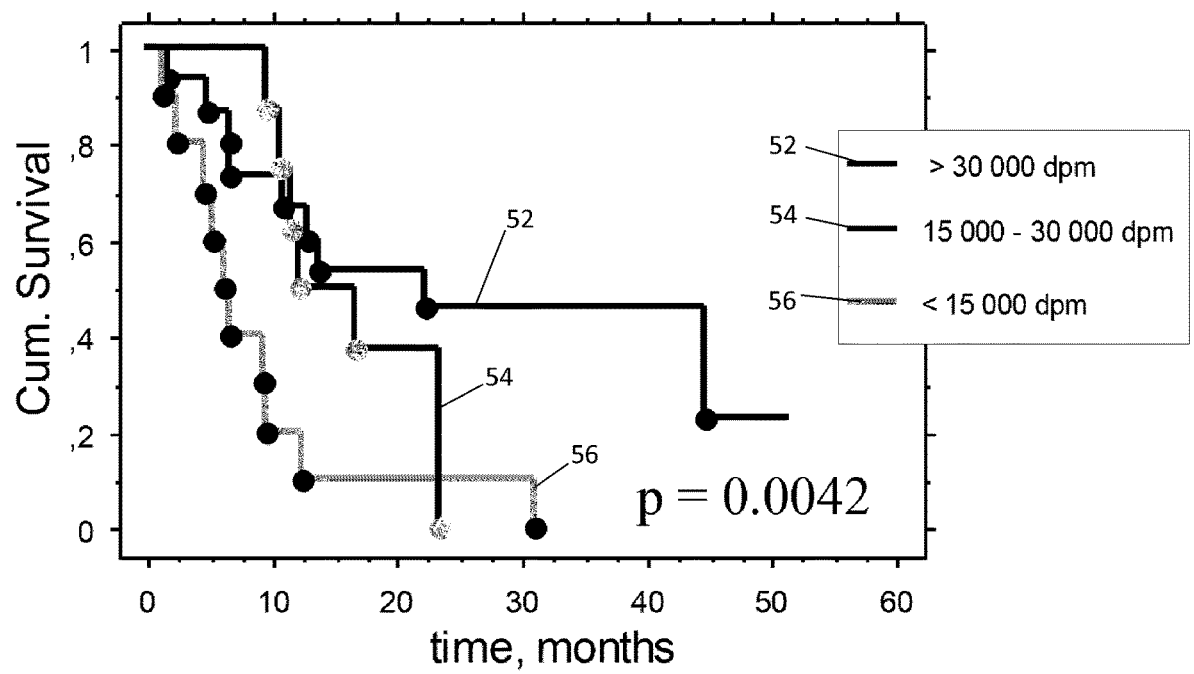
FIG. 5 illustrates a Kaplan Meyer analysis of renal cell carcinoma patients according to proliferative response to IL-2.

FIG. 5 illustrates a Kaplan Meyer analysis of renal cell carcinoma patients according to proliferative response to IL-2. Patients were classified as having a proliferative response of >30,000 dpm 52, 15,000-30,000 dpm 54, or <15,000 dpm 56. A log rank analysis we performed, and overall patient survival correlated with proliferative response (p=0.0042). As illustrated in FIG. 5, patients with the lowest IL-2 induced proliferation of PBMCs in autologous serum in the ex vivo model 56 also had the lowest overall survival time. Thus, a low proliferative rate indicates a poor survival.

Effect of Different Peptides on IL-2 Induced Proliferation

Figure 6:
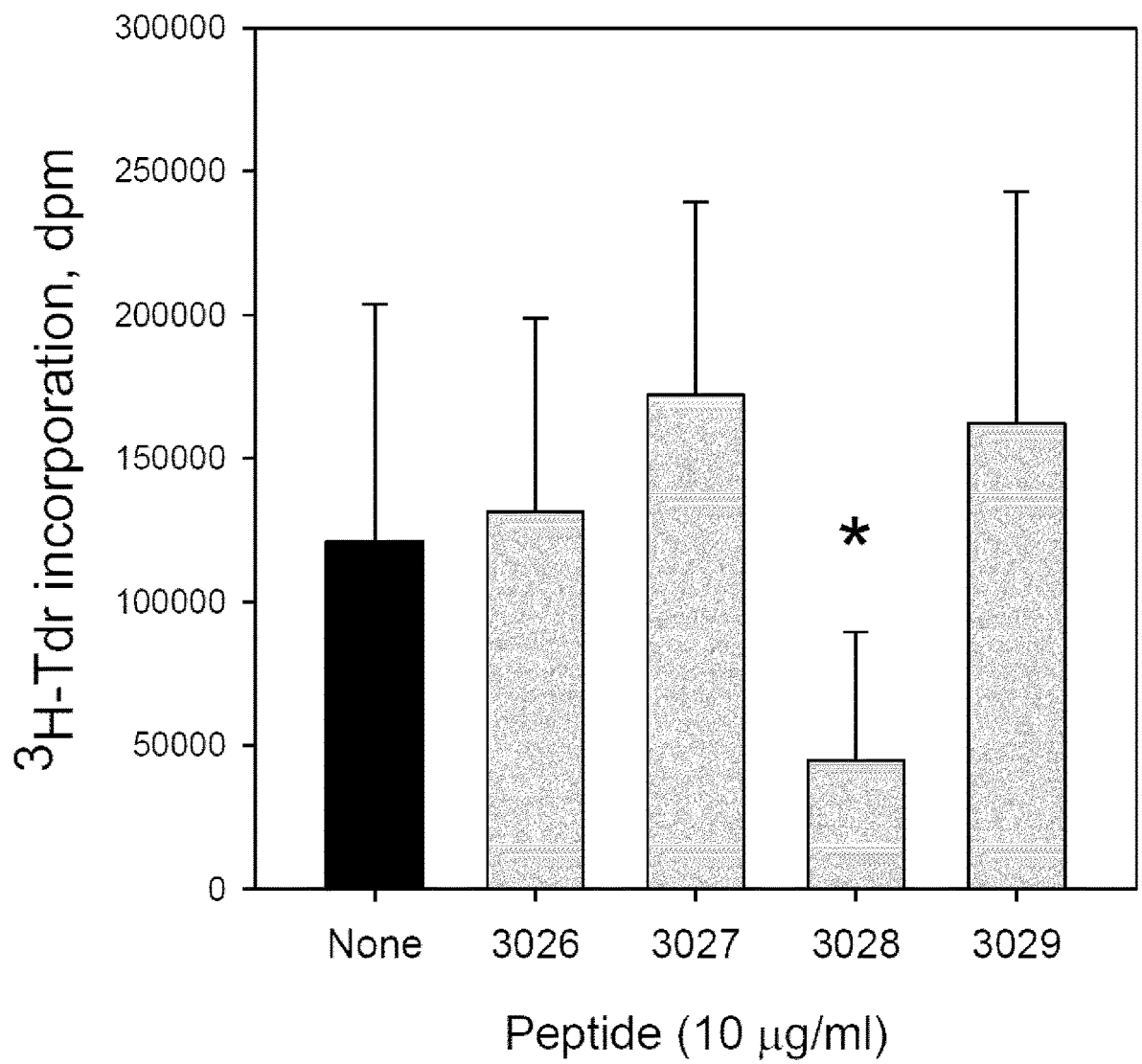
FIG. 6 illustrates analysis of the effect of four different peptides on IL-2 induced proliferation of PBMCs from healthy control samples.

The effect of different peptides on IL-2 induced proliferation was analyzed in the human ex vivo model, using PBMCs from healthy control samples. PBMCs were cultured for 7 days in the presence of IL-2 (20 U/ml) and the peptides. A control sample was also performed in which no peptide was added ("None"). Proliferation was measured as incorporation of $^3$H-thymidine during the final 18 hours. The peptides included P3026 (SEQ ID NO: 183), P3027 (SEQ ID NO: 184), P3028 (SEQ ID NO: 185), and P3029 (SEQ ID NO: 186). One of the peptides, P3028, regularly inhibited IL-2 induced proliferation (p<0.0006, as compared to control sample; n=17), but none of the other peptides identified by their binding to the artificial cell surface had any inhibitory activity (For P3026, P3027, P3029 n=4 or 5). FIG. 6 illustrates the analysis of the effect of the four different peptides.

Figure 7:
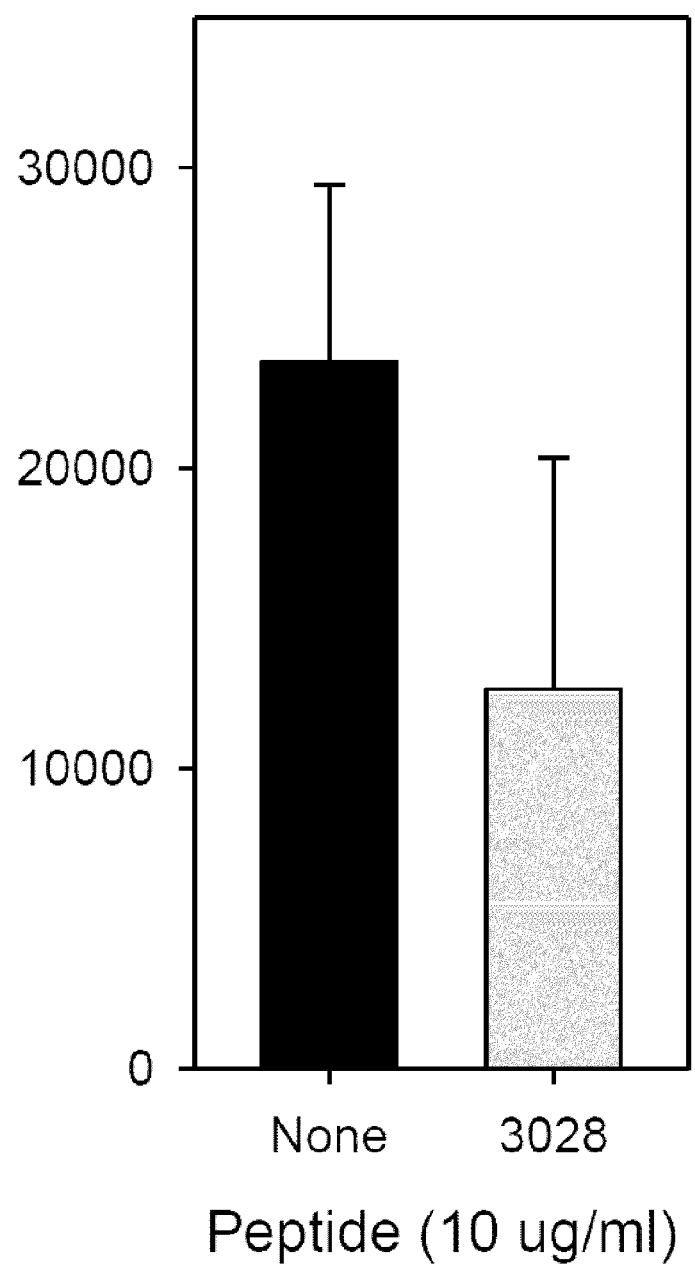
FIG. 7 illustrates inhibition of the proliferative response to IL-2 by P3028 in the human ex vivo model using cancer patient PBMCs.

The inhibition of the proliferative response to IL-2 by P3028 was also observed for cancer patient PBMCs studied in the human ex vivo model. The ex vivo model of IL-2 stimulation was constituted using the PBMCs of a cancer patient, and IL-2 stimulation was compared in the presence and absence of P3028. As illustrated in FIG. 7, the inhibitory activity of P3028 on IL-2 induced proliferation can be demonstrated also in cultures with cancer patient PBMCs, even if the response to IL-2 was already suppressed (see FIG. 7).

Example 3: Effect of P3028 on T-Cell Receptor Stimulation

To examine the effects of P3028 on T cell receptor stimulation, Blood for PBMC isolation was provided from healthy control samples in 50 ml transfusion bags with acid dextrose citrate solution A. Whole blood was diluted 1:1 in PBS containing 2 mM EDTA. PBMCs were then isolated by Ficoll-Paque® Plus (GE® Healthcare Bio-Sciences AB, Sweden) density gradient centrifugation after which the cells were washed first in PBS with 2 mM EDTA and second in lymphocyte culture media. Cell viability was assessed by exclusion of 0.02% Trypan Blue and was always above 95%. The cell suspension was counted in a haemocytometer. PBMCs were suspended in the culture medium without sera and the cell concentration adjusted to $1\times10^6$ lymphocytes/ml for proliferation assays and $6.4\times10^5$ for migration assays respectively. The lymphocyte culture medium RPMI 1640 (Invitrogen®, Sweden) was complemented with 1% Penicillin/Streptomycin (Invitrogen®, Sweden) and 4 mM Gluta-Max (Invitrogen®, Sweden). For CD3 induced proliferation the plates were coated with purified anti-human CD3 antibodies (BD® Pharmingen, Sweden). Therefore 50 µl of 2.5 µg/ml antibody PBS solution were pipetted into each well incubated for 1 hour. Cells were cultured for 4, 5 or 7 days in a humidified, 5% CO2-atmosphere at 37° C. Cell proliferation was assayed by the mitochondrial activity test CellTiter 96® AQueous Non-Radioactive Cell Proliferation Assay (MTS, Promega®, Sweden) during the last 4 hours. To each well 10 µl of the MTS solution was added and measured after 4 hours of incubation at 37° C. The measured values of the reference dye were subtracted of each well. The peptide solutions were prepared by dissolving peptides 3028, SCF28R, 28209 and SCF27 (Schafer-N, Copenhagen, Denmark) in lymphocyte media to a concentration of 25 µg/ml. The final concentration in the cultures was 5 or 10 µg/ml.

Figure 8:
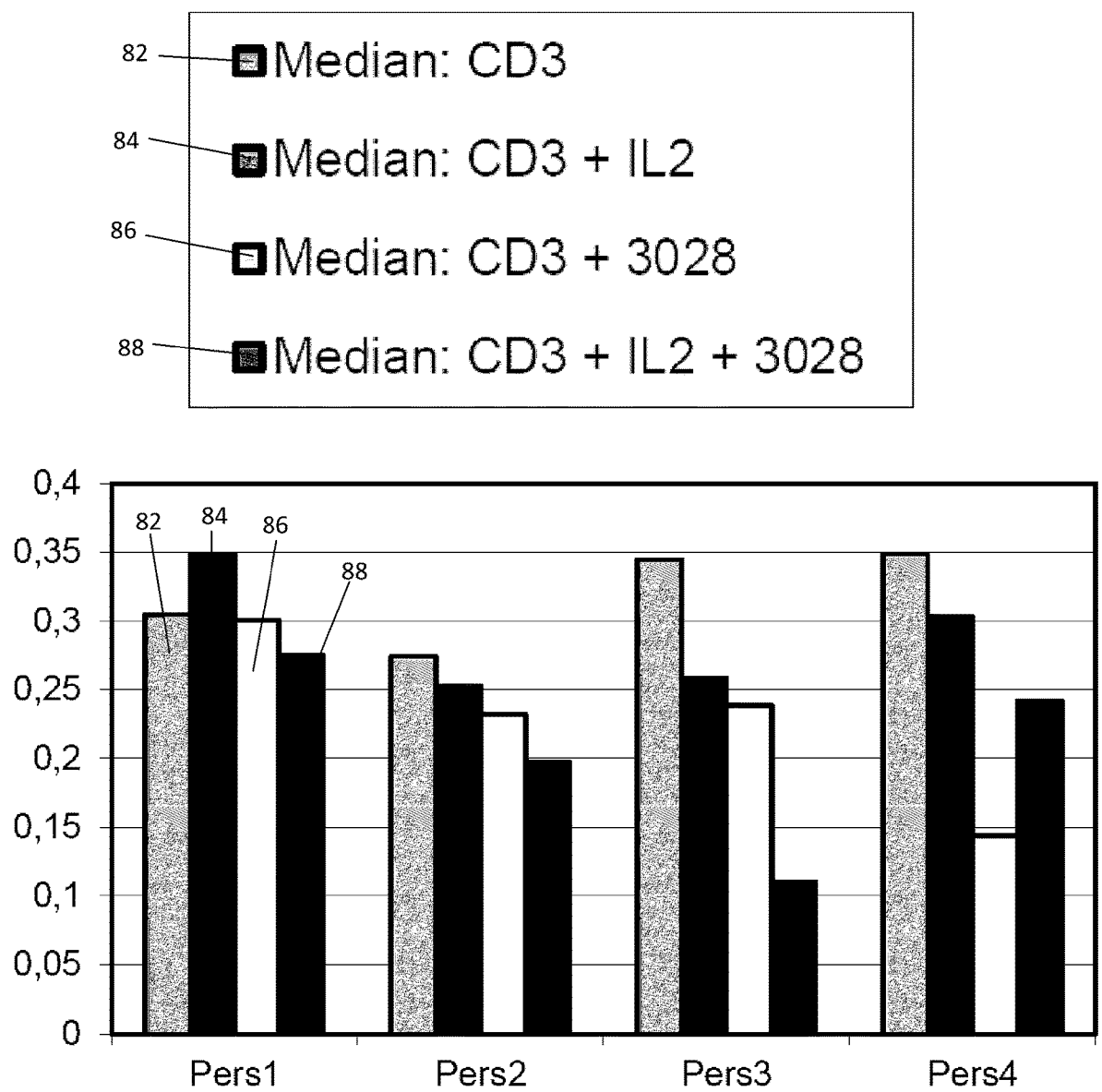
FIG. 8 illustrates effect of P3028 on TCR stimulated lymphocyte proliferation of PBMCs from four healthy persons.

T cells were stimulated in cultures on plates pre-coated with a monoclonal antibody directed against CD3 and the number of metabolically active cells (i.e., cell proliferation) was determined using MTS staining after 3 to 7 days of culture. Detection of solid phase CD3 monoclonal antibody was used as a measurement of T cell proliferation. FIG. 8 illustrates the effect of P3028 on TCR stimulated lymphocyte proliferation of PBMCs from four healthy persons. For each person, proliferation of lymphocytes was measured in the absence of stimulation 82, IL-2 stimulation 84, treatment with P3028 alone 86, and IL-2 stimulation plus P3028 88. Bars of the bar graph of FIG. 8 are in the same order for each person.

As can be seen in FIG. 8, P3028 had an inhibitory effect in at least three out of four experiments ($p<0.001$). It is unlikely that reduced MTS staining caused by P3028 was be due to a reduced cell metabolism. Taken together, the results from both models of lymphocyte proliferation, a reduced metabolism should reasonably reduce the endogenous thymidine pools and thereby result in an increased uptake of exogenous thymidine/specific activity of the thymidine pools, which then should be erroneously registered as an enhanced proliferation. The $^3$H-TdR was actually reduced in these experiments, indicating inhibition of proliferation.

Example 4: Effect of P3028 on NK-Cell Cytotoxicity

The NK-cell cytotoxic activity of blood mononuclear cells from four healthy donors was tested. Mononuclear cells were separated by standard Ficoll-Paque® Plus (Pharmacia AB, Sweden) density gradient centrifugation from heparinized blood obtained from healthy donors. NK cell cytotoxic activity of the mononuclear cells was then tested using a commercial kit (NKTEST, Orpegen Pharma GmbII, Heidelberg, Germany) following the manufacturers protocol. Briefly, the kit contains cryopreserved, NK-sensitive target cells (K562) labeled with a lipophilic green fluorescent membrane dye, which enables discrimination of effector and target cells. After incubation with effector cells, killed target cells are identified by a DNA-stain, which penetrates and specifically stain the nuclei of dead target cells. This way the percentage of killed targets can be determined by flow cytometry. The mononuclear cells were preincubated for 30 min at 37° C. with the indicated peptides (peptides have been described previously) at 10 ug/ml. Target cells were then added, giving an effector:target ratio of 40:1, and the cell mixture incubated at 37° C. for 3-4 hours. Samples were analysed on a FACSCalibur (BD® Biosciences, San Jose, Calif.).

Figure 9A:
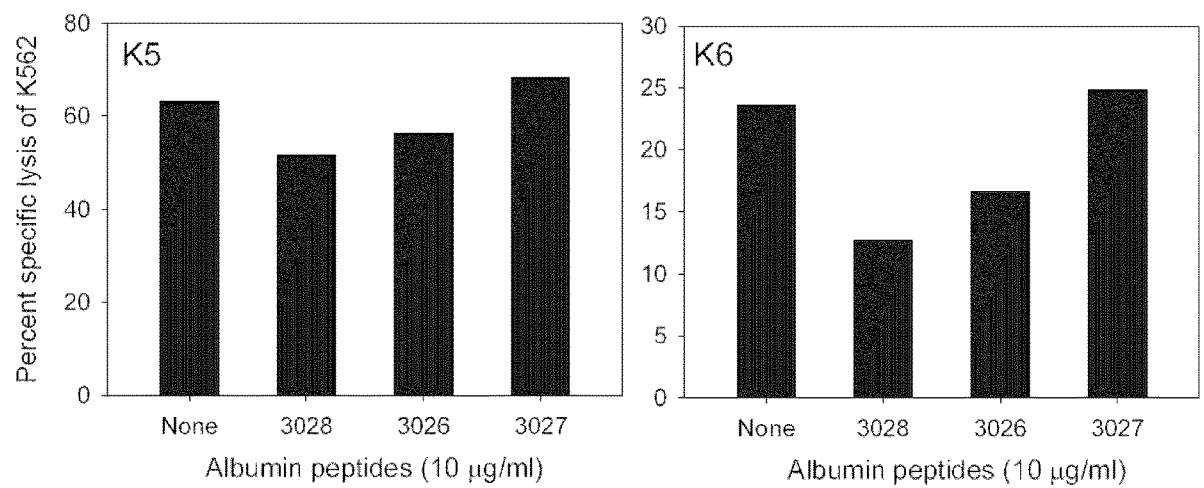
FIGS. 9A-9B illustrates effect of albumin peptides on NK-cell cytotoxicity.
Figure 9B:
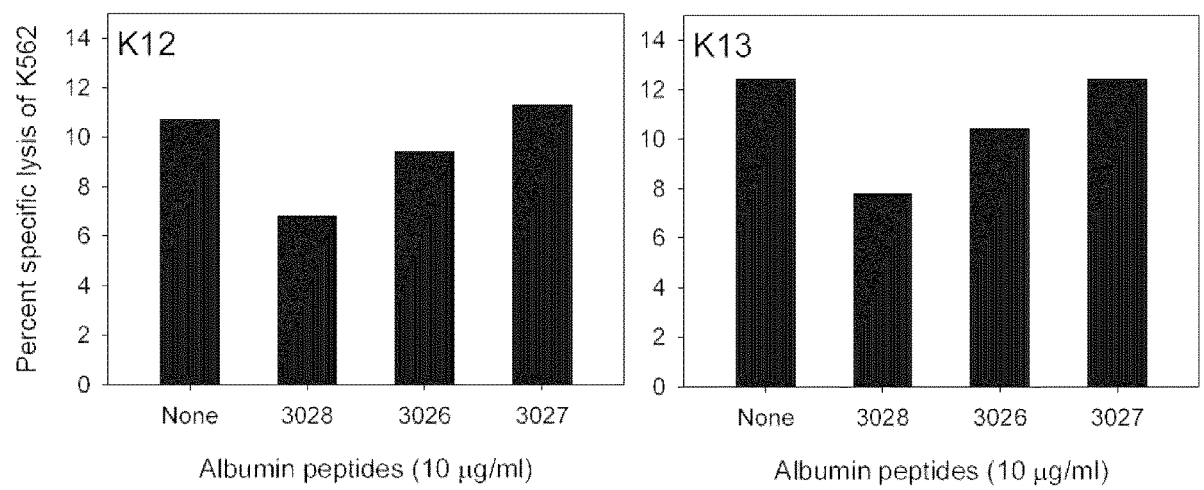

FIGS. 9A-B illustrate the effect of albumin peptides on NK-cell cytotoxicity ($p=0.015$, paired t-test, normal transformation log-values). As shown in FIG. 9A-B, the presence of P3028 and, to a lesser degree, peptide 3026 reduced the percent specific lysis of K562 target cells by all four donors. Inhibition was not seen in the presence of the control sample peptide 3027 with no structural relationship with P3028. Inhibition of NK-cell cytotoxicity, in this model, was not due to an effect of P3028 on the activity of IL-2 as no IL-2 was added to the short-term cultures.

Example 5: Effect of P3028 on Leukocyte Spreading and Immune Cell Migration

In properly functioning immune systems, immune cells are recruited to tissues, and migrate within tissues. The effect of P3028 in two functional tests, leukocyte spreading and immune cell migration was investigated.

Leukocyte Spreading

Figure 10:
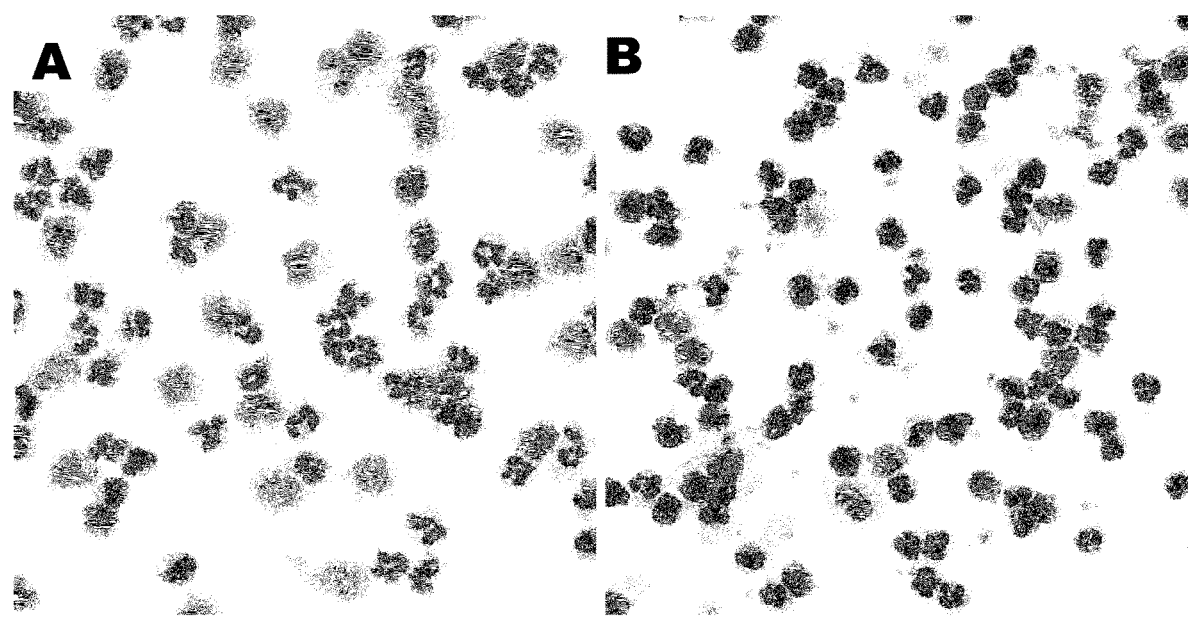
FIG. 10 illustrates effect of P3028 on the spreading on peripheral blood leukocytes.

To analyze the effect of P3028 on leukocyte spreading, buffy coat cells were prepared from heparinized blood by Dextran assisted sedimentation. These cells were then washed twice in PBS and transferred to slides washed in 70% and 96% ethanol. The cell suspension was dropped onto the slides and incubated for 15 min in a moist chamber with or without P3028, 10 µg/ml, the solution was carefully drained off, the slides were air dried and stained in May Grünewals Giemsa for 1 minute. As shown in FIG. 10A, the cells strongly adhered to the glass surface and spread out. Pre-treatment of these cells with P3028 efficiently inhibited the spreading (see FIG. 10B).

Immune Cell Migration

Blood for PBMC isolation was provided from healthy control samples in 50 ml transfusion bags with acid dextrose citrate solution A. Whole blood was diluted 1:1 in PBS containing 2 mM EDTA. PBMCs were then isolated by Ficoll-Paque® Plus (GE® Healthcare Bio-Sciences AB, Sweden) density gradient centrifugation after which the cells were washed first in PBS with 2 mM EDTA and second in lymphocyte culture media. Cell viability was assessed by exclusion of 0.02% Trypan Blue and was always above 95%. The cell suspension was counted in a haemocytometer. PBMCs were suspended in the culture medium without sera and the cell concentration adjusted to $1\times10^6$ lymphocytes/ml for proliferation assays and $6.4\times10^5$ for migration assays respectively. The lymphocyte culture medium RPMI 1640 (Invitrogen®, Sweden) was complemented with 1% Penicillin/Streptomycin (Invitrogen®, Sweden) and 4 mM Gluta-Max (Invitrogen®, Sweden). For CD3 induced proliferation the plates were coated with purified anti-human CD3 antibodies (BD® Pharmingen, Sweden). Therefore 50 µl of 2.5 µg/ml antibody PBS solution were pipetted into each well incubated for 1 hour. Cells were cultured for 4, 5 or 7 days in a humidified, 5% $CO_2$-atmosphere at 37° C. Cell proliferation was assayed by the mitochondrial activity test CellTiter 96® AQueous Non-Radioactive Cell Proliferation Assay (Promega®, Sweden) during the last 4 hours. To each well 10 µl of the MTS solution was added and measured after 4 hours of incubation at 37° C. The measured values of the reference dye were subtracted of each well. The peptide solutions were prepared by dissolving peptides 3028, SCF28R, 28209 and SCF27 (Schafer-N, Copenhagen, Denmark) in lymphocyte media to a concentration of 25 µg/ml. The final concentration in the cultures was 5 or 10 µg/ml.

Figure 11:
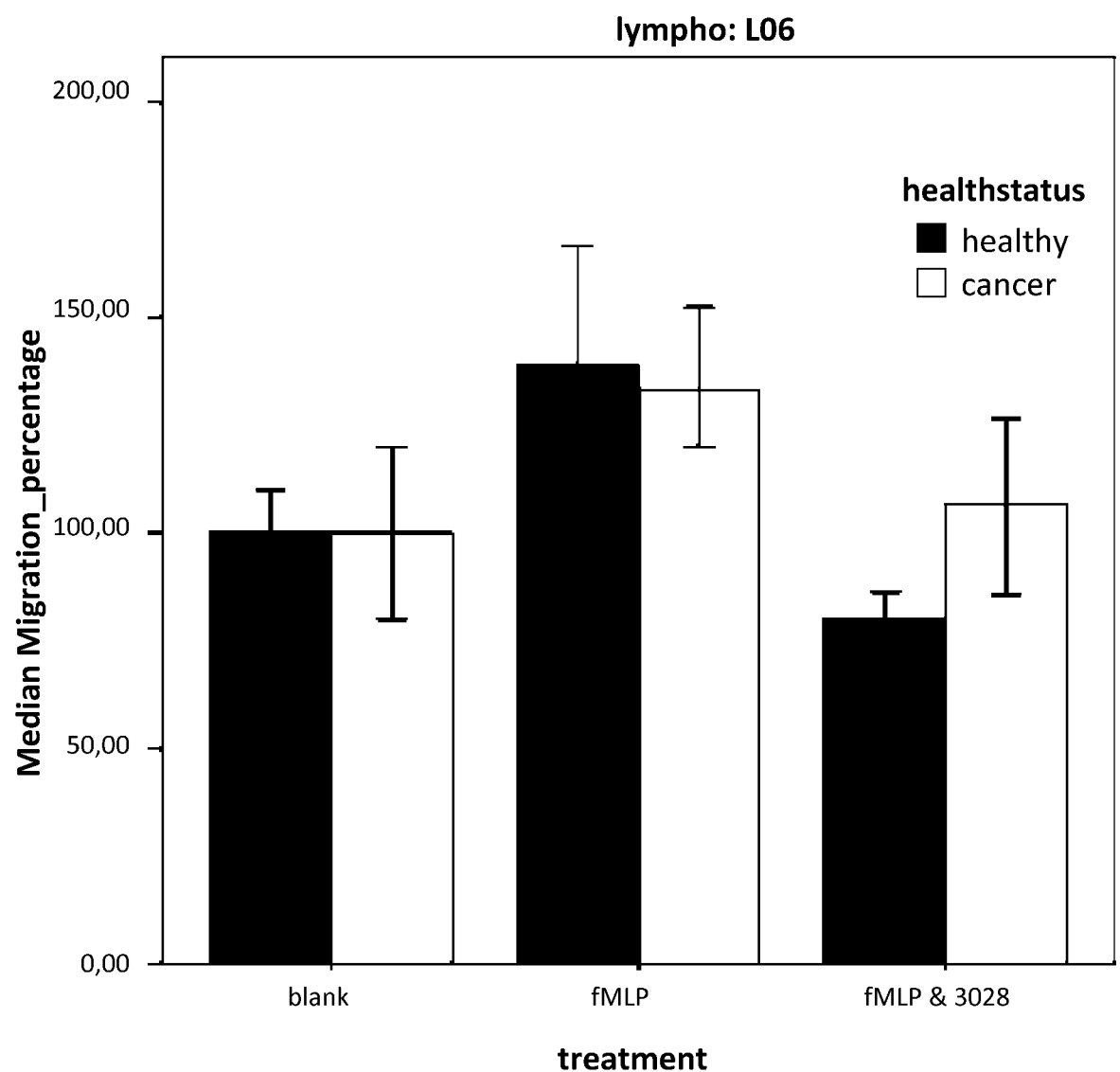
FIG. 11 illustrates effect of P3028 on migration of PBMCs studied using the Boyden chamber technique.

50 µl of the prepared $6.4 \times 10^5$ PBMC dilution were pipetted into Eppendorfs tubes and centrifuged for 5 minutes at 400 g, then the prepared dilutions of blank, P3028 and the inhibitors were added. The PBMCs were incubated at the 37° C. with the test substances for one hour. Meanwhile the Boyden Chamber was prepared by pipetting 25 µl of either media without fMLP or media containing $1 \times 10$-8M fMLP to the lower wells. Then 50 µl of the PBMCs final concentration, $3.2 \times 104$, were transferred to the upper wells of the chamber. The PBMCs were allowed to migrate for one hour at the 37° C. The filters were removed and stored in 70% ethanol overnight. Thereafter the filters were dehydrated in increasing alcohol concentration and finally placed in Xylene. Subsequently they were placed on slides, mounted and counted with a microscope, containing a µm scale. Each test was done in duplicates and migration was calculated as percentage of the mean of the blank duplicates without fMLP. As shown in FIG. 11, P3028 is a potent inhibitor of immune cell migration across the membrane of the Boyden chamber ($p<0.002$). Migration for healthy control samples (N=6) is illustrated in FIG. 11 using dark bars (left), while cancer patients (N=3) are shown as light bars (right). In FIG. 11, Error bars: 95% CI. P3028 reduced the migration of PBMCs of both healthy cells and cancer patients.

Figure 12:
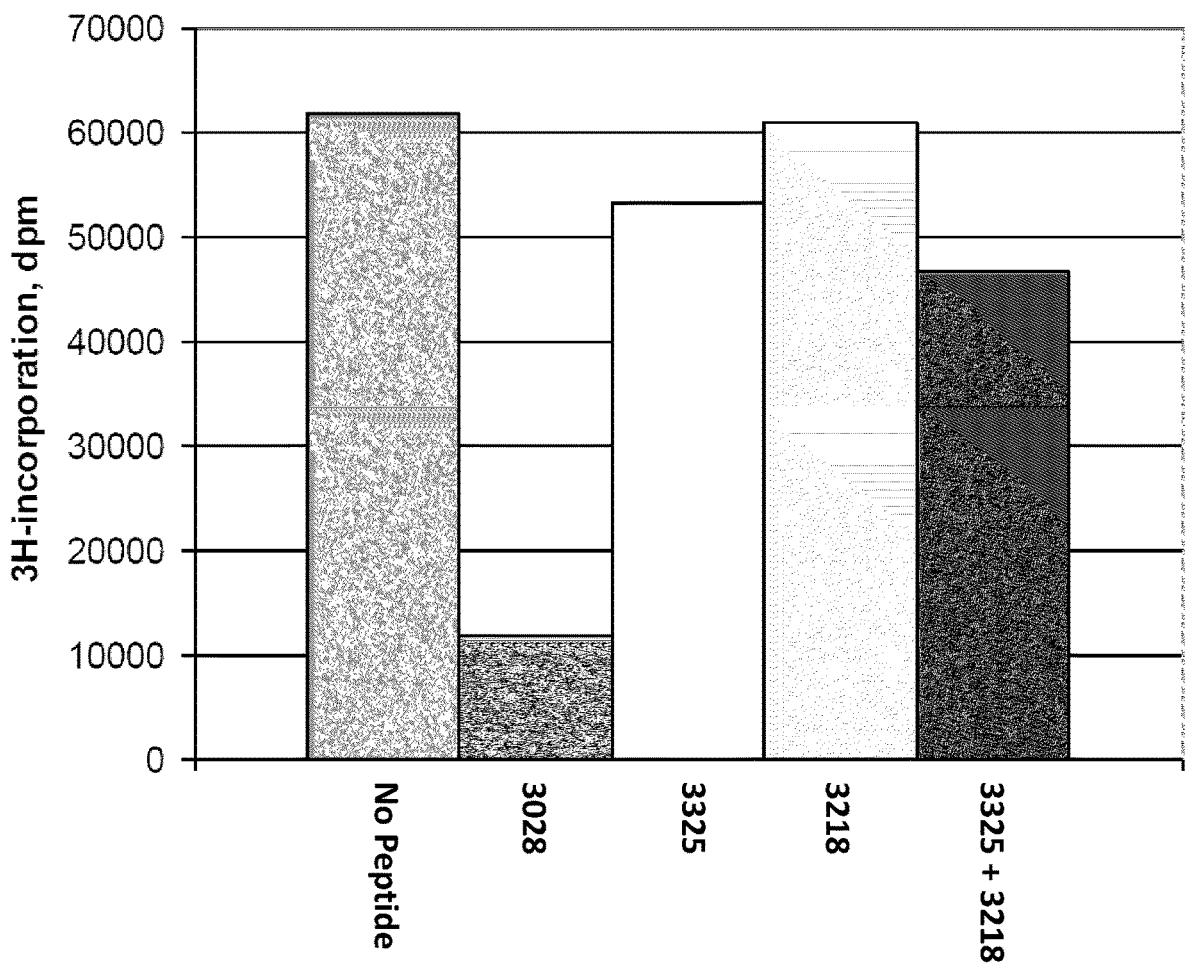
FIG. 12 illustrates effect of the C- (3218) and N-terminal (3325) parts of P3028 on 11-2 induced proliferation in comparison with the effect of the full length P3028.
Figure 13:
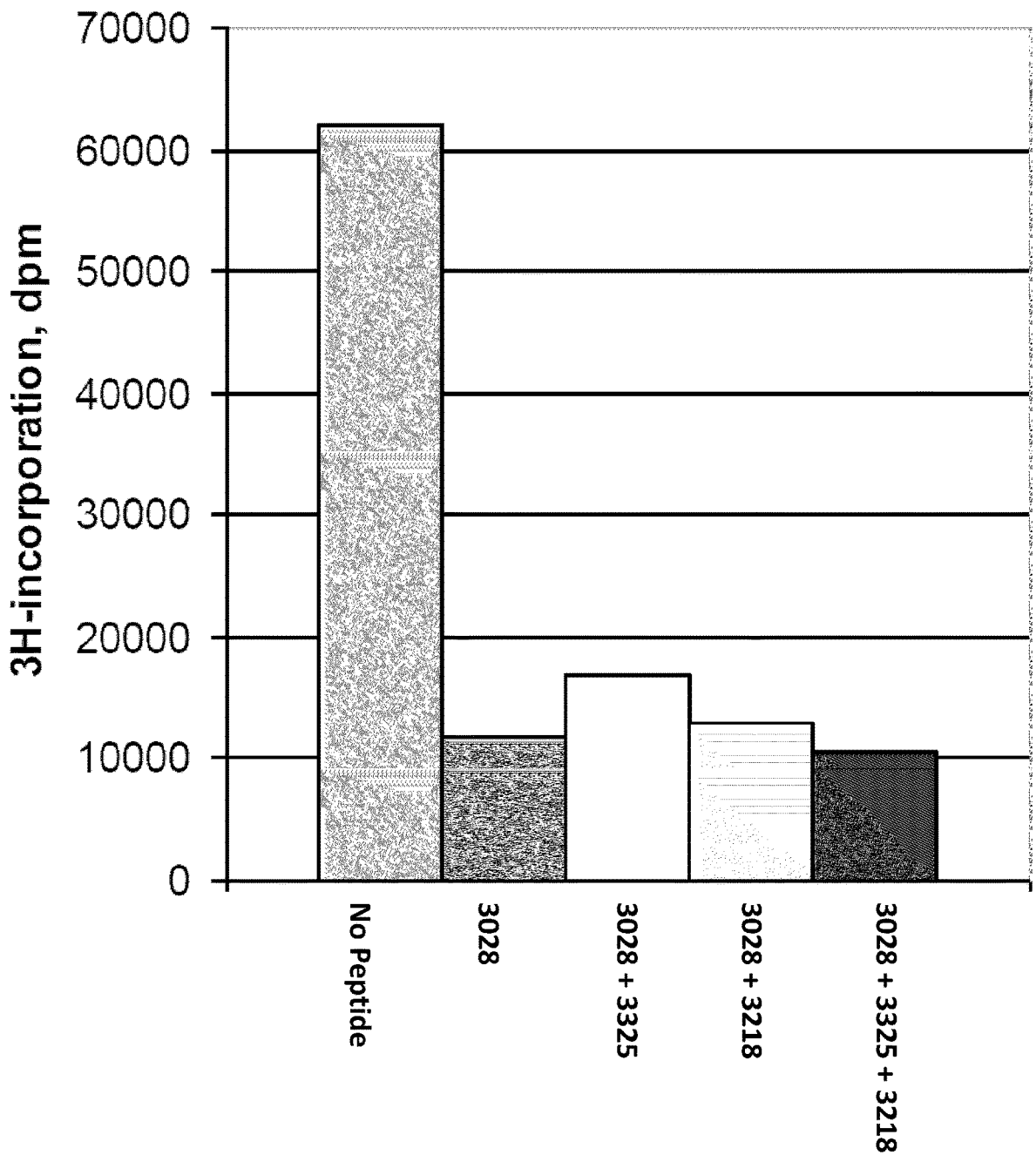
FIG. 13 illustrates the inhibitory effect of P3028 on IL-2 induced proliferation is not neutralized by the C- (3218) and N-terminal (3325) parts of P3028 alone or in combination.

Example 6: Further Characterization of the Effect of P3028 on IL-2 Induced Proliferation The C and N-terminal parts of P3028 were synthesized and analyzed separately and in combination. The inhibitory activity of these two parts of P3028 alone or in combination is much weaker (see FIG. 12) and they do not inhibit the effect of P3028 on IL-2 induced proliferation (see FIG. 13) in the ex vivo human model. FIG. 12 illustrates effects of the C- (P3218) (SEQ ID NO: 187) and N-terminal (P3325) (SEQ ID NO: 186) parts of P3028 on 11-2 induced proliferation in comparison with the effect of the full length P3028. One representative experiment is shown. FIG. 13 illustrates that the inhibitory effect of P3028 on IL-2 induced proliferation is not neutralized by the C- (P3218) and N-terminal (P3325) parts of P3028 alone or in combination.

Example 7: Binding of P3028 to LFA-1

The presence of β2-integrins on PBMCs was demonstrated by immunocytochemical staining. The occurrence of factors interfering with the binding of monoclonal antibodies directed against β2-integrins in cancer patient sera was analysed by staining of β2-integrins on PBMCs. A standard immunohistochemical staining procedure using acetone fixation, 10% human AB-serum for blocking, incubation with anti-LFA-1 antibody. PBMCs were separated as described above and immediately spun down on pre-cleaned microscope slides in a Shandon Cytospin® (Shandon Scientific Ltd, UK) at 1000 RPM for 7 min at $5 \times 104$ cells per slide. The slides were left to dry at room temperature over night, after which they were wrapped in parafilm and stored at 70° C. Immediately before use, the cytospins were thawed and fixed with acetone for 5 min at room temperature. The Cytospins® were first blocked with 10% normal human AB-serum with and without albumin peptides (40 µg/ml) or serum from cancer patients for 1 h before staining. Primary antibody, consisting of a monoclonal mouse anti-human CD11a (BD® Biosciences) diluted in Tris buffered saline (TBS, pH 7.6) at 1 µg/ml (PBMC), was added. The slides were incubated for 30 min and then washed in TBS followed by Envision-Alkaline Phosphatase (Dako® Norden A/S, Denmark) or, alternatively, Ultravision-Alkaline Phosphatase (Lab Vision® Co) for 30 min. After additional washing in TBS, the slides were incubated in alkaline phosphatase substrate consisting of Fast Red TR salt (Sigma®), naphtol AS-MX (Sigma®) and 5 mM levamisol (Sigma®) to block endogenous alkaline phosphatase activity, for 20 min followed by washing in TBS. They were then counterstained in Mayer's haematoxylin for 1 minute and mounted in Glycergel® (Dako® Norden A/S). Monoclonal mouse IgG1 against an irrelevant antigen (*Aspergillus niger* glukosoxidase, Dako® Norden A/S) was used as a negative control sample. All incubations were performed at room temperature in a moist chamber.

Pre-incubation with peptides added to the AB serum was either no peptide added (see FIG. 15A), or P3028 added (see FIG. 15B). Notably, the anti-LFA-1 antibody used in these experiments was a potent inhibitor of IL-2 induced proliferation.

Figure 14:
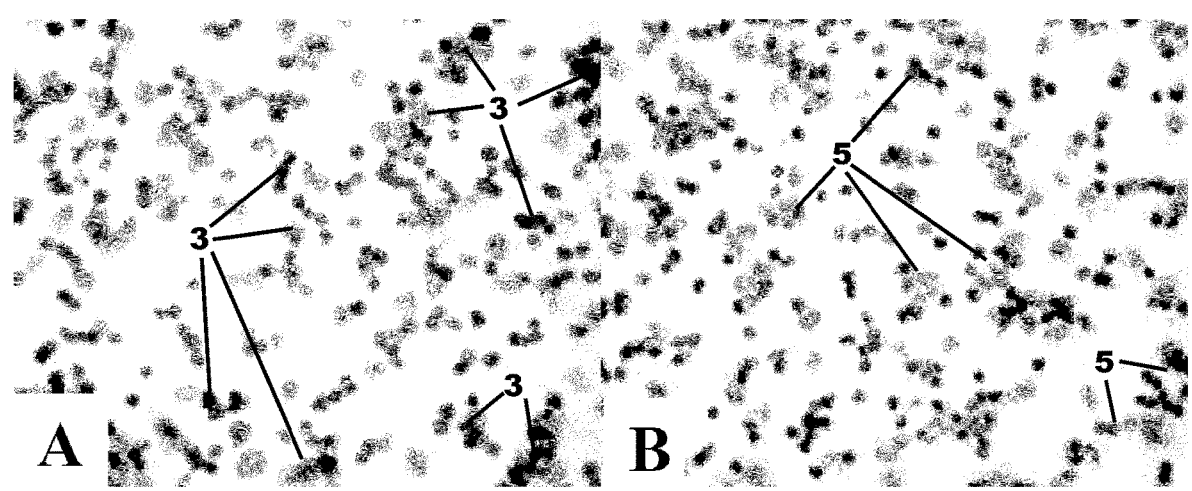
FIG. 14 illustrates inhibition of the binding of anti-LFA-1 antibody directed to CD11a by incubation of normal PBMCs with patient sera.

As shown in FIG. 14, the presence of β2-integrin blocking factors was then demonstrated as a reduced stainability 5 of these cells after incubation with cancer patient sera (see FIG. 14B), compared to preparations pre-incubated with control serum sample (see FIG. 14A) which showed strong staining 3 for LFA-1.

As shown in FIG. 15, similar to the results described for cancer patient sera, treatment with P3028 can modulate the binding of the LFA-1 antibody to LFA-1 of mononuclear blood cells, FIG. 15 illustrates inhibition of the binding of an anti-LFA-1, mAb, to mononuclear blood cells by P3028. Strong staining 3 for LFA-1 was observed in cells in which no peptide was added (see FIG. 15A), while weak staining 5 for LFA-1 was observed in cells in which P3028 was added (see FIG. 15B).

In order to further demonstrate the blockade of LFA-1 by the P3028 structure, the staining of this integrin on PBMCs from healthy control samples and cancer patients was compared. FIG. 16 illustrates staining of LFA-1 on PBMCs from a healthy control sample (see FIG. 16A), and a cancer patient before (see FIG. 16B) and after (see FIG. 16C) treatment with an antibody directed against P3028. As shown in FIG. 16A, a clear membrane staining 3 is found on PBMCs from healthy control samples in contrast to PBMCs from a patient with advanced cancer, which exhibited weak staining 5. However, when the PBMCs from this patient were incubated with an antibody directed towards the P3028 structure for 24 hours the membrane staining appeared 3, indicating that the antibody bound the P3028-structure and thereby unblocked LFA-1 (see FIG. 16C).

Figure 17:
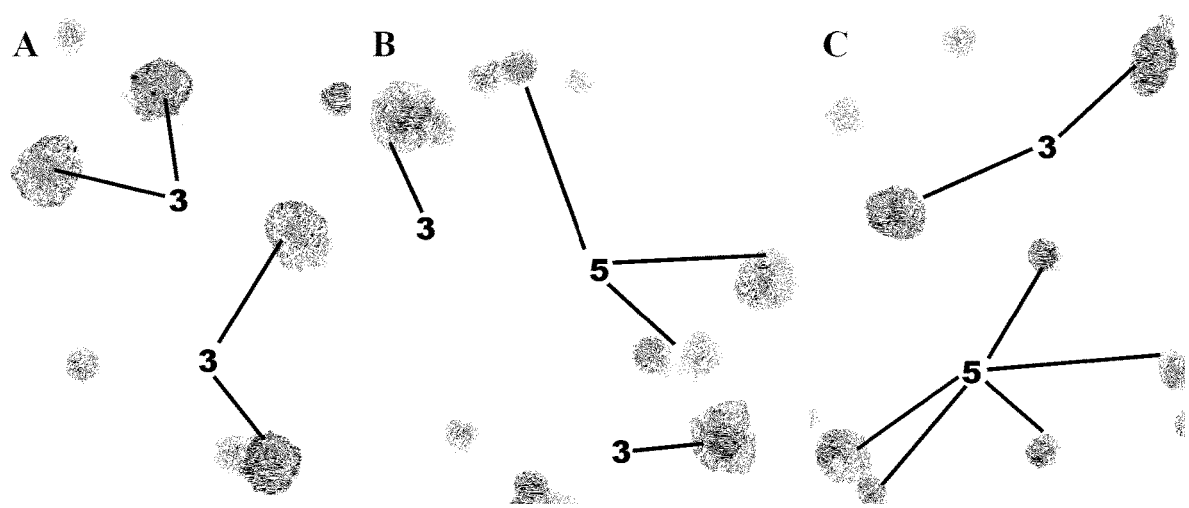
FIG. 17 illustrates staining of mononuclear blood cells by an anti-LFA-1 antibody (A) is blocked by P3028 (B) or cancer patient serum (C).

Similarly, as shown in FIG. 17, incubation of PBMCs from a healthy control sample with either P3028 or serum from a cancer patient blocked the membrane staining of LFA-1. FIG. 17 illustrates staining 3 of mononuclear blood cells by an anti-LFA-1 antibody (A) is blocked 5 by P3028 (B) or cancer patient serum (C).

Example 8: Binding of P3028 to the α-Chain (CD25) of the IL-2 Receptor

Figure 18A:
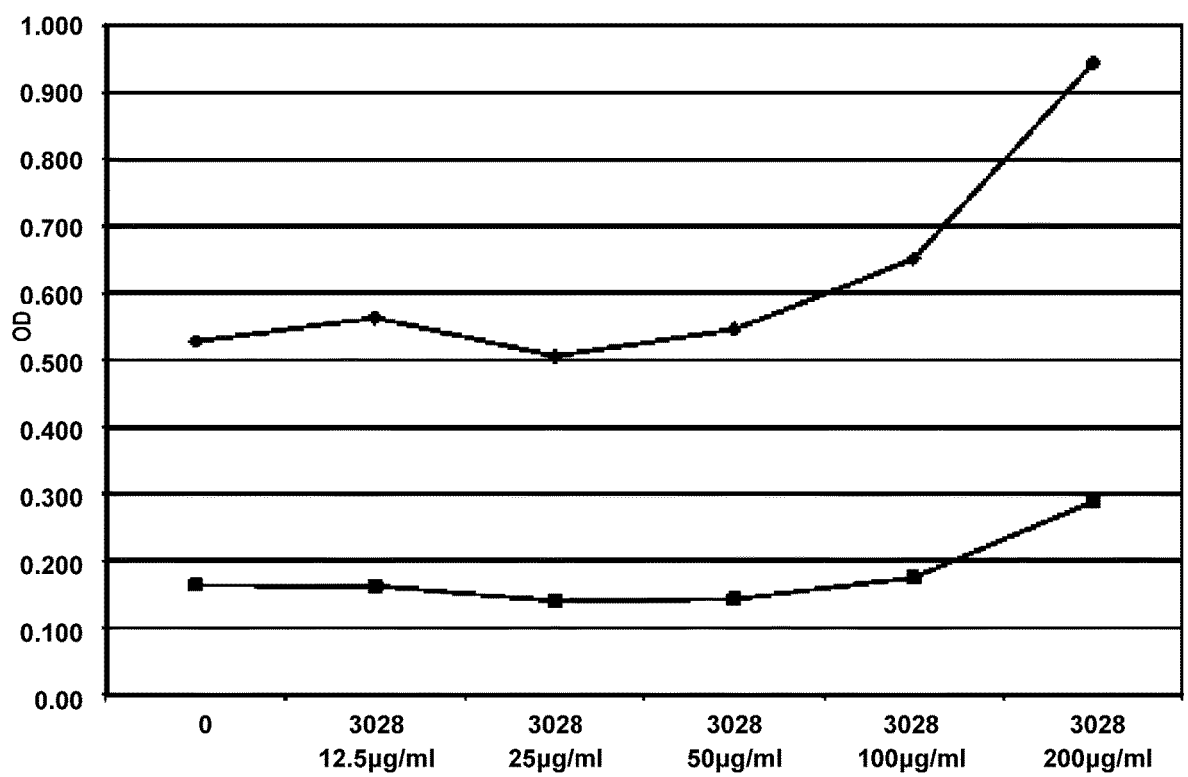
FIGS. 18A and 18B illustrates ELISA analysis showing that the binding of biotinylated IL-2 to rhuIL-2R.
Figure 18B:
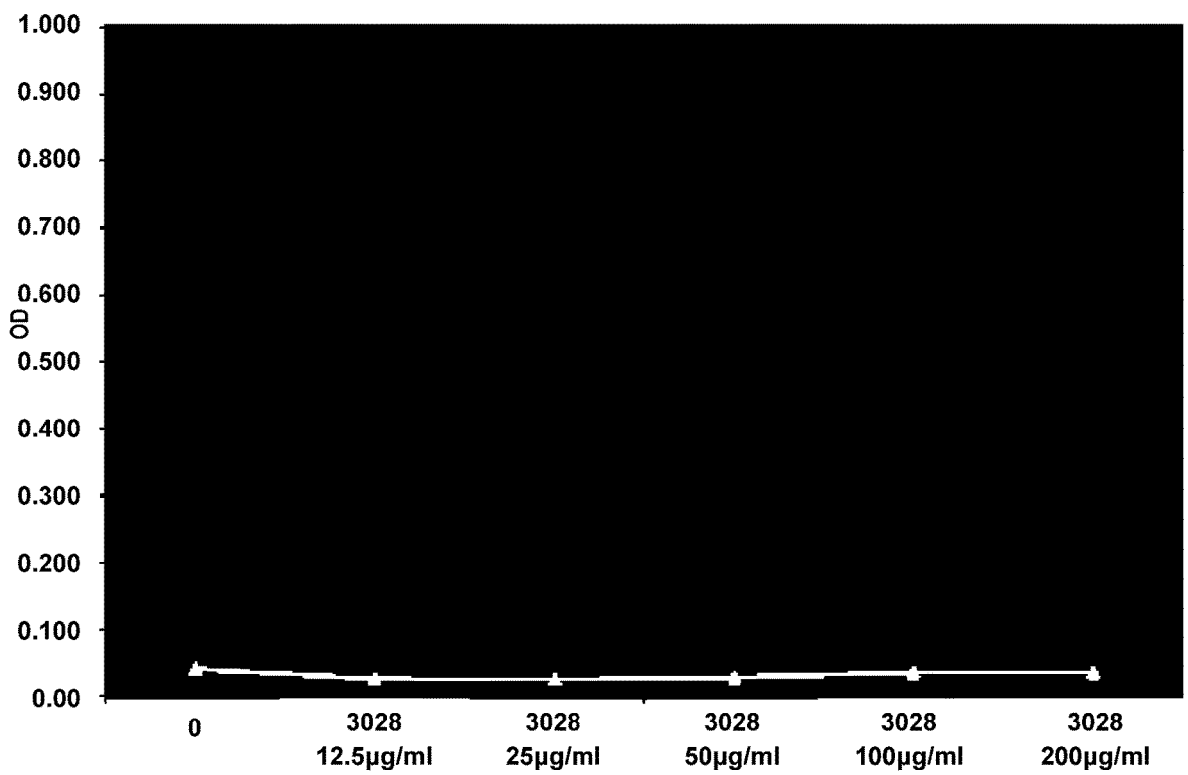

Because P3028 significantly inhibits the proliferative response to IL-2, the effect of P3028 on the binding of IL-2 to its receptor, CD25 was studied. The fusion protein of CD25 and the Fc-part of IgG was bound to protein G coated micro-plates/ELISA plates and the plates were incubated with biotinylated IL-2 with or without P3028 present. FIGS. 18-B illustrate the results of this ELISA analysis for dilution of biotinylated IL-2 that were as follows: (diamond ♦) 1:300, (square ■) 1:600, (triangle ▲; see FIG. 18B) no biotinylated IL-2. The binding of biotinylated IL-2 to rhuIL-2R alpha was increased by increasing amounts of P3028. Surprisingly, the binding of IL-2 to CD25 was enhanced by P3028, indicating a three-part interaction between IL-2, CD25 and P3028 (see FIG. 18-B). Even if the binding of IL-2 to CD25 is enhanced the proper assembly of the high affinity receptor and/or signal transduction is blocked as P3028 is a potent inhibitor of IL-2 induced proliferation.

It was demonstrated using computer assisted molecular modeling that P3028 binds to CD25 at the IL-2 binding site (see FIG. 19). The crystal structure of the IL-2 receptor bound to IL-2 is known in the art (see Wang et al., Science 2005, 310(5751): 1159-1163, and Stauber et al, Proc. Natl. Acad. Sci. USA 2006, 103(8): 2788-2793, each of which is hereby incorporated by reference in its entirety), and binding of P3028 was modeled according. In FIG. 19, the α-chain 190 of the IL-2 receptor (CD25) binding P3028 192 (A) at the IL-2 binding site 194 (B) is depicted. IL-2 196 is also shown.

Example 9: Antibodies that Bind to P3028

Rabbit antisera directed against the albumin P3028 were generated. P3028 was synthesized with a cysteine added to the N-terminus end and then conjugated with keyhole limpet hemocyanin (KLH) as a carrier protein. Polyclonal antisera were generated by repeated immunizations of rabbits with KLH-conjugated P3028 and Freund's adjuvants. For some experiments, the antisera were affinity purified by chromatography on P3028-conjugated Ultralink® Iodoacetyl gels (Pierce® Biotechnology Inc.). For cell culture experiments, buffer exchange to RPMI 1640 Dutch's modification (Gibco®, InVitrogen® AB, Stockholm, Sweden) was performed by passage over PD-10 Sephadex® columns (Amersham® Biosciences, Uppsala, Sweden) followed by filter sterilization on 0.22 µm Millex® syringe filters (Millipore® Co., MA, USA). Rabbit immunizations and purification of antisera were carried out by Agrisera AB, Sweden.

Figure 20:
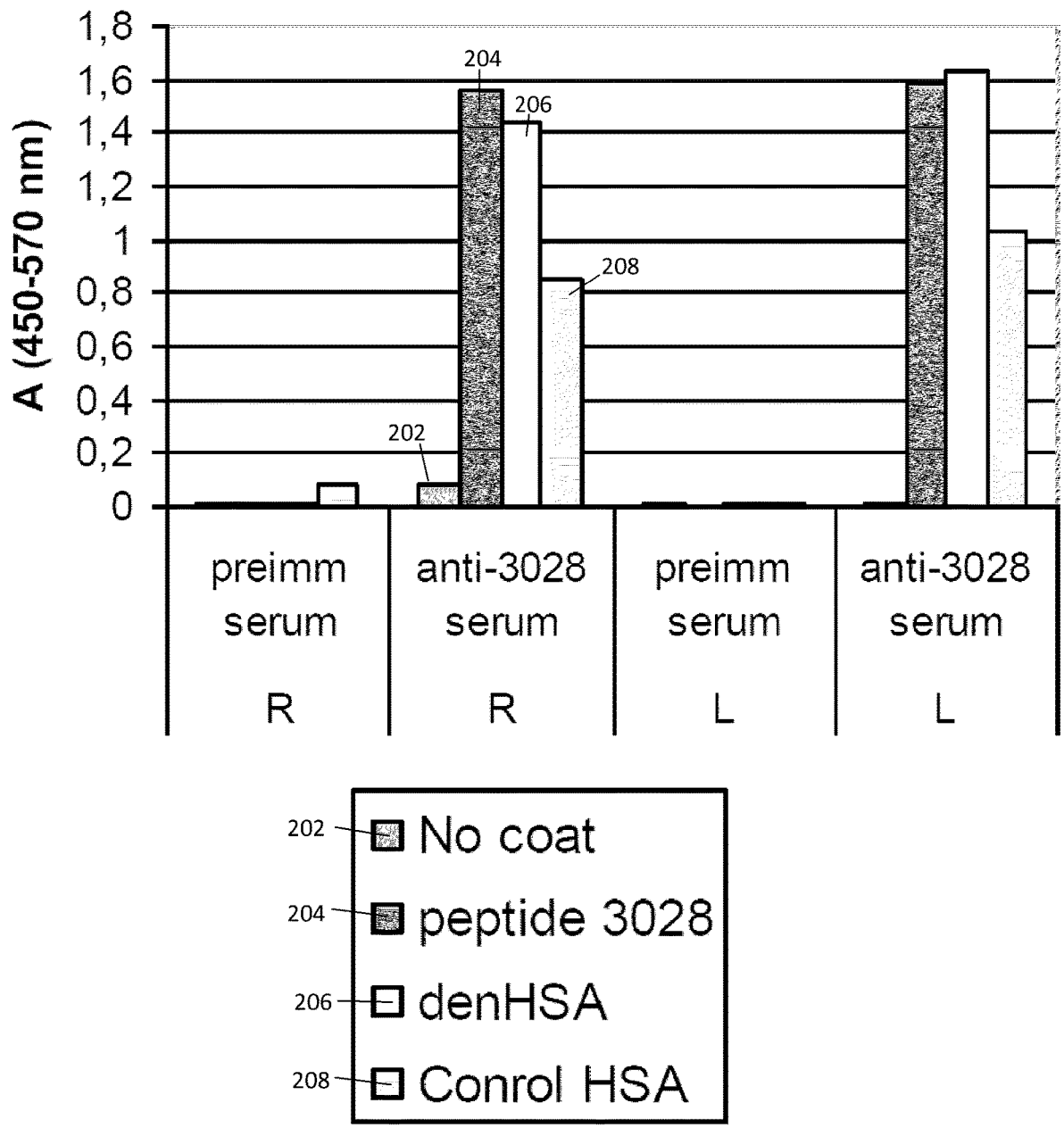
FIG. 20 illustrates antisera from rabbits immunized with P3028 binds to P3028.

Two antisera, R and L, from two different rabbits were tested for their ability to bind human serum and denatured Human Serum Albumin (dHSA). Human serum albumin commercially available for therapeutic purposes was tested, heated 10 times in order to be virus free. Wells were coated with the P3028, dHSA, or control sample treated (not denatured, but heated 10 times) HSA, which has been prepared just as the denatured HSA except for the denaturation procedure. As shown in FIG. 20, antisera, but not preimmune sera, from two rabbits immunized with the albumin P3028 bind to plates coated with the P3028 204, dHSA 206 and, to a lesser extent, to control sample treated HSA 208. No substantial binding was detected for wells with no coat 202. Thus, rabbit antisera directed against the albumin P3028 binds to dHSA and to a lesser extent to control sample HSA.

Figure 21:
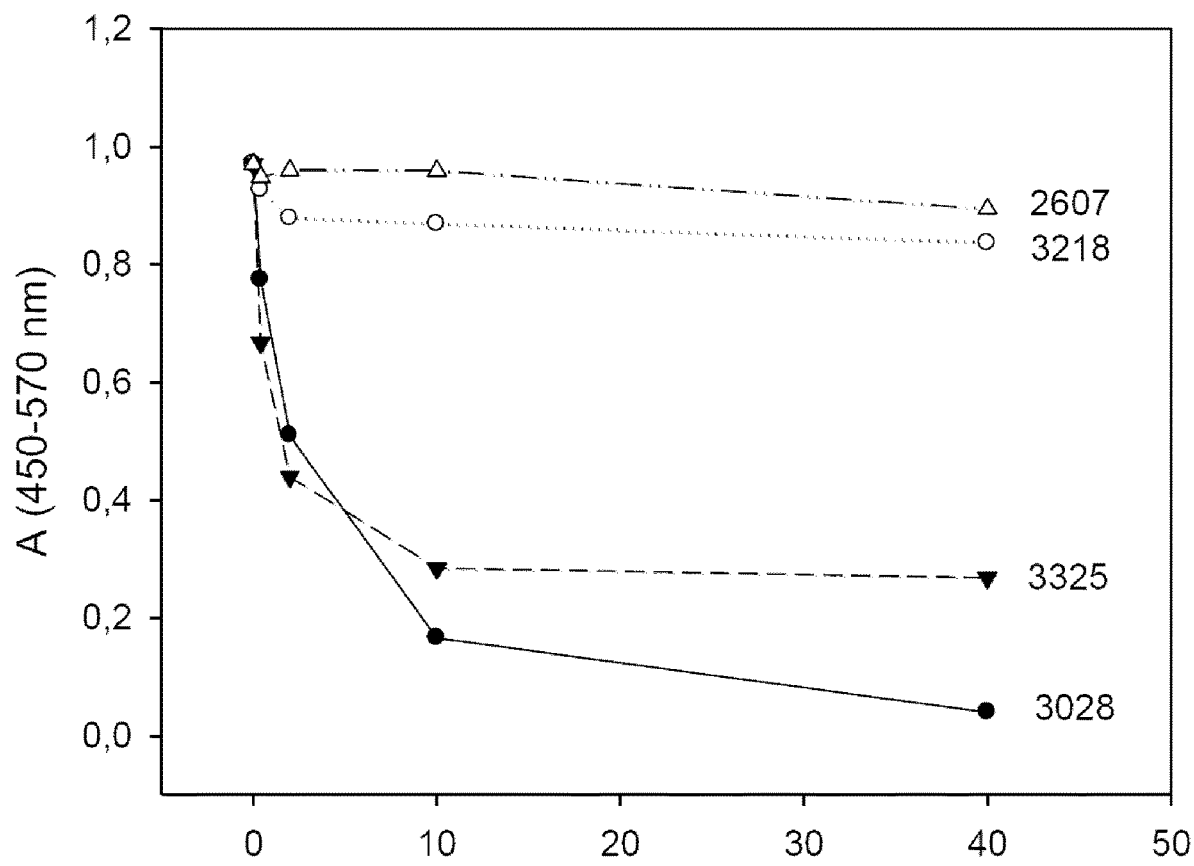
FIG. 21 illustrates inhibition of the binding of rabbit-anti 3028 serum L to wells coated with the P3028 in an ELISA by albumin peptides

The binding of the rabbit anti-P3028 serum to P3028 fragments was assayed using competition ELISA assay. Rabbit antisera, diluted 1/1000 000 in ELISA reagent diluent, was pre-incubated for 1 hr at room temperature with the indicated concentrations of the peptides. 100 µl of the monoclonal antibody alone, or, alternatively, the monoclonal antibody mixed with peptides, was then added to P3028 coated wells and the ELISA carried out. Inhibition of the binding of rabbit anti-P3028 serum L to wells coated with the P3028 was determined for albumin peptides 2607 (SEQ ID NO: 192), 3218 (C terminal of P3028) (SEQ ID NO: 187), 3325 (N terminal of P3028) (SEQ ID NO: 186), and full-length P3028 (SEQ ID NO: 185). Peptide 2607, containing the E5K structure, was used as a negative control sample. As shown in FIG. 21, these serum antibodies bound preferentially to the 3325 but not to the 3218 fragment of P3028. Similar results are also obtained with the affinity purified antibodies.

The effects of affinity purified antibodies directed against P3028 on the proliferative response to IL-2 were studied in the ex vivo model, using PBMCs from immunosuppressed cancer patients and normal control samples. Cultures to test the immunomodulatory effect of affinity purified rabbit antibodies specific for 3028 were performed as described above for IL-2 induced proliferation with the following exceptions; 2% HSA was omitted from the washing medium and from the PBMC suspension medium. Serum containing culture medium (100 µl/well) was pre-incubated with 20 µg/ml of rabbit antibodies for 30 min at room temperature before the addition of 100 µl PBMC suspension to the culture wells.

Figure 22A:
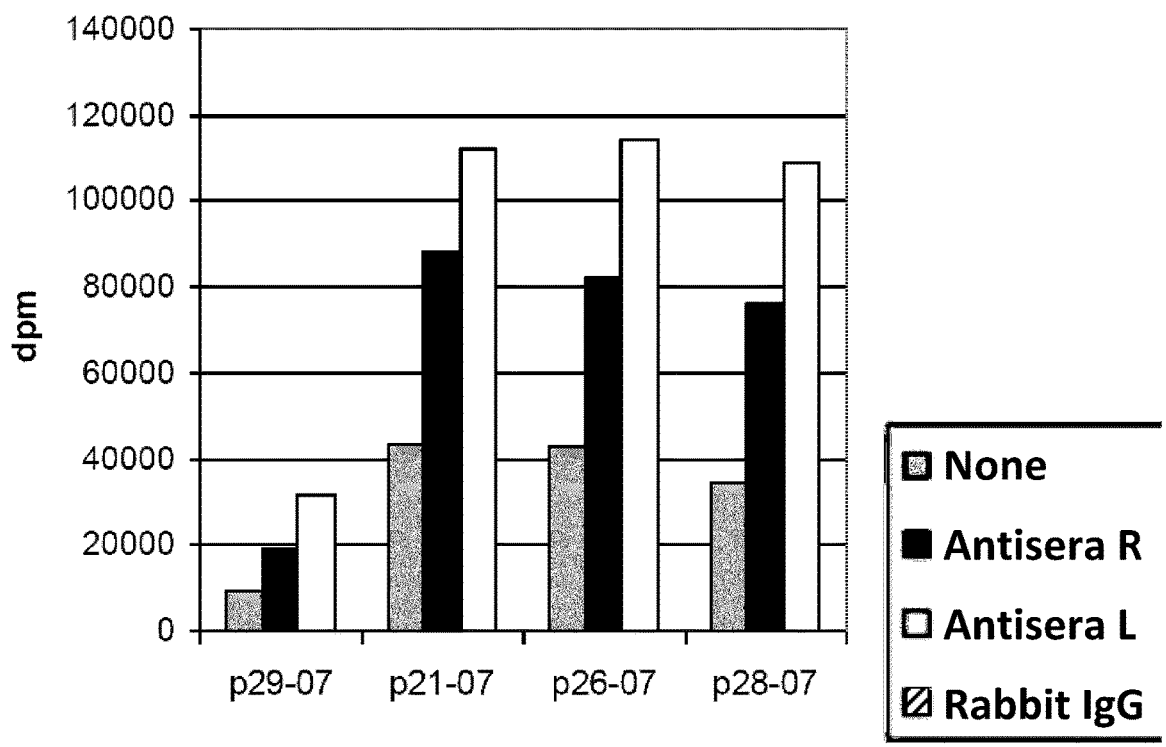
FIG. 22 illustrates effect of affinity purified antibodies directed against P3028 on the proliferative response to IL-2 of PBMCs from immunosuppressed cancer patients (FIG. 22A) and normal control samples (FIG. 22B).
Figure 22B:
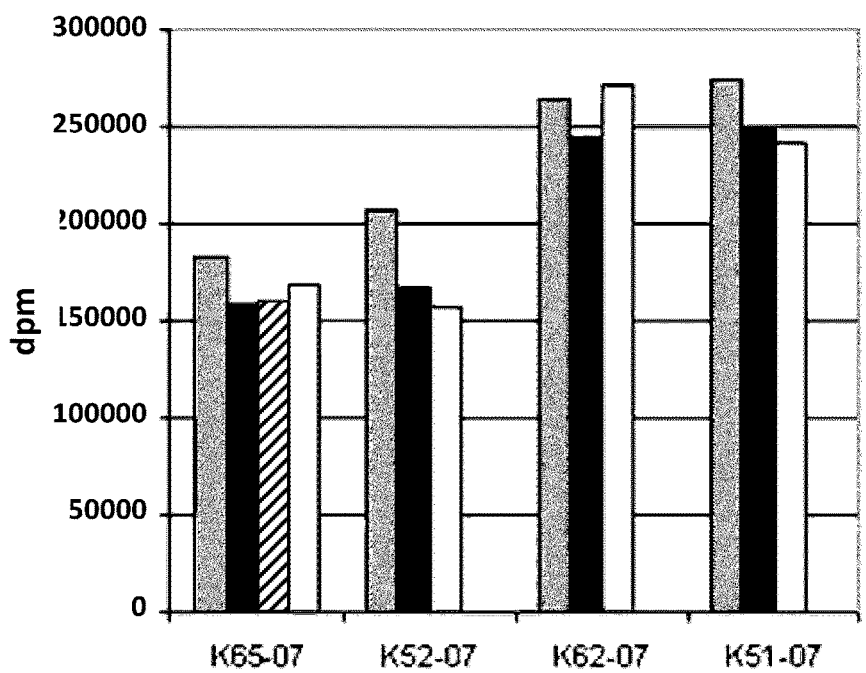

P21 had renal cell carcinoma and p26, p28 and p29 had malignant melanoma. As shown in FIG. 22, affinity-purified rabbit antibodies against P3028 overcame inhibition of the proliferative response to IL-2 in immunosuppressed cancer patients (FIG. 22A). In normal control samples with normal proliferative response to IL-2, no effect of addition of these antibodies was seen (see FIG. 22B) (antibody: R., cancer patients, p=0.0002, paired t-test, normal transformation log-values). In normal control samples with down-regulation of the immune reactivity having a proliferative rate of less than 100,000 dpm, the proliferative rate was stimulated similar to the situation in cultures from cancer patients.

Polyclonal rabbit IgG was added to control sample cultures in order to make sure that the effect of the affinity purified antibodies was not due to an unspecific activity of rabbit IgG in this model. Rabbit IgG had only minimal activity. The specificity of the anti-P3028 antibodies was further demonstrated as the stimulatory effect of these antibodies was neutralized by a small amount of P3028 having no inhibitory activity per se. Similar to the results in the autologous ex vivo model, the immunosuppressor activity of sera from persons with a low proliferative response to IL-2 was over-come by addition of the anti-P3028 antibodies to the cultures.

Example 10: Peptides that Bind to P3028

The information obtained by studying the effect of cancer patient sera and the synthetic peptide P3028, on staining of the α-chain, CD11a, of LFA-1 on PBMCs was used in order to design the structure of a potential binder/inhibitor of the immunomodulatory peptide P3028. The epitope of the particular monoclonal mouse antibody used, HI 111, was mapped to residues 249-300 of CD11a (Ma Q, et al., J Biol Chem. 2002; 277:10638-41). Based on complementarity of charged and hydrophobic amino acid sequences the first candidate binding to the P3028 peptide was designed. This sequence was then optimized by synthesizing and testing the binding efficacy of candidate peptides where each amino acid was substituted for all 19 L-amino acids.

Three candidate peptide inhibitors of P3028 sequences/ structures were identified and their blocking capacity in solution was tested. Potential peptide inhibitors of P3028 were synthesized on a chip. The linear and/or CLIPS peptides were synthesized based on the amino acid sequence of the target protein using standard Fmoc-chemistry and deprotected using trifluoric acid with scavengers. The constrained peptides were synthesized on chemical scaffolds in order to reconstruct conformational epitopes, using Chemically Linked Peptides on Scaffolds (CLIPS) technology (Timmerman et al. (2007)). For example, the single looped peptides were synthesized containing a dicysteine, which was cyclized by treating with alpha, alpha'-dibromoxylene and the size of the loop is varied by introducing cysteine residues at variable spacing. If other cysteines besides the newly introduced cysteines are present, they were replaced by alanine. The side-chains of the multiple cysteines in the peptides are coupled to CLIPS templates by reacting onto credit-card format polypropylene PEPSCAN cards (455 peptide formats/card) with a 0.5 mM solution of CLIPS template such as 1,3-bis (bromomethyl) benzene in ammonium bicarbonate (20 mM, pH 7.9)/acetonitrile (1:1 (v/v)). The cards were gently shaken in the solution for 30 to 60 minutes while completely covered in solution. Finally, the cards are washed extensively with excess of $H_2O$ and sonicated in disrupt-buffer containing 1 percent SDS/0.1 percent beta-mercaptoethanol in PBS (pH 7.2) at 70° C. for 30 minutes, followed by sonication in $H_2O$ for another 45 minutes. The binding of His-tagged P3028 to each peptide was tested in a PEPSCAN-based ELISA. The 455-well credit card format polypropylene cards containing the covalently linked peptides are incubated with peptide solution for example consisting of 1 micrograms/mL diluted in blocking solution, for example 4% horse serum, 5% ovalbumin (w/v) in PBS/1% Tween. After washing, the peptides were incubated with a monoclonal mouse anti-his tag antibody (1/1000, Novagen®, 70796-3) and subsequently after washing with a rabbit-anti-mouse antibody peroxidase conjugate (1/1000, Southern Biotech®, 6175-05) for one hour at 25° C. After washing, the peroxidase substrate 2,2'-azino-di-3-ethylbenzthiazoline sulfonate (ABTS) and 2 microlitres of 3 percent $H_2O_2$ were added. After one hour, the color development was measured. The color development was quantified with a charge coupled device (CCD)—camera and an image processing system.

The raw data (Raw Data: Optical density, Arbitrary OD units) are optical values obtained by a CCD-camera. The values mostly range from 0 to 3000, a log scale similar to 1 to 3 of a standard 96-well plate ELISA-reader. First the CCD-camera makes a picture of the card before peroxidase coloring and then again a picture after the peroxidase coloring. These two pictures are subtracted from each other which results in the data which is called raw-data. This is copied into the Peplab™ database. Then the values are copied to excel and this file is labeled as raw-data file. One follow-up manipulation is allowed. Sometimes a well contains an air-bubble resulting in a false-positive value, the cards are manually inspected and any values caused by an air-bubble are scored as 0.

As shown in Position 17, 22 and 26 contained good binders of P3028 (PGE73=His-tag-P3028). As shown in the diagram, peptide SCF28 and SCF29 efficiently block the binding of P3028 (PGE73) but SCF27 does not. Peptide SCF28 (SEQ ID NO: 1), had a solubility good enough to allow testing in biological human ex vivo models. Based on this structure, peptide P28R (SEQ ID NO: 2) was developed. For each position, shown are data for no peptide added assay in PBS buffer 230, SCF027 assay in PBS buffer 232, SCF029 assay in PBS buffer+10% DMSO 234, no peptide added in PBS buffer+10% DMSO 236, and SCF028 assay in PBS buffer+10 DMSO 238. In the bar graph of FIG. 23, bars representing each assay were in the same left-to-right order for each position. Each peptide, when present in an assay, was at a concentration of 0.5 mg/mL.

Example 11: Peptide Interactions with P3028

The information obtained by studying the effect of cancer patient sera and the synthetic peptide P3028, on staining of the alpha-chain, CD11a (SEQ ID NO: 248), of LFA-1 on PBMCs was used in order to design the structure of a potential binder/inhibitor of the immunoinhibitory peptide P3028. The epitope of the particular monoclonal mouse antibody used, HIM, was mapped to residues 274-325 of CD11a, (SEQ ID NO: 248) (UniProt accession code P20701; Ma Q, et al., J Biol Chem. 2002; 277: 10638-41). Based on complementarity of charged and hydrophobic amino acid sequences (see FIG. 31) the first candidate binding to the P3028 peptide was designed using the sequence comprising 312-326 of CD11a. This resulted in the peptide KKL15 (SEQ ID NO: 1).

Peptide KKL15 (SEQ ID NO: 1), for example appears to be complementary to P3028. As shown in FIG. 31, positively charged amino acids interact with negatively charged amino acids of P3028 and hydrophobic amino acids make hydrophobic contacts enhancing the interaction.

Example 12: Peptides that Bind to P3028

Based on the structure of peptide P28R, additional peptides were identified that bind to P3028. The additional binders included deletions, truncations, and or amino acid substitutions of peptide P28R. Binding of peptides to P3028 was assayed using PEPSCAN technology. PEPSCAN technology, or "rampo" assays are biochemical binding assays, details of which are provided below:

A peptide microarray screening technology was used to measure binding of P28R (SEQ ID NO: 2) and variants of P28R to P3028 (SEQ ID NO: 185). In this technology libraries of synthetic peptides are synthesized and covalently linked onto polypropylene microarray chips. The linear peptides were synthesized onto credit-card format polypropylene cards (455 peptide formats/card) as described by (Timmerman et al., 2004) using standard Fmoc-chemistry using hexamethylenediamine (HMDA) as linker and deprotection using trifluoroacetic acid (TFA) with scavengers.

The binding of His-tagged P3028 to each peptide on the card was tested in an ELISA assay. The 455-well credit card format polypropylene cards containing the covalently linked peptides were incubated with His-tagged P3028 peptide (PGE73) solution consisting of 0.5 μg/mL diluted in blocking solution (4% horse serum, 5% ovalbumin (w/v) in PBS/1% Tween). After washing, the peptides were incubated with a monoclonal mouse anti-His-tag antibody (Novagen®, 70796-3, diluted 1/1000 in the incubation buffer) and subsequently after washing with a rabbit-anti-mouse antibody peroxidase (Rampo) conjugate (Southern Biotech®, 6175-05, diluted 1/1000), for one hour at 25° C. After washing, the peroxidase substrate 2,2'-azine-di-3-ethylbenzthiazoline sulfonate (ABTS) and 2 µL of 3% $H_2O_2$ were added. The binding capacity of the mAb was measured as a color development at 405 nm (optical density, OD405). The color development was quantified with a charge-coupled device (CCD)—camera and an image processing system.

The OD405-values obtained by a CCD-camera was considered as raw data values ("rampo values," "rampo units," or "rampo scores"). The values mostly ranged from 0 to 3000, a log scale similar to 1 to 3 of a standard 96-well plate ELISA-reader. First the CCD-camera made a picture of the card before peroxidase coloring and then again a picture after the peroxidase coloring. These two pictures were subtracted from each other, which resulted in the data which was considered raw data. These values were copied into an excel file and labeled as a raw data file. One follow-up manipulation was allowed. Sometimes a well can contain an air-bubble resulting in a false-positive value. If manual inspection of the cards detect an air-bubble the value are set to 0 for that well.

A library of peptides tested for binding to peptide P3028 included all substitutions for each position of the peptide P28R (SEQ ID NO: 2) (i.e., 19 substitutions for each position). The results of the binding experiments are shown in FIGS. 27, 28, 29 and 30 and Table 5.1. Rampo scores ranged between 102 and 1190 for all substitutions in each of the 16 positions of P28R. P28R had rampo values ranging between 262 and 460 with a mean value of 370. As shown in FIG. 28, 31 single-amino acid substitutions of the peptide P28R (SEQ ID NO: 2) had a rampo score above 500. These 31 substituted peptides include SEQ ID NOs: 3-31, and are shown in Table 6.1. Significant higher values were observed for the substitutions M, Q, H, N in position 13 (SEQ ID NOs: 22 to 25, respectively), all with values above 800. In addition, M and S in position 7 (SEQ ID NOs: 9 and 10, respectively), and Q and M in position 11 (SEQ ID NOs: 15 and 16, respectively) all have rampo values over 700.

TABLE 6.1

Peptides that bind to P3028 with a rampo score above 500

| SEQ ID NO | Sequence |
| --- | --- |
| 3 | RKLDTFFVKLSLFTER |
| 4 | KKGDTFFVKLSLFTER |
| 5 | KKEDTFFVKLSLFTER |
| 6 | KKLDQFFVKLSLFTER |
| 7 | KKLDTAFVKLSLFTER |
| 8 | KKLDTVFVKLSLFTER |
| 9 | KKLDTFMVKLSLFTER |
| 10 | KKLDTFSVKLSLFTER |
| 11 | KKLDTFVVKLSLFTER |
| 12 | KKLDTFTVKLSLFTER |
| 13 | KKLDTFLVKLSLFTER |
| 14 | KKLDTFFVKVSLFTER |
| 15 | KKLDTFFVKLQLFTER |

TABLE 6.1-continued

Peptides that bind to P3028 with a rampo score above 500

| SEQ ID NO | Sequence |
| --- | --- |
| 16 | KKLDTFFVKLMLFTER |
| 17 | KKLDTFFVKLTLFTER |
| 18 | KKLDTFFVKLHLFTER |
| 19 | KKLDTFFVKLSQFTER |
| 20 | KKLDTFFVKLSVFTER |
| 21 | KKLDTFFVKLSMFTER |
| 22 | KKLDTFFVKLSLMTER |
| 23 | KKLDTFFVKLSLQTER |
| 24 | KKLDTFFVKLSLHTER |
| 25 | KKLDTFFVKLSLNTER |
| 26 | KKLDTFFVKLSLPTER |
| 27 | KKLDTFFVKLSLSTER |
| 28 | KKLDTFFVKLSLGTER |
| 29 | KKLDTFFVKLSLATER |
| 30 | KKLDTFFVKLSLRTER |
| 31 | KKLDTFFVKLSLFNER |
| 32 | KKLDTFFVKLSLFPER |
| 33 | KKLDTFFVKLSLFRER |

For each position of P28R, the rampo scores of the group of 19 different peptides containing an L-amino acid substitution were compared to the rampo score of a control sample P28R peptide (SEQ ID NO: 2) for that group. Single-amino acid substitutions having a rampo score greater than or substantially equivalent to P28R were identified. As used herein, a rampo score "substantially equivalent to P28R" is a rampo score that is at least 98% of the rampo score of P28R. Thus, variants of P28R having equivalent or better binding to P3028 were identified.

For example, at position 8 of P28R (SEQ ID NO: 2) is a V. The control sample P28R peptide had a rampo score of 308, and peptides having an F, G, L, P or R at position 8 (SEQ ID NOs: 326-330, respectively) each had a rampo score greater than or equal to 302 (98% of 308). The single amino acid substitutions of P28R having a score greater than or equal to that of the P28R control sample peptide for that group are shown in Table 6.2.

TABLE 6.2

Peptides that bind to a rampo score greater than or substantially equivalent to that of P28R

| SEQ ID NO | Position | Sequence | Rampo Score | Rampo score of P28R control sample |
| --- | --- | --- | --- | --- |
| 268 | 1 | AKLDTFFVKLSLFTER | 466 | 308 |
| 269 | 1 | DKLDTFFVKLSLFTER | 373 | 308 |

TABLE 6.2-continued

Peptides that bind to a rampo score greater than or substantially equivalent to that of P28R

| SEQ ID NO | Position | Sequence | Rampo Score | Rampo score of P28R control sample |
|---|---|---|---|---|
| 270 | 1 | EKLDTFFVKLSLFTER | 396 | 308 |
| 271 | 1 | GKLDTFFVKLSLFTER | 367 | 308 |
| 272 | 1 | HKLDTFFVKLSLFTER | 428 | 308 |
| 273 | 1 | IKLDTFFVKLSLFTER | 483 | 308 |
| 274 | 1 | LKLDTFFVKLSLFTER | 449 | 308 |
| 275 | 1 | MKLDTFFVKLSLFTER | 457 | 308 |
| 276 | 1 | NKLDTFFVKLSLFTER | 445 | 308 |
| 277 | 1 | PKLDTFFVKLSLFTER | 387 | 308 |
| 278 | 1 | QKLDTFFVKLSLFTER | 455 | 308 |
| 279 | 1 | RKLDTFFVKLSLFTER | 523 | 308 |
| 280 | 1 | TKLDTFFVKLSLFTER | 493 | 308 |
| 281 | 1 | VKLDTFFVKLSLFTER | 442 | 308 |
| 282 | 3 | KKADTFFVKLSLFTER | 427 | 375 |
| 283 | 3 | KKCDTFFVKLSLFTER | 432 | 375 |
| 284 | 3 | KKDDTFFVKLSLFTER | 492 | 375 |
| 285 | 3 | KKEDTFFVKLSLFTER | 528 | 375 |
| 286 | 3 | KKFDTFFVKLSLFTER | 393 | 375 |
| 287 | 3 | KKGDTFFVKLSLFTER | 563 | 375 |
| 288 | 3 | KKHDTFFVKLSLFTER | 477 | 375 |
| 289 | 3 | KKIDTFFVKLSLFTER | 454 | 375 |
| 290 | 3 | KKKDTFFVKLSLFTER | 386 | 375 |
| 291 | 3 | KKMDTFFVKLSLFTER | 460 | 375 |
| 292 | 3 | KKNDTFFVKLSLFTER | 374 | 375 |
| 293 | 3 | KKQDTFFVKLSLFTER | 473 | 375 |
| 294 | 3 | KKRDTFFVKLSLFTER | 370 | 375 |
| 295 | 3 | KKSDTFFVKLSLFTER | 393 | 375 |
| 296 | 3 | KKTDTFFVKLSLFTER | 451 | 375 |
| 297 | 3 | KKVDTFFVKLSLFTER | 377 | 375 |
| 298 | 4 | KKLATFFVKLSLFTER | 494 | 414 |
| 299 | 4 | KKLETFFVKLSLFTER | 417 | 414 |
| 300 | 4 | KKLITFFVKLSLFTER | 430 | 414 |
| 301 | 4 | KKLVTFFVKLSLFTER | 424 | 414 |
| 302 | 4 | KKLWTFFVKLSLFTER | 443 | 414 |
| 303 | 4 | KKLYTFFVKLSLFTER | 422 | 414 |
| 304 | 5 | KKLDCFFVKLSLFTER | 449 | 424 |
| 305 | 5 | KKLDMFFVKLSLFTER | 475 | 424 |
| 306 | 5 | KKLDNFFVKLSLFTER | 436 | 424 |
| 307 | 5 | KKLDPFFVKLSLFTER | 427 | 424 |
| 308 | 5 | KKLDQFFVKLSLFTER | 535 | 424 |
| 309 | 5 | KKLDRFFVKLSLFTER | 430 | 424 |
| 310 | 5 | KKLDSFFVKLSLFTER | 458 | 424 |
| 311 | 5 | KKLDWFFVKLSLFTER | 418 | 424 |
| 312 | 5 | KKLDYFFVKLSLFTER | 425 | 424 |
| 313 | 6 | KKLDTAFVKLSLFTER | 575 | 437 |
| 314 | 6 | KKLDTIFVKLSLFTER | 466 | 437 |
| 315 | 6 | KKLDTMFVKLSLFTER | 467 | 437 |
| 316 | 6 | KKLDTNFVKLSLFTER | 446 | 437 |
| 317 | 6 | KKLDTPFVKLSLFTER | 497 | 437 |
| 318 | 6 | KKLDTTFVKLSLFTER | 481 | 437 |
| 319 | 6 | KKLDTVFVKLSLFTER | 547 | 437 |
| 320 | 7 | KKLDTFLVKLSLFTER | 517 | 460 |
| 321 | 7 | KKLDTFMVKLSLFTER | 712 | 460 |
| 322 | 7 | KKLDTFQVKLSLFTER | 511 | 460 |
| 323 | 7 | KKLDTFSVKLSLFTER | 700 | 460 |
| 324 | 7 | KKLDTFTVKLSLFTER | 517 | 460 |
| 325 | 7 | KKLDTFVVKLSLFTER | 527 | 460 |
| 326 | 8 | KKLDTFFFKLSLFTER | 358 | 308 |
| 327 | 8 | KKLDTFFGKLSLFTER | 379 | 308 |
| 328 | 8 | KKLDTFFLKLSLFTER | 411 | 308 |
| 329 | 8 | KKLDTFFPKLSLFTER | 456 | 308 |
| 330 | 8 | KKLDTFFRKLSLFTER | 365 | 308 |
| 331 | 9 | KKLDTFFVRLSLFTER | 374 | 377 |
| 332 | 10 | KKLDTFFVKASLFTER | 426 | 348 |
| 333 | 10 | KKLDTFFVKFSLFTER | 403 | 348 |
| 334 | 10 | KKLDTFFVKGSLFTER | 495 | 348 |
| 335 | 10 | KKLDTFFVKISLFTER | 415 | 348 |
| 336 | 10 | KKLDTFFVKMSLFTER | 460 | 348 |
| 337 | 10 | KKLDTFFVKNSLFTER | 365 | 348 |
| 338 | 10 | KKLDTFFVKPSLFTER | 436 | 348 |
| 339 | 10 | KKLDTFFVKQSLFTER | 470 | 348 |
| 340 | 10 | KKLDTFFVKRSLFTER | 439 | 348 |
| 341 | 10 | KKLDTFFVKSSLFTER | 351 | 348 |
| 342 | 10 | KKLDTFFVKTSLFTER | 399 | 348 |

TABLE 6.2-continued

Peptides that bind to a rampo score greater than or substantially equivalent to that of P28R

| SEQ ID NO | Position | Sequence | Rampo Score | Rampo score of P28R control sample |
|---|---|---|---|---|
| 343 | 10 | KKLDTFFVKVSLFTER | 658 | 348 |
| 344 | 10 | KKLDTFFVKYSLFTER | 382 | 348 |
| 345 | 11 | KKLDTFFVKLHLFTER | 535 | 442 |
| 346 | 11 | KKLDTFFVKLMLFTER | 744 | 442 |
| 347 | 11 | KKLDTFFVKLNLFTER | 451 | 442 |
| 348 | 11 | KKLDTFFVKLQLFTER | 768 | 442 |
| 349 | 11 | KKLDTFFVKLTLFTER | 520 | 442 |
| 350 | 12 | KKLDTFFVKLSAFTER | 462 | 428 |
| 351 | 12 | KKLDTFFVKLSHFTER | 460 | 428 |
| 352 | 12 | KKLDTFFVKLSIFTER | 456 | 428 |
| 353 | 12 | KKLDTFFVKLSMFTER | 499 | 428 |
| 354 | 12 | KKLDTFFVKLSNFTER | 462 | 428 |
| 355 | 12 | KKLDTFFVKLSQFTER | 651 | 428 |
| 356 | 12 | KKLDTFFVKLSRFTER | 483 | 428 |
| 357 | 12 | KKLDTFFVKLSSFTER | 478 | 428 |
| 358 | 12 | KKLDTFFVKLSTFTER | 437 | 428 |
| 359 | 12 | KKLDTFFVKLSVFTER | 545 | 428 |
| 360 | 12 | KKLDTFFVKLSWFTER | 409 | 428 |
| 361 | 13 | KKLDTFFVKLSLATER | 525 | 402 |
| 362 | 13 | KKLDTFFVKLSLCTER | 400 | 402 |
| 363 | 13 | KKLDTFFVKLSLGTER | 531 | 402 |
| 364 | 13 | KKLDTFFVKLSLHTER | 1046 | 402 |
| 365 | 13 | KKLDTFFVKLSLITER | 468 | 402 |
| 366 | 13 | KKLDTFFVKLSLLTER | 448 | 402 |
| 367 | 13 | KKLDTFFVKLSLMTER | 1190 | 402 |
| 368 | 13 | KKLDTFFVKLSLNTER | 862 | 402 |
| 369 | 13 | KKLDTFFVKLSLPTER | 696 | 402 |
| 370 | 13 | KKLDTFFVKLSLQTER | 1144 | 402 |
| 371 | 13 | KKLDTFFVKLSLRTER | 502 | 402 |
| 372 | 13 | KKLDTFFVKLSLSTER | 635 | 402 |
| 373 | 13 | KKLDTFFVKLSLTTER | 494 | 402 |
| 374 | 13 | KKLDTFFVKLSLVTER | 446 | 402 |
| 375 | 13 | KKLDTFFVKLSLWTER | 430 | 402 |
| 376 | 14 | KKLDTFFVKLSLFFER | 348 | 319 |
| 377 | 14 | KKLDTFFVKLSLFGER | 343 | 319 |
| 378 | 14 | KKLDTFFVKLSLFHER | 463 | 319 |
| 379 | 14 | KKLDTFFVKLSLFIER | 375 | 319 |
| 380 | 14 | KKLDTFFVKLSLFLER | 360 | 319 |
| 381 | 14 | KKLDTFFVKLSLFMER | 501 | 319 |
| 382 | 14 | KKLDTFFVKLSLFNER | 599 | 319 |
| 383 | 14 | KKLDTFFVKLSLFPER | 551 | 319 |
| 384 | 14 | KKLDTFFVKLSLFSER | 369 | 319 |
| 385 | 14 | KKLDTFFVKLSLFVER | 380 | 319 |
| 386 | 14 | KKLDTFFVKLSLFWER | 374 | 319 |
| 387 | 15 | KKLDTFFVKLSLFTDR | 404 | 371 |
| 388 | 16 | KKLDTFFVKLSLFTEF | 297 | 260 |
| 389 | 16 | KKLDTFFVKLSLFTEK | 291 | 260 |
| 390 | 16 | KKLDTFFVKLSLFTEN | 311 | 260 |
| 391 | 16 | KKLDTFFVKLSLFTER | 260 | 260 |
| 392 | 16 | KKLDTFFVKLSLFTET | 292 | 260 |
| 393 | 16 | KKLDTFFVKLSLFTEY | 311 | 260 |

The positional substitutions of P28R in Table 6.2, (SEQ ID NOs: 268-393) are summarized in FIG. 32. It is noted that positions 2 (K), 9 (K) and 15 (E) tolerate relatively few substitutions while still binding to P3028. Substitution of the residue at positions 2, 9, and/or 15 of P28R can result in binding to P3028 (as measured by rampo scores) substantially lower than unsubstituted P28R. Thus, it is contemplated herein that these 3 positions appear to modulate signal transduction. One skilled in the art will appreciate that signal transduction modulatory activity of these positions can be useful in designing inhibitors of immunomodulatory peptides.

Figure 29:
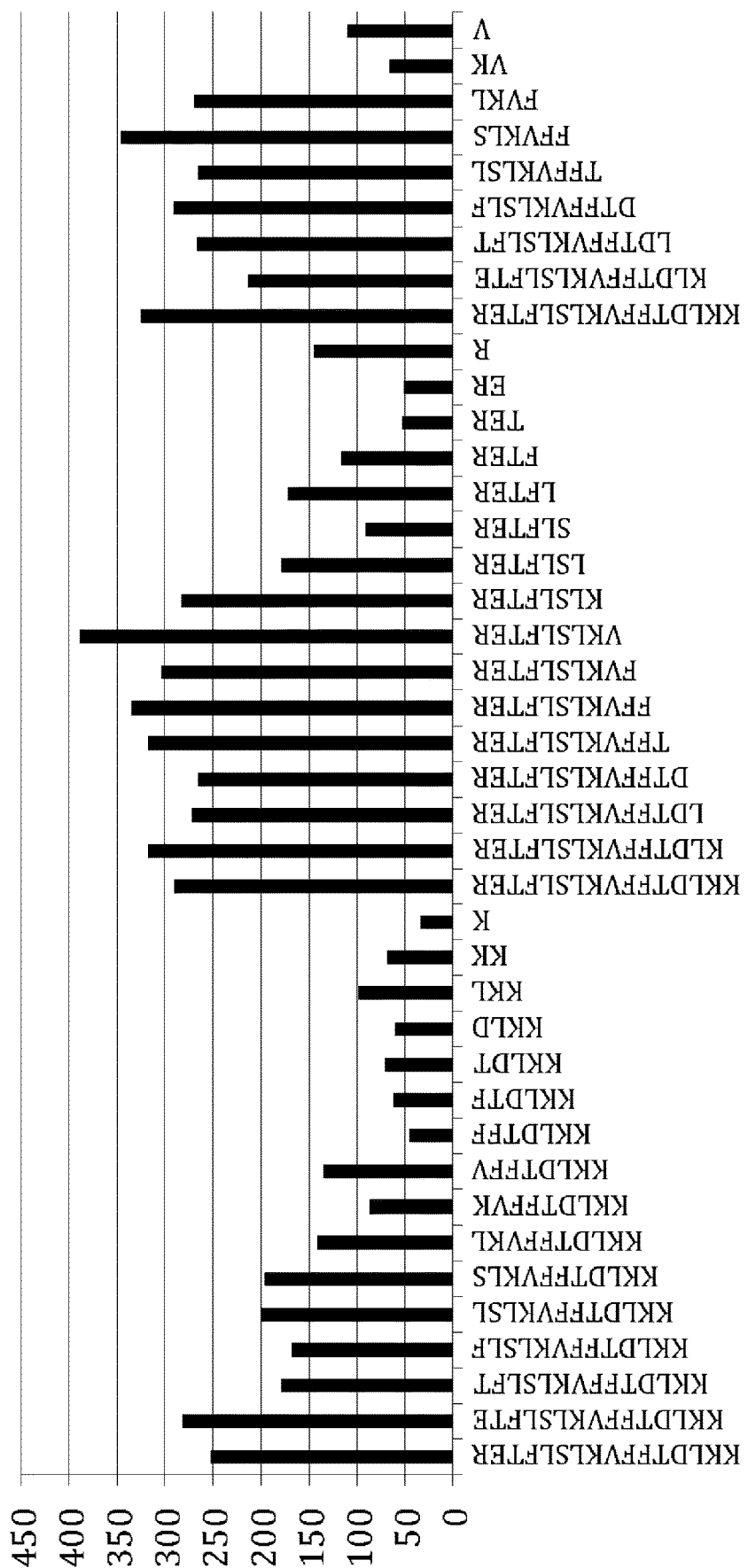
FIG. 29 illustrates rampo scores for binding of P3028 to P28R and N-terminal and/or C-terminal truncations of peptide P28R.

PEPSCAN analysis was also performed on truncations and internal deletions of peptide P28R. Shown in FIG. 29 are rampo scores for peptides having the sequences KKLDTFFVKLSLFTER (SEQ ID NO: 2); KKLDTFFVKLSLFTE (SEQ ID NO 34); KKLDTFFVKLSLFT (SEQ ID NO: 35); KKLDTFFVKLSLF (SEQ ID NO 36); KKLDTFFVKLSL (SEQ ID NO: 37); KKLDTFFVKLS (SEQ ID NO: 38); KKLDTFFVKL (SEQ ID NO: 39); KKLDTFFVK (SEQ ID NO: 40); KKLDTFFV (SEQ ID NO: 41); KKLDTFF (SEQ ID NO: 42); KKLDTF (SEQ ID NO: 43); KKLDT (SEQ ID NO: 44); KKLD (SEQ ID NO: 45); KLDTFFVKLSLFTER (SEQ ID NO: 46); LDTFFVKLSLFTER (SEQ ID NO: 47); DTFFVKLSLFTER (SEQ ID NO: 48); TFFVKLSLFTER (SEQ ID NO: 49); FFVKLSLFTER (SEQ ID NO: 50); FVKLSLFTER (SEQ ID NO:51); VKLSLFTER (SEQ ID NO: 52); KLSLFTER (SEQ ID NO: 53); LSLFTER (SEQ ID NO: 54); SLFTER (SEQ ID NO: 55); LFTER (SEQ ID NO: 56); FTER (SEQ ID NO: 57); KLDTFFVKLSLFTE (SEQ ID NO: 58); LDTFFVKLSLFT (SEQ ID NO: 59); DTFFKLSLF (SEQ ID NO: 60); TFFVKLSL (SEQ ID NO: 61); FFVKLS (SEQ ID NO: 62); FVKL (SEQ ID NO: 63).

Figure 30A:
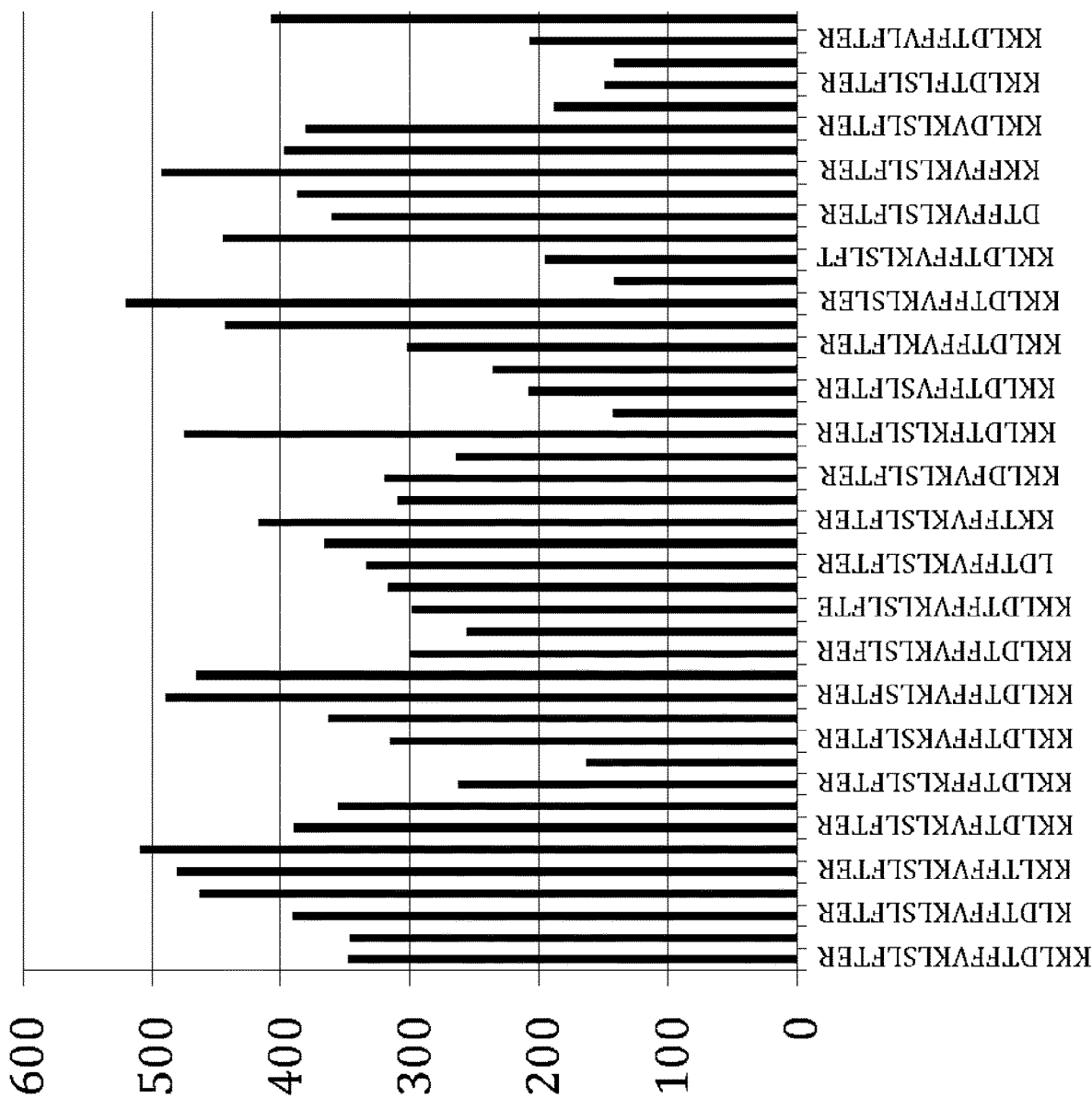
FIGS. 30A and 30B represent the left and right sides, respectively, of a single graph that was enlarged to show the text more clearly. For reference, the Y axis has been reproduced in FIG. 30B.
Figure 30B:
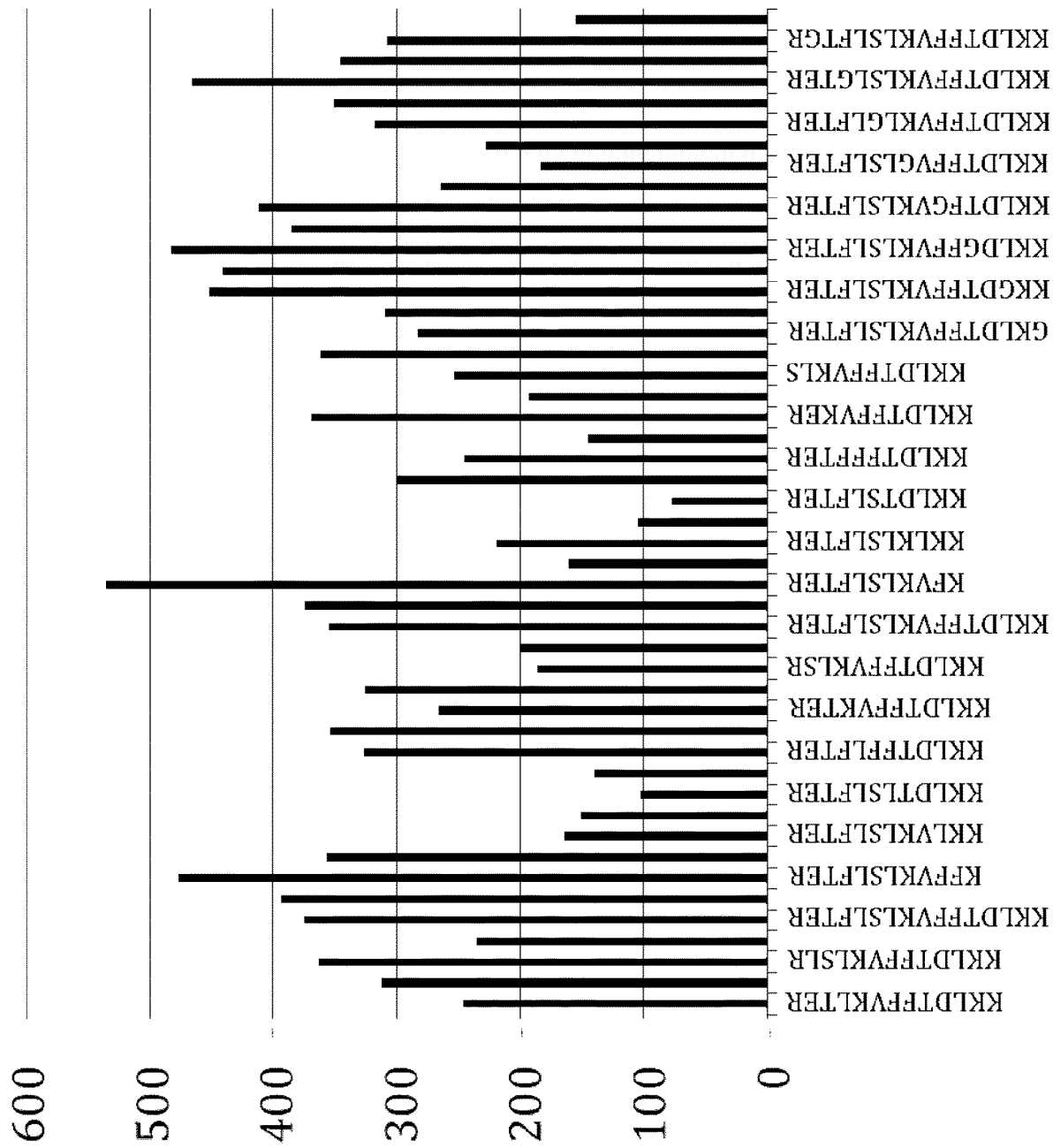

Shown in FIG. 30 are rampo scores for peptides having the sequences KKLDTFFVKLSLFTER (SEQ ID NO: 2); KLDTFFVKLSLFTER (SEQ ID NO: 46); KKLTFFVKLSLFTER (SEQ ID NO: 64); KKLDTFVKLSLFTER (SEQ ID NO: 65); KKLDTFFKLSLFTER (SEQ ID NO: 66); KKLDTFFVKSLFTER (SEQ ID NO: 67); KKLDTFFVKLSFTER (SEQ ID NO: 68); KLDTFFVKLSLFER (SEQ ID NO: 69); KLDTFFVKLSLFTE (SEQ ID NO: 58); LDTFFVKLSLFTER (SEQ ID NO: 47); KKTFFVKLSLFTER (SEQ ID NO: 70); KKLDFVKLSLFTER (SEQ ID NO: 71); KKLDTEKLSLFTER (SEQ ID NO: 72); KKLDTFFVSLFTER (SEQ ID NO:73); KKLDTFFVKLFTER (SEQ ID NO: 74); KKLDTFFVKLSLER (SEQ ID NO: 75); LDTFFVKLSLFT (SEQ ID NO: 59); DTFFVKLSLFTER (SEQ ID NO: 48); KKFFVKLSLFTER (SEQ ID NO: 76); KKLDVKLSLFTER (SEQ ID NO: 77); KKLDTFLSLFTER (SEQ ID NO: 78); KKLDTFFVLFTER (SEQ ID NO: 79); KKLDTFFVKLTER (SEQ ID NO: 80); KKLDTFFVKLSLR (SEQ ID NO: 81); KFFVKLSLFTER (SEQ ID NO: 82); KKLVKLSLFTER (SEQ ID NO: 83); KKLDTLSLFTER (SEQ ID NO: 84); KKLDTFFLFTER (SEQ ID NO: 85); KKLDTFFVKTER (SEQ ID NO: 86); KKLDTFFVKLSR (SEQ ID NO: 87); KFVKLSLFTER (SEQ ID NO: 88); KKLKLSLFTER (SEQ ID NO: 89); KKLDTSLFTER (SEQ ID NO:90); KKLDTFFFTER (SEQ ID NO: 91); KKLDTFFVKER (SEQ ID NO: 92); KKLDTFFVKLS (SEQ ID NO: 38); GKLDTFFVKLSLFTER (SEQ ID NO: 93); KKGDTFFVKLSLFTER (SEQ ID NO: 94); KKLDGFFVKLSLFTER (SEQ ID NO: 95); KKLDTFGVKLSLFTER (SEQ ID NO: 96); KKLDTFFVGLSLFTER (SEQ ID NO: 97); KKLDTFFVGLSLFTER (SEQ ID NO: 98); KKLDTFFVKLGLFTER (SEQ ID NO: 99); KKLDTFFVKLSLGTER (SEQ ID NO: 100); KKLDTFFVKLSLFTGR (SEQ ID NO: 101).

As shown in FIG. 30, several deletions and truncations of peptide P28R have a rampo score comparable to, or higher than peptide P28R, including peptides of the sequences SEQ ID NOs: 64, 65, 68, and 76. Additionally several glycine substitutions had rampo scores comparable to P28R, including peptides of SEQ ID NOs: 94, 95, 96, 98, and 99. Deleting up to at least 8 amino acids from the N terminal of P28R (SEQ ID NOs: 46 to 53) retained a high affinity to P3028 as measured by rampo score. Deleting the C terminal R of P28R (SEQ ID NO: 34) retained a high affinity to P 3028.

Example 13: Effect of a Low Molecular Weight Inhibitor of P3028 on Lymphocyte Activation Analyses of the inhibitor of P3028, P28R, were performed in human ex vivo models. The stimulatory activity on PBMCs, measured using the MTS or CFSE techniques, were studied in 7 healthy control samples and 7 cancer patients of various diagnoses. Interestingly, even in the absence of other types of stimulation P28R has a significant stimulatory activity in 6 out of 7 cancer patients whereas PBMCs from control samples showed only a weak or no stimulation.

As shown in FIG. 24, stimulatory activity of P28R on suppressed proliferative response to IL-2. PBMCs were cultured for 7 days with IL-2 and the proliferative rate was determined as incorporation of BrdU. Each bar represents mean value of triplets. Similar to the studies on the efficacy of antibodies (see FIG. 22) directed against P3028 to reverse cancer related immunosuppression determined as a poor proliferative response of PBMCs from cancer patients to IL-2, the efficacy of the low molecular weight inhibitor P28R on reversal of suppressed IL-2 induced proliferation was investigated. The results of cultures of PBMCs from four different treatment naïve patients are shown in FIG. 24. For each quantity of added P28R, IL-2 stimulated cells 240 are shown in the left, and unstimulated 242 are shown on the right. PBMCs with a low initial proliferation (see FIGS. 24A and 24B) were markedly stimulated by P28R whereas a high initial proliferation was essentially unaffected by the drug (see FIGS. 24C and 24D). As expected, systemic immunosuppression was not present in all patients and only those with immunosuppression were stimulated.

Figure 25:
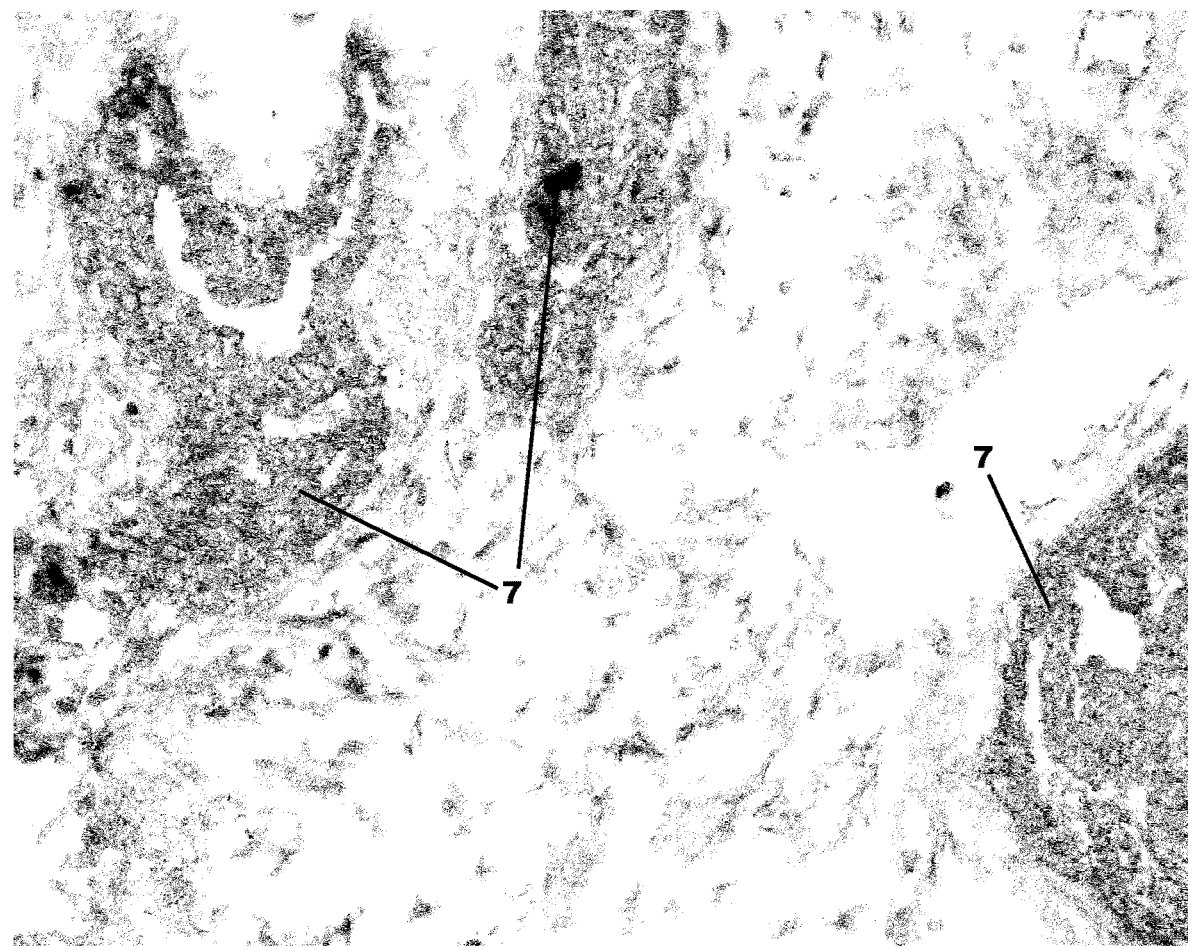
FIG. 25 illustrates binding of biotinylated P28R to a fresh frozen breast cancer tumor.

Example 14: Binding of a Low Molecular Weight Inhibitor of P3028 to Tumor Cells As demonstrated herein, P3028 structures are present in tumors. A biotinylated inhibitor of P3028, P28R, was used to further study the distribution of 3028 structures and the binding of the inhibitor in tumor tissue. Three breast cancers, two renal cell carcinomas and four malignant melanomas were analyzed. All investigated tumors bound the inhibitor. An example of a stained breast cancer is shown in FIG. 25, and a strong positive reaction 7 is seen indicating the presence of the inhibitory 3028-structure in this tumor. As the P3028-structure inhibits lymphocyte migration as well as cytotoxic activity (described above), an immune mediated attack against positively staining tumor areas can be efficiently suppressed as long as exposed P3028 is not blocked by binding P28R. However, lymphocytes were not stained by this procedure since the P3028 structure was blocked by binding to LFA-1 on these cells.

Example 15: Unblocking the LFA-1 Receptor by P28R

As described herein, β2-integrins play a role in the normal function of the immune system. Also described herein are immunosuppressor mechanisms based on the binding of an endogenous inhibitor, P3028, to the β2-integrin LFA-1. As described in Example 7, the membrane staining of PBMCs from cancer patients is markedly decreased compared to normal control samples. The exposure of LFA-1 could, however, be enhanced by incubating PBMCs from cancer patients with an antibody directed against the inhibitor P3028 (see Example 7 and FIG. 16). Staining for LFA-1 was performed using anti-LFA-1 antibody of Example 7 and a secondary antibody (Ultravision®) followed by development with Fast Red. Fresh frozen tumor sections without any fixation were incubated for 4-20 hours with the drug candidate, P28R before staining for LFA-1 (see FIG. 26B). For comparison, control sample tumor sections were incubated with phosphate buffered saline only (see FIG. 26A).

As is shown in FIG. 26, P28R unblocked LFA-1, and thereby markedly enhanced the functional expression of LFA-1 enabling migration and cytotoxic activity of these cells. Strong LFA-1 staining 3 in P28R-treated cells is contrasted with weak LFA-1 staining 5 in untreated cells. These results show that LFA-1 was unblocked by removal of the P3028 structure by the P28R.

Example 16: Delivery of Immunoregulatory Peptide Inhibitors Via Nanodosing to Cancer Patients Cancer patients with immunosuppression due to the presence of P3028 structures and having subcutaneous melanoma metastases are selected. A micro-dialysis catheter is inserted into one of these metastases after the inflammatory infiltrate has been determined using a fine needle biopsy. The base line: inflammatory infiltrate, cytokine profile and concentration of P3028 structures are determined before infusion of the P3028-specific immunoregulatory peptide inhibitor. Changes of the cytokine profile and concentration of P3028 structures are then determined during and after the infusion. The infusion will continue for 24 or 48 hours and the area supplied by the micro-dialysis catheter will be excised immediately after the infusion and then after one and two weeks in order to study the inflammatory infiltrate and tumor regressive changes. It is expected that the administration of the immunoregulatory peptide inhibitor will reduce the immunosuppression of the cancer patient, as measured, for example, by de-blocking LFA-1, binding P3028 structures, and/or enhancing immune cell recruitment.

Example 17: Albumin Peptide Binders of Cell Surface Molecules

Albumin Fragments that Bind to Cell Surface Molecules

As taught in US Publication No: 2011/0262470 (hereby expressly incorporated by reference in its entirety) some albumin fragments can bind to cell surface molecules. U.S. Publication No: 2011/0262470 reports the identification of serum peptides that bind to Artificial Cell Surface (ACS) columns. The ACS columns were prepared as follows:

First, biotinylated cell surface proteins were prepared. Buffy coats generated from 450 ml blood each were collected from 4 healthy donors. Erythrocytes were removed by sedimentation on 2% dextran T500 solution (Amersham® Pharmacia Biotech AB, Uppsala Sweden) in 0.9% NaCl. Mononuclear cells (PBMC) were then isolated by Ficoll-Paque® Plus (GE® Healthcare BioscienceAB Sweden) density gradient centrifugation. The PBMCs were then suspended in phosphate buffered saline (PBS) containing Ca and Mg (GIBCO) at a concentration of $10\times10^6$/ml. EZ Link® Sulfo-NHS-biotin (Pierce® USA) was added at a final concentration of 0.2 mg/ml and the mixture incubated on a shaker at room temperature for 10 min. Excess biotin was then removed by washing the PBMC in PBS. Biotinylated PBMC were then lysed by adding 1.0 ml ice-cold lysing buffer (50 mM Tris-HCL, pH 7.5, with 0.15 MNaCl, 5 mM MgCl2 containing 100 mM Octyl glucoside and 1 mM Phenylmethylsulfonyl fluoride) per $2\times10^7$ pelleted cells with gentle shaking, then incubated for 30 min. on ice. Debris was removed by centrifugation at 5000×g at 4° C. for 10 min and the supernatants were collected and pooled from all four donors. The lysate was then stored at −70° C. in polypropylene plastic tubes.

To study the absorptions by trypsin-fragment dHSA, affinity columns with biotinylated cell surface proteins from mononuclear cells coupled to streptavidin-sepharose were prepared as follows: 18 ml biotinylated cell lysate in lysate buffer was diluted 1/10 in binding buffer (20 mM NaH2P04, 0.15 M NaCl, pH 7.5). This amount of lysate corresponds to $36\times10^7$ mononuclear cells. It was added to a 1 ml Hitrap® Streptavidin HP affinity column (Amersham® Biosciences). To block possible remaining free biotin, 5 ml of 0.1 M glycine (Sigma®) was added to the column. Unsaturated streptavidin on the column was then reacted with 150 ug biotin (Sigma®) in binding buffer. The column was carefully washed with PBS and stored in PBS with 0.1% NaN3 at 4° C. until use.

To study the absorptions by of ASP-N fragmented dHSA, affinity columns with biotinylated cell surface proteins from mononuclear cells coupled to streptavidin-sepharose were prepared as follows: Biotinylated cell lysate in lysate buffer underwent buffer exchange by dialysis with Spectrapore 4 dialysis tubing (Spectrum Europe, Breda, The Netherlands) in binding buffer (20 mM NaH2P04, 0.15 MNaCl pH 7.5). 27 ml biotinylated cell lysate in binding buffer (corresponding to $54\times10^7$ mononuclear cells) was added to 1.5 ml washed Streptavidin Sepharose HP (Amersham® Biosciences). To block possible remaining free biotin, 25 ml of 0.1 M glycine (Sigma®) was added to the Streptavidin Sepharose. Unsaturated streptavidin was then reacted with 225 ug biotin (Sigma®) in binding buffer. The Streptavidin Sepharose was carefully washed in PBS. One ml of the biotinylated cell lysate coupled Streptavidin Sepharose was then packed in an empty column (Tricorn® Empty High Performance Column, Amersham® Bioscience) and washed with phosphate buffered saline (PBS) containing $Ca^{2+}$ and $Mg^{2+}$ (GIBCO).

Digestion with trypsin or ASP-N was performed as follows. Freeze dried dHSA (0.5 mg) was reconstituted in 25 mM NH4HCO3, pH 8, containing 10 mg sequencing grade modified trypsin (Promega® Corporation, WI) or 2 mg Endoproteinase ASP-N(Sigma®) and incubated at 37° C. overnight. To remove unfragmented albumin and enzyme, the sample was ultra filtered through an Amicon® Ultra 4 (mw cut-off of 5000) or a Centriplus (mw cut-off 10000) centrifugal filter (Millipore® AB, Solna, Sweden). The filtrate, containing fragmented dHSA without enzymes, was collected and diluted with PBS with Ca and Mg (GIBCO).

dHSA was trypsinated, and the mixture of peptides obtained after trypsination was adsorbed by ACS. Two ml of enzyme-fragmented dHSA in PBS, corresponding to a total of 0.2 mg protein, was passaged over the ACS column. The flow-through was collected with consideration taken to void volume and dilution of adsorbed sample by collecting in small portions of 0.2 ml. Thirty microliters of each sample, including a control sample that has not been adsorbed, were dried in a Speed-Vac centrifuge. The binding peptides were identified by comparing adsorbed and unadsorbed peptide solutions using the MALDI TOF mass spectrometry technique. Dried samples were reconstituted in 10 ul of 0.1% TFA. Zip Tip pipette tips (Millipore®, USA) containing C18 reversed-phase media were used for desalting reconstituted samples. For analysis of samples in the mass range 700-3600 Da, one µl of each Zip Tip eluted sample was mixed with 1 µl of a saturated solution of α-cyano-4-hydroxycinamic acid (0.02 mg/ml) in 70% acetonitrile/0.3% trifluoro acetic acid. For the analysis of samples in the mass range 1500-9000 Da, one ul of each Zip Tip eluted sample was mixed with 1 µl of sinapinic acid (3-methoxy-4-hydroxycinnamic acid). 1 µl of the mixture was spotted on the MALDI plate and analysed using MALDI-TOF MS (Voyager-DE PRO, Applied Biosystems®, CA, US). Mass identity search of resulting spectra was performed in the SwissProt or NCBI databases using MS-Fit.

These peptides are shown in Table 7.

TABLE 7

| | Trypsin-generated albumin fragments that bind to ACS | | |
|---|---|---|---|
| SEQ ID NO: | Percent Absorbed | Sequence | Albumin Positions |
| 194 | 71% | KYLYEIAR | 161-168 |
| 195 | 64% | KVPQVSTPTLVEVSR | 438-452 |
| 196 | 60% | VFDEFKPLVEEPQNLIK | 397-413 |

TABLE 7-continued

Trypsin-generated albumin fragments that bind to ACS

| SEQ ID NO: | Percent Absorbed | Sequence | Albumin Positions |
|---|---|---|---|
| 197 | 59% | VPQVSTPTLVEVSR | 439-452 |
| 198 | 42% | RPCFSALEVDETYVPK | 509-524 |
| 199 | 41% | FQNALLVR | 427-434 |
| 200 | 36% | SLHTLFGDK | 89-97 |
| 201 | 36% | LKECCEKPLLEK | 299-310 |
| 202 | 35% | LCTVATLR | 98-105 |
| 203 | 34% | YLYEIAR | 162-168 |
| 204 | 32% | CCAAADPHECYAK | 384-396 |
| 205 | 29% | AAFTECCQAADK | 187-198 |
| 206 | 26% | CCTESLVNR | 500-508 |
| 207 | 25% | QEPERNECFLQHK | 118-130 |
| 208 | 23% | AVMDDFAAFVEK | 570-581 |
| 209 | 22% | NECFLQHK | 123-130 |
| 210 | 20% | ONCELFEQLGEYK | 414-426 |
| 211 | 18% | QEPERNECFLQHK | 118-130 |
| 212 | 13% | VHTECCHGDLLECADDR | 265-281 |
| 213 | 8% | FKDLGEENFK | 35-44 |
| 214 | 3% | YICENQDSISSK | 287-298 |
| 215 | 2% | LDELRDEGK | 206-214 |
| 216 | 1% | DDNPNLPR | 131-138 |

Because the full peptide sequence of albumin is not recovered using the MALDI-TOF technique after trypsin degradation, and because some sequences with the capacity to bind to cell surface receptors of immune cells, might have been degraded by trypsin treatment, dHSA was also degraded by asparaginase (ASN-N), and the mixture of peptides obtained after degradation was adsorbed by ACS. The binding peptides were identified by comparing adsorbed and unadsorbed peptide solutions using the MALDI TOF ms technique. These peptides are shown in Table 8.

TABLE 8

Asp-N-generated albumin fragments that bind to ACS

| SEQ ID NO: | Percent Absorbed | Sequence | Albumin Positions |
|---|---|---|---|
| 217 | 100% | DHVKLVNEVTEFAKTCVA | 62-79 |
| 218 | 100% | DDKETCFAEEGKKLVAASQAALGL | 586-609 |
| 219 | 87% | DRVTKCCTESLVNRRPCFSALEV | 495-517 |
| 220 | 86% | DETYVPKEFNAETFTHA | 518-535 |
| 221 | 65% | DSISSKLKECCEKPLLEKSHCIAEVEN | 293-319 |
| 222 | 65% | DKLCTVATLRETYGEM | 96-112 |
| 223 | 100% | YSVVLLLRLAKTYETTLEKCCAAADPHECYAKVF | 364-398 |
| 224 | 100% | KLCTVATLRETYGEMADCCAKQEPERNECFLQHK | 96-130 |
| 225 | 100% | ICTLSEKERQIKKQTALVELVKHKPKATKEQLKAVM | 536-572 |
| 226 | 100% | LAKYICENQDSISSKLKECCEKPLLEKHCIAEVEN | 283-319 |
| 227 | 100% | VFLGMFLYEYARRHPDYSVVLLLRLAKTYETT LEKCCAAA | 348-388 |
| 228 | 100% | LGEENFKALVLIAFAQYLQQCPFEDHVKLVNEVTEFAKTCVA | 37-79 |
| 229 | 100% | RVTKCCTESLVNRRPCFSALEVDETYVPKEFNAETFTFHA | 495-535 |
| 230 | 37% | YLSVVLNQLCVLHEKTPVSDRVTKCCCTESLVNRRPFSALEV | 475-517 |

Additionally, nine synthetic albumin peptides were synthesized, as shown in Table 9.

TABLE 9

Synthetic albumin peptides

| SEQ ID NO: | Peptide Name | Sequence | Albumin Positions |
|---|---|---|---|
| 183 | 3026 | NEETFLKKYLYEIARRHPYFYAP | 153-176 |
| 184 | 3027 | ELFEQLGEYKFQNALLVR | 417-434 |
| 185 | 3028 | VFDEFKPLVEEPQNLIK | 397-413 |
| 188 | 3029 | KVPQVSTPTLVEVSR | 438-452 |
| 189 | 2604 | KLVNEVTEFAKT | 65-76 |
| 190 | 2605 | NEETFLKKYLYE | 153-168 |
| 191 | 2606 | LDELRDEGKAS | 205-217 |
| 192 | 2607 | EMADCCAKQEPE | 110-122 |
| 193 | 2608 | ELFEQLGEYKF | 417-427 |

Example 18: Albumin Peptide Binders of Cell Surface Molecules

Monoclonal antibody mAb A was shown to have immunomodulatory activity. Structures of the epitope bound by mAb A were further investigated. Briefly, albumin fragments were incubated with antibody, and Matrix-Assisted Laser Desorption/Ionisation Time-of-Flight mass spectrometry (MALDI-TOF ms) were used in order to define the possible site or sites on human serum albumin to which a mouse monoclonal antibody specific for denatured albumin binds. One approach took advantage of the fact that some tryptic peptides to which an antibody is bound will not generate characteristic mass spectra in MALDI as they are "hidden"

from the analysis. Another approach takes advantage of the fact that sites on a protein where an antibody has bound are protected from proteolysis.

Purified human serum albumin (HSA) was denatured with urea, reduced with DTT and alkylated. The denatured HSA was then subjected to trypsin treatment with a low concentration (0.02-2 ng/ml) of trypsin. However, the spectra obtained with MALDI were unsatisfactory, as the peptides masses typical for albumin were not found. Based on gel electrophoresis this preparation (digested by 0.02 ng/ml of trypsin) was found to contain substantial amounts of undigested albumin. Therefore, trypsin digestion was continued, at a higher concentration (5 ug/ml) in order to obtain the mass spectra usually used for identification of proteins by MALDI.

To identify albumin fragments bound by mAb A, some of the now completely cleaved albumin solution was incubated with the mAb A. MALDI-TOF ms was performed and spectra of enzyme-treated denatured albumin obtained in the presence or absence of mAb A were compared. Fourteen albumin (SEQ ID NOs: 231-244) massed were absent or reduced after incubation with mAb A. The amino acid sequence of these peptides is shown in Table 10. The spectra represent multiple areas encompassing residues 66 to 508 of the albumin molecule.

In order to further confirm these results the monoclonal antibody mAb A was allowed to bind to the denatured albumin (previously digested by trypsin at a concentration of 0.02 ng/ml) in order to protect the peptide sequences of the epitope. The complex was then again treated with trypsin. MALDI-TOF ms was then performed and the peptide mass spectra generated from albumin were compared with spectra generated from denatured albumin trypsin-treated in the absence of antibody. The same fourteen masses out of 39 albumin masses disappeared completely or were significantly reduced in the sample were the mAb was present during trypsin treatment (see Table 10, Column 6). Multiple readings were taken to verify the results.

TABLE 10

Albumin peptides that bind to monoclonal antibody mAb A

| SEQ ID NO: Sequence | Albumin Positions | Peak area before Ab incub. (2 spectra) | Peak area after Ab incub. (5 spectra) | Peak area trypsiniated Albumin + Ab (6 spectra) |
|---|---|---|---|---|
| 231 LVNEVTEFAK | 066-075 | 1970, 4092 | 0, 0, 0, 0, 0, | 0, 0, 0, 0, 0, 0, |
| 232 SLHTLFGDK | 089-097 | 1695, 5089 | 0, 0, 0, 0, 0, | 0, 0, 0, 0, 0, 0, |
| 233 LCTVATLR | 098-105 | 1862, 4869 | 0, 0, 132, 0, 0 | 0, 0, 0, 0, 0, 0, |
| 234 ETYGEMADCCAK | 106-117 | 809, 1010 | 0, 0, 0, 0, 0, | 0, 0, 0, 0, 0, 0, |
| 235 YLYEIAR | 162-168 | 6036, 13066 | 504, 118, 473, 281, 288 | 448, 895, 216, 724, 2346, 1571 |
| 236 LDELRDEGK | 206-214 | 3064, 7917 | 0, 0, 0, 0, 0 | 0, 0, 0, 0, 0, 0 |
| 237 YICENQDSISSK | 287-298 | 583, 1394 | 0, 0, 0, 0, 0, | 0, 0, 53, 0, 0, 0, |
| 238 LKECCEKPLLEK | 299-310 | 2283, 4675 | 0, 0, 0, 0, 0, | 0, 0, 0, 0, 0, 0, |
| 239 HPDYSVVLLLR | 362-372 | 1036, 1482 | 0, 0, 0, 0, 0, | 0, 0, 51, 0, 407 (1312), 226(1312) |
| 240 CCAAADPHECYAK | 384-396 | 2186, 3327 | 0, 0, 0, 0, 0, | 0, 0, 0, 0, 0, 0, |
| 241 QNCELFEQLGEYK | 414-426 | 2519, 2978 | 0, 0, 0, 0, 0, | 0, 0, 0, 0, 0, 212(1656.64) |
| 242 FQNALLVR | 427-434 | 15276, 32846 | 267, 315, 931, 494, 309 | 591, 1284, 199, 1015, 2963, 1998 |
| 243 CCTESLVNR | 500-508 | 1360, 4659 | 0, 0, 0, 0, 0, | 0, 258, 0, 0, 0, 204 (1139) |
| 244 AVMDDFAAFVEK | 570-581 | 2720, 3758 | 0, 0, 0, 0, 0 | 0, 0, 0, 0, 0, 0 |

Some peptide fragments of albumin might not be identified by binding an antibody to trypsinated fragments of albumin because of the possibility that the mAb binding epitope of albumin is cleaved by trypsin, resulting in fragments of the epitope with too low binding affinity to bind to the mAb. Therefore, an additional method was used to identify fragments bound by the antibody. MALDI epitope mapping of mAb A based on antibody protection of proteolysis was repeated. This time a slightly different approach was used. Denatured HSA was incubated with mAb A. Albumin not bound by the antibody, was removed from the sample by size exclusion on an ultra filter. The remaining free mAbs and the complexes of mAb-albumin was then digested with trypsin (sequences of the albumin molecule to which mAb is bound should resist the trypsin digestion). Small cleaved fragments of mAb and unprotected albumin was then removed from the sample by ultrafiltration (30 kD). The complexes of mAb and bound albumin fragments were dissociated by lowering the pH to 2.7. Again ultrafiltration at 30 kD was performed to separate whole mAb from albumin fragments smaller than 30 kD. MALDI TOF analysis of these fragments did not identify spectra typical for albumin Reasonably, because the fragments containing the epitope of mAb A were still too large. This filtrate (<30 kD) was then further digested with trypsin (for cleavage of sites previously protected by the mAb) in order to generate peptide masses suitable for analysis with MALDI TOF ms.

After this second trypsin treatment, eight of 32 masses detected by MALDI TOF ms matched to albumin (see Table 11). Thus, these new amino acid sequences represent a part of the epitope, which also contains sequences on the other side of the trypsin cleavage point. Six of the eight peptide masses ((SEQ ID NOs: 231, 233, 235, 236, 242, and 243) were peptide masses that also disappeared when analysed previously when completely cleaved albumin was incubated with the mAb A before the MALDI-TOF analysis (see Table 10). Two of the eight peptides (SEQ ID NOs: 245 and 346) had not been identified in the binding assays with completely cleaved albumin. The epitope/s of this antibody was thus established. It is important to note that multiple such structures are present in the albumin molecule, which can then cause cross-linking of the receptors to which they are bound. However, multiple epitope sites for mAb A can indeed exist on albumin.

TABLE 11

Albumin peptides that bind to monoclonal antibody mAb A

| SEQ ID NO: | Sequence | Albumin Positions |
|---|---|---|
| 245 | LSQRFPK | 243-249 |
| 246 | DDNPNLPR | 131-138 |
| 235 | YLYEIAR | 162-168 |
| 233 | LCTVATLR | 98-105 |
| 242 | FQNALLVR | 427-434 |
| 236 | LDELRDEGK | 206-214 |
| 243 | CCTESLVNR | 500-508 |
| 231 | LVNEVTEFAK | 66-75 |

Example 19: Cyclic Peptides that Bind P3028

In order to identify cyclic peptides that bind to P3028, all possible variants of di- and tripeptides were synthesized on chips and the binding of the His-tag labeled P 3028 was analyzed using the ELISA-technique. Based on the identified binding motifs, looped 6-meres were produced and tested. These results together enable the construction of a lead cyclic peptide CLALNVMCG (SEQ ID NO: 264). Positional scans were performed in each position of the lead cyclic peptide was replaced with each of the other 19 L-amino acids. Binding of each of the substituted peptides was tested, and peptide sequences with even better binding capacity than that of the lead peptide were identified. The two peptides with the highest affinity were CLRLNVFCG (SEQ ID NO: 265) and CLRLIVMCG (SEQ ID NO: 266). The two best looped peptides that bind to P3028 based on the positional scan binding assay are summarized in Table 12.

TABLE 12

Cyclic peptides that bind to P3028

| SEQ ID NO: | SEQUENCE |
|---|---|
| 264 | CLALNVMCG |
| 265 | CLRLNVFCG |
| 266 | CLRLIVMCG |

Substitutable amino acid residues in the lead looped peptide that were identified in the positional scans as providing improved binding to P3028 (SEQ ID NO: 185) are summarized in FIG. 33 (i.e., SEQ ID NOs: 264 to 266). Positional substitutions of P28R that result in equivalent or better binding to P28R to P3028 that were identified as providing higher or substantially equal binding to P3028 (see Tables 6.1 and 6.2) are also summarized in FIG. 33. It was observed that there was very good homology between looped peptide sequences that bind to P3028 based on the scan data (SEQ ID NOs: 264-266), and sequences of linear peptides that identified as binding to P3028 (SEQ ID NOs: 2-31 and 268-393) (see FIG. 33). It is noted that the N-terminal C residues and C-terminal CG residues of the cyclic peptides are involved in cyclization of the peptide. Thus, as shown by shaded boxes in FIG. 33, there is strong homology between 6-mere cyclic peptides identified as binders of P3028 (SEQ ID NOs: 264-266) and either the N terminus of C-terminus of P28R-related peptide (SEQ ID NOs: 2-31 and 268-393). It is contemplated that additional cyclic peptides that bind to and inhibit albumin-derived immunoregulatory peptides can be identified.

Example 20: Effect of Albumin Peptides on IL-2 Induced Proliferation

The effect of albumin peptides including at least one of SEQ ID NOs: 183-185 or 188-246 is determined using the ex vivo human model as described in Example 2.

PBMCs are isolated from venous blood samples from healthy blood donors (control samples) or cancer patients. One hundred pl of culture medium (RPMI 1640 Dutch's modification (Gibco®, InVitrogenAB®, Stockholm, Sweden) supplemented with 200 IV/ml penicillin, 200 ul/ml streptomycin, 4 mM L-glutamine (all from Sigma® Chemical Co. MO, US) and 20% heat-inactivated human serum) is added to roundbottomed, 96-well tissue culture plates (Costar®, Corning® Inc. NY, US). For experimental cultures, the culture medium of each well is supplemented with a peptide of SEQ ID NOs: 183-185 or 188-246. One hundred pl of PBMCs in RPMI/2% HAS (5×104 lymphocytes) is then added per well followed by IL-2 (Proleukin®, Chiron®, NL) at a final concentration of 120 IU/well. Control wells without IL-2 are set up in parallel. Cells are cultured for 7 days in a humidified, 5% CO2-atmosphere at 37° C. Cell proliferation is assayed by incorporation of 1.6 μCi/well of [$^3$H]-thymidine (Amersham® Int., UK) during the last 18-24 h hrs. Mean values of dpm (disintegrations per minute) of triplicate wells are used for the calculations.

Thus, albumin peptides that inhibit IL-2 stimulation of PBMCs are identified.

Example 21: Effect of Albumin Peptides on T Cell Receptor Stimulation

The effect of albumin peptides including at least one of SEQ ID NOs: 183-185 or 188-246 on T Cell receptor stimulation is determined as in Example 3. Cells are stimulated in cultures on plates pre-coated with a monoclonal antibody directed against CD3 and the number of metabolically active cells (i.e., cell proliferation) is determined using MTS staining after 3 to 7 days of culture. Detection of solid phase CD3 monoclonal antibody is used as a measurement of T cell proliferation.

Thus, albumin peptides that inhibit T cell receptor stimulation are identified.

Example 22: Effect of Albumin Peptides on NK Cell Cytotoxicity

The effect of albumin peptides including at least one of SEQ ID NOs: 183-185 or 188-246 on NK cell cytotoxicity is determined as in Example 4.

Mononuclear cells are separated by standard Ficoll-Paque® Plus (Pharmacia AB, Sweden) density gradient centrifugation from heparinized blood obtained from healthy donors. NK cell cytotoxic activity of the mononuclear cells is then tested using a commercial kit (NKTEST, Orpegen Pharma GmbII, Heidelberg, Germany) following the manufacturers protocol. Briefly, the kit contains cryo-preserved, NK-sensitive target cells (K562) labeled with a lipophilic green fluorescent membrane dye, which enables discrimination of effector and target cells. After incubation with effector cells, killed target cells are identified by a DNA-stain, which penetrates and specifically stain the nuclei of dead target cells. This way the percentage of killed targets can be determined by flow cytometry. The mononuclear cells were preincubated for 30 min at 37° C. with the indicated peptides (peptides have been described previously) at 10 ug/ml. Target cells were then added, giving an effector:target ratio of 40:1, and the cell mixture incubated at 37° C. for 3-4 hours. Samples are analysed on a FACSCalibur (BD® Biosciences, San Jose, Calif.).

Thus, albumin peptides that inhibit NK cell cytotoxicity are identified.

Example 23: Effect of Albumin Peptides on Leukocyte Spreading

The effect of albumin peptides including at least one SEQ ID NOs: 183-185 or 188-246 on leukocyte spreading is determined as in Example 5. Buffy coat cells are prepared from heparinized blood by Dextran assisted sedimentation. To test the effects of each peptide, a samples of cells are treated with of one of the peptides of (SEQ ID NOs: 183-185 or 188-246 at a concentration of 10 µg/ml for 15 minutes efficiently inhibited the spreading. These cells are then washed twice in PBS and transferred to clean slides. Cells adherance to the glass surface and spreading is detected.

Thus, albumin peptides that inhibit leukocyte spreading are identified.

Example 24: Effect of Albumin Peptides on Immune Cell Migration

The effect of albumin peptides including at least one of SEQ ID NOs: 183-185 or 188-246 on immune cell migration is determined as in Example 5. PBMC migration is studied using the Boyden chamber technique. Migration for PBMCs of healthy control samples and cancer patients is assessed in both the presence and absence of each of the peptides of SEQ ID NOs: 183-185 or 188-246. Thus, albumin peptides that inhibit immune cells migration are identified.

Example 25: Binding of Albumin Peptides to LFA-1

The binding of albumin peptides including at least one of SEQ ID NOs: 183-185 or 188-246 to LFA-1 is determined as in Example 7. A standard immunohistochemical staining procedure is performed using acetone fixation, 10% human AB-serum for blocking, incubation with anti-LFA-1 antibody and a secondary antibody (Ultravision®) followed by development with Fast Red. Pre-incubation with peptides added to the AB serum is either no peptide added, or a peptide of SEQ ID NOs: 183-185 or 188-246 is added.

Peptides that bind to LFA-1 prevent the binding of the antibody, thus decreasing the amount of Fast Red staining in antibody-treated cells as compared to untreated control samples.

Example 26: Antibodies that Bind Albumin Peptides

Antibodies that specifically bind to peptides including at least one of SEQ ID NOs: 183-185 or 188-246 are generated as in Example 9. Rabbit antisera directed against each of the peptides of SEQ ID NOs: 183-185 or 188-246 are generated. Each peptide of SEQ ID NOs: 183-185 or 188-246 is synthesized with a cysteine added to the N-terminus end and then conjugated with keyhole limpet hemocyanin (KLH) as a carrier protein. Polyclonal antisera is generated by repeated immunizations of rabbits with KLH-conjugated P3028 and Freund's adjuvants. The antisera are affinity purified by chromatography on P3028-conjugated Ultra-link® Iodoacetyl gels (Pierce® Biotechnology Inc.).

The antisera are tested for their ability to bind human serum and dHSA. Human serum commercially available for therapeutic purposes is tested, heated 10 times in order to be virus free. Thus, rabbit antisera that specifically binds the albumin peptide binds to dHSA and/or control sample HSA.

The binding of the rabbit antiserum to peptides of SEQ ID NOs: 183-185 or 188-246 is assayed using competition ELISA assay.

Effects of affinity purified antibodies directed against of SEQ ID NOs: 183-185 or 188-246 on the proliferative response to IL-2 are examined the ex vivo model, using PBMCs from immunosuppressed cancer patients and normal control samples.

Thus, antibodies that bind peptides of SEQ ID NOs: 183-185 or 188-246 are identified.

Example 27: Peptides that Bind to Albumin-Derived Peptides

Peptides that bind to peptides including at least one of SEQ ID NOs: 183-185 or 188-246 are identified as in Example 10. Potential binders of the peptides are synthesized. For each peptide of SEQ ID NOs: 183-185 or 188-246 a His-tagged peptide is contacted with the potential binders in solution, and then isolated from solution using the His tag. Binders of each peptide are isolated along with the peptide, and subsequently identified.

Additionally, substitutions, truncations, and deletions of peptides that bind to each of the albumin peptides are identified as in Example 12. Substitutions, truncations, and deletions are synthesized on a chip, and contacted with the albumin peptide of one of SEQ ID NOs: 183-185 or 188-246 to determine binding. The amount of bound peptide is quantified using a rampo assay as in Example 12. The binders with the highest rampo scores are isolated.

The highest-score binders of each peptide are assessed for their ability to reduce immunosuppression, as in Examples 13 and 15. Each binder is assessed for its ability to induce lymphocyte activation, and unblock the LFA-1 receptor. Additionally, each binder is assessed to bind to tumor cells, as in Example 14.

Example 28: Effect of P28R on Mitochondrial Metabolism and Conversion of MTS

PBMCs from eight healthy control samples and nine cancer patients with various diagnoses (including renal cell cancer, malignant melanoma, rectal cancer, small cell lung cancer, non-small cell lung cancer (adenocarcinoma), squamous cell carcinoma, bladder cancer, osteosarcoma, pancreatic cancer, or bronchial cancer) were cultured in a modified version of the ex vivo model of Example 2 for seven days in the presence of various quantities of P28R (SEQ ID NO: 2), and control samples were untreated with P28R. As shown in FIGS. 33A and 33B, the cells were cultured in either no P28R 322, 5 µg/mL 324, 10 µg/ml 326, or 20 µg/ml 328 of P28R. A dose dependent stimulation of the mitochondrial metabolism measured as conversion of MTS was observed in 5/8 (see FIG. 33A) control samples and 9/9 cancer patients (see FIG. 33B). Similar results were obtained when the PBMCs were cultured for only three days.

Example 29: Effects of Inhibitors of Immunoregulatory Peptides on Mitochondrial Metabolism and Conversion of MTS The effect of P28R (SEQ ID NO: 2) on mitochondrial metabolism based on MTS conversion was compared to the effect of a closely related peptide P27. P27 (aka "SCF 27") has the sequence KKLDTFFKKLSLFTER (SEQ ID NO: 264), and is a variant of P28R that differs in that V8 of P28R is substituted to K8 in P27. P28R binds to P3028 more efficiently than P27 (P27 binds P3028 with a rampo score of 253, while a P28R control sample binds P3028 with a rampo score of 308; see Example 12).

PBMCs from cancer patients with various diagnoses were cultured in a modified version of the ex vivo model of Example 2 with various concentrations of P28R or P27 (N=9 for P28R: N=8 for P27). The concentrations were either untreated control samples, 5 µg/mL ("SCF28-R5" and "SCF275"), 10 µg/ml ("SCF28-R10" and "SCF2710"), 20 µg/ml ("SCF28-R20" and "SCF2720"), or 40 µg/ml ("SCF28-R40" and "SCF2740"). The results are shown in FIG. 34. While P28R stimulated the cells of cancer patients in a dose-dependent manner, P27 had no effect.

Example 30: Effect of P28R on IL-2 Induced Proliferation (BrdU Incorporation)

The effect of P28R (SEQ ID NO: 2) on IL-2 induced proliferation was measured in a BrdU incorporation assay. PBMCs from six healthy control samples and ten cancer patients (including renal cell cancer, malignant melanoma, rectal cancer, small cell lung cancer, non-small cell lung cancer (adenocarcinoma), squamous cell carcinoma, bladder cancer, osteosarcoma, pancreatic cancer, or bronchial cancer) were harvested in a modified version of the ex vivo model of Example 2. One hundred pl of culture medium (RPMI 1640 Dutch's modification (Gibco®, InVitrogenAB®, Stockholm, Sweden) supplemented with 200 IV/ml penicillin, 200 ul/ml streptomycin, 4 mM L-glutamine (all from Sigma® Chemical Co. MO, US) and 20% heat-inactivated human serum) were added to roundbottomed, 96-well tissue culture plates (Costar®, Corning® Inc. NY, US). One hundred pl of PBMCs in RPMI/2% HAS (5×104 lymphocytes) was then added per well followed by IL-2 (Proleukin®, Chiron®, NL) at a final concentration of 120 IU/well. Control sample wells without IL-2 was set up in parallel. Cells were cultured for 7 days in a humidified, 5% CO2-atmosphere at 37° C. Cell proliferation was assayed by incorporation of BrdU.

Figure 35:
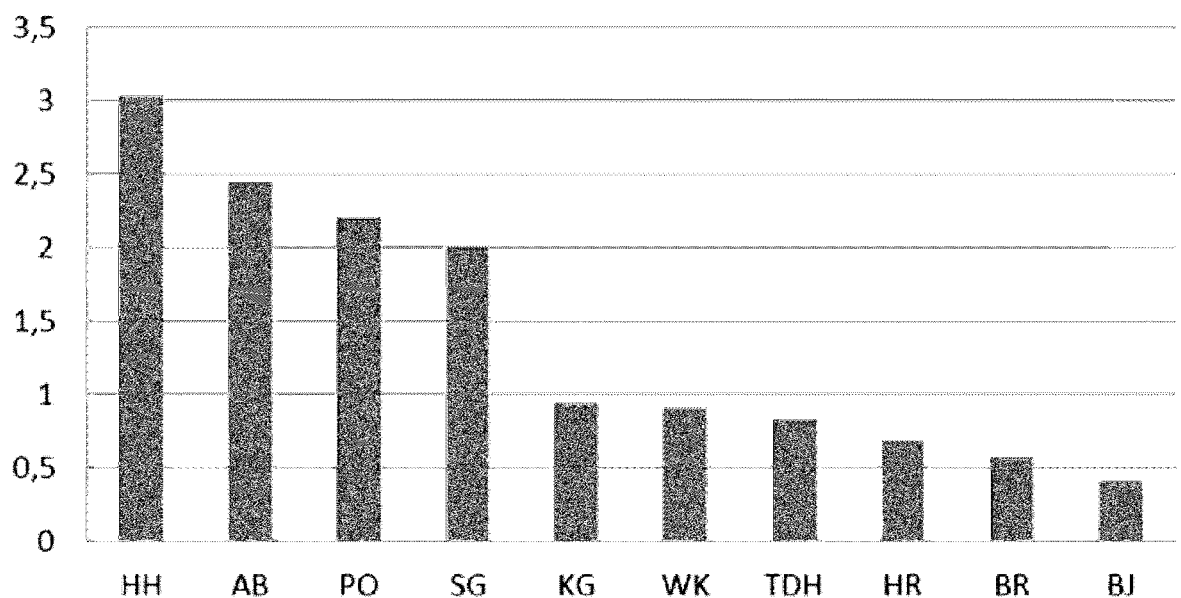
FIG. 35 illustrates response to IL-2 in cancer patients cells, measured by BrdU incorporation.

As shown in FIG. 35, four out of six control samples had a high proliferative response to IL-2 compared to four out of ten cancer patients. These differences in proliferative response to IL-2 in PBMCs demonstrated the difference existence of high and low responders to IL-2.

Figure 36A:
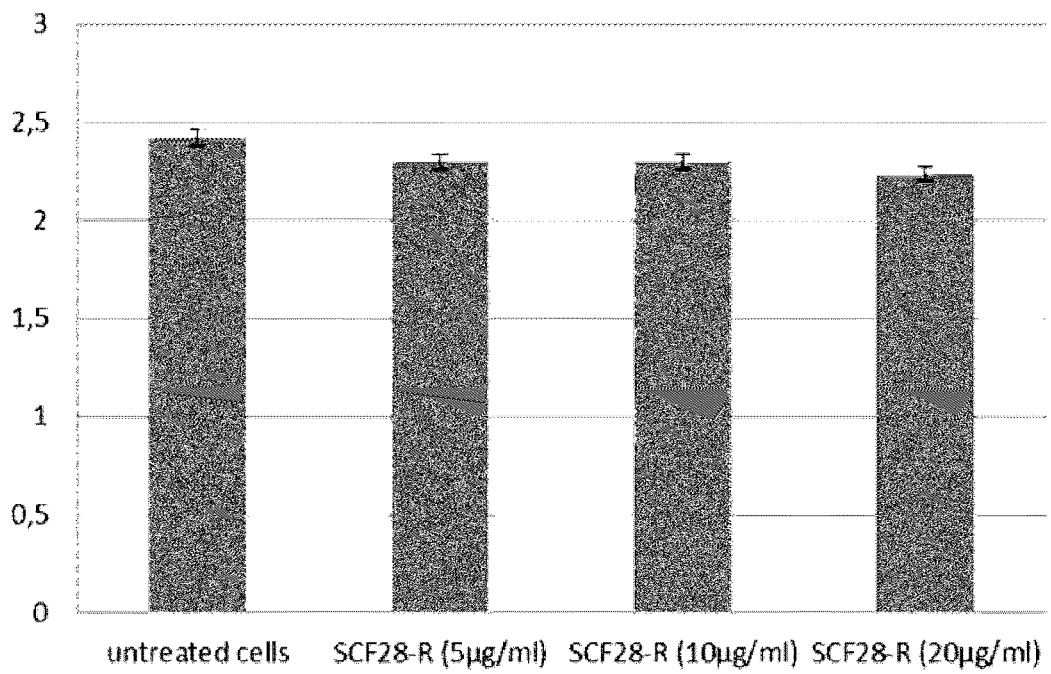
FIG. 36 illustrates effect of P28R (aka "P28") on IL-2 induced proliferation in cells of (FIG. 36A) high responders, and (FIG. 36B) low responders.
Figure 36B:
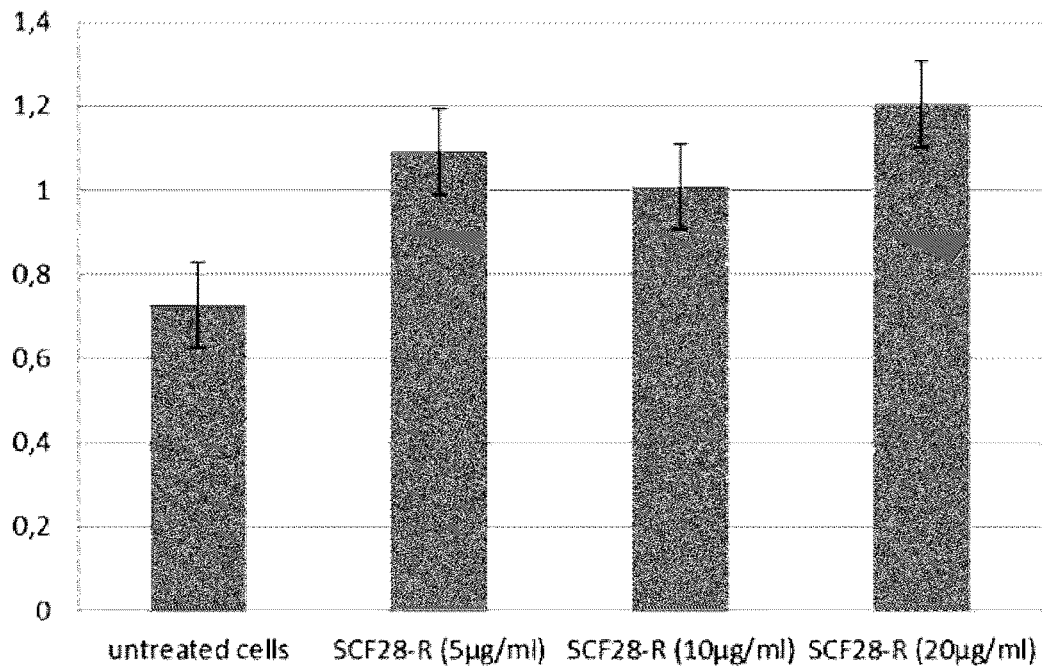

The response of high responders and low responders to various doses of P28R was compared. Cells from either high responders or low responders were cultured for 7 days with either no P28R, 5 µg/mL, 10 µg/ml, or 20 µg/ml of P28R. IL-2-induced proliferation was measured as BrdU incorporation, as in the above example, and the results are shown for high responders in FIG. 36A, and low responders in FIG. 36B. While P28R had no stimulatory effect in cells from patients with a high response to IL-2 (N=4) (see FIG. 36A), P28R had a stimulatory effect on cells from patients with a low response to IL-2 (N=6) (see FIG. 36B).

Example 31: Effects of Inhibitors of Immunoregulatory Peptides on IL-2 Induced Proliferation (BrdU Incorporation and MTS Conversion)

The effect of P27, a peptide related to P28R was compared to the effect of P28R on Il-2induced proliferation as measured by BrdU Incorporation. P27 (aka "SCF 27") has the sequence KKLDTFFKKLSLFTER (SEQ ID NO: 264), and is a variant of P28R that differs in that V8 of P28R is substituted to K8 in P27. P28R binds to P3028 more efficiently than P27 (P27 binds P3028 with a rampo score of 253, while a P28R control sample binds P3028 with a rampo score of 308; see Example 12).

PBMCs from low responder cancer patients of Example 30 were cultured as in Example 30, except that some samples were cultured with various concentrations P28R (aka "SCF28-R"), and others were cultured with various concentrations of P27 (aka "SCF27"). The concentrations were either no peptide ("untreated cells"), 5 µg/mL, 10 µg/ml, or 20 µg/ml. BrdU incorporation was measured as in Example 30. As shown in FIG. 37, both P28R and P27 enhanced the proliferative rate of PBMCs induced by IL-2. A comparison can be drawn to the data of Example 29 and FIG. 34, in which P28R, but not P27 enhanced IL-2 stimulation of mitochondrial metabolism, as measured by MTS conversion. P27 was observed to enhance IL-2 stimulation of cell proliferation as measured by BrdU incorporation, but not mitochondrial metabolism as measured by MTS conversion. On the other hand, P28R was observed to enhance both parameters. The inhibitory peptide P3028 binds to different receptors, including CD25 (see Example 8 and FIGS. 18-19) and LFA-1 (see Example 7 and FIGS. 15-16), as described herein. It is contemplated that the more efficient binder of P3028, P28R, is capable of removing P3028 from LFA-1 and/or unblocking CD25. However, it is contemplated that P27 with a lower/weaker binding to P3028, does not have the capacity to unblock LFA-1 but can unblock CD25. Thus, it is contemplated that different populations of patients may be affected in different ways by immunoregulatory peptides such as P3028. Moreover, it is contemplated that different inhibitors of immunoregulatory peptides can modulate the activity of different receptors, and/or different signal transduction pathways.

Example 32: Comparison of MTS and BrdU Assays

The two cell proliferation assays in this study are both widely used in order to measure cell proliferation. Peptide P28R had a stimulatory activity of MTS conversion in seven day cultures of PBMCs in 9/9 patients and in 5/8 healthy control samples. In contrast, P28R stimulated incorporation of BrdU in seven day cultures of PBMCs from only 1/6 and 2/10 patients.

IL-2 induced proliferation, measured as incorporation of BrdU, was stimulated by P28R in PBMC cultures from cancer patients with a low proliferative response to IL-2 (experimental conditions were as described in Example 30). PBMCs from 2/3 healthy control samples and 2/4 cancer patients were not stimulated by IL-2 when the effect was measured as MTS conversion (experimental conditions were as described in Example 28). However, PBMCs from all these persons ("non-responders") who did not respond when measured with MTS were significantly stimulated by IL-2 when the effect was measured as incorporation of BrdU.

The above results are illustrated in FIG. 38. PBMC cultures from two different patients (A, B) and (C, D), with IL-2 382 (bars on left) or without IL-2 384 (bars on right). The effect of IL-2 and the peptides P28R (aka "SCR28R") and P27 (aka "SCF27") were measured at concentrations of either no peptide ("untreated cells"), 5 µg/mL, 10 µg/ml, or 20 µg/ml of peptide.

Figure 38A:
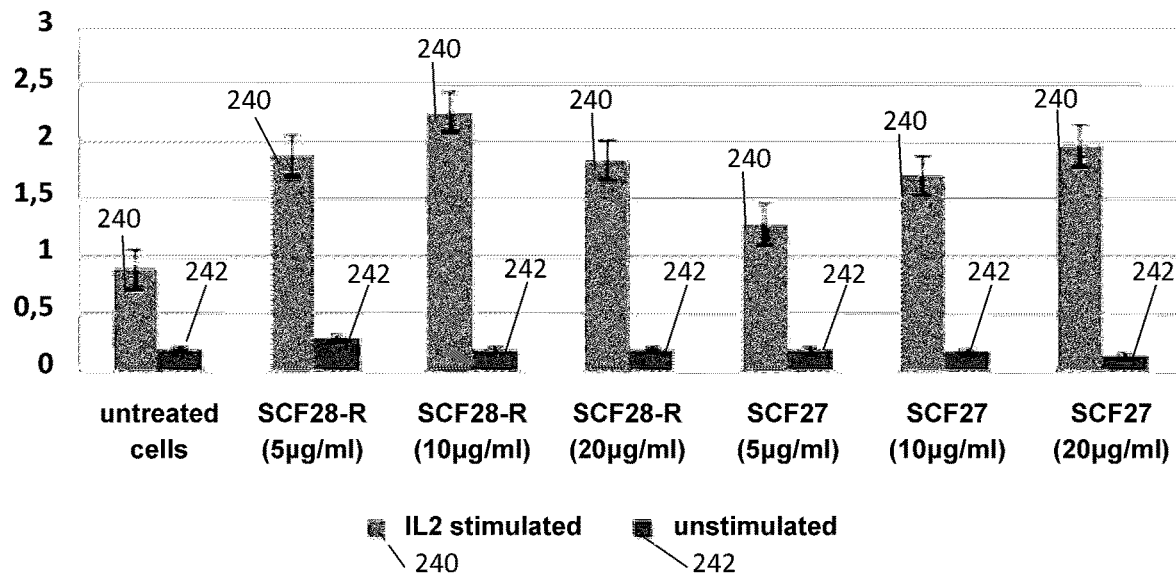
FIG. 38 illustrates effect of P28R (aka "SCF 28R") and P27 (aka "SCF 27") on IL-2-induced proliferation based on BrdU incorporation (FIGS. 38A, 38C) and MTS incorporation (FIGS. 38B, 38D). Shown are cells of two different patients, (FIGS. 38A, 38B) and (FIGS. 38C, 38D) respectively.
Figure 38B:
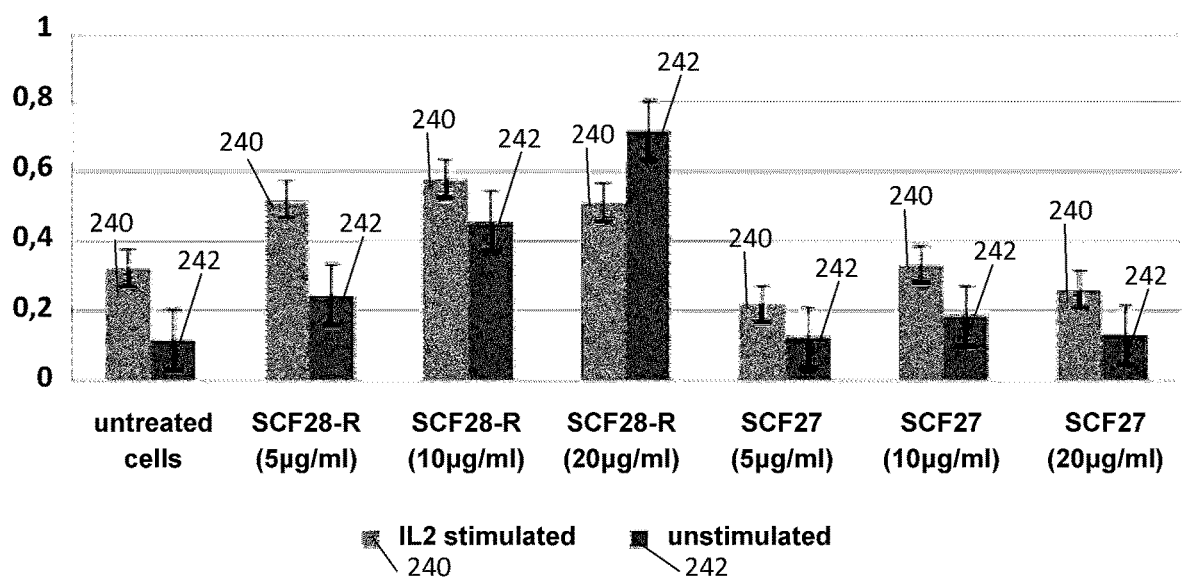
Figure 38C:
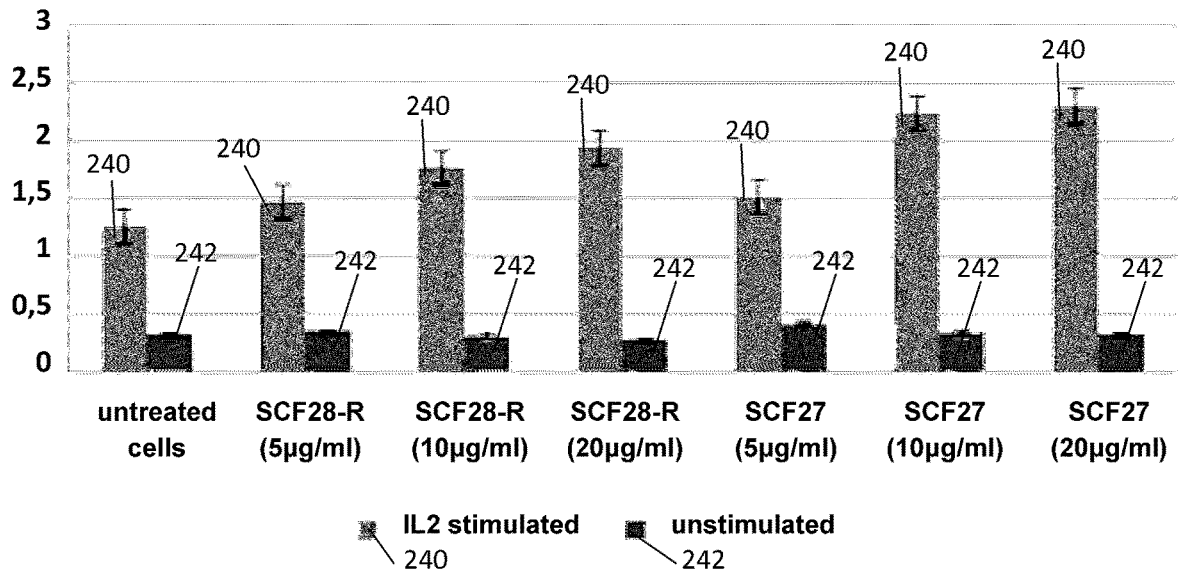
Figure 38D:
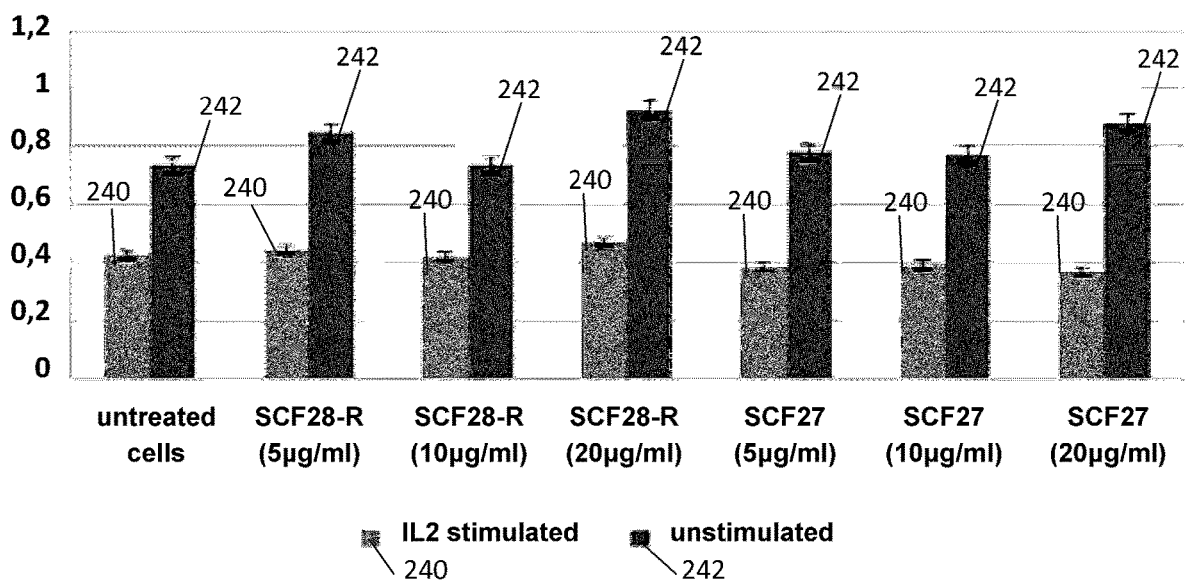
Figure 39:
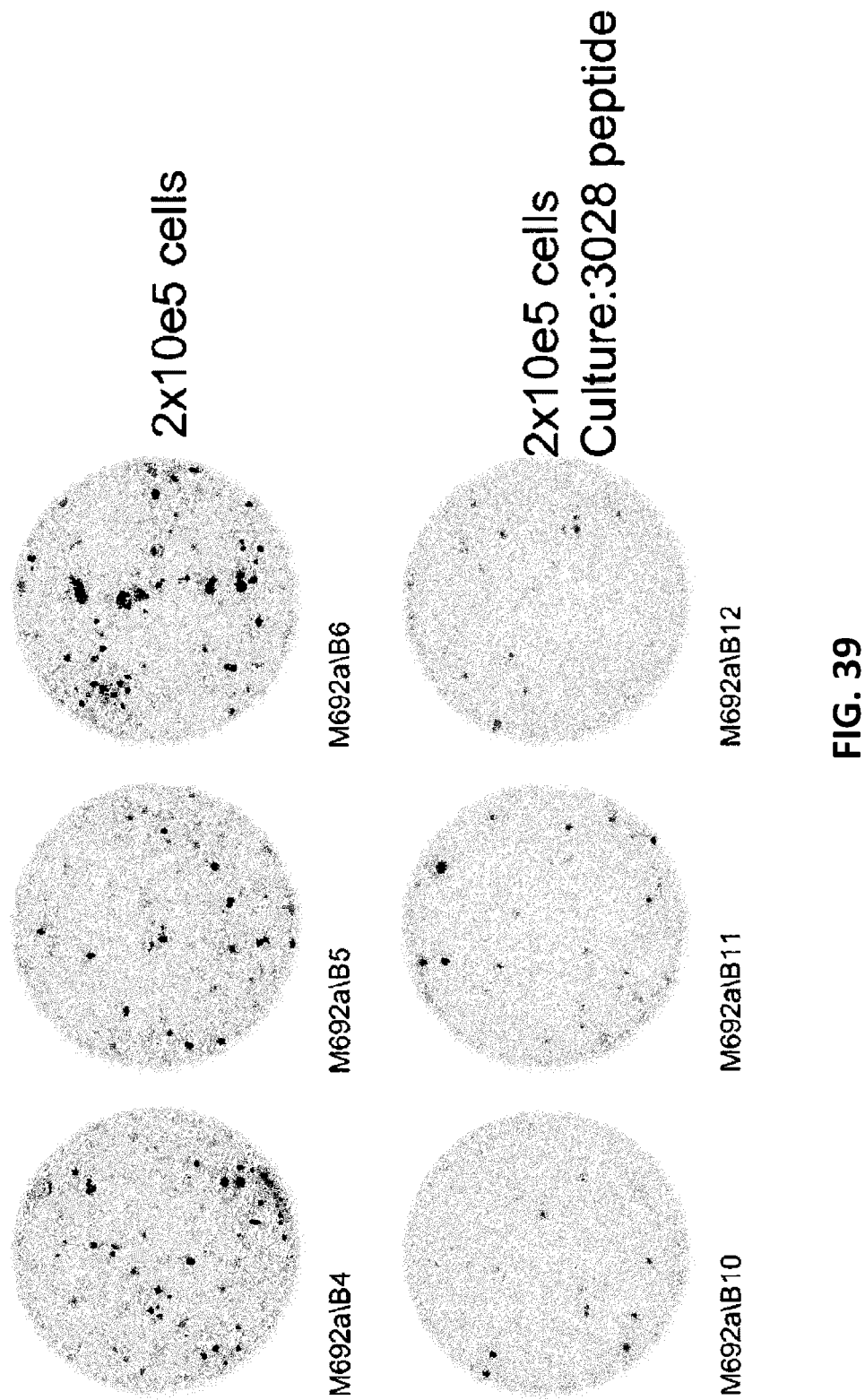
FIG. 39 illustrates enzyme linked immunosorbent spot assays of cells with (bottom row) and without (top row) P3028 peptide.
Figure 40:
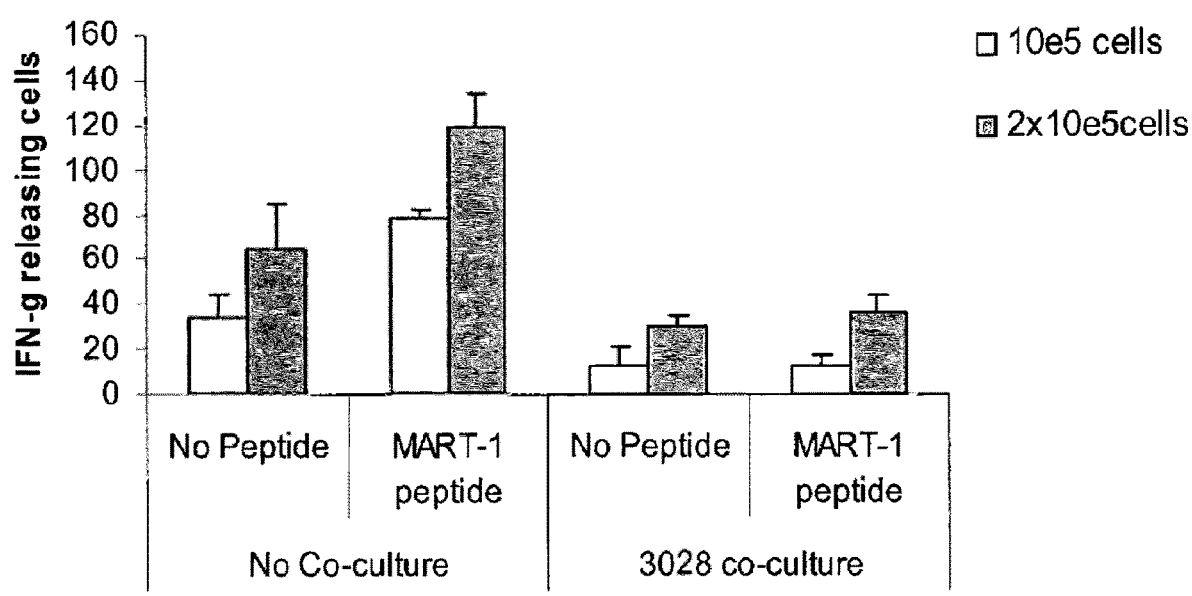
FIG. 40 illustrates data from enzyme linked immunosorbent spot assays of cells with and without P3028 peptide.

In two patients, the response to IL-2, measured as BrdU incorporation, was enhanced by P28R (see FIGS. 38A and 38C), but this effect of P28R was only observed in one of these patients when MTS conversion was used (see FIG. 38B). Thus, while in one patient (see FIGS. 38A and 38B) the stimulatory activity of IL-2 was registered using both BrdU and MTS, in the other patient, the stimulatory activity of IL-2 was registered using BrdU only (see FIG. 38C). Based on these observations, it is concluded that effects on the metabolic activity measured as MTS conversion does not always correlate with DNA synthesis measured as incorporation of BrdU.

Additionally, P28R enhanced the effect of IL-2 measured both with BrdU and MTS, but the stimulatory effect of SCF27 was observed only when BrdU incorporation is measured. In the patient shown in C the results are very similar to those shown in A, but in D no stimulatory effect is seen when the effect is determined using MTS conversion.

These results indicate that albumin-derived immunomodulatory structures such as P3028 appear to modulate signal transduction through different mechanisms. Thus, different patient populations can respond differently to inhibitors of immunomodulatory peptides. It is contemplated that in vitro diagnostic assays can be helpful in identifying which patients have albumin-derived immunomodulatory structures, and can be further helpful in identifying which patients will respond to certain inhibitors (or combinations of inhibitors) of immunomodulatory structures.

Example 33: Effects of Binders of Immunoregulatory Peptides on Lymphocyte Activation Binders of immunoregulatory peptides, for example the peptides of Tables 5.1, 6.1, 6.2, or 12 (SEQ ID NOs: 1-32, 265-393), or SEQ ID NOs: 34, 46-53, 64-66, 68, 76, 94-96, 98, or 264, are assayed for effects on lymphocyte activation, as in Example 13. Analyses of these peptides are performed in human ex vivo models. The stimulatory activity on PBMCs, measured using the MTS or CFSE techniques, are studied in 7 healthy control samples and 7 cancer patients of various diagnoses. The peptides are assayed for stimulatory activity even in the absence of other types of stimulation, and are compared to untreated control samples.

Stimulatory activity of the peptides of Tables 5.1, 6.1, 6.2, or 12 (SEQ ID NOs: 1-32, 265-393), or SEQ ID NOs: 34, 46-53, 64-66, 68, 76, 94-96, 98, or 264 on a proliferative response to IL-2 suppressed by a P3028 sequence or structure. PBMCs are cultured for 7 days with IL-2 and the proliferative rate is determined as incorporation of BrdU. Each set of conditions is assayed in triplicate. Initial proliferation of PBMCs is compared to proliferation of PBMCs from the same donor after treatment with each peptide.

Example 34: Binding of Inhibitors of Immunoregulatory Peptides to Tumor Cells

A biotinylated version of each of the P28R peptides of Tables 5.1, 6.1, 6.2, or 12 (SEQ ID NOs: 1-32, 265-393), or SEQ ID NOs: 34, 46-53, 64-66, 68, 76, 94-96, 98, or 264, each of which has been shown to bind to P3028, is used to assay binding of the peptide to tumor cells. Five breast cancers, two renal cell carcinomas and four malignant melanomas are analyzed, as in Example 14.

Example 35: Unblocking the LFA-1 Receptor by Inhibitors of Immunoregulatory Peptides As described herein, β2-integrins play a role in the normal function of the immune system. Also described herein are immunosuppressor mechanisms based on the binding of an endogenous inhibitor, P3028, to the β2-integrin LFA-1. As described in Example 7, the membrane staining of PBMCs from cancer patients is markedly decreased compared to normal control samples. The exposure of LFA-1 could, however, be enhanced by incubating PBMCs from cancer patients with an antibody directed against the inhibitor P3028 (see Example 7 and FIG. 16).

Staining for LFA-1 is performed with the anti-LFA-1 antibody of Example 7 and a secondary antibody (Ultravision®) followed by development with Fast Red. Fresh frozen tumor sections without any fixation are incubated for 4-20 hours with each of the P28R peptides of Tables 5.1, 6.1, 6.2, or 12 (SEQ ID NOs: 1-32, 265-393), or SEQ ID NOs: 34, 46-53, 64-66, 68, 76, 94-96, 98, or 264, each of which has been shown to bind to P3028, before staining for LFA-1. For comparison, control sample tumor sections were incubated with phosphate buffered saline only. The amount of anti-LFA-1 antibody staining is observed, and used to determine the amount of blocking, if any, of the LFA-1 receptor. Migration and cytotoxic activity of treated cells is also ongoing.

Example 36: Positional Scans of Amino Acid Residues in SEQ ID NO: 2

Positional scan data was used to study the influence of substitution of different types of amino acids in each position of P28R (SEQ ID NO: 2) on the binding of P3028 (SEQ ID NO: 185). Each amino acid in the peptide sequence of P28R (SEQ ID NO: 2) was exchanged with all of the naturally occurring amino acids, and immobilized on a solid phase chip. The binding of P3028 to these "mutated" P28 R peptides synthesized on a chip was determined using the ELISA technique. The results are summarized in Table 13. In view of the results, Table 13 includes a column identifying optional substitutions at each position that can maintain binding to P3028.

TABLE 13

Analysis of P3028 Binding to Solid Phase P28R Variants

| Position | Substitution Category | ELISA signal | | | | Avg | Optional Substitutions that maintain 3028 binding |
|---|---|---|---|---|---|---|---|
| K1 | RHK | 523 | 428 | 366 | | 439 | any type of |
| | DE | 373 | 396 | | | 385 | amino acid |
| | AVIL | 466 | 442 | 483 | 449 | 460 | possible |
| | M | 457 | | | | 457 | |
| | FYW | 332 | 315 | 284 | | 310 | |
| | STNQ | 344 | 493 | 445 | 455 | 434 | |
| K2 | RHK | 417 | 394 | 445 | | 419 | positively |
| | DE | 335 | 349 | | | 342 | charged |
| | AVIL | 309 | 317 | 331 | 343 | 325 | amino acids |
| | M | 400 | | | | 400 | preferable, |
| | FYW | 390 | 301 | 304 | | 332 | F and N |
| | STNQ | 281 | 331 | 432 | 350 | 349 | possible* |
| L3 | RHK | 370 | 477 | 386 | | 411 | any type of |
| | DE | 492 | 528 | | | 510 | amino acid |
| | AVIL | 427 | 377 | 454 | 375 | 408 | possible |
| | M | 460 | | | | 460 | |
| | FYW | 393 | 344 | 341 | | 359 | |
| | STNQ | 393 | 451 | 374 | 473 | 423 | |
| D4 | RHK | 317 | 317 | 274 | | 303 | any type of |
| | DE | 414 | 417 | | | 416 | amino acid |
| | AVIL | 494 | 424 | 430 | 303 | 413 | possible |
| | M | 384 | | | | 384 | |
| | FYW | 380 | 422 | 443 | | 415 | |
| | STNQ | 344 | 405 | 296 | 345 | 348 | |
| T5 | RHK | 430 | 391 | 237 | | 353 | polar |
| | DE | 295 | 341 | | | 318 | uncharged |
| | AVIL | 346 | 374 | 293 | 311 | 331 | amino acids |
| | M | 475 | | | | 475 | preferable, |
| | FYW | 290 | 425 | 418 | | 378 | R, Y and W |
| | STNQ | 458 | 424 | 436 | 535 | 463 | are possible* |
| F6 | RHK | 309 | 332 | 309 | | 317 | hydrophobic |
| | DE | 193 | 229 | | | 211 | and uncharged |
| | AVIL | 575 | 547 | 466 | 408 | 499 | polar amino |
| | M | 467 | | | | 467 | acids are |
| | FYW | 437 | 364 | 348 | | 383 | preferable; |
| | STNQ | 432 | 481 | 446 | 410 | 442 | avoid positively and negatively charged |
| F7 | RHK | 369 | 364 | 232 | | 322 | hydrophobic |
| | DE | 301 | 381 | | | 341 | and uncharged |
| | AVIL | 426 | 527 | 446 | 517 | 479 | polar amino |
| | M | 712 | | | | 712 | acids are |
| | FYW | 460 | 334 | 380 | | 391 | preferable; |
| | STNQ | 700 | 517 | 348 | 511 | 519 | avoid positively and negatively charged |
| V8 | RHK | 365 | 213 | 253 | | 277 | hydrophobic |
| | DE | 122 | 139 | | | 131 | non-aromatic |
| | AVIL | 299 | 308 | 401 | 411 | 355 | carbon chain |
| | M | 221 | | | | 221 | amino acids |
| | FYW | 358 | 211 | 228 | | 266 | are preferable, |
| | STNQ | 216 | 298 | 203 | 271 | 247 | F possible, avoid negatively charged |
| K9 | RHK | 374 | 306 | 377 | | 352 | positively |
| | DE | 149 | 240 | | | 195 | charged amino |
| | AVIL | 191 | 248 | 190 | 166 | 199 | acids preferable, |
| | M | 283 | | | | 283 | polar uncharged |
| | FYW | 174 | 198 | 245 | | 206 | T and Q possible |
| | STNQ | 274 | 347 | 256 | 330 | 302 | |
| L10 | RHK | 439 | 293 | 285 | | 339 | any type of |
| | DE | 102 | 81 | | | 92 | amino acid |
| | AVIL | 426 | 658 | 415 | 348 | 462 | except |
| | M | 460 | | | | 460 | negatively |

TABLE 13-continued

Analysis of P3028 Binding to Solid Phase P28R Variants

| Position | Substitution Category | ELISA signal | | | | Avg | Optional Substitutions that maintain 3028 binding |
|---|---|---|---|---|---|---|---|
| | FYW | 403 | 382 | 316 | | 367 | charged are |
| | STNQ | 351 | 399 | 365 | 470 | 396 | possible |
| S11 | RHK | 333 | 535 | 323 | | 397 | polar uncharged |
| | DE | 322 | 234 | | | 278 | amino acids are |
| | AVIL | 318 | 392 | 289 | 213 | 303 | preferable, |
| | M | 744 | | | | 744 | H is |
| | FYW | 250 | 402 | 324 | | 325 | possible* |
| | STNQ | 442 | 520 | 451 | 768 | 545 | |
| L12 | RHK | 483 | 460 | 355 | | 433 | any type of |
| | DE | 89 | 82 | | | 86 | amino acid |
| | AVIL | 462 | 545 | 456 | 428 | 473 | except |
| | M | 499 | | | | 499 | negatively |
| | FYW | 389 | 320 | 409 | | 373 | charged |
| | STNQ | 478 | 437 | 462 | 651 | 507 | |
| F13 | RHK | 502 | 1046 | 220 | | 589 | any type of |
| | DE | 112 | 98 | | | 105 | amino acid |
| | AVIL | 525 | 446 | 468 | 448 | 472 | except |
| | M | 1190 | | | | 1190 | negatively |
| | FYW | 402 | 291 | 430 | | 374 | charged* |
| | STNQ | 635 | 494 | 862 | 1144 | 784 | |
| T14 | RHK | 264 | 463 | 259 | | 329 | any type of |
| | DE | 159 | 110 | | | 135 | amino acid |
| | AVIL | 305 | 380 | 375 | 360 | 355 | except |
| | M | 501 | | | | 501 | negatively |
| | FYW | 348 | 270 | 374 | | 331 | charged |
| | STNQ | 369 | 319 | 599 | 301 | 397 | |
| E15 | RHK | 237 | 318 | 324 | | 293 | negatively |
| | DE | 404 | 371 | | | 388 | charged amino |
| | AVIL | 174 | 163 | 163 | 246 | 187 | acids |
| | M | 247 | | | | 247 | preferable, |
| | FYW | 137 | 340 | 226 | | 234 | possibly |
| | STNQ | 165 | 152 | 161 | 344 | 206 | Y or Q |
| R16 | RHK | 260 | 239 | 291 | | 263 | any type of |
| | DE | 133 | 107 | | | 120 | amino acid |
| | AVIL | 226 | 254 | 176 | 217 | 218 | except |
| | M | 238 | | | | 238 | negatively |
| | FYW | 297 | 311 | 202 | | 270 | charged |
| | STNQ | 184 | 292 | 311 | 133 | 230 | |

*It is noted that M has a sulfur atom in the side chain, and without being limited by any theory, it is contemplated that substitution of M only at positions 8, 9, and/or 15 can result in reduced binding of the inhibitor peptide to P3028.

It was noted that the following categories of amino acid residues at the following positions are likely to be involved in binding of P3028 to P28R (some additional "possible" substitutions are noted in Table 13):

K2 positive charged amino acids
T5 polar uncharged amino acids
F6 hydrophobic and uncharged polar
F7 hydrophobic and uncharged polar
V8 hydrophobic, non-aromatic carbon chain amino acids
K9 positively charged amino acids
S11 polar uncharged amino acids
E15 negatively charged amino acids Thus, in some embodiments, a central core, T5-S11, and two additional amino acids, K2 and E15, are identified to be involved in the binding of the peptide P3028.

From the positional scan data it is also noted that a "core peptide" can be identified, FFVKLS (SEQ ID NO: 62) (also referred to herein as "P28 core"), bind the 3028 peptide as efficiently as the full length peptide P28R. However, the P28 core peptide does not stimulate PBMC activation (CD69 and CD71) in short term cultures of this model, while the P28R peptide does stimulate PBMC activation in short term cultures of this model.

However, in cultures with human and dog cancer sera, P28 core has a stimulatory activity. As such, without being limited by any theory, it is contemplated that P28 core can be useful in de-blocking inhibitory effects of P3028 (e.g. displacing bound 3028 structures from the cellular receptors). For example, in some embodiments, P28 core can be useful in de-blocking P3028-mediated inhibition of the LFA-1 receptor.

Based on the positional scan data, it is contemplated that substitutions of SEQ ID NO: 2 could be useful in binding P3028, de-blocking the LFA-1 receptor from P3028-mediated inhibition, and/or stimulating immune cells.

Example 37: Effect of Modified Peptides on PBMC Activation

The activity of peptide P28R (SEQ ID NO: 2) and modifications of P28R was studied in a human ex vivo model using PBMCs in short term cultures, 24 or 48 hours. Effects of P28R and modifications of P28R on PBMCs from a healthy control person were studied. Activation was measured as percentage of cells with enhanced marker CD69 using flow cytometry. PBMCs were incubated with the peptides (40 µg/mL) for 24 hours in RPMI plus 10% human AB serum.

Figure 41A:
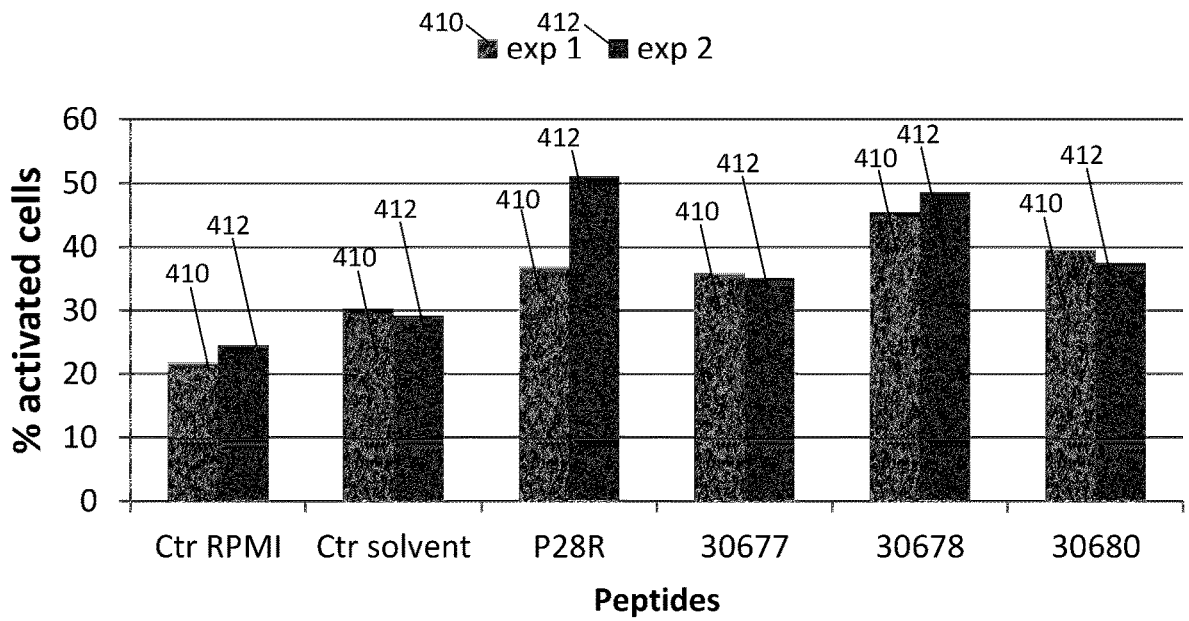
FIG. 41A illustrates results of two experiments (410 and 412) performed for each peptide.

The influence of various amino acid substitutions on the stimulatory effect (measured as expression of CD69) in this ex vivo model was studied. Stimulatory effects of P28R and amino acid substitutions that exhibit a good binding capacity according to the positional scan were assessed. P28R (KKLDTFFVKLSLFTER)(SEQ ID NO: 2), peptide 30677 (KKLDTFFVKLSLMTER)(SEQ ID NO: 583), peptide 30678 (KKLDTFFVKLQLFTER)(SEQ ID NO: 584), and peptide 30680 (KKLDTVMVKLQLMTER)(SEQ ID NO: 585) were examined (see FIG. 41A). FIG. 41A illustrates the results of two experiments (410 and 412) for each peptide. All four peptides induced activation of PBMCs from the healthy control person.

Figure 41B:
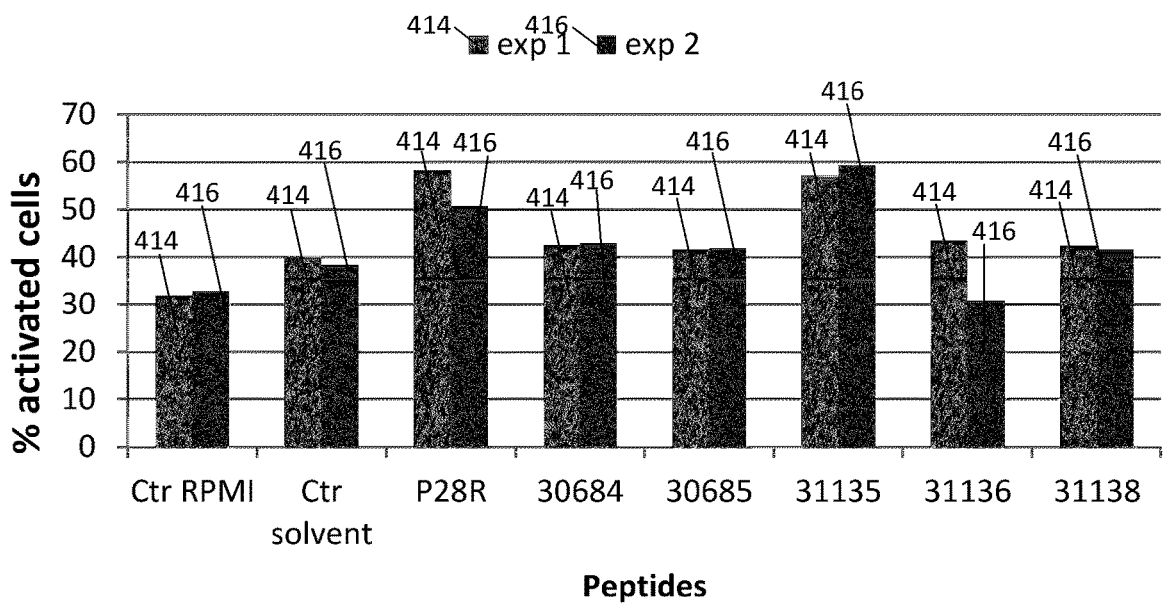
FIG. 41B illustrates results of two experiments (414 and 416) performed for each peptide.

P28R (SEQ ID NO: 2), peptide 30864 (KSLDTFFVKLSLFTER, SEQ ID NO: 586); peptide 30685 (KKLDTFFVKLSLFTFR, SEQ ID NO: 587); peptide 31135 (KKLDTFFVYLSLFTER)(SEQ ID NO: 588); peptide 31136 (KKLDTFFVNLSLFTER)(SEQ ID NO: 589), and peptide 31138 (KKLDTFFVDLSLFTER)(SEQ ID NO: 590) were examined (see FIG. 41B). FIG. 41B shows two experiments (414 and 416) for each peptide. Peptide 31135 also stimulated immune cells. Accordingly, in addition to the analysis of Table 13, tyrosine may also be substituted in position 9 of SEQ ID NO: 2 in accordance with some embodiments herein.

These results show general agreement with the data from the analysis based on the positional scan in Table 13 (see Example 36). Without being limited by any theory, some differences between the position scan data and immune cell stimulation data are not inconsistent with the disclosure herein. It is noted that Table 13 relates to ability to bind to P3028 in an ELISA assay, while FIGS. 41A-B relates to an assay for PBMC activation. In some embodiments, a peptide comprising, consisting essentially of, or consisting of SEQ ID NO 2 or 583-585 stimulates healthy immune cells, for example PBMCs.

Example 38: Effect of P28 Core Peptide on PBMC Activation

As observed in Example 37, P28R (SEQ ID NO: 2) can stimulate PBMCs from healthy controls in short term cultures when RPMI plus 10% normal human AB serum is used as culture medium. Truncations of P28R were also assessed for their ability to activate PBMCs. PBMCs were incubated with the peptides (40 µg/mL) for 24 hours in RPMI plus 10% human AB serum. PBMC activation was measured as percent cells with enhanced expression of either CD69 (FIG. 42A) or CD71 (FIG. 42B) using flow cytometry. Two experiments were performed for each peptide.

As shown in FIGS. 42A and 42B, peptide P28R (SEQ ID NO: 2) effectively activated healthy PBMCs in this model, but peptide 32251 (SEQ ID NO: 592) and peptide 32230 ("P28 core")(FFVKLS)(SEQ ID NO: 62) did not activate healthy PBMCs in this model.

Figure 43:
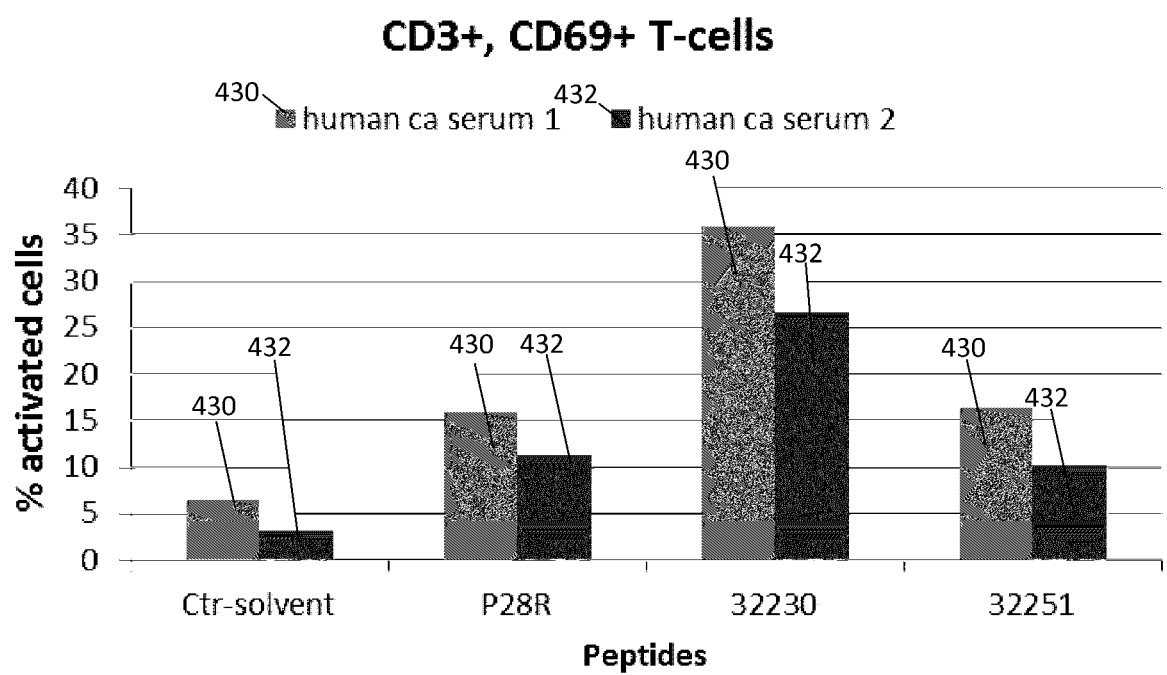
FIG. 43 is a graph illustrating a comparison of the full length peptide P28R and the 6 amino acid central sequence (32230, FFVKLS, SEQ ID NO: 62) in culture medium containing sera from two different cancer patients ("human ca serum 1" 430 and ("human ca serum 2" 432).

However, in PBMC cultures where normal human AB-serum in the culture medium was substituted for by sera from dogs with cancer or human patients with cancer, P28R (SEQ ID NO: 2) and P28 core (peptide 32230)(FFVKLS) (SEQ ID NO: 62) each activated PBMCs, measured as enhanced expression of CD69 (see FIG. 43). FIG. 43 shows a comparison between the full length peptide P28R (SEQ ID NO: 2) and the 6 amino acid P28 core sequence (peptide 32230)(FFVKLS)(SEQ ID NO: 62) in culture medium containing sera from two different cancer patients (human ca serum 1 430 and human ca serum 2 432). Both P28R (SEQ ID NO: 2) and P28 core (SEQ ID NO: 62) activated PBMCs in the presence of cancer serum.

In addition, biotinylated P28R has been shown to bind directly to PBMCs as demonstrated by immunocytochemistry or rosetting of P28R coated beads (binding of beads to the cells).

Taken together, these results show that P28R (SEQ ID NO: 2) can bind to P3028 and de-block cellular receptors and can also have a direct stimulatory activity on immune cells. Additionally, P28 core (SEQ ID NO: 62) can bind to P3028 and de-block cellular receptors.

Example 39: Cytotoxic Activity of P28R

Figure 44A:
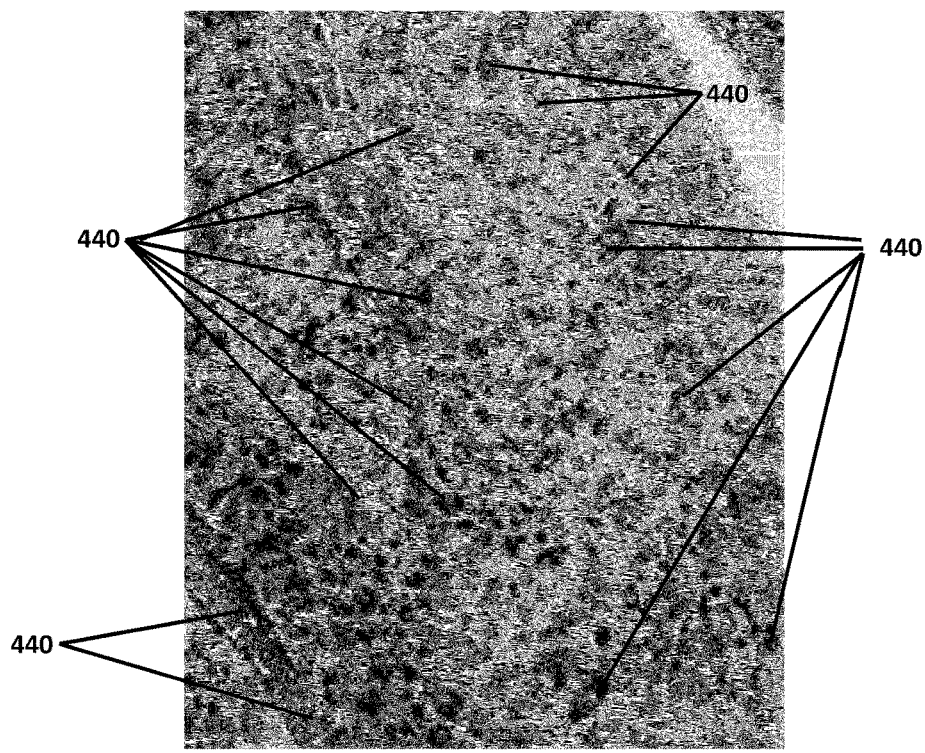
FIG. 44 is a series of microscope images illustrating P28R treatment of human prostate cancer, PC3, in a xenograft model in nude mice. Tumor was injected intra-tumorally with P28R (FIG. 44A) and only the drug solvent (FIG. 44B). Staining for Caspase 3 440 (demonstrating induction of apoptosis) and an absence of staining 442 are depicted.
Figure 44B:
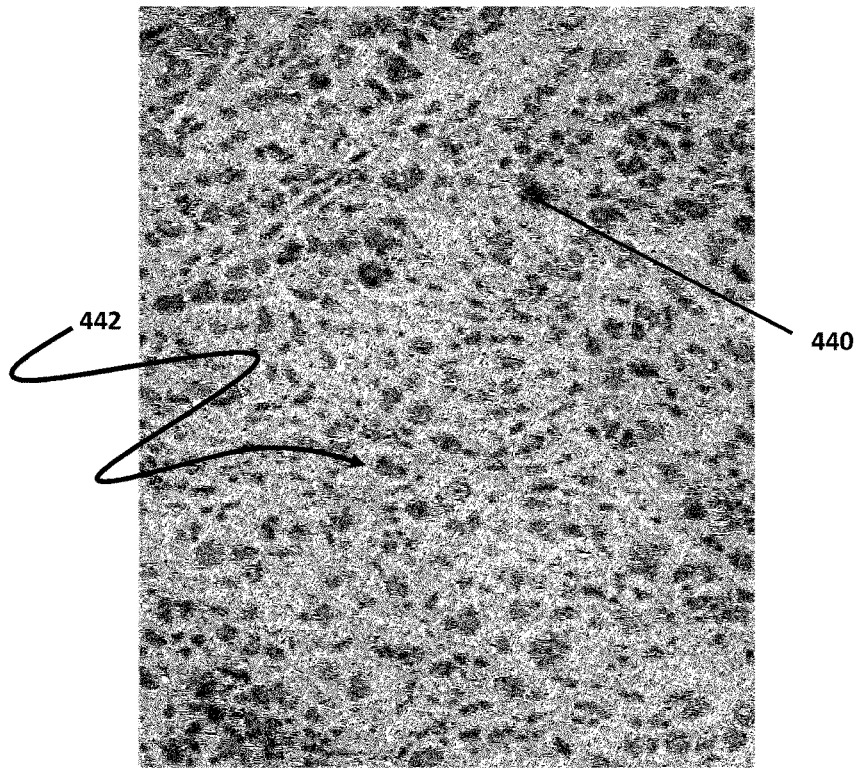

The effect of P28R (SEQ ID NO:2) was further studied in in vivo models in nude and immunocompetent mice. Injection of P28R intra-tumorally into human pancreas cancer in a xenograft model in nude mice demonstrated a capacity to induce tumor cell apoptosis after one day. FIGS. 44A and 44B shows immunohistochemical staining for Caspase 3 (440), indicating an ongoing apoptosis with a significantly enhanced activation of this enzyme in P28R treated tumors (FIG. 44A) compared to tumors which were treated with the drug solvent only (FIG. 44B). An absence of staining is also indicated 442. It is noted that the results shown were obtained only one day after administration of P28R in animals with no capacity to form an immune reactivity to the tumor.

As such, intra-tumoral administration of P28R a can have a cytotoxic action on tumor cells in accordance with some embodiments herein. In some embodiments, P28R has a direct cytotoxic action on tumor cells.

Example 40: Therapeutic Activity of P28R

The capacity of P28R (SEQ ID NO: 2) to activate the immune system and thereby induce tumor cell-lysis was studied in immunocompetent mice, C57B1, with inoculated B16 melanoma. P28R, 40 microgram in 100 microliter, was injected intra-tumorally and the tumors were taken out after 3 days. As shown in FIG. 45, the dominating cells in the tumors after this treatment are inflammatory cells, which were identified by immunohistochemical staining 450 using a polyclonal rabbit anti-CD45 antibody (FIG. 45A). For comparison a control tumor section was incubated with rabbit IgG at the same concentration (FIG. 45B). An absence of staining is also indicated 452.

Accordingly, it was demonstrated that P28R can induce infiltration of a B16 melanoma tumor by inflammatory cells. In accordance with some embodiments herein, P28R can induce infiltration of tumors, for example melanomas, by immune cells.

Example 41: Effects of Modified Peptides on Immune Cell Stimulation

The influence of various amino acid substitutions and additions on the immunostimulatory effect was studied. Effects of modified peptides on activation of PBMCs from healthy control person were assessed. Activation was determined as percentage of cells with enhanced marker CD69 or CD71 using flow cytometry. PBMCs were incubated with the peptides (40 µg/mL) for 48 hours in RPMI plus 10% human AB serum. Two experiments (460 and 462 in FIG. 46A; 464 and 466 in FIG. 46B, respectively) were performed for each peptide. Peptides P28R (SEQ ID NO: 2), P28 core (peptide 32230)(SEQ ID NO: 62), 32251 (KKLDTFFPKLSLFTER)(SEQ ID NO: 592), 32814 (RKLDTFFVKLSLFTERRR)(SEQ ID NO: 591), 32815 (KKLDQFFVKLSQHNER)(SEQ ID NO: 595), 32665 (SEQ ID NO: 593), and 32819 (SEQ ID NO: 594) were tested.

As shown in FIG. 46, peptide 32814 (SEQ ID NO: 591), had a stimulatory effect in short term cultures similar to that of P28R (SEQ ID NO: 2) (batch CS8040). Accordingly, peptide 32814 (SEQ ID NO: 591) activated healthy PBMCs as indicated by enhanced CD69 (FIG. 46A) and also by enhanced CD71 (FIG. 46B).

Example 42: Diagnostic Uses

In addition to therapeutic applications, diagnostic applications of P28R and truncations and modifications thereof were also contemplated. For example, information about patients systemic and local (intra-tumoural) immune status can be obtained using reagents comprising P28R, or a truncation or modification thereof.

It is contemplated that the occurrence of immunoinhibitory 3028-structures in tumors can be identified by immunohistochemical staining using either an antibody directed against P3028 or using labeled P28R (SEQ ID NO: 2) or P28 core (SEQ ID NO: 62), for example biotinylated P28R or P28 core. FIG. 47 shows two areas of a human breast cancer stained using biotinylated P28R. Staining 470 is observed in FIG. 47B. Staining is not observed in FIG. 47A. An absence of staining is indicated 472.

As such, areas of tumors comprising P3028 structures (as well as areas not comprising these structures) can be identified using labeled peptides in accordance with embodiments herein.

Example 43: Treatment of a Tumor Using a P28 Peptide Inhibitor

A patient having a melanoma is identified. A pharmaceutical composition comprising 40 µg/100 ml of a peptide consisting of the amino acid sequence SEQ ID NO: 2 and a PBS buffer formulated as a gel-like substance is injected peri-tumorally in the patient once a week for three weeks. Tumor cytotoxicity is observed. Immune cell invasion of the tumor is observed.

Example 44: Treatment of a Tumor Using a P28 Core Peptide Inhibitor

A patient having breast cancer is identified. A pharmaceutical composition comprising a 80 µg/100 ml of a peptide consisting the amino acid sequence SEQ ID NO: 62 and a tris buffer formulated as a gel-like substance is injected peri-tumorally in the patient. Immune cell invasion of the tumor is observed.

Example 45: Treatment of a Tumor Using a P28R-Modification Peptide Inhibitor

A patient having prostate cancer is identified. A pharmaceutical composition comprising 1 mg/kg of a peptide consisting of the amino acid sequence SEQ ID NO: 586 dissolved in an aqueous buffer is administered systemically to the patient once every two days for five total administrations. Tumor cytotoxicity is observed. Immune cell invasion of the tumor is observed.

Example 46: Generation of Immunoinhibitory P3028 Structures by Cancer Cells

Human prostate cancer cells were cultured in the absence of serum proteins, and exhibited minimal immunostaining for P3028 structures, based on detection by rabbit antibodies (FIG. 48A). The human prostate cancer cells were fed human serum albumin for 2 hours, and were stained for the presence of P3028 structures using rabbit antibodies (FIG. 48B). The albumin-fed cancer cells exhibited substantially higher levels of P3028 structures (as depicted by red staining 480 in FIG. 48B) as compared to the non-albumin-fed cells (as indicated by substantially lower levels 482 of red staining 480 in FIG. 48A).

As such, it has been shown that immunoinhibitory structures such as 3028 structures can be generated by cancer cells. It is contemplated that inhibitors of immunoregulatory proteins in accordance with some embodiments herein can be useful for countering the effects of such immunohibitory structures on cancer cells.

Example 47: Nanoparticle-Inhibitors of Albumin-Derived Immunoregulatory Peptide Compositions Magnetic Dynabead® beads were bound to P28 core peptide (FFVKLS)(SEQ ID NO: 62). The Dynabeads® coated with P28 core peptide were incubated with PBMCs for 24 hours. As shown in FIG. 49A-B, untreated control PBMCs had substantial amounts of bound dHSA (shown as red staining 490 in FIG. 49A). After incubation with the Dynabead®-P28 core particles, the PBMCs had significantly reduced bound dHSA 492 (as indicated by substantially lower levels of staining 490 in FIG. 49B) in comparison to the untreated PBMCs.

Accordingly, it has been shown that nanoparticles associated with immunoregulatory peptide inhibitors such as P28 core peptide in accordance with some embodiments herein can be delivered to immune cells bound by immunoregulatory peptides, and further can reduce inhibition of immune cell receptors by immunoregulatory peptides.

Example 48: Expression of P3028 Epitopes

Figure 50A:
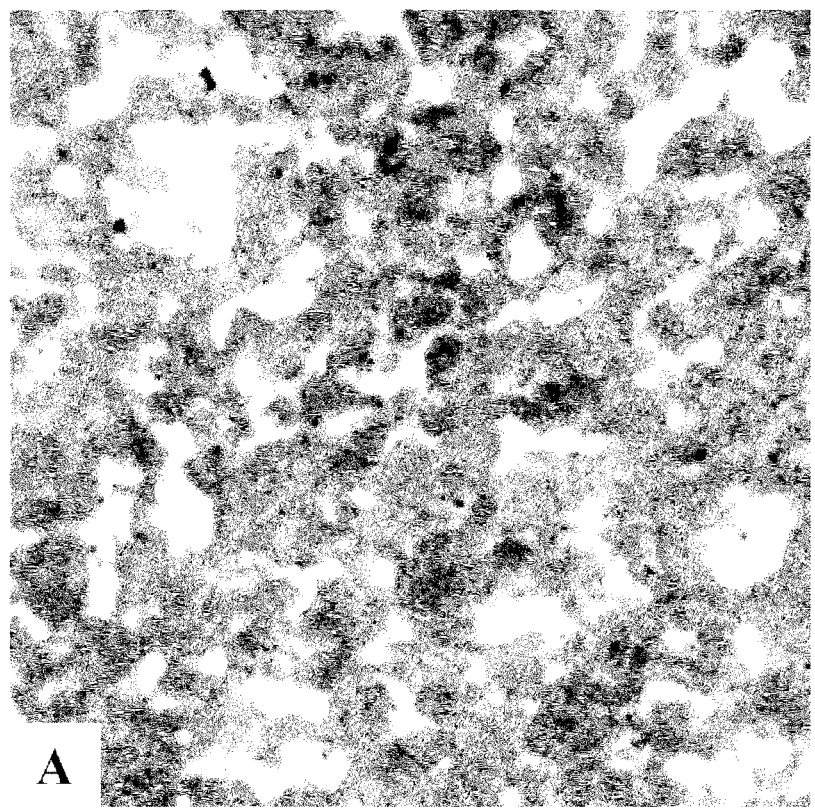
FIG. 50 is a series of microscope images illustrating immunohistochemical (MC) staining of Xenograft of a human prostate cancer, PC3, in nude mice. A first tumour biopsy (FIG. 50A) and a second tumour biopsy (FIG. 50B) are shown. IHC staining of tumour biopsies for the P3028-structure using oligoclonal rabbit antibodies. The expression of the epitope showed considerable heterogeneity with strongly stained areas.
Figure 50B:
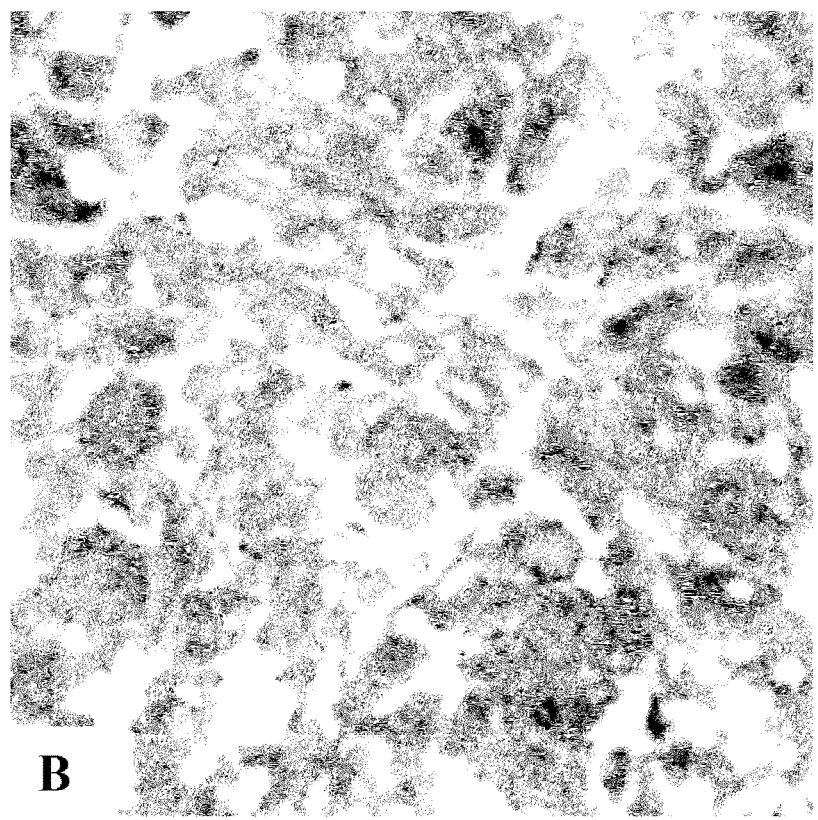

IHC staining of P3028 of human tumours using a rabbit oligo-clonal anti-P3028 antibody (Rimbo) generally shows high expression of this epitope. Some tumours even show a high expression intra-tumorally, in the cytoplasm. This phenomenon has been further investigated in a mouse xenograft model of prostate cancer, PC3. As shown in FIG. 50A, the cytoplasm was strongly stained in certain areas, however, a remarkable heterogeneity in the expression of this epitope was seen with extensive faintly staining areas (FIG. 50B). The P3028 epitope has also been observed to be expressed by damaged HSA, and unexpectedly, this tumour (shown in FIGS. 50A-B) shows a high expression of the P3028 epitope although it is grown in a mouse with no HSA present. Without being limited by any theory, there can be several explanations, e.g. cross reactivity of the antibody with unknown prostate cancer structures/epitopes, uptake of mouse albumin by the tumour cells followed by generation of the 3028 epitope also in mouse albumin (fragmentation or denaturation).

Figure 51A:
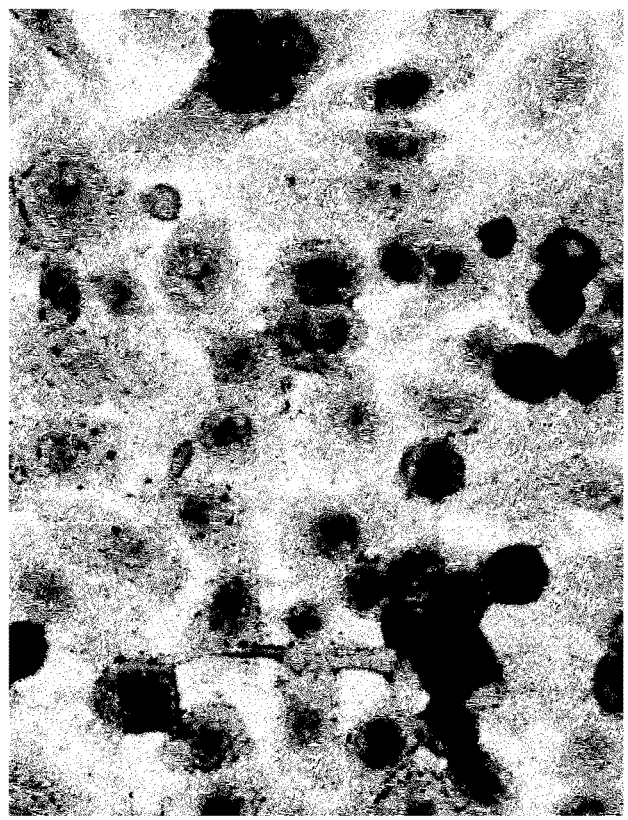
FIG. 51 is a series of microscope images illustrating cultured human prostate carcinoma cells, starved for proteins for 18 hours in accordance with some embodiments herein. A first image of such cells (FIG. 51A) and a second image of such cells (FIG. 51B) are shown. IHC staining for the P3028-structure using oligoclonal rabbit antibodies.
Figure 51B:

In order to further analyze then latter possibility (uptake of albumin) the PC3 cell line was set up in cell culture. FIG. 51A-B clearly shows that when the cells were "starved" (cultured only medium F12 without proteins) for 18 hours the stainability was markedly reduced, in particular in confluent areas but also in peripherally growing tumour cells, compared to sections of the same tumour.

Figure 52:
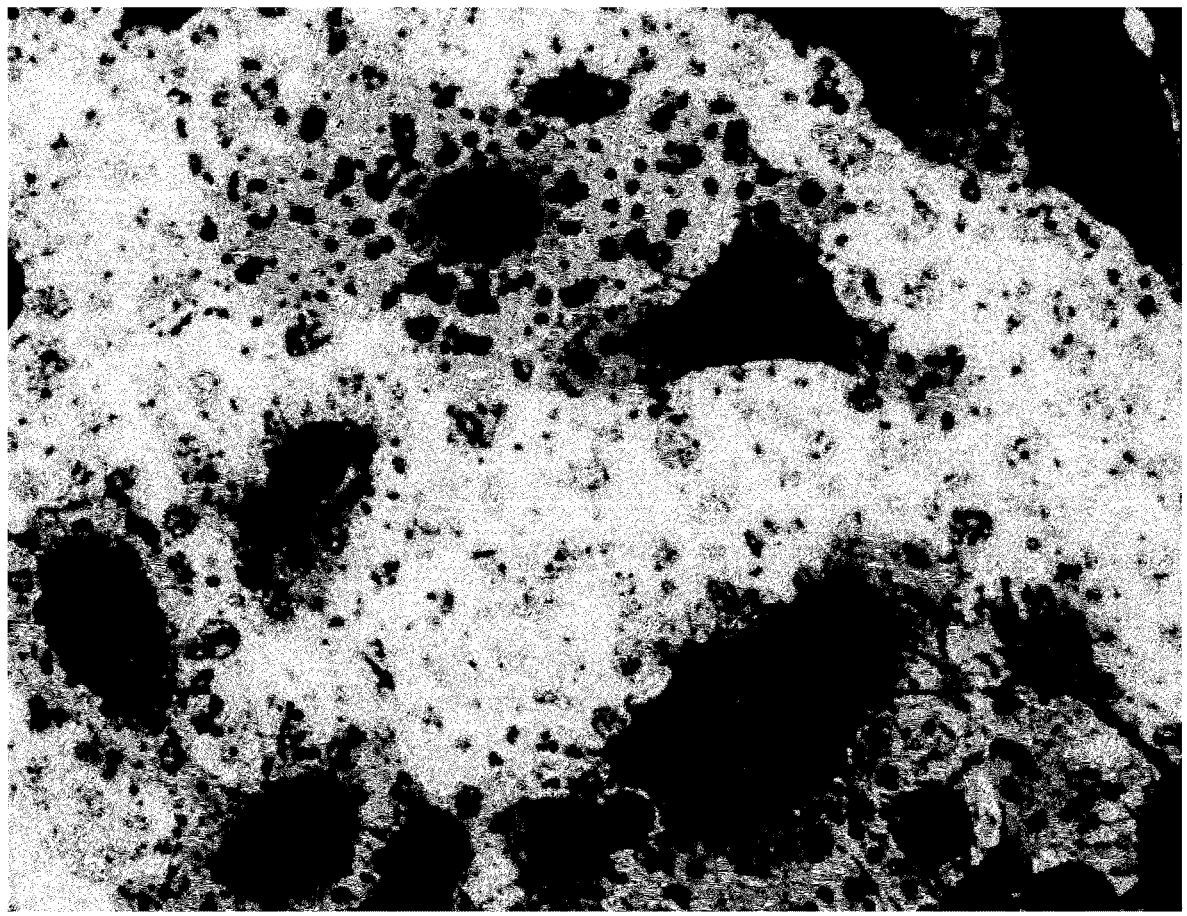
FIG. 52 is a microscope image illustrating cultured human prostate carcinoma cells, starved for proteins for 18 hours and then incubated with human serum albumin for 2 hours in accordance with some embodiments herein. IHC staining for the P3028-structure using oligoclonal rabbit antibodies.

The cultures were then supplemented with HSA, MSA or BFS for 30 or 120 minutes. FIG. 52 shows cultured human prostate carcinoma cells, starved for proteins for 18 hours and then incubated with human serum albumin for 2 hours. IHC staining for the 3028-structure using oligoclonal rabbit antibodies. Strong expression of the P3028 epitope was observed (FIG. 52). Based on these observations it is highly unlikely that the antibody directed against the P3028 epitope cross-reacts with some unknown prostate cancer structures, reasonably in tumour sections from the prostate cancer mouse albumin has been transformed to expose some epitope binding the anti-P3028 antibody.

The P3028 structure has been demonstrated to be a very potent immunoinhibitor, and now has been shown to be efficiently produced by the tumour cells themselves. This reasonably means that these types of tumours have the capacity to efficiently inhibit immune mediated anti-tumour reactivity. Human breast cancers were stained using a biotinylated peptide binding to the P3028 structure. Interestingly, great differences in the staining patterns were obtained where the malignant cells in some tumours did not show any cytoplamatic expression of the P3028 structure. It is contemplated that in accordance with some embodiments herein, the intra-tumoural expression of this structure can be of prognostic or predictive value.

The production or immunoregulatory effect of this immunosuppressor can to be blocked in accordance with some embodiments herein. Considering the rapid and extensive production of the P3028 structure by tumour cells, it is contemplated that conventional approaches might be difficult to supply substances blocking the P3028 structure (antibodies or low molecular weight blockers) in sufficient amounts in order to maintain control of this type of immunosuppression long enough to achieve a therapeutic anti-tumour effect. There are then at least two alternatives: Block the uptake and generation of the P3028 structure by the tumour cells or use binders to the P3028 structure to target toxins to the tumour cells.

Example 49: Activation of the Immune System by P28R in Immunocompetent Mice

Figure 53A:
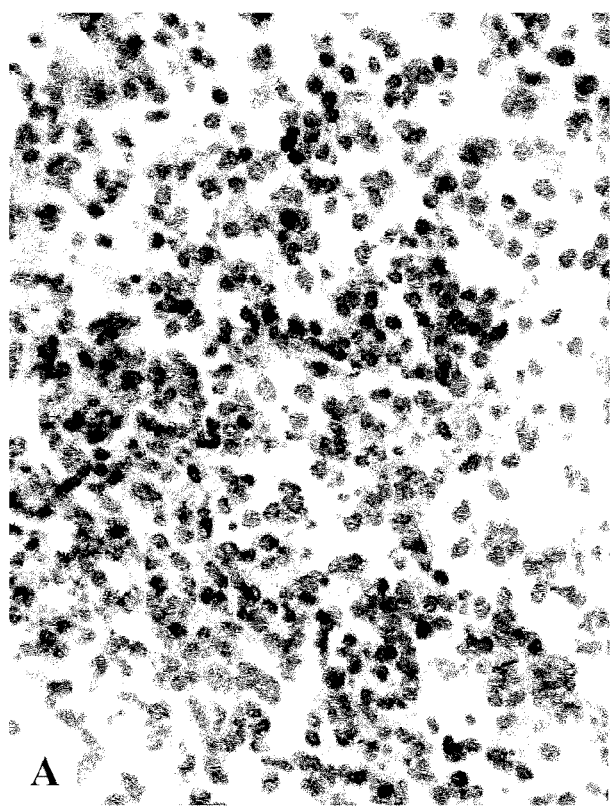
FIG. 53 is a series of microscope images illustrating intra-tumoral treatment of B16 melanoma P28R in accordance with some embodiments herein. The inflammatory infiltrate was demonstrated after 3 days of treatment using a polyclonal rabbit antibody directed against CD45 (FIG. 53A), control sections were incubated with rabbit IgG at the same concentration (FIG. 53B).
Figure 53B:
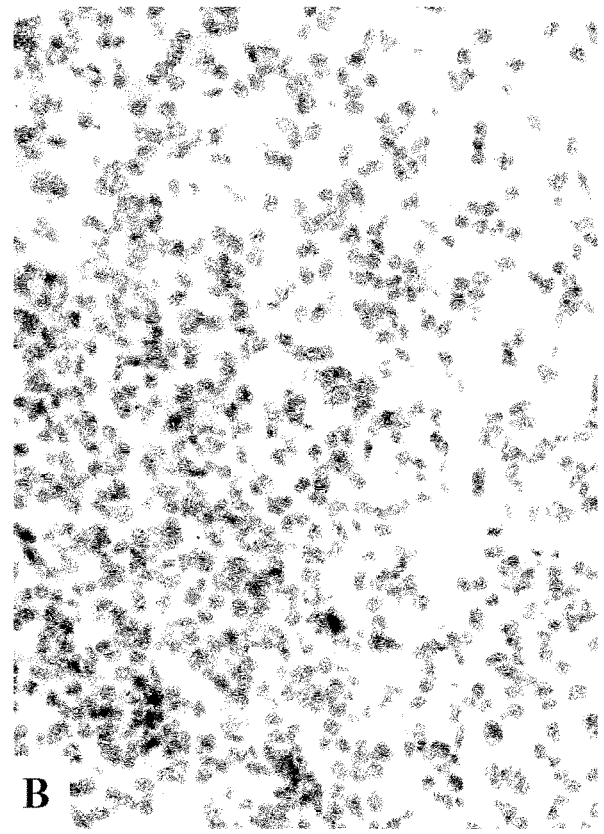

The capacity of P28R to activate the immune system and thereby induce tumor cell-lysis was studied in immunocompetent mice, C57B1, with inoculated B16 melanoma. P28R, 20 nM in 100 microliter, was injected intra-tumorally and the tumors were taken out after 3-5 days. As shown in FIG. 53, the tumors were permeated by CD45+ inflammatory cells after this treatment (FIG. 53A). For comparison a control tumor section was incubated with rabbit IgG at the same concentration (FIG. 53B). It is noted that in animals treated intra-tumorally with P28R a regional lymph node reaction was regularly found. Accordingly, these findings provide evidence of an inhibition of the cancer and such a systemic immune activation against the cancer, a vaccination effect, was achieved.

Figure 54:
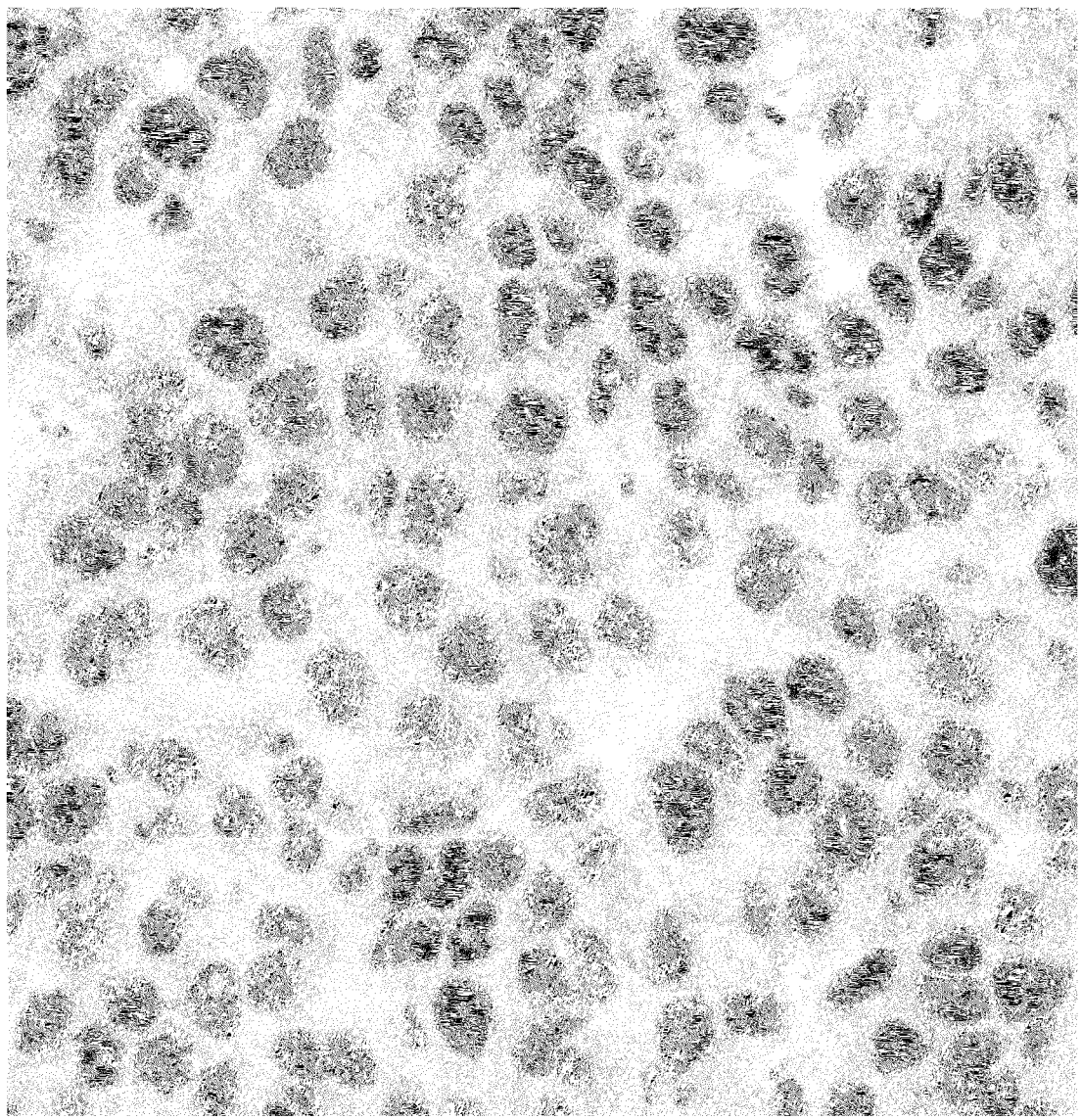
FIG. 54 is a series of microscope images illustrating a B16 melanoma in accordance with some embodiments herein. Contralateral tumour injected with vehicle one day after treatment and with hematoxylin staining is shown.
Figure 55A:
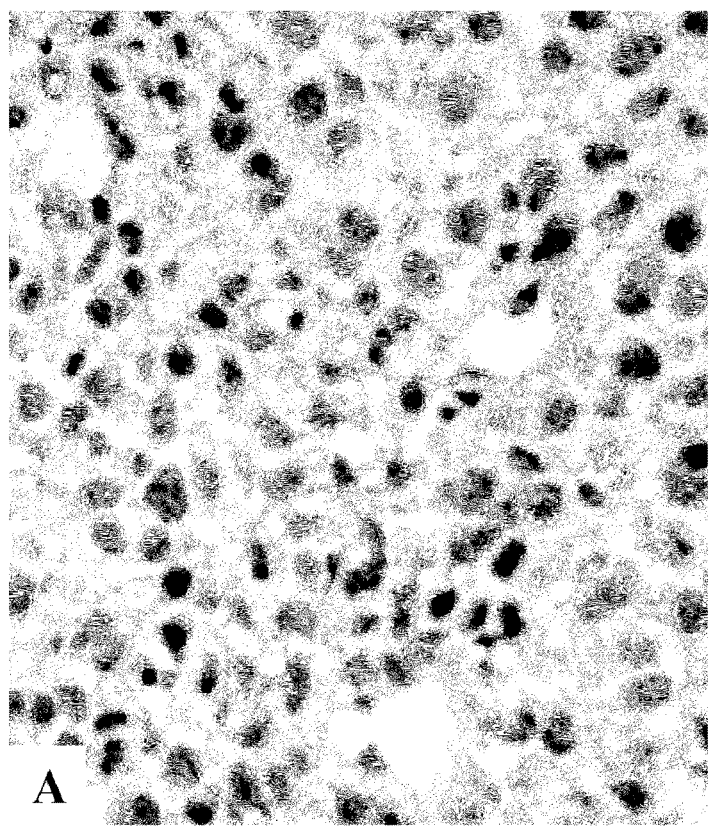
FIG. 55 is a series of microscope images illustrating B16 melanoma 5 days after intra-tumoral injection of P28R (FIGS. 55A and 55C) and the contralateral uninjected tumour (FIGS. 55B and 55D) in accordance with some embodiments herein. MC staining for CD45+ inflammatory cells. Extensive tumour regressive changes and heavy infiltration of CD45+ cells are seen in both treated (FIGS. 55A and 55C) and untreated tumours (FIGS. 55B and 55D).
Figure 55B:
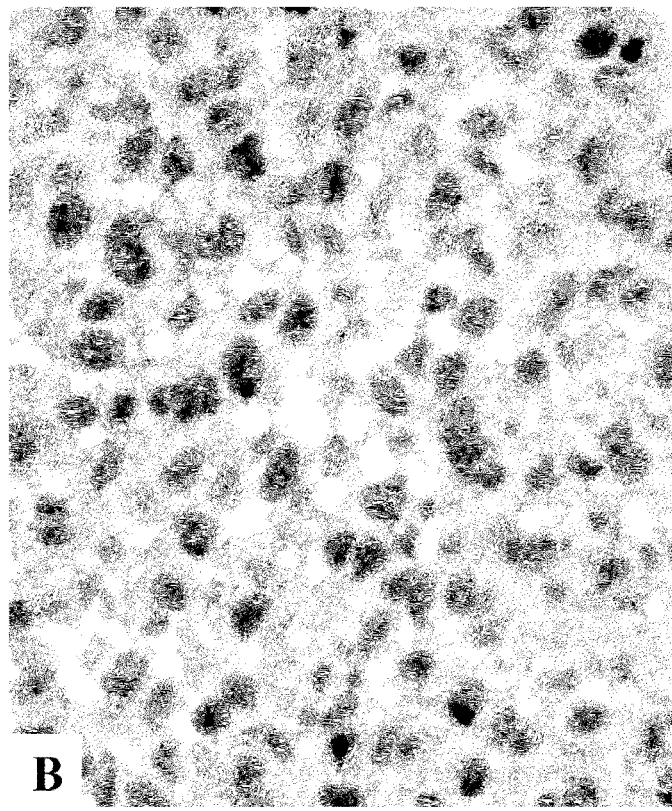
Figure 55C:
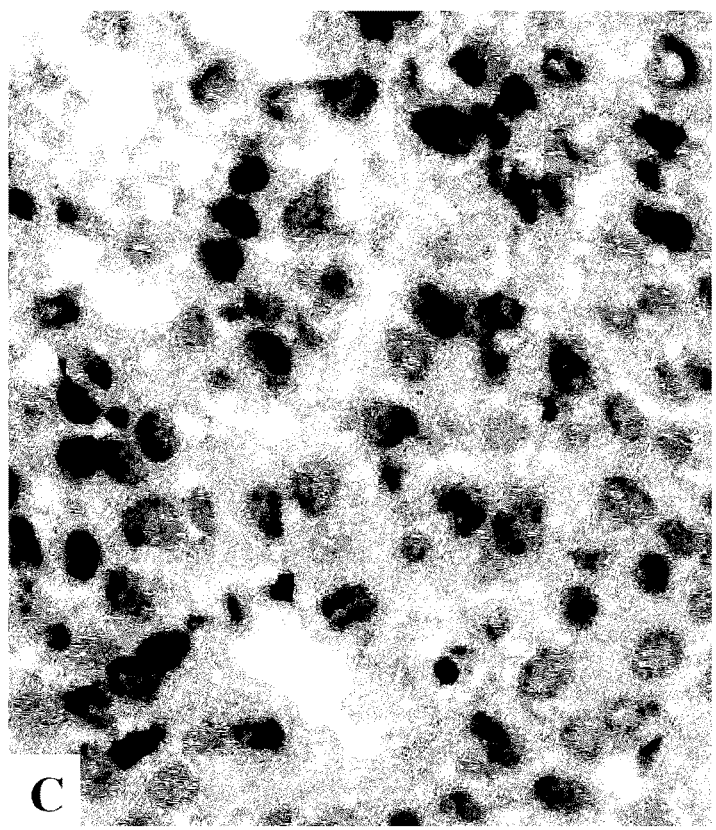
Figure 55D:
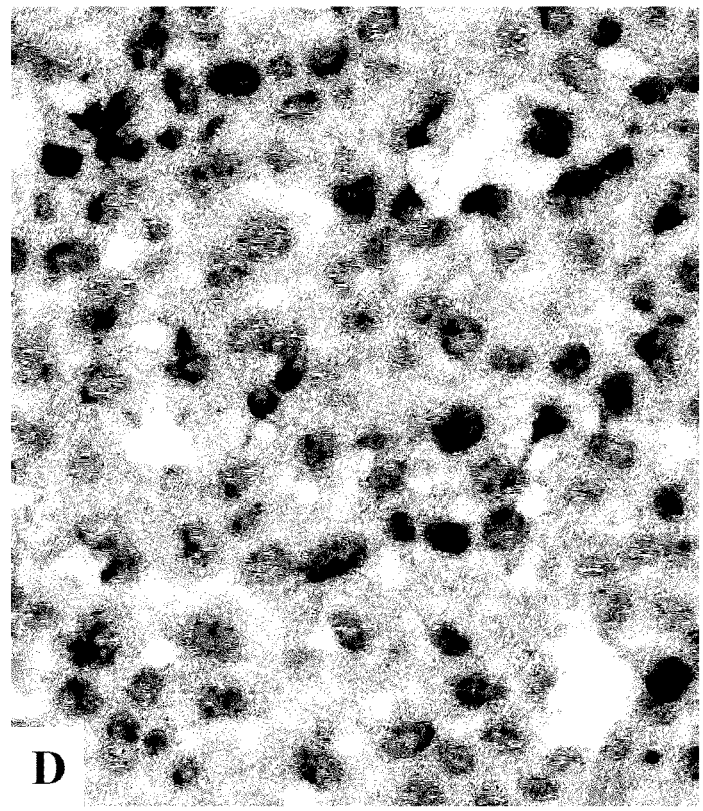

In this tumour model bilateral tumours were inoculated, one in each flank. P28R was injected into one of these tumours and tumour regressive changes were studied in these tumours as well as in the contralateral tumours either left uninjected or injected with the vehicle only. FIG. 54 shows a tumour injected with the vehicle after one day with only minor tumour regressive changes.

It is noted that intra-tumoral injection of P28R resulted in remarkable tumour regressive changes not only in P28R treated tumours but also in uninjected contralateral tumour (FIG. 55A-D) or tumours injected with saline only. The effect in the untreated distant/contralateral tumours increased with time after injection of P28R into the treated tumour.

Figure 56:
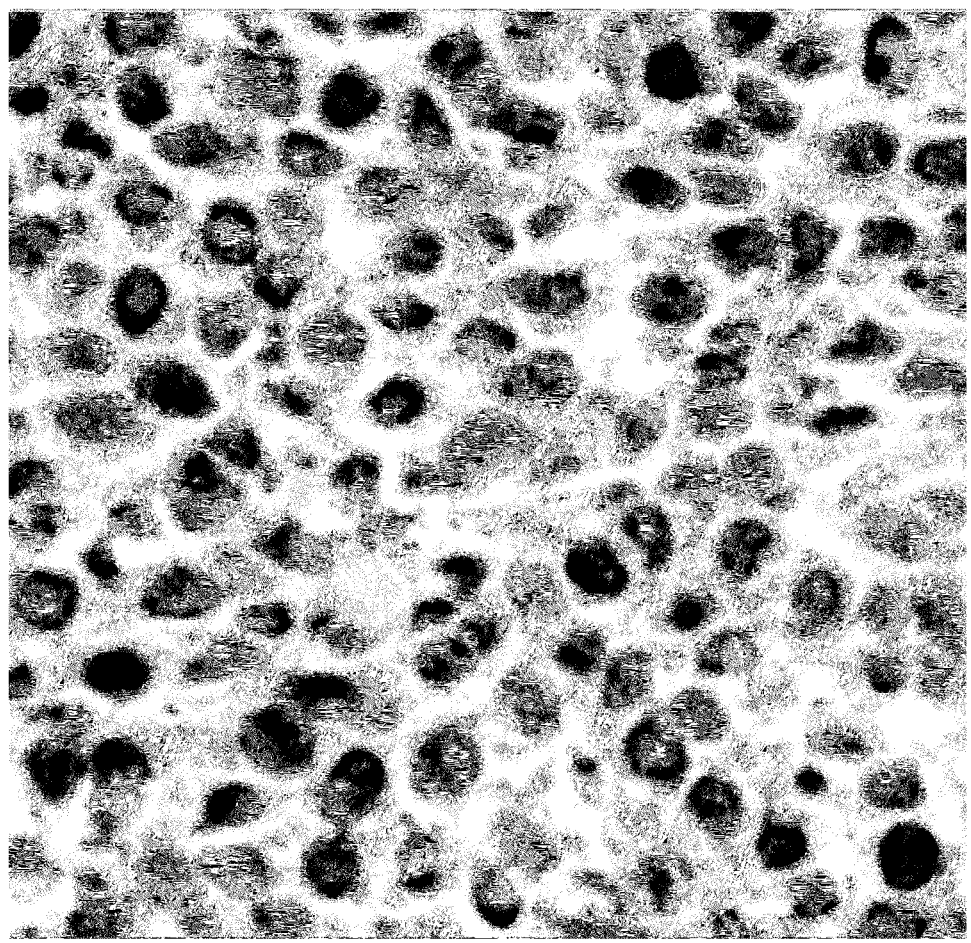
FIG. 56 is a microscope image illustrating Lewis lung carcinoma grown in C57B1 mice in accordance with some embodiments herein. Untreated tumour stained with hematoxylin.

Similar results were obtained in a Lewis lung carcinoma model in B57Bl mice. Compared to tumours in animals treated with P28R, tumours in untreated animals showed a predominance of tumour cells with only minor tumour regressive changes (FIG. 56).

Injection of P28R into the Lewis lung carcinoma tumours resulted in extensive tumour regressive changes; both in the treated tumour (FIG. 57A) and in the untreated contralateral tumour (FIG. 57B). Effects of intra-tumoural treatment of spontaneous tumours in dogs with P28R in accordance with some embodiments herein are summarized below.

Accordingly, it is shown that administration of immunoregulatory peptide inhibitors in accordance with some embodiments herein can induce regressive changes in tumors, including tumors that receive the immunoregulatory peptide inhibitor intratumorally, as well as tumors in other parts of the subject (e.g. tumors contralateral to the tumor that received the immunoregulatory peptide inhibitor).

Examples 50-60: Intratumoral Treatment of Spontaneous Tumors in Dogs with P28R

Seventeen spontaneous canine tumours, of variable histology have been treated by intra-tumoral injection of 40 nmol P28R in 200 microliters. The tumours were resected 3-5 days later, immediately snap frozen and stored at −80° C. until further processed. A detailed description of treatment of the tumors is provided below (see Examples 50-60). In these examples, 15 control dogs with untreated tumours (5 snap frozen and 10 FFPE) were also examined.

Figure 88:
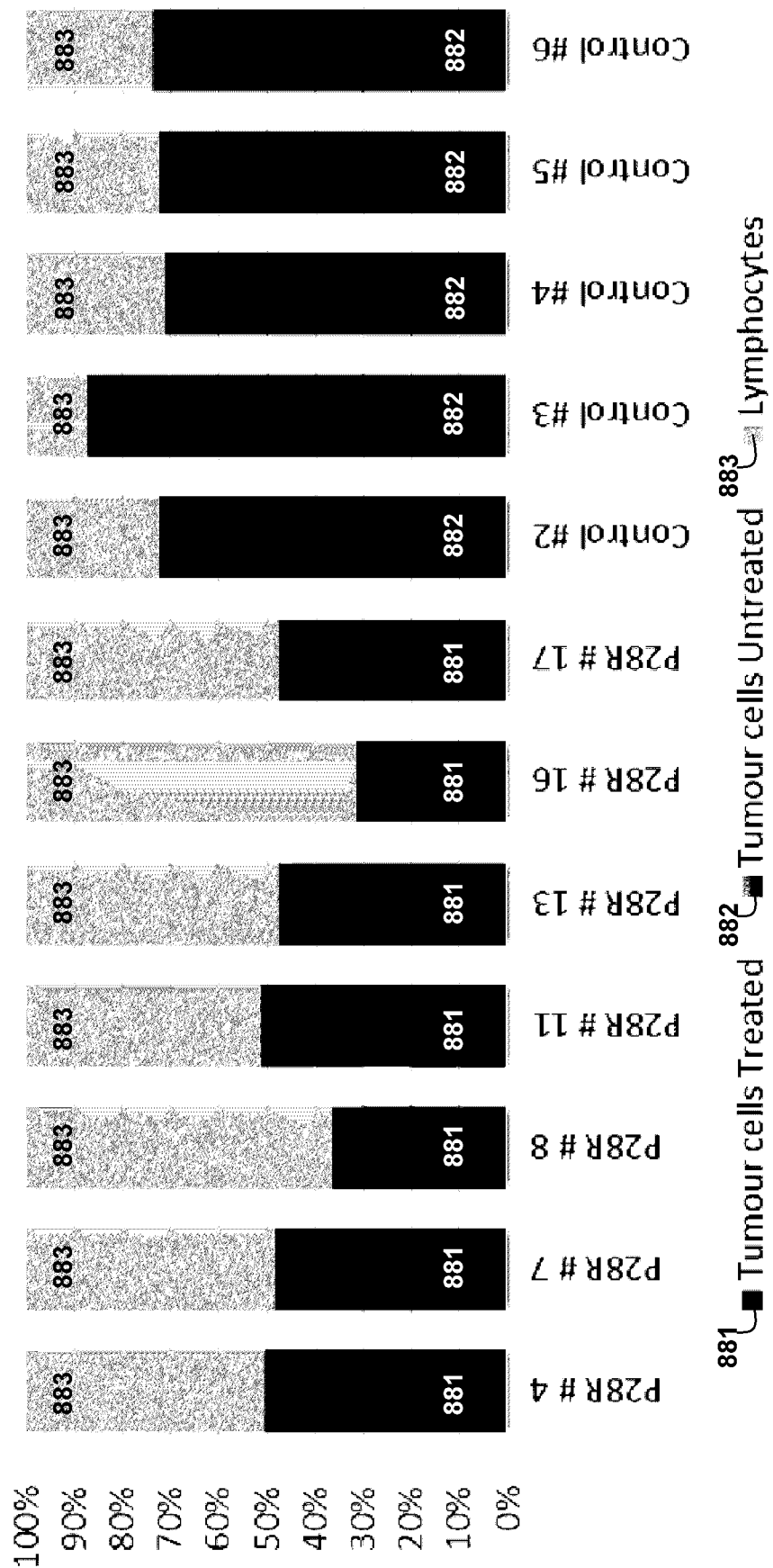
FIG. 88 is a graph showing evaluation of P28R treatment in 7 dogs with breast tumours compared with 5 untreated control dogs, in accordance with some embodiments herein. In representative pictures (n=1-5), the total number of tumour cells from treated (dark bars 881 in P28R #4, #7, #8, #11, #13, #16, and #17) and from control tumours (dark bars 882 in Controls #2, #3, #4, #5, and #6) was counted and compared with the number of inflammatory cells (light grey bars 883).
Figure 89A:
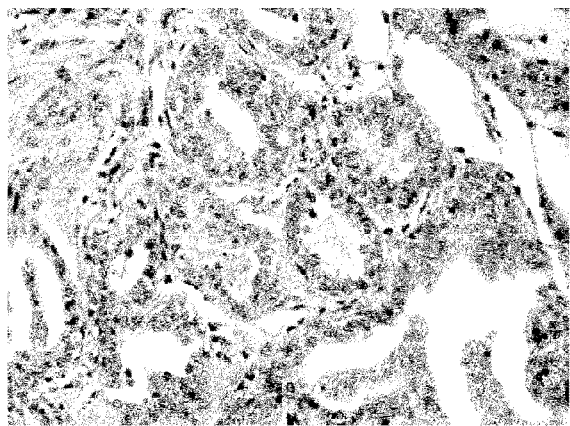
FIGS. 89A-D. are a series of microscope images illustrating four examples of formalin fixed and paraffin embedded canine breast tumours with very sparse infiltration of inflammatory cells close to the tumour cells. The inflammatory cells are mainly located in the stromal areas.
Figure 89B:
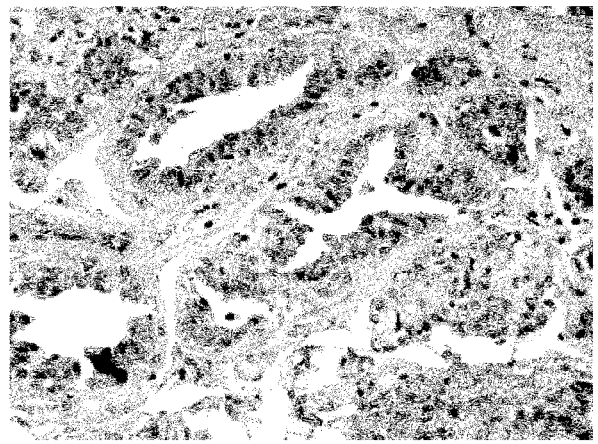
Figure 89C:
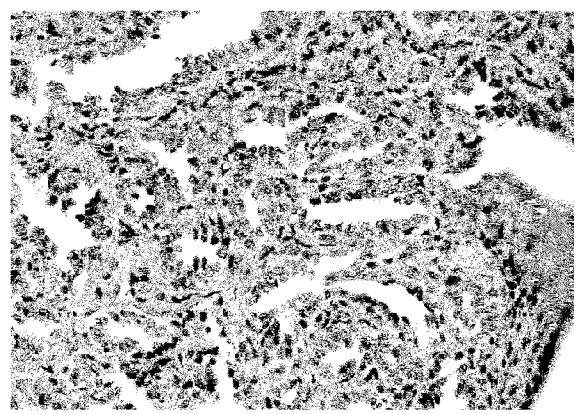
Figure 89D:
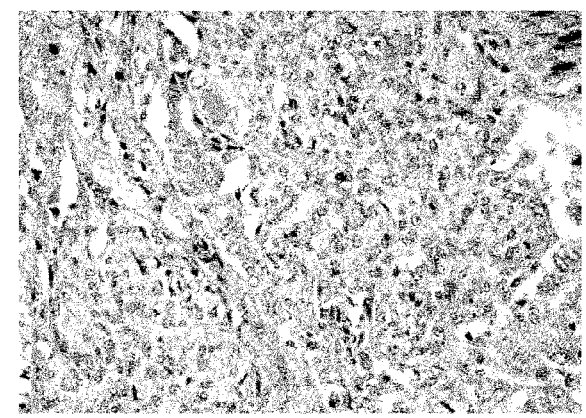
Figure 90A:
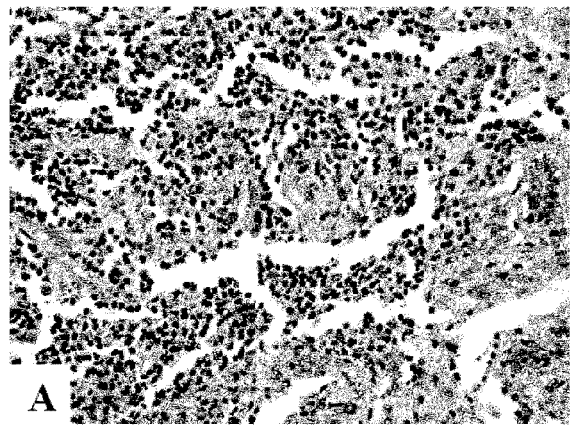
FIGS. 90A-D are a series of microscope images illustrating two formalin fixed and paraffin embedded canine breast tumours with very small areas of inflammatory cells infiltrating into the tumour cell areas close to the tumour cells. These areas were located at the very periphery of the tumour section (FIGS. 90A and 90C). In the main area of the tumours, the infiltration of inflammatory cells close to tumour cells was very sparse as seen in the same section (FIGS. 90B and 90D) even if the stroma of the tumour is heavily infiltrated (FIG. 90D), indicating immunosuppression with blockade of cell migration at this level.
Figure 90B:
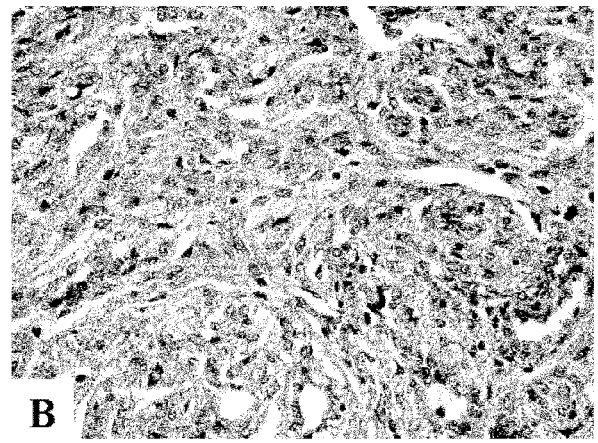
Figure 90C:
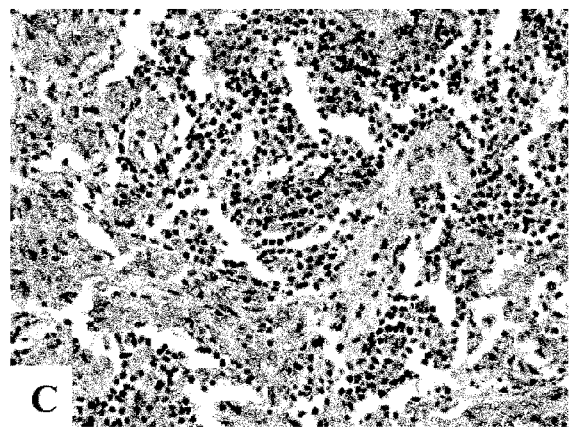
Figure 90D:
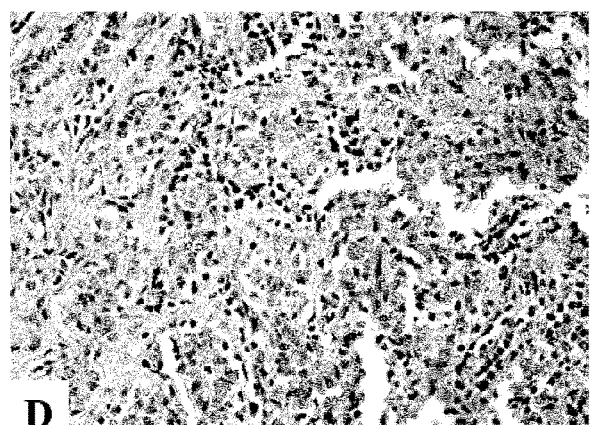

A summary is provided for 7 dogs with treated mammary tumours and 5 untreated control dogs (see FIG. 88). Tumour cells (881 for treated dogs, 882 for untreated control dogs) and lymphocytes (883 for both treated dogs and untreated control dogs) were counted at 400× magnification. The ratio between these cells was used as a measure on the inflammatory infiltrate (FIG. 88). The reproducibility and the influence of tumour heterogeneity on cell counts were evaluated by counting several areas from each tumour section.

The therapeutic efficacy was evaluated as the presence of an inflammatory infiltrate and the occurrence of tumour cell regressive changes. As migration of effector cells close to tumour cells is one important, but often inhibited function of these cells, the effect of P28R was specifically evaluated as the presence of inflammatory cells infiltrating into the tumour cell areas close to the tumour cells. Antibodies against the following markers of inflammatory cells have been used: CD3, CD8, CD45 and CD68.

Figure 78A:
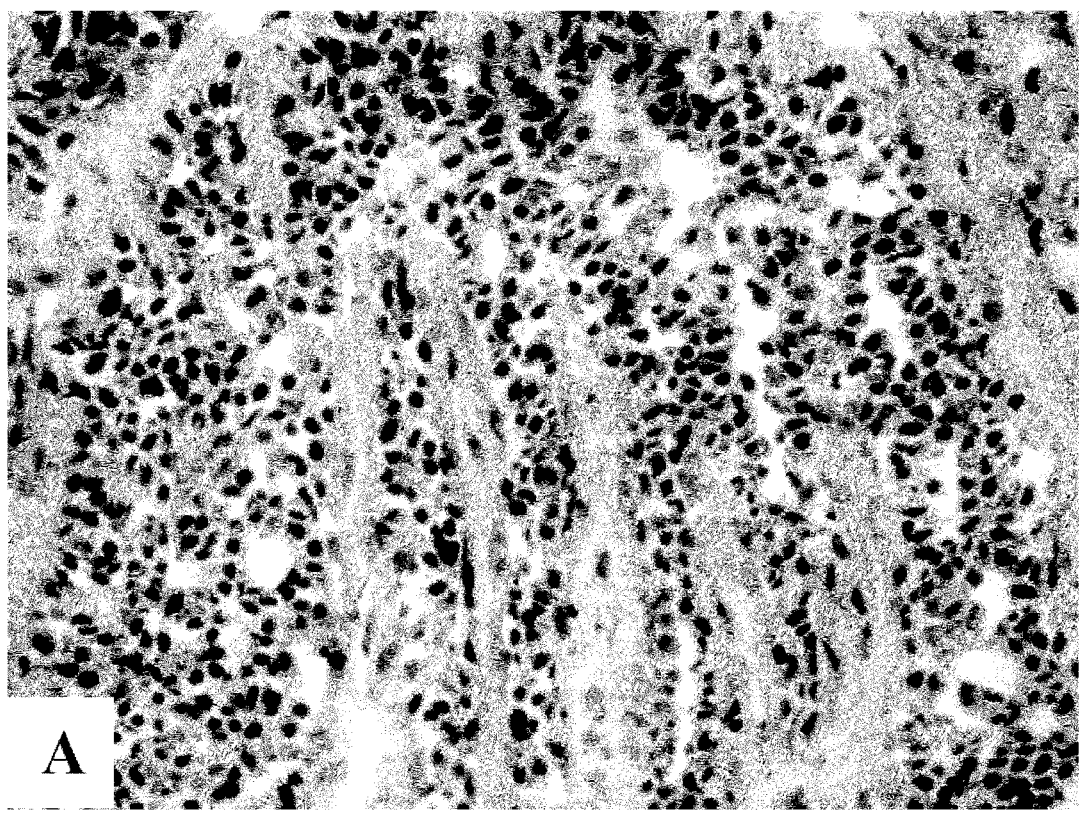
FIG. 78 is a series of microscope images illustrating a dog breast tumour after intra-tumoral injection of vehicle in accordance with some embodiments herein. The section was stained with hematoxylin showing a fairly well preserved glandular structure (FIG. 78A). The inflammatory infiltrate was visualized by staining for CD45+ cells (FIG. 78B).
Figure 78B:
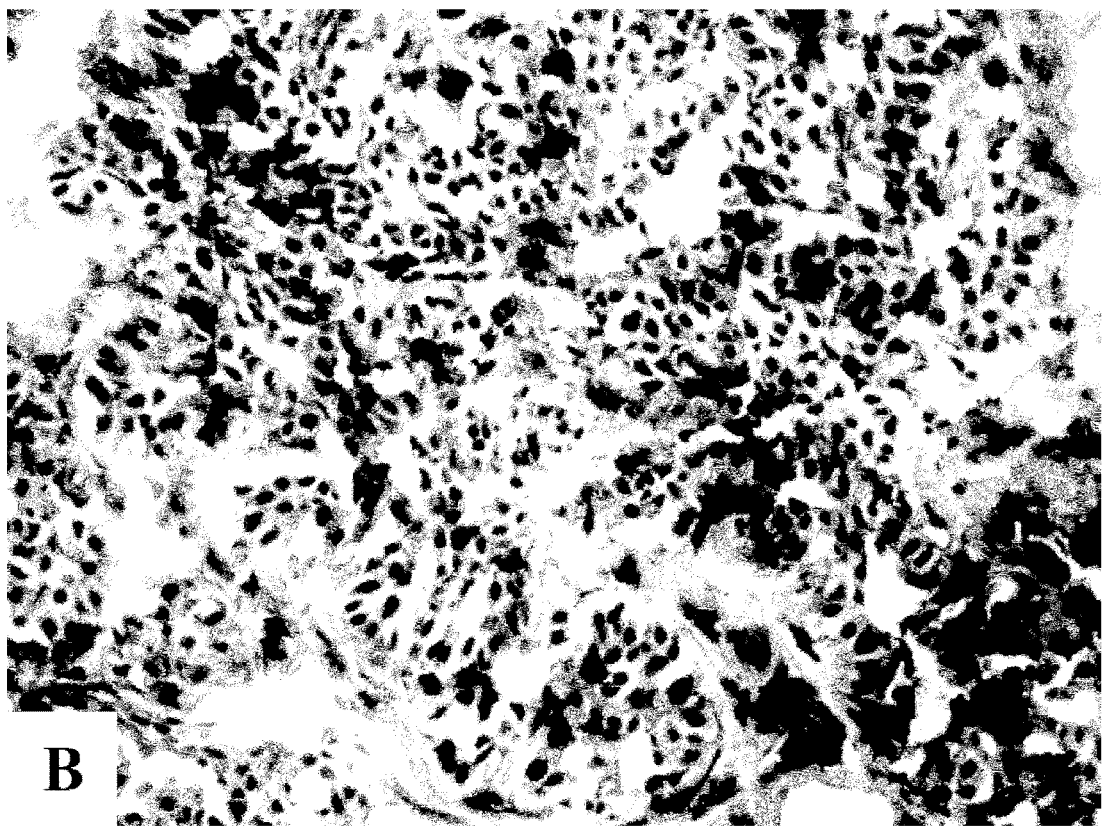

As outlined in Examples 50-54, five spontaneous tumours were treated intra-tumorally with P28R, in all of these a strong inflammatory infiltrate was observed, mainly characterized as CD45+ cells and NK cells stained by antibodies directed against CD56 and NCR1 (see FIG. 78A-B). Extensive tumour regressive changes were found in three of these and in one, the apocrine gland carcinoma, with thick tumour nodules, regressive changes were seen at least in thin lesions and at the periphery of the tumour nodules. The thick tumour nodules were, however, heavily infiltrated by NK-cells. Interestingly, in a breast tumour with regional metastases, also these lesions were heavily infiltrated with inflammatory cells and showed extensive tumour regressive changes (FIG. 58). Two tumours were injected with the vehicle, in one of these, a breast tumour, a spontaneous inflammatory infiltrate was found. The other, a testis tumour, did not show any inflammatory reaction.

More than 20 dogs have been treated with P28R, including 4 in the toxicological study (CiToxLab®, Denmark) with 200 nM administered in 1 mL subcutaneously and 17 dogs in the treatment study reported here with 40 nM in 200 microliters intra-tumourally. None of these dogs showed any systemic side effects.

Treatment schedule/strategy: The drug, P28R, is injected intra-tumorally, 40 nM in 200 µl. The tumours are then resected within 3-5 days and representative biopsis are immediately "snap frozen" and stored frozen/at −80° C. until further investigated.

Objective of the treatments, performed in accordance with some embodiments herein, include:

1. Evaluate infiltration of inflammatory cells in H&E stained sections
2. Characterize inflammatory cells immunohistochemically. (Based on the pronounced stimulation CD3+ lymphocytes 48 h after exposure to P28R in a human ex vivo model, staining for T-cells was included in the analysis of the inflammatory infiltrate)
3. Analyse occurrence of tumour regressive changes, morphologically and immunohistochemically.

Dog tumor tissues were removed, snap-frozen in isopentane in dry ice and kept at −80° C. until further processed. Frozen tissues were embedded in OCT cryomount (Histolab, Goteborg, Sweden) and sectioned with 5-7 µm thickness using Cryostat (CM3050S, Leica®, Sweden) and the tissue sections were kept at −80° C. until used. Tissue sections were fixed either in aceton or with 4% formalin for 10 min followed by rinsing in distilled water. Tissue sections were then washed with PBS for 5 min for three times and blocked with 1× animal free blocker (VECTOR, Goteborg, Sweden) and 10% serum (human AB serum (Sigma-Aldrich®, Schnelldorf, Germany) or normal dog serum (Abcam®, Cambridge, UK) for 30 min followed by incubation with primary antibody for 1h at room temperature and then washed three times with PBS for 5 min Immunohistochemistry staining was visualized with alkaline phosphatase (AP) or diaminobenzidine (DAB). After primary antibody incubation and washing, AP staining was carried out using EXPOSE Mouse and Rabbit specific AP (Abcam®, Cambridge, UK) by applying AP-conjugate (Expose Mouse and Rabbit specific AP, Abcam®, Cambridge, Cambridge, UK) on the tissue sections and incubating for 30 min, followed by washing four times with PBS for 5 min. Thereafter tissue sections were incubated with Enhancer (Expose Mouse and Rabbit specific AP, Abcam®, Cambridge, UK) for 4 min. Without rinsing off the Enhancer, mixture of equal volume of Naphtol Phosphate (Expose Mouse and Rabbit specific AP, Abcam®, Cambridge, UK) and Fast Red (Expose Mouse and Rabbit specific AP, Abcam®, Cambridge, UK) (1:1) and levamisole (DAKO, carpinteria, USA) (1 drop/ml) were applied on tissue sections and incubated for 8 min at room temperature. Tissues were then washed with PBS four times. After rinsing in distilled water counter-staining was carried out with Mayers hematoxylin (Histolab, Goteborg, Sweden) for 10 min, following washing with running tap water for 10 min and rinsing in distilled water before mounting tissue sections with aqueous mounting medium (AQUA PERTEX, Histolab, Goteborg, Sweden). For immunohistochemistry with DAB, staining was performed using DAKO Autostainer plus (DAKO, Glostrup, Denmark) using the EnVision Flex High pH-kit (DAKO, Glostrup, Denmark) according to the company's instruction. The stained sections were mounted with CYTOSEAL XYL (Thermo Scientific®, Cheshire, UK).

Antibodies that have been used in this study were the following. Rabbit active pro caspase 3 (ab13847, Abcam®, Cambridge, UK), mouse pan-cytokeratin (C1801, Sigma-Aldrich®, Schnelldorf, Germany), Rabbit mouse NCR1 (bs10027R, BioSite®, Sweden), Rabbit IgG (ab27478, Abcam®, Cambridge, UK), mouse CD3 (ab699, Abcam®, Cambridge, UK), mouse CD8a (ab34105, Abcam®, Cambridge, UK), mouse CD45 (ab34126, Abcam®, Cambridge, UK), goat anti-Rabbit IgG Envision FLEX/HRP (DAKO, Glostrup, Denmark), goat anti-Rabbit and mouse IgG Envision FLEX/HRP (DAKO, Glostrup, Denmark).

Accordingly, intra-tumoral administration of immunoregulatory peptide inhibitors to subjects in accordance with some embodiments herein can treat, ameliorate, eliminate, and/or destroy tumors.

Example 50: D Dog Tumour 1

Clinical Data

Breed of dog: Cross breed. Weight: 15.1 kg. Sex: Spayed. Age: 85 months. Type of tumour: Apocrine gland carcinoma of the anal sac (primary tumour). Size of tumour: 25 mm Clinical observations immediately after injection of the P28R and during the time interval until resection: No systemic adverse events were observed.

Biopsies Obtained:

A large biopsy was taken from the site of injection in direction of drug injection from the periphery towards the centre of the tumour. This was divided into two equal parts, biopsy 1 and 2. At the "bottom" of first biopsy a small haemorrhage, 2-3 mm in diameter was observed. Another biopsy was cut out, injection site 1, and still at the bottom of this third biopsy the haemorrhage continued. A fourth biopsy was obtained from this area, injection site 2.

Histopathological Examination.

H&E stained sections were obtained from all biopsies described above. These were investigated for occurrence of tumour growth, infiltration of inflammatory cells and various degrees/types of tumour regressive changes.

H&E Stained Sections

This tumour grew in large bulky tumour nodules, sometimes with central necroses, surrounded by stromal tissue.

Figure 59:
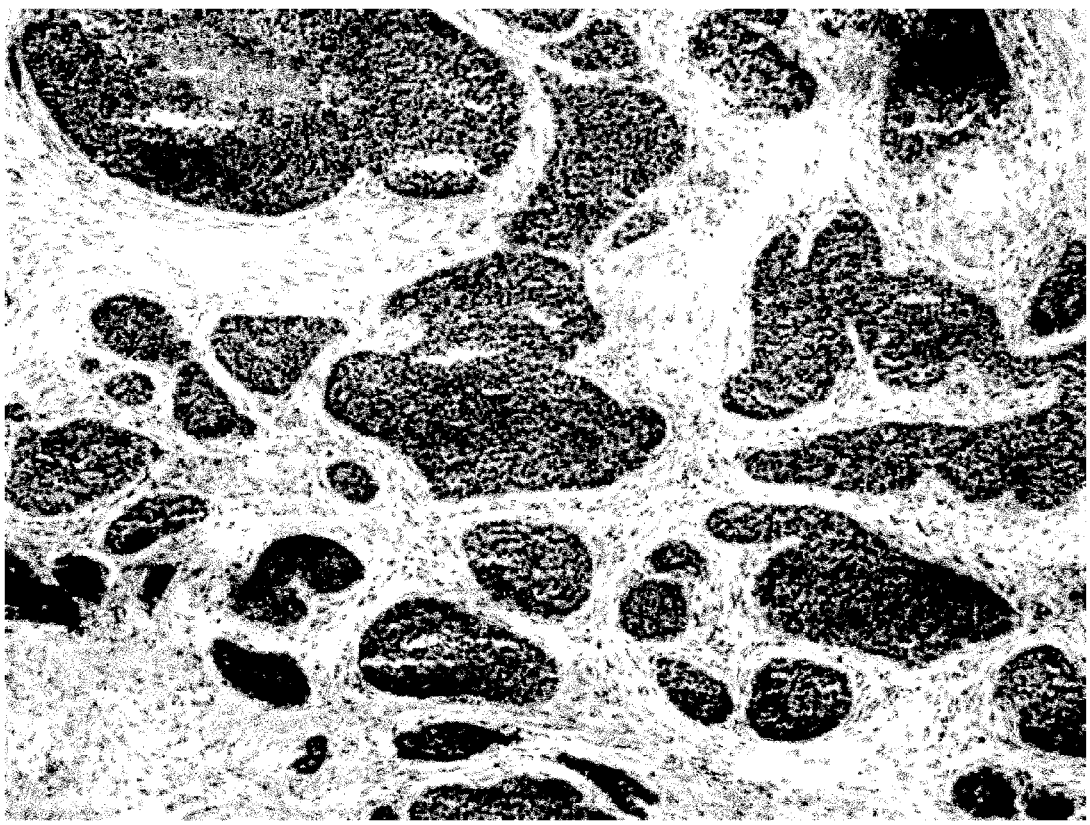
FIG. 59 is a microscope image illustrating H&E staining of a dog anal adenocarcinoma in accordance with some embodiments herein.

Tumour regressive areas were only observed at the periphery of such nodules or in areas of thin tumour growth (see FIG. 59).

Figure 60:
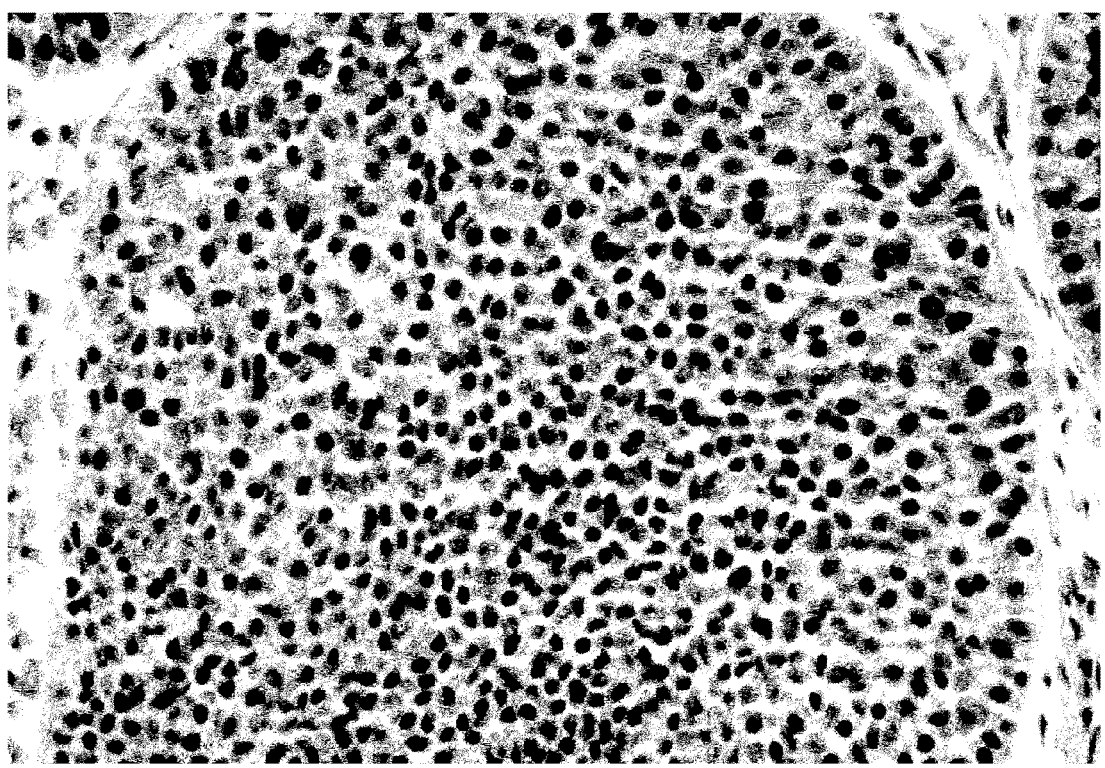
FIG. 60 is a microscope image illustrating H&E staining of a major tumour nodule of a dog, apparently with two cell types, in accordance with some embodiments herein.
Figure 61A:
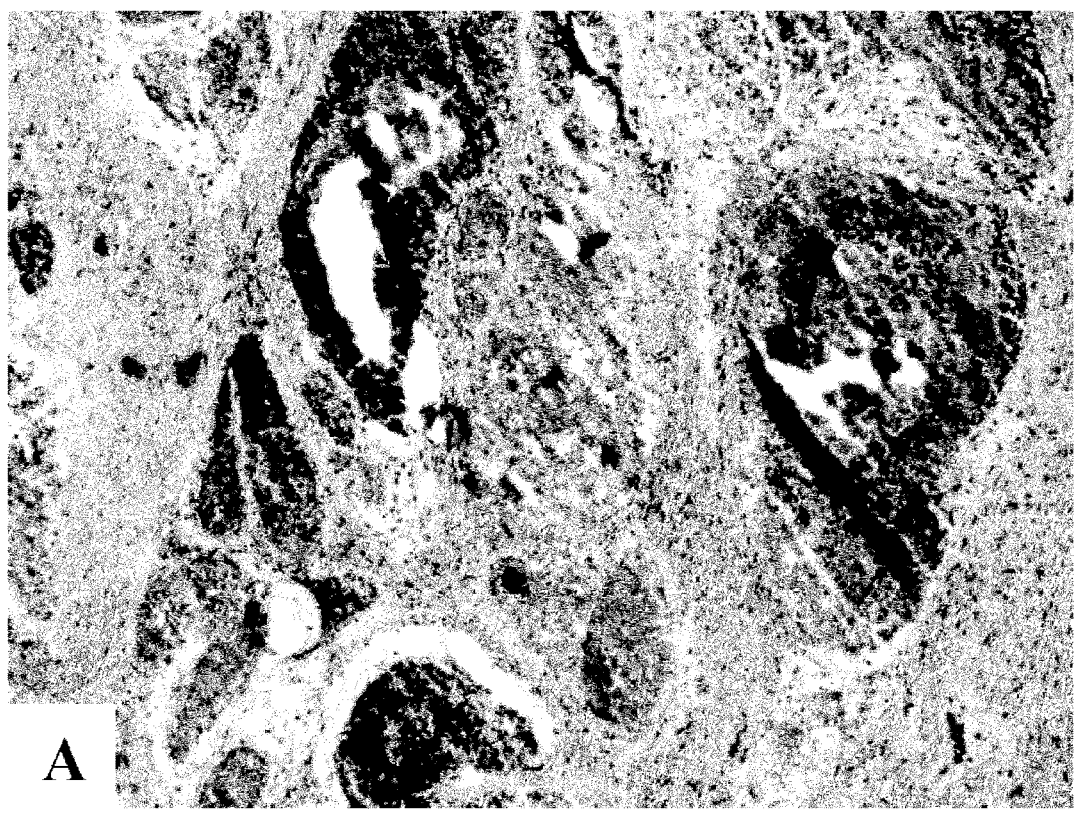
FIG. 61A illustrates staining of the central part of the injection site with some destruction.
Figure 61B:
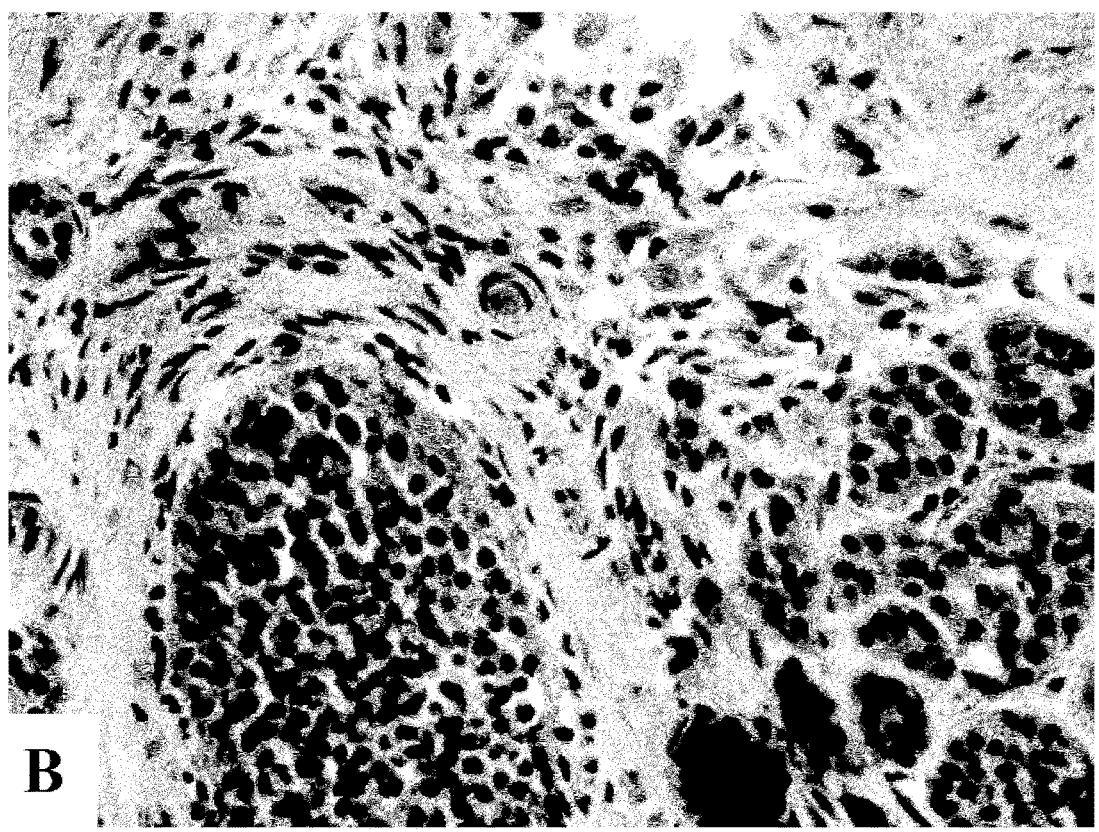
FIG. 61B illustrates staining of an area with an inflammatory infiltrate and some tumour regressive changes.

A careful examination of such tumour nodules revealed the existence of at least two types of cells, large cells with faintly staining nuclei and small cell with dense nuclei (FIGS. 60-61).

IHC Characterization of the Inflammatory Infiltrate

Characterization of the inflammatory cells has mainly focused on the innate immune response as the tumours were resected 3 days after intra-tumoral injection of the drug. Staining with an antibody directed against CD45 is shown in FIG. 62.

As shown in FIG. 62, the CD45+ inflammatory cells are mainly localized in the stromal areas surrounding the tumour nodules, which are not infiltrated by these cells. Tumour regressive changes, immune mediated tumour cell lysis, is only observed at the periphery of the tumour nodules or in "thin" tumour areas.

Figure 63A:
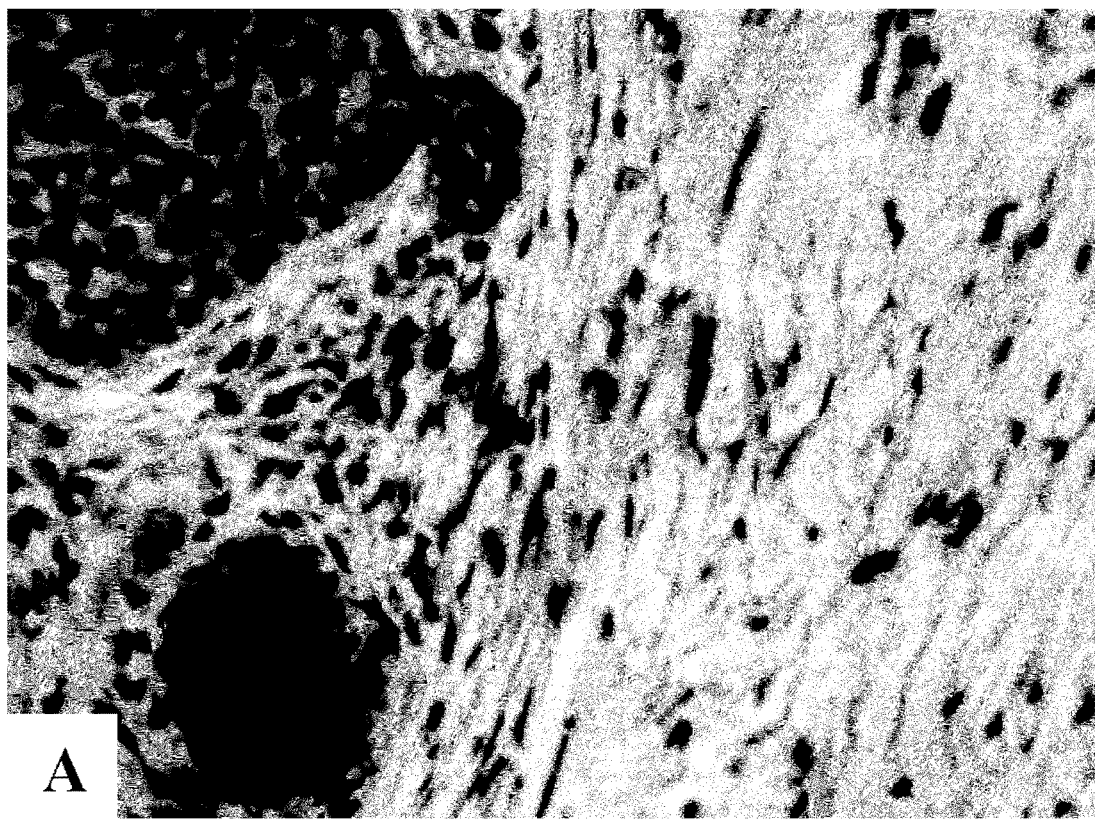
FIG. 63A and FIG. 63B are shown.
Figure 63B:
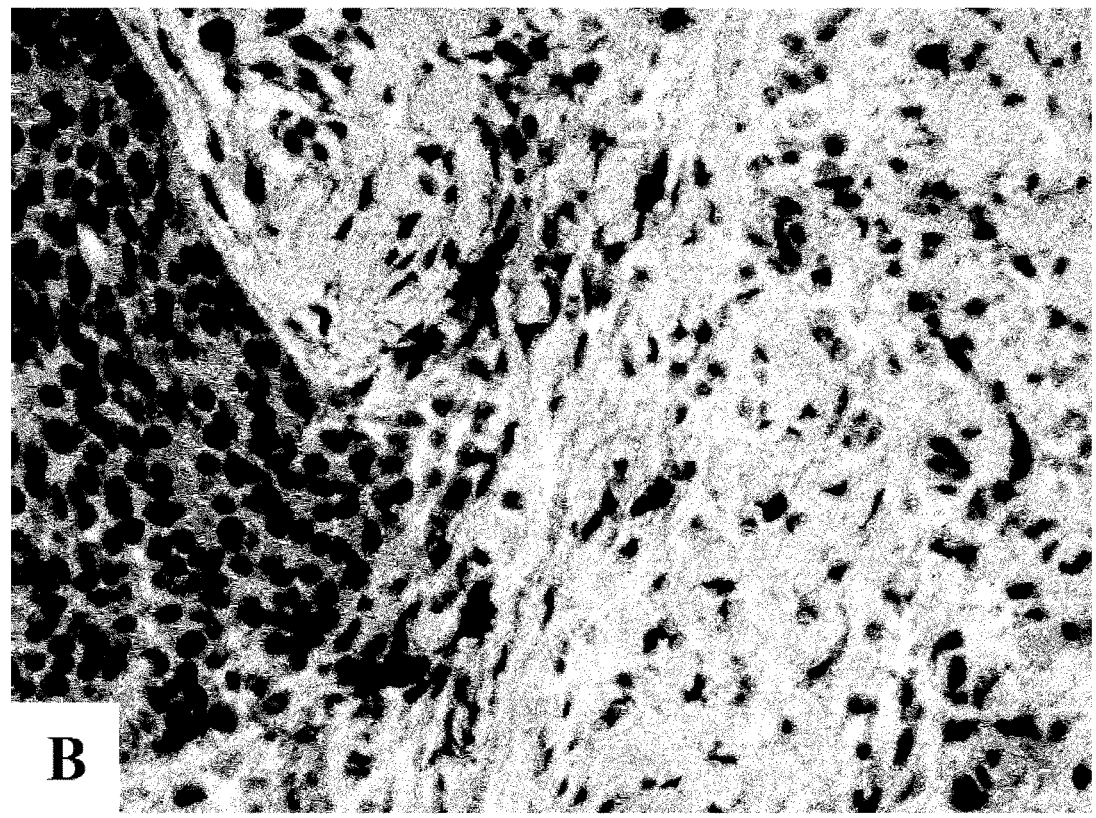
Figure 64A:
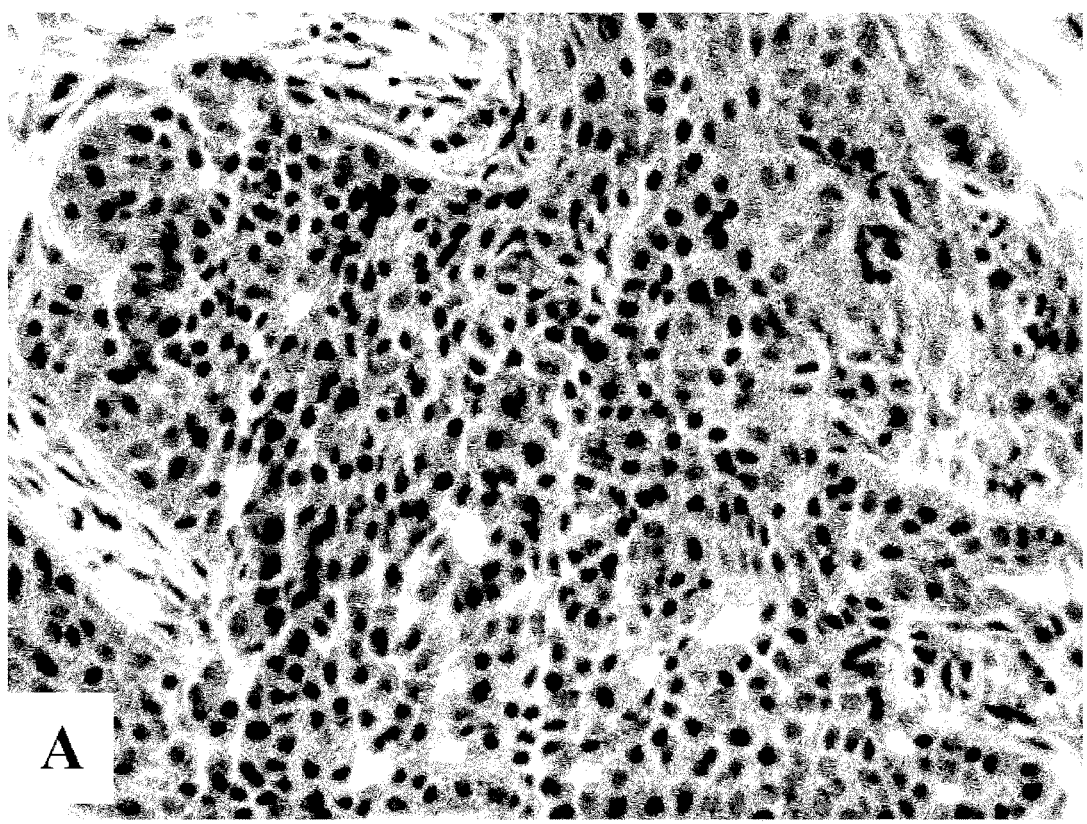
FIG. 64 is a series of microscope images illustrating inflammatory cells infiltrating into a dog tumour nodule in accordance with some embodiments herein. The inflammatory cells infiltrating into a tumour nodule are stained for CD56 (FIG. 64A) and NCR1 (FIG. 64B).
Figure 64B:
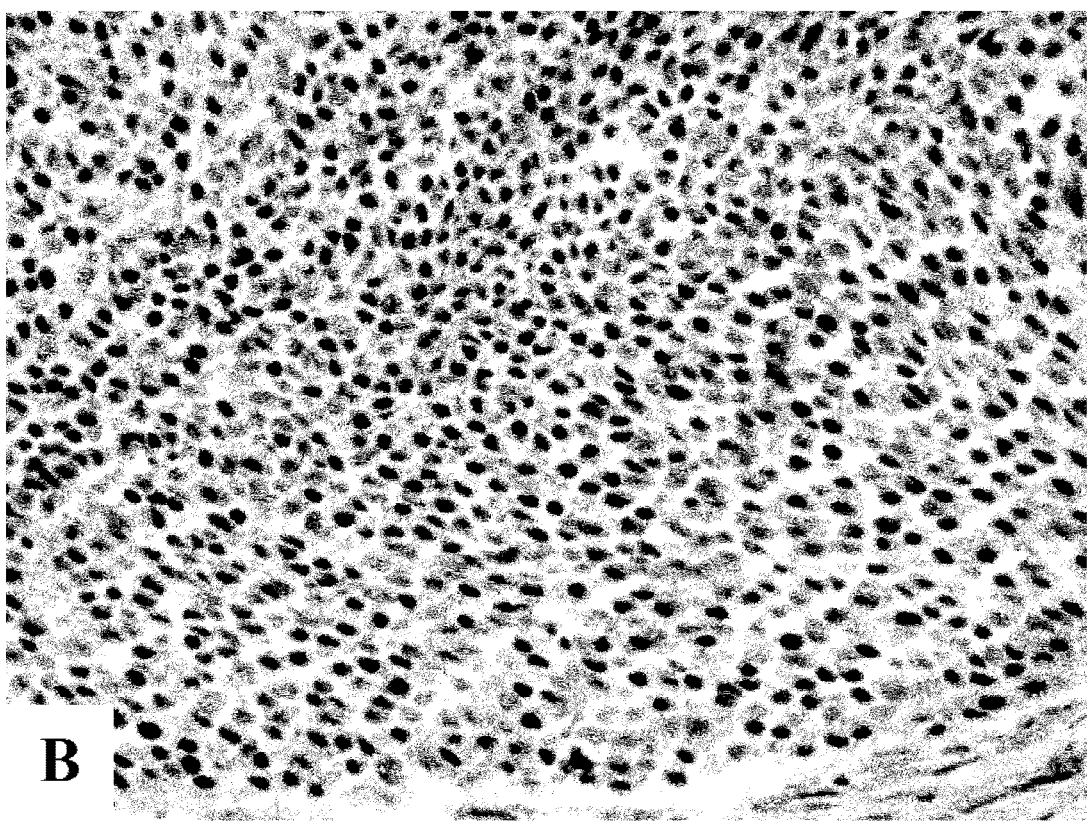
Figure 65A:
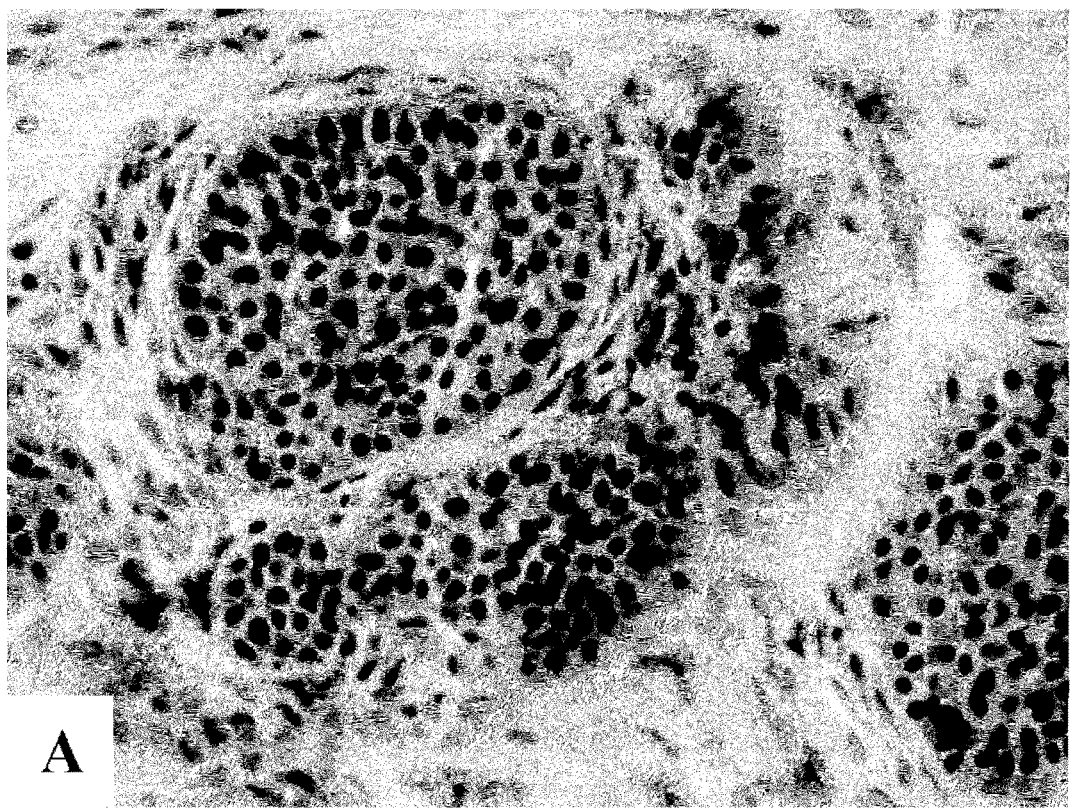
FIG. 65 is a series of microscope images illustrating CD56+ cells are found both infiltrating tumour nodules and stromal area of a dog in accordance with some embodiments herein. Both of FIG. 65A and FIG. 65B are pictures from the same section. It is noted that the staining of the tumour nodule infiltrating cells is much weaker and there seems to be a gradient with more strongly stained cells at the periphery of the nodules.
Figure 65B:
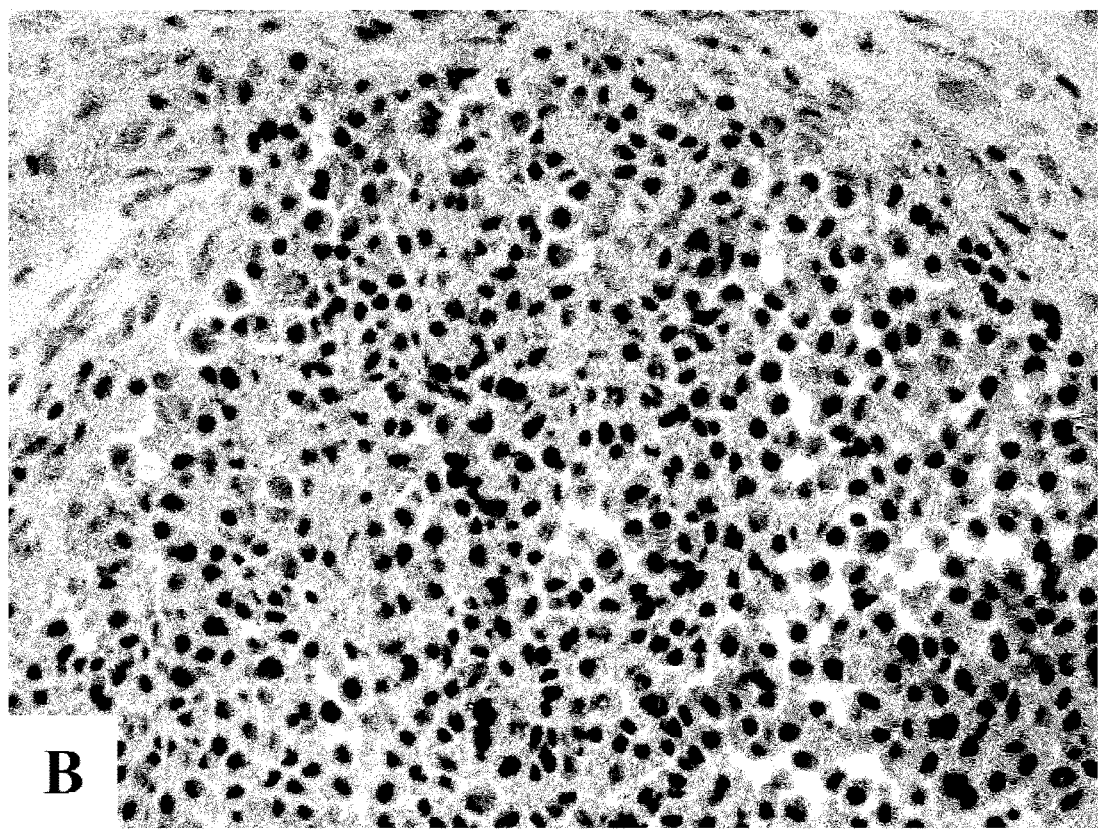

As shown in FIG. 63, only few scattered CD3+ or CD8+ cells were found after treatment in this tumour.

Staining for NK-cells, CD56 and NCR1

As the tumour was resected three days after intra-tumoural treatment and only minor T-cell recruitment was found, the innate response was investigated by staining for NK-cells and macrophages (see FIGS. 64-65).

As shown in FIGS. 64-65, The more intense staining of CD56+ cells in the stromal areas and the gradient of staining intensity of these cells in the tumour nodules indicate that the CD56 marker might be lost from the cells (shedding) possibly due to high proteolytic activity in these areas.

Accordingly, it has been shown that apocrine gland carcinoma of the anal sac, resected 3 days after intra-tumoural treatment with P28R in accordance with some embodiments herein. A strong mainly stromal infiltration of CD45+ cells was found with infiltration close to tumour cells with tumour regressive changes found in "thin" tumour areas and the peripheral parts of some tumour nodules. CD56+ cells were found to permeate the tumour nodules.

Accordingly, intra-tumoral administration of immunoregulatory peptide inhibitors to subjects in accordance with some embodiments herein can cause regressive changes in carcinoma tumors of the anal sac, and can treat, ameliorate, eliminate, and/or destroy such tumors.

Example 51: D Dog Tumour 2

Clinical Data

Breed of dog: N/A. Weight: 36.0 kg. Age: 106 months. Sex: Male. Type of tumour: Testis tumour (primary tumour). Size of tumour: 50 mm Clinical observations immediately after injection of the vehicle and during the time interval until resection: No systemic adverse events were observed.

Biopsies Obtained:

One large biopsy was taken from the site of injection in direction of drug injection from the periphery towards the centre of the tumour.

Histopathological Examination.

H&E stained sections were investigated for occurrence of tumour growth, infiltration of inflammatory cells and various degrees/types of tumour regressive changes.

H&E Stained Sections

All three biopsies were carefully analysed and showed the same result, a testicular tumour with no signs of tissue destruction and only a weak inflammatory reaction of the degree usually found in these tumours (FIG. 66A). The degree of inflammatory reaction was confirmed using staining for CD45 (FIG. 66B).

Accordingly, it has been shown that no inflammatory reaction or tumour regressive changes were observed in this tumour after intra-tumoral injection of the vehicle of the drug formulation in accordance with some embodiments herein.

Example 52: D Dog Tumour 3

Clinical Data

Breed of dog: Pug. Weight: 12.5 kg. Sex: Spayed. Age: 88 months. Type of tumour: Mast cell tumour (primary tumour). Size of tumour: 10 mm Clinical observations immediately after injection of the P28R and during the time interval until resection: No systemic adverse events were observed.

Biopsies Obtained:

A large biopsy was taken from the site of injection in direction of drug injection from the periphery towards the centre of the tumour.

Histopathological Examination.

Figure 67A:
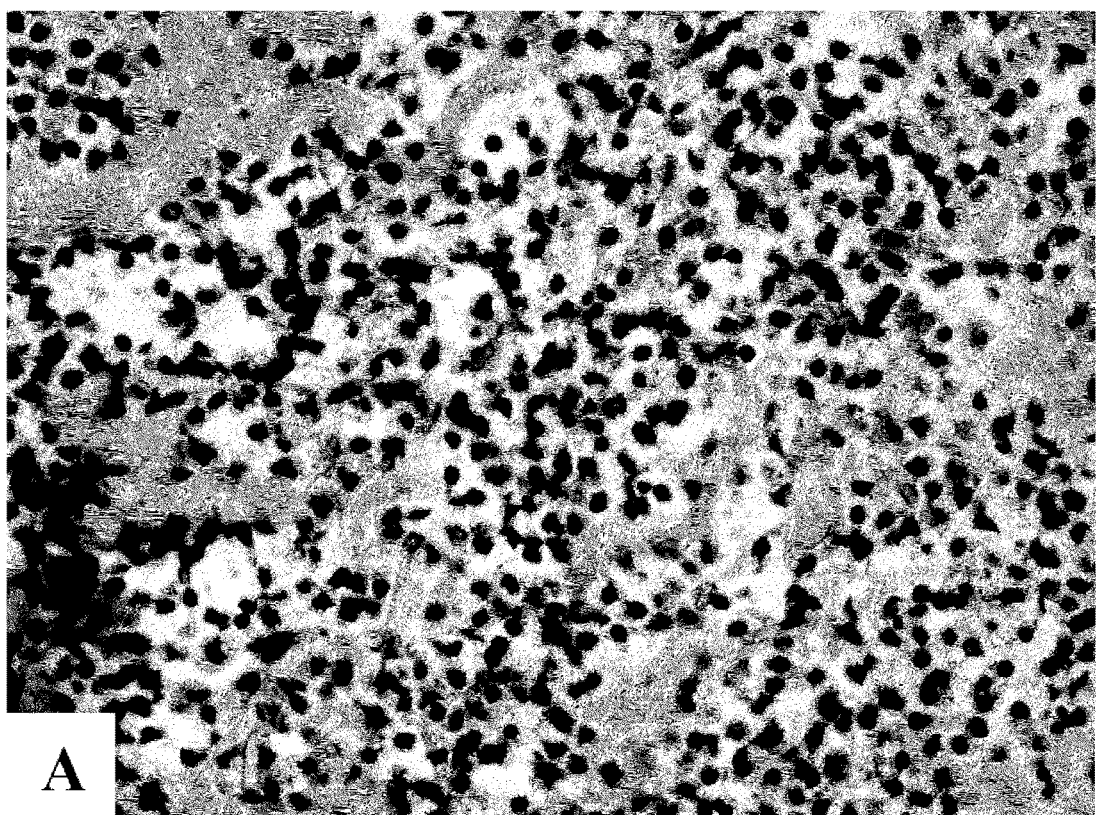
FIG. 67 is a series of microscope images illustrating H&E stained sections of a dog mastocytoma with pronounced tumour regressive changes (FIG. 67A and FIG. 67B represent different sections of the mastocytoma, in accordance with some embodiments herein.
Figure 67B:
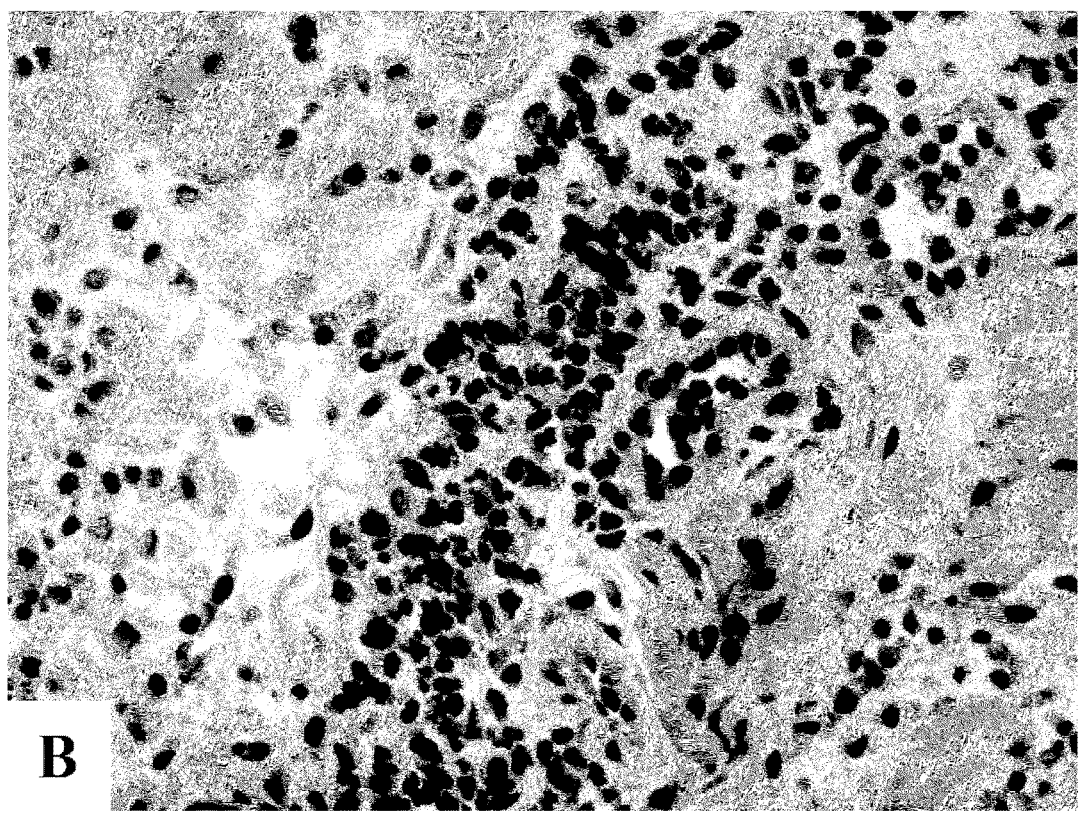

H&E stained sections were investigated for occurrence of tumour growth, infiltration of inflammatory cells and various degrees/types of tumour regressive changes (see FIGS. 67A-B).

Figure 68A:
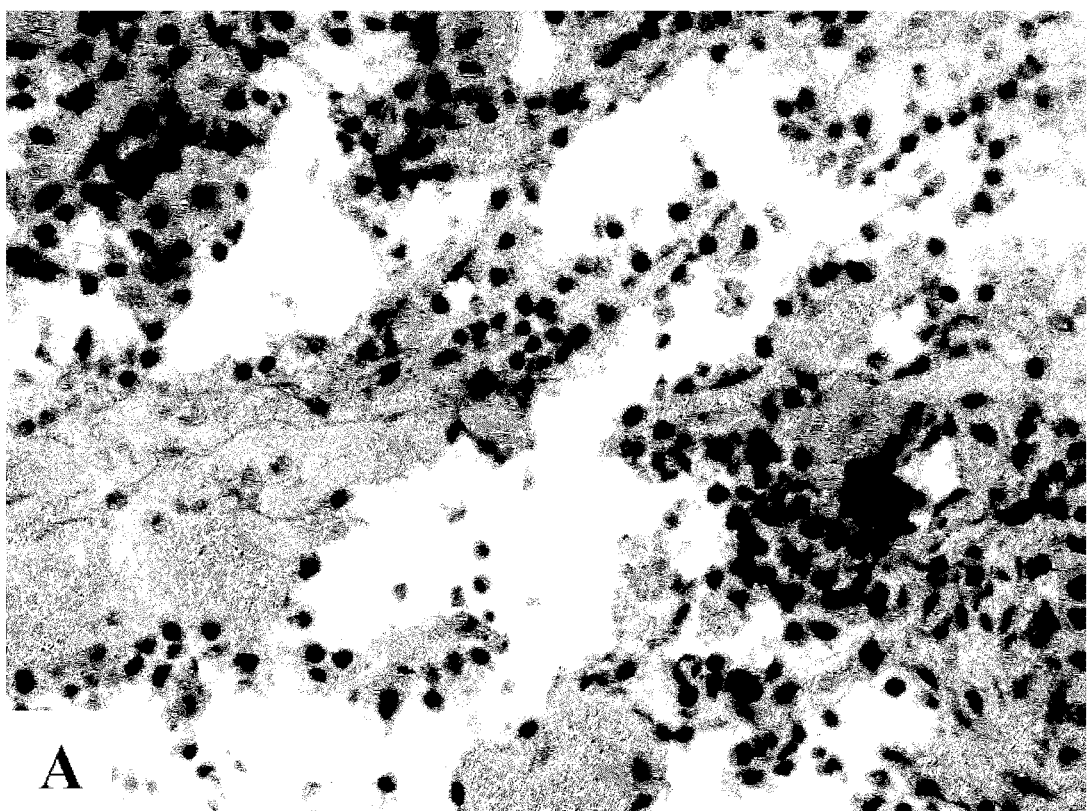
FIG. 68 is a series of microscope images illustrating a dog mastocytoma after intra-tumoral treatment with P28R in accordance with some embodiments herein. Staining for CD3+(FIG. 68A) and CD8+T-lymphocytes (FIG. 68B) show very low infiltration of these cells, with a highly variable, usually very faint, staining intensity
Figure 68B:
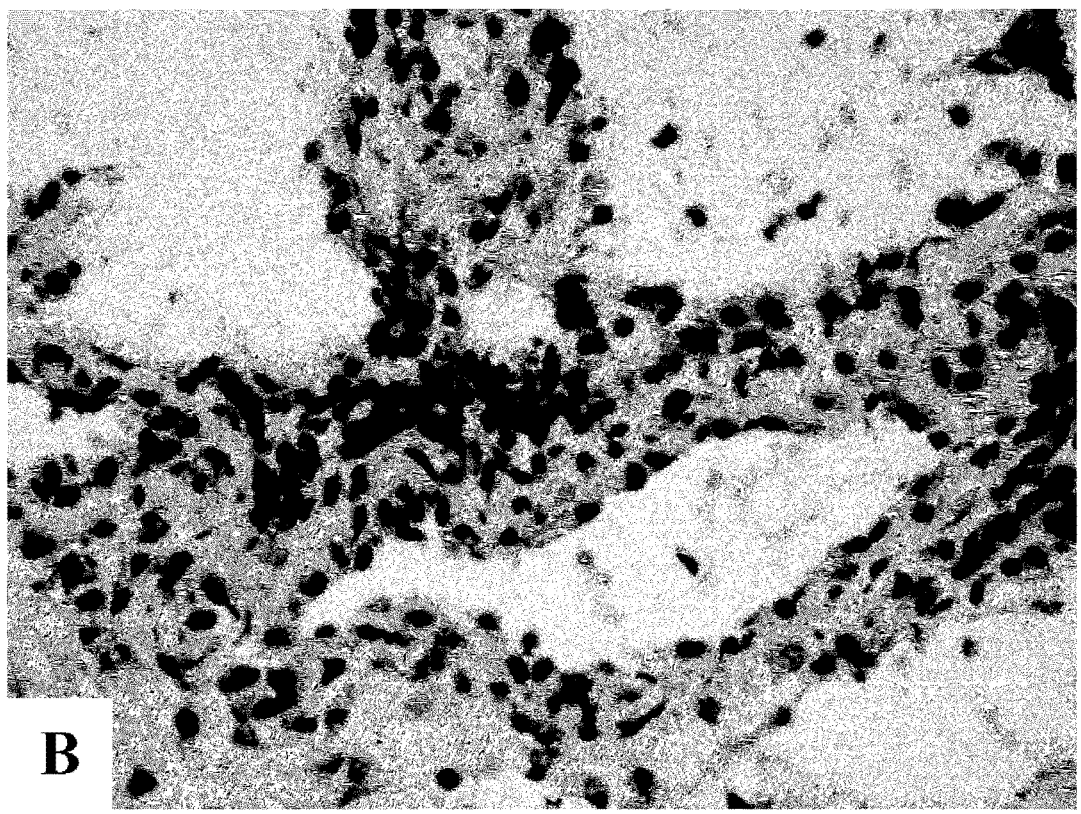

Only few scattered CD3+ or CD8+ cells were found after treatment in this tumour (see FIGS. 68A-68B).

Figure 69:
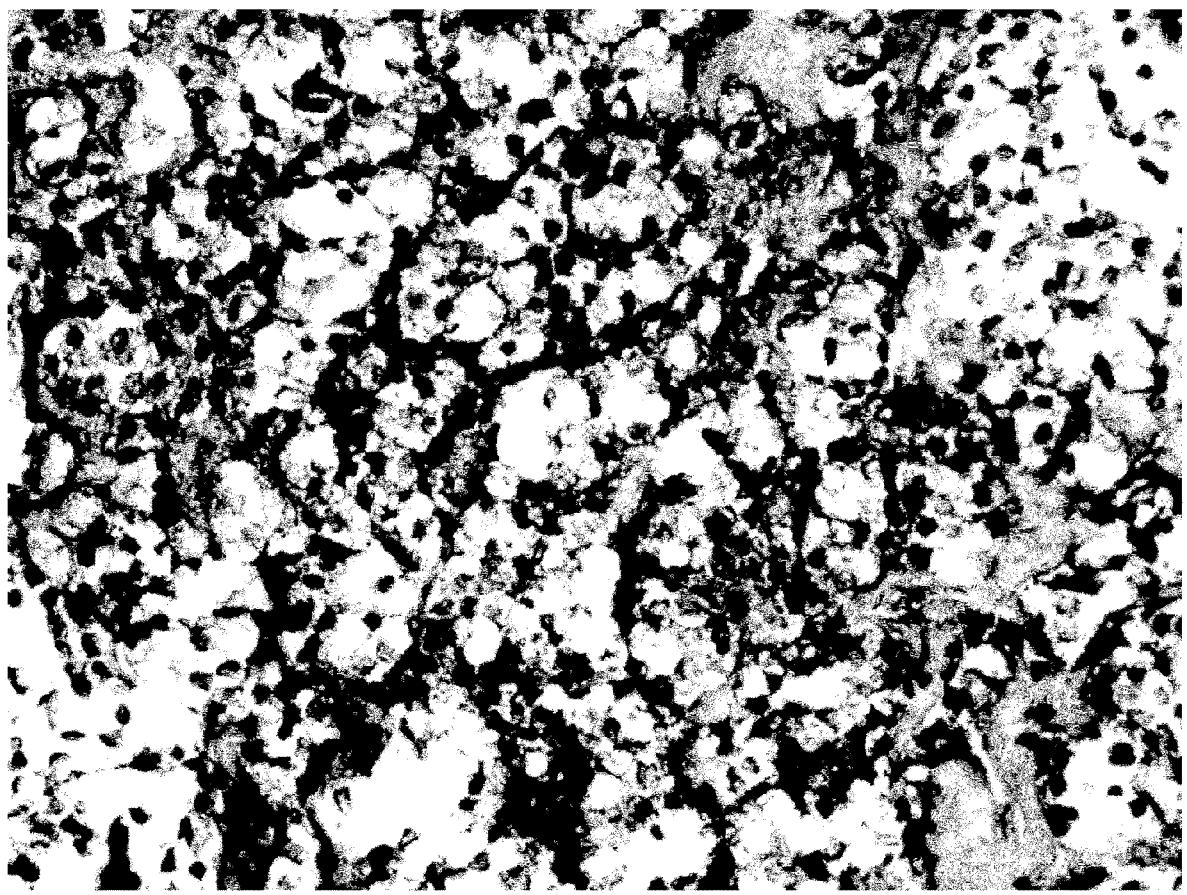
FIG. 69 is a series of microscope images illustrating a dog mastocytoma after intra-tumoral treatment with P28R in accordance with some embodiments herein.
Figure 70A:
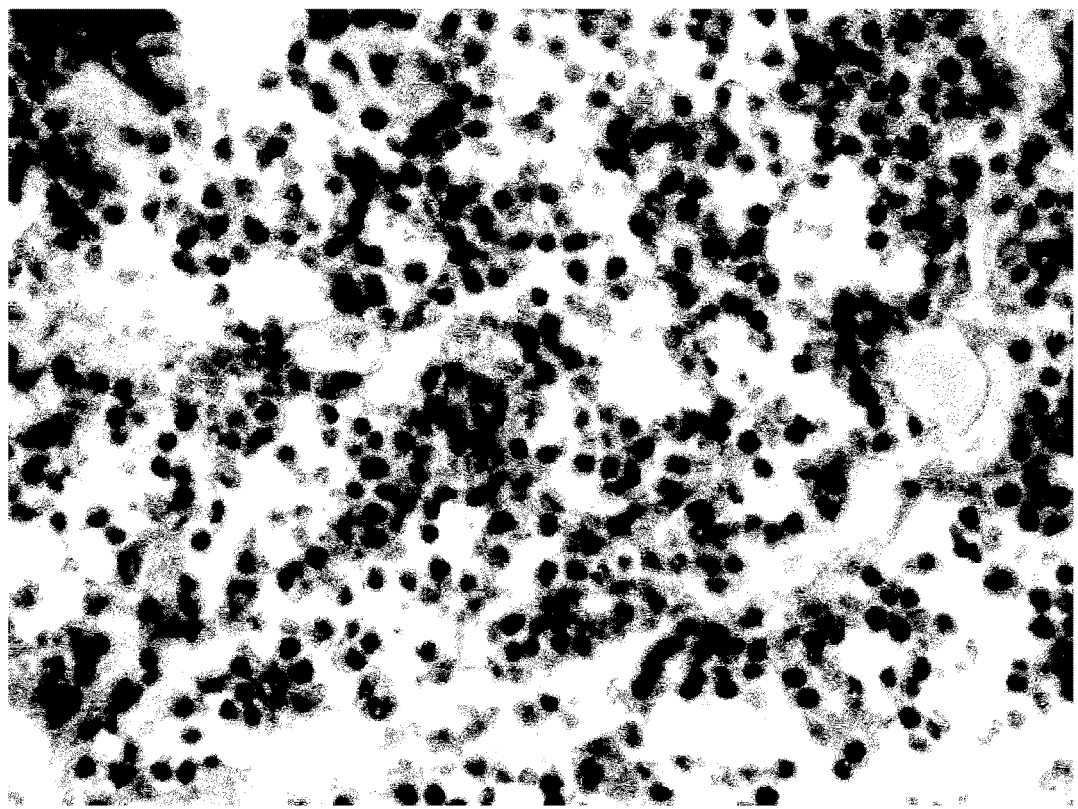
FIG. 70A, FIG. 70B, FIG. 70C, and FIG. 70D represent different images of the mastocytoma. A massive tumour destruction and an extensive infiltration of CD56+ inflammatory cells are shown.
Figure 70B:
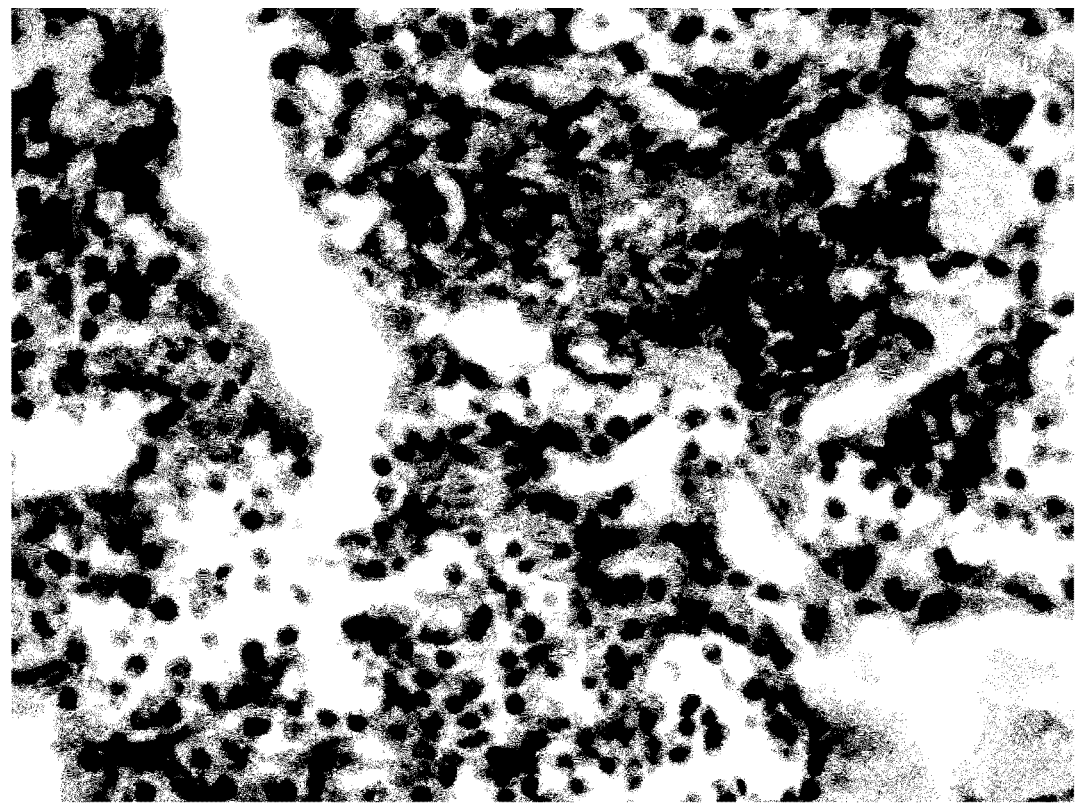
Figure 70C:
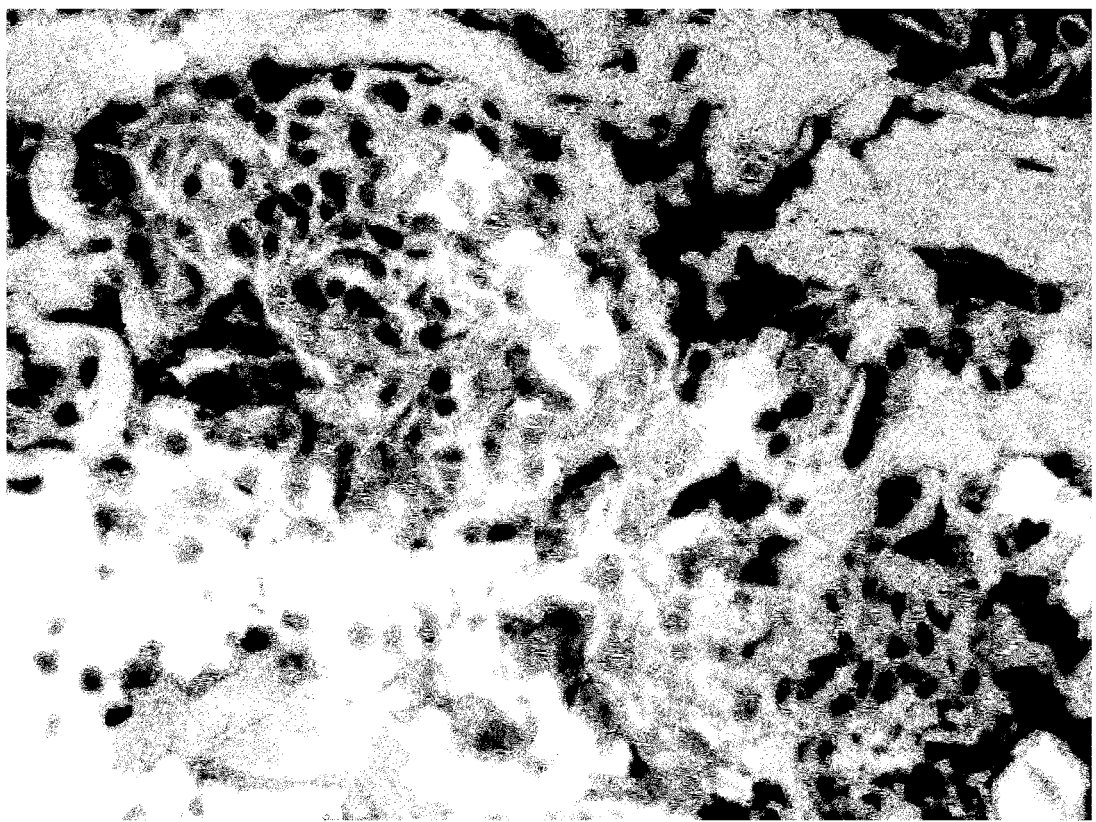
Figure 70D:
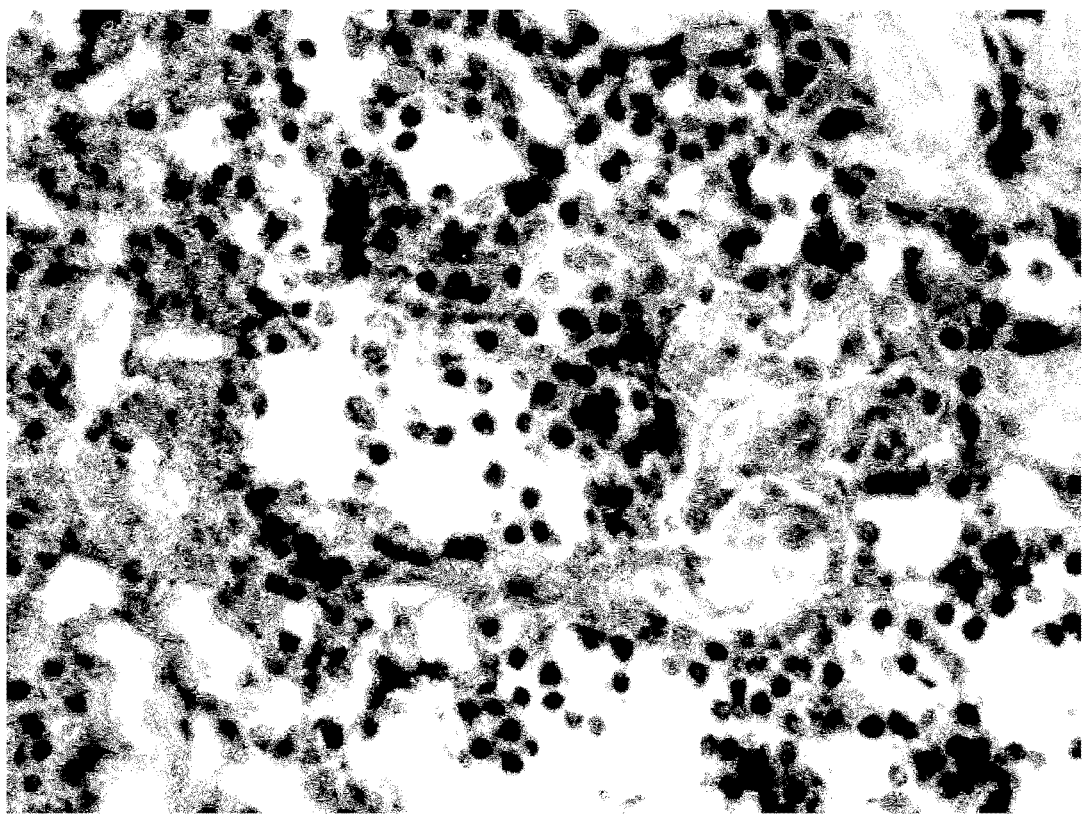

In FIG. 69, a mastocytoma after intra-tumoral treatment with P28R is shown. A massive tumour destruction and as extensive infiltration of CD45+ inflammatory cells are shown.

Staining for NK-cells, CD56 and NCR1 was performed (see FIGS. 70A-D). As the tumour was resected three days after intra-tumoural treatment and only minor T-cell recruitment was found, the innate response was investigated by staining for NK-cells and macrophages.

As such, mastocytoma after intra-tumoral injection of P28R in accordance with some embodiments herein was observed. The tumour, resected after 3 days, is permeated with CD56+ cells and shows extensive tumour regressive changes.

Accordingly, intra-tumoral administration of immunoregulatory peptide inhibitors to subjects in accordance with some embodiments herein can cause regressive changes in mast cell tumors, and can treat, ameliorate, eliminate, and/or destroy such tumors.

Example 53: D Dog Tumour 4

Clinical Data

Breed of dog: Farm dog. Weight: 8.6 kg. Sex: Female. Age: 86 months. Type of tumour: Benign mixed mammary tumour (primary tumour and metastases). Size of tumour: 25 mm Clinical observations immediately after injection of the P28R and during the time interval until resection: No systemic adverse events were observed.

Biopsies Obtained:

The primary tumour was localized in a distal breast gland close to the groin:
1. A central slice, 5-7 mm thick, of the primary tumour corresponding to the injection site was cut out.
2. A peripheral biopsy close to the central slice
3. In the peripheral slice a small haemorrhage was observed, probably the centre of the injection, called injection site.

4. A separate metastasis close to the primary tumour, about 3 cm in diameter
5. A second separate metastasis close to the primary tumour
6. An additional tumour localized in the upper most breast gland close to the axilla.

Histopathological Examination.

H&E stained sections were obtained from all biopsies described above. These were investigated for occurrence of tumour growth, infiltration of inflammatory cells and various degrees/types of tumour regressive changes.

All areas of all biopsies were infiltrated by inflammatory cells. Only small areas completely without infiltration of such cells were observed in any of the biopsies. In general, the vast majority of the tumour cell areas had a marked infiltration often with strongly distorted morphology of the tumour growth. The following types of tumour regressive areas were identified.

1. Regressive changes related to the injection site
2. Clear glandular structure with inflammatory infiltrate
3. Highly distorted glandular structure with inflammatory infiltrate
4. Diffuse, confluent growth of tumour cells with pronounced tumour regressive changes and often a strong inflammatory infiltrate H&E stained sections from different parts of the primary tumour, a regional metastasis and a distant tumour were analysed, The results are shown FIGS. 71-74.

The characterization of the inflammatory infiltrate of this tumour has so far been performed using antibodies directed against CD45 and CD8 (see, e.g. FIG. 75).

Figure 76:
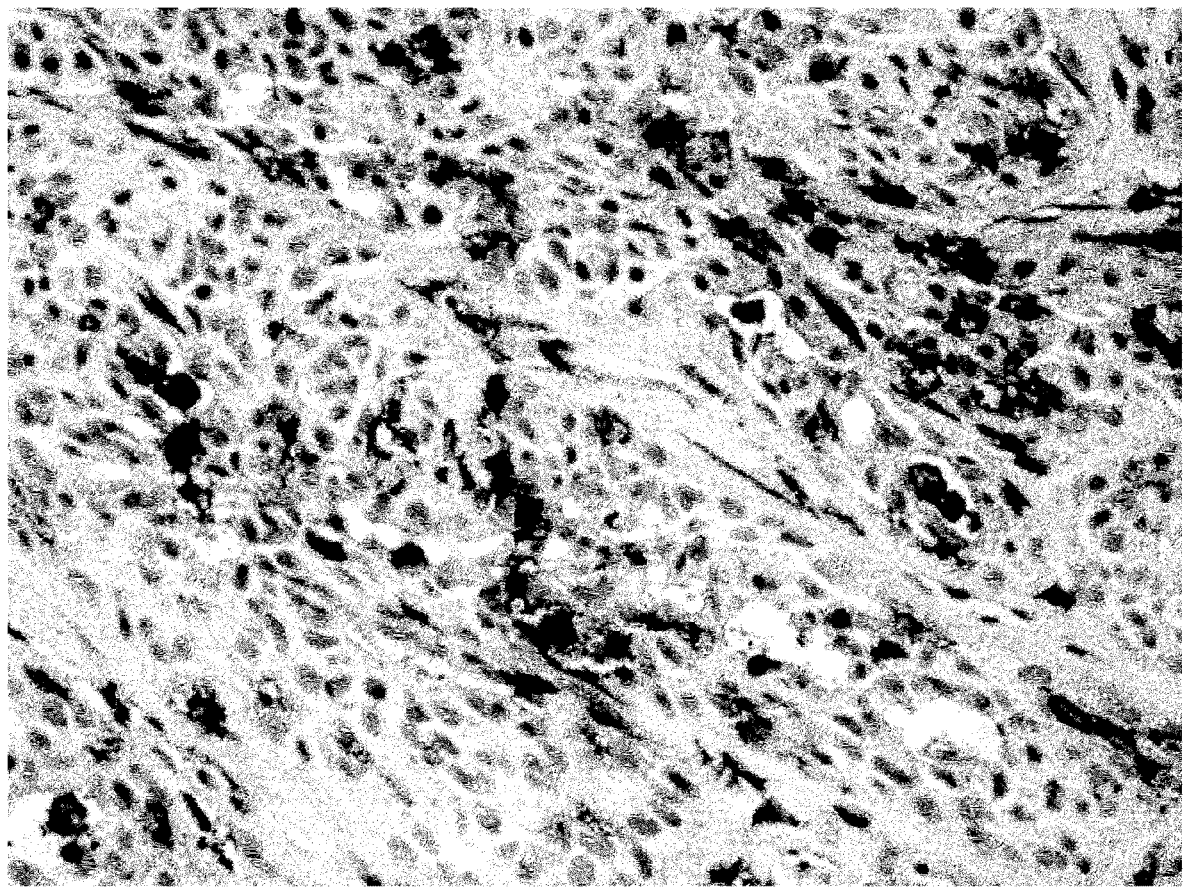
FIG. 76 is a microscope image illustrating distant metastases/new primary tumour of a dog breast tumor showing infiltration of CD45+ cells into the tumour cell areas in accordance with some embodiments herein.
Figure 77A:
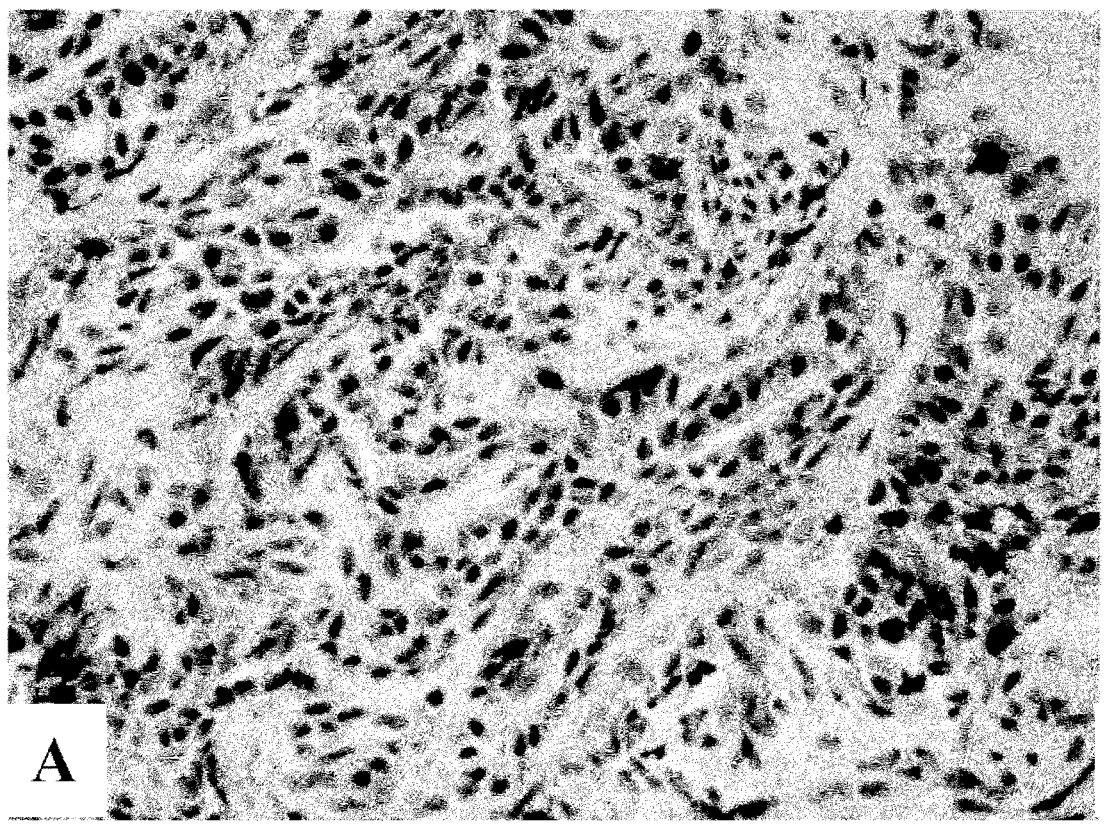
FIG. 77A, FIG. 77B, FIG. 77C, and FIG. 77D are images from the lesion showing various degrees of tumour regressive changes.
Figure 77B:
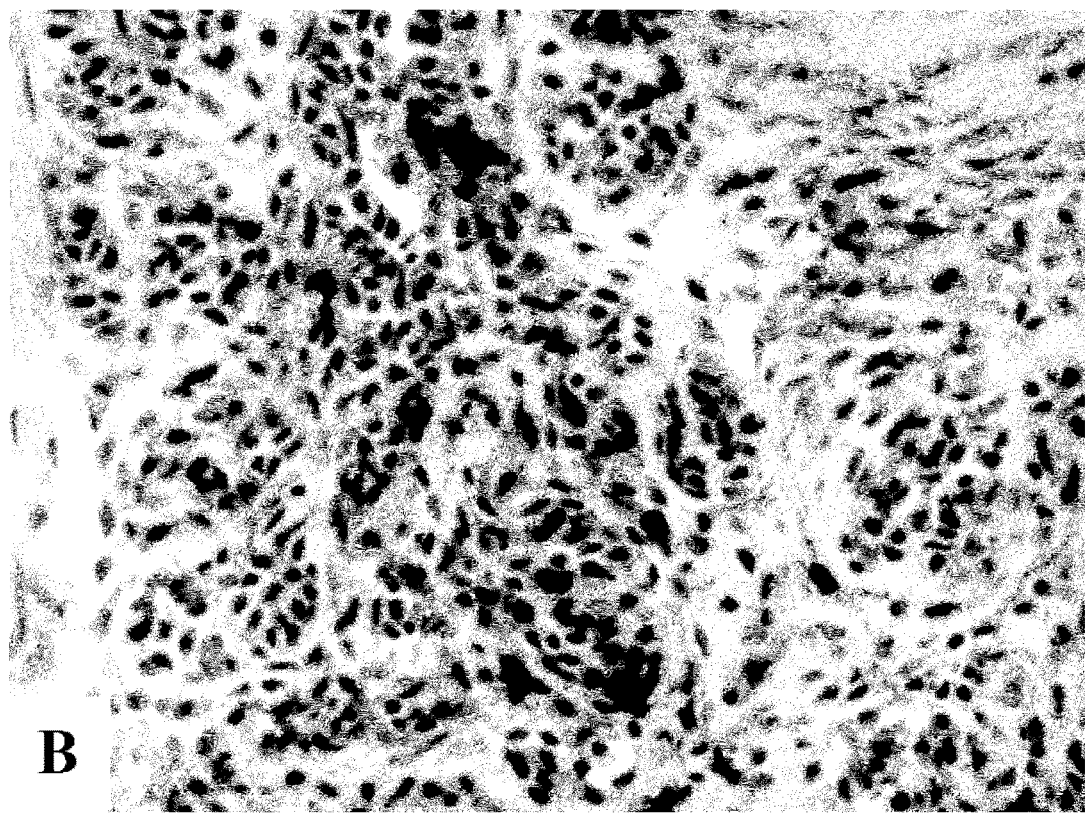
Figure 77C:
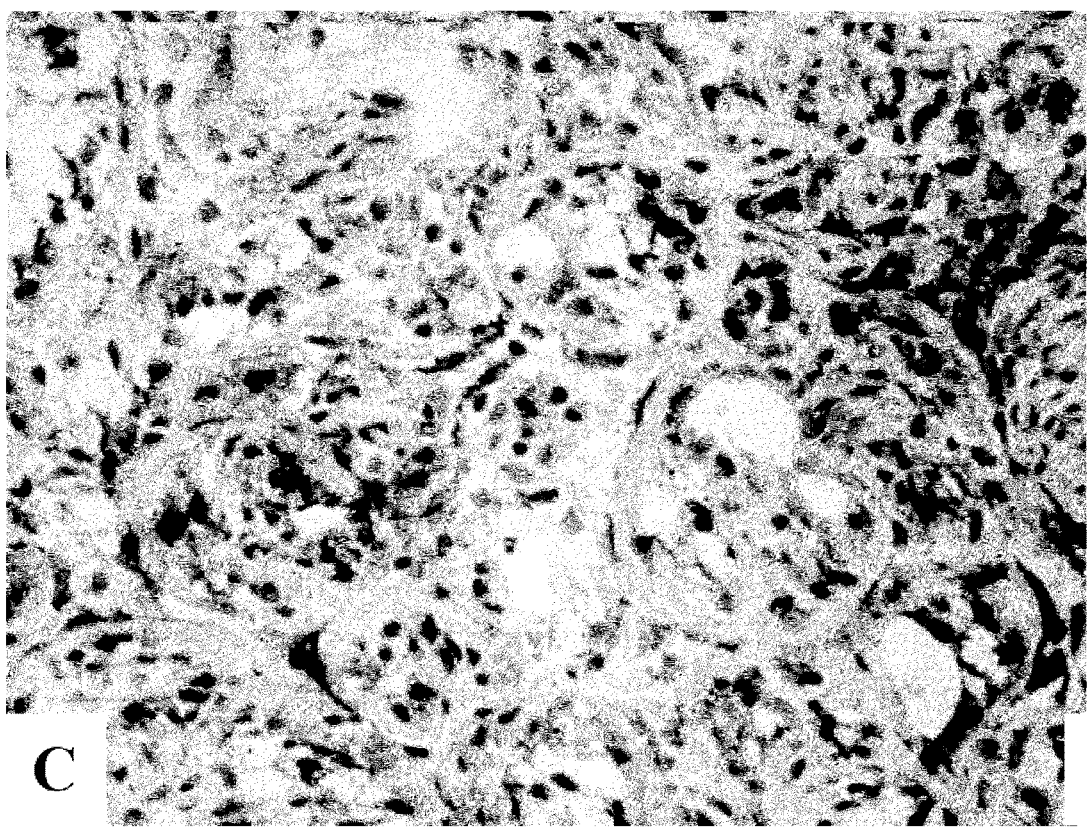
Figure 77D:
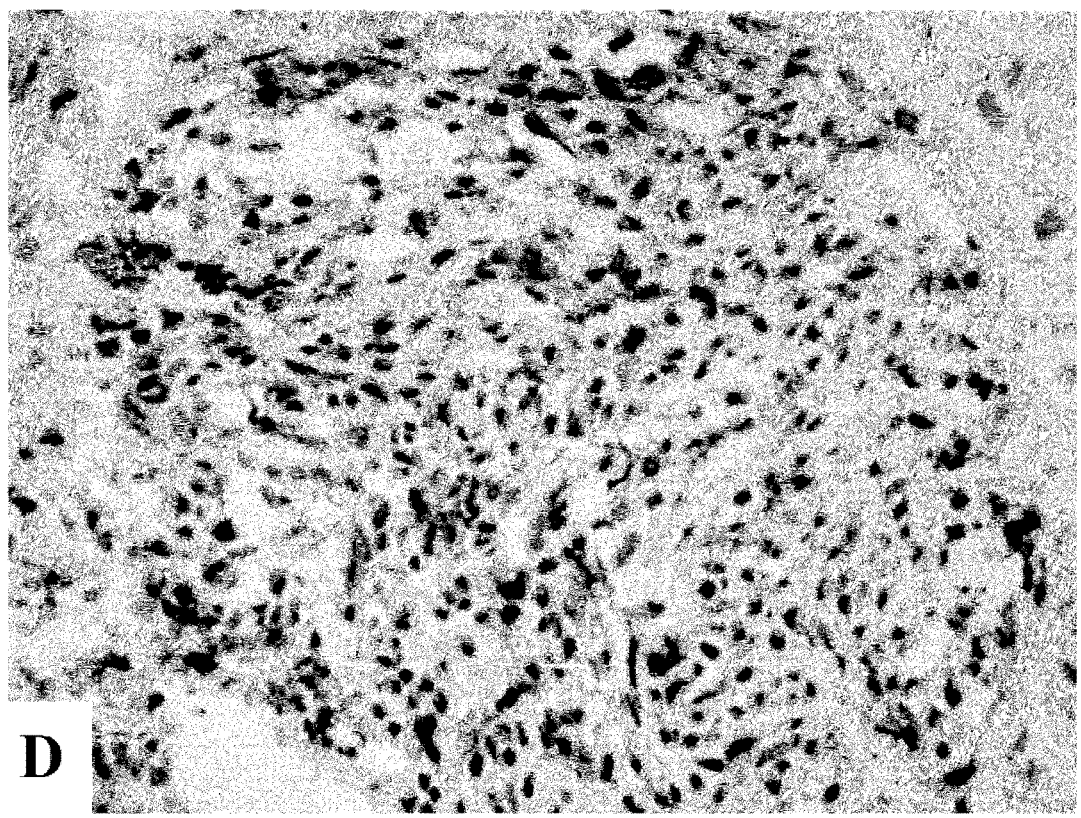

FIGS. 76 and 77 show additional staining of samples from the tumors of this dog.

Accordingly, observed herein was a breast tumour after intra-tumoral treatment with P28R in accordance with some embodiments herein. The tumour was resected after 4 days. The analysis showed infiltration of inflammatory cells with tumour cell destruction in all areas, injection site, central parts, local and distant metastases.

Accordingly, intra-tumoral administration of immuno-regulatory peptide inhibitors to subjects in accordance with some embodiments herein can cause regressive changes in mixed mammary tumors with metasteses, and can treat, ameliorate, eliminate, and/or destroy such tumors and metastases.

Example 54: D Dog Tumour 5

Clinical Data

Breed of dog: Dwarf Pincher. Weight: 8.0 kg. Sex: Spayed. Age: 155 months. Type of tumour: Mammary gland: mucinous carcinoma (primary tumour) Size of tumour: 20 mm Clinical observations immediately after injection of the P28R and during the time interval until resection: No systemic adverse events were observed.

Biopsies Obtained:

A large biopsy was taken from the site of injection in direction of drug injection from the periphery towards the center of the tumour.

Histopathological Examination.

Hematoxylin stained sections were obtained (see FIG. 78). These were investigated for occurrence of tumour growth, infiltration of inflammatory cells and various degrees of tumour regressive changes.

As such, a quite strong inflammatory infiltration was seen in this tumour injected only with the vehicle of the drug formulation in accordance with some embodiments herein. The extensive tumour regressive changes found in treated tumours (3, 4 and 6) in this tumour. The tumour is considered to have a spontaneous inflammatory reaction, which usually is found only rarely.

Accordingly, intra-tumoral administration of immuno-regulatory peptide inhibitors to subjects in accordance with some embodiments herein can cause regressive changes in mucinous carcinoma tumors, and can treat, ameliorate, eliminate, and/or destroy such tumors.

Example 55: D Dog Tumour 6

Clinical Data

Breed of dog: Labrador. Weight: 28.0 kg. Sex: Spayed. Age: 30 months. Type of tumour: Histiocytoma (primary tumour). Size of tumour: 6 mm Clinical observations immediately after injection of the P28R and during the time interval until resection: No systemic adverse events were observed.

Biopsies Obtained:

A biopsy was taken from the site of injection in direction of drug injection from the periphery towards the center of the tumour.

Histopathological Examination.

Hematoxylin stained sections were investigated for occurrence of tumour growth, infiltration of inflammatory cells and various degrees/types of tumour regressive changes (see FIGS. 79-80). As the tumour cells in histiocytoma might express CD45, the inflammatory infiltrate of this tumour was mainly explored regarding infiltration of NK-cells using an antibody directed against CD56 and NCR1 (see FIG. 80).

As such, it was shown that histiocytoma treated intra-tumorally with P28R and resected after 3 days. The analysis shows extensive tumour regressive changes and a heavy infiltration of CD56+ and NCR1+NK-cells.

Example 56: D Dog Tumour 7

Clinical Data

Breed of dog: Cocker spaniel. Weight: 27.0 kg. Sex: Female. Age 123 months. Type of tumour: Intraductal papillary adenoma in mammary gland (primary tumour). Size of tumour: 10 mm Clinical observations immediately after injection of the P28R and during the time interval until resection: No systemic adverse events were observed.

Biopsies Obtained:

A large biopsy was taken from the site of injection in direction of drug injection from the periphery towards the centre of the tumour.

Histopathological Examination.

Figure 81:
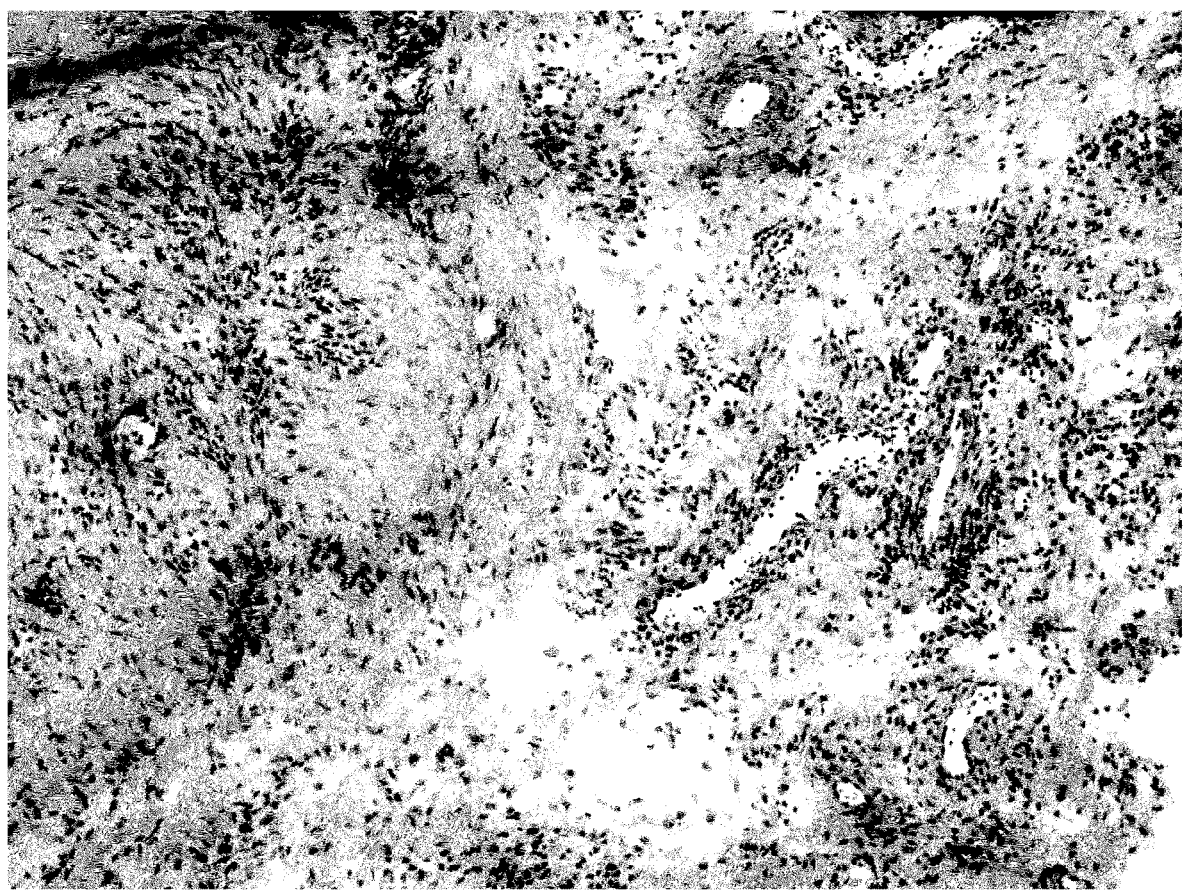
FIG. 81 is a microscope image illustrating an overview of H&E staining of breast tumour treated with P28R for 5 days in accordance with some embodiments herein. A heavy inflammatory infiltrate is demonstrated.
Figure 82A:
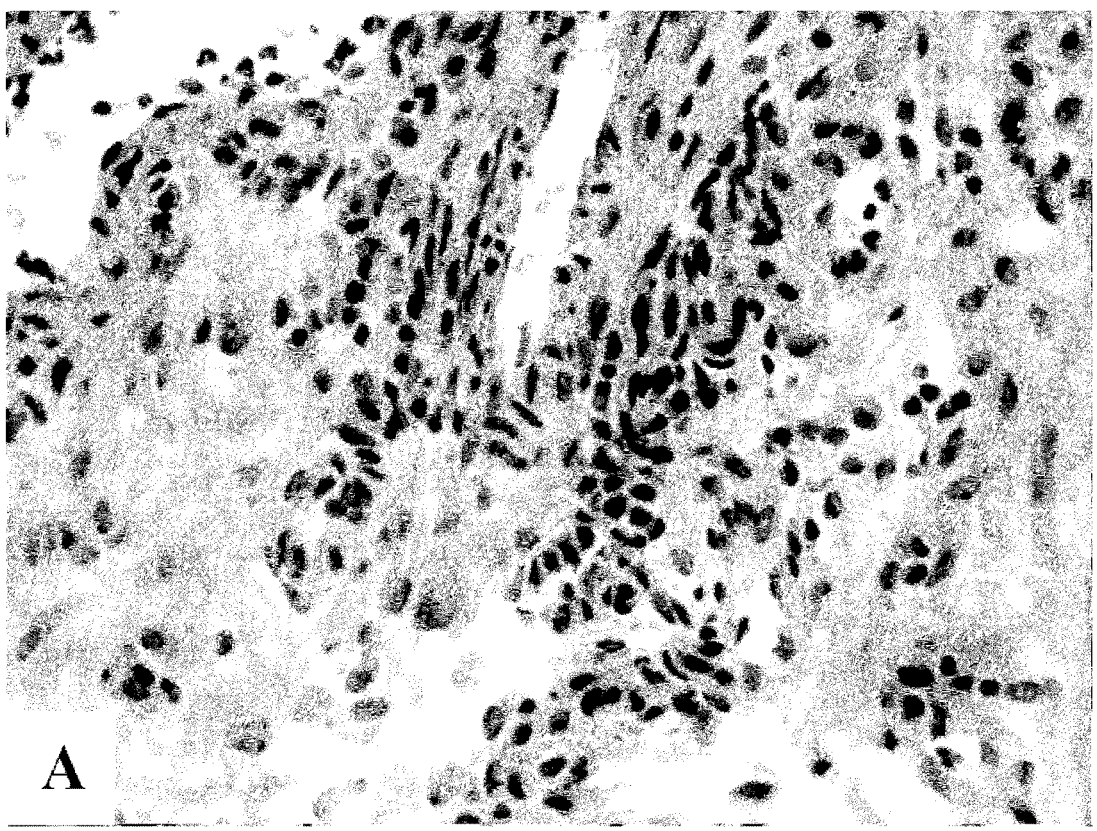
FIG. 82 is a series of microscope images illustrating H&E staining of a breast tumour in accordance with some embodiments herein. An intense inflammatory infiltration with extensive destruction of tumour glands (FIG. 82A, FIG. 82B, FIG. 82C, and FIG. 82D provide different images of the breast tumor).
FIG. 82D also demonstrates the occurrence of macrophages with hemosiderin (yellow, arrow).
Figure 82B:
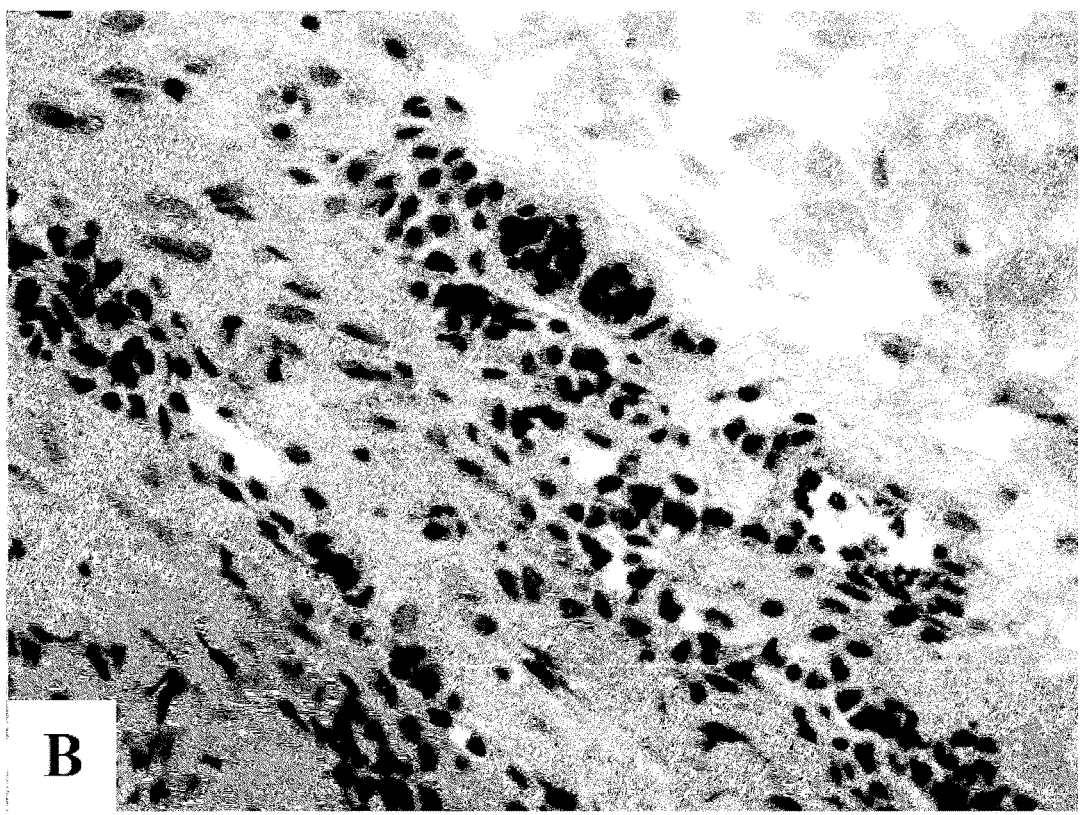
Figure 82C:
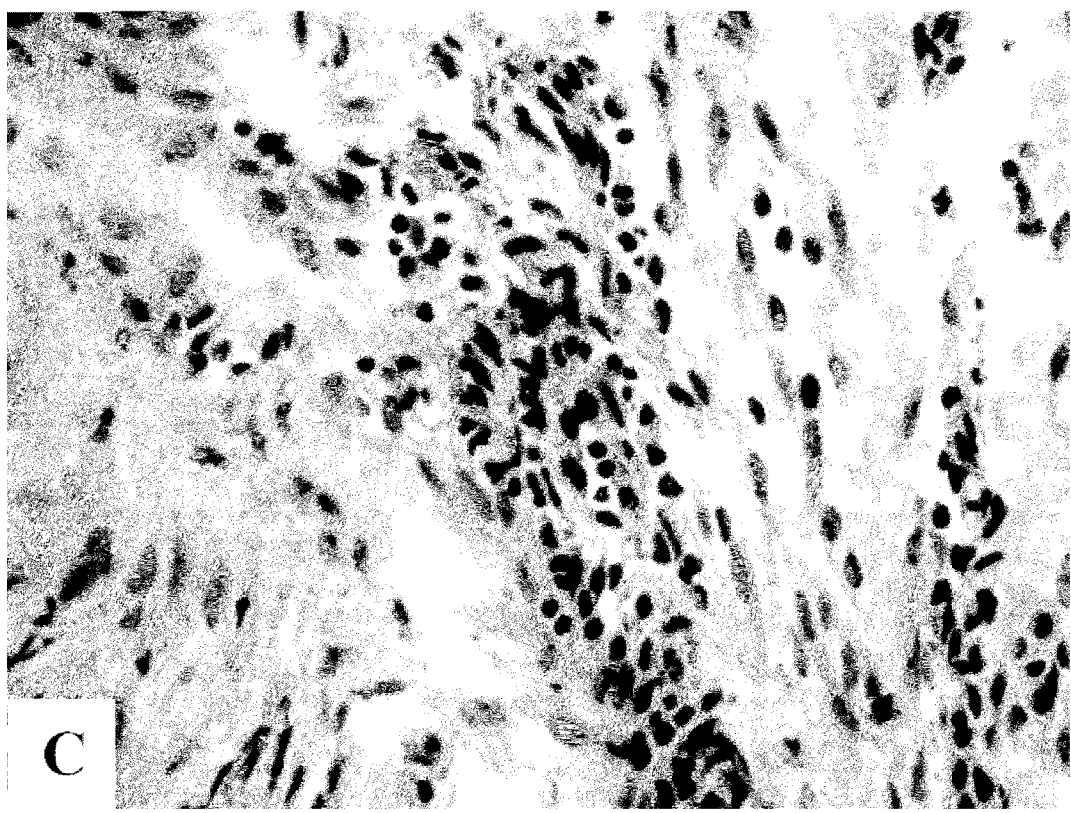
Figure 82D:
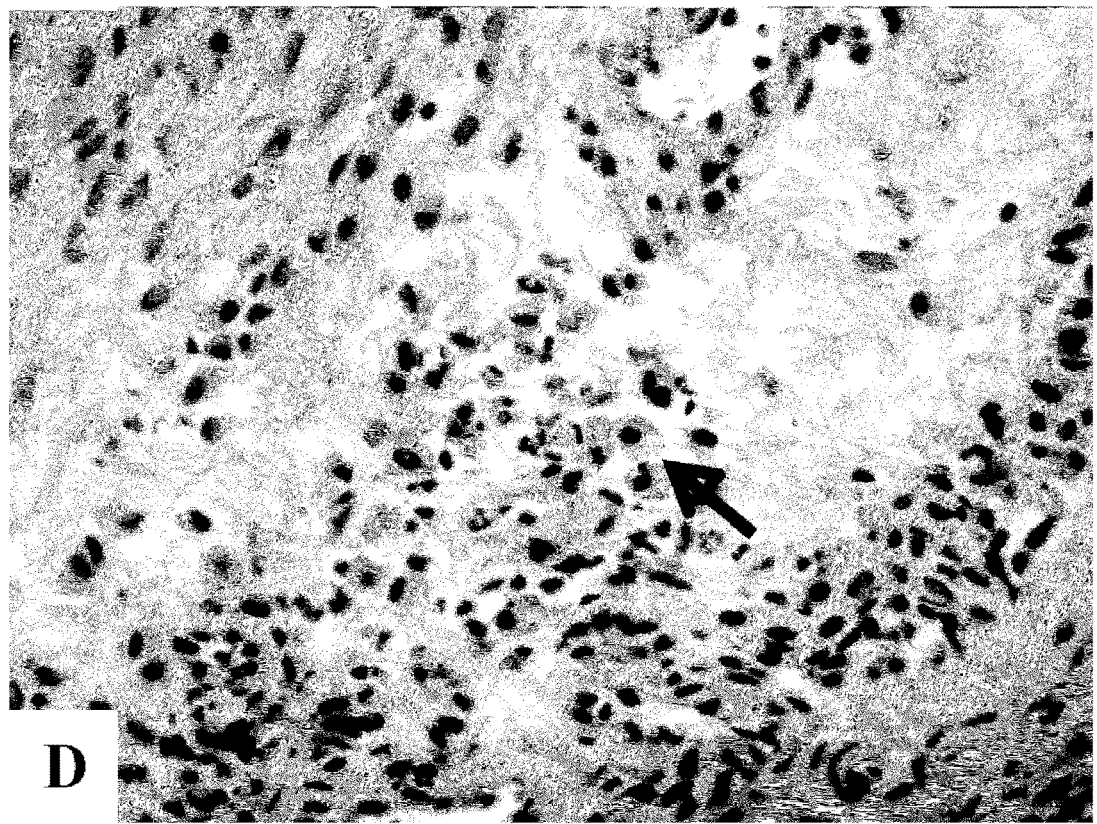

H&E stained sections were investigated for occurrence of tumour growth, infiltration of inflammatory cells and various degrees/types of tumour regressive changes (see FIGS. 81-82).

As such, it has been shown that breast tumour injected with 40 nM P28R in accordance with some embodiments herein, resulted in an intense inflammatory infiltrate and an extensive eradication of tumour cells after 5 days.

Figure 83:
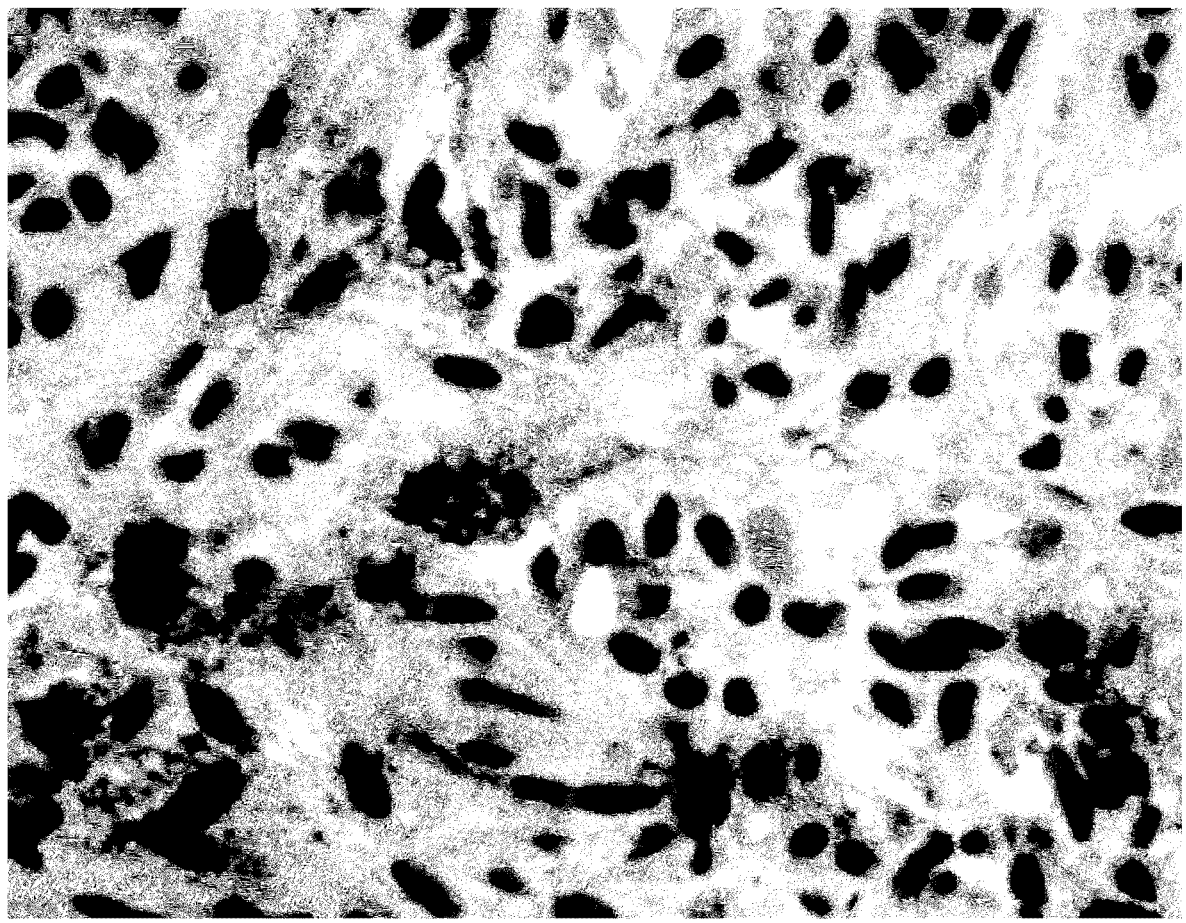
FIG. 83 is a microscope image illustrating canine breast tumour stained for CD8 treated intra-tumorally with 40 nmol P28R in accordance with some embodiments herein. Apparently, the lymphocytes in the stroma have an increased staining intensity compared to some faintly stained cells infiltrating the tumour cell areas.

Example 57: Observation of Inflammatory Cells and Tumor Cells Upon Administration of P28R The expression of some markers CD3, CD8 and CD45 was down-regulated/lost when inflammatory cells infiltrated into the tumour-cell-areas. As shown in FIG. 83, inflammatory cells in stromal areas generally had a stronger expression as compared to tumour-cell-areas. FIG. 83 shows canine breast tumour (from D Dog 4) stained for CD8 treated intra-tumorally with 40 nmol P28R. It appears that the lymphocytes in the stroma have an increased staining intensity compared to some faintly stained cells infiltrating the tumour cell areas.

Based on morphological criteria, a considerable number of lymphocytes close to tumour cells were completely unstained. This interpretation was further confirmed by comparing "standard" staining with a more intense staining, allowing some background/unspecific staining of the tumour tissue (FIGS. 84A and 84B, showing D Dog 17). In order to get a true evaluation of the degree of infiltration of inflammatory cells, H&E/Haematoxylin stained sections were used and the inflammatory cells were identified by their morphological characteristics.

In light microscopy tumour regressive changes can be identified as: 1. Deteriorated architecture of the tumour tissue. 2 Degenerative tumour cells, appearing as nuclear "shadows" often with irregular shape. 3. "Missing" tumour cells, typical holes in the tumour tissue, often surrounded by inflammatory cells.

The architecture of mammary glands and ducts is often deteriorated already by tumour growth; tumour regressive changes were therefore mainly registered as appearance of damaged tumour cells/tumour cell shadows or missing tumour cells/"holes" in the tumour cell areas. The criteria for damaged tumour cells are: Extremely faintly-staining often irregular nuclei and disruption of the nuclear membrane. These cells are apoptotic as demonstrated by the TUNEL staining (FIG. 85, showing D Dog 17).

Figure 86A:
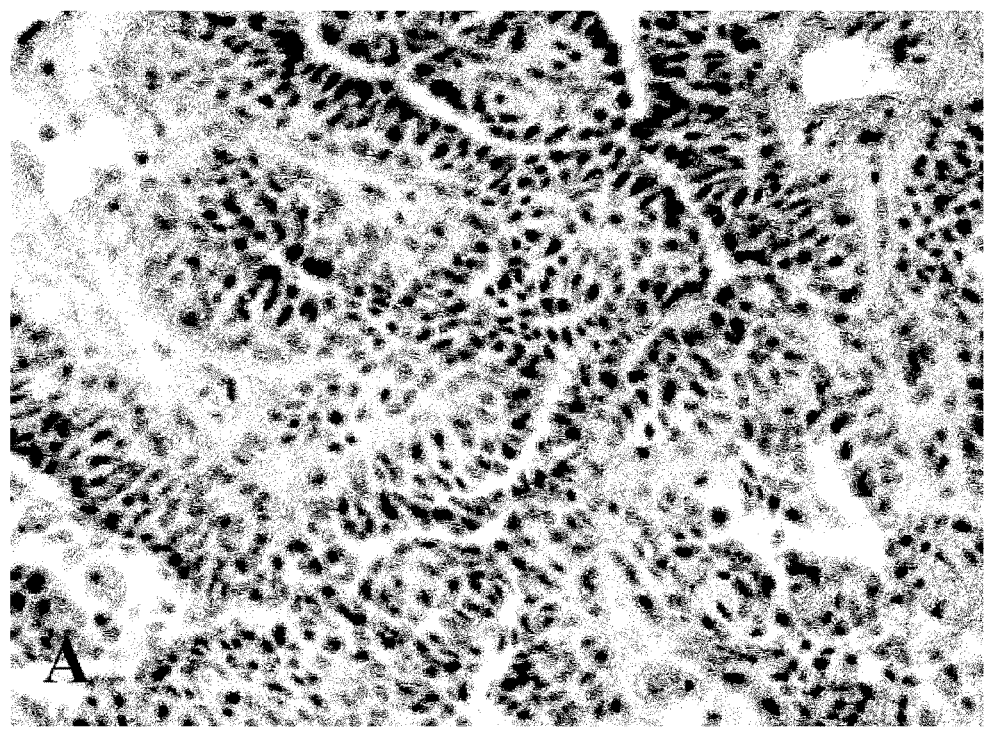
FIGS. 86A-B are a series of microscope images illustrating untreated (FIG. 86A) and treated (FIG. 86B) canine breast tumours, in accordance with some embodiments herein. The tumour cell density is significantly reduced in the treated tumour and at the same time, a large number of "damaged" tumour cells can still be found.
Figure 86B:
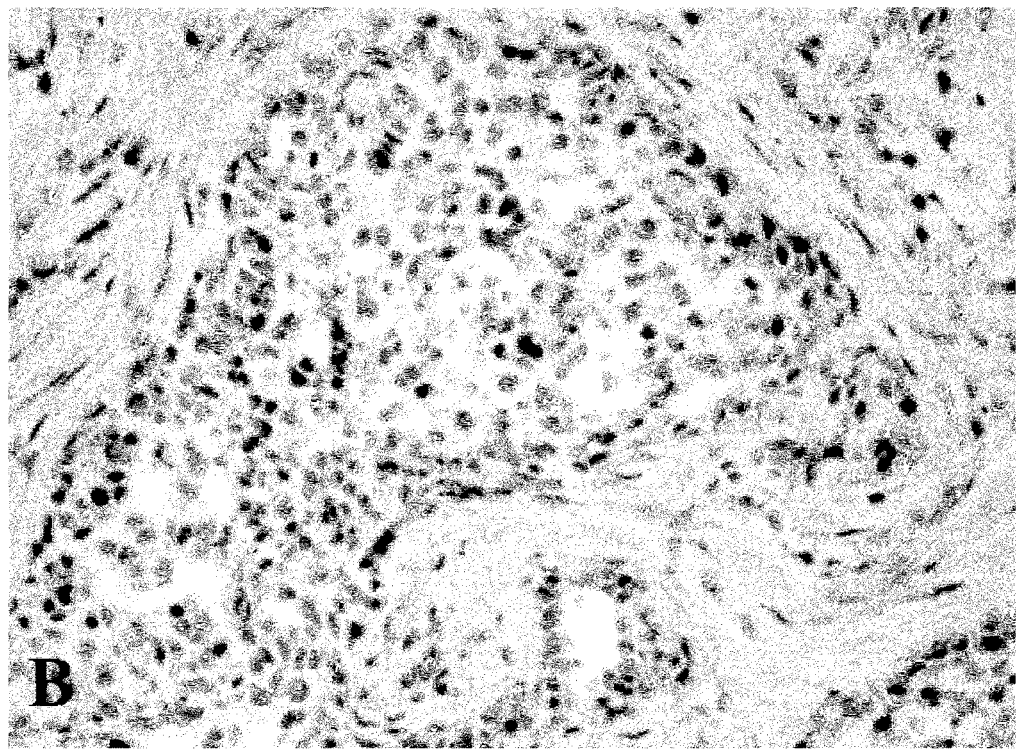
Figure 87A:
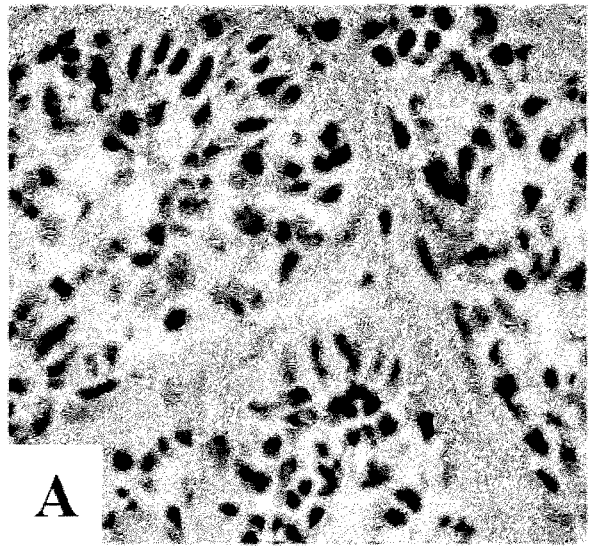
FIGS. 87A-D are a series of microscope images illustrating four different untreated canine breast tumours showing a high density of unaffected tumour cells and few degenerative cells. The number of lymphocytes is low except for tumour C, but even with this degree of inflammatory cells in an untreated tumour the number of degenerated tumour cells is low.
Figure 87B:
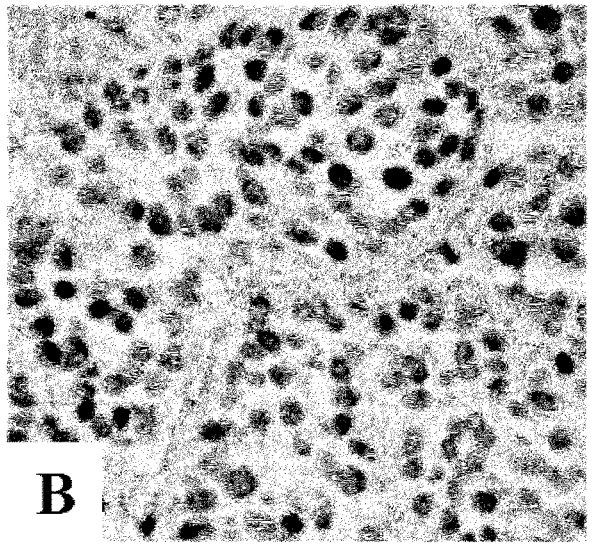
Figure 87C:
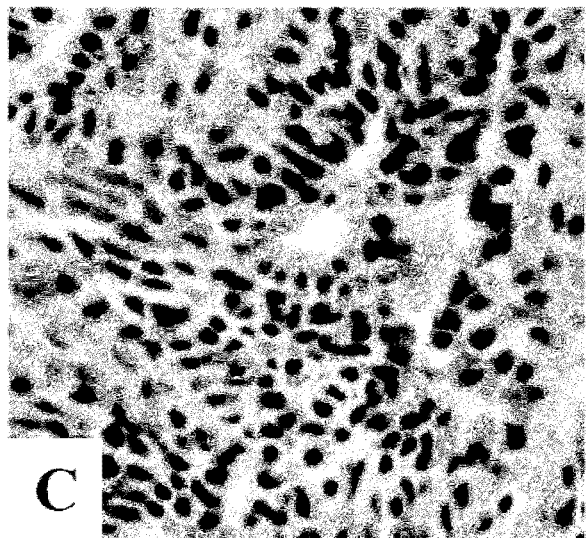
Figure 87D:
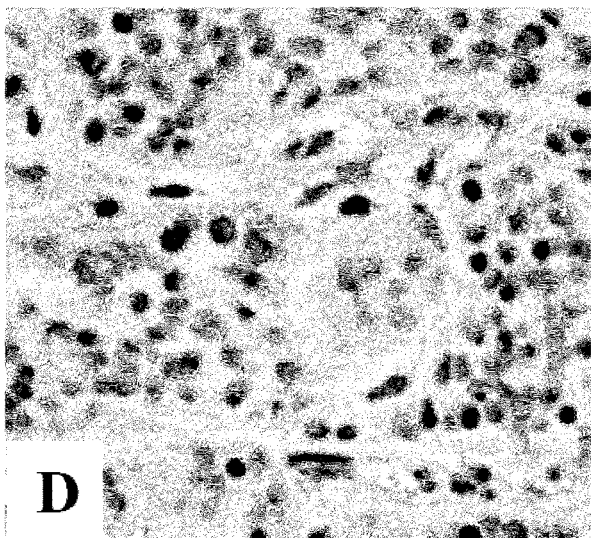

The ratio between normal looking and "damaged" tumour cells was used as a measure of tumour cell regressive changes. The destruction of tumour cells results in a significantly lower tumour cell density in treated tumours (FIG. 86B, showing D Dog 17) compared with tumours from untreated control dogs (FIG. 86A, showing D Dog C4, and FIGS. 87A-D).

Some minor tumour cell areas in some tumours were found to have an unaffected morphology/architecture and low numbers of inflammatory cells. Without being limited by any theory, this observation could possibly be due to the short treatment period with only one injection not allowing enough time for the immune attack to take place. Alternatively, without being limited by any theory, it is contemplated that these parts of the tumours possibly do not expose the necessary antigen to be recognized by the immune system.

In conclusion, in general, in treated tumours, an inflammatory infiltrate with tumour cell regressive changes was found throughout the tumours. Accordingly, it is contemplated that administration of immunoregulatory peptide inhibitors in accordance with some embodiments herein induce an inflammatory infiltration of, and cell regressive changes in tumor tissues.

Example 58: Quantification of Inflammatory Infiltrate in Dogs Treated with P28R

The inflammatory infiltrate in tissues of treated dogs (as outlined in Examples 50-57 above), was quantified and compared with the total tumour cell number in breast tumours from 7 P28R treated and 5 untreated dogs (FIG. 88).

It was observed that treated tumours contained more than 3-fold higher ratio between inflammatory cells and tumour cells compared with untreated. Accordingly, it is contemplated that administration of immunoregulatory peptide inhibitors in accordance with some embodiments herein induce an inflammatory infiltration of tumor tissues.

Example 59: Analysis of Inflammatory Infiltrate in Formalin Fixed and Paraffin Embedded Tumours In addition, the inflammatory infiltrate was evaluated in ten formalin fixed and paraffin embedded tumours. Generally the infiltration of inflammatory cells was very low, representative examples of four different tumours are shown in FIG. 89. There is at most a very sparse infiltration of the inflammatory cells in the tumour cell areas in eight of these tumours. In two out of ten FFPE tumours, small infiltrated areas, not exceeding 10 percent of the total area of the section, were registered at the very periphery of the tumour section. The major part of these tumours had low grade inflammatory infiltrate with the inflammatory cells mainly localized to the stromal areas (FIG. 90).

Figure 91A:
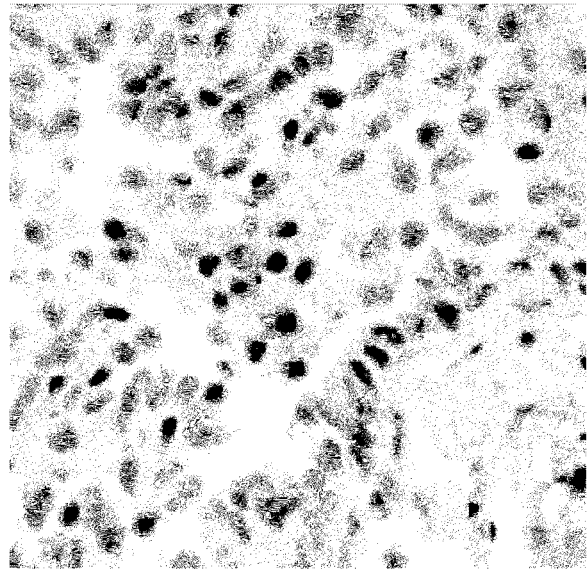
FIGS. 91A-D are a series of microscope images illustrating a comparison of inflammatory response and occurrence of degenerative tumour cells in directly injected breast tumors (FIGS. 91A and 91C) and uninjected breast tumors (FIGS. 91B and 91D) in two dogs treated with P28R in accordance with some embodiments herein. A large number of inflammatory cells and degenerated tumour cells were found also in the tumors that were not directly injected with P28R. That is, when each of the two dog was treated with P28R, degenerative tumor cells were observed in the tumors that were directly injected with P28R, and also in other tumors in the same animal, even though these tumors were not directly injected with P28R.
Figure 91B:
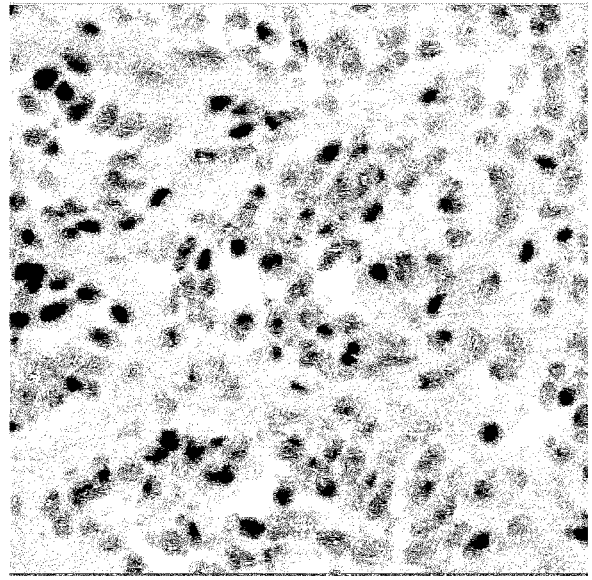
Figure 91C:
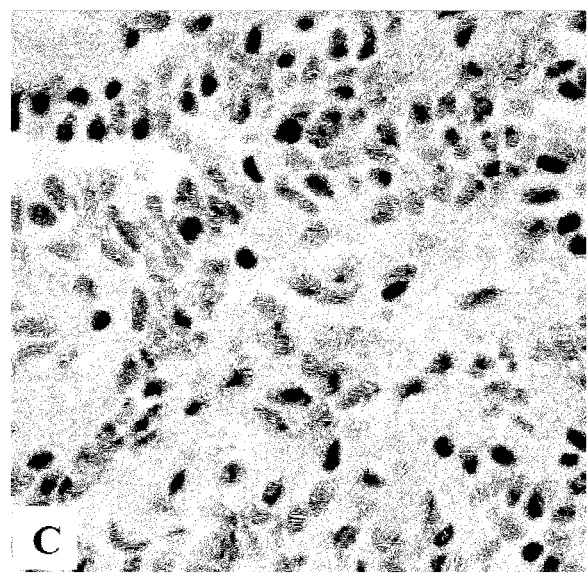
Figure 91D:
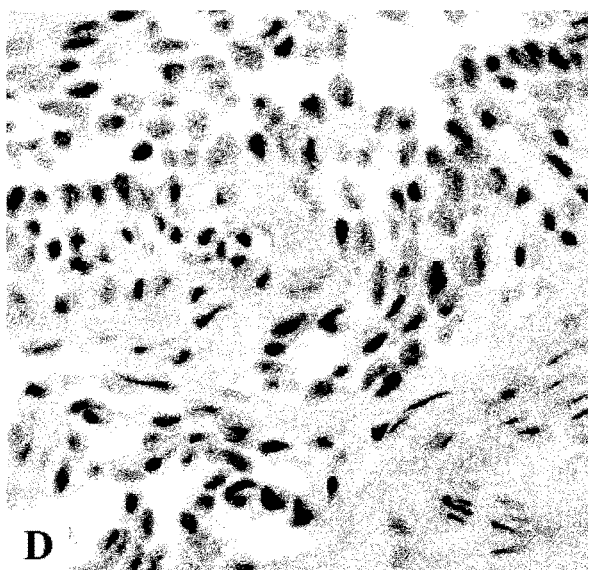

Example 60: Comparison Between Treated and Untreated Tumours in the Same Dog—the Distant Effect Remarkably, a treatment effect (enhanced inflammatory infiltrate and an enhanced amount of "damaged" tumour cells) was found in large tumours after injection of only 200 μL of P28R, indicating a distant effect of the drug. Such an effect was also found in two dogs with multiple tumours where only one tumour was injected with P28R and a treatment effect was observed also in the untreated tumours (FIGS. 91A-D; FIGS. 91A and 91C show tumours that were directly injected with P28R, while FIGS. 91B and 91D show tumours that were uninjected).

Accordingly, it is shown that systemic administration, in addition to direct tumoral injection, of immunoregulatory peptide inhibitors in accordance with some embodiments herein can induce an inflammatory infiltration, regressive changes, and/or eradication of tumor tissues. As such, in some embodiments, an immunoregulatory peptide inhibitor as described herein is administered systemically, and induces inflammatory infiltration, regressive changes, and/or eradication of a tumor located in a different tissue or organ from the site(s) of administration.

Summary of Examples 50-60

In summary, the anti-tumour activity of the immunomodulatory peptide P28R, administered intra-tumorally, was evaluated in 7 dogs with spontaneous breast tumours. A marked inflammatory infiltrate was found in all treated tumours and the number of degenerative tumour cells increased compared to these parameters in 14 untreated tumours. Interestingly, the anti-tumour effect was observed throughout large tumours even if the drug was injected in only 2004. Similarly, in two dogs with multiple tumours the same response to P28R was found not only in the injected tumours but also in uninjected tumours. Thus, this intra-tumoral treatment results in a distant anti-tumour effect in untreated tumours.

Example 61: Toxicological Aspects of P28R in Dogs

Twenty-one dogs have been treated with P28R, 4 in the toxicological study (CiToxLab®, Denmark) with 200 nM administered in 1 mL subcutaneously and 17 dogs in the treatment study reported here with 40 nM in 200 microliters intra-tumourally.

None of these dogs showed any systemic side effects.

Example 62: Systemic Effect of P28R

Based on the observation that a therapeutic effect was obtained in untreated distant tumours in animals where one tumour was injected with P28R intra-tumorally, a study on the effect of systemic, subcutaneous administration of the drug was started.

Figure 92A:
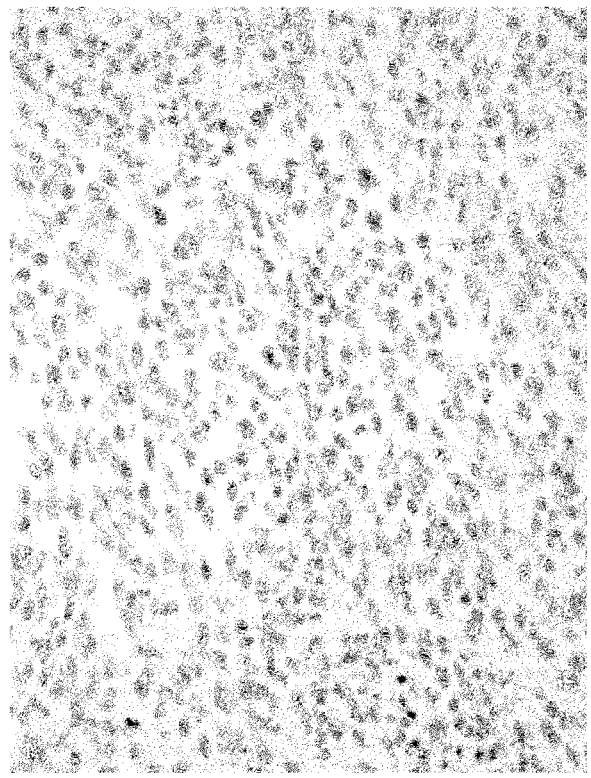
FIGS. 92A-B are a series of microscope images illustrating tumours in a CT26 colon cancer model. Apoptotic tumour cells are identified using the TUNEL staining technique. The tumours are counterstained using methyl-green pyronin.
Figure 92B:
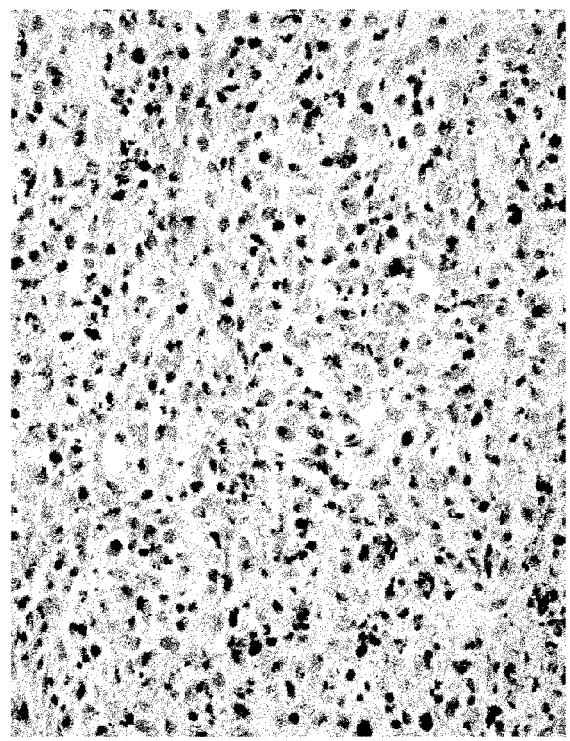

Mice with inoculate CT26 colon cancer were treated with 12 microgram P28R, twice weekly for two weeks. As shown in FIGS. 92A-B, apoptosis, identified using the TUNEL staining technique, was induced in the majority of tumour cells. A summary of these results are presented in Table 16.

Table 16 shows effects of subcutaneous administration of P28R twice weekly for two weeks on survival of CT26 colon cancer cells in BALBc mice. Two dose levels, 4 (D10) or 12 mg (D30) per injection were compared with injection of the vehicle. Apoptotic tumour cells were identified by staining using the TUNEL staining technique.

TABLE 16

| TUMOUR<br>MIC 11 TUNEL J84 | Number of viable<br>tumour cells | Number of<br>apoptotic tumour | Percent<br>Viable<br>tumour cells |
| --- | --- | --- | --- |
| Ctr 2 #24 4 2 | 65 | 44 | 59.6 |
| Ctr 4 #26 4 2 | 48 | 69 | 41.0 |
| Ctr 6 #28 1 2 | 61 | 48 | 56.0 |
| Ctr 7 #30 1 2 | 47 | 47 | 50.0 |
| Ctr 8 #33 3 2 | 52 | 57 | 47.7 |
| D10 3 #2 1 2 | 0 | 105 | 0.0 |
| D10 4 #4 1 2 | 36 | 57 | 38.7 |
| D10 5 #6 2 2 | 9 | 101 | 8.2 |
| D10 7 #9 3 2 | 11 | 59 | 15.7 |
| D10 8 #11 2 2 | ? | ? | n/a |
| D30 1 #13 1 2 | 7 | 65 | 9.7 |
| D30 2 #15 3 2 | 7 | 66 | 9.6 |
| D30 5 #17 3 2 | 25 | 82 | 23.4 |
| D30 6 #19 3 2 | 11 | 87 | 11.2 |
| D30 8 #22 2 2 | 7 | 85 | 7.6 |

Accordingly, it is shown that systemic administration, in addition to direct tumoral injection, of immunoregulatory peptide inhibitors in accordance with some embodiments herein can induce an inflammatory infiltration, regressive changes, and/or eradication of tumor tissues throughout the subject, and can induce programmed cell death in the tumor cells. As such, in some embodiments, an immunoregulatory peptide inhibitor as described herein is administered systemically, and induces inflammatory infiltration, regressive changes, programmed cell death, and/or eradication of a tumor located in a different tissue or organ from the site(s) of administration.

Example 63: Effects of Polyclonal Sera Against P3028 in a Mouse Model of Colon Cancer Oligoclonal rabbit antibodies against P3028 were shown to induce regressive changes in tumors in a mouse model of colon cancer. CT26 colon cancers in Balb/c mice were injected with an oligoclonal rabbit antibody against the denatured human albumin fragment (oligoclonal antibody "R") at 100 micrograms in 100 microliters, or with the same volume of saline as a control ("A").

Eradication of the tumor cells was readily observed in the antibody-injected mice after five days. As summarized in Table 17, the number of tumor cells was substantially reduced in oligoclonal antibody-injected mice (injected with oligoclonal antibody "R") compared to saline controls.

TABLE 17

| | Tumor | Number<br>of tumor cells<br>in injected tumor | Number of tumor cells in<br>uninjected<br>(contralateral) tumor |
| --- | --- | --- | --- |
| Saline-injected<br>control mice | A1 | 109 | 85 |
| | A2 | 64 | — |
| | A3 | 100 | 95 |
| | A4 | 81 | 91 |
| Antibody-<br>injected mice | B1 | 58 | 62 |
| | B2 | 42 | 39 |
| | B3 | 47 | 44 |
| | B4 | 41 | 32 |
| | B5 | 39 | 43 |
| | B6 | 53 | 42 |

In the mice injected with antibodies, eradication of tumor cells was observed in tumors that were directly injected with the antibody, and also in uninjected tumors, contralateral to the antibody-injected tumors (see FIGS. 93A-93B). Both FIGS. 93A and 93B show haematoxylin staining of uninjected tumours on the contralateral side of the injected tumours (FIG. 93A shows saline controls, and FIG. 93B shows antibody-injected animal). The tumour cell density is clearly reduced by antibody treatment.

Accordingly, an abscopal and/or systemic effect in an uninjected tumour from a treated mouse is observed. This effect is summarized numerically in the right-hand column of Table 16. As such, it is shown that in accordance with some embodiments herein, treatment of immunoregualtory peptides such as P3028 with an immunoregulatory peptide inhibitor (such as antibody, for example oligoclonal antibody against P3028) can have a systemic effect, and result in regressive changes both in tumors injected intratumorally or peri-tumorally with the immunoregulatory peptide inhibitor, and also in other tumors that were not directed intratumorally or peritumorally with the immunoregulatory peptide inhibitor.

What is claimed is:

1. A method of inhibiting a metastatic cancer in a subject, the method comprising:
   selecting a subject that has a metastatic cancer having at least a first tumor and a second tumor;
   administering a composition comprising an isolated peptide comprising the amino acid sequence FFVKLS (SEQ ID NO: 62) systemically;
   wherein the isolated peptide comprises no more than 30 amino acid residues and binds to an albumin fragment comprising the sequence of P3028 (SEQ ID NO: 185);
   thereby inhibiting the metastatic cancer.

2. The method of claim 1, wherein the administering induces regressive changes in the metastatic tumor, eradication of tumor cells of the metastatic tumor, immune cell infiltration of the metastatic tumor, or two or more of these, thereby inhibiting or eradicating the metastatic tumor.

3. The method of claim 1, wherein the first tumor is a primary tumor and the second tumor is a metastasis thereof.

4. The method of claim 1, wherein the metastatic cancer comprises a prostate tumor, a melanoma, a lung carcinoma, a colon cancer, an Apocrine gland carcinoma, a testis tumor, a mast cell tumor, a mammary tumor, a mucinous carcinoma, or a histicytoma.

5. The method of claim 1, wherein administering systemically inhibits a tumor of the metastatic cancer that is not at a site of administration.

6. The method of claim 1, wherein the isolated peptide is administered to the subject at a dose of at least about 1 ng/kg.

7. The method of claim 1, wherein said isolated peptide comprises the amino acid sequence KKLDTFFVKLSLFTER (SEQ ID NO: 2).

8. The method of claim 1, wherein said isolated peptide comprises the amino acid sequence RKLDTFFVKLSLFTERRR (SEQ ID NO: 586).

9. A composition comprising:
   an isolated peptide consisting of the amino acid sequence FFVKLS (SEQ ID NO: 62); and
   a support, in which the isolated peptide is immobilized on the support.

10. The method of claim 1, wherein said administration is done by subcutaneous, intravenous, intraperitoneal, or intramuscular administration.

* * * * *